(12) United States Patent
Park et al.

(10) Patent No.: US 11,665,958 B1
(45) Date of Patent: May 30, 2023

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Hyoung Keun Park, Cheonan-si (KR); Min Ji Jo, Cheonan-si (KR); Sun Hee Lee, Cheonan-si (KR); Soung Yun Mun, Cheonan-si (KR); Yong Wook Park, Cheonan-si (KR); Jin Woo Shin, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 93 days.

(21) Appl. No.: 17/807,495

(22) Filed: Jun. 17, 2022

(30) Foreign Application Priority Data

Nov. 26, 2021 (KR) ......................... 10-2021-0165118
Dec. 14, 2021 (KR) ......................... 10-2021-0178806

(51) Int. Cl.
| | | |
|---|---|---|
| *C07C 211/61* | (2006.01) | |
| *C07D 307/91* | (2006.01) | |
| *C07D 335/04* | (2006.01) | |
| *C07D 401/12* | (2006.01) | |
| *C09K 11/06* | (2006.01) | |
| *H01L 51/00* | (2006.01) | |
| *H01L 51/50* | (2006.01) | |

(52) U.S. Cl.
CPC .......... *H01L 51/006* (2013.01); *C07C 211/61* (2013.01); *C07D 307/91* (2013.01); *C07D 335/04* (2013.01); *C07D 401/12* (2013.01); *H01L 51/0061* (2013.01); *H01L 51/0072* (2013.01); *H01L 51/0058* (2013.01); *H01L 51/0067* (2013.01); *H01L 51/0073* (2013.01); *H01L 51/0074* (2013.01); *H01L 51/5056* (2013.01)

(58) Field of Classification Search
CPC . C07C 211/61; H01L 51/006; H01L 51/0061; H01L 51/0071; H01L 51/0072; H01L 51/0073; H01L 51/0074; H01L 51/5056
See application file for complete search history.

(56) References Cited

U.S. PATENT DOCUMENTS

2019/0016666 A1* 1/2019 Jeong ............... H01L 51/0073

FOREIGN PATENT DOCUMENTS

| KR | 10-2017-0080432 A | 7/2017 | |
|---|---|---|---|
| KR | 10-2017-0083765 A | 7/2017 | |
| KR | 10-2020-0018229 A | 2/2020 | |
| WO | WO-2014015935 A2 * | 1/2014 | .......... C07C 13/567 |

OTHER PUBLICATIONS

Notice of Allowance dated Feb. 21, 2022 for corresponding KR Application No. 10-2021-0178806, with English Translation, 4 pages.

* cited by examiner

*Primary Examiner* — Vu A Nguyen
(74) *Attorney, Agent, or Firm* — Vorys, Sater, Seymour and Pease LLP; Mih Suhn Koh

(57) ABSTRACT

Provided are a compound capable of improving the luminous efficiency, stability and lifespan of an organic electronic device, an organic electronic element using the same, and an electronic device thereof.

20 Claims, 3 Drawing Sheets

$$\Delta G = | E_A^{\text{site}} - E_B^{\text{site}} |$$

COMPOUND FOR ORGANIC ELECTRONIC ELEMENT, ORGANIC ELECTRONIC ELEMENT USING THE SAME, AND AN ELECTRONIC DEVICE THEREOF

BACKGROUND

Technical Field

The present invention relates to compound for organic electronic element, organic electronic element using the same, and an electronic device thereof.

Background Art

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function.

Currently, the portable display market is a large-area display, and the size thereof is increasing, and thus, more power consumption than the power consumption required for the existing portable display is required. Therefore, power consumption has become a very important factor for a portable display having a limited power supply such as a battery, and the problem of efficiency and lifespan must also be solved.

Efficiency, lifespan, and driving voltage are related to each other, and when the efficiency is increased, the driving voltage is relatively decreased, and as the driving voltage is decreased, crystallization of organic materials due to Joule heating generated during driving decreases, and consequently, the lifespan tends to increase.

However, the efficiency cannot be maximized simply by improving the organic material layer. This is because, when the energy level and T1 value between each organic material layer, and the intrinsic properties (mobility, interfacial properties, etc.) of materials are optimally combined, long lifespan and high efficiency can be achieved at the same time.

In other words, in order to fully exhibit the excellent characteristics of an organic electronic element, the material constituting the organic material layer in the device, such as a hole injection material, a hole transport material, a light emitting material, an electron transport material, an electron injection material, etc., is supported by a stable and efficient material should take precedence, but the development of a stable and efficient organic material layer material for an organic electronic device has not yet been sufficiently made. Therefore, the development of new materials is continuously required, and in particular, the development of a host material for the emitting layer is urgently required.

DETAILED DESCRIPTION OF THE INVENTION

Summary

In order to solve the problems of the above-mentioned background art, the present invention has revealed a compound having a novel structure, and when this compound is applied to an organic electronic element, it has been found that the luminous efficiency, stability and lifespan of the device can be significantly improved.

Accordingly, an object of the present invention is to provide a novel compound capable of improving the stability of the compound during device fabrication, used in a hole transport layer to finely control charge mobility, an organic electronic element using the same, and an electronic device thereof.

Technical Solution

An object of the present invention is to provide a compound capable of improving luminous efficiency, stability and lifespan of an element, an organic electronic element using the same, and an electronic device thereof.

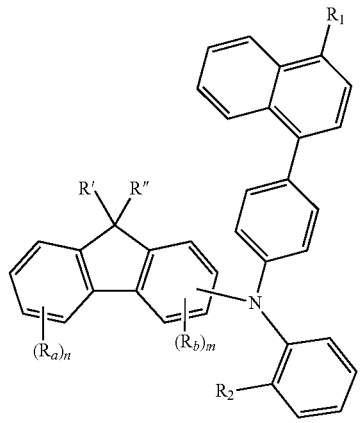

Formula 1

Effects of the Invention

By using the compound according to the present invention, high luminous efficiency, low driving voltage and high heat resistance of the device can be achieved, and color purity and lifespan of the device can be greatly improved.

DETAILED DESCRIPTION

Figure 1:
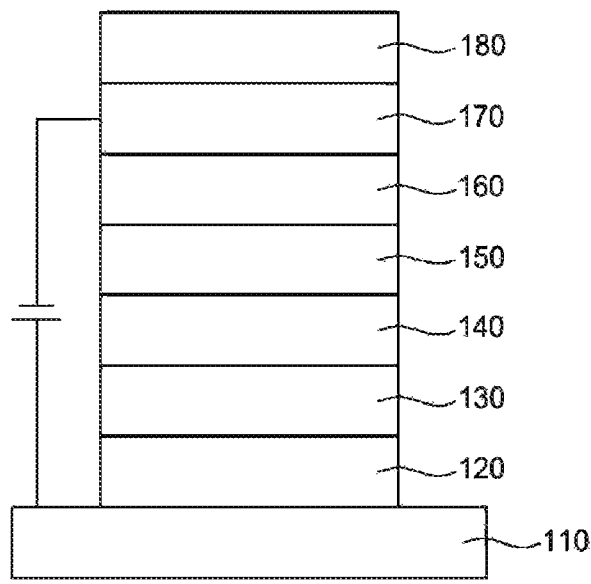
FIG. 1 to FIG. 3 are exemplary diagram of an organic electroluminescent device according to the present invention.

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

The terms "aryl group" and "arylene group" used in the present invention have 6 to 60 carbon atoms, respectively, unless otherwise specified, but are not limited thereto. In the present invention, an aryl group or an arylene group means a single ring or multiple ring aromatic, and includes an aromatic ring formed by an adjacent substituent joining or participating in a reaction.

For example, the aryl group may be a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, includes any one of a single ring or multiple ring, and may include heteroaliphadic ring and heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including $SO_2$ instead of carbon consisting of cycle. For example, "heterocyclic group" includes the following compound.

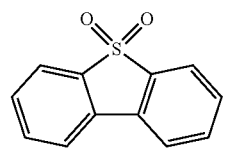 [SMILES: O=S1(=O)c2ccccc2-c2ccccc21]

Unless otherwise stated, the term "fluorenyl group" or "fluorenylene group", as used herein, means a monovalent or divalent functional group, in which R, R' and R" are all hydrogen in the following structures, and the term "substituted fluorenyl group" or "substituted fluorenylene group" means that at least one of the substituents R, R', R" is a substituent other than hydrogen, and include those in which R and R' are bonded to each other to form a spiro compound together with the carbon to which they are bonded.

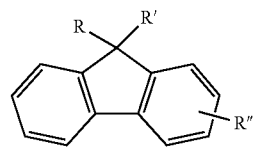

The term "spiro compound", as used herein, has a 'spiro union', and a spiro union means a connection in which two rings share only one atom. At this time, atoms shared in the two rings are called 'spiro atoms', and these compounds are called 'monospiro-', 'di-spiro' and 'tri-spiro', respectively, depending on the number of spiro atoms in a compound.

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Also, unless expressly stated, as used herein, "substituted" in the term "substituted or unsubstituted" means substituted with one or more substituents selected from the group consisting of deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group, but is not limited to these substituents.

Also, unless there is an explicit explanation, the formula used in the present invention is the same as the definition of the substituent by the exponent definition of the following formula.

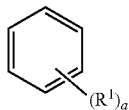

Here, when a is an integer of zero, the substituent $R^1$ is absent, when a is an integer of 1, the sole substituent $R^1$ is linked to any one of the carbon constituting the benzene ring, when a is an integer of 2 or 3, each is combined as follows, where $R^1$ may be the same or different from each other, when a is an integer of 4 to 6, it is bonded to the carbon of the benzene ring in a similar manner, while the indication of the hydrogen bonded to the carbon forming the benzene ring is omitted.

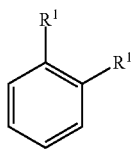

(a = 2)

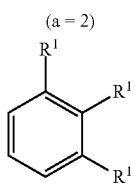

(a = 3)

Hereinafter, a compound according to an aspect of the present invention and an organic electronic element including the same will be described.

The present invention provides a compound represented by Formula 1.

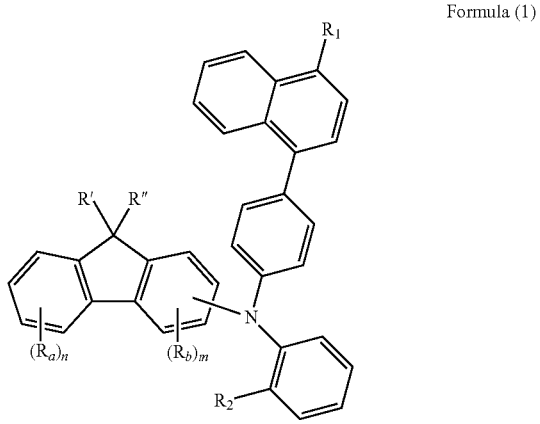

Formula (1)

Wherein, each symbol may be defined as follows.

1) R' and R" are each independently selected from the group consisting of hydrogen; $C_6$-$C_{60}$ aryl group; $C_2$-$C_{60}$ heterocyclic group including at least one heteroatom of O, N, S, Si or P, fused ring group of a $C_3$-$C_{60}$ aliphatic ring and a $C_6$-$C_{60}$ aromatic ring; $C_1$-$C_{50}$ alkyl group; $C_2$-$C_{20}$ alkenyl group; $C_2$-$C_{20}$ alkynyl group; $C_1$-$C_{30}$ alkoxy group; $C_6$-$C_{30}$ aryloxy group; or R' and R" may be bonded to each other to form a spiro.

When R' and R" are aryl groups, they may be preferably $C_6$-$C_{30}$ aryl groups, more preferably $C_6$-$C_{25}$ aryl groups, such as phenylene, biphenyl, naphthalene, terphenyl, and the like.

When R' and R" are heterocyclic groups, they may be preferably $C_2$-$C_{30}$ heterocyclic groups, and more preferably $C_2$-$C_{24}$ heterocyclic groups, for example, it may be pyrazine, pyridine, pyrimidoindole, 5-phenyl-5H-pyrimido[5,4-b]indole, quinazoline, benzoquinazoline, carbazole, dibenzoquinazole, dibenzofuran, dibenzothiophene, benzothienopyrimidine, benzofuropyrimidine, phenothiazine, phenylphenothiazine, etc.

When R' and R" are fused ring groups, they may be preferably fused ring groups of a $C_3$-$C_{30}$ aliphatic ring and a $C_6$-$C_{30}$ aromatic ring, more preferably fused ring groups of a $C_3$-$C_{24}$ aliphatic ring and a $C_6$-$C_{24}$ aromatic ring.

When R' and R" are alkyl groups, they may be preferably $C_1$-$C_{30}$ alkyl groups, and more preferably $C_1$-$C_{24}$ alkyl groups.

When R' and R" are alkoxy groups, they may be preferably $C_1$-$C_{24}$ alkoxy groups.

When R' and R" are aryloxy groups, they may be preferably $C_6$-$C_{24}$ aryloxy groups.

2) $R_1$ and $R_2$ are each independently selected from the group consisting of $C_6$-$C_{60}$ aryl group; fluorenyl group; $C_2$-$C_{60}$ heterocyclic group including at least one heteroatom of O, N, S, Si or P; fused ring group of a $C_3$-$C_{60}$ aliphatic ring and a $C_6$-$C_{60}$ aromatic ring; $C_1$-$C_{60}$ alkyl group; $C_2$-$C_{20}$ alkenyl group; $C_2$-$C_{20}$ alkynyl group; $C_1$-$C_{30}$ alkoxy group; $C_6$-$C_{30}$ aryloxy group; and $C_3$-$C_{60}$ cycloalkyl group;

When $R_1$ and $R_2$ are aryl groups, they may be preferably $C_6$-$C_{30}$ aryl groups, more preferably $C_6$-$C_{25}$ aryl groups, such as phenylene, biphenyl, naphthalene, terphenyl, and the like.

When $R_1$ and $R_2$ are heterocyclic groups, they may be preferably $C_2$-$C_{30}$ heterocyclic groups, and more preferably $C_2$-$C_{24}$ heterocyclic groups, for example, they may be pyrazine, pyridine, pyrimidoindole, 5-phenyl-5H-pyrimido[5,4-b]indole, quinazoline, benzoquinazoline, carbazole, dibenzoquinazole, dibenzofuran, dibenzothiophene, benzothienopyrimidine, benzofuropyrimidine, phenothiazine, phenylphenothiazine, etc.

When $R_1$ and $R_2$ are fused ring groups, they may be preferably fused ring groups of a $C_3$-$C_{30}$ aliphatic ring and a $C_6$-$C_{30}$ aromatic ring, more preferably fused ring groups of a $C_3$-$C_{24}$ aliphatic ring and a $C_6$-$C_{24}$ aromatic ring.

When $R_1$ and $R_2$ are alkyl groups, they may be preferably $C_1$-$C_{30}$ alkyl groups, and more preferably $C_1$-$C_{24}$ alkyl groups.

When $R_1$ and $R_2$ are alkoxy groups, they may be preferably $C_1$-$C_{24}$ alkoxy groups.

When $R_1$ and $R_2$ are aryloxy groups, they may be preferably $C_6$-$C_{24}$ aryloxy groups.

When $R_1$ and $R_2$ are cycloalkyl groups, they may be preferably $C_3$-$C_{30}$ cycloalkyl groups, and more preferably $C_3$-$C_{24}$ cycloalkyl groups.

3) $R_a$ and $R_b$ are the same or different from each other, and are each independently selected from the group consisting of a hydrogen; deuterium; halogen; $C_6$-$C_{60}$ aryl group; fluorenyl group; $C_2$-$C_{60}$ heterocyclic group including at least one heteroatom of O, N, S, Si or P, fused ring group of a $C_3$-$C_{60}$ aliphatic ring and a $C_6$-$C_{60}$ aromatic ring; $C_1$-$C_{50}$ alkyl group; $C_2$-$C_{20}$ alkenyl group; $C_2$-$C_{20}$ alkynyl group; $C_1$-$C_{30}$ alkoxy group; $C_6$-$C_{30}$ aryloxy group; $C_3$-$C_{60}$ cycloalkyl group or an adjacent plurality of $R_a$s, or a plurality of $R_b$s may be bonded to each other to form a ring.

When $R_a$ and $R_b$ are aryl groups, they may be preferably $C_6$-$C_{30}$ aryl groups, more preferably $C_6$-$C_{25}$ aryl groups, such as phenylene, biphenyl, naphthalene, terphenyl, and the like.

When $R_a$ and $R_b$ are heterocyclic groups, they may be preferably $C_2$-$C_{30}$ heterocyclic groups, and more preferably $C_2$-$C_{24}$ heterocyclic groups, for example, it may be pyrazine, pyridine, pyrimidoindole, 5-phenyl-5H-pyrimido[5,4-b]indole, quinazoline, benzoquinazoline, carbazole, dibenzoquinazole, dibenzofuran, dibenzothiophene, benzothienopyrimidine, benzofuropyrimidine, phenothiazine, phenylphenothiazine, etc.

When $R_a$ and $R_b$ are fused ring groups, they may be preferably fused ring groups of a $C_3$-$C_{30}$ aliphatic ring and a $C_6$-$C_{30}$ aromatic ring, more preferably fused ring groups of a $C_3$-$C_{24}$ aliphatic ring and a $C_6$-$C_{24}$ aromatic ring.

When $R_a$ and $R_b$ are alkyl groups, they may be preferably $C_1$-$C_{30}$ alkyl groups, and more preferably $C_1$-$C_{24}$ alkyl groups.

When $R_a$ and $R_b$ are alkoxy groups, they may be preferably $C_1$-$C_{24}$ alkoxy groups.

When $R_a$ and $R_b$ are aryloxy groups, they may be preferably $C_6$-$C_{24}$ aryloxy groups.

When $R_a$ and $R_b$ are cycloalkyl groups, they may be preferably $C_3$-$C_{30}$ cycloalkyl groups, and more preferably $C_3$-$C_{24}$ cycloalkyl groups.

4) m is an integer of 0 to 3, n is an integer of 0 to 4, 5) wherein the aryl group, heterocyclic group, fluorenyl group, aliphatic ring, fused ring group, alkyl group, alkenyl group, alkynyl group, alkoxy group, aryloxy group and cycloalkyl group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group; also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Also, the compound represented by Formula 1 is represented by any one of Formulas 2 to 5

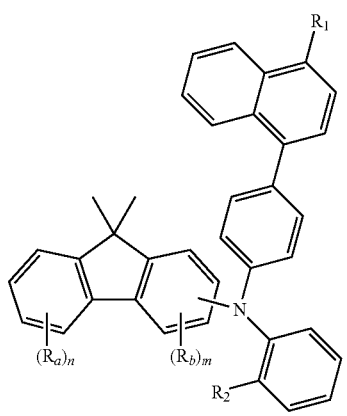

Formula 2

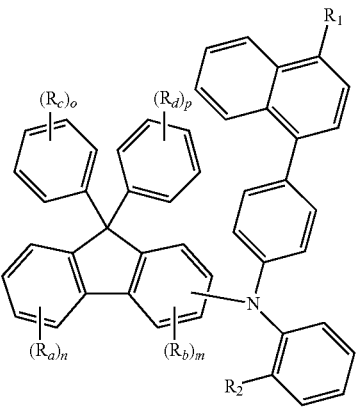

Formula 3

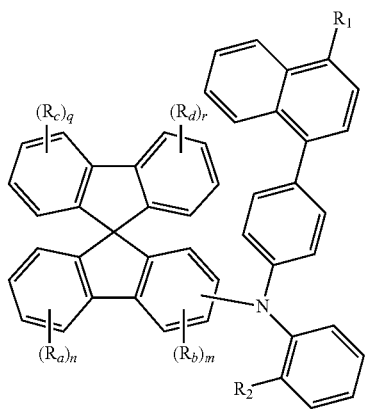

Formula 4

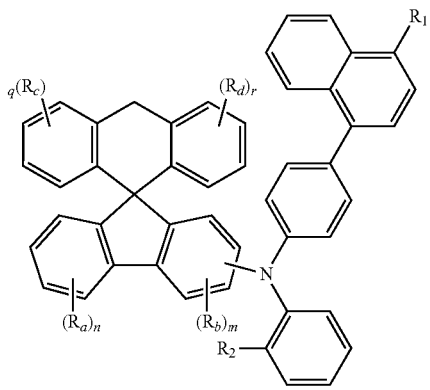

Formula 5

Wherein,

1) $R_1$, $R_2$, $R_a$, $R_b$, m and n are the same as defined above,

2) X is O or S,

3) $R_c$ and $R_d$ are the same as definition of $R_a$ 4) o and p are each independently an integer from 0 to 5, q and r are each independently an integer from 0 to 4.

Also, the compound represented by Formula 1 is represented by Formula 6.

Formula 6

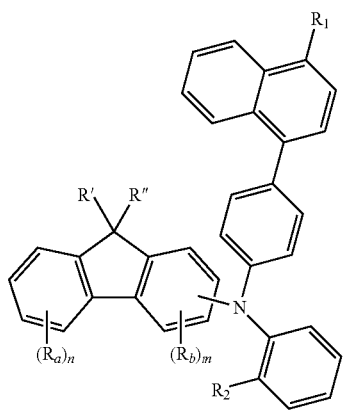

Wherein
1) R', R", $R_1$, $R_2$, m and n are the same as defined above,
2) $R_a$ and $R_b$ are hydrogen.

Also, the compound represented by Formula 1 is represented by Formula 7.

Formula 7

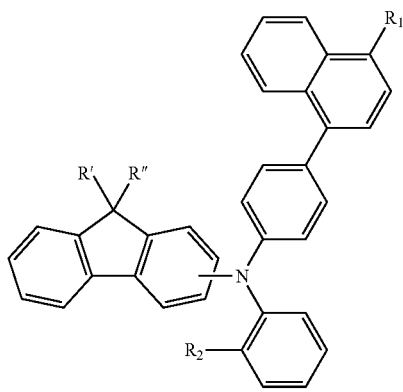

Wherein,
1) R' and R" are the same as defined above,
2) $R_1$ and $R_2$ are each independently $C_6$-$C_{25}$ aryl groups.

Also, the compound represented by Formula 1 is represented by any one of Formulas 8 to 11.

Formula 8

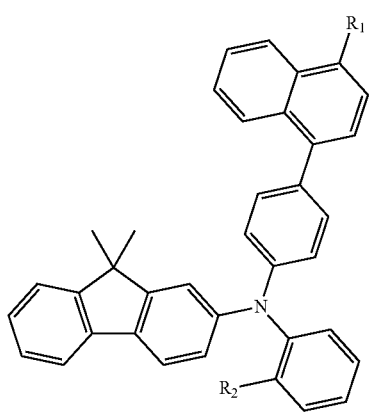

Formula 9

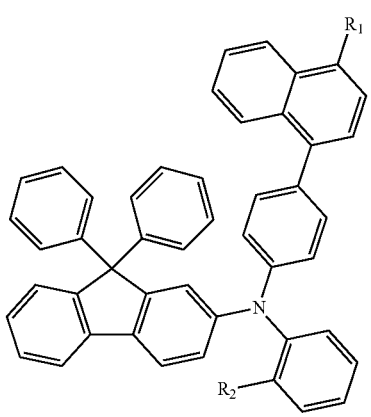

Formula 10

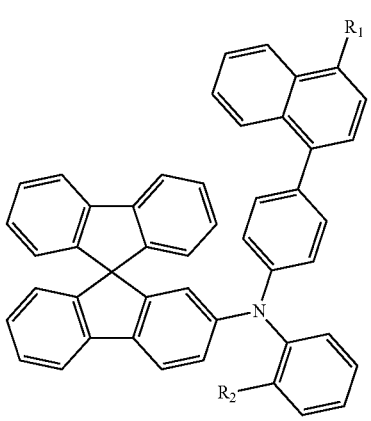

Formula 11

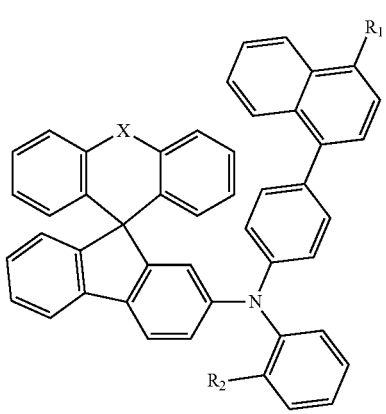

Wherein, $R_1$, $R_2$ and X are the same as defined above.

Also, the present invention provides compounds in which both $R_1$ and $R_2$ of Formulas 8 to 11 are $C_6$ aryl groups.

Also, the compound represented by Formula 1 is for the hole transport layer (HTL) of the hole transport region.

Specifically, the compound represented by Formula 1 may be any one of the following compounds.

P-1
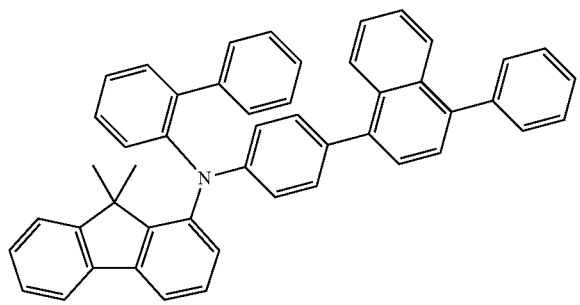
P-2
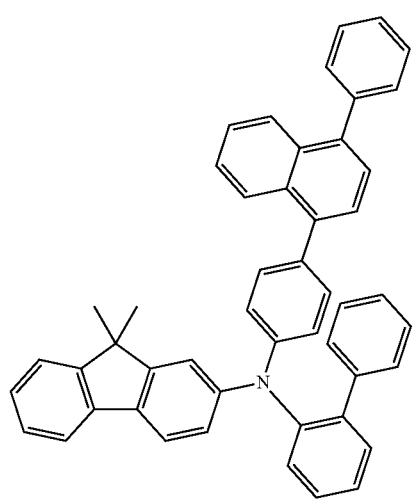
P-3
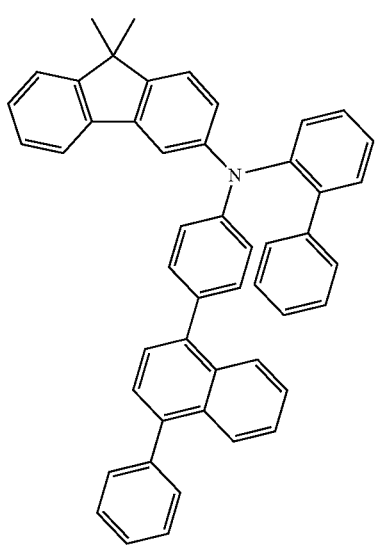
P-4
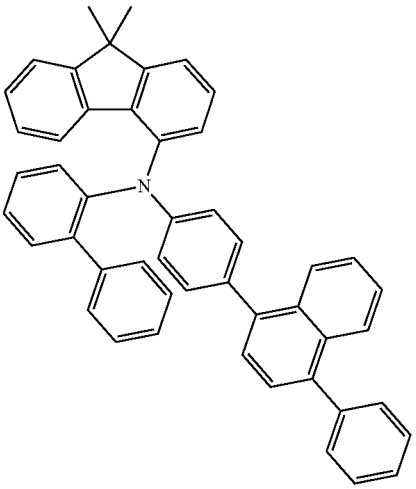
P-5
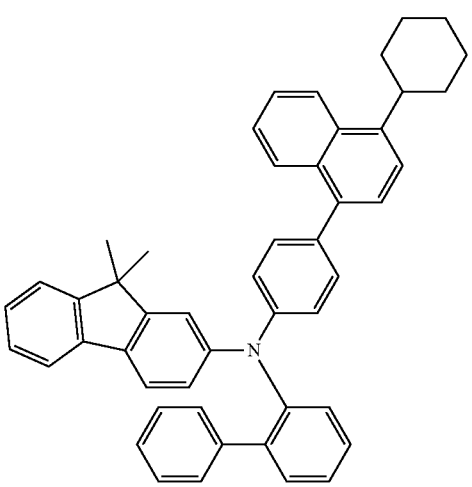
P-6
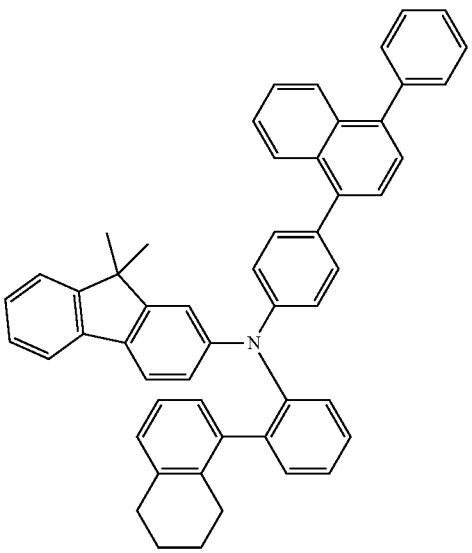

P-7
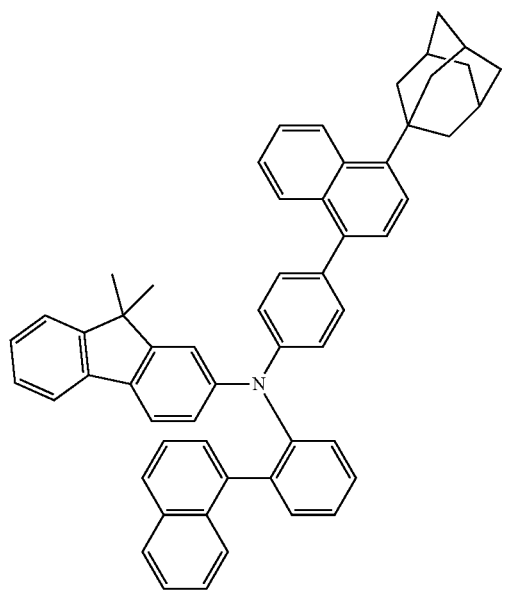
P-8
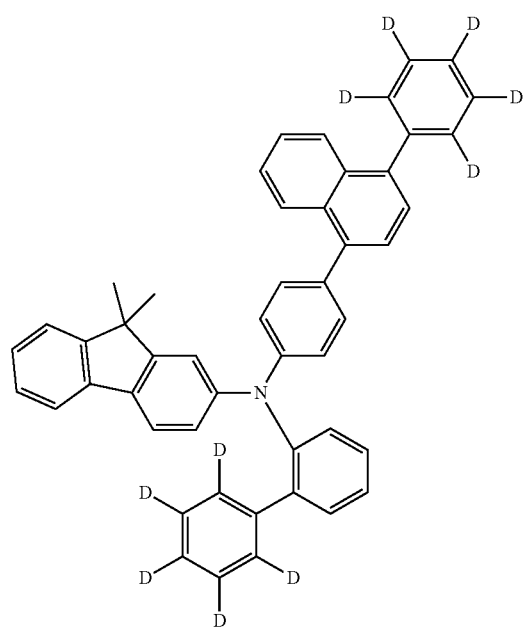
P-9
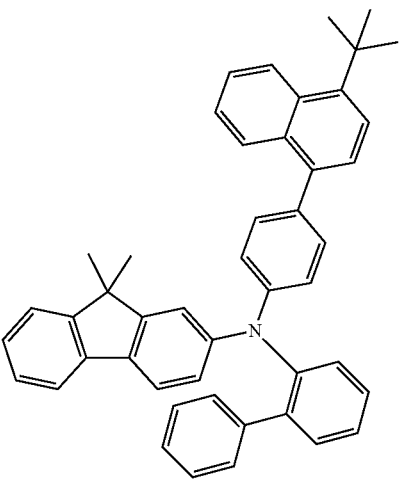
P-10
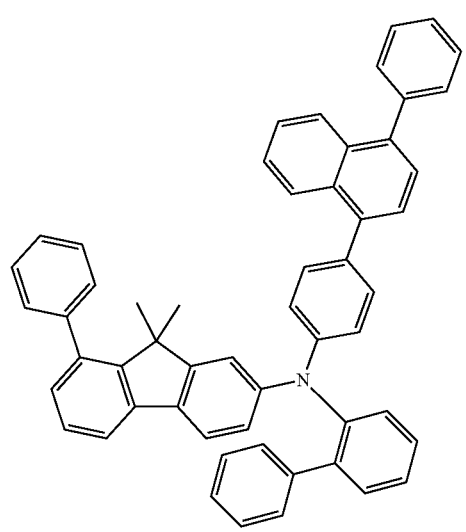
P-11
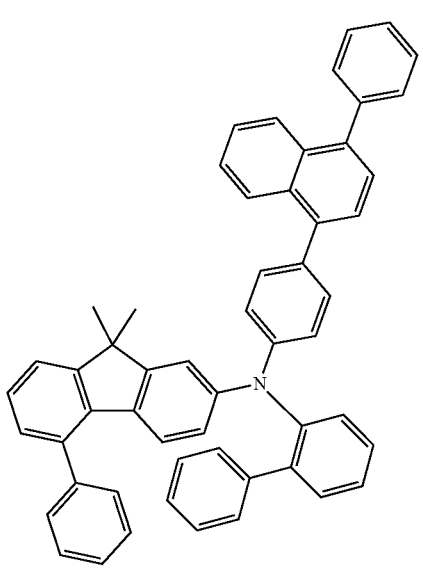

P-12
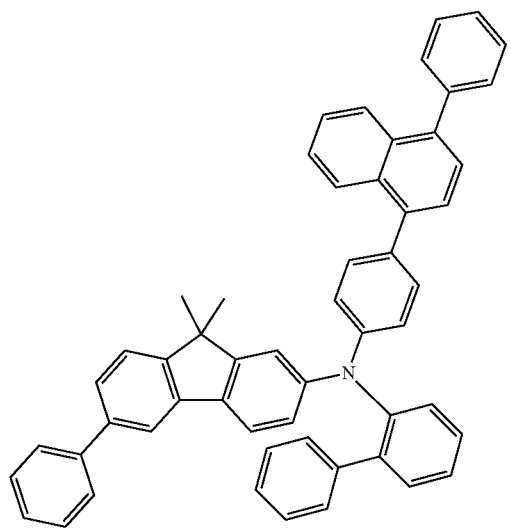
P-13
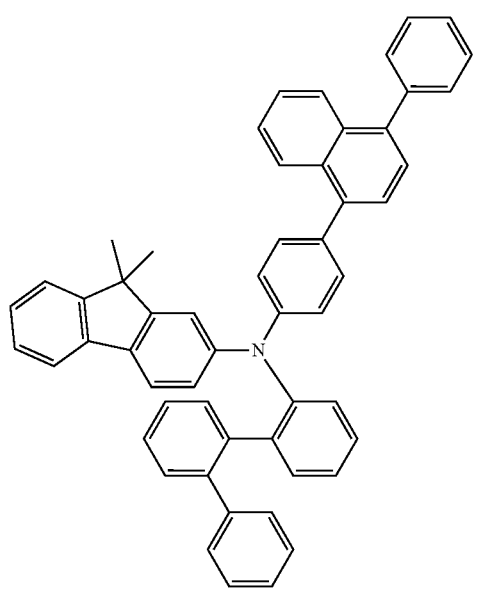
P-14
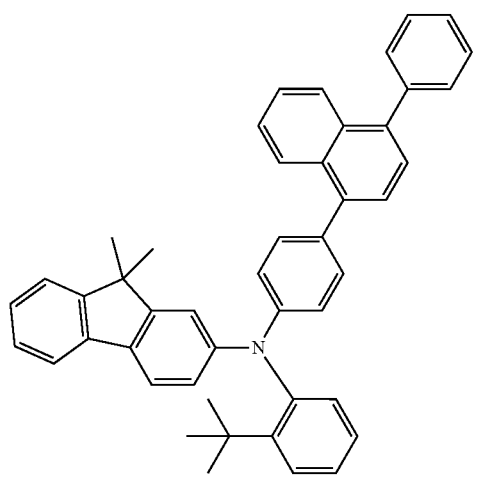
P-15
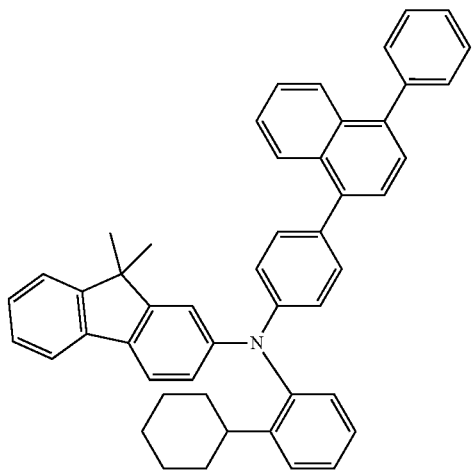
P-16
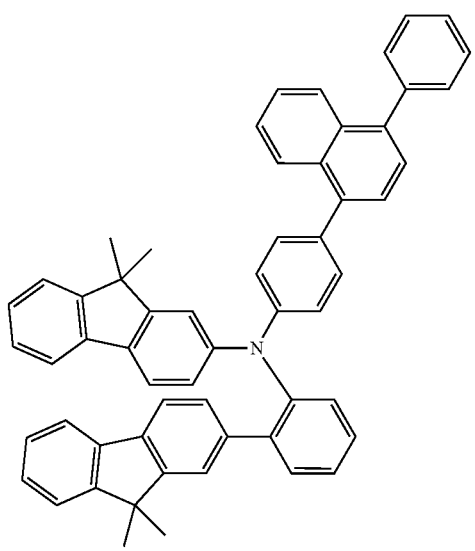
P-17
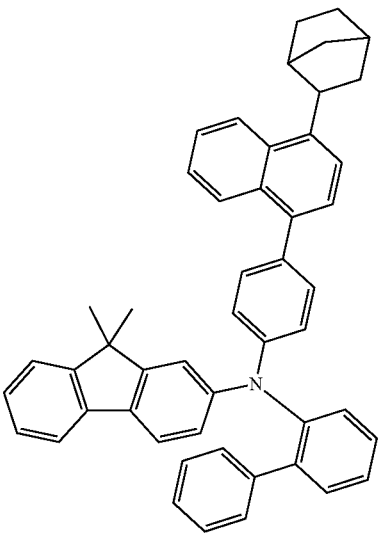

P-18
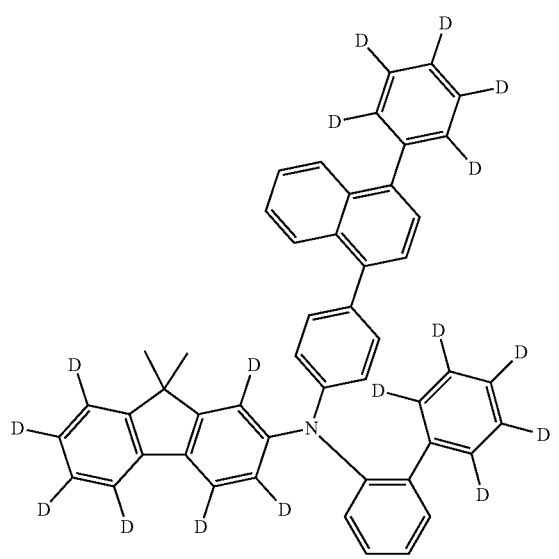
P-19
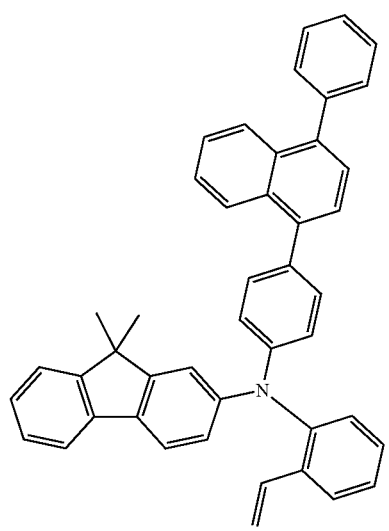
P-20
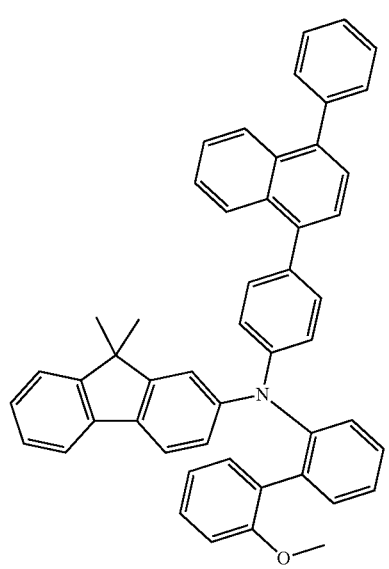
P-21
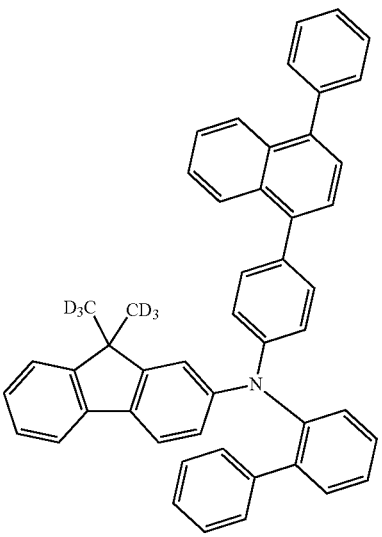
P-22
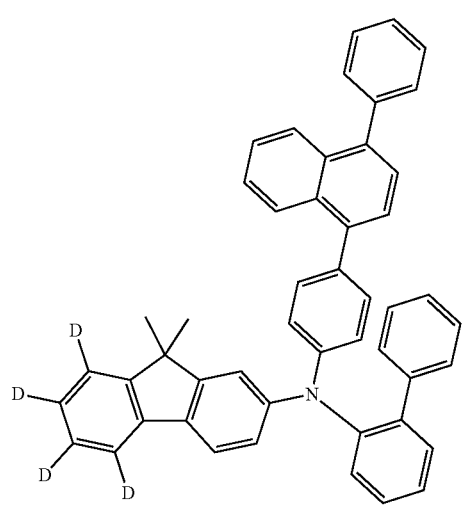
P-23
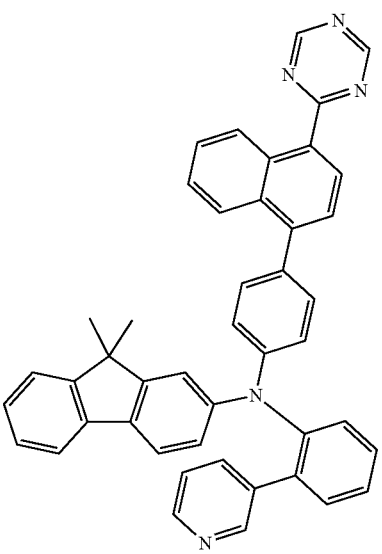

-continued
P-24
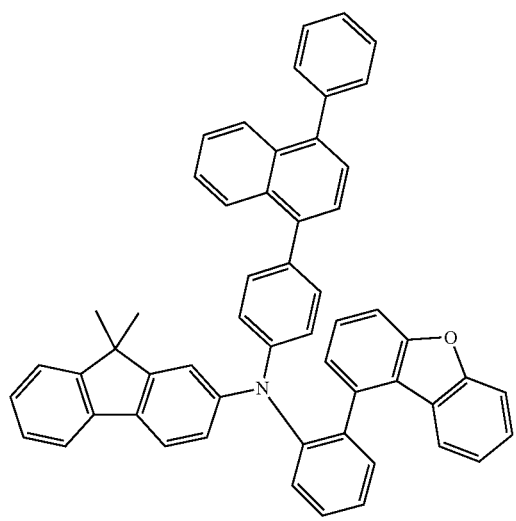
P-25
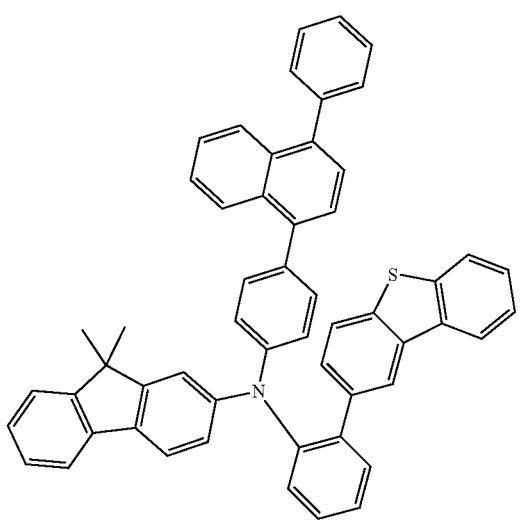
P-26
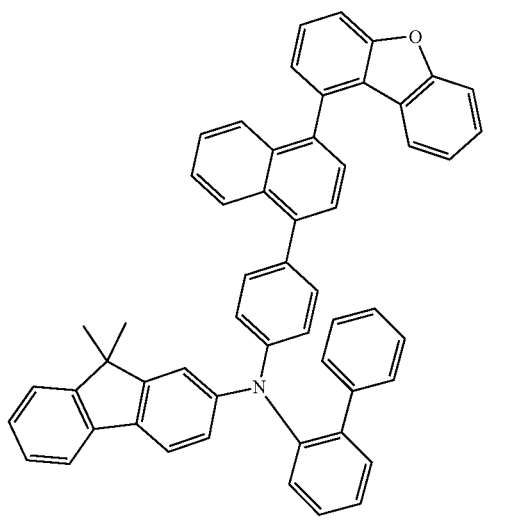
P-27
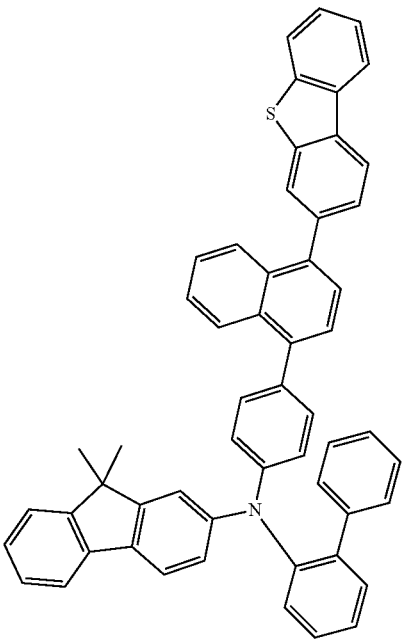
P-28
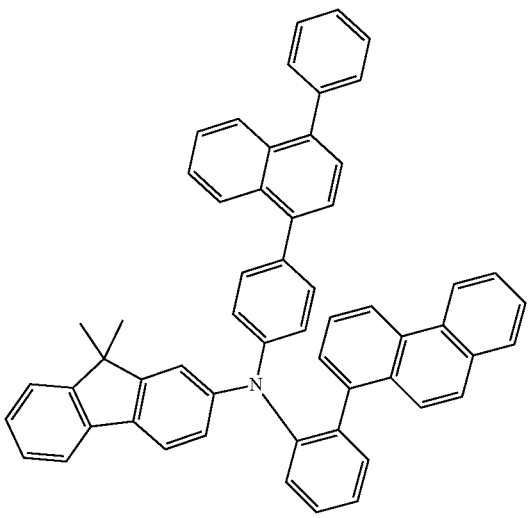

P-29
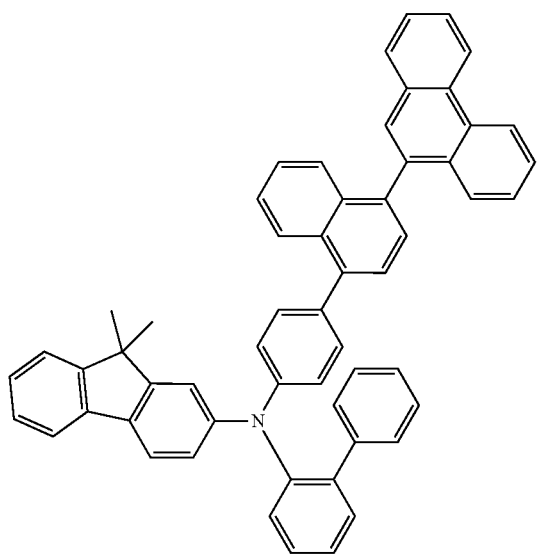
P-31
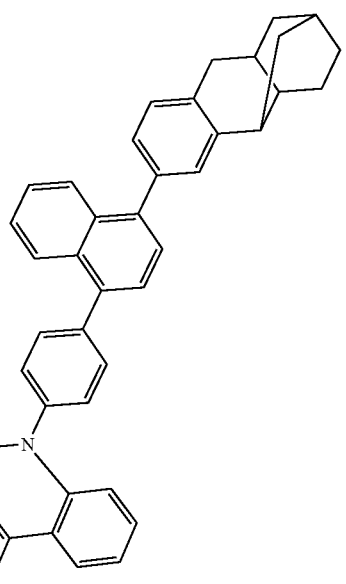
P-32
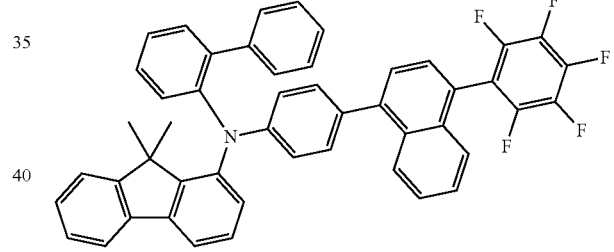
P-30
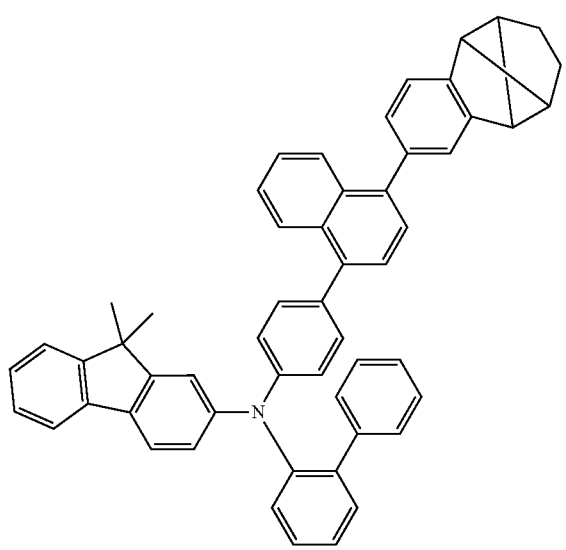
P-33
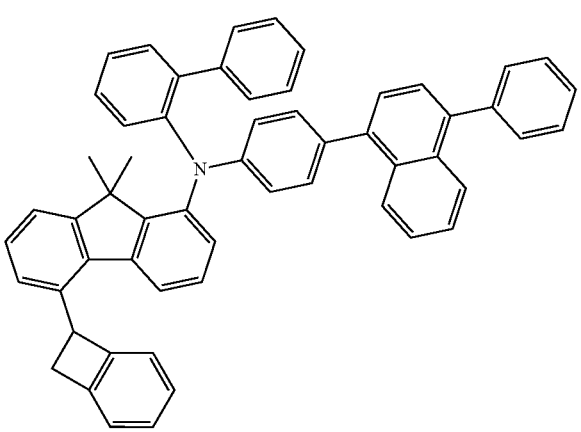

P-34
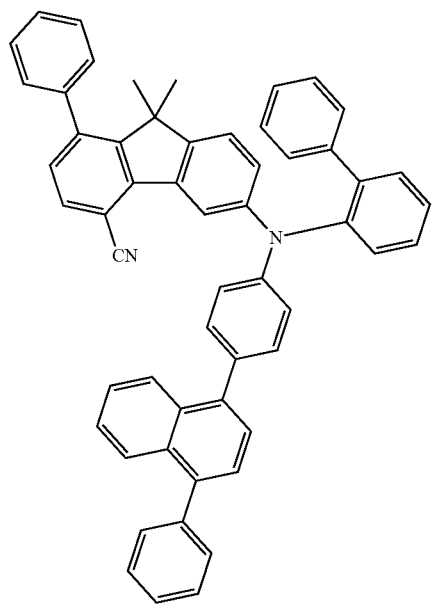
P-35
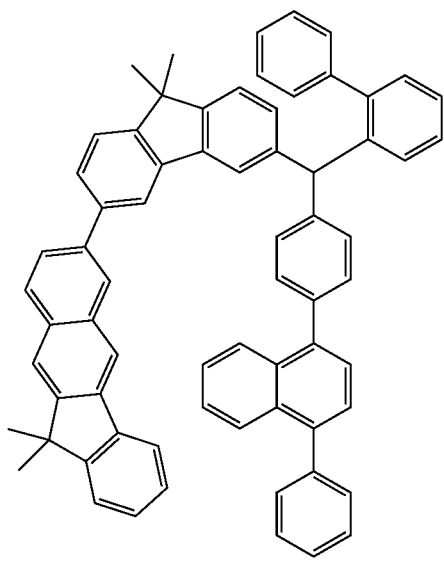
P-36
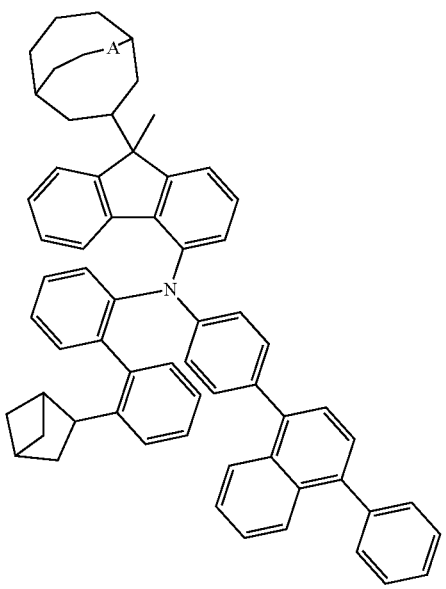
P-37
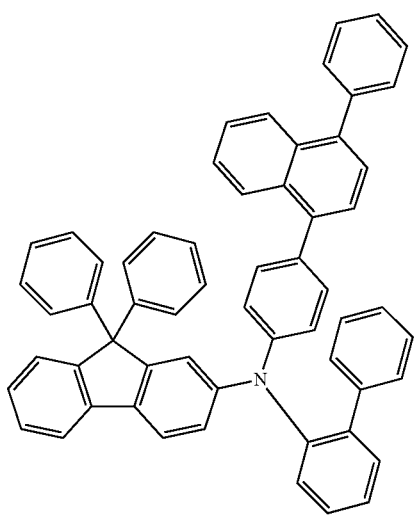

P-39
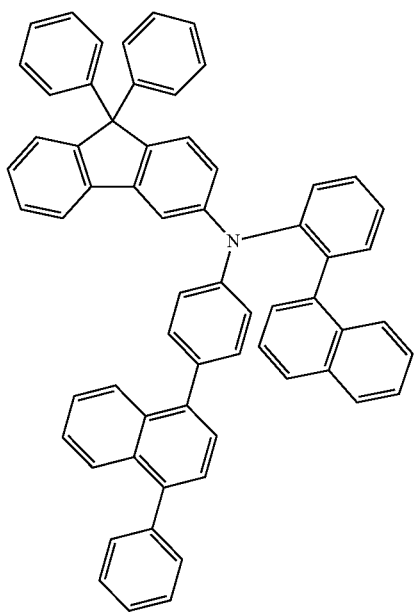
P-42
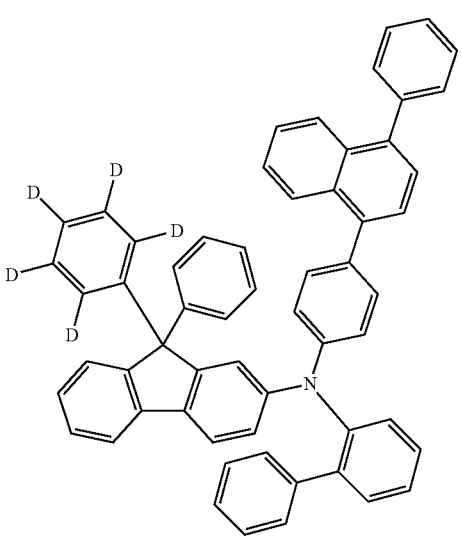
P-40
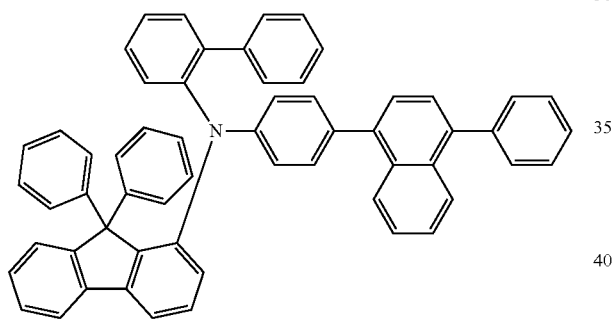
P-41
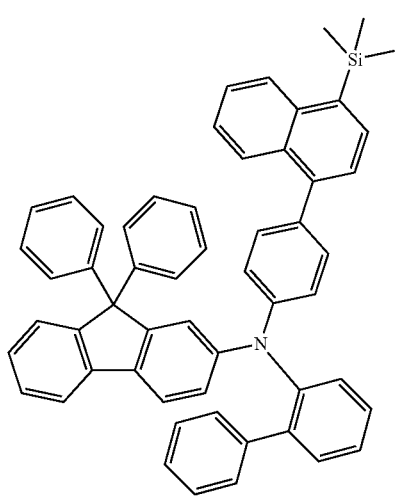
P-43
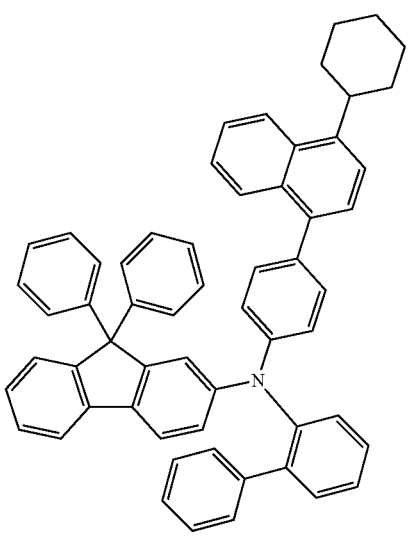

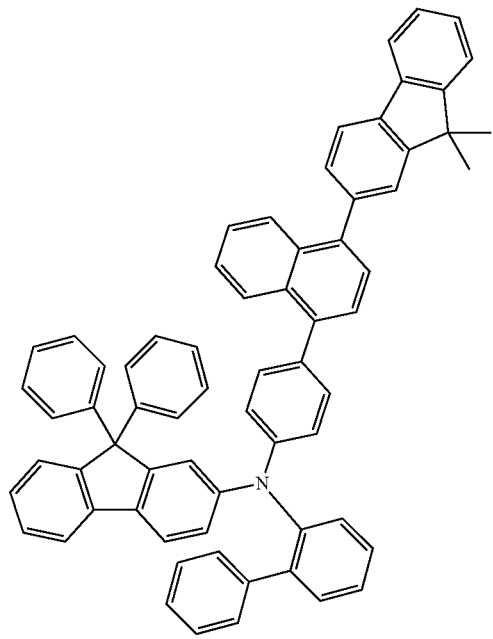
P-44
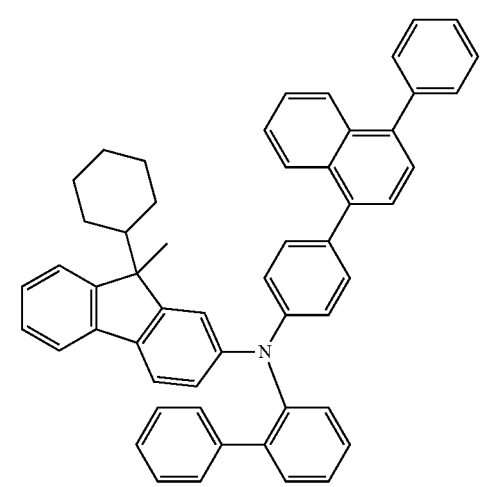
P-45
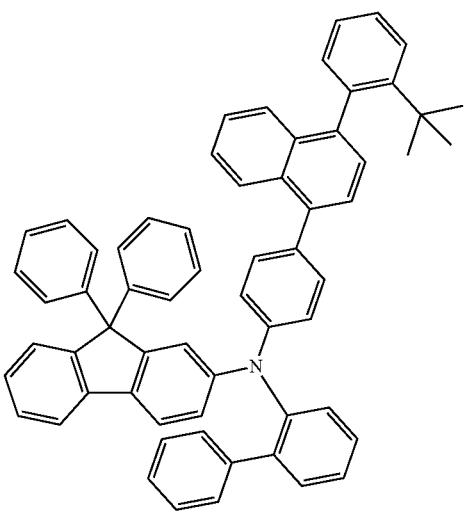
P-46
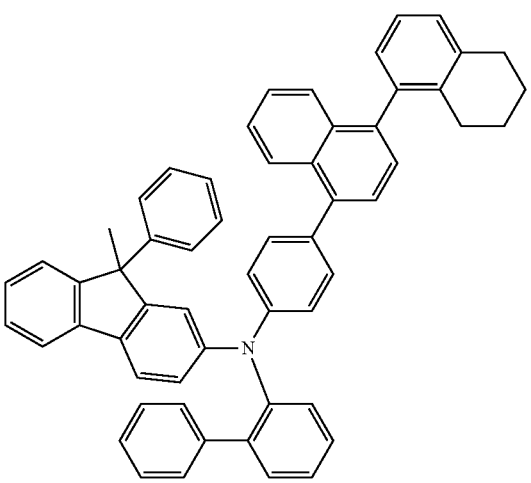
P-47
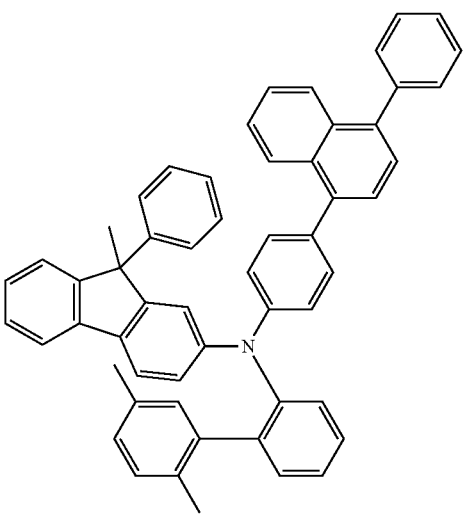
P-48
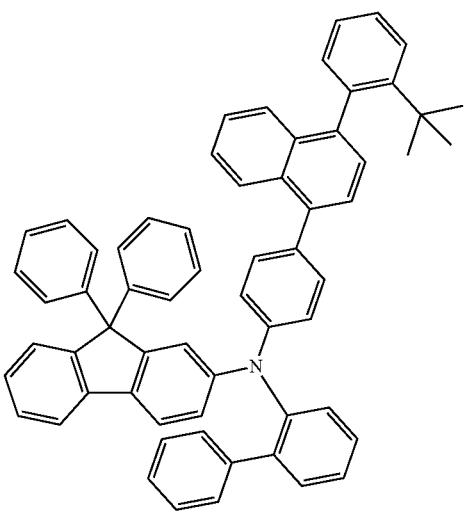
P-49

P-50
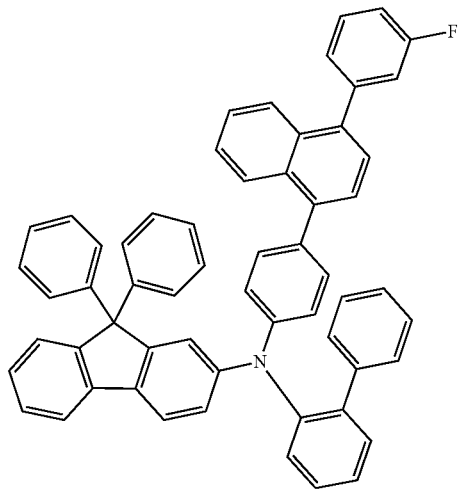
P-51
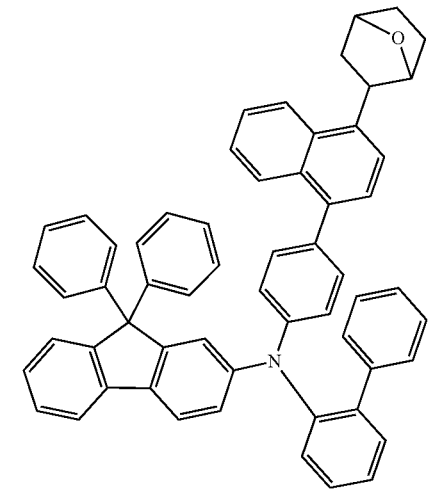
P-52
P-53
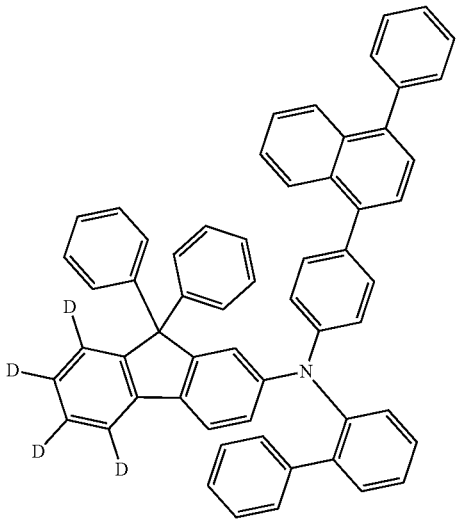
P-54
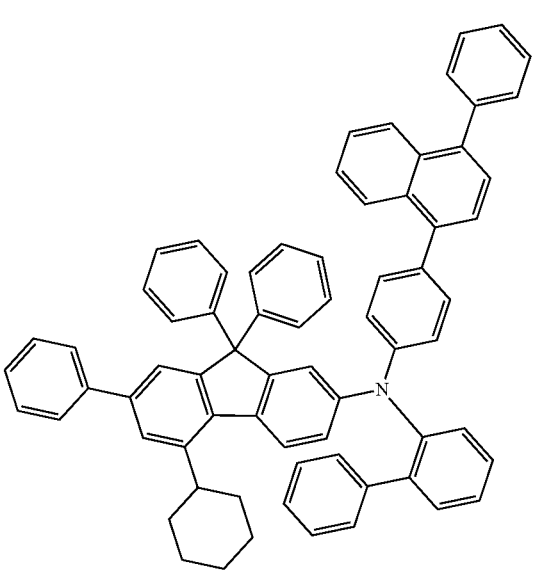
P-55
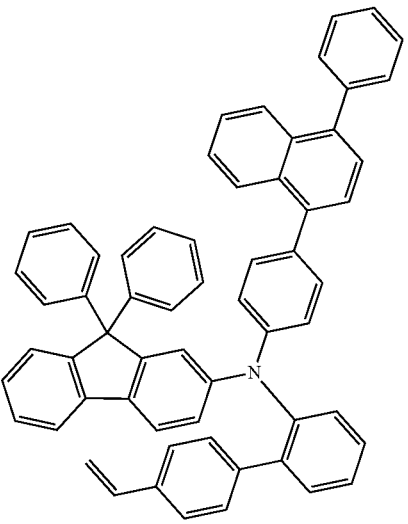

P-56
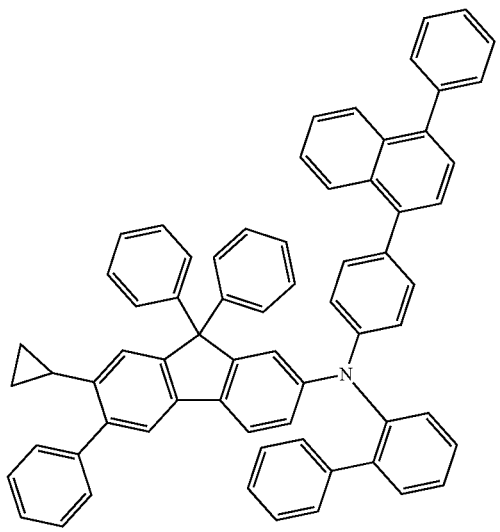
P-57
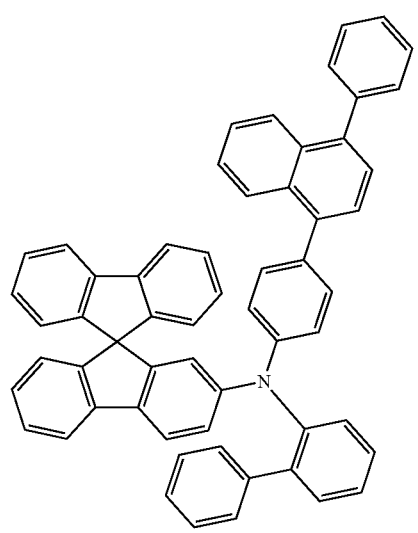
P-58
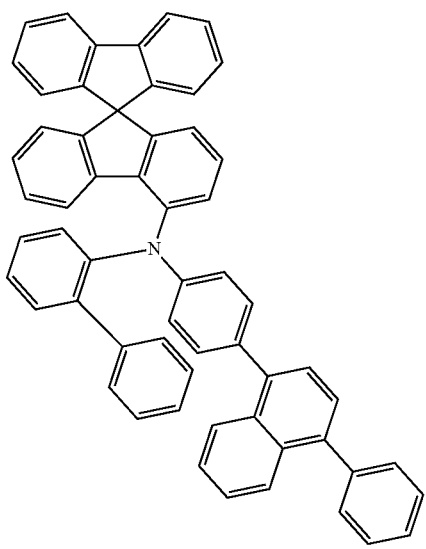
P-59
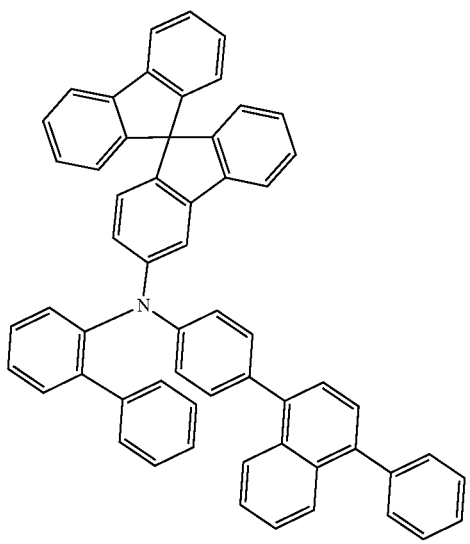
P-60
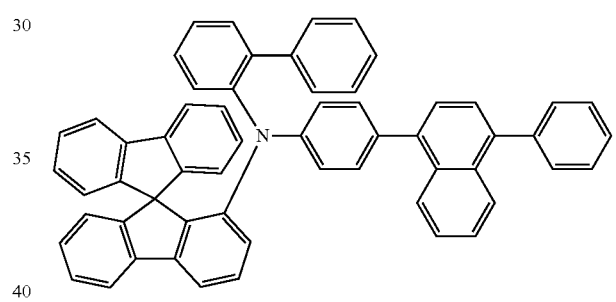
P-61
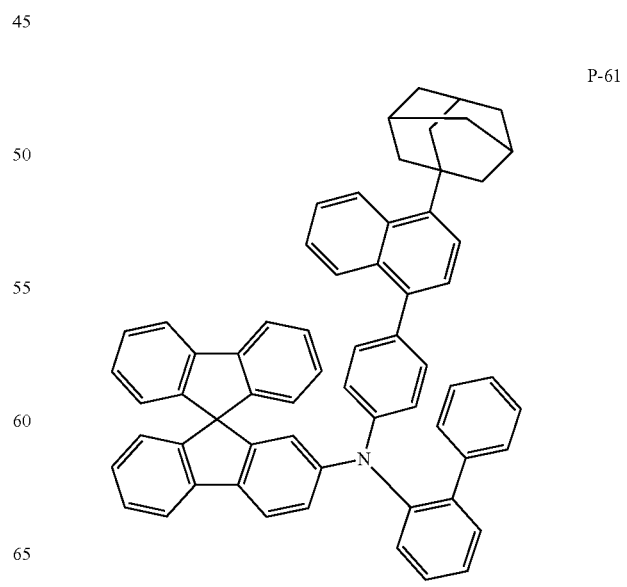

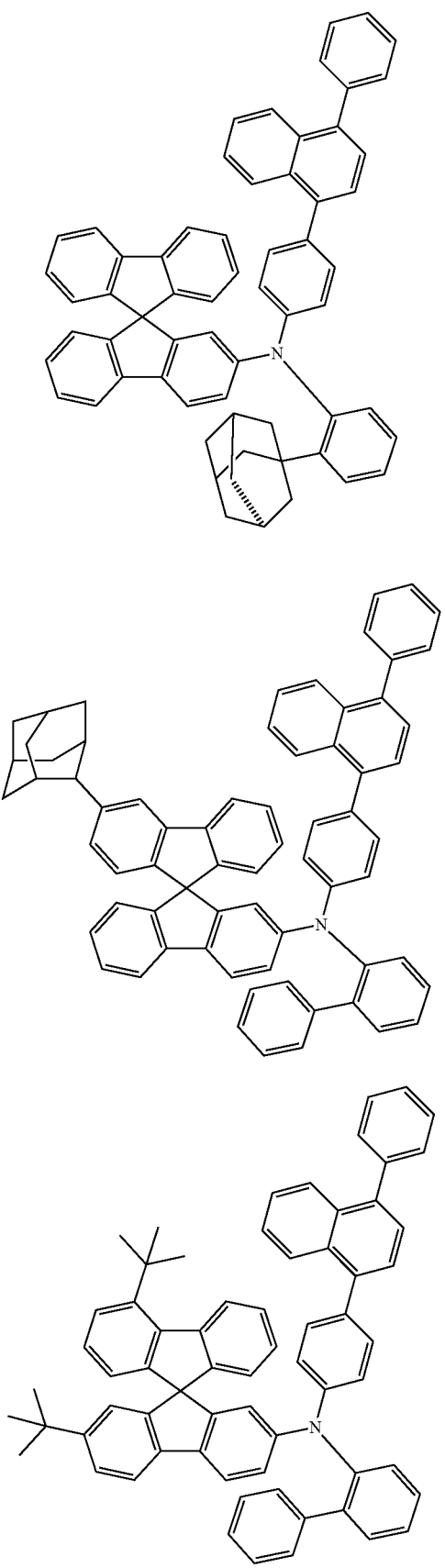
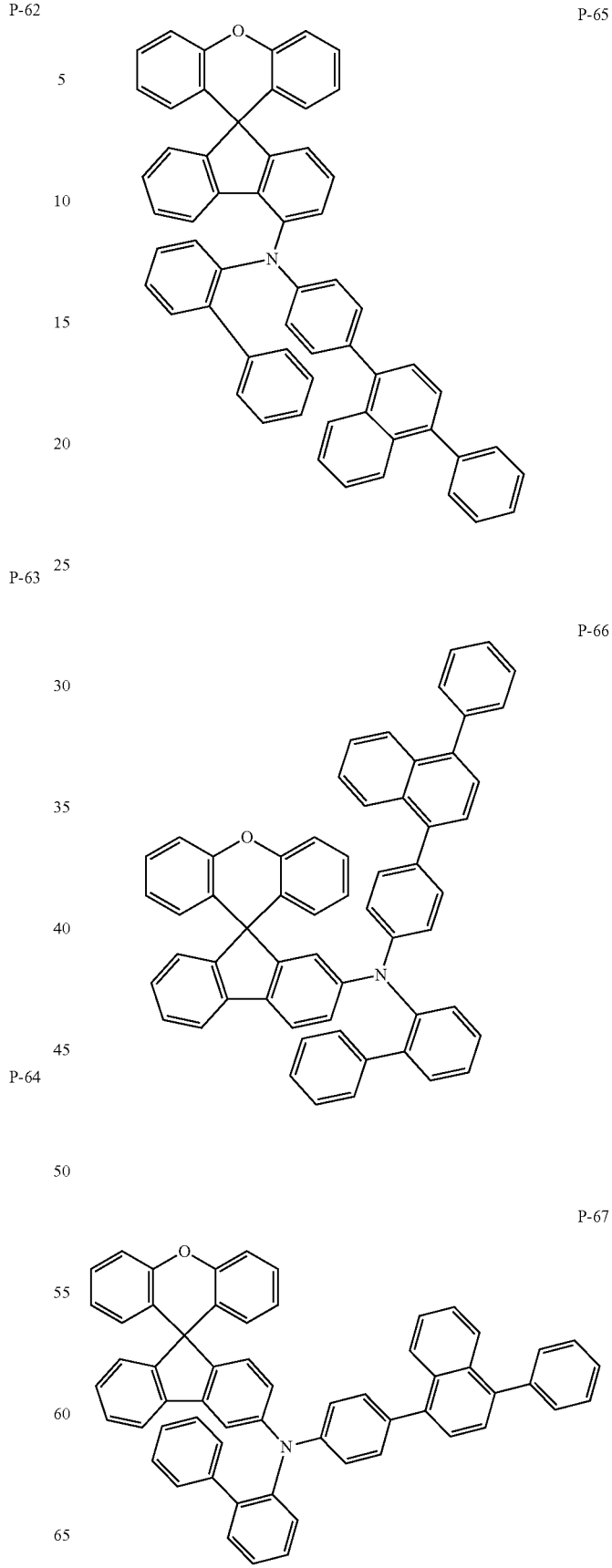

P-68

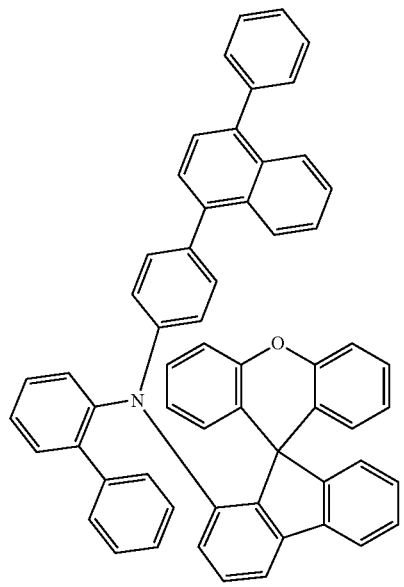

P-69

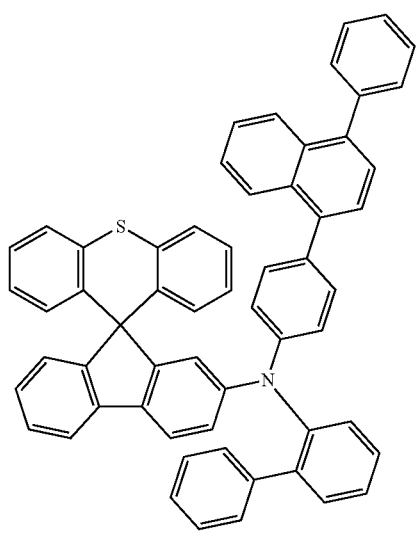

P-70

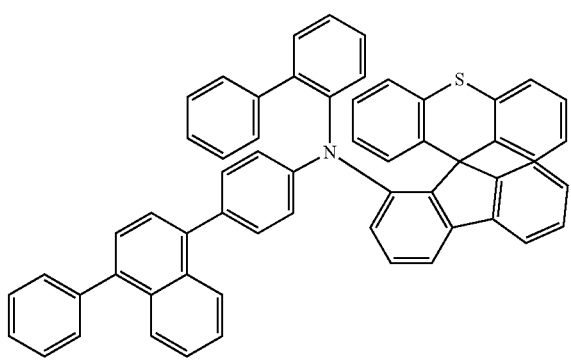

P-71

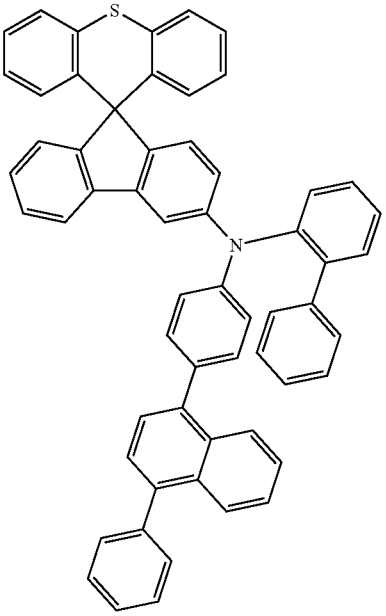

P-72

Also, in another aspect, the present invention provides an organic electronic element comprising an anode, a cathode, and an organic material layer formed between the anode and the cathode, wherein the organic material layer comprises a single compound or 2 or more compounds represented by Formula 1.

Also, the present invention provides an organic electronic element comprising at least one of a hole injection layer, a hole transport layer, an emitting auxiliary layer, an emitting layer, an electron transport auxiliary layer, an electron transport layer and an electron injection layer as the organic material layer.

Also, the present invention provides an organic electronic element comprising at least one of the compounds represented by Formulas 12 to 14 as the emitting layer.

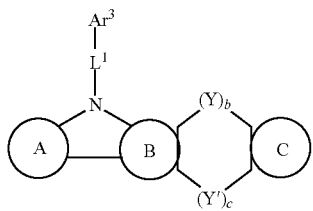

Formula 12

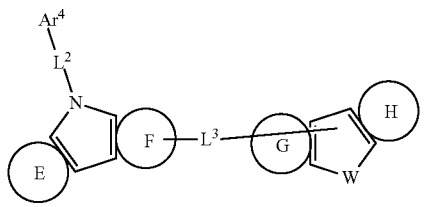

Formula 13

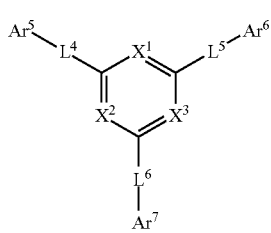

Formula 14

Wherein, each symbol may be defined as follows.

1) $X^1$, $X^2$ and $X^3$ are each independently $C(R_3)$ or N, provided that at least two of $X^1$, $X^2$ and $X^3$ are N, 2) $R_3$ is selected from the group consisting of a hydrogen; deuterium; halogen; a $C_6$-$C_{60}$ aryl group; a $C_2$-$C_{60}$ heterocyclic group including at least one heteroatom of O, N, S, Si or P, a fused ring group of a $C_3$-$C_{60}$ aliphatic ring and a $C_6$-$C_{60}$ aromatic ring; $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group.

When $R_3$ is an aryl group, it may be preferably a $C_6$-$C_{30}$ aryl group, more preferably a $C_6$-$C_{25}$ aryl group, such as phenylene, biphenyl, naphthalene, terphenyl, and the like.

When $R_3$ is a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazole, dibenzofuran, benzothienopyrimidine, benzofuropyrimidine, phenothiazine, phenylphenothiazine, etc.

When $R_3$ is a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

When $R_3$ is an alkyl group, it may be preferably a $C_1$-$C_{30}$ alkyl group, and more preferably a $C_1$-$C_{24}$ alkyl group.

When $R_3$ is an alkoxyl group, it may be preferably a $C_1$-$C_{24}$ alkoxyl group.

When $R_3$ is an aryloxy group, it may be preferably a $C_6$-$C_{24}$ aryloxy group.

3) Y and Y' are each independently O, S, $CR^eR^f$ or N-L'-$Ar^8$,

4) W is O, N, S, $CR^eR^f$ or N-L'-$Ar^8$, 5) wherein $R^e$ and $R^f$ are each independently selected from the group consisting of hydrogen; deuterium; $C_6$-$C_{60}$ aryl group; fluorenyl group; $C_2$-$C_{60}$ heterocyclic group including at least one heteroatom of O, N, S, Si or P, fused ring group of a $C_3$-$C_{60}$ aliphatic ring and a $C_6$-$C_{60}$ aromatic ring; $C_1$-$C_{50}$ alkyl group; $C_2$-$C_{20}$ alkenyl group; $C_2$-$C_{20}$ alkynyl group; $C_1$-$C_{30}$ alkoxy group; $C_6$-$C_{30}$ aryloxy group, or $R^e$ and $R^f$ may be bonded to each other to form a spiro.

wherein $R^e$ and $R^f$ are aryl groups, they may be preferably $C_6$-$C_{30}$ aryl groups, more preferably $C_6$-$C_{25}$ aryl groups, such as phenylene, biphenyl, naphthalene, terphenyl, and the like.

When $R^e$ and $R^f$ are heterocyclic groups, they may be preferably $C_2$-$C_{30}$ heterocyclic groups, and more preferably $C_2$-$C_{24}$ heterocyclic groups, for example, they may be pyrazine, thiophene, pyridine, pyrimidoindole, 5-phenyl-5H-pyrimido[5,4-b]indole, quinazoline, benzoquinazoline, carbazole, dibenzoquinazole, dibenzofuran, benzothienopyrimidine, benzofuropyrimidine, phenothiazine, phenylphenothiazine, etc.

When $R^e$ and $R^f$ are fused ring groups, they may be preferably fused ring groups of a $C_3$-$C_{30}$ aliphatic ring and $C_6$-$C_{30}$ aromatic rings, more preferably fused ring groups of a $C_3$-$C_{24}$ aliphatic ring and a $C_6$-$C_{24}$ aromatic ring.

When $R^e$ and $R^f$ are alkyl groups, they may be preferably $C_1$-$C_{30}$ alkyl groups, and more preferably $C_1$-$C_{24}$ alkyl groups.

When $R^e$ and $R^f$ are alkoxyl groups, they may be preferably $C_1$-$C_{24}$ alkoxyl groups.

When $R^e$ and $R^f$ are aryloxy groups, they may be preferably $C_6$-$C_{24}$ aryloxy groups.

6) $L^1$, $L^2$, $L^3$, $L^4$, $L^5$, $L^6$ and L' are each independently selected from the group consisting of single bond; a $C_6$-$C_{60}$ arylene group; a $C_2$-$C_{60}$ heterocyclic group including at least one heteroatom of O, N, S, Si or P, Wherein $L^1$, $L^2$, $L^3$, $L^4$, $L^5$, $L^6$ and L' are arylene group, they may be preferably $C_6$-$C_{30}$ arylene groups, and more preferably $C_6$-$C_{24}$ arylene groups, such as phenylene, biphenyl, naphthalene, terphenyl, and the like.

Wherein $L^1$, $L^2$, $L^3$, $L^4$, $L^5$, $L^6$ and L' are heterocyclic groups, they may be preferably $C_2$-$C_{30}$ heterocyclic groups, and more preferably $C_2$-$C_{24}$ heterocyclic groups, for example, they may be pyrazine, thiophene, pyridine, pyrimidoindole, 5-phenyl-5H-pyrimido[5,4-b]indole, quinazoline, benzoquinazoline, carbazole, dibenzoquinazole, dibenzofuran, benzothienopyrimidine, benzofuropyrimidine, phenothiazine, phenylphenothiazine, etc.

7) $Ar^3$, $Ar^4$, $Ar^5$, $Ar^6$, $Ar^7$ and $Ar^8$ are each independently selected from the group consisting of $C_6$-$C_{60}$ aryl group; fluorenyl group; $C_2$-$C_{60}$ heterocyclic group including at least one heteroatom of O, N, S, Si or P, fused ring group of a $C_3$-$C_{60}$ aliphatic ring and a $C_6$-$C_{60}$ aromatic ring; $C_1$-$C_{60}$ alkyl group; $C_2$-$C_{20}$ alkenyl group; $C_2$-$C_{20}$ alkynyl group; $C_1$-$C_{30}$ alkoxy group; $C_6$-$C_{30}$ aryloxy group, Wherein $Ar^3$, $Ar^4$, $Ar^5$, $Ar^6$, $Ar^7$ and $Ar^8$ are aryl groups, they may be preferably $C_6$-$C_{30}$ aryl groups, more preferably $C_6$-$C_{25}$ aryl groups, such as phenylene, biphenyl, naphthalene, terphenyl, and the like.

Wherein $Ar^3$, $Ar^4$, $Ar^5$, $Ar^6$, $Ar^7$ and $Ar^8$ are heterocyclic groups, they may be preferably $C_2$-$C_{30}$ heterocyclic groups, and more preferably $C_2$-$C_{24}$ heterocyclic groups, for example, they may be pyrazine, thiophene, pyridine, pyrimidoindole, 5-phenyl-5H-pyrimido[5,4-b]indole, quinazoline, benzoquinazoline, carbazole, dibenzoquinazole, dibenzofuran, benzothienopyrimidine, benzofuropyrimidine, phenothiazine, phenylphenothiazine, etc.

Wherein Ar³, Ar⁴, Ar⁵, Ar⁶, Ar⁷ and Ar⁸ are fused ring groups, they may be preferably fused ring groups of a $C_3$-$C_{30}$ aliphatic ring and $C_6$-$C_{30}$ aromatic rings, more preferably fused ring groups of a $C_3$-$C_{24}$ aliphatic ring and a $C_6$-$C_{24}$ aromatic ring.

When Ar³, Ar⁴, Ar⁵, Ar⁶, Ar⁷ and Ar⁸ are alkyl groups, they may be preferably $C_1$-$C_{30}$ alkyl groups, and more preferably $C_1$-$C_{24}$ alkyl groups.

When Ar³, Ar⁴, Ar⁵, Ar⁶, Ar⁷ and Ar⁸ are alkoxyl groups, they may be preferably $C_1$-$C_{24}$ alkoxyl groups.

When Ar³, Ar⁴, Ar⁵, Ar⁶, Ar⁷ and Ar⁸ are aryloxy groups, they may be preferably $C_6$-$C_{24}$ aryloxy groups.

8) Ring A, ring B and ring C are each independently a $C_6$-$C_{14}$ aryl group; or, ring A, ring B and ring C may be substituted with $R^1$, 9) E ring, F ring, G ring and H ring are each independently a $C_6$-$C_{20}$ aryl group; or $C_2$-$C_{20}$ heterocyclic group; or, E ring, F ring, G ring and H ring may be substituted with $R^2$, 10) wherein $R^1$ and $R^2$ are each independently selected from the group consisting of a hydrogen; deuterium; halogen; cyano group; $C_6$-$C_{60}$ aryl group; $C_2$-$C_{60}$ heterocyclic group including at least one heteroatom of O, N, S, Si or fused ring group of a $C_3$-$C_{60}$ aliphatic ring and a $C_6$-$C_{60}$ aromatic ring; $C_1$-$C_{50}$ alkyl group; $C_2$-$C_{20}$ alkenyl group; $C_2$-$C_{20}$ alkynyl group; $C_1$-$C_{30}$ alkoxy group; $C_6$-$C_{30}$ aryloxy group; -L"-N(R''')(R''); and adjacent groups can bond to form a ring.

wherein $R^1$ and $R^2$ are aryl groups, they may be preferably $C_6$-$C_{30}$ aryl groups, more preferably $C_6$-$C_{25}$ aryl groups, such as phenylene, biphenyl, naphthalene, terphenyl, and the like.

wherein $R^1$ and $R^2$ are heterocyclic groups, they may be preferably $C_2$-$C_{30}$ heterocyclic groups, and more preferably $C_2$-$C_{24}$ heterocyclic groups, for example, they may be pyrazine, thiophene, pyridine, pyrimidoindole, 5-phenyl-5H-pyrimido[5,4-b]indole, quinazoline, benzoquinazoline, carbazole, dibenzoquinazole, dibenzofuran, benzothienopyrimidine, benzofuropyrimidine, phenothiazine, phenylphenothiazine, etc.

wherein $R^1$ and $R^2$ are fused ring groups, they may be preferably fused ring groups of a $C_3$-$C_{30}$ aliphatic ring and $C_6$-$030$ aromatic rings, more preferably fused ring groups of a $C_3$-$C_{24}$ aliphatic ring and a $C_6$-$C_{24}$ aromatic ring.

When $R^1$ and $R^2$ are alkyl groups, they may be preferably $C_1$-$C_{30}$ alkyl groups, and more preferably $C_1$-$C_{24}$ alkyl groups.

When $R^1$ and $R^2$ are alkoxyl groups, they may be preferably $C_1$-$C_{24}$ alkoxyl groups.

When $R^1$ and $R^2$ are aryloxy groups, they may be preferably $C_6$-$C_{24}$ aryloxy groups.

11) wherein L" is selected from the group consisting of single bond; a $C_6$-$C_{60}$ arylene group; a fluorenylene group; a $C_3$-$C_{60}$ aliphatic ring a $C_2$-$C_{60}$ heterocyclic group including at least one heteroatom of O, N, S, Si or and a combination thereof, wherein R''' and R'' are each independently $C_6$-$C_{60}$ aryl group; fluorenyl group; $C_3$-$C_{60}$ aliphatic ring; $C_2$-$C_{60}$ heterocyclic group including at least one heteroatom of O, N, S, Si or P; and a combination thereof.

Wherein L" is an arylene group, it may be preferably a $C_6$-$C_{30}$ arylene group, more preferably a $C_6$-$C_{24}$ arylene group, such as phenylene, biphenyl, naphthalene, terphenyl, and the like.

Wherein L" is an aliphatic group, it may be preferably a $C_3$-$C_{30}$ aliphatic ring, more preferably a $C_3$-$C_{24}$ aliphatic ring.

Wherein L" is a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazole, dibenzofuran, benzothienopyrimidine, benzofuropyrimidine, phenothiazine, phenylphenothiazine, etc.

Wherein R''' and R'' are aryl groups, they may be preferably $C_6$-$C_{30}$ aryl groups, more preferably $C_6$-$C_{25}$ aryl groups, such as phenylene, biphenyl, naphthalene, terphenyl, and the like.

Wherein R''' and R'' are aliphatic ring, they may be preferably $C_3$-$C_{30}$ aliphatic ring, more preferably $C_3$-$C_{24}$ aliphatic ring.

Wherein R''' and R'' are heterocyclic groups, they may be preferably $C_2$-$C_{30}$ heterocyclic groups, and more preferably $C_2$-$C_{24}$ heterocyclic groups, for example, they may be pyrazine, thiophene, pyridine, pyrimidoindole, 5-phenyl-5H-pyrimido[5,4-b]indole, quinazoline, benzoquinazoline, carbazole, dibenzoquinazole, dibenzofuran, benzothienopyrimidine, benzofuropyrimidine, phenothiazine, phenylphenothiazine, etc.

12) b and c are each independently 0 or 1, provided that b+c≥1;

13) wherein the aryl group, arylene group, heterocyclic group, fluorenyl group, fluorenylene group, aliphatic ring, fused ring group, alkyl group, alkenyl group, alkoxyl group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group; also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Also, the compound represented by Formula 1 is represented by any one of Formulas 2-1 to 2-3

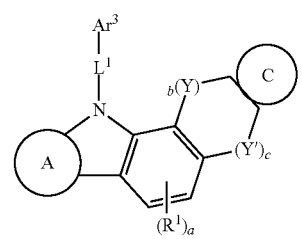

Formula 2-1

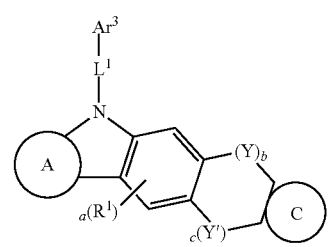

Formula 2-2

Formula 2-3
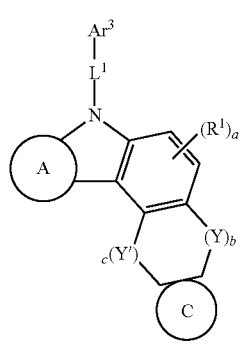
Wherein,
1) A ring, C ring, Y, Y', b, c, $Ar^3$, $L^1$ and $R^1$ are the same as defined above, 2) a is an integer of 0 to 2.
Specifically, the compound represented by Formula 12 may be any one of the following compounds.
2-1
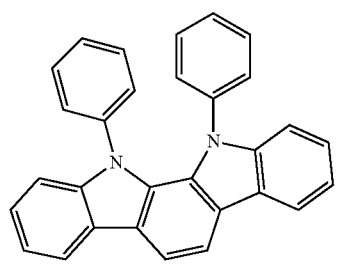
2-2
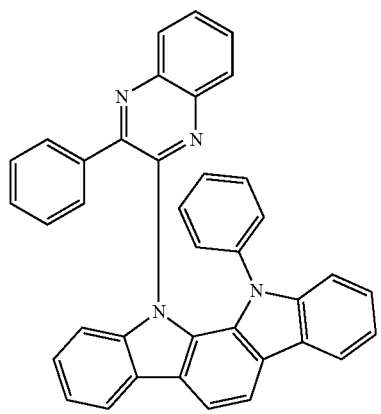
2-3
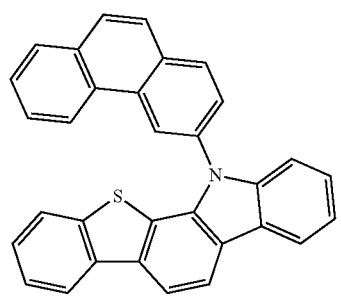
2-4
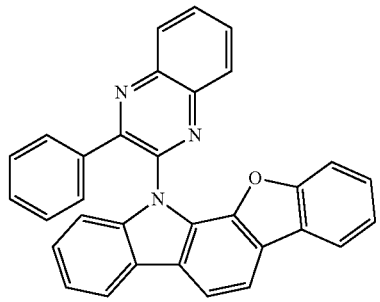
2-5
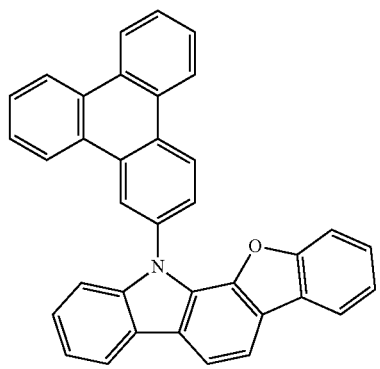
2-6
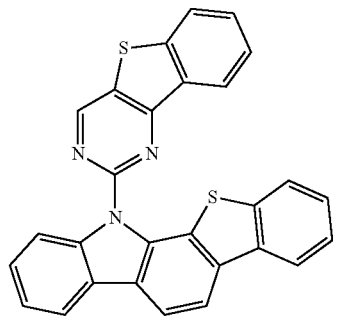
2-7
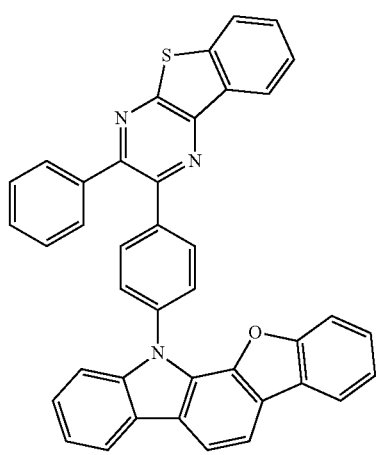

2-8
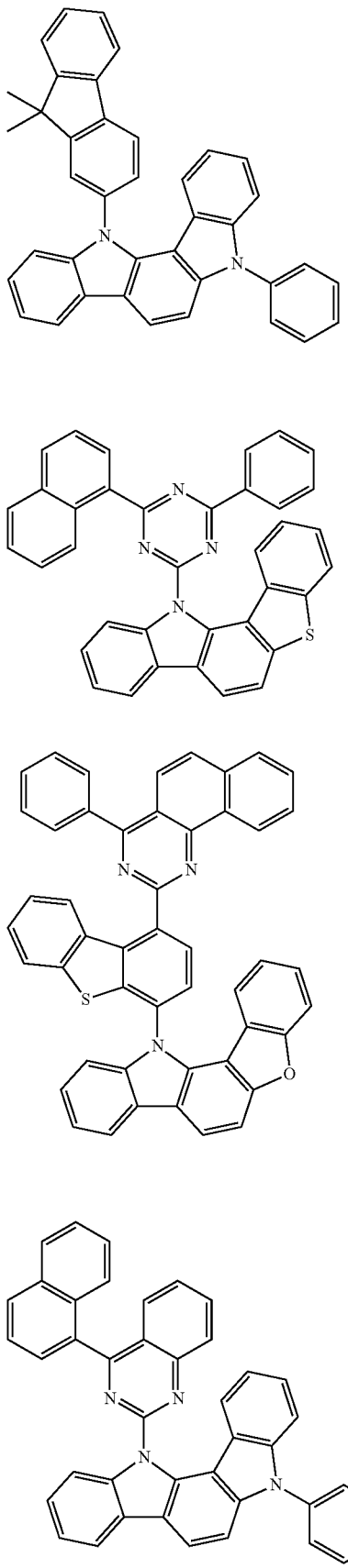
2-9
2-10
2-11
2-12
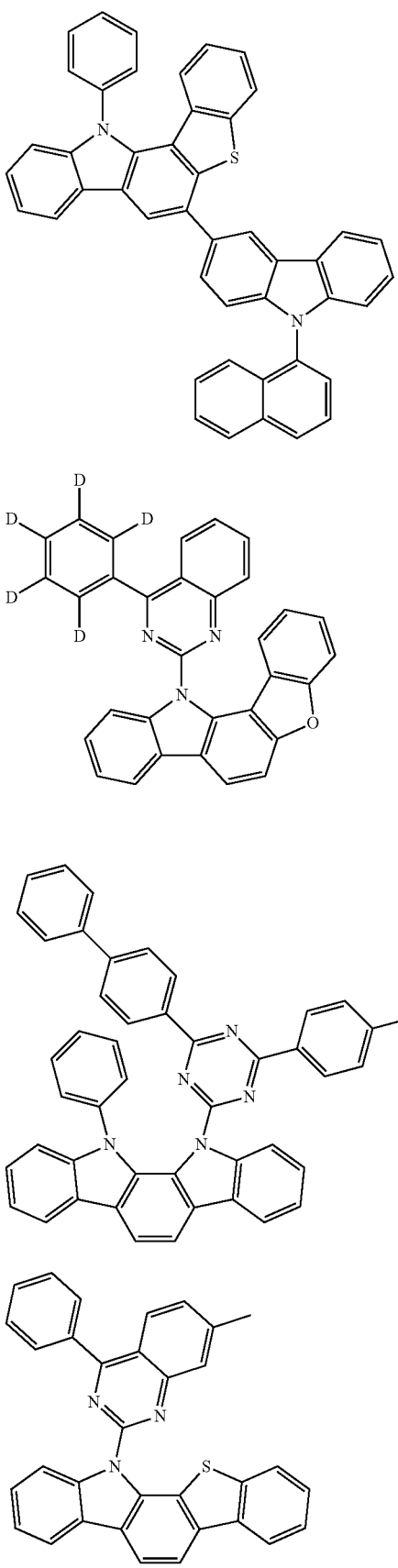
2-13
2-14
2-15

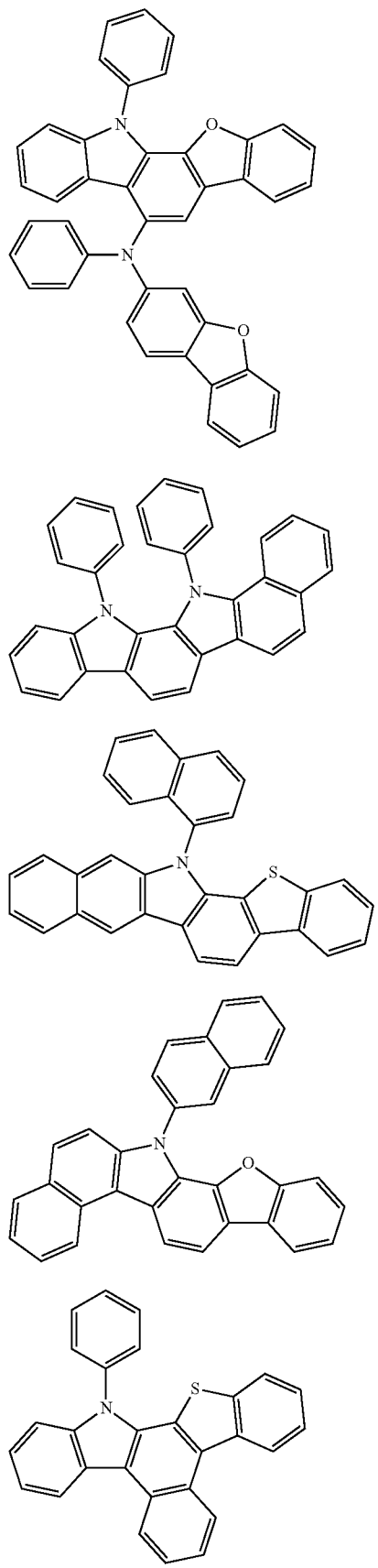
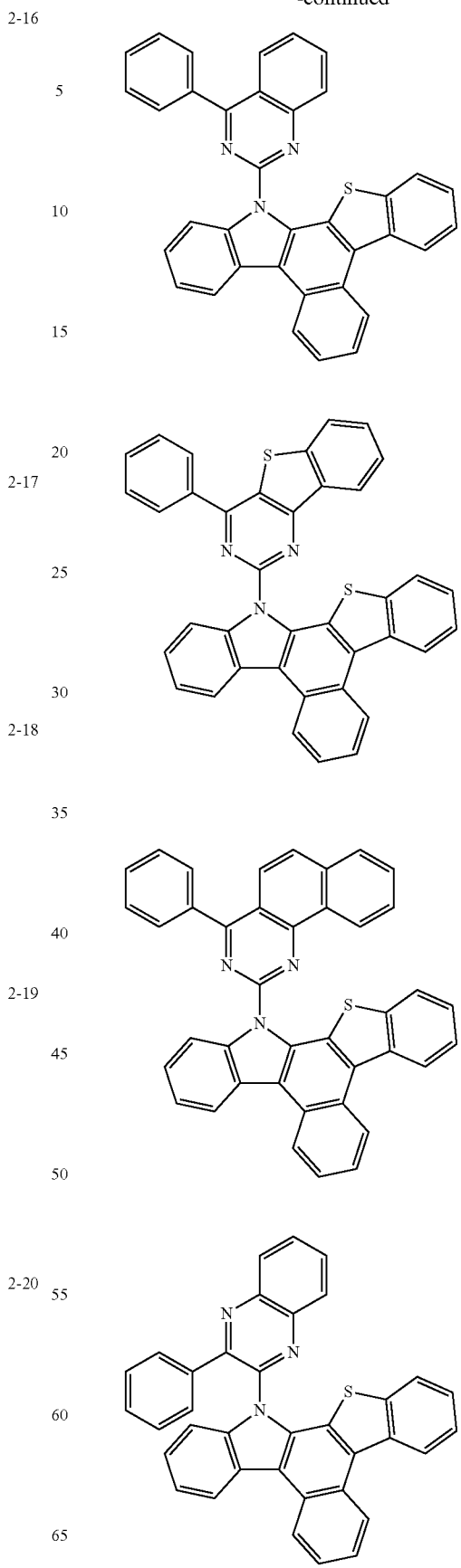

2-25
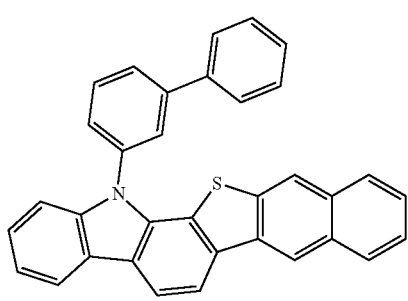
2-26
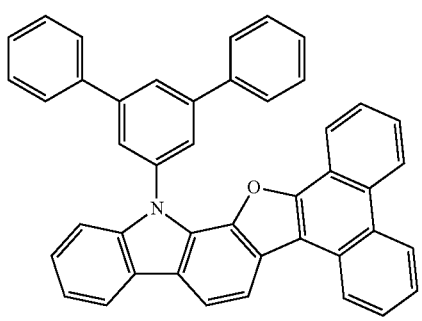
2-27
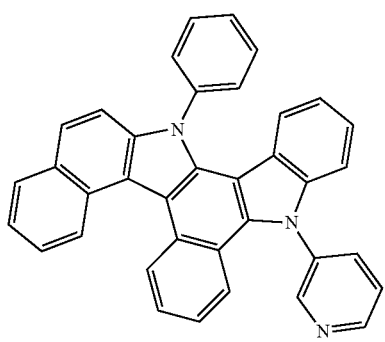
2-28
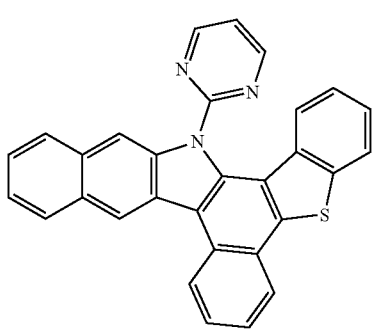
2-29
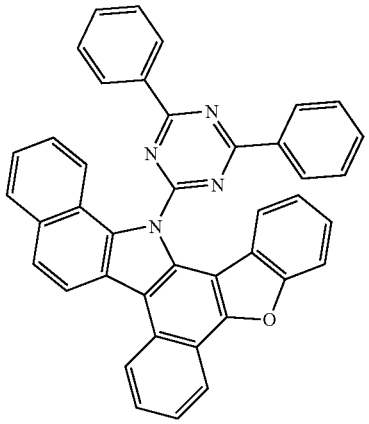
2-30
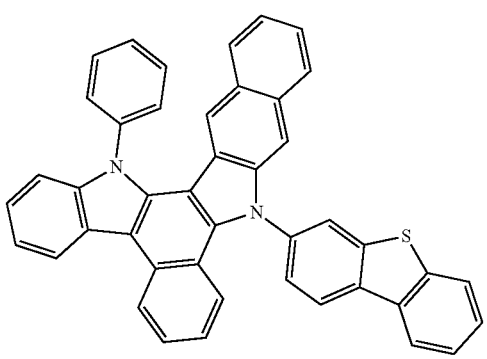
2-31
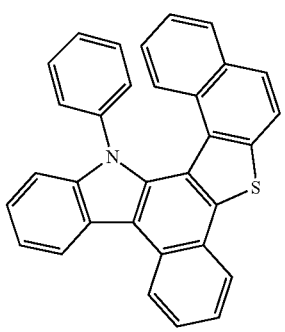
2-32
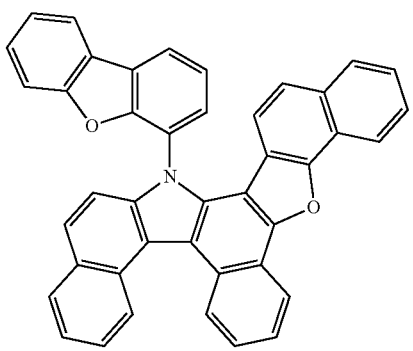

2-33
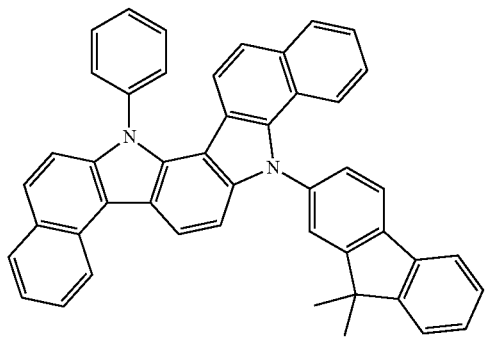
2-34
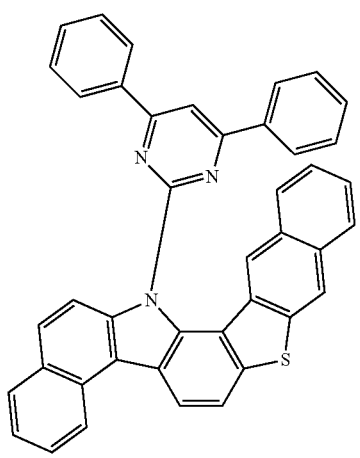
2-35
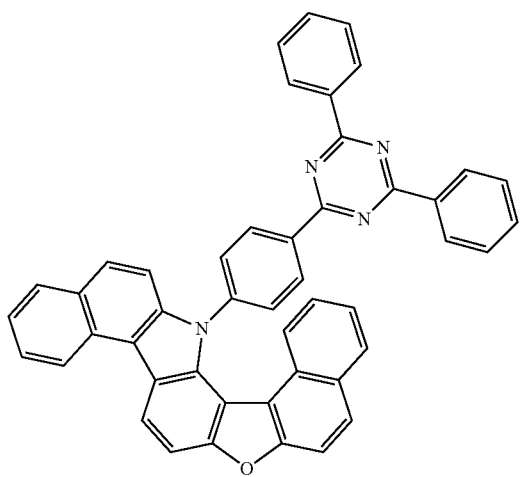
2-36
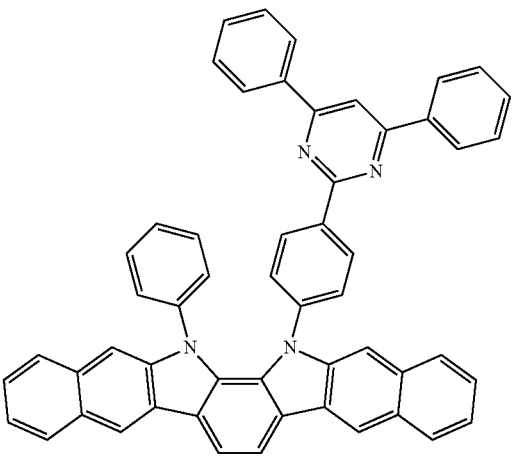
2-37
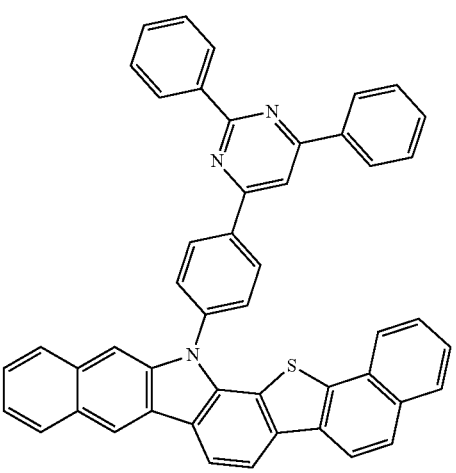
2-38
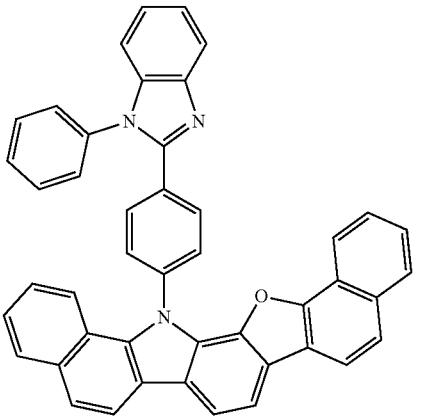
2-39
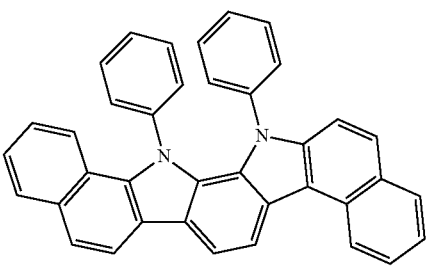

2-40 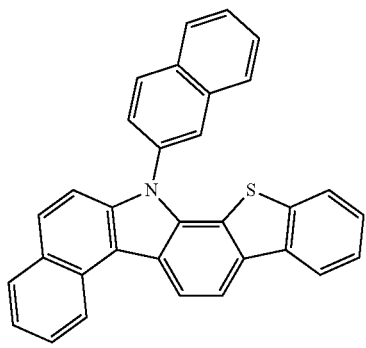
2-41 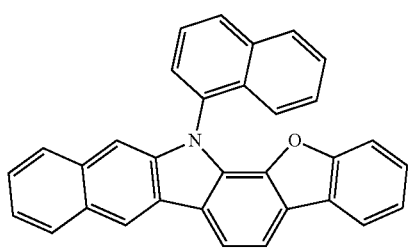
2-42 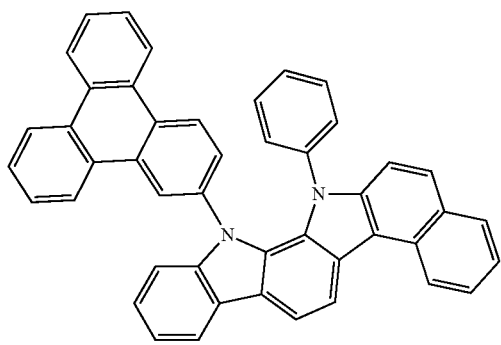
2-43 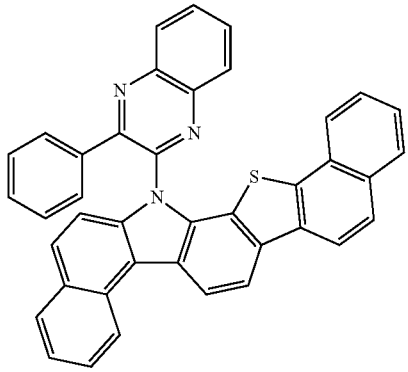
2-44 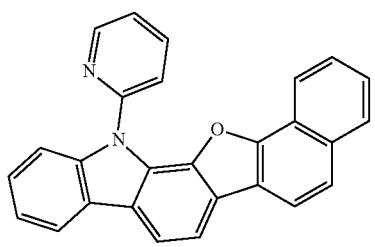
2-45 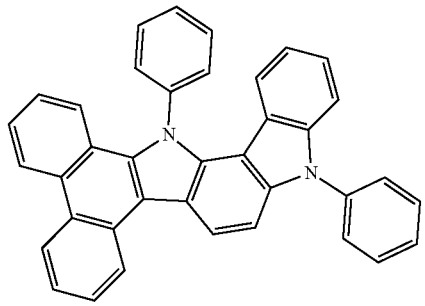
2-46 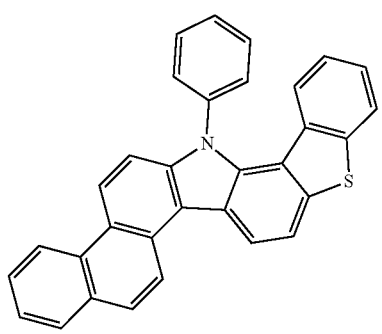
2-47 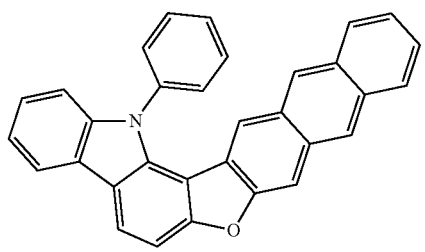
2-48 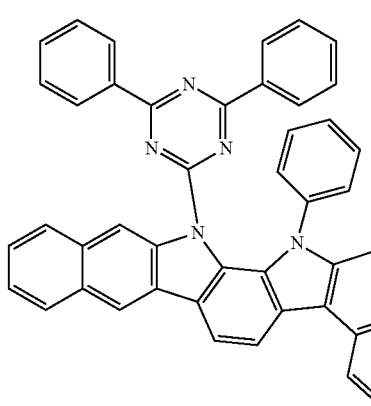

2-49
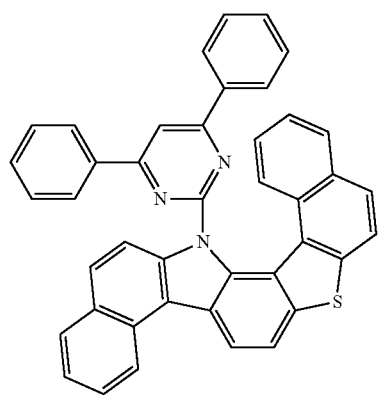
2-50
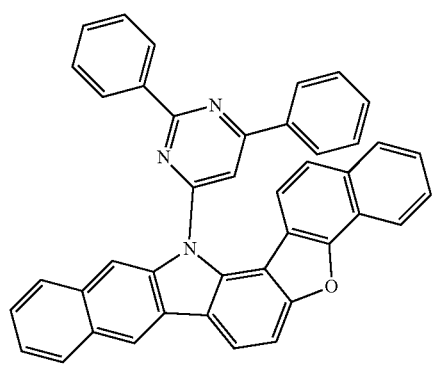
2-51
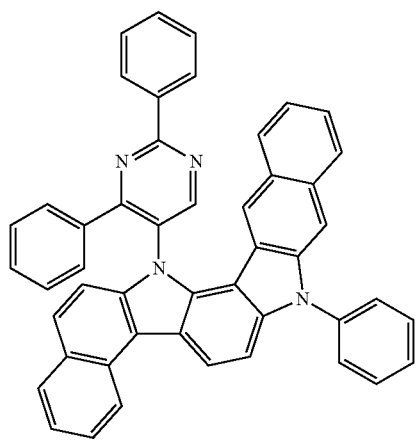
2-52
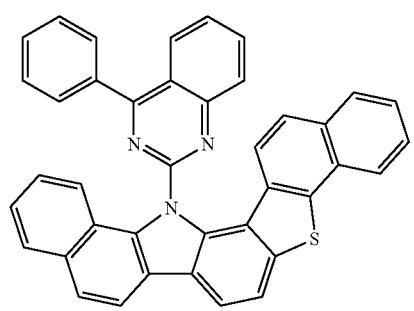
2-53
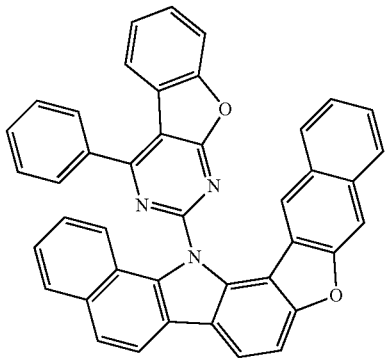
2-54
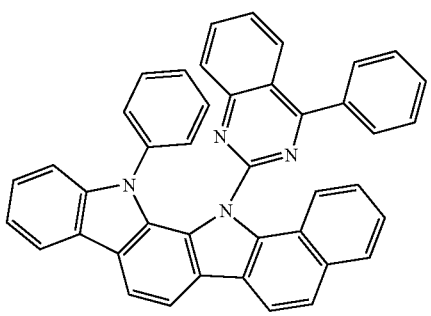
2-55
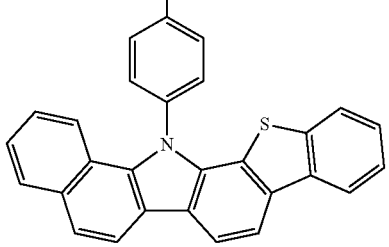
2-56
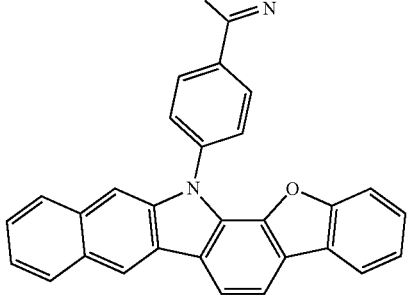

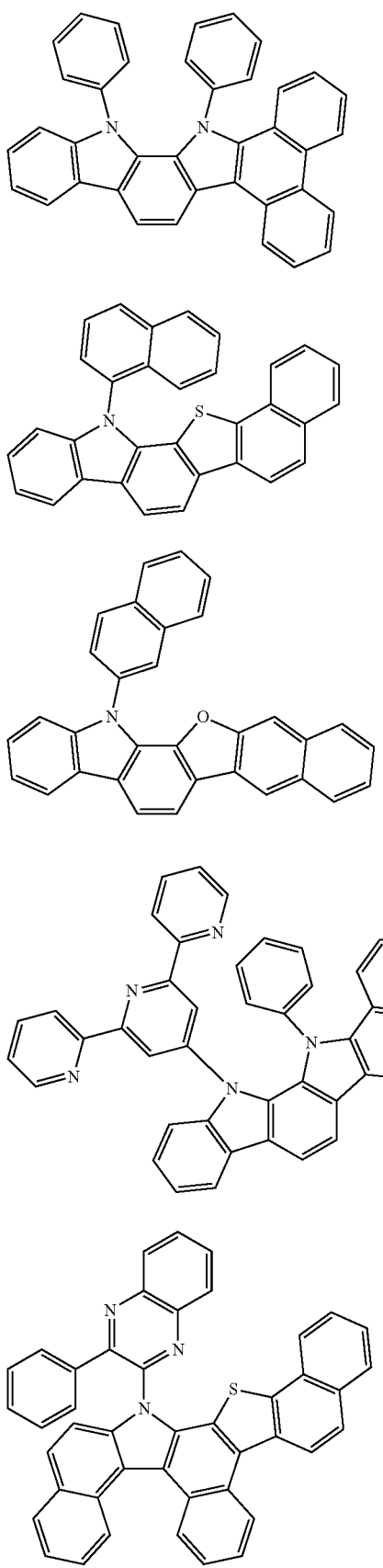
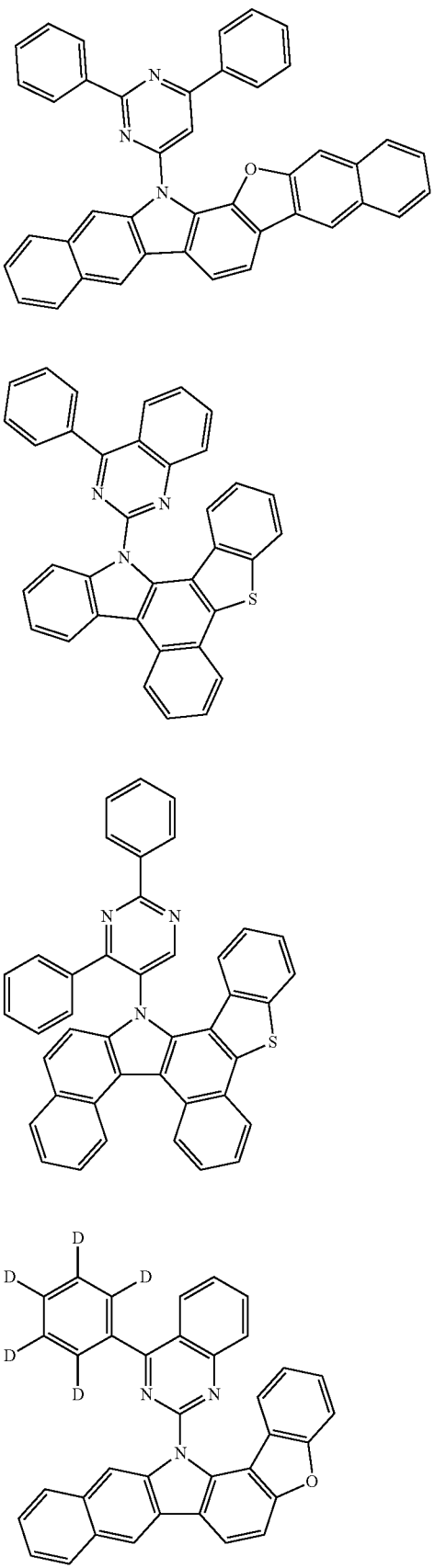

2-66
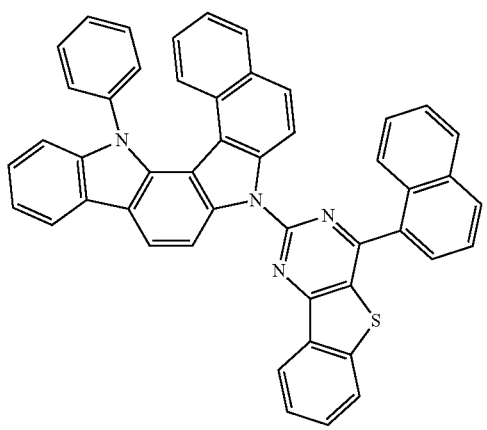
2-67
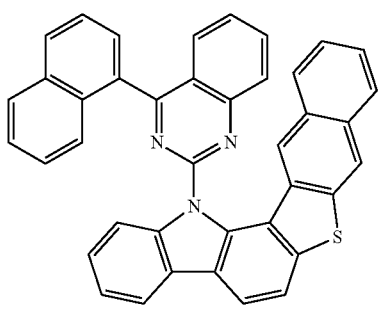
2-68
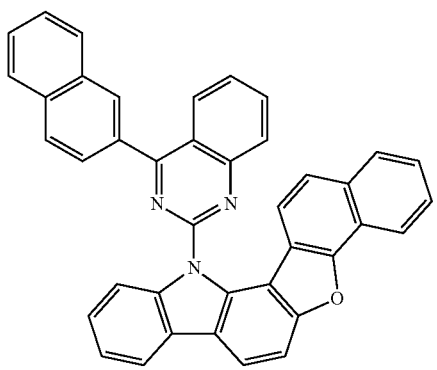
2-69
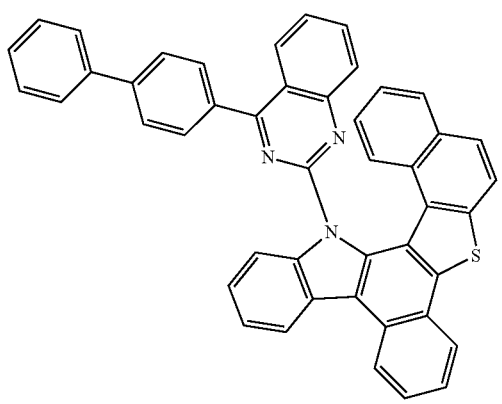
2-70
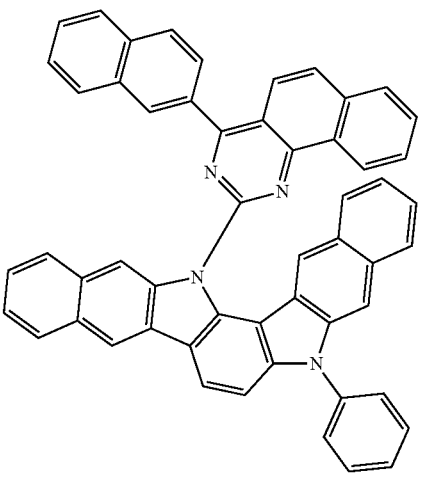
2-71
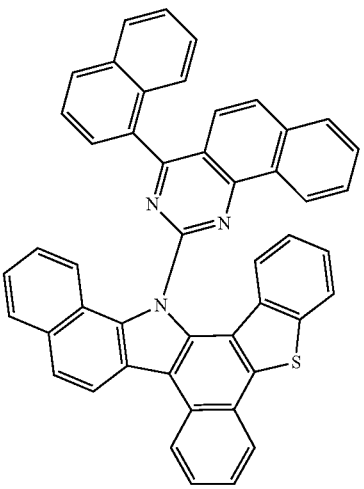
2-72
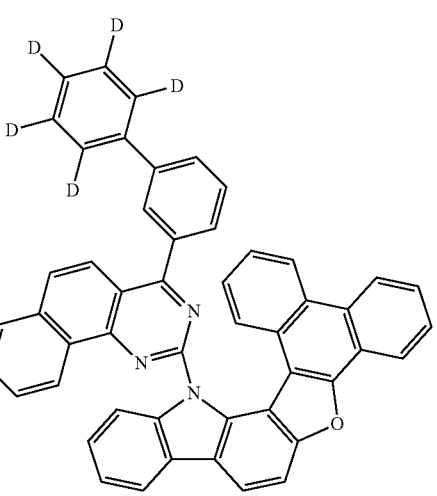

2-73
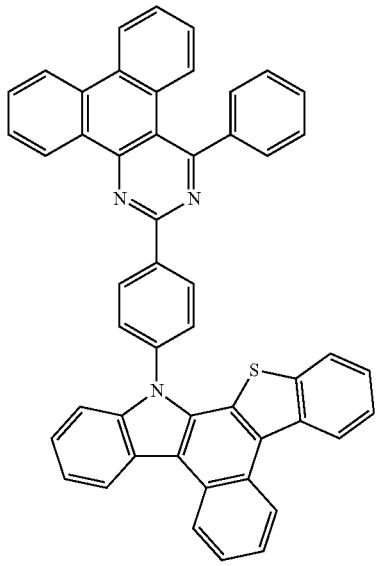
2-74
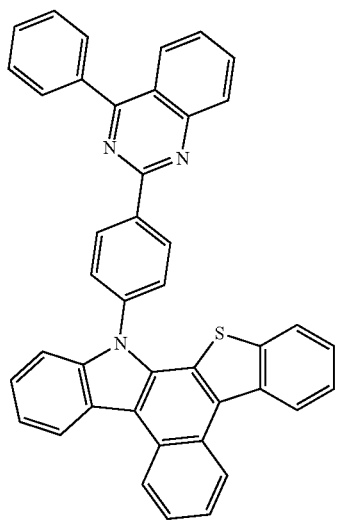
2-75
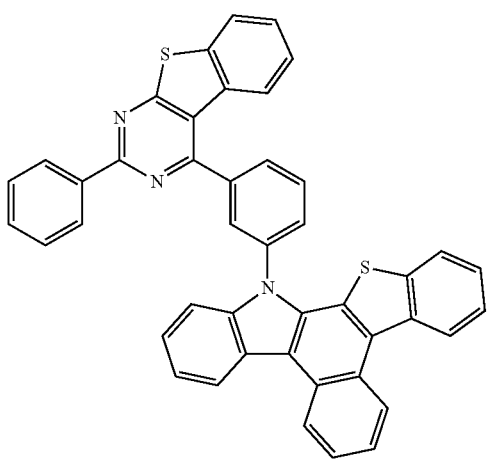
2-76
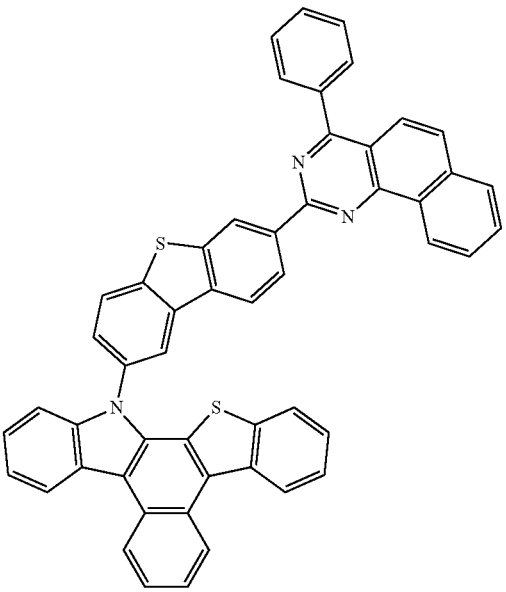
2-77
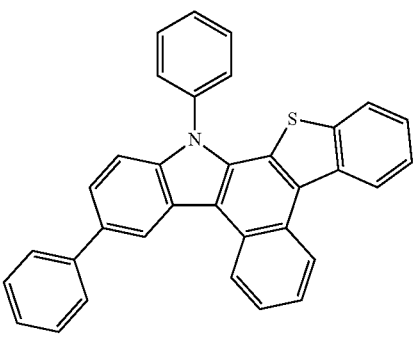
2-78
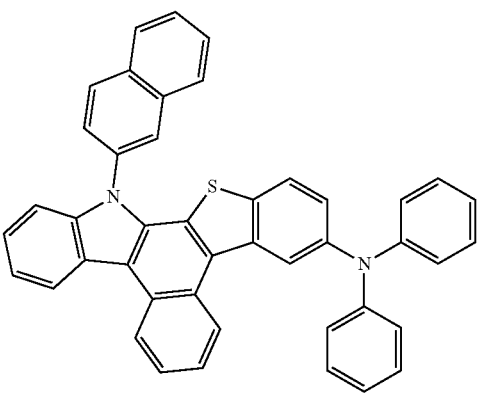

2-79
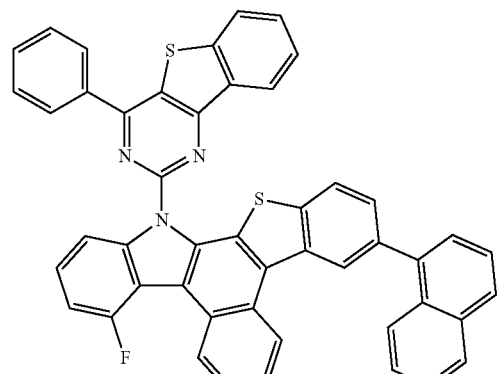
2-80
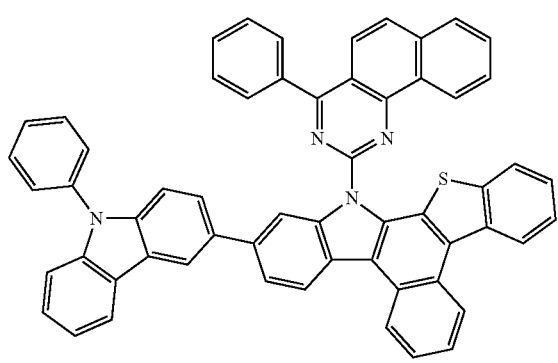
2-81
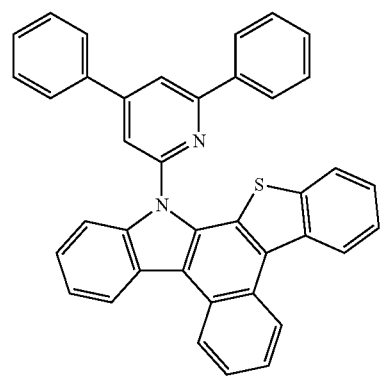
2-82
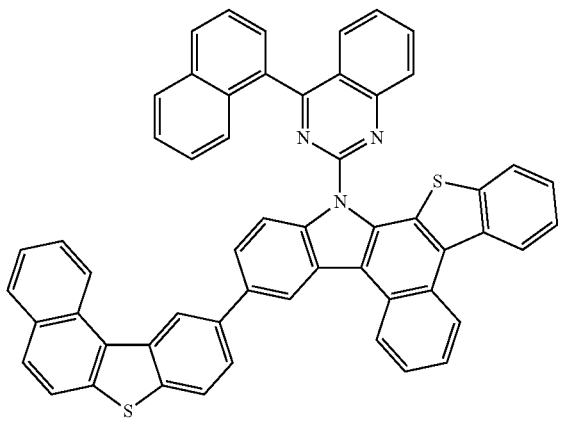
2-83
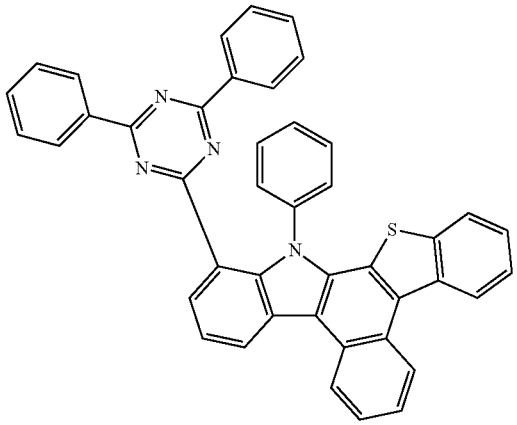
2-84
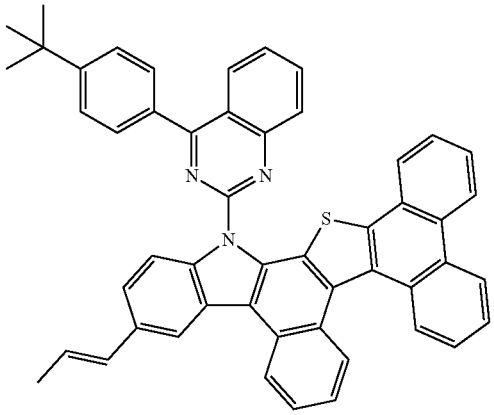
2-85
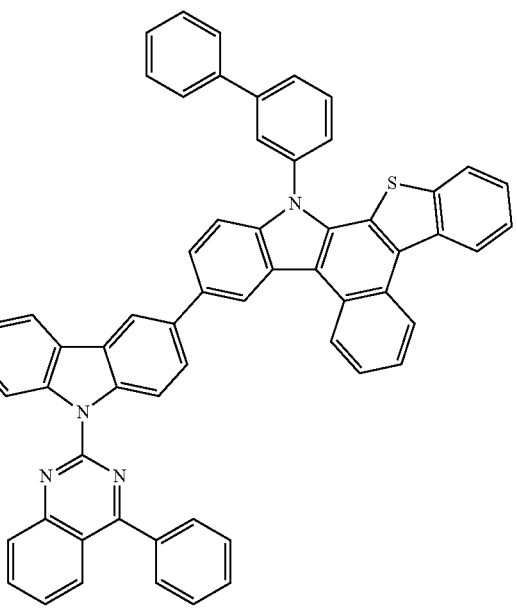

2-86
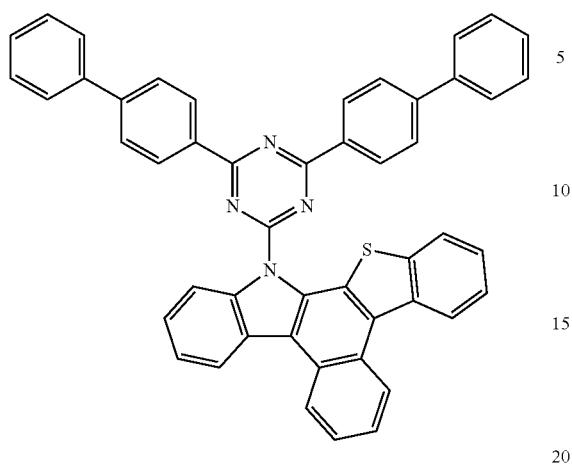
2-89
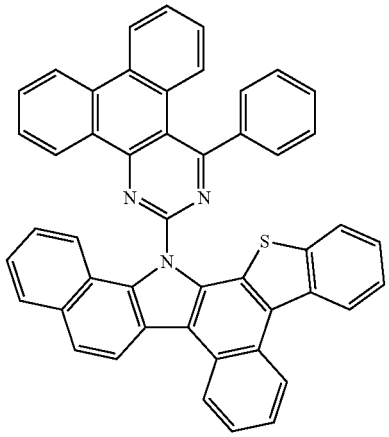
2-87
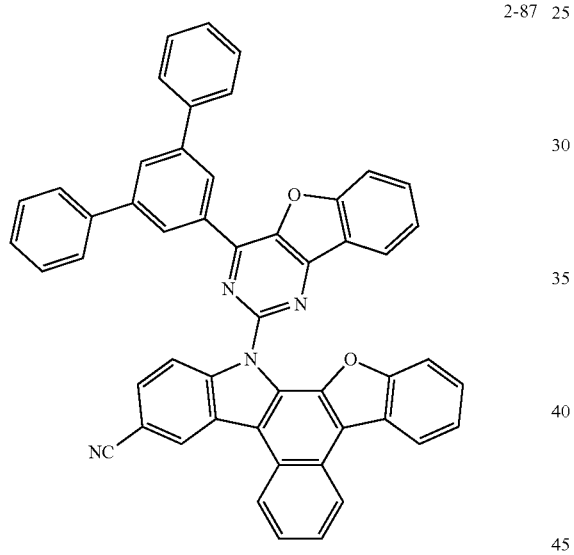
2-90
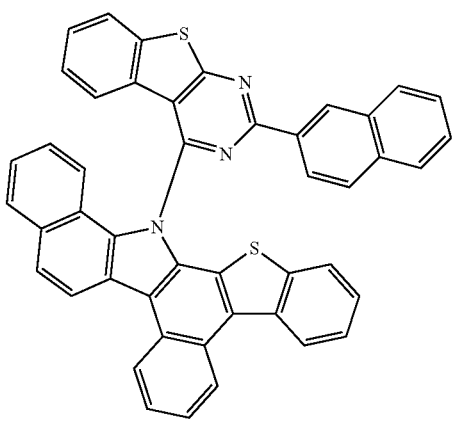
2-88
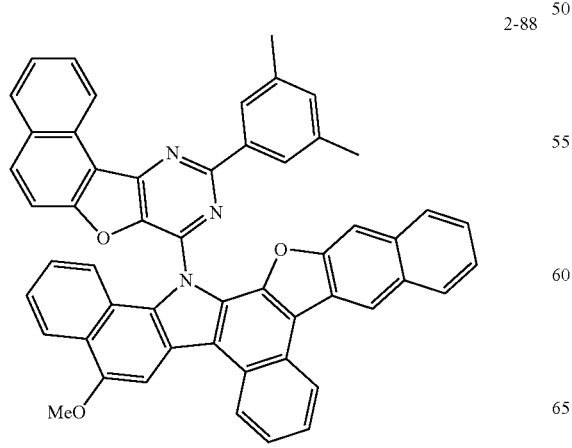
2-91
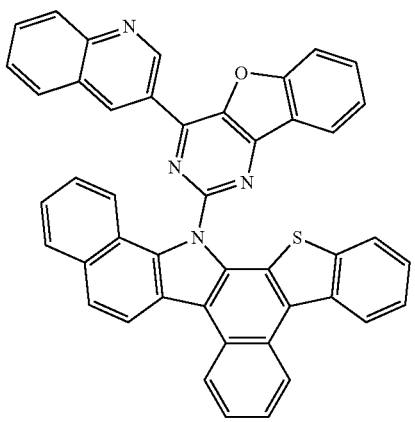

2-92
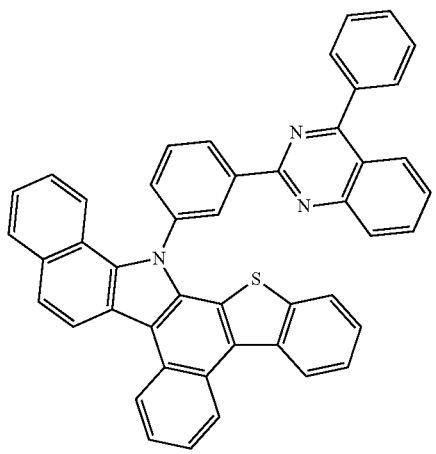
2-93
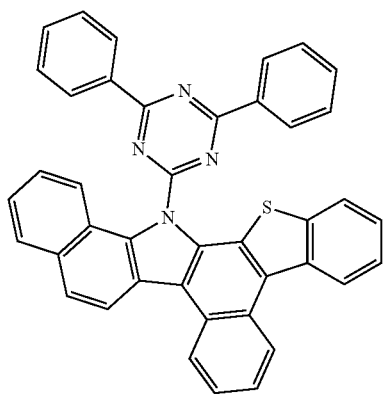
2-94
2-95
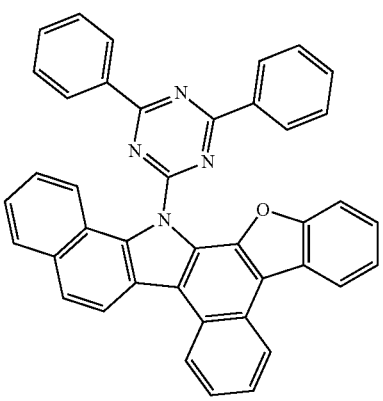
2-96
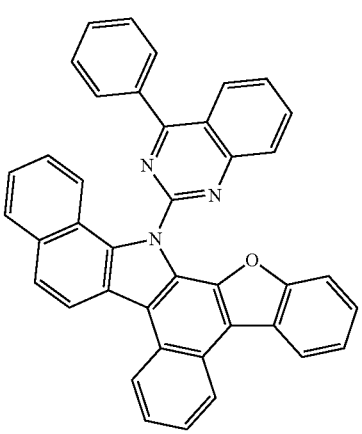
2-97
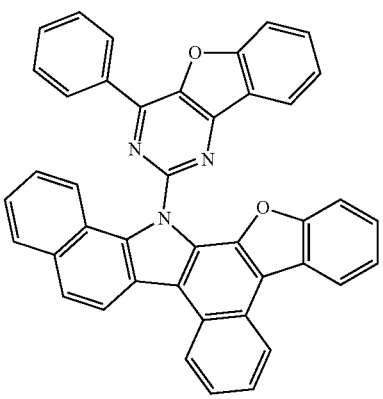

2-98
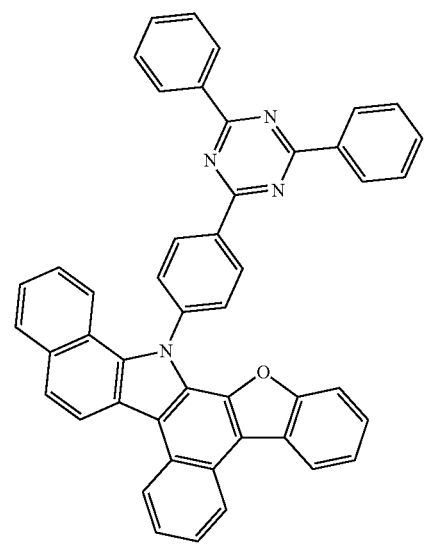
2-99
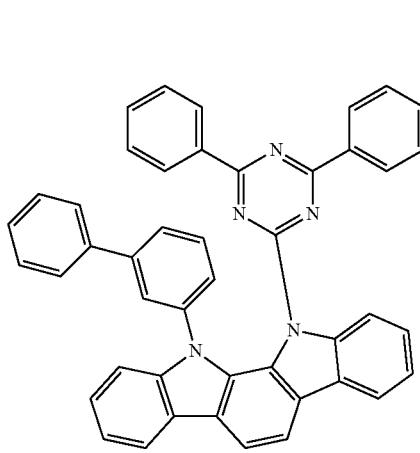
2-100
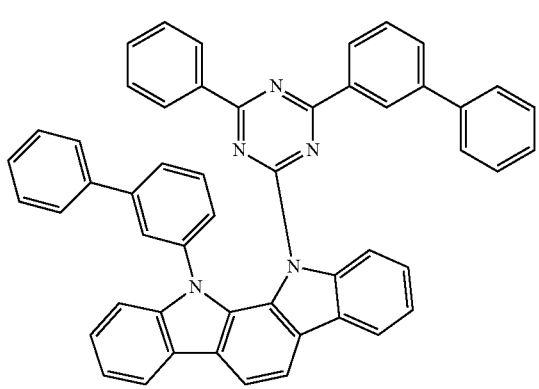
2-101
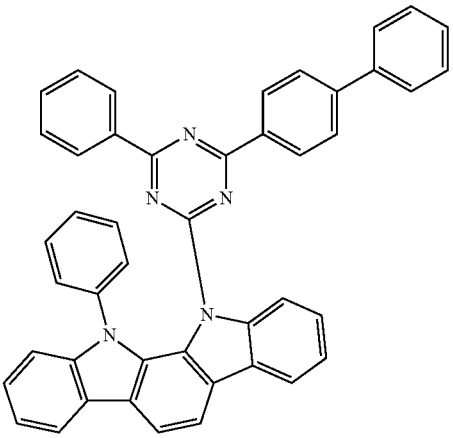
2-102
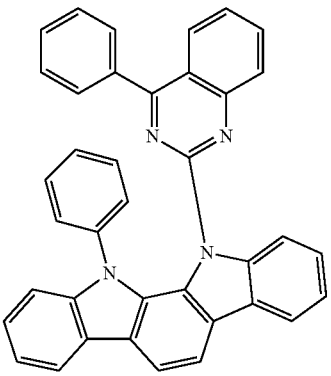
2-103
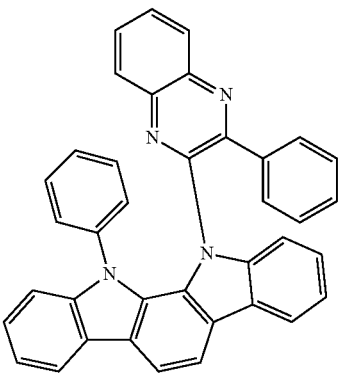
2-104
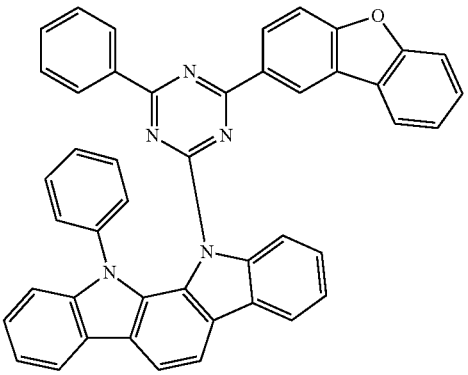

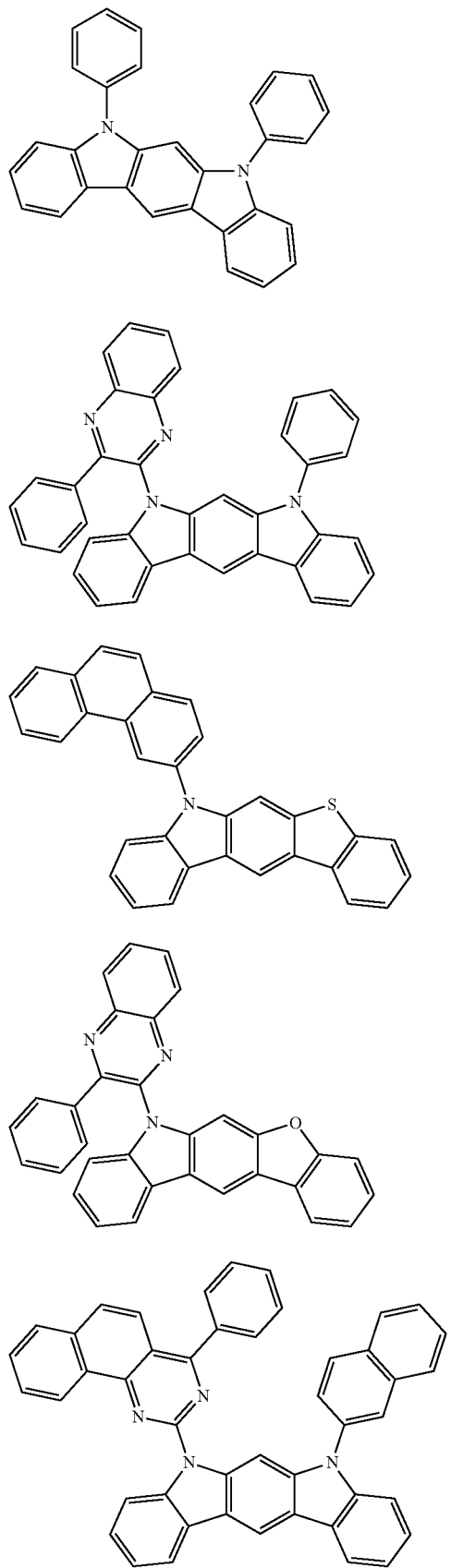
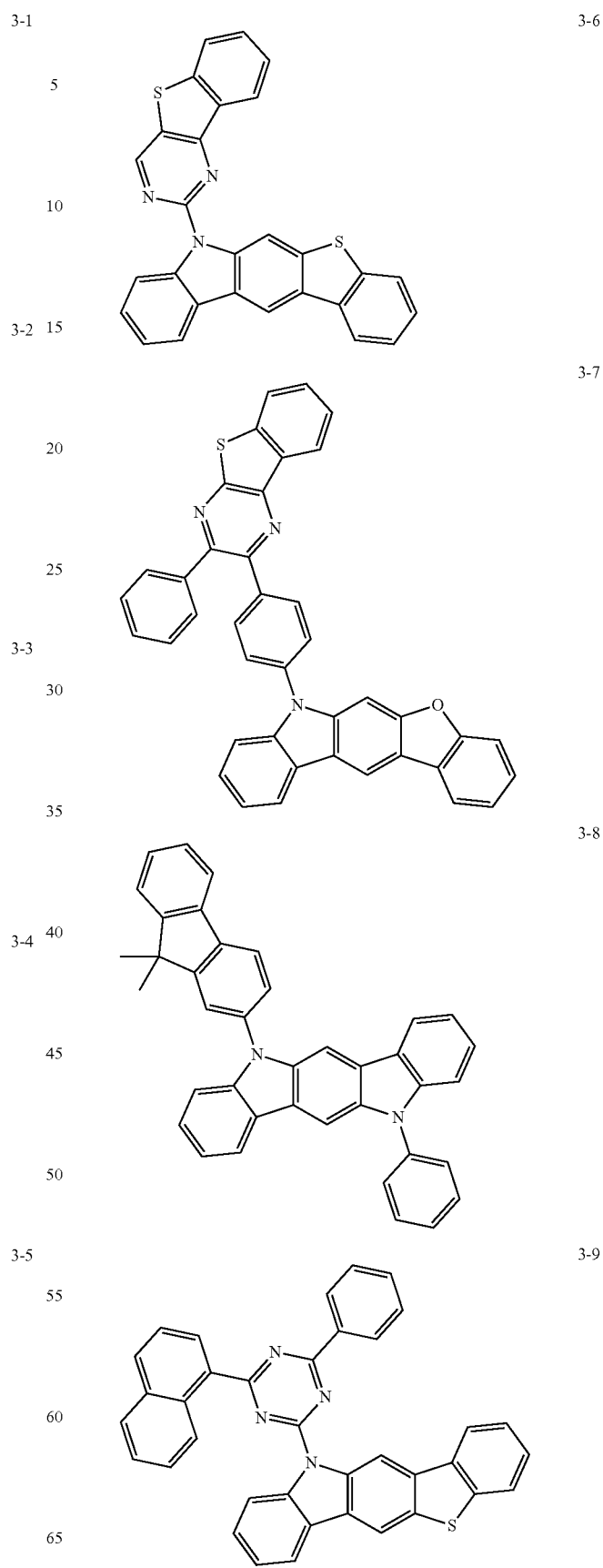

US 11,665,958 B1
-continued
3-10
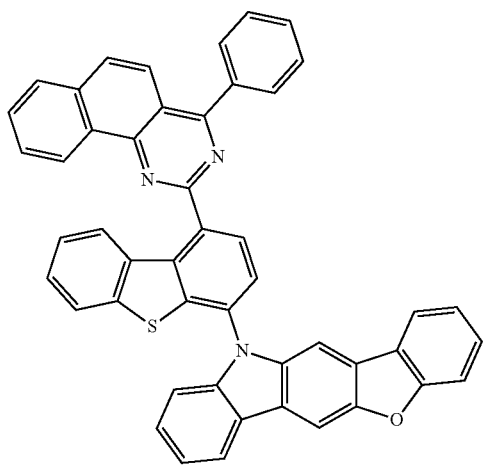
3-11
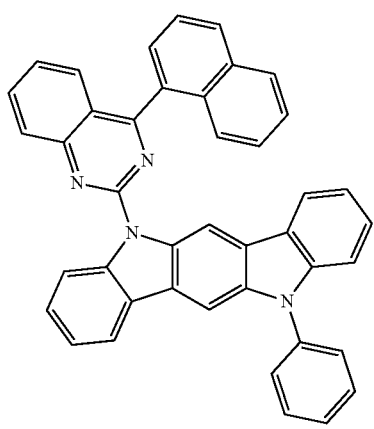
3-12
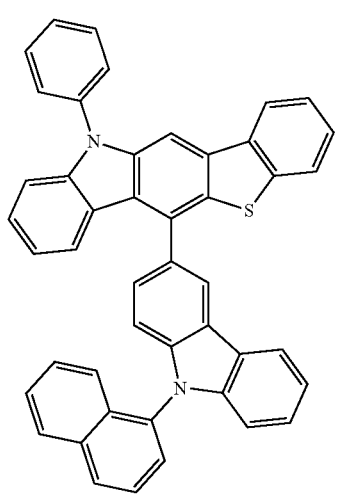
-continued
3-13

3-14
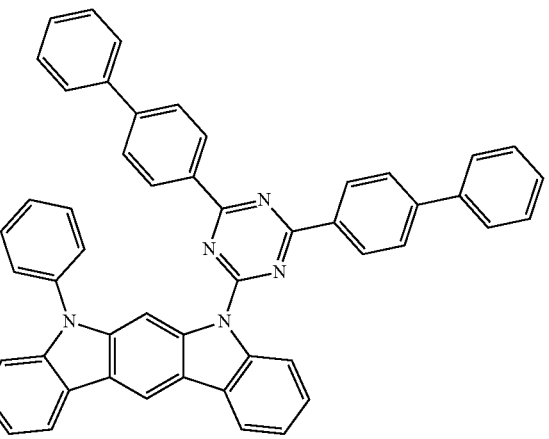
3-15

3-16
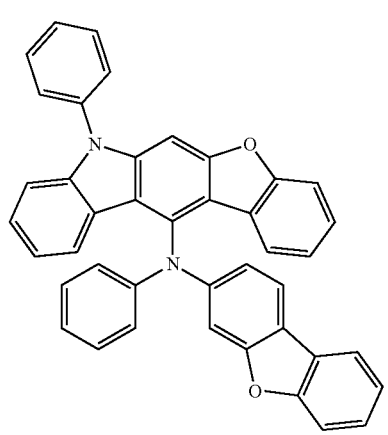

73
-continued
3-17
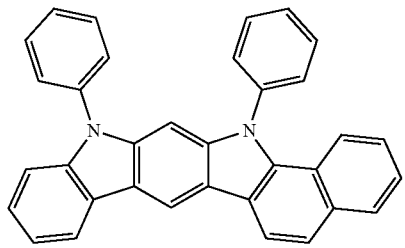
3-18
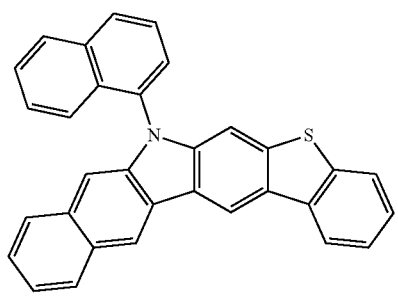
3-19
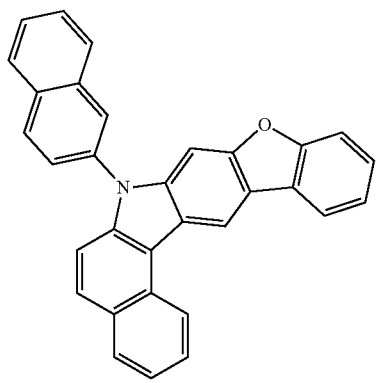
3-20
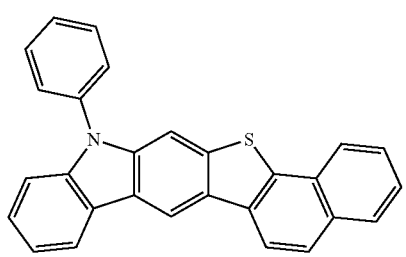
3-21
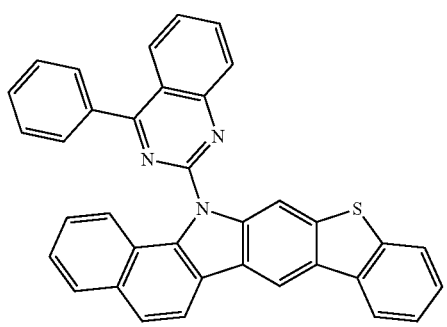
74
-continued
3-22
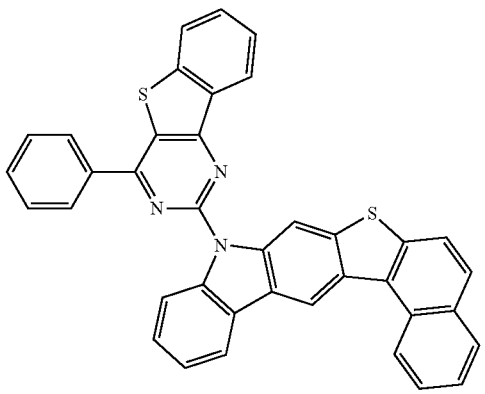
3-23
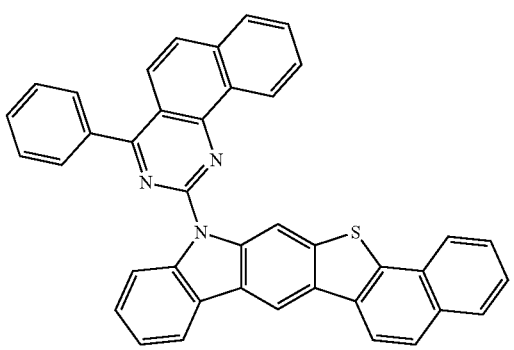
3-24
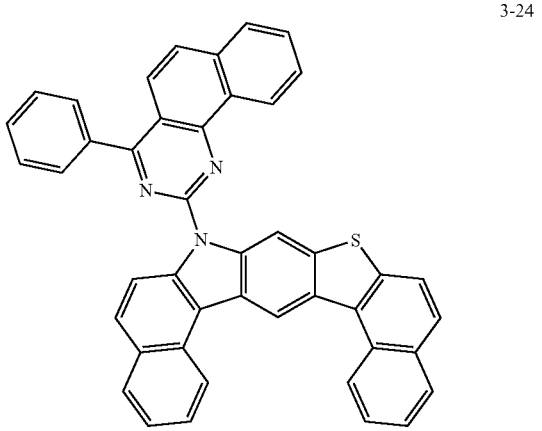
3-25
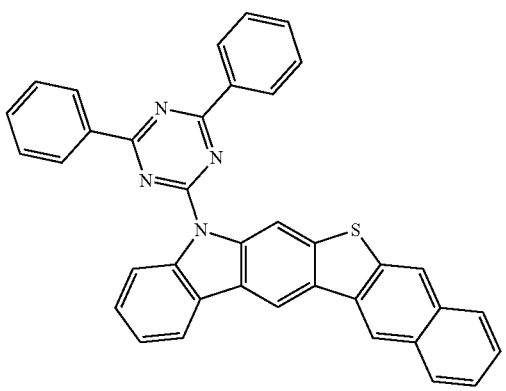

-continued
3-26
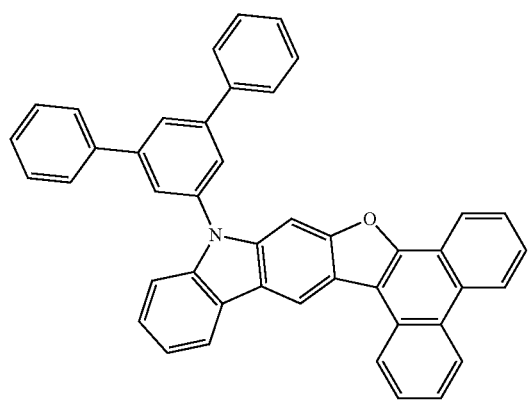
3-27
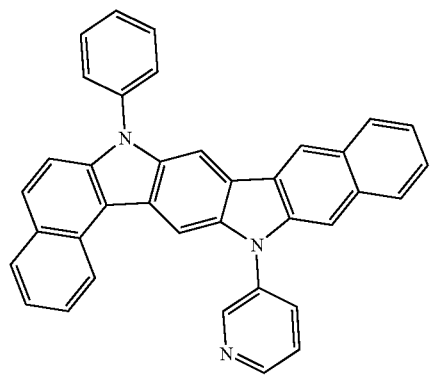
3-28
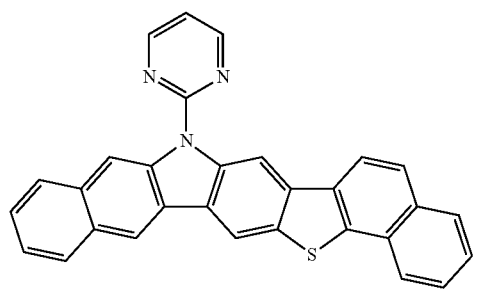
3-29
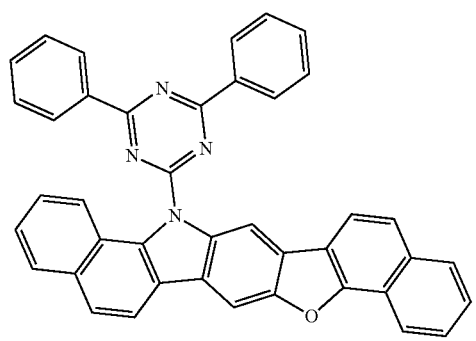
-continued
3-30
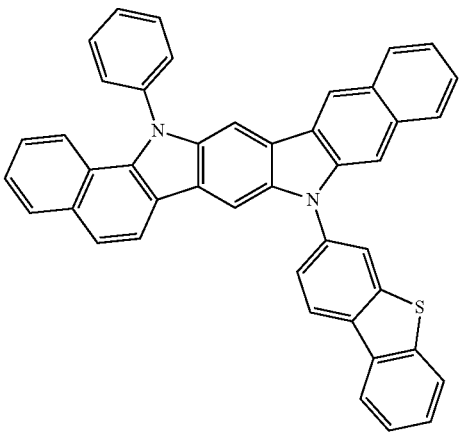
3-31
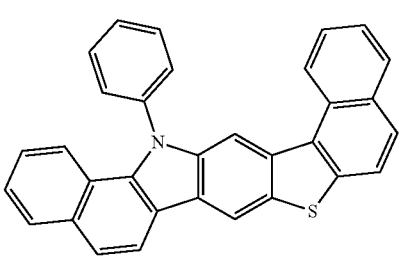
3-32
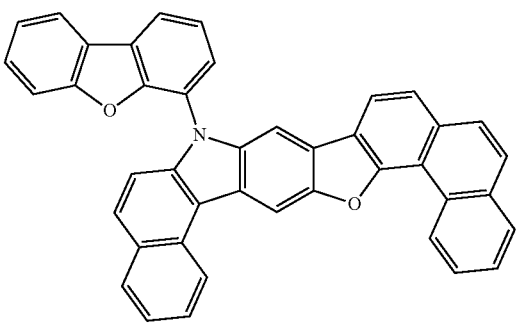
3-33
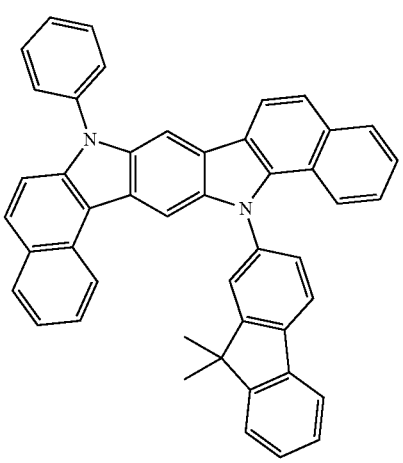

3-34
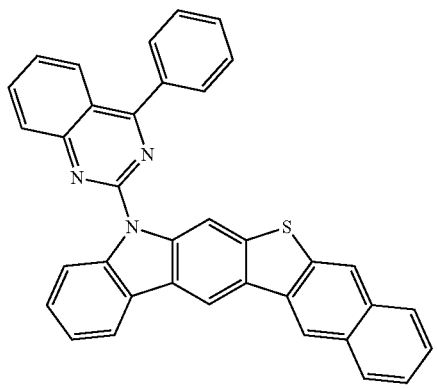
3-35
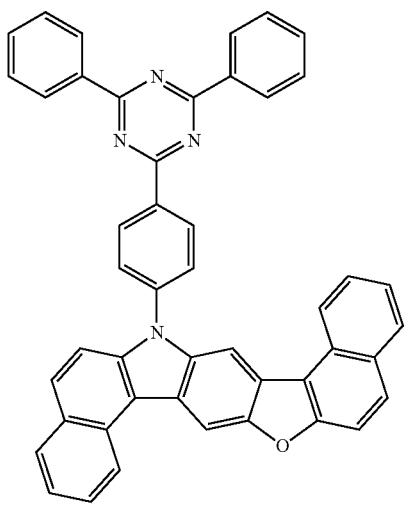
3-36
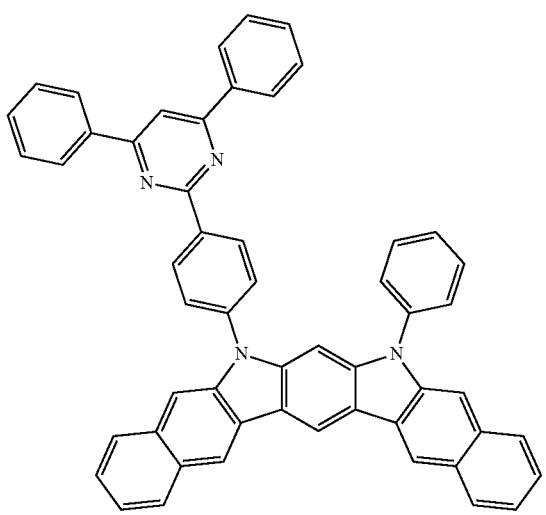
3-37
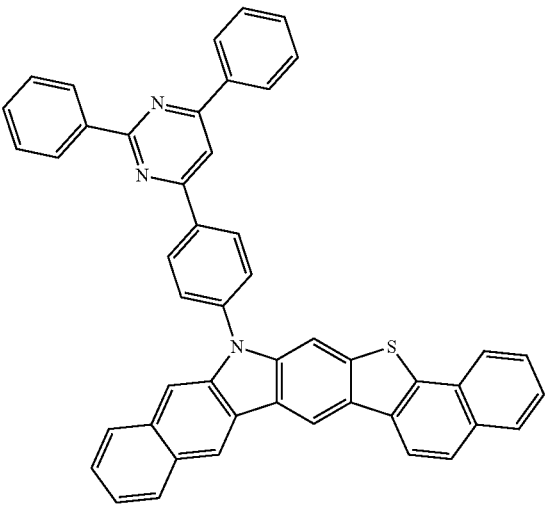
3-38
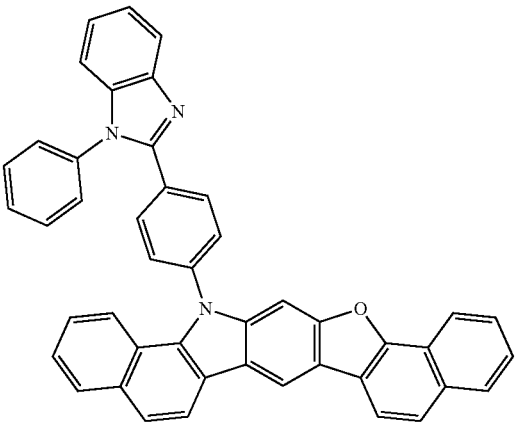
3-39
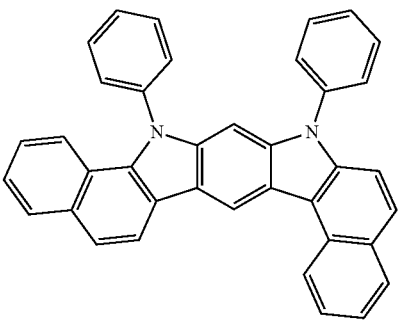

3-40
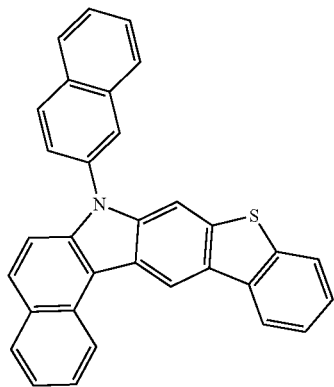
3-41
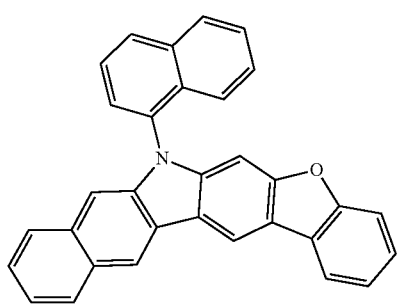
3-42
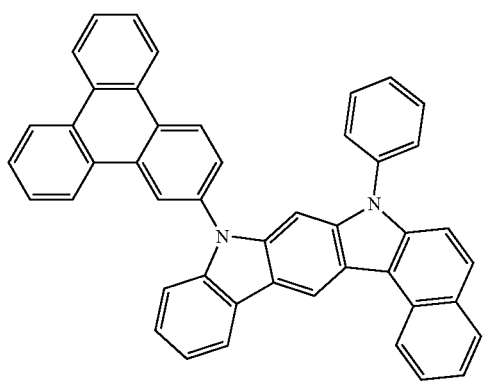
3-43
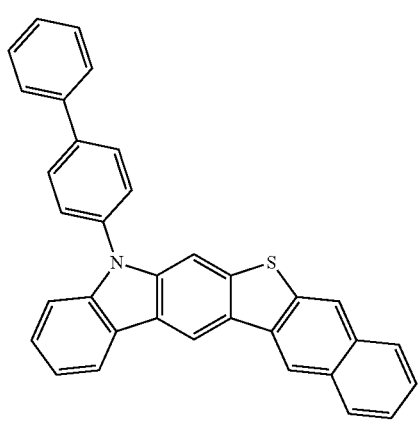
3-44
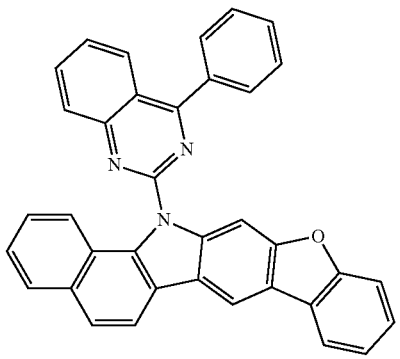
3-45
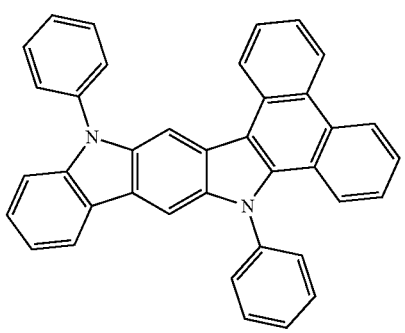
3-46
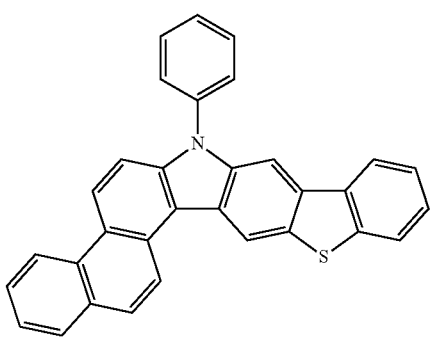
3-47
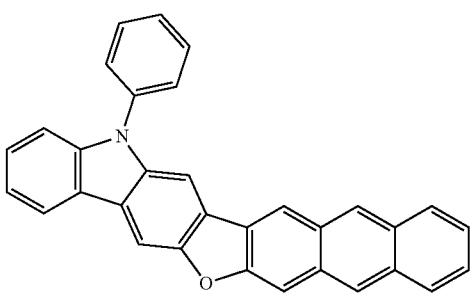

-continued
3-48
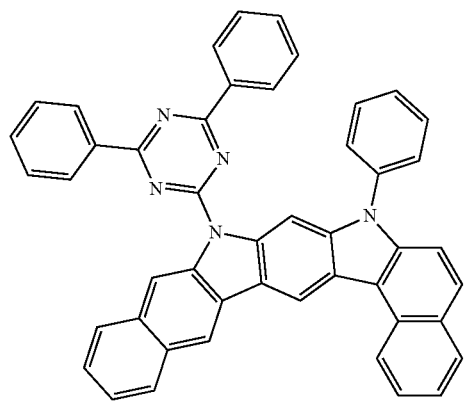
3-49
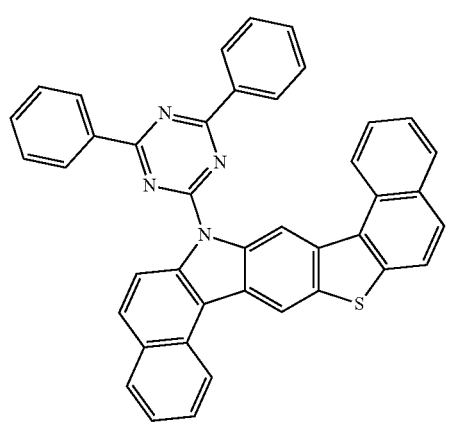
3-50
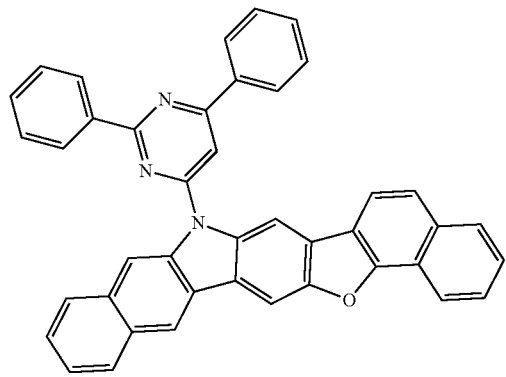
3-51
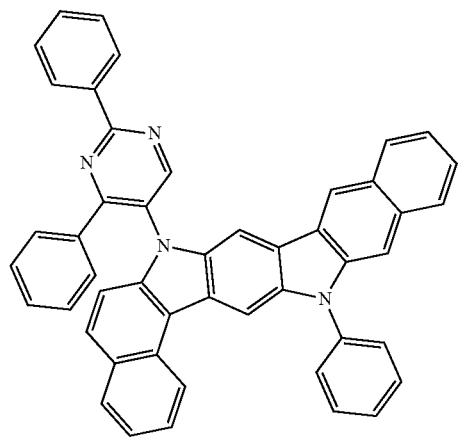
-continued
3-52
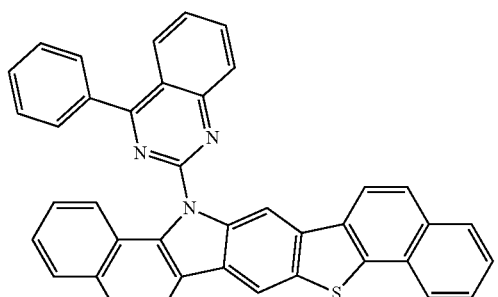
3-53
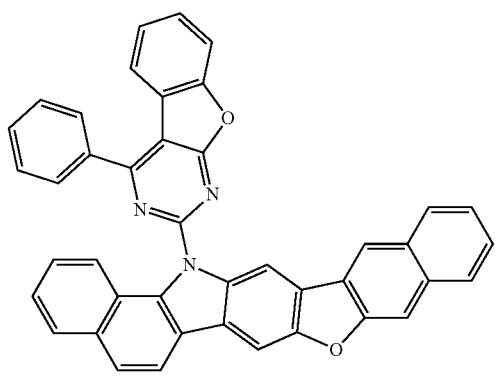
3-54
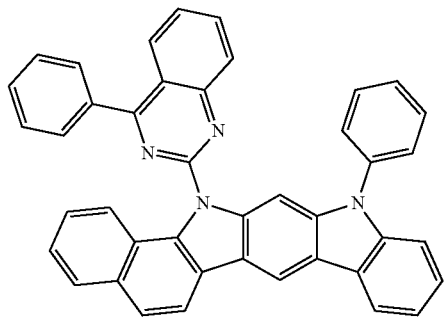
3-55
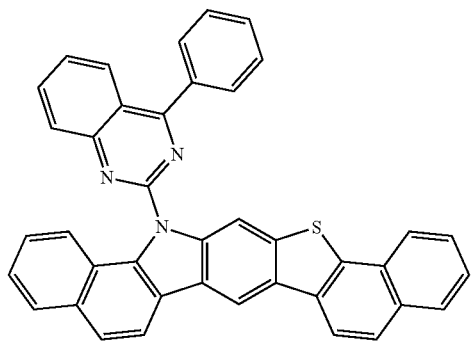

3-56
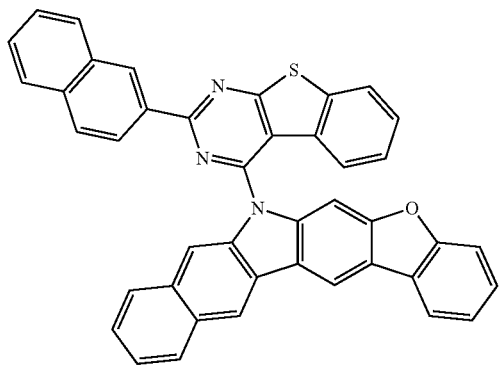
3-57
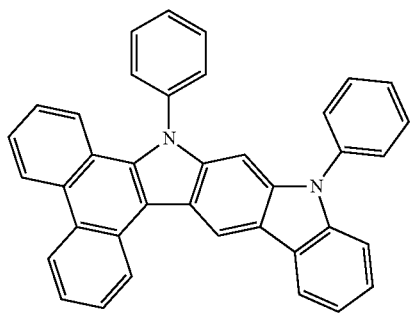
3-58
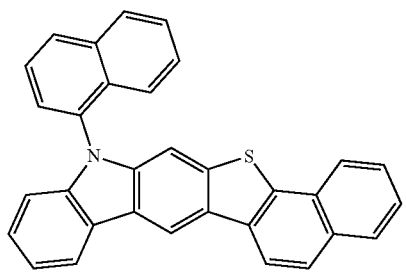
3-59
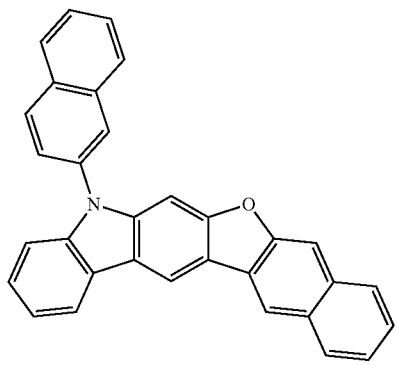
3-60
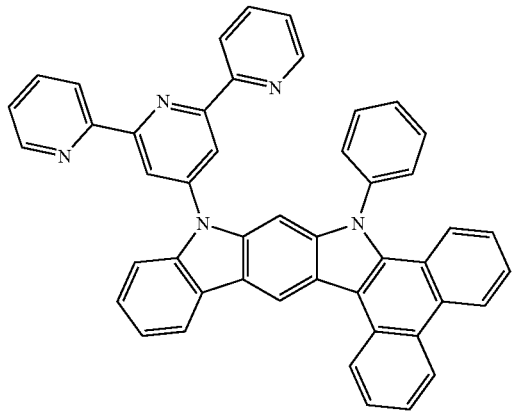
3-61
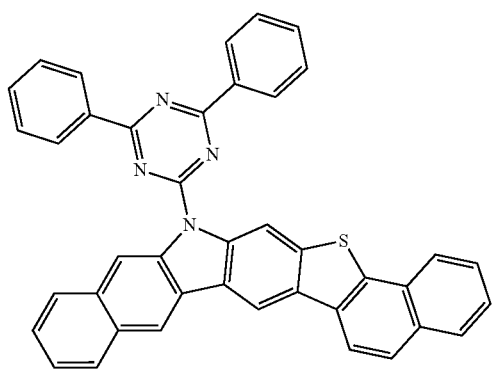
3-62
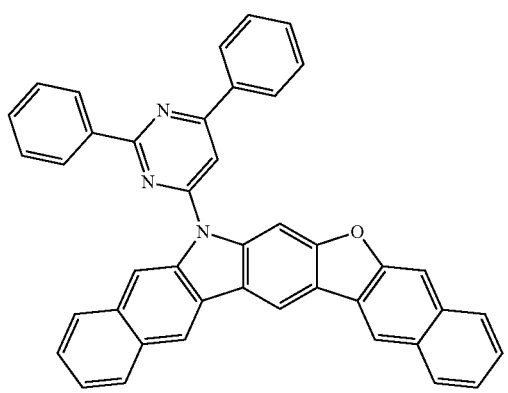
3-63
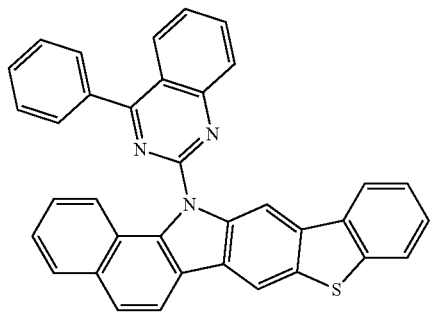

3-64
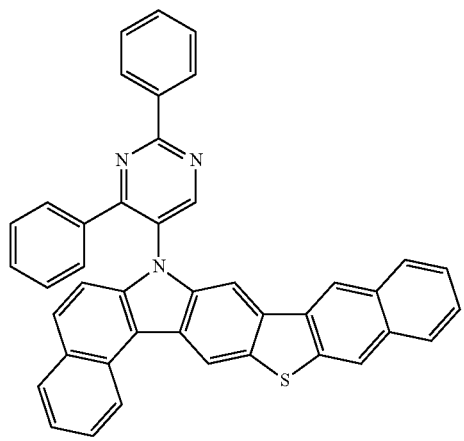
3-65
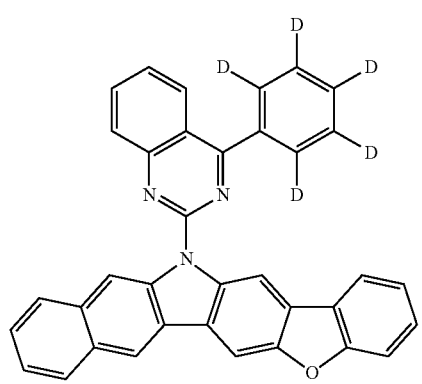
3-66
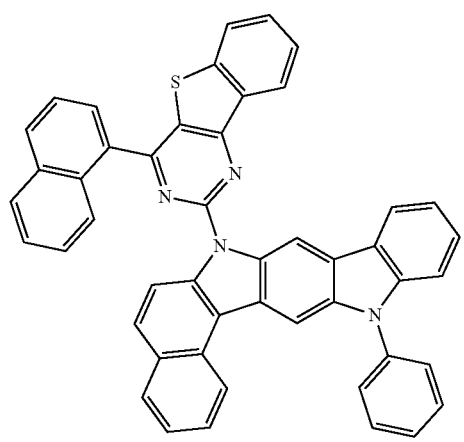
3-67
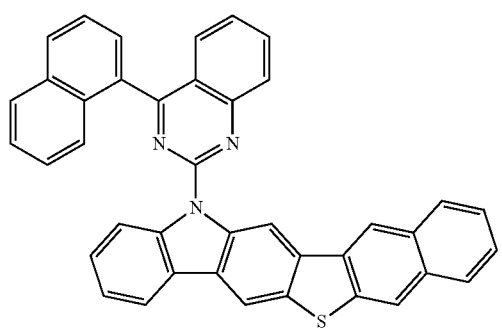
3-68
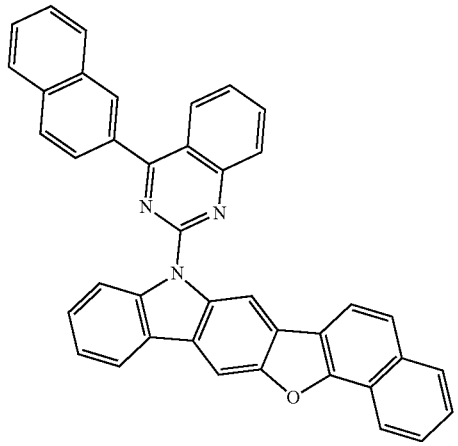
3-69
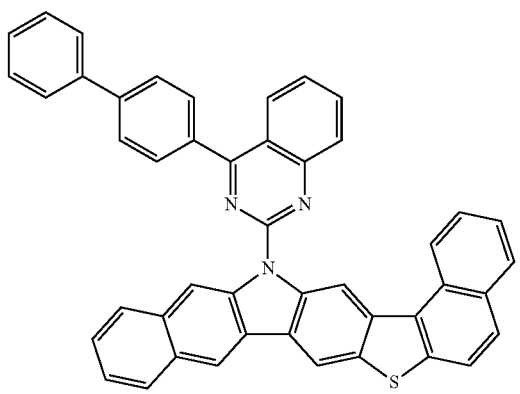
3-70
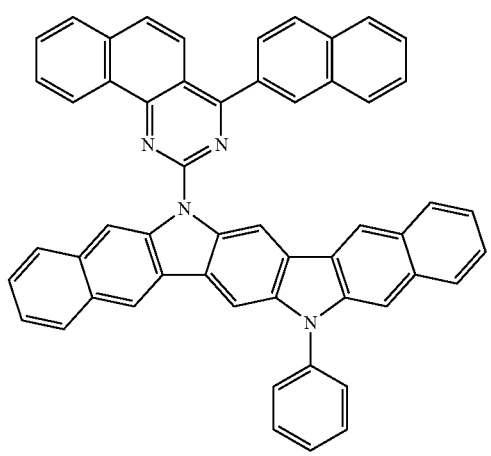

87
-continued
3-71
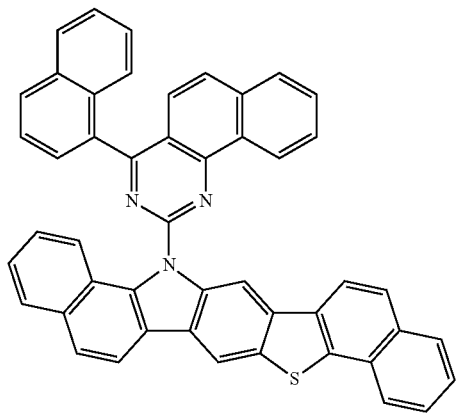
3-72
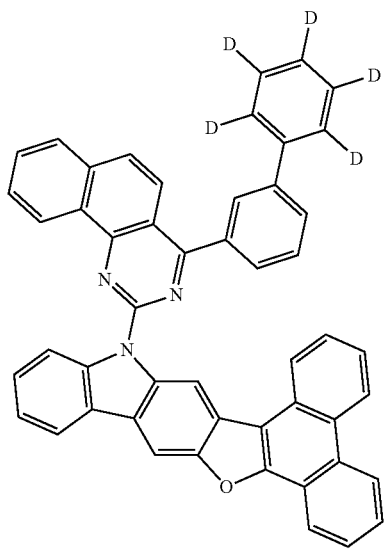
3-73
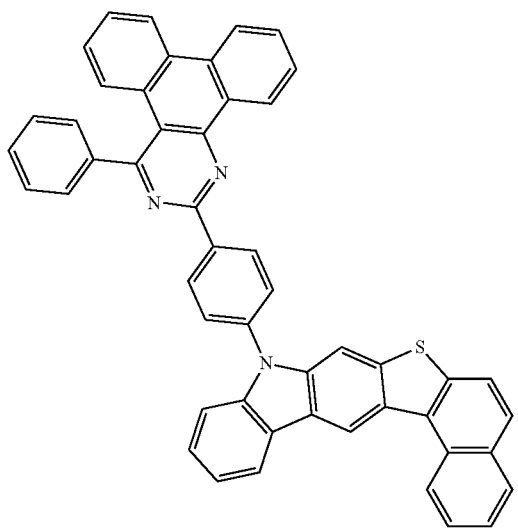
88
-continued
3-74
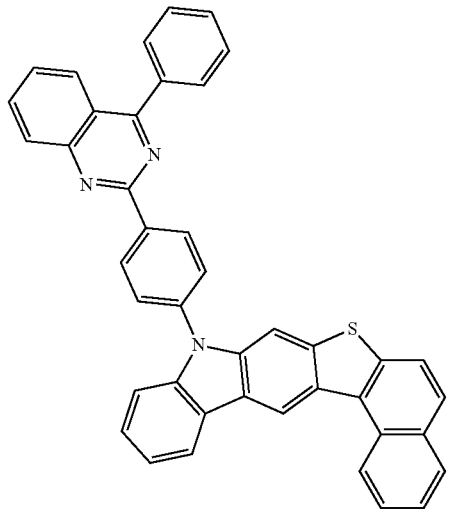
3-75
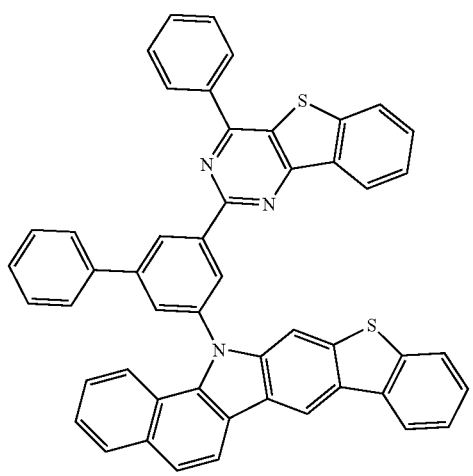
3-76
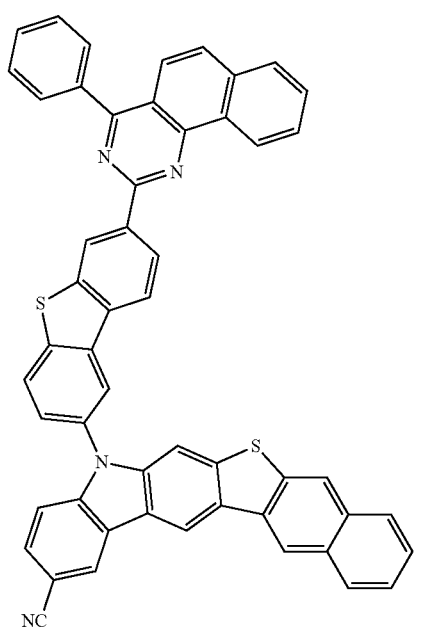

-continued
3-77
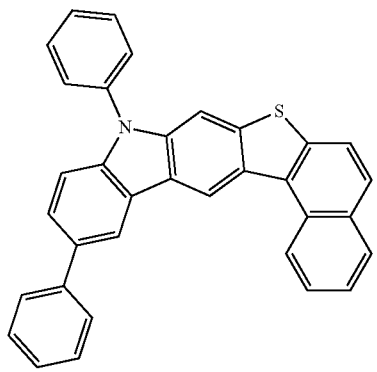
3-78
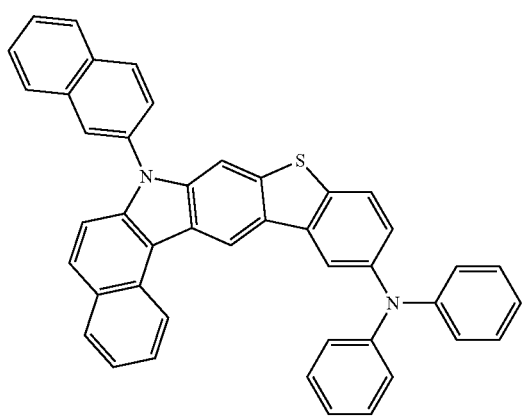
3-79
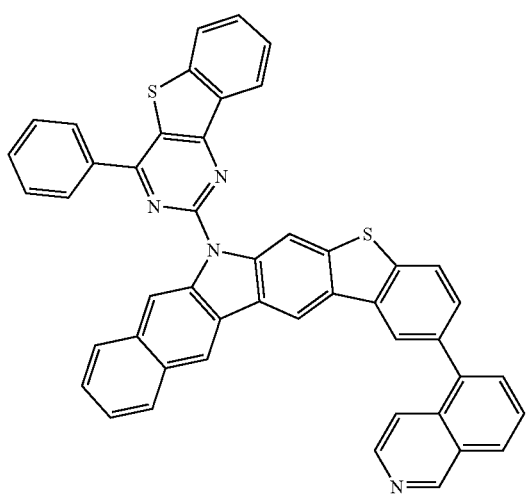
-continued
3-80
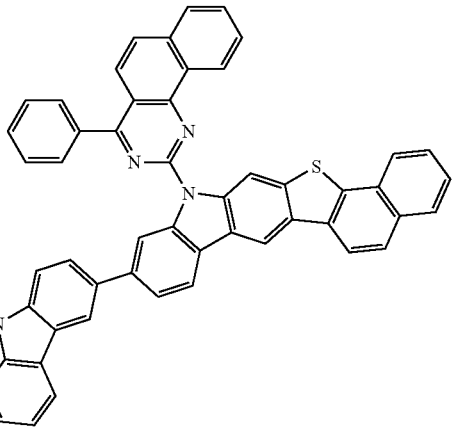
3-81
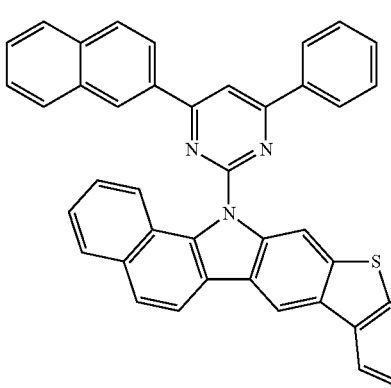
3-82
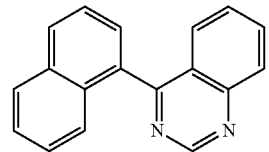
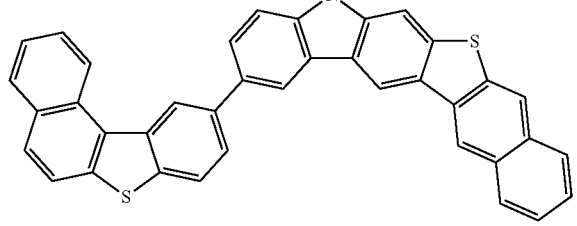
3-83
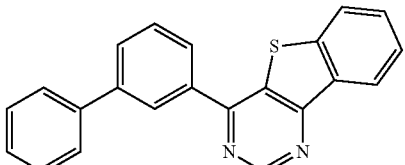
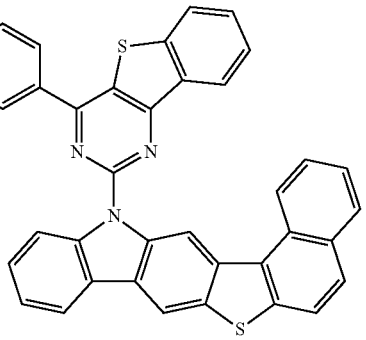

3-84
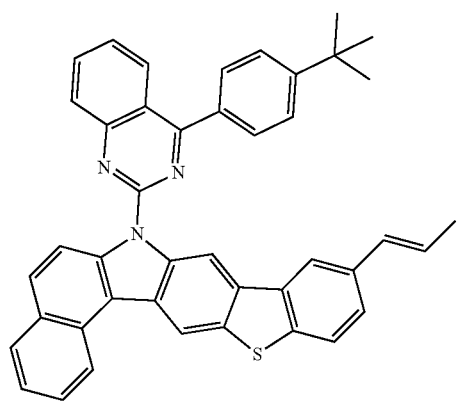
3-85
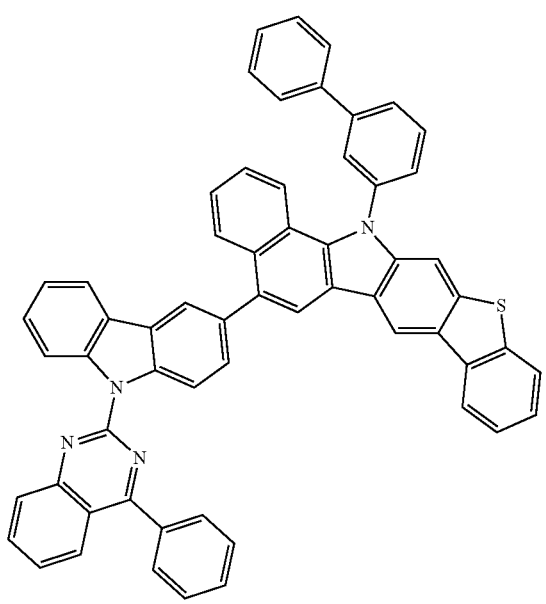
3-86
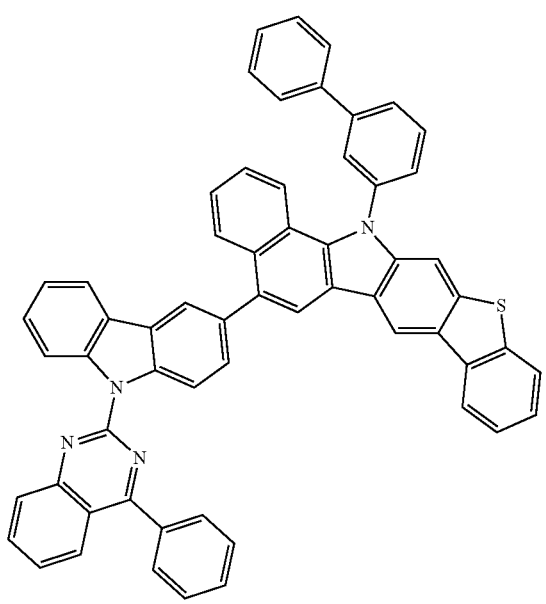
3-87
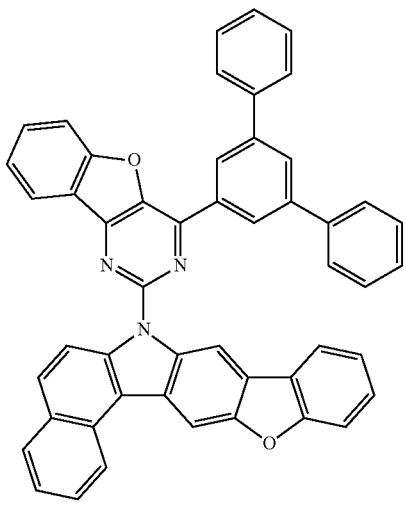
3-88
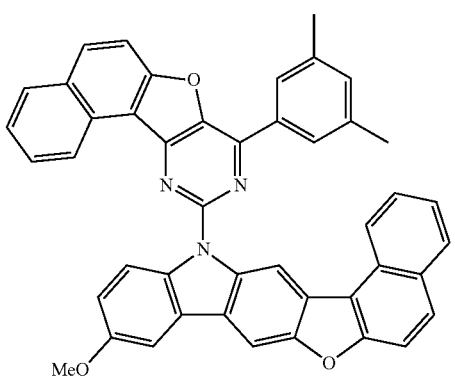
3-89
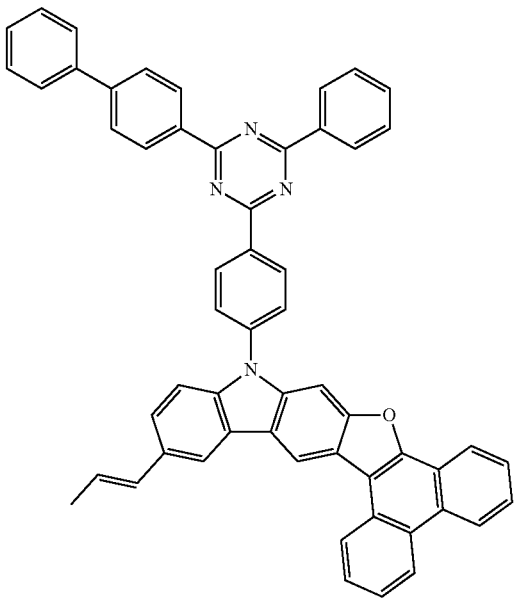

93
-continued
3-90
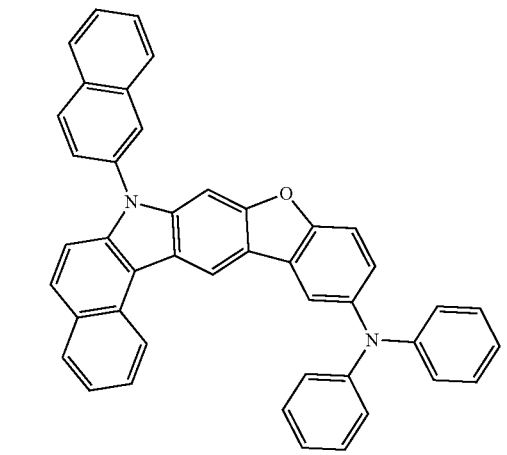
3-91
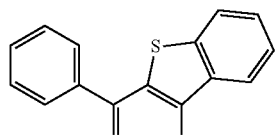
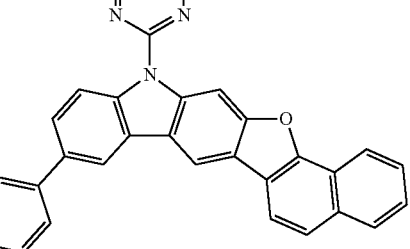
3-92
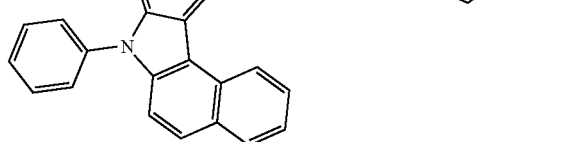
94
-continued
3-93
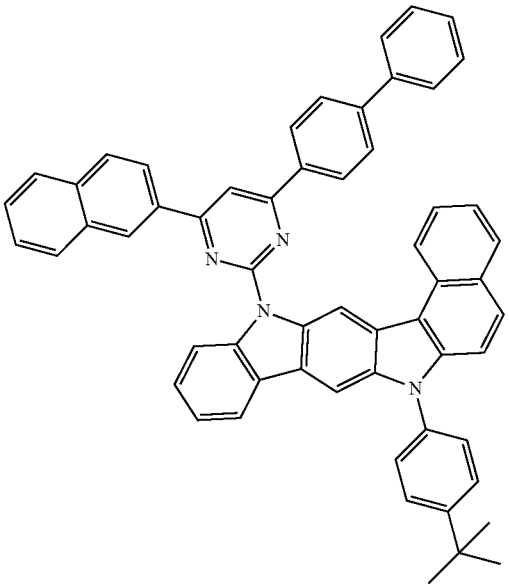
3-94
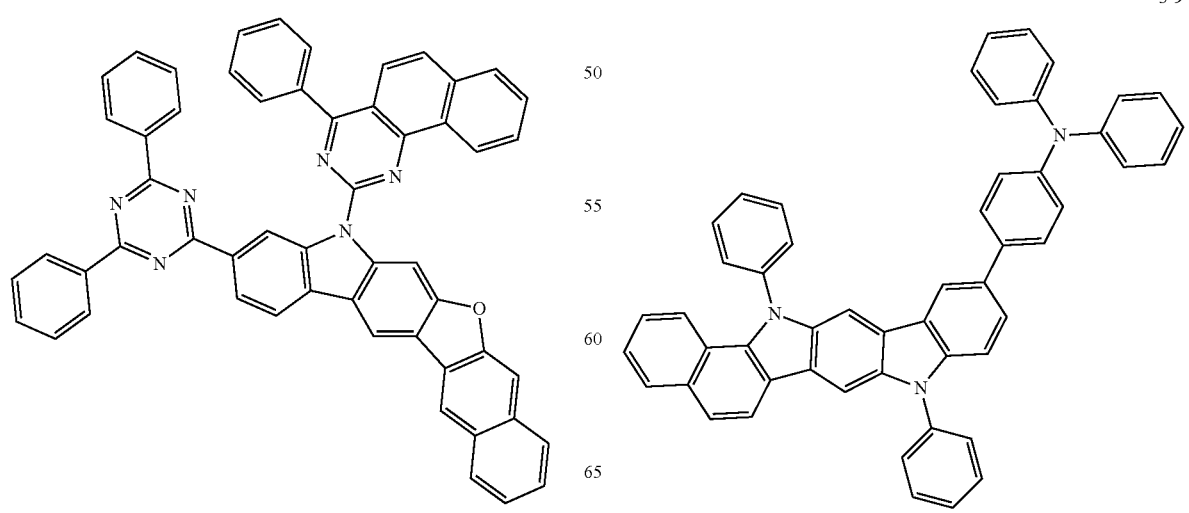

3-95
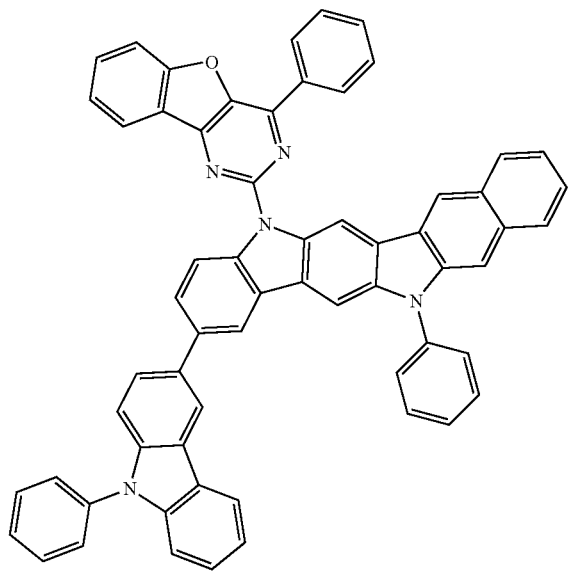
3-96
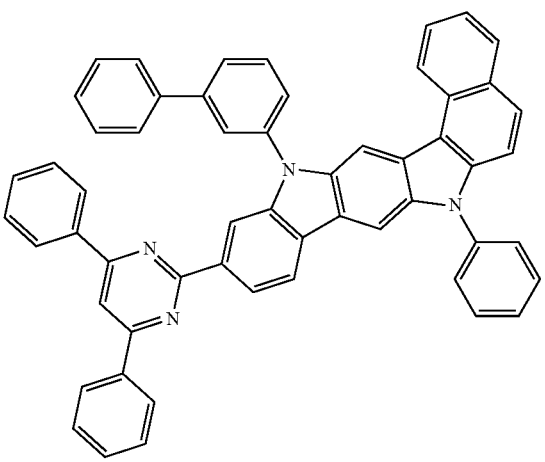
3-97
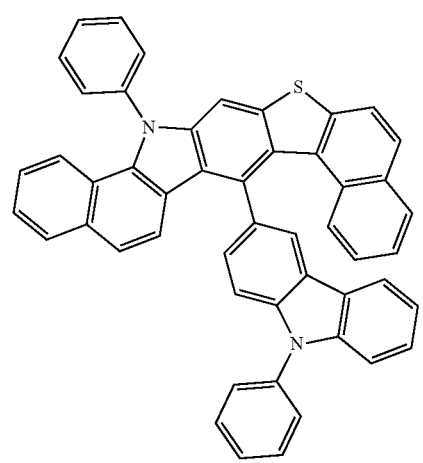
3-98
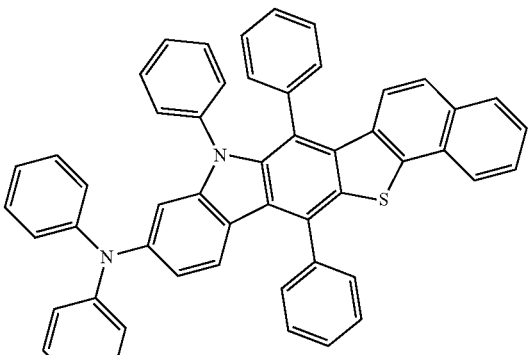
3-99
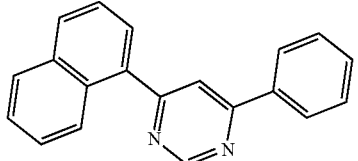
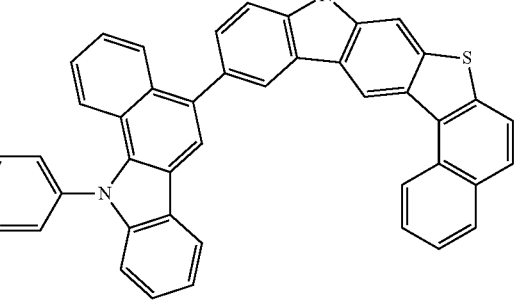
3-100
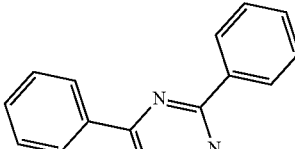
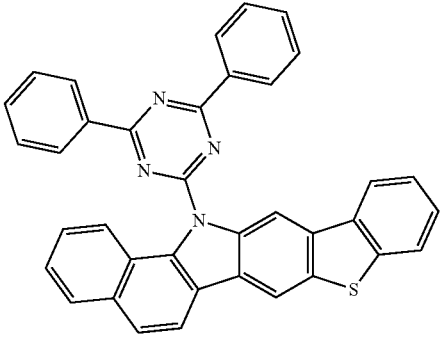
3-101
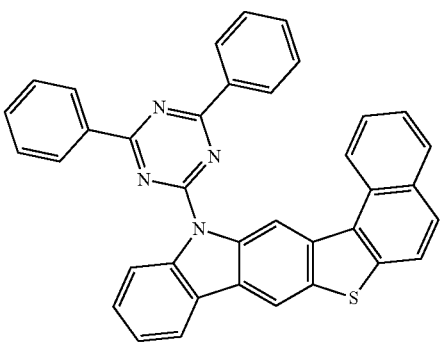

3-102
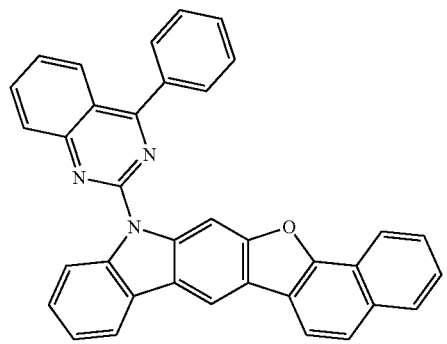
3-103
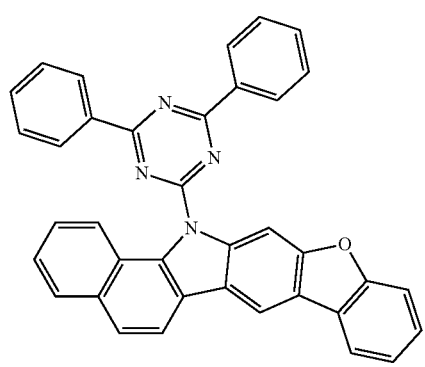
3-104
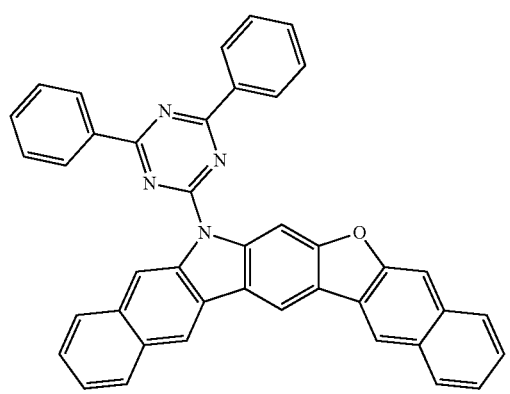
4-1
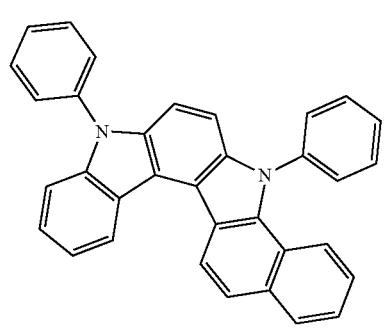
4-2
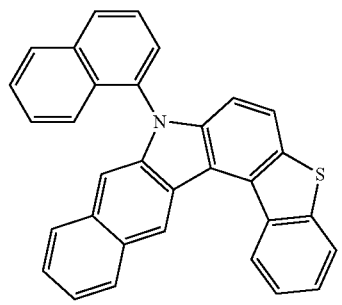
4-3
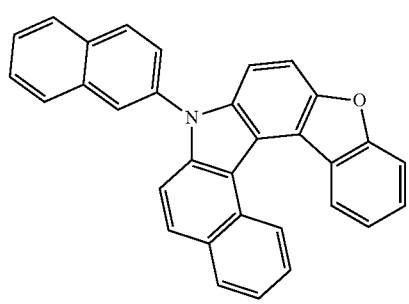
4-4
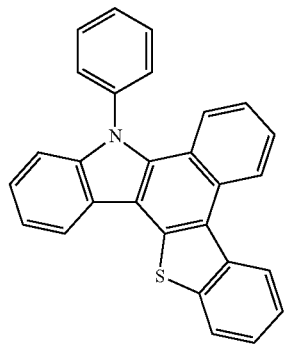
4-5
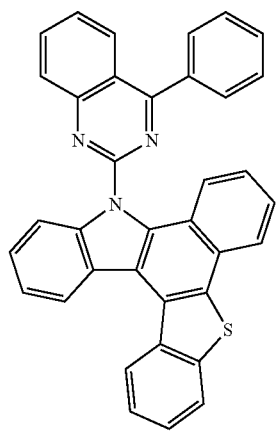

4-6
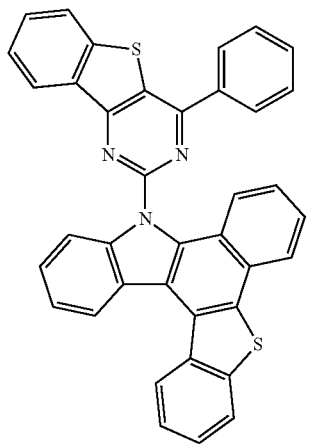
4-7
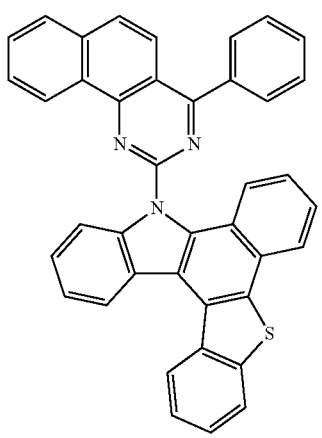
4-8
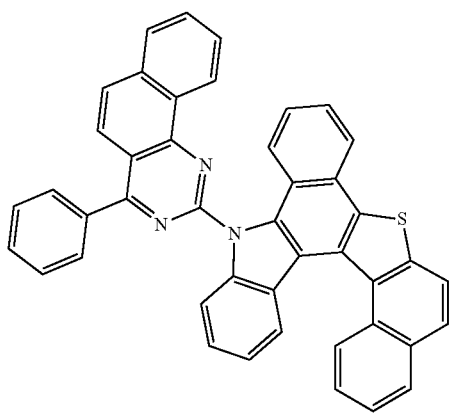
4-9
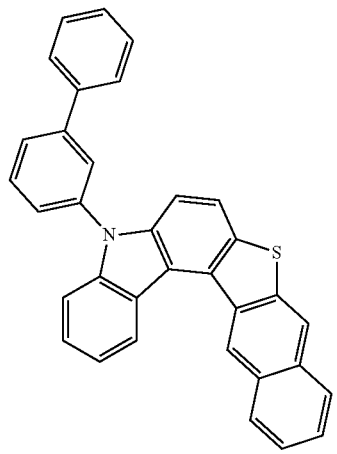
4-10
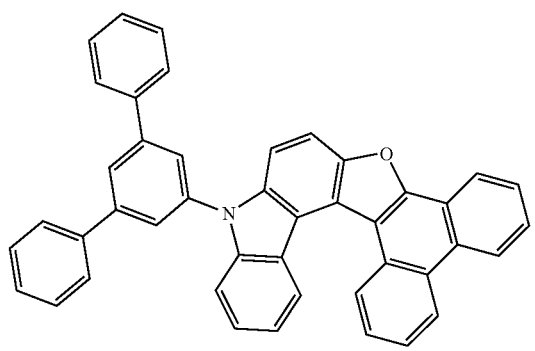
4-11
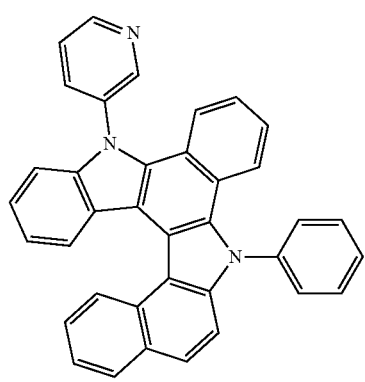
4-12
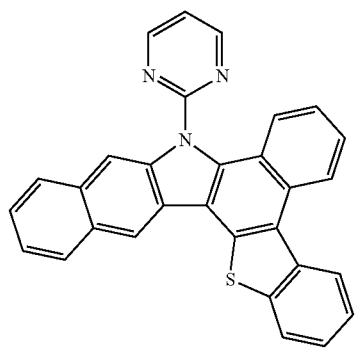

US 11,665,958 B1
101
-continued
4-13
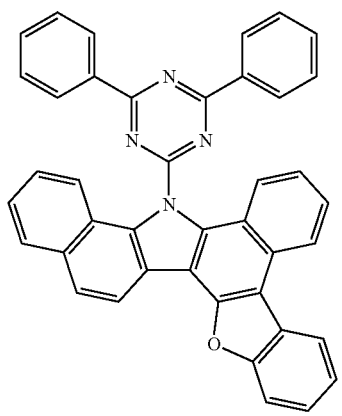
4-14
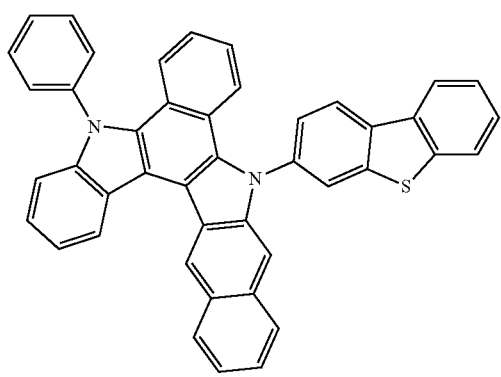
4-15
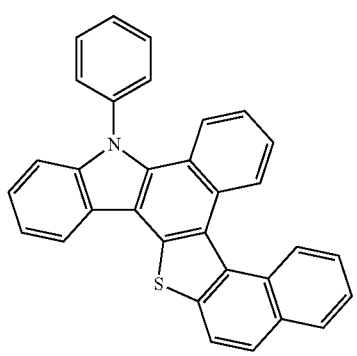
4-16
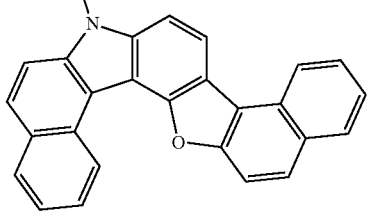
102
-continued
4-17
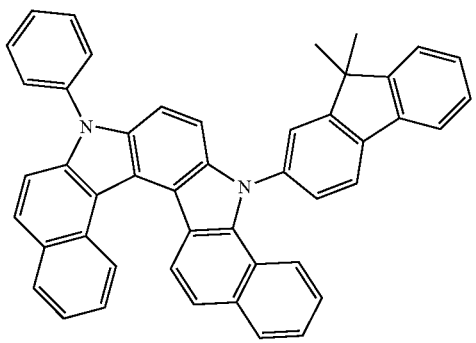
4-18
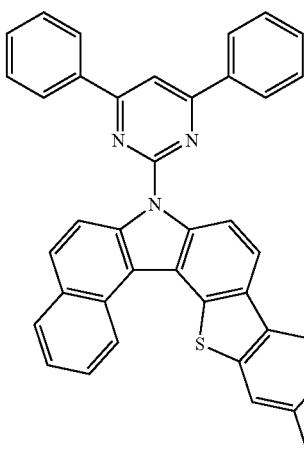
4-19
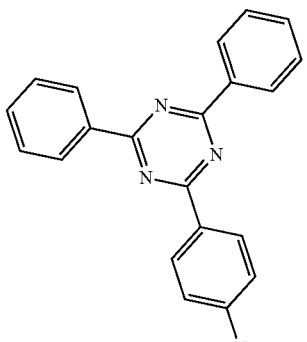

103
-continued
4-20
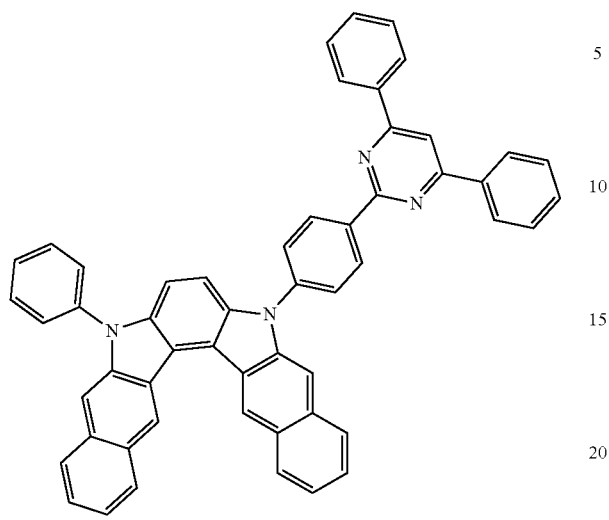
4-21
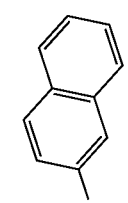
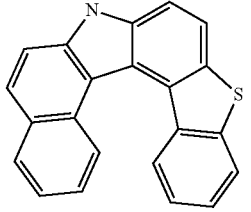
4-22
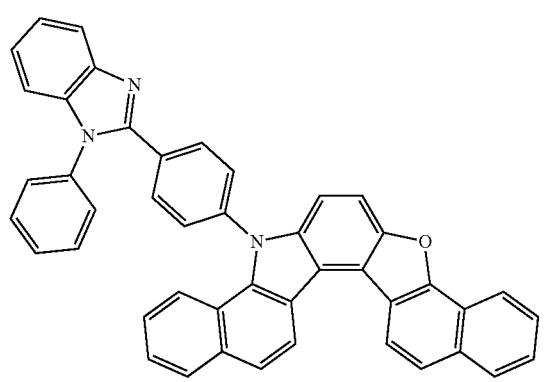
104
-continued
4-23
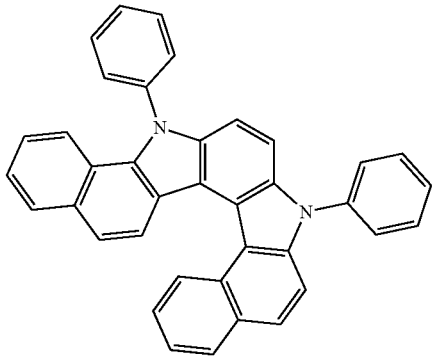
4-24
4-25
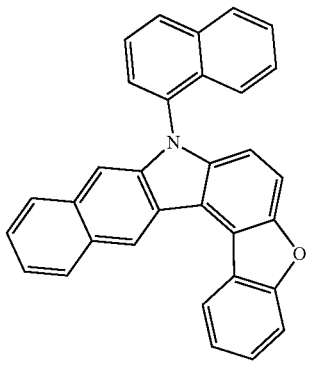
4-26
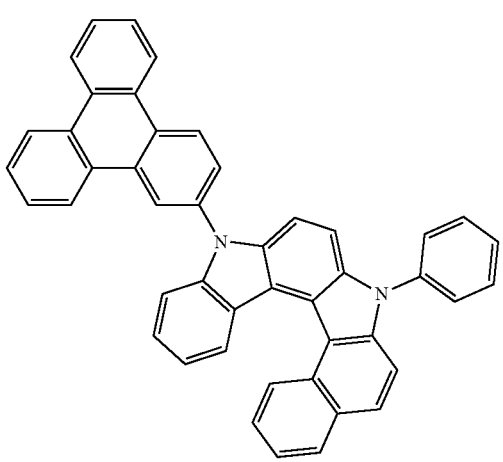

4-27
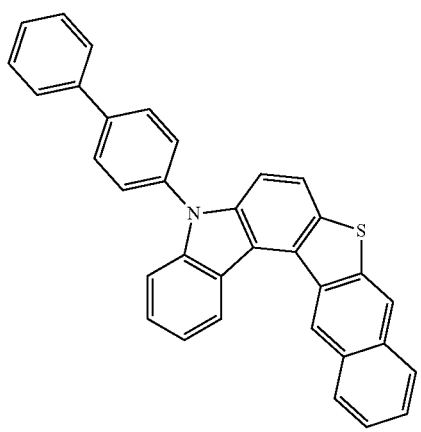
4-28
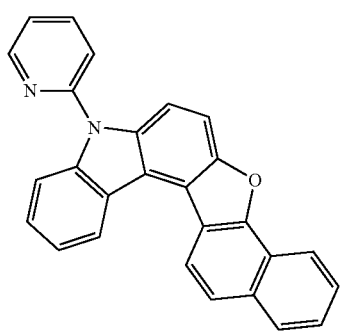
4-29
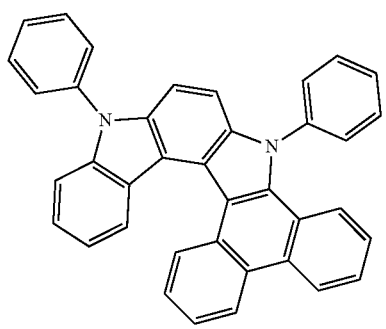
4-30
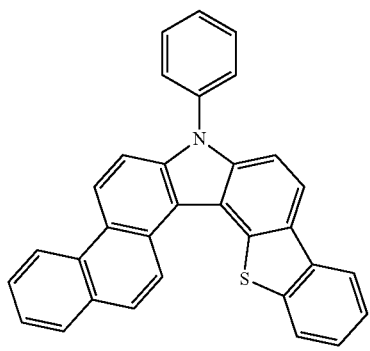
4-31
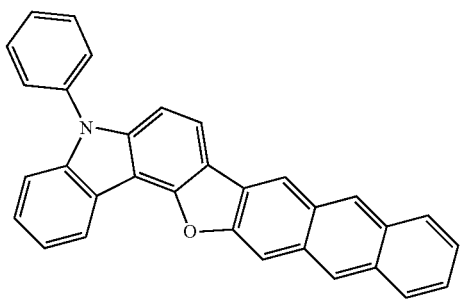
4-32
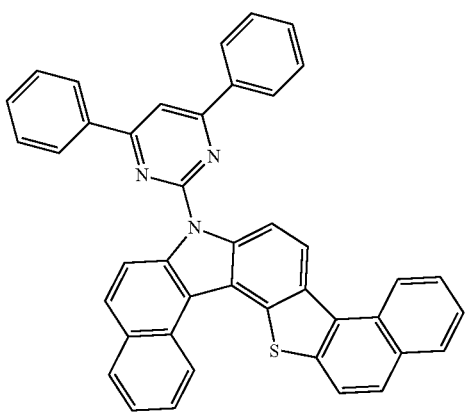
4-33
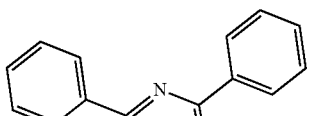
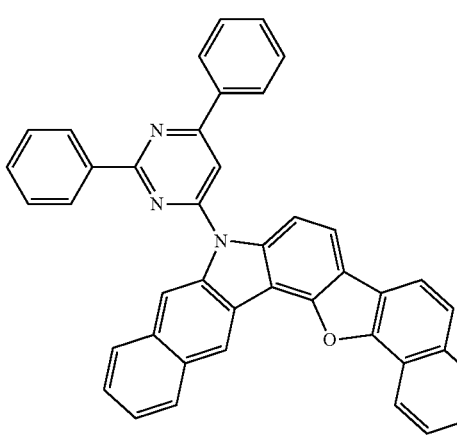
4-34

107
-continued
4-35
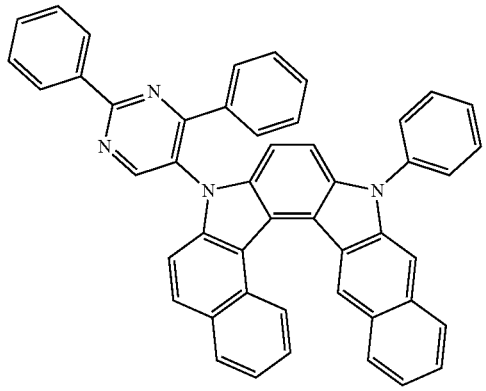
4-36
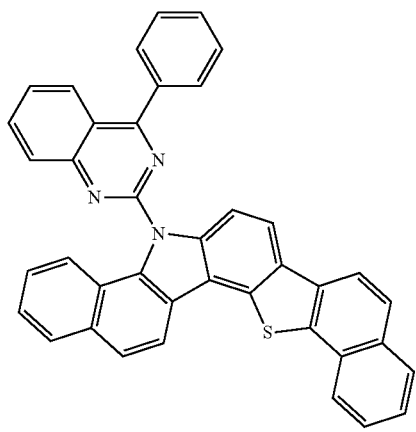
4-37
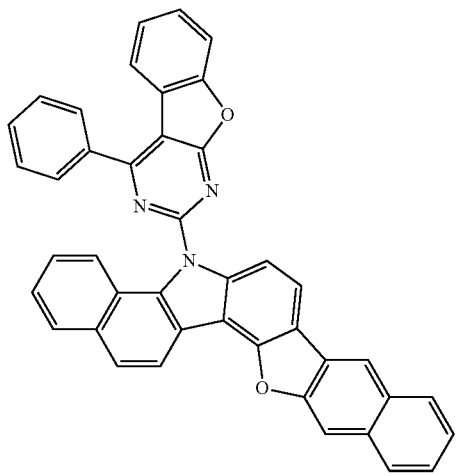
108
-continued
4-38
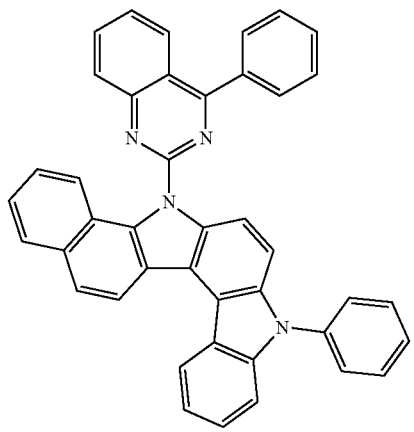
4-39
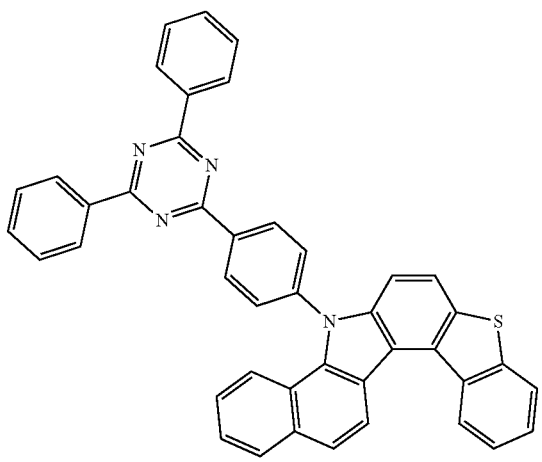
4-40
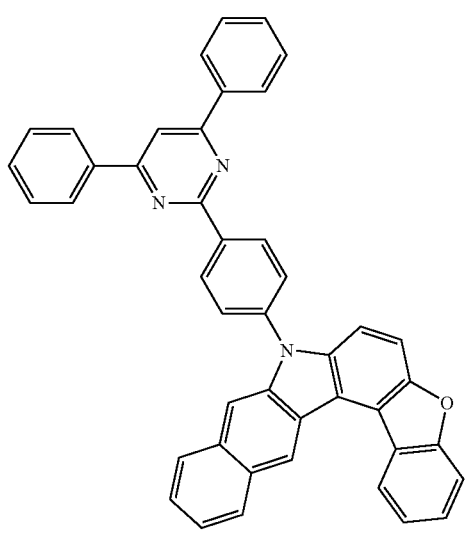

4-41
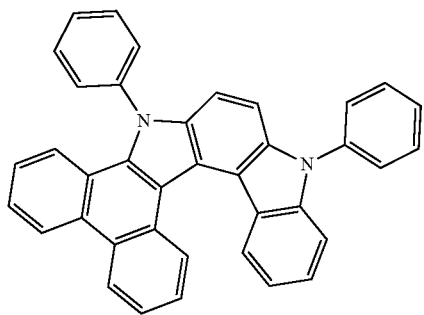
4-42
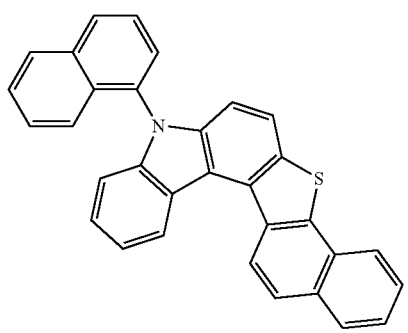
4-43
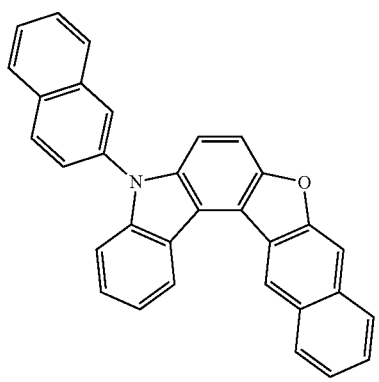
4-44
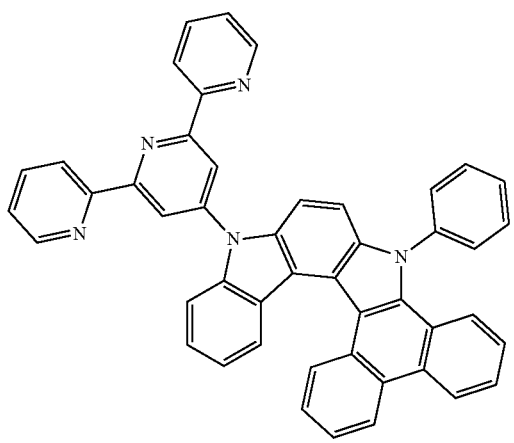
4-45
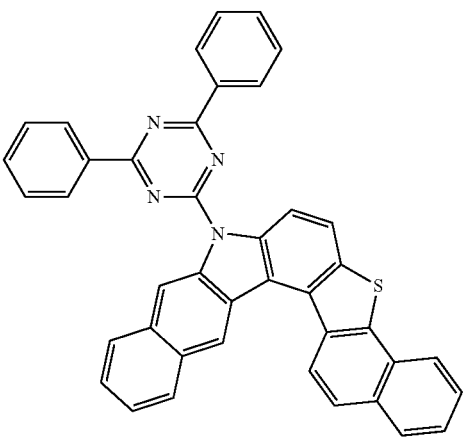
4-46
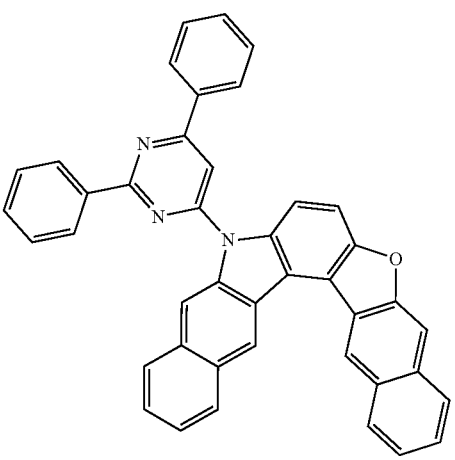
4-47
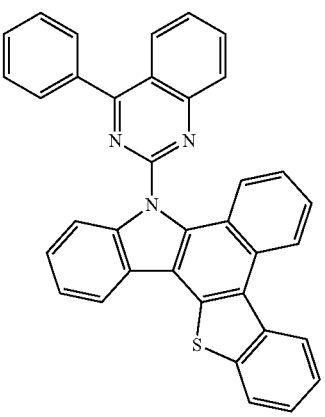

4-48
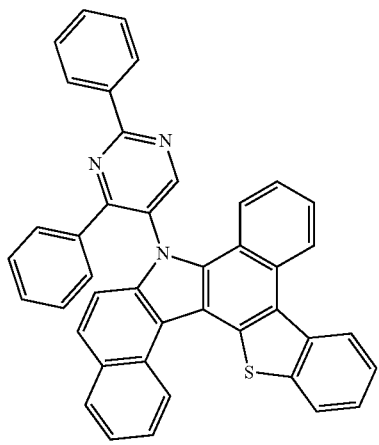
4-49
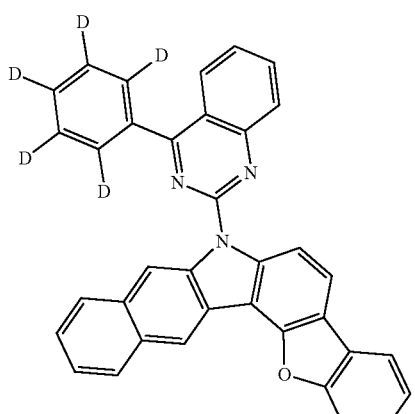
4-50
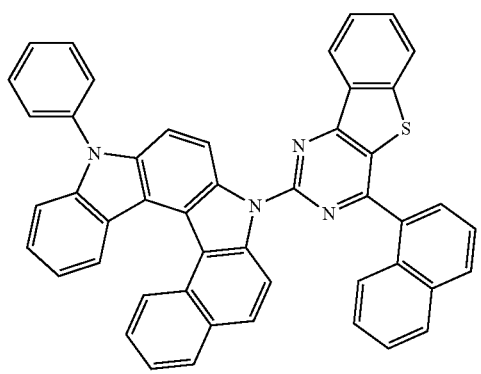
4-51
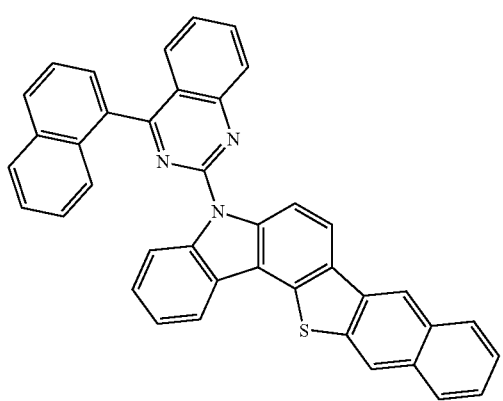
4-52
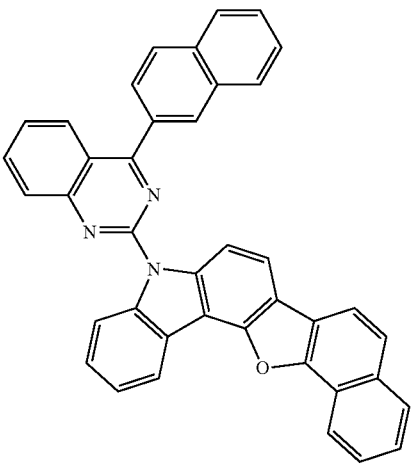
4-53
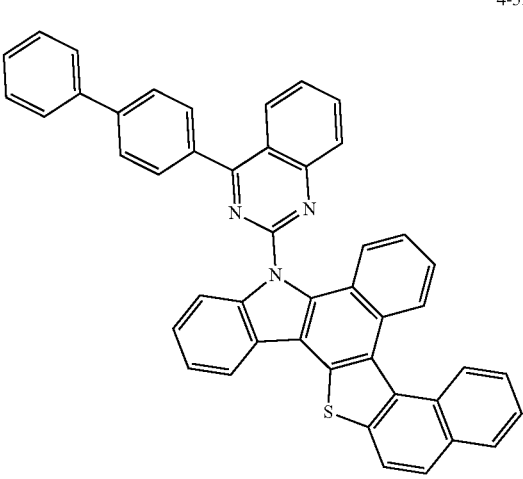
4-54
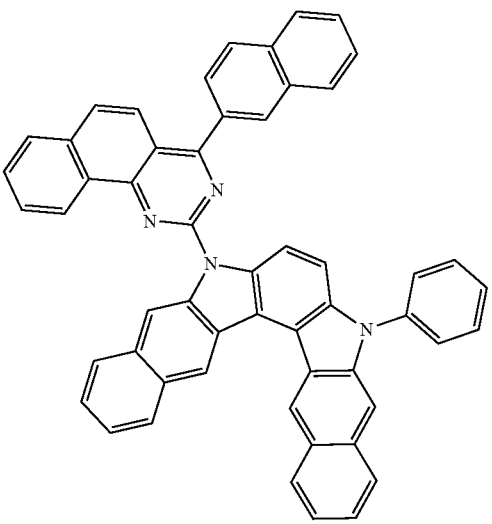

4-55
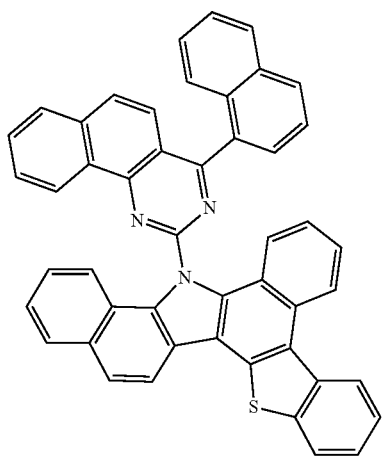
4-58
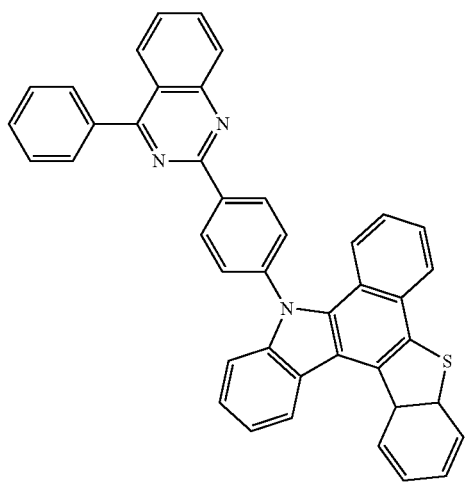
4-56
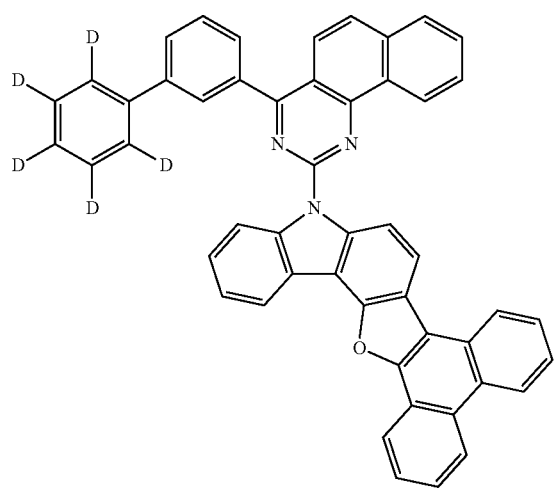
4-59
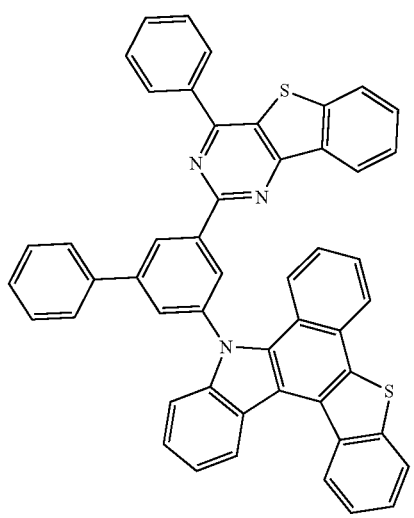
4-57
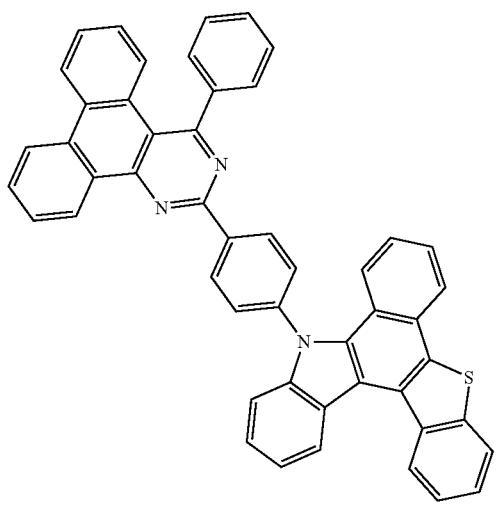
4-60
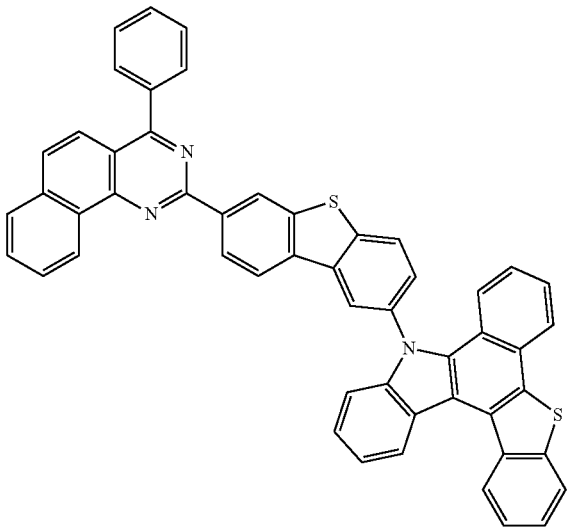

-continued
4-61
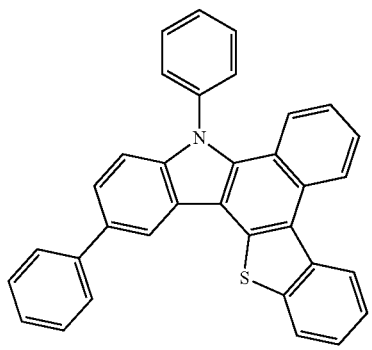
4-64
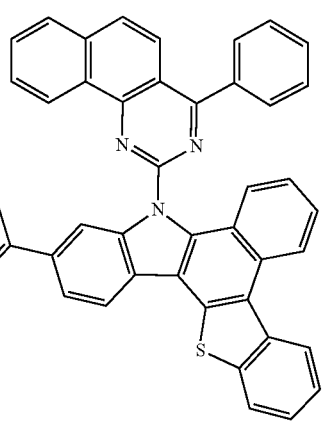
4-62
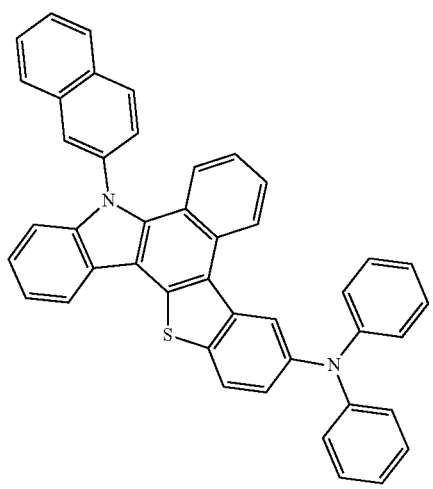
4-65
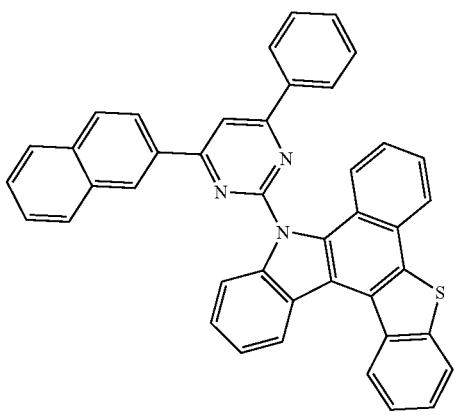
4-63
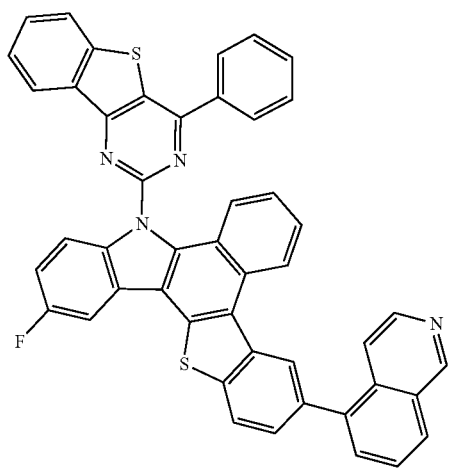
4-66
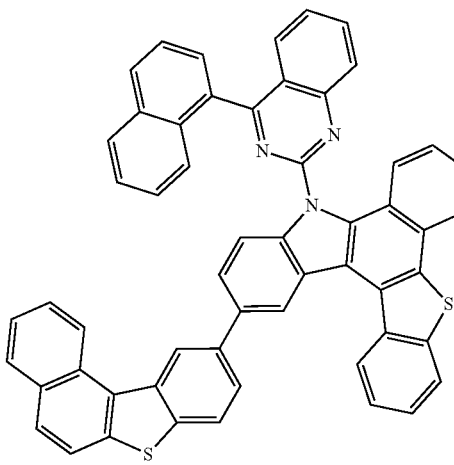

-continued
4-67
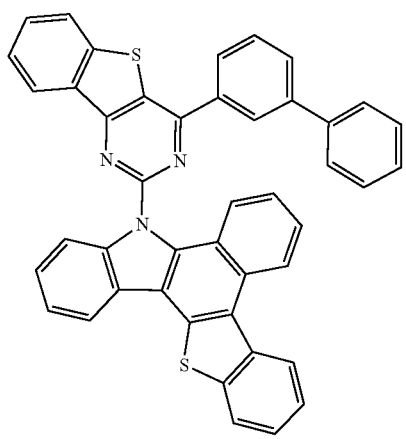
4-68
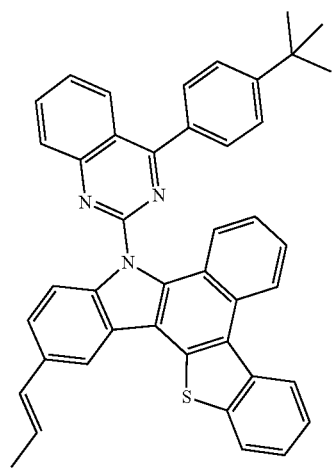
4-69
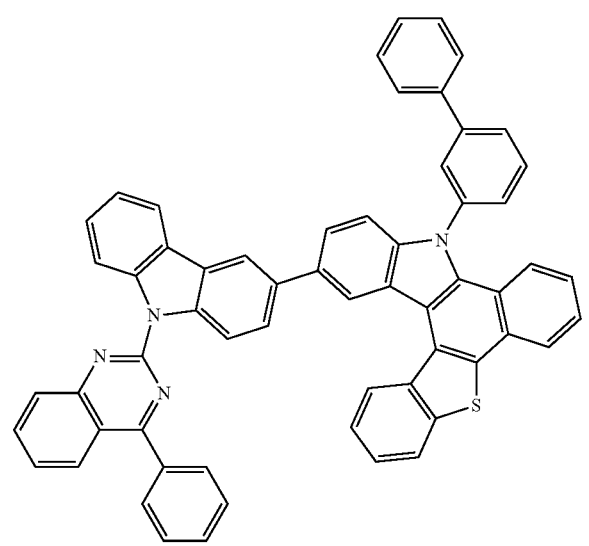
-continued
4-70
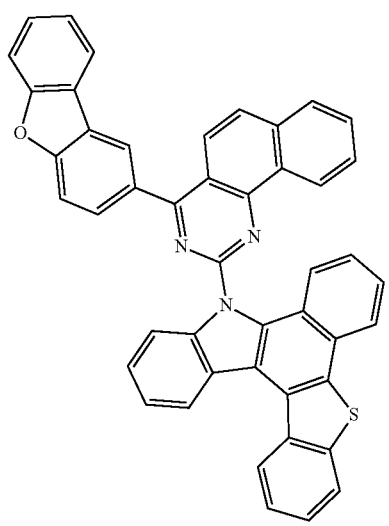
4-71
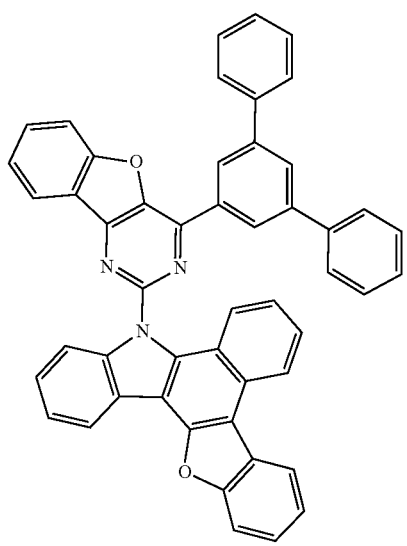
4-72
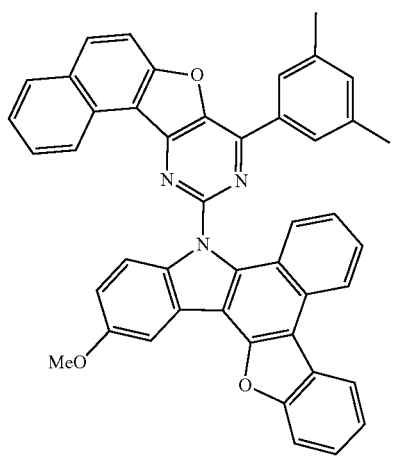

-continued
4-73
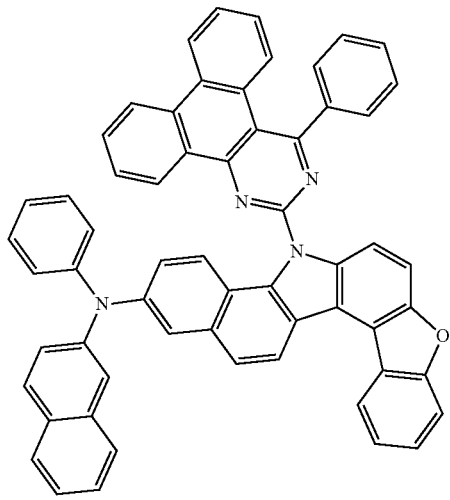
4-74
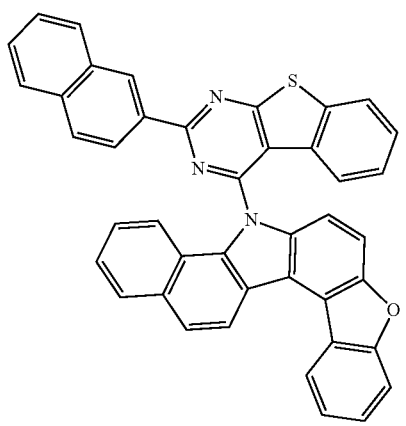
4-75
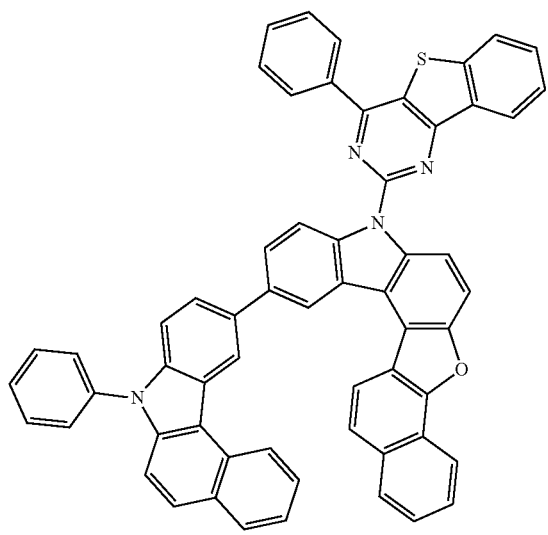
-continued
4-76
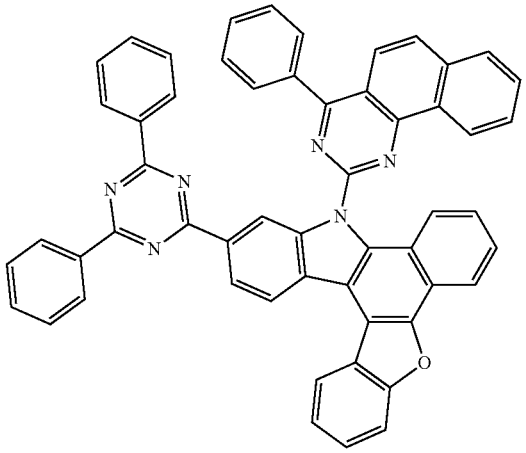
4-77
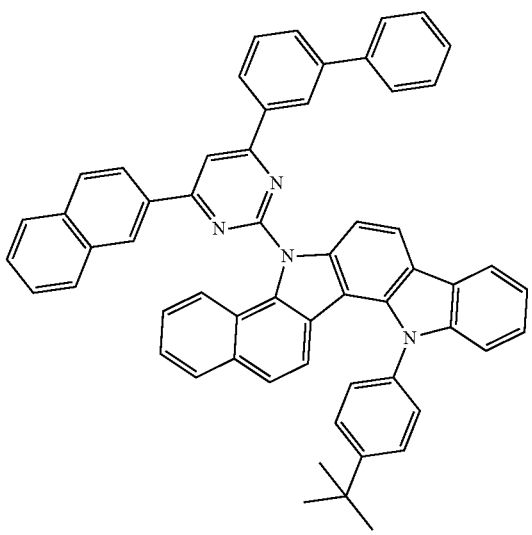
4-78
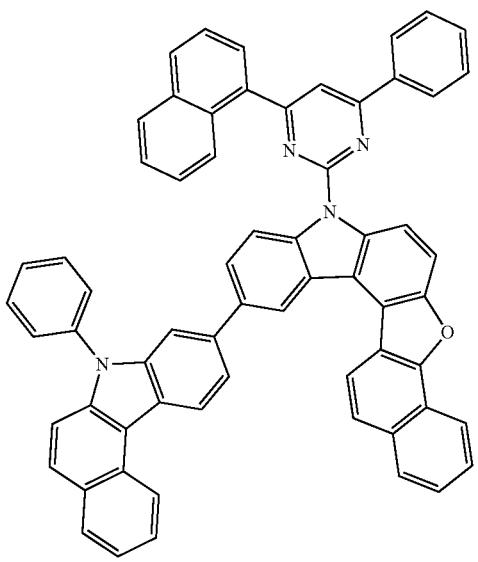

-continued
4-79
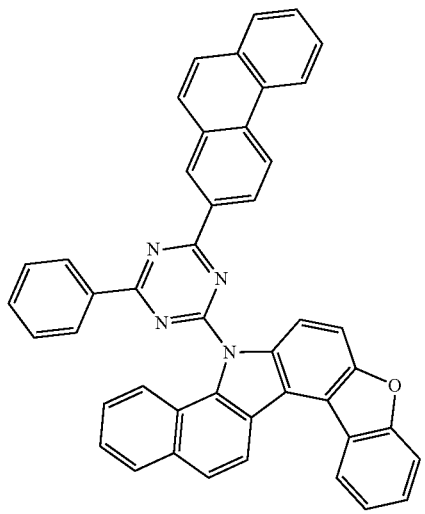
4-80
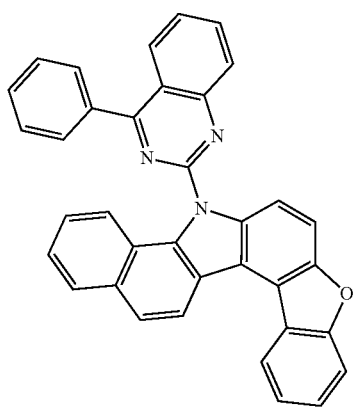
4-81
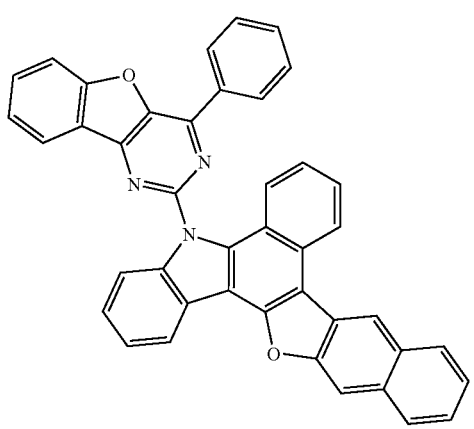
-continued
4-82
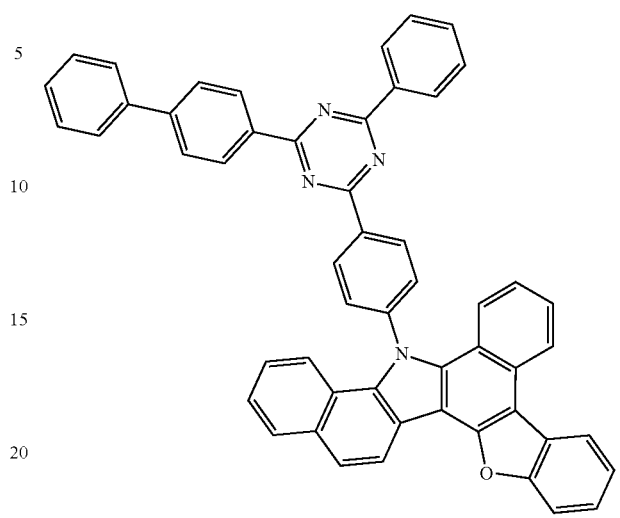
4-83
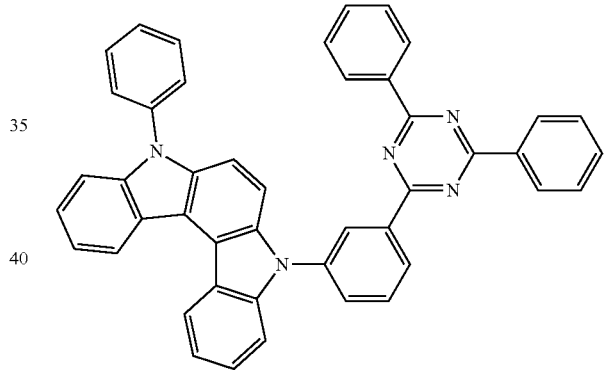
4-84
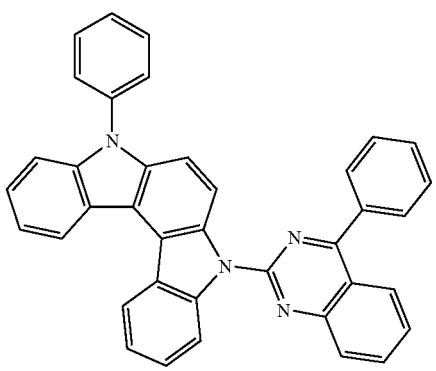

4-85
4-86
4-87
4-88
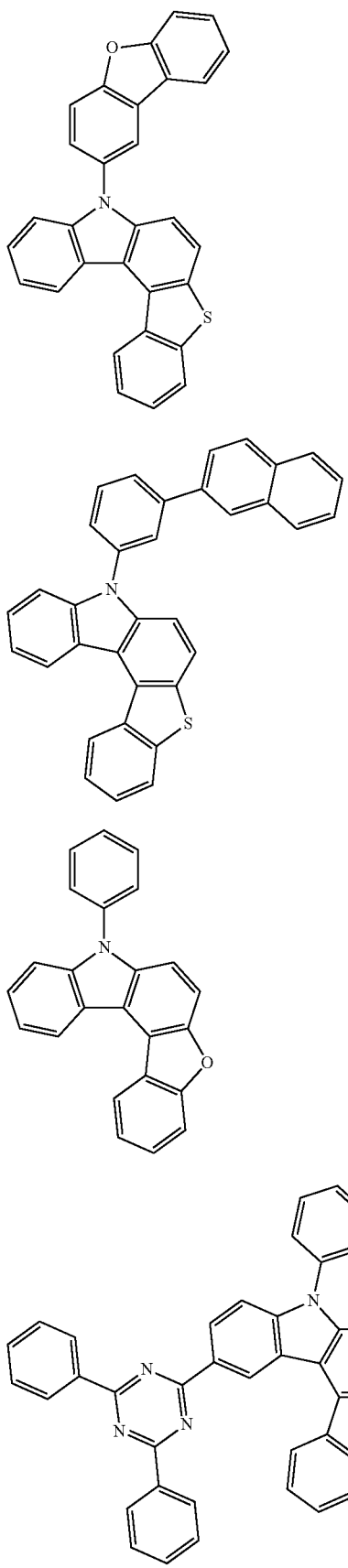
4-89
4-90
4-91
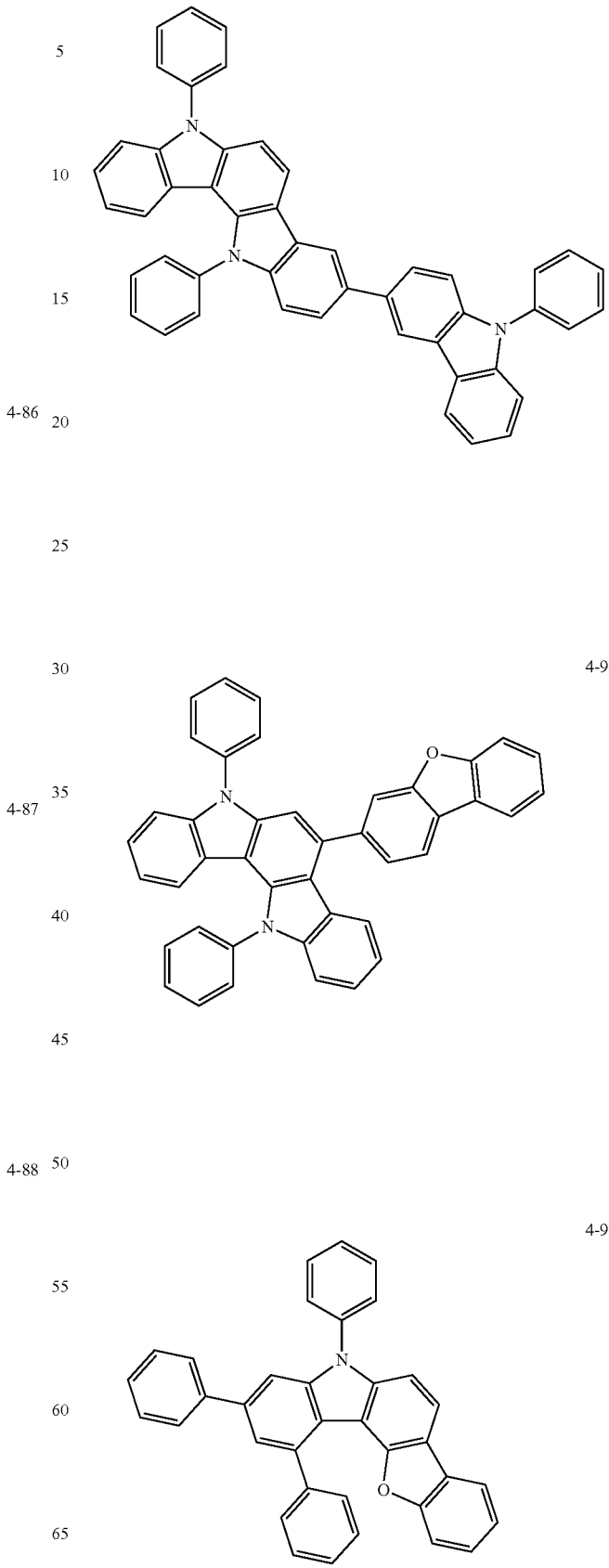

4-92
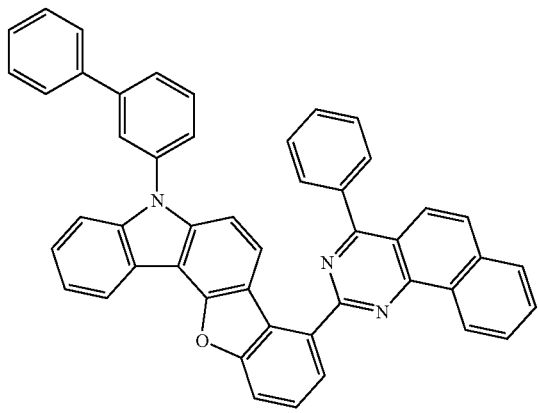
4-93
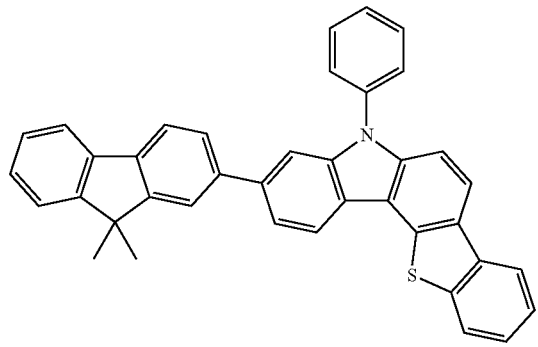
4-94
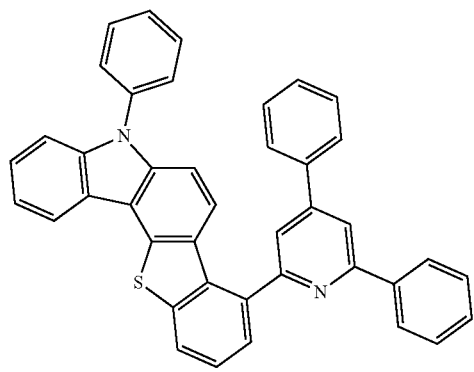
Also, Formula 13 is represented by any one of Formulas 3-1 to 3-5
Formula 3-1
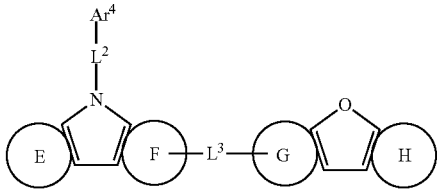
Formula 3-2
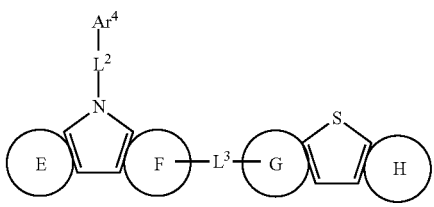
Formula 3-3
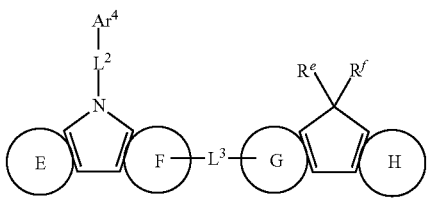
Formula 3-4
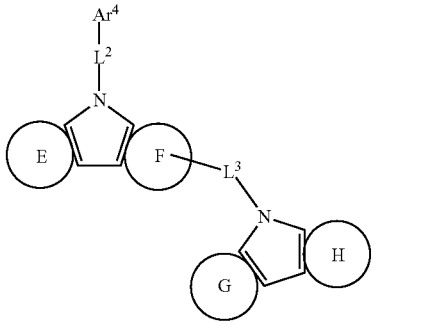
Formula 3-5
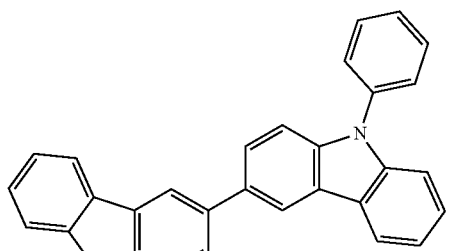
Wherein E ring, F ring, G ring, H ring, $Ar^4$, $Ar^8$, $L^2$, $L^3$, $L'$, $R^e$ and $R^f$ are the same as defined above.
Specifically, the compound represented by Formula 13 may be any one of the following compounds.
5-1
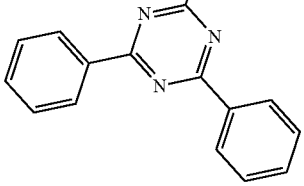

-continued
5-2
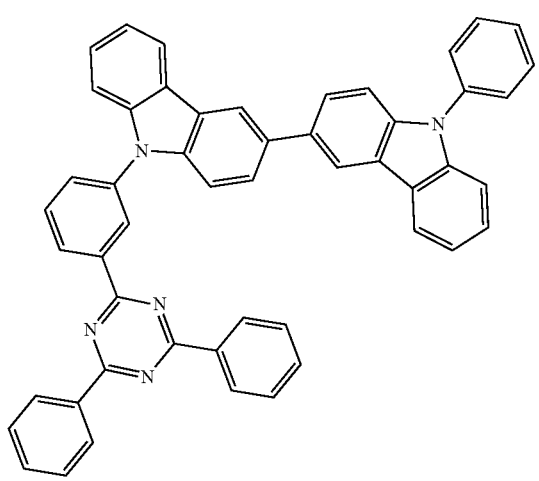
5-3
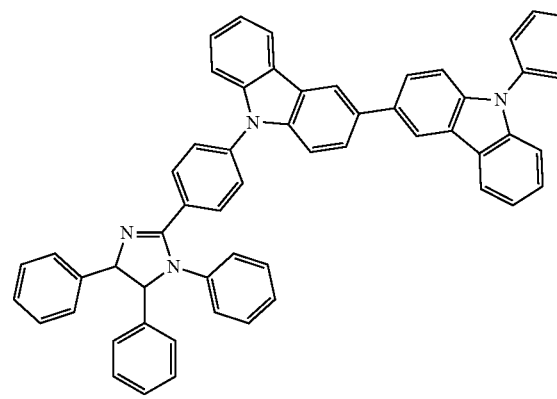
5-4
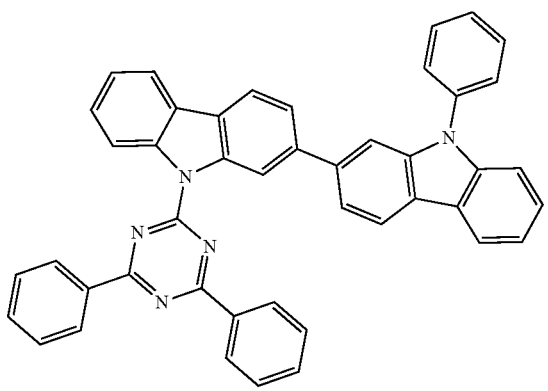
5-5
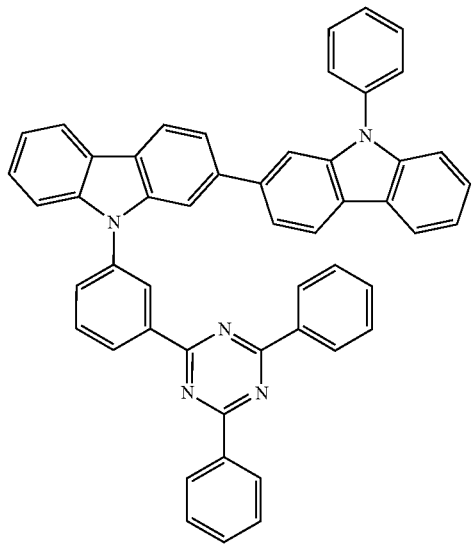
5-6
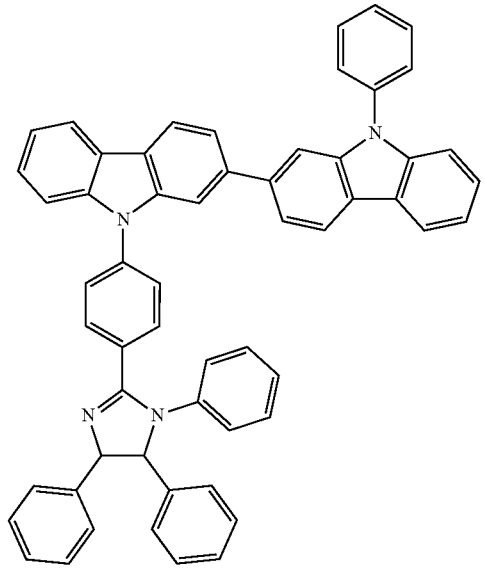
5-7
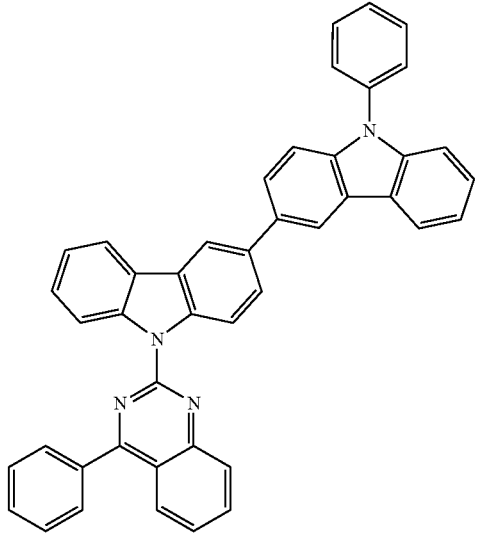

5-8
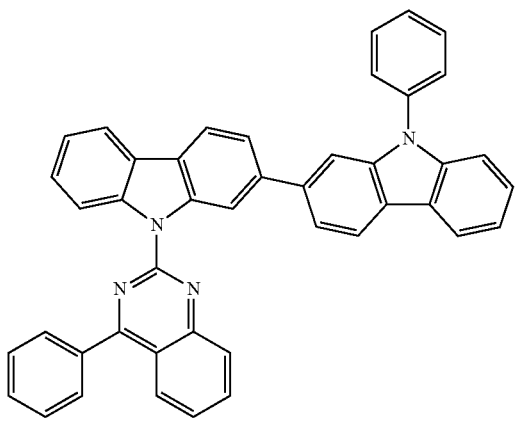
5-11
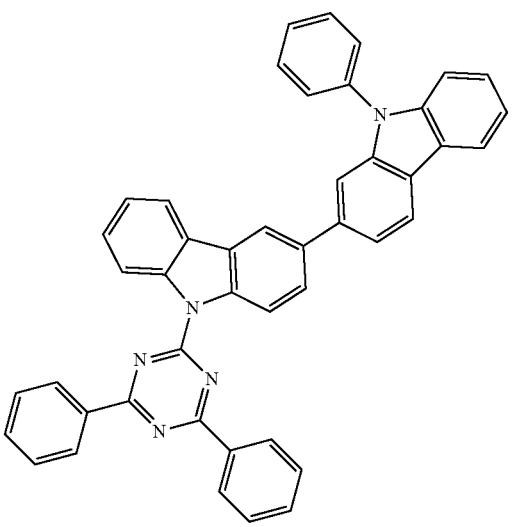
5-9
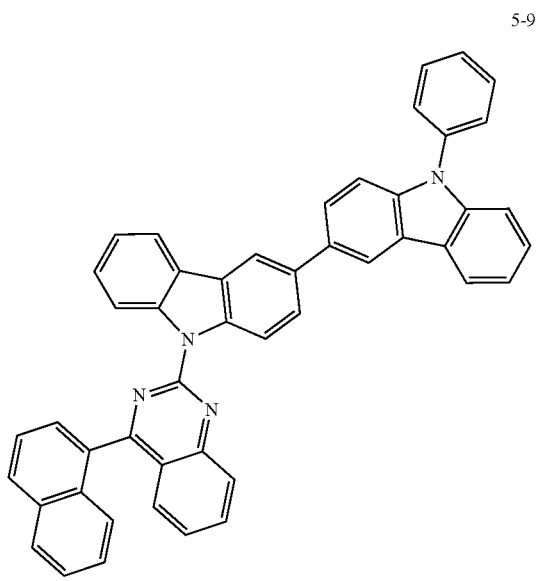
5-12
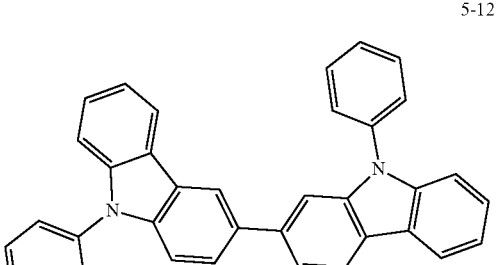
5-10
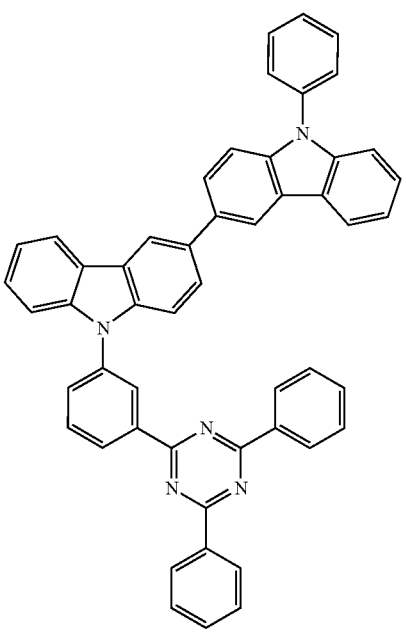
5-13

-continued
5-14
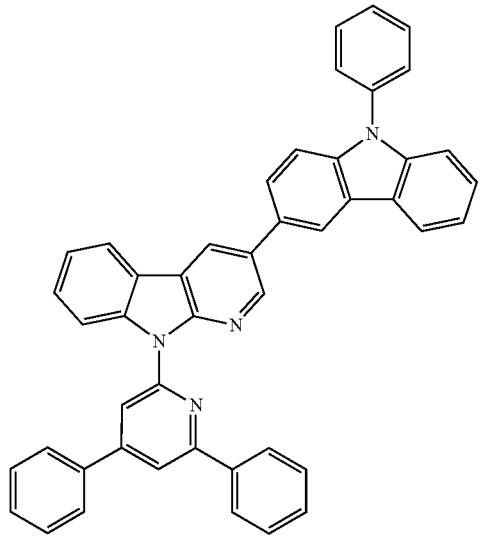
5-15
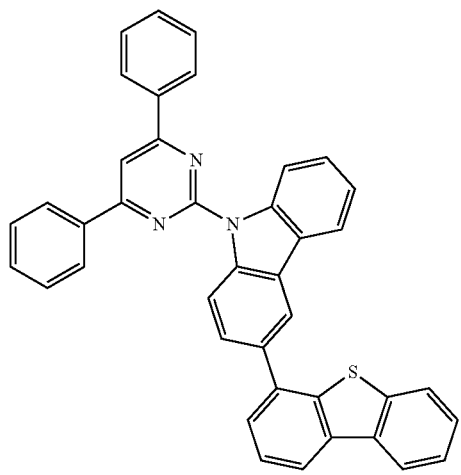
5-16
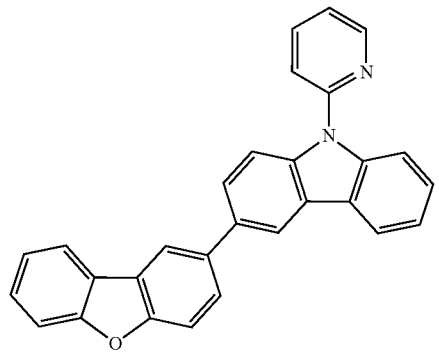
-continued
5-17
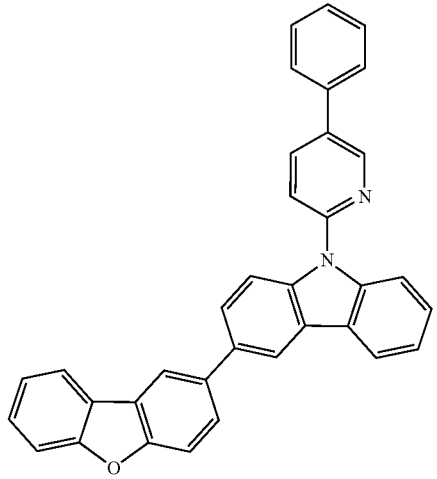
5-18
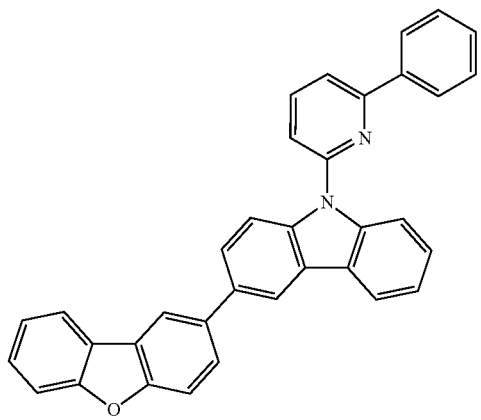
5-19
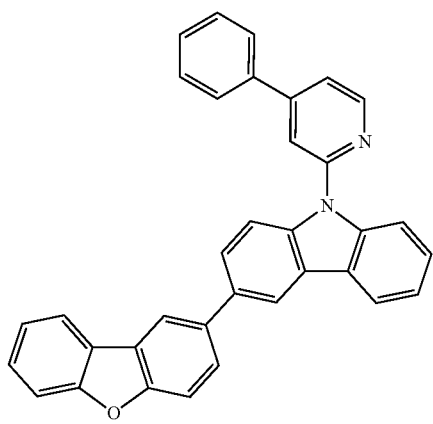

5-20
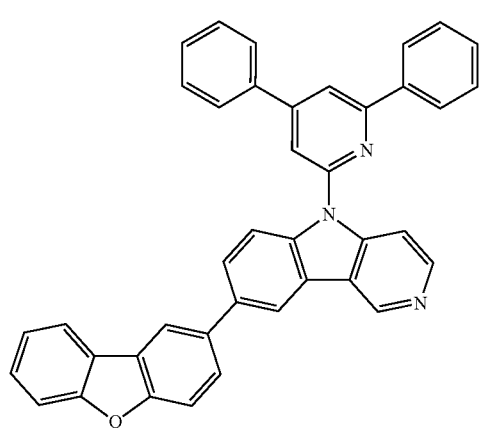
5-21
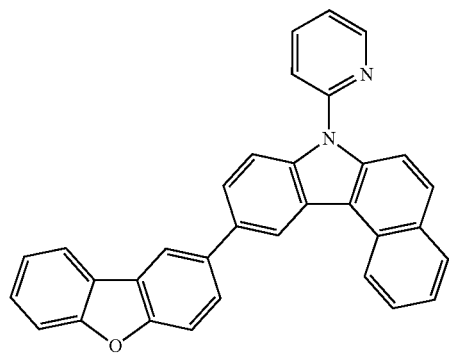
5-22
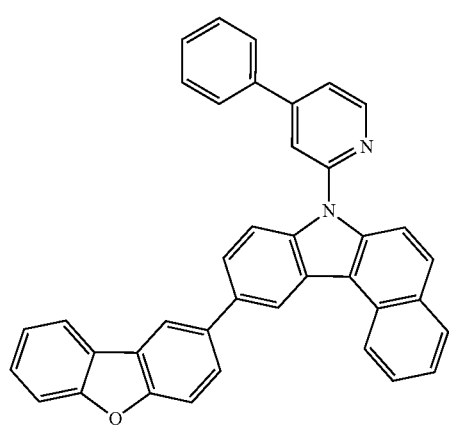
5-23
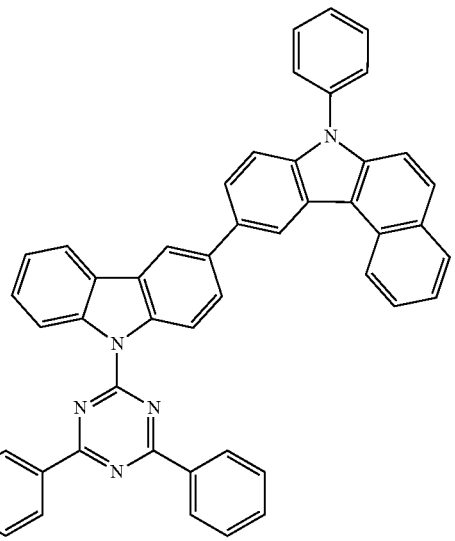
5-24
5-25
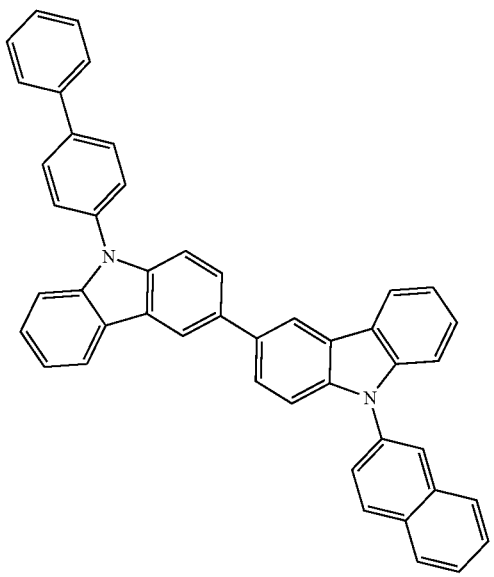

-continued
5-26
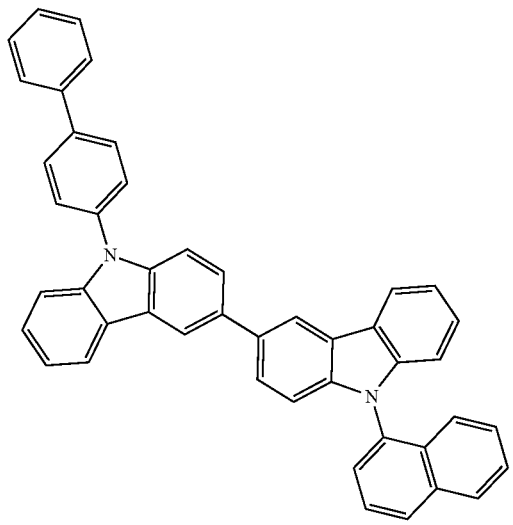
5-27
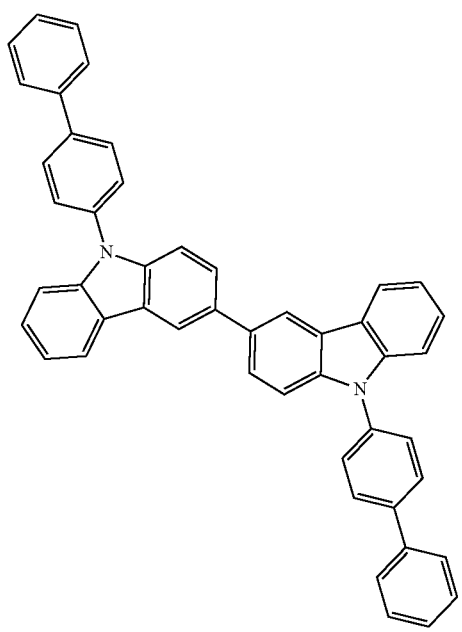
5-28
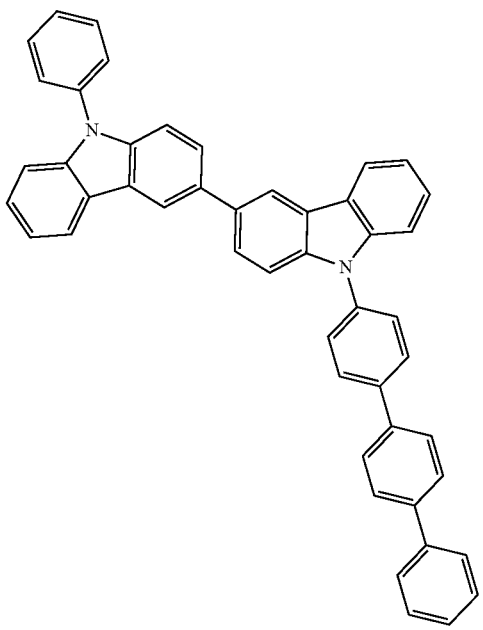
5-29
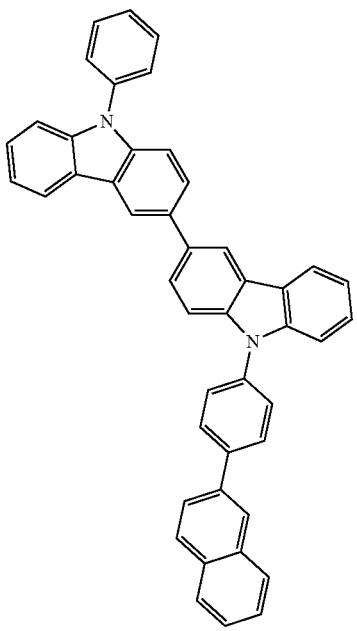

5-30
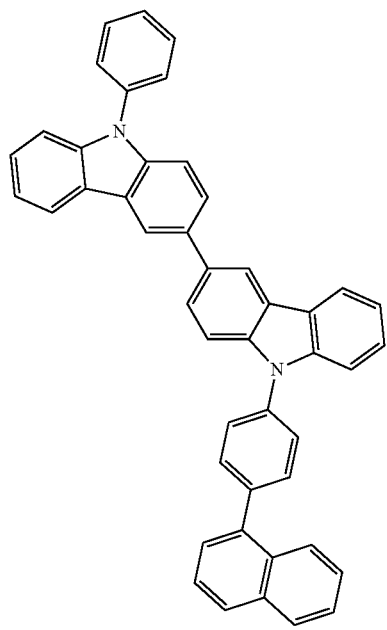
5-31
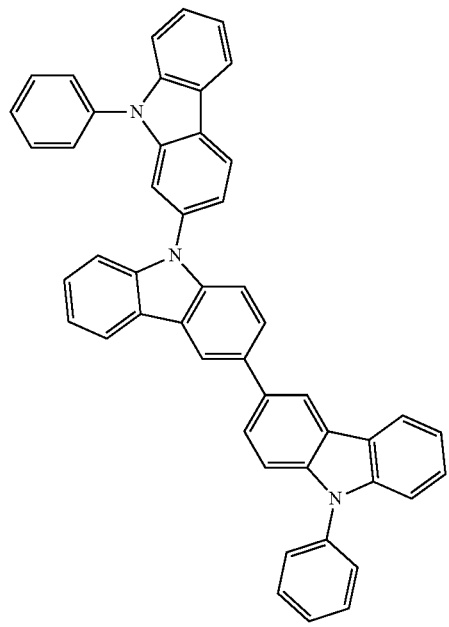
5-32
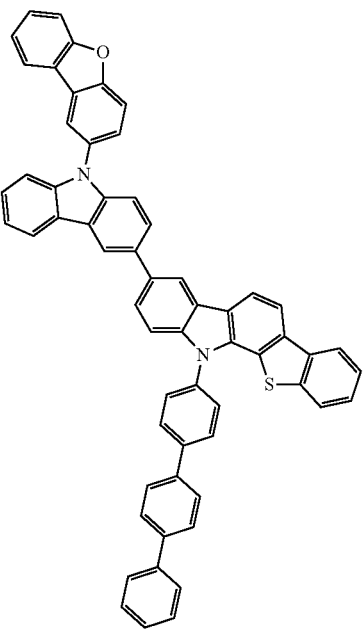
5-33
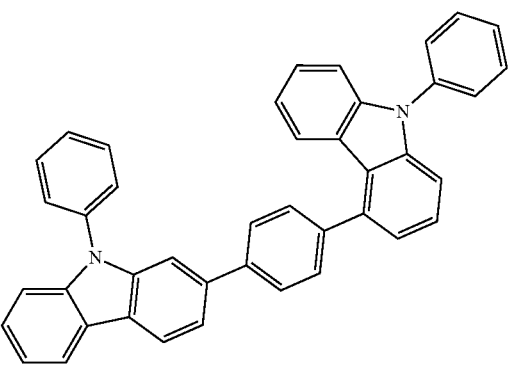
5-34
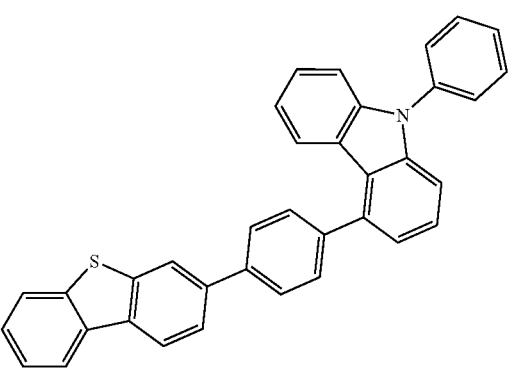

5-35
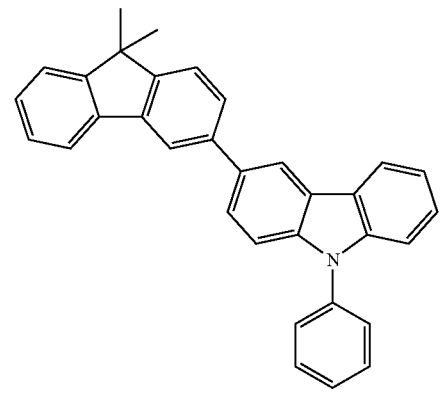
5-36
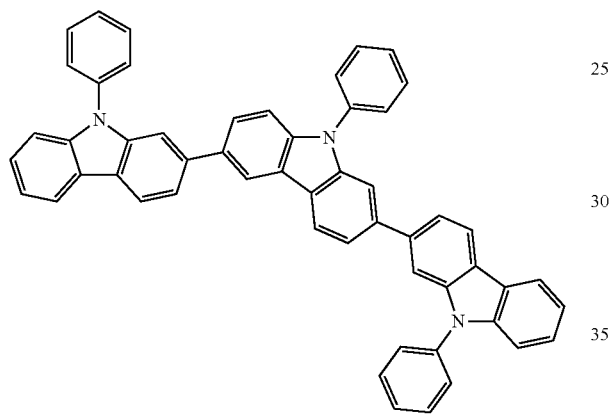
5-37
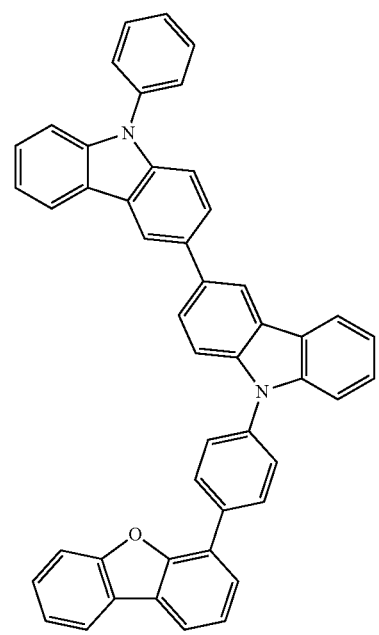
5-38
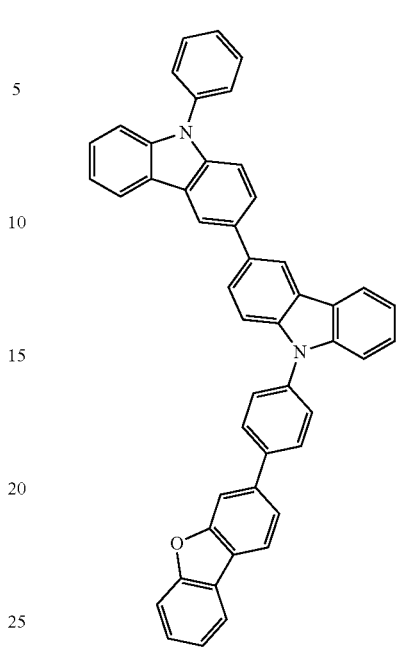
5-39
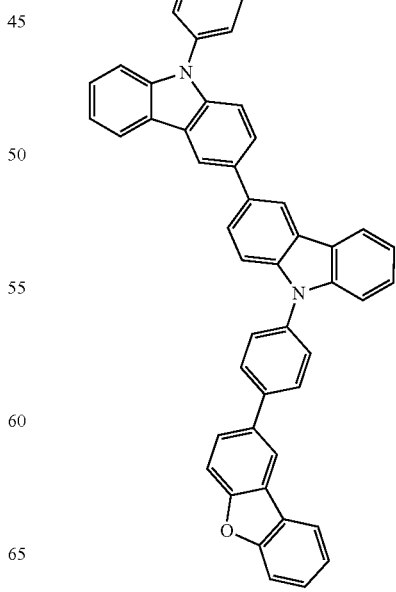

5-40
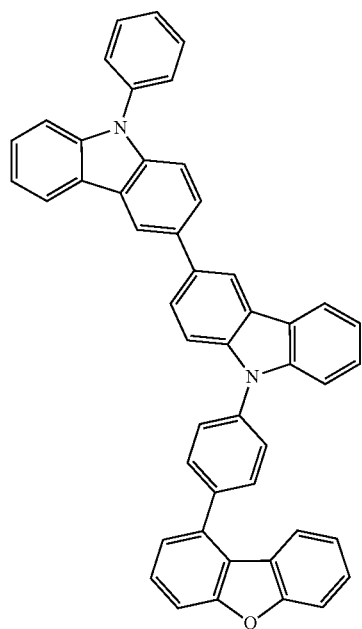
5-41
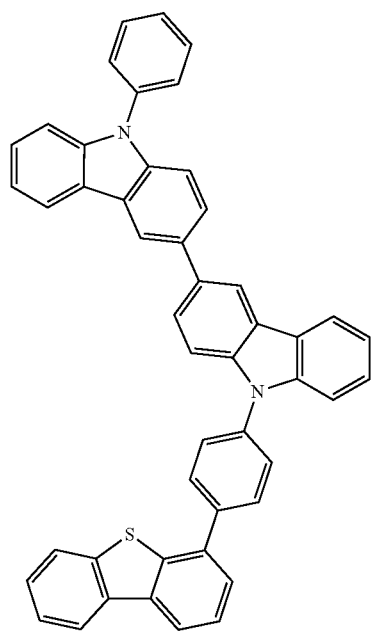
5-42
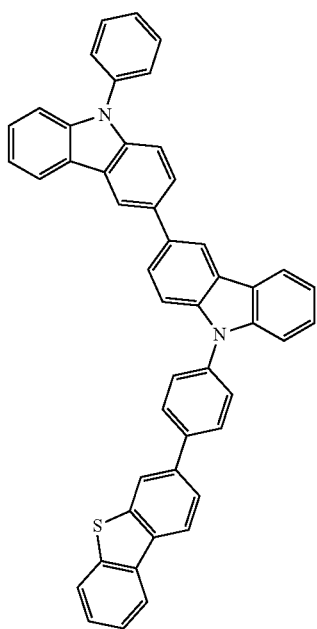
5-43
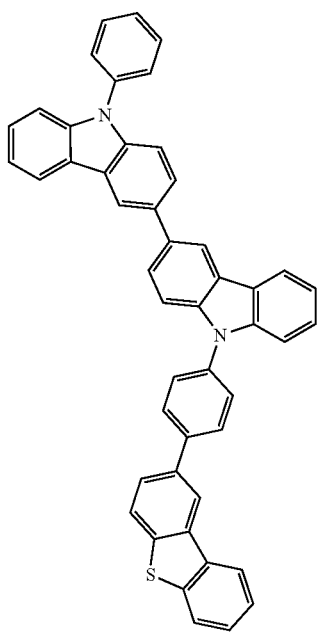

5-44
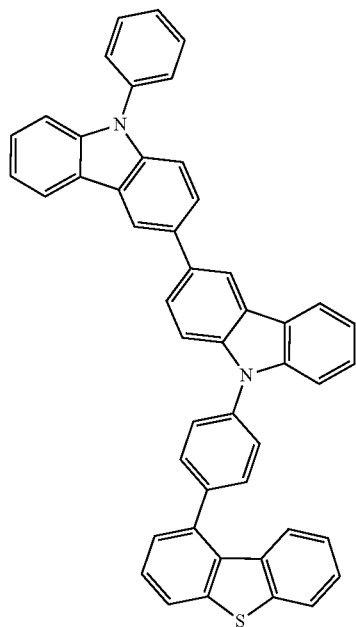
5-46
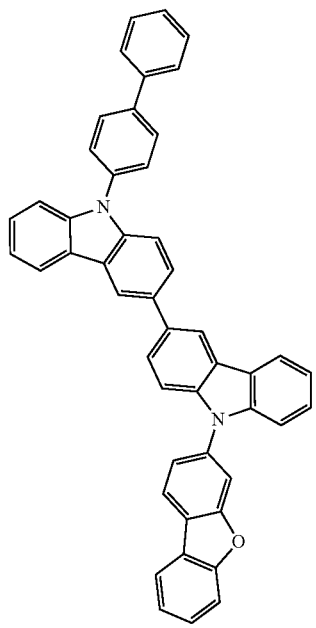
5-45
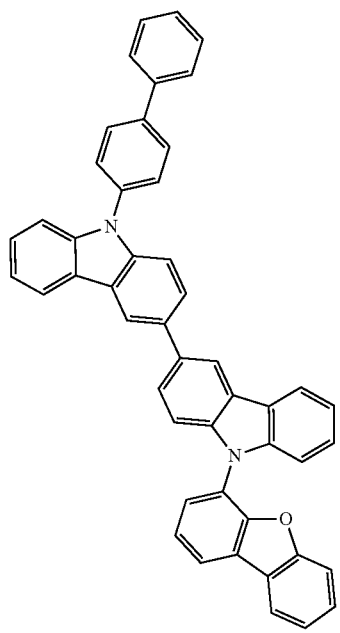
5-47
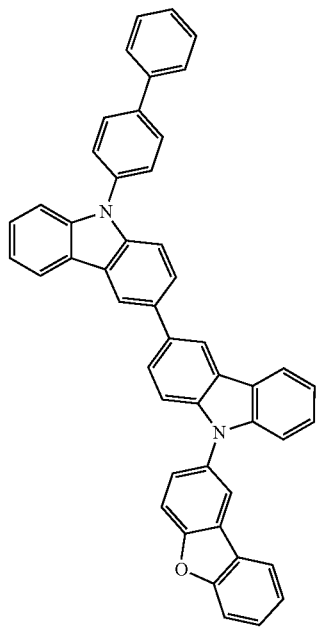

5-48
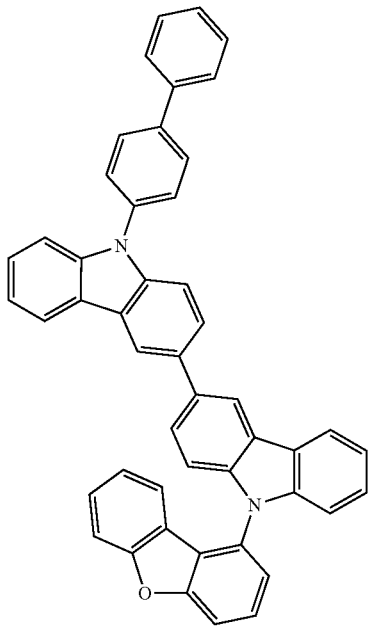
5-49
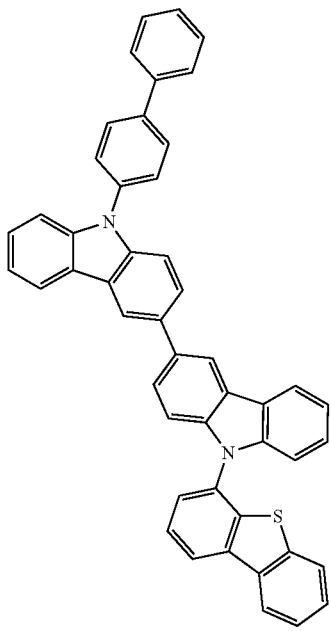
5-50
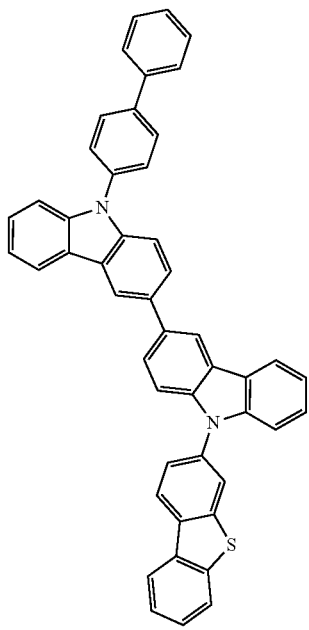
5-51
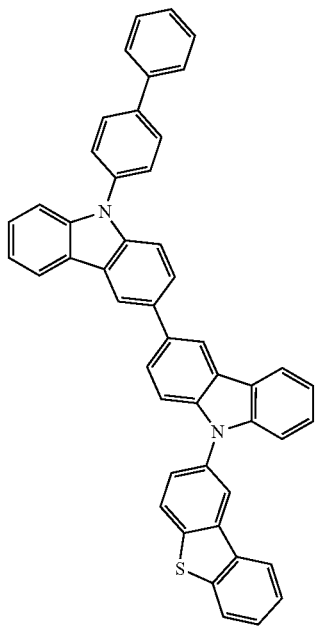

5-52
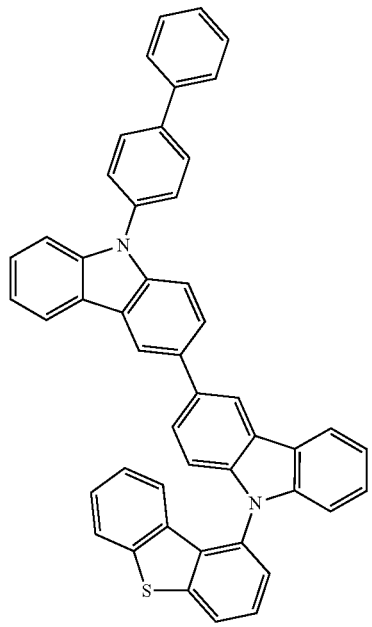
5-53
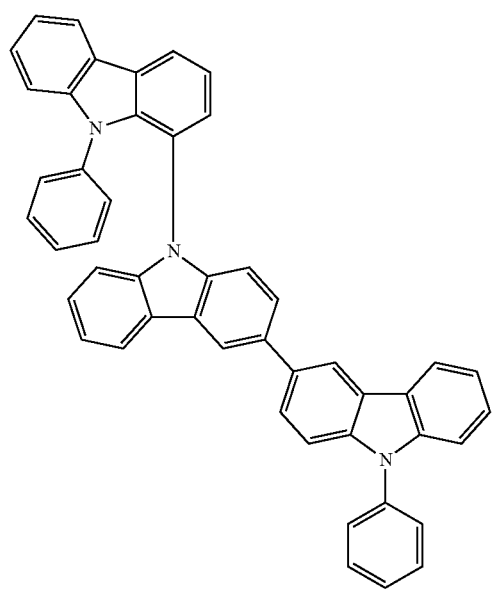
5-54
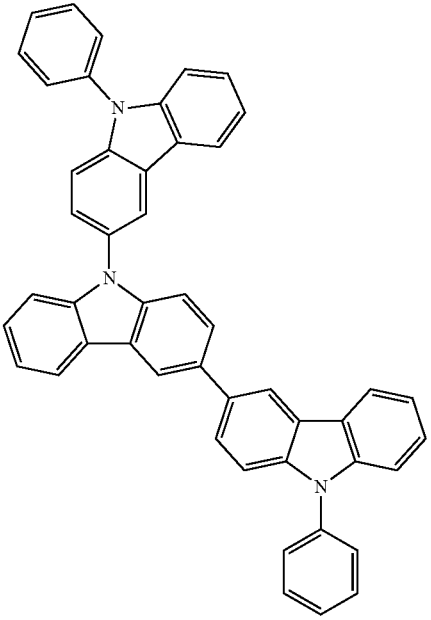
5-55
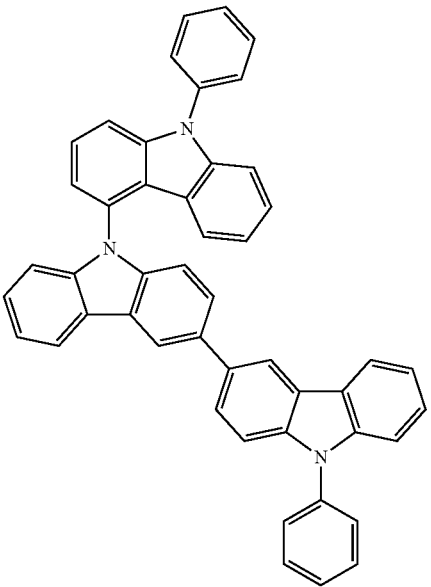

149
-continued
5-56
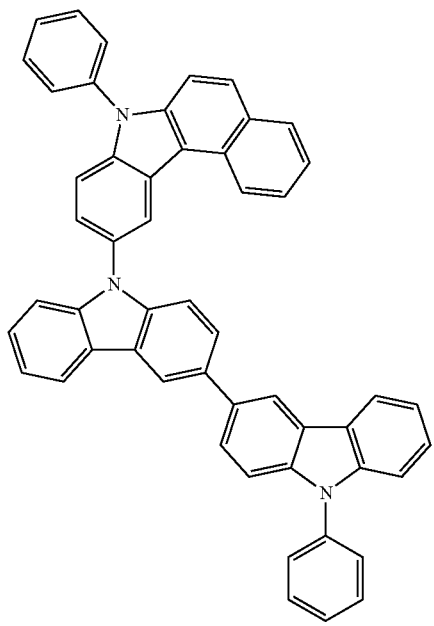
5-57
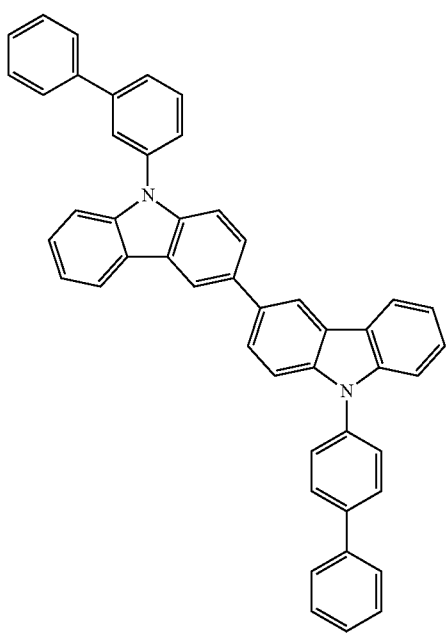
150
-continued
5-58
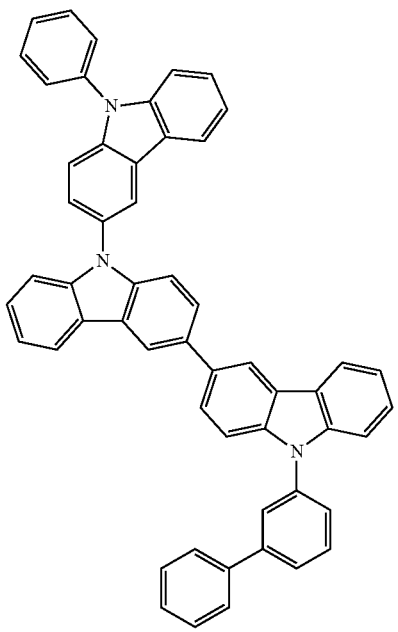
5-59
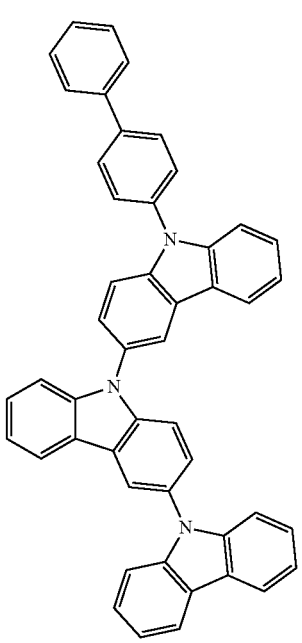

5-60
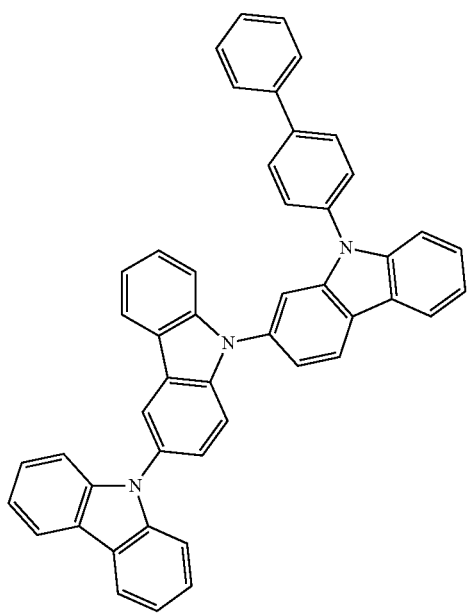
5-61
5-62
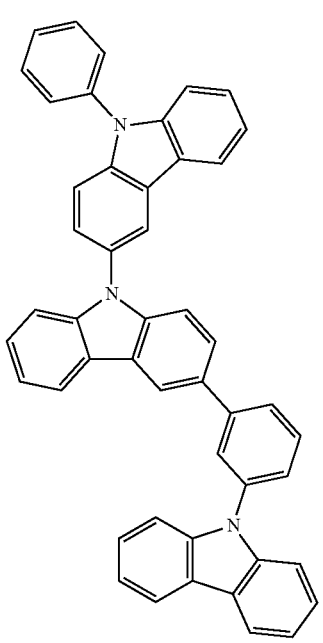
5-63
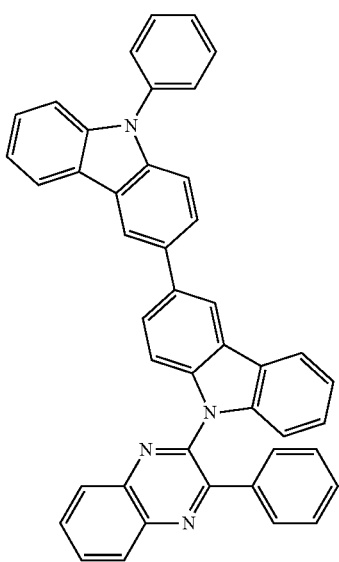

5-64
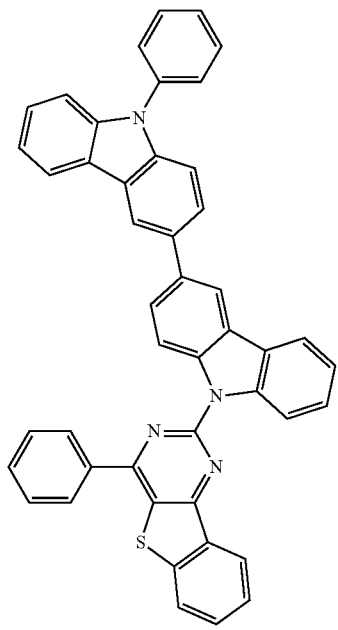
5-66
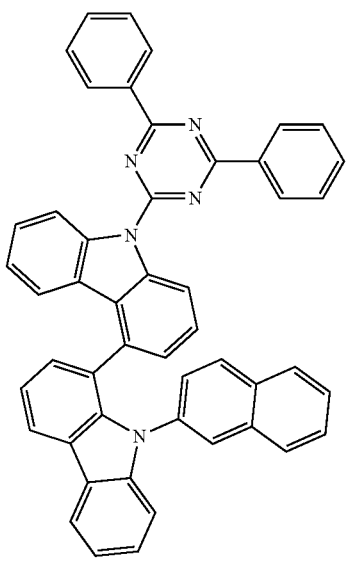
5-67
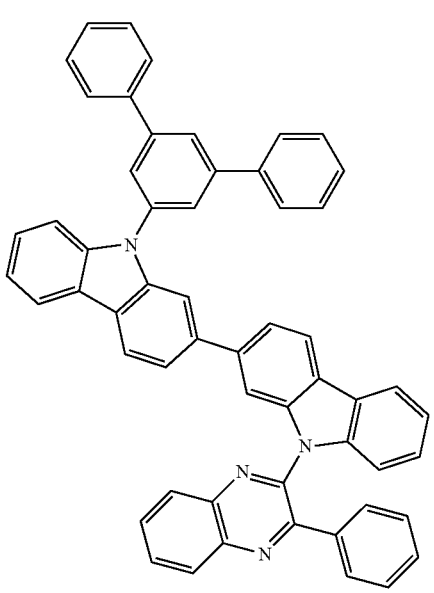
5-65
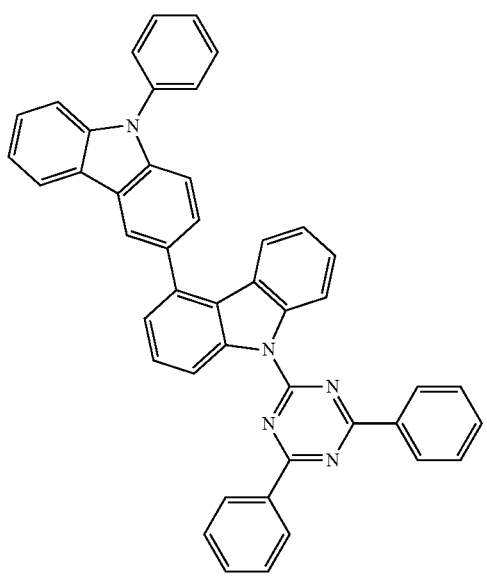
5-68

5-69
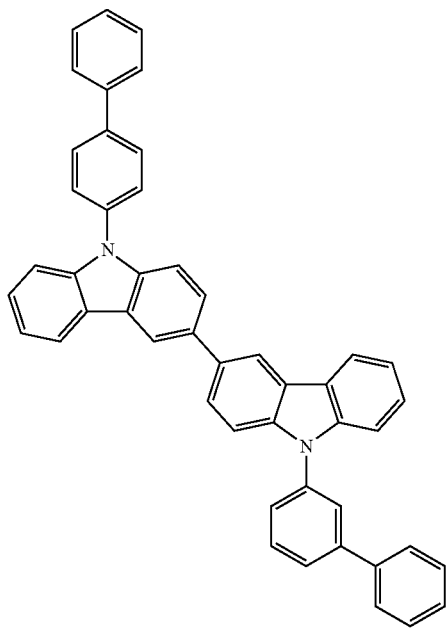
5-70
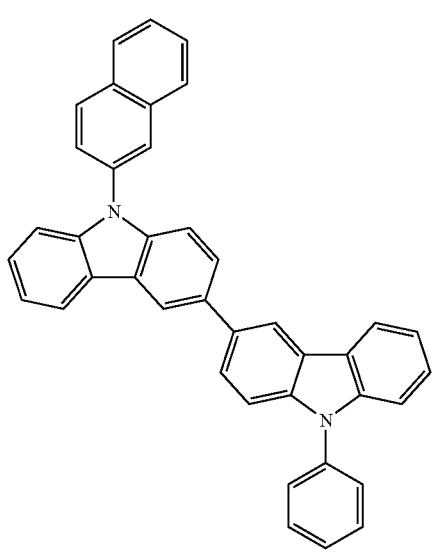
5-71
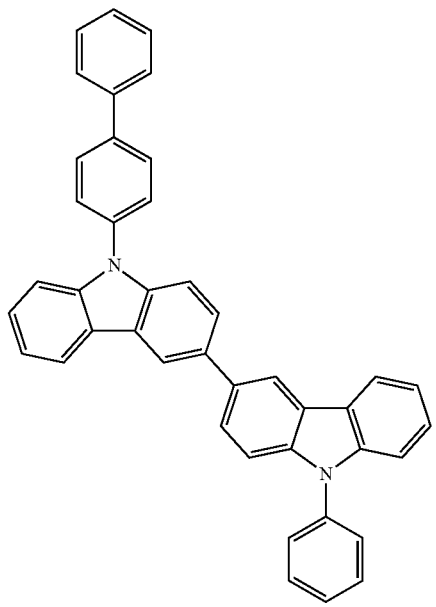
5-72
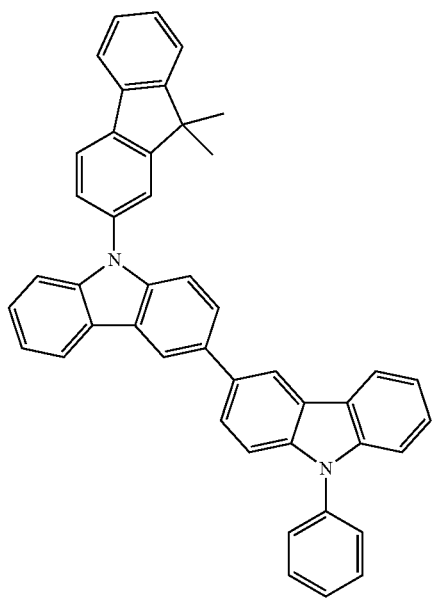
Also, the compound represented by Formula 14 is represented by any one of Formulas 4-1 to 4-6
Formula 4-1
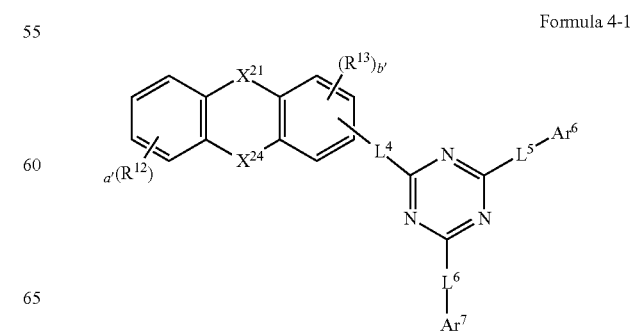

-continued

Formula 4-2

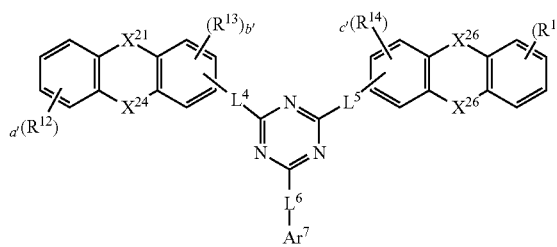

Formula 4-3

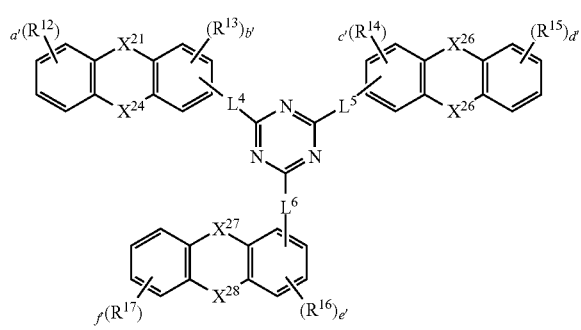

Formula 4-4

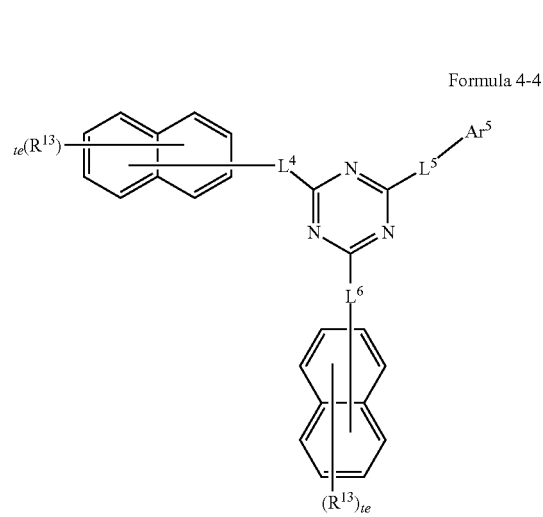

-continued

Formula 4-5

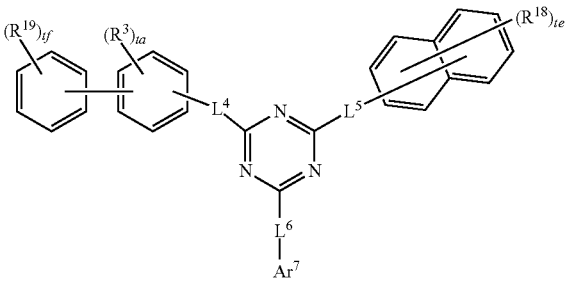

Formula 4-6

Wherein
1) $X^{21}$, $X^{25}$ and $X^{27}$ are each independently $NAr^{11}$, O, S or $C(R^{10})(R^{11})$,
2) $X^{24}$, $X^{26}$ and $X^{28}$ are each independently $NAr^{12}$, O, S, $C(R^{20})(R^{21})$ or single bond,
3) wherein $Ar^{11}$ and $Ar^{12}$ are the same as the definition of $Ar^3$,
4) a', d' and f' are each independently an integer of 0 to 4, b', c', e' and ta' are each independently integer of 0 to 3,
5) $L^4$, $L^5$, $L^6$, $Ar^6$ and $Ar^7$ are the same as defined above,
6) to and tb are each independently integer of 0 to 4, te is an integer of 0 to 7, tf is an integer of 0 to 5,
7) $R_3$, $R_4$, $R_{10}$, $R_{11}$, $R_{12}$, $R_{13}$, $R_{14}$, $R_{15}$, $R_{16}$, $R_{17}$, $R_{18}$, $R_{19}$, $R_{20}$ and $R_{21}$ are the same or different from each other, and are each independently selected from the group consisting of a hydrogen; deuterium; halogen; a silane group unsubstituted or substituted with a $C_1$-$C_{20}$ alkyl group or a $C_6$-$C_{20}$ aryl group; cyano group; nitro group; $C_1$-$C_{20}$ alkoxy group; $C_6$-$C_{20}$ aryloxy group; $C_1$-$C_{20}$ alkyl group; $C_2$-$C_{20}$ alkenyl group; $C_2$-$C_{20}$ alkynyl group; $C_6$-$C_{20}$ aryl group; fluorenyl group; $C_2$-$C_{20}$ heterocyclic group including at least one heteroatom of O, N, S, Si or $C_3$-$C_{20}$ aliphatic ring; or adjacent groups may be bonded to each other to form a ring, or may be bonded to adjacent substituents to form a ring.

Specifically, the compound represented by Formula 14 may be any one of the following compounds.

6-1

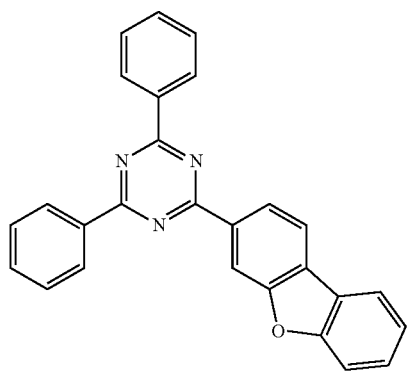

6-2

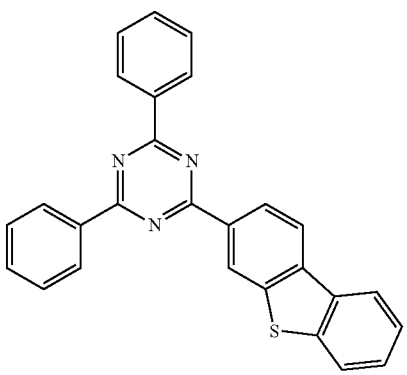

-continued
6-3
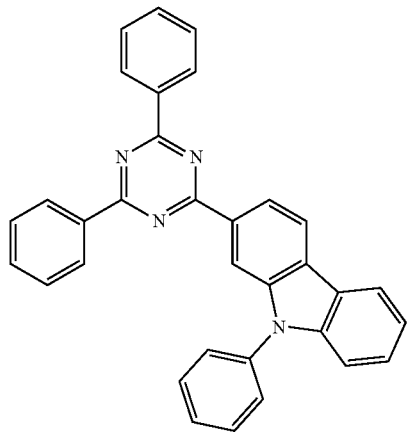
6-4
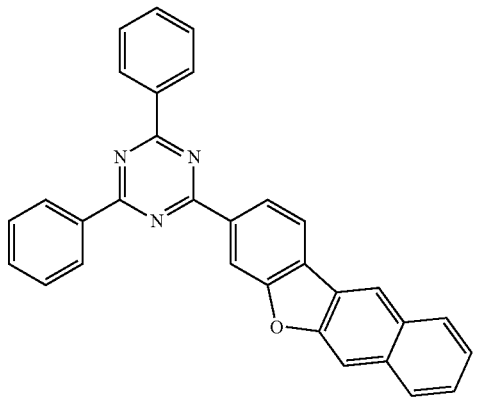
6-5
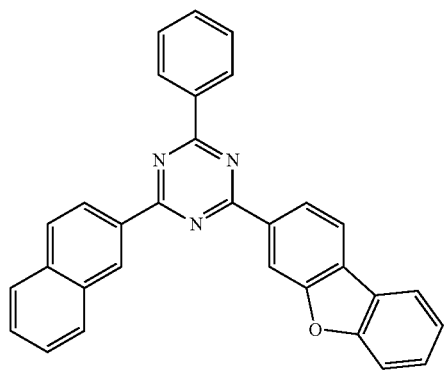
6-6
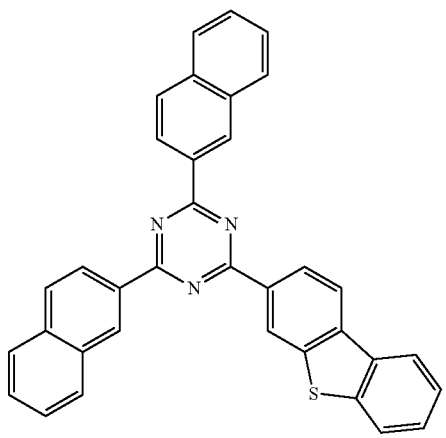
6-7
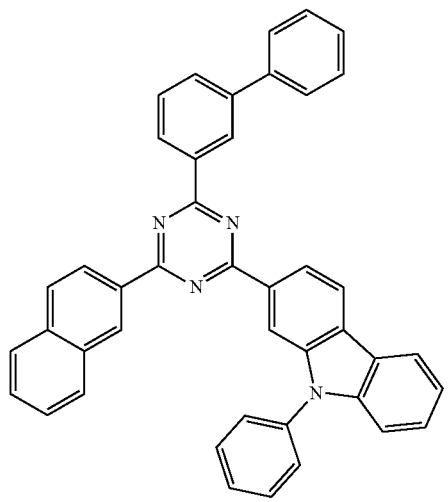
6-8
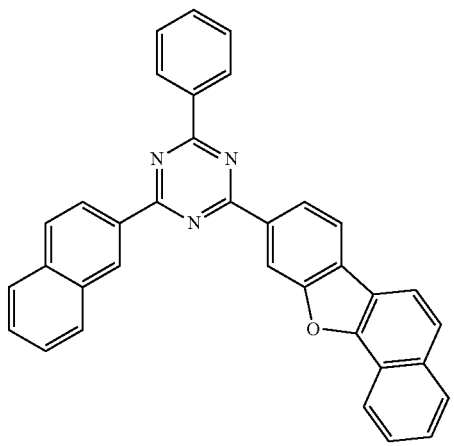

-continued
6-9
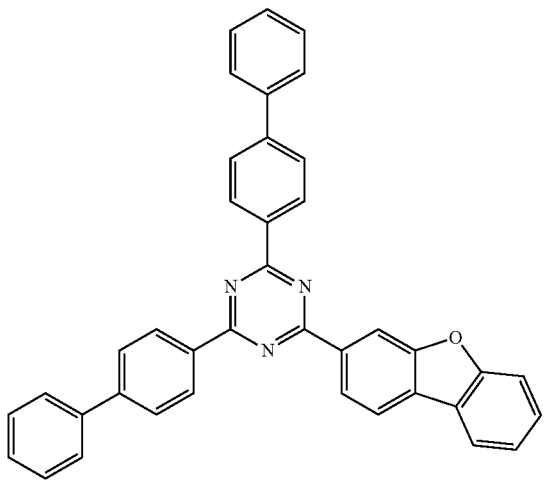
6-10
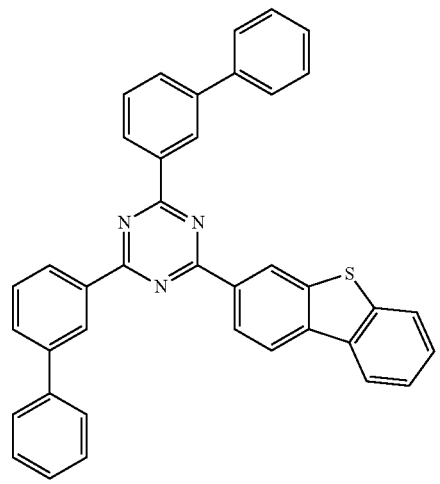
6-11
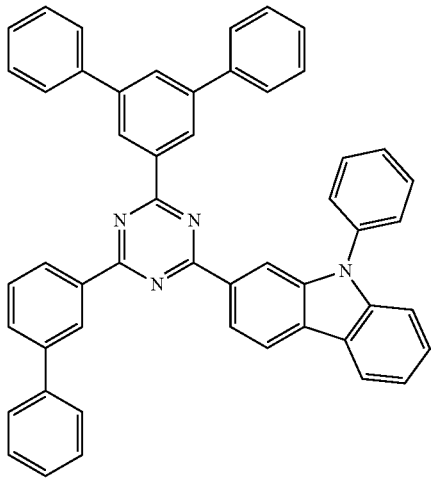
6-12
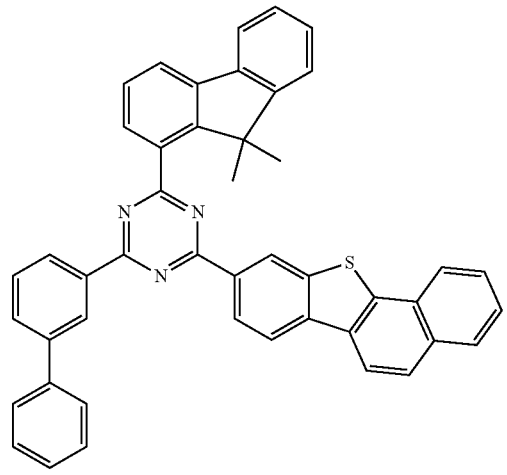
6-13
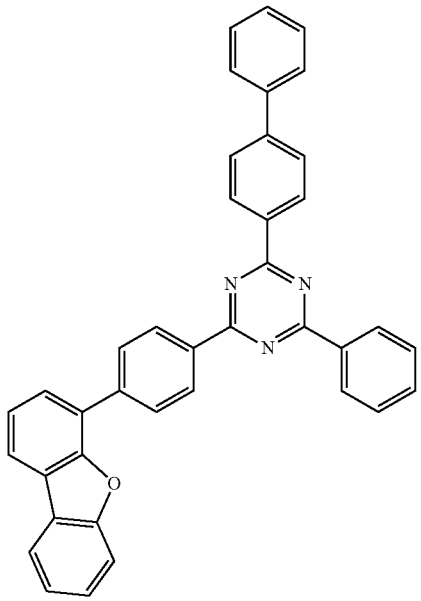
6-14
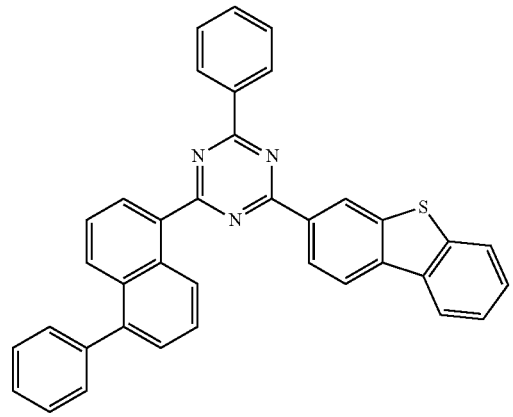

6-15
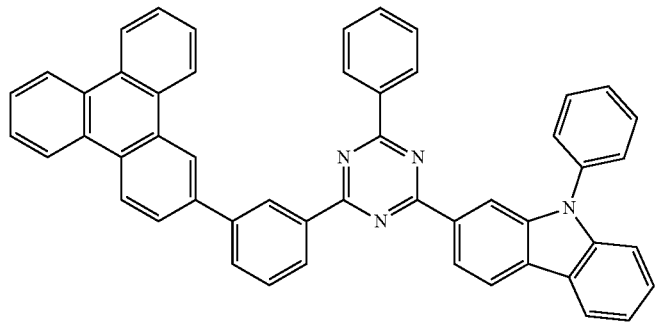
6-16
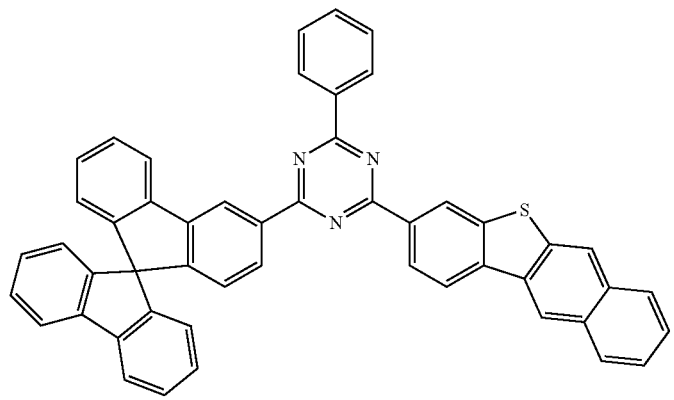
6-17
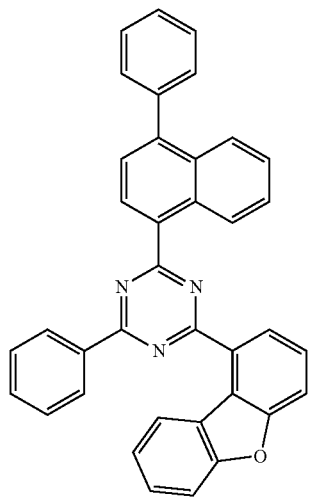
6-18
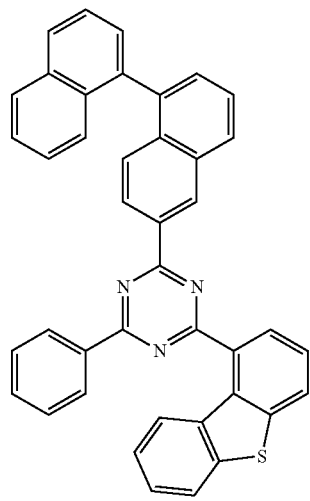

-continued
6-19
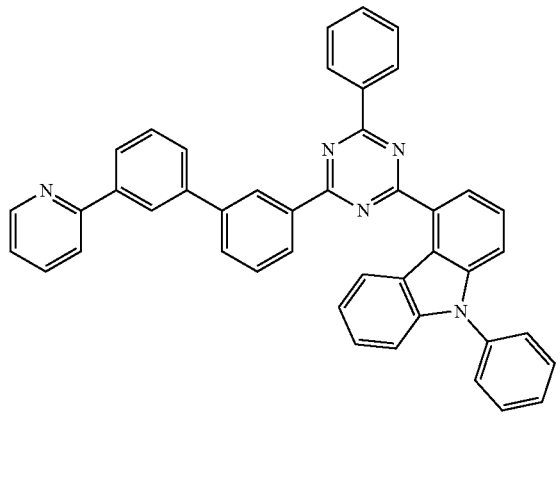
6-20
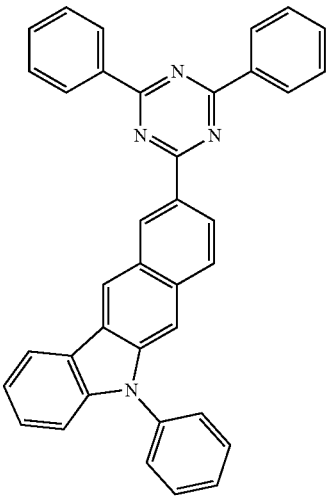
6-21
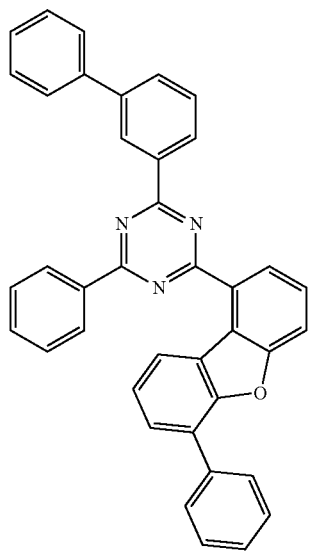
6-22
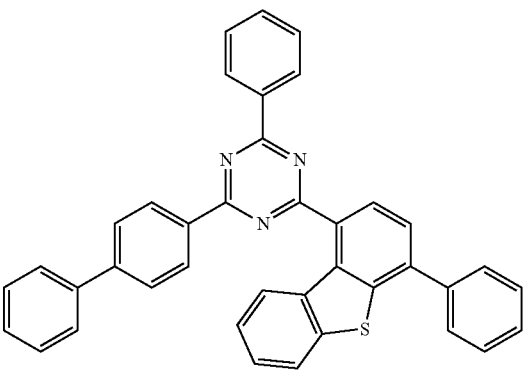
6-23
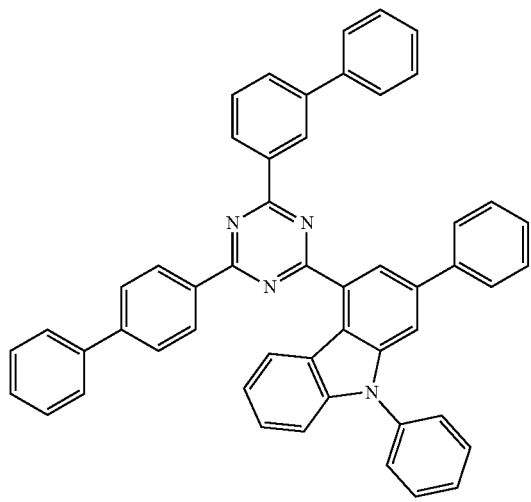
6-24
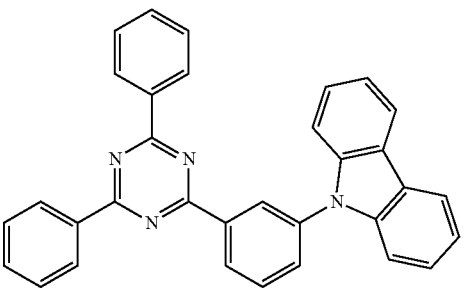

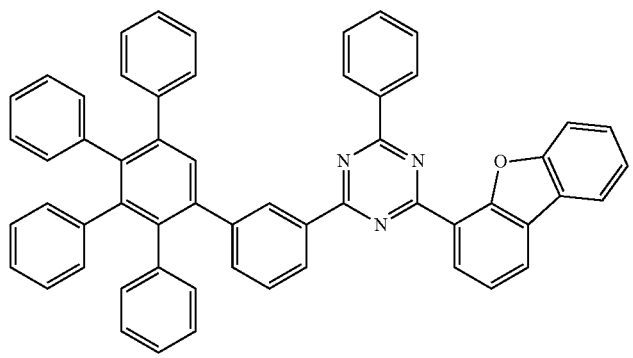
6-25
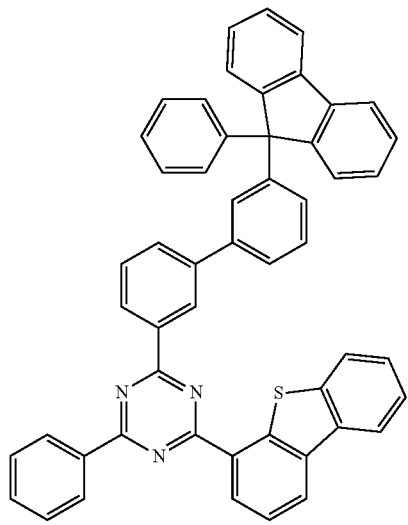
6-26
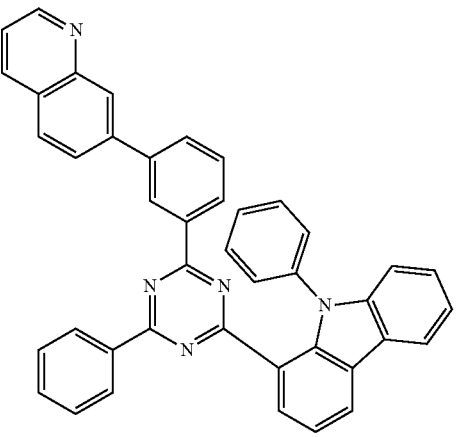
6-27
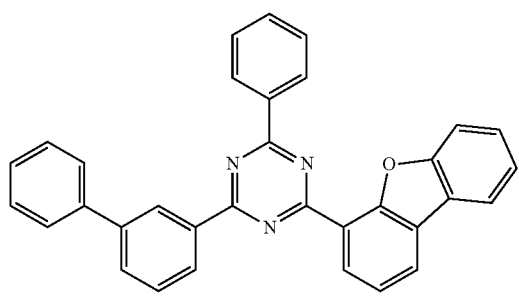
6-28
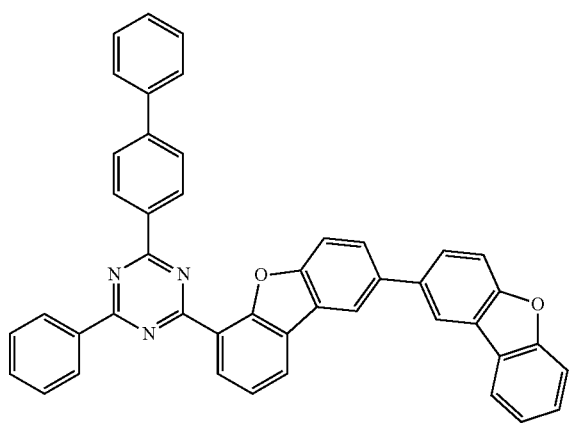
6-29

6-30
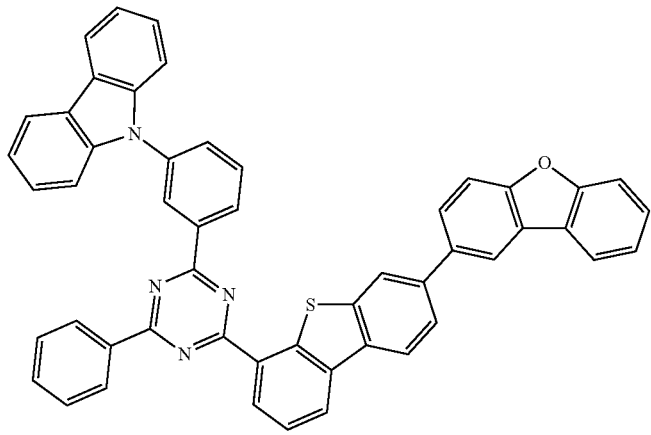
6-31
6-32
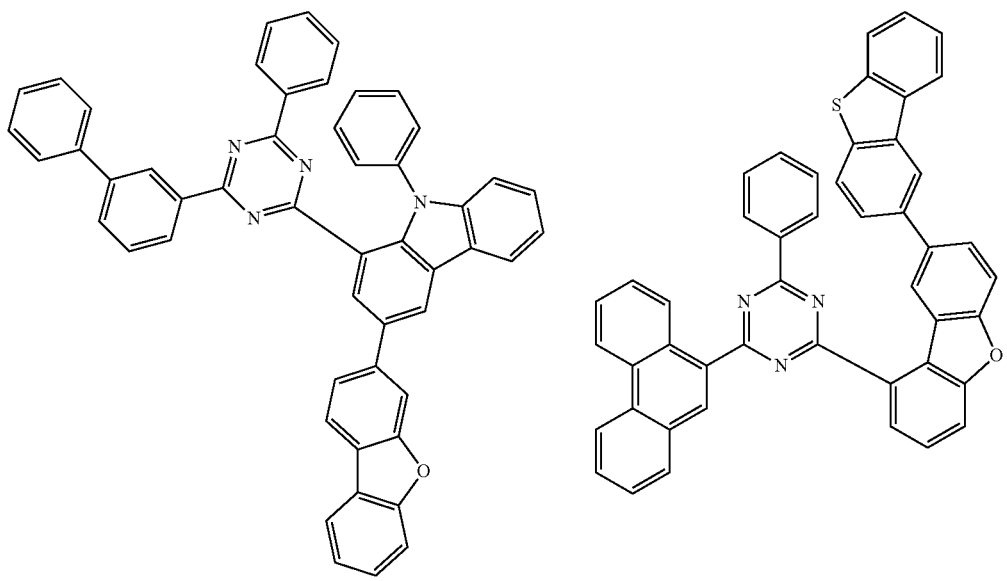
6-33
6-34
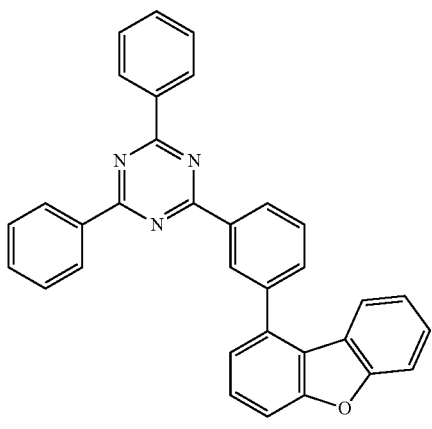

-continued
6-35
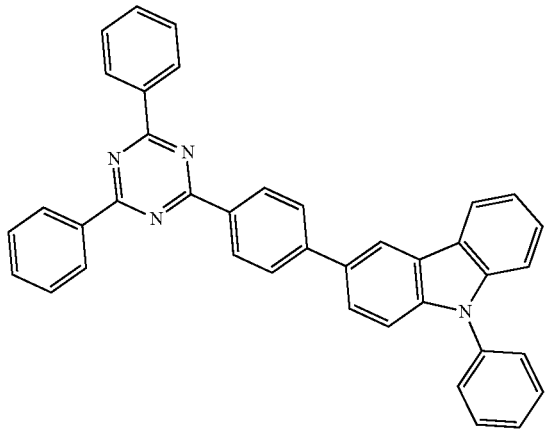
6-36
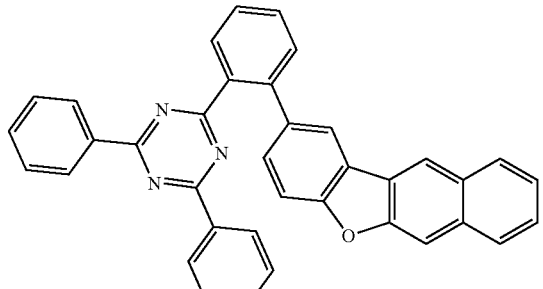
6-37
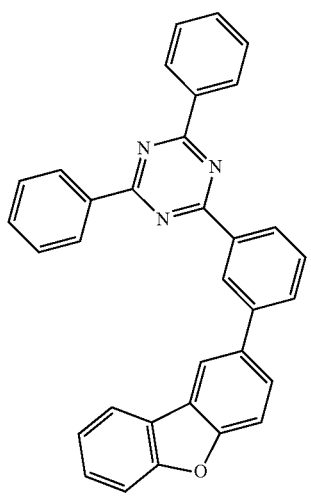
6-38
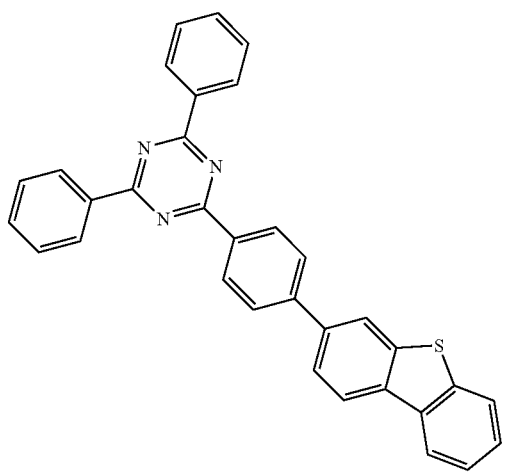
6-39
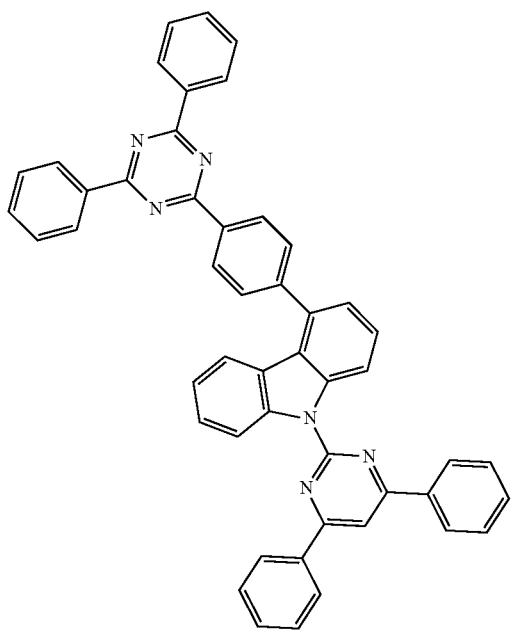
6-40
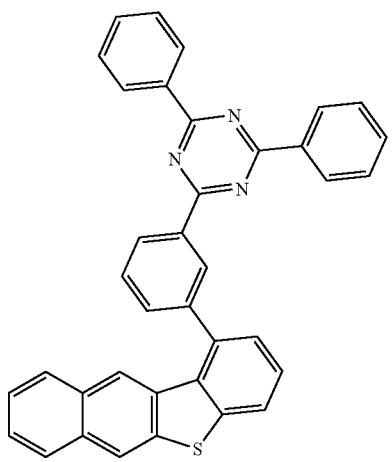

-continued
6-41
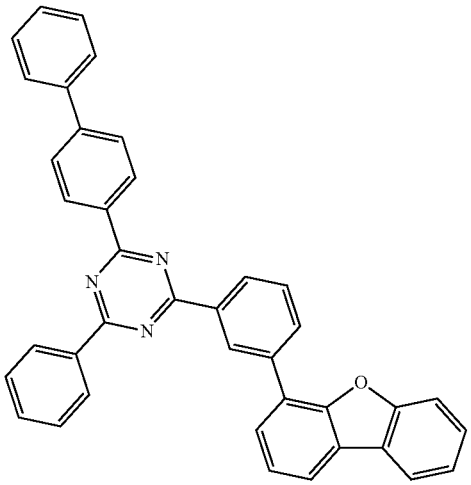
6-42
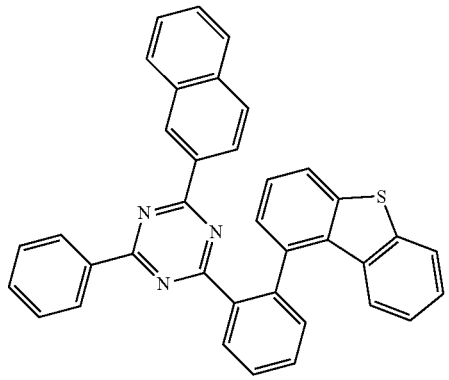
6-43
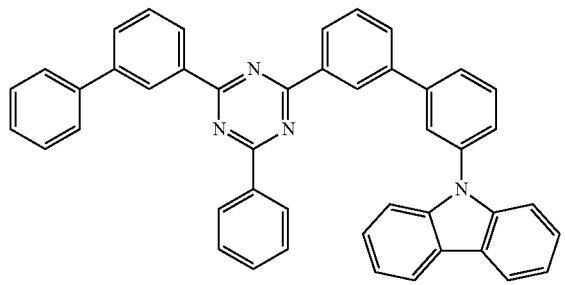
6-44
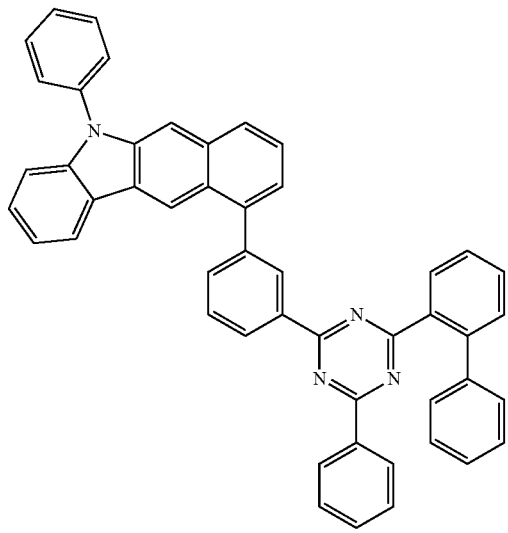
6-45
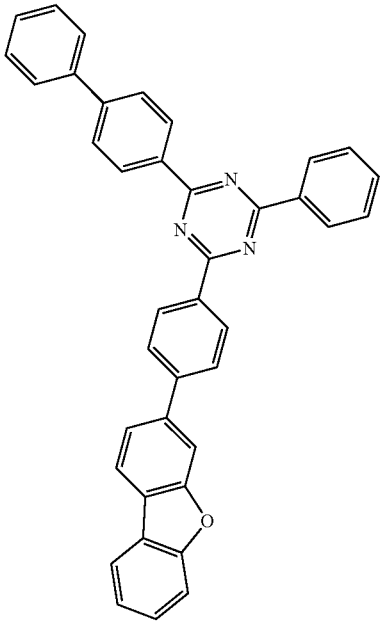
6-46
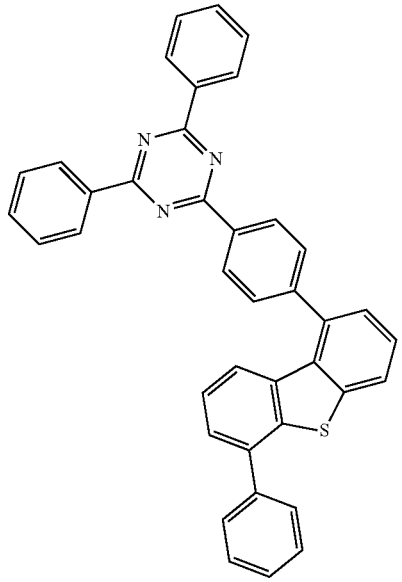

-continued
6-47
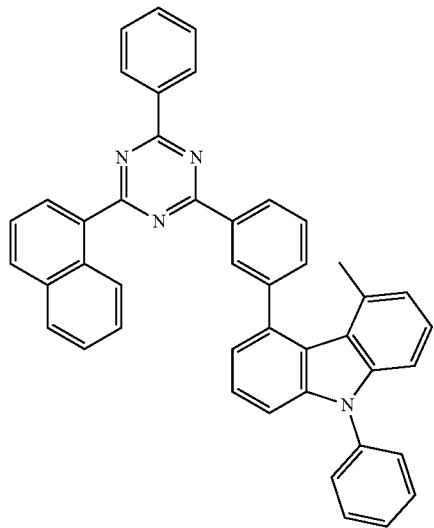
6-48
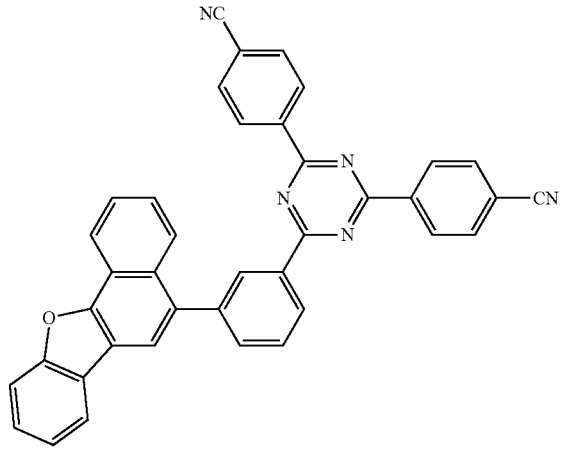
6-49
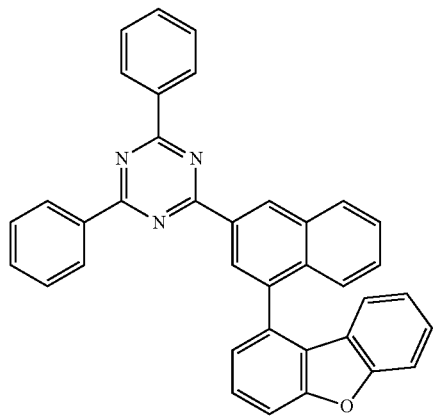
6-50
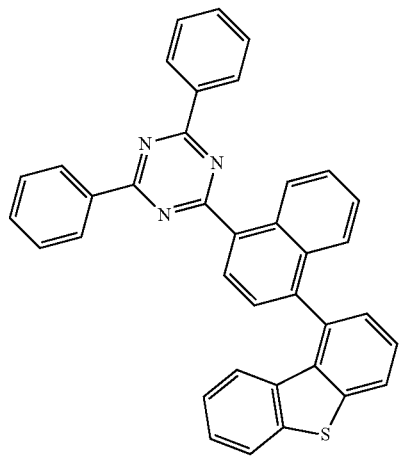
6-51
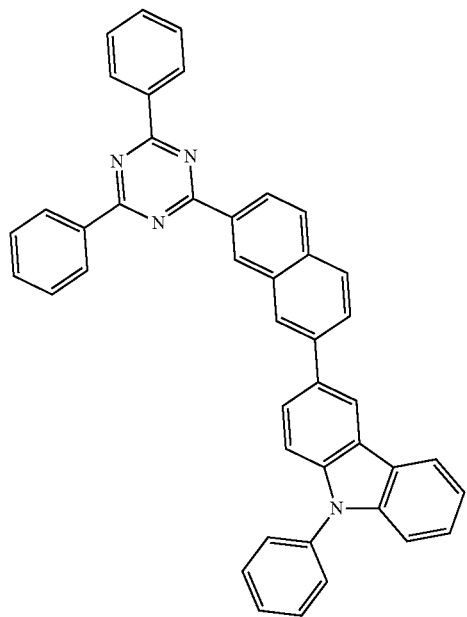

6-52
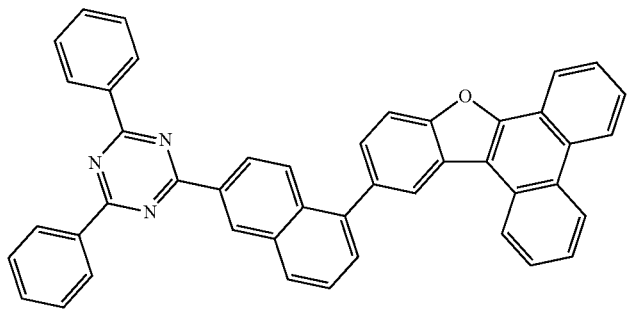
6-53
6-54
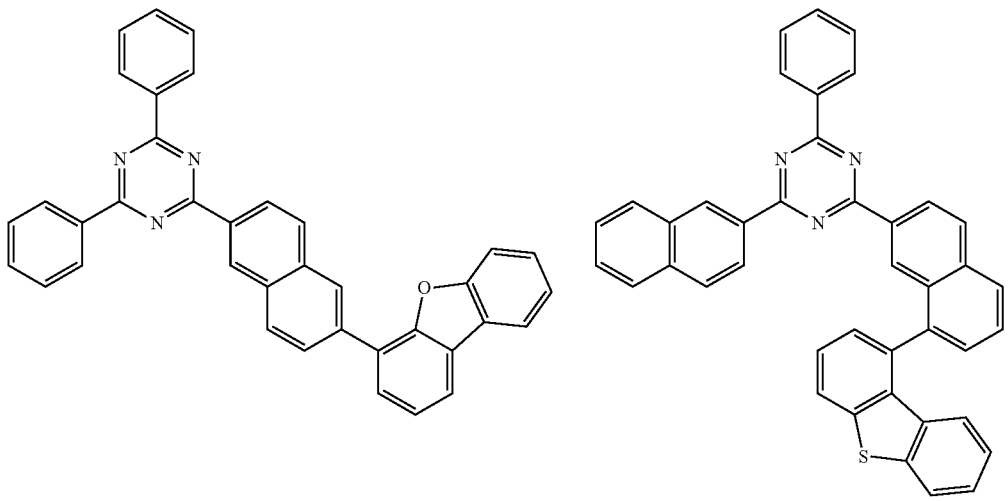
6-55
6-56
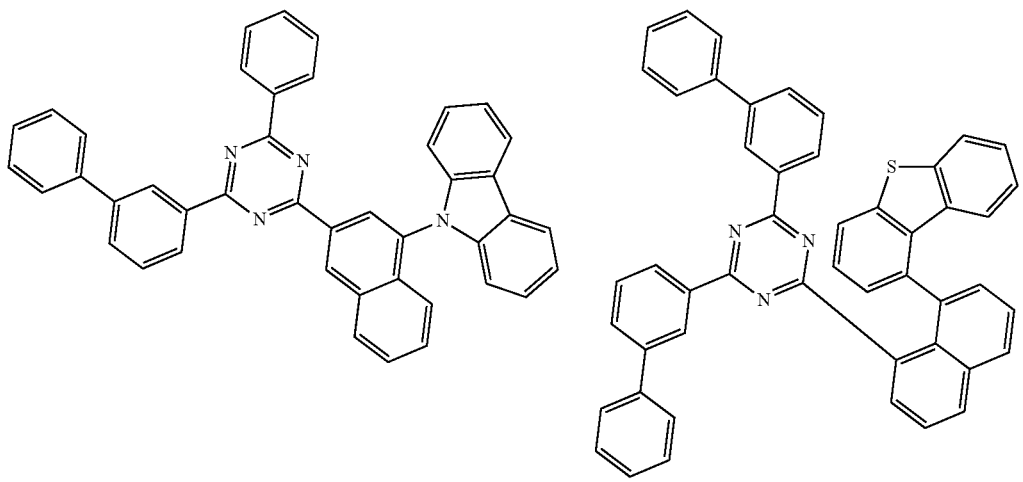

-continued
6-57
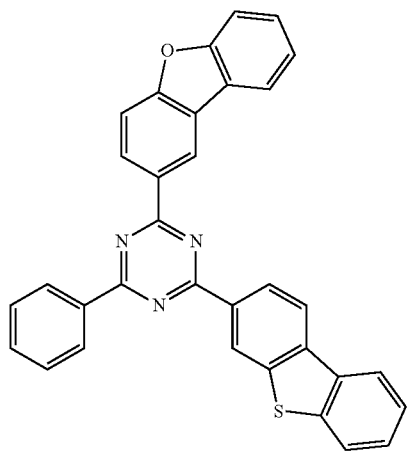
6-58
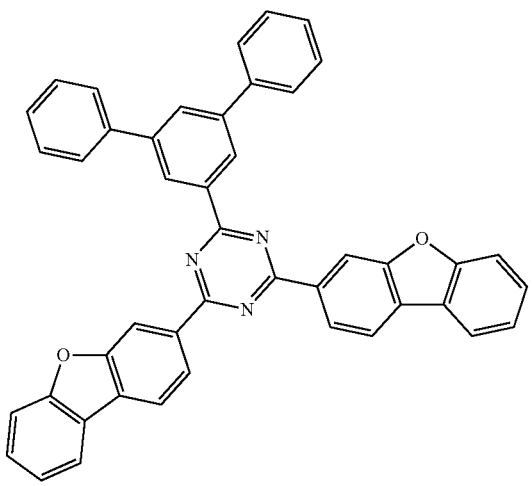
6-59
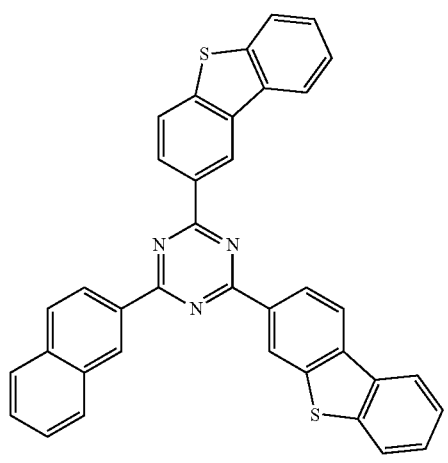
6-60
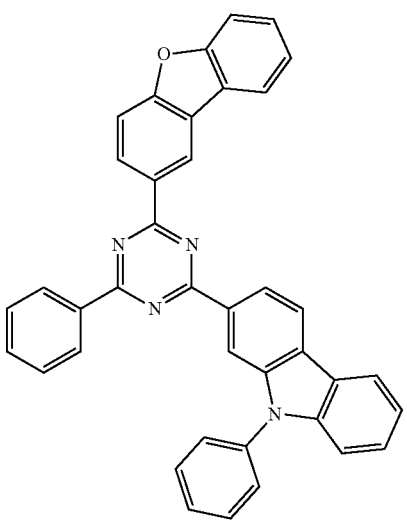
6-61
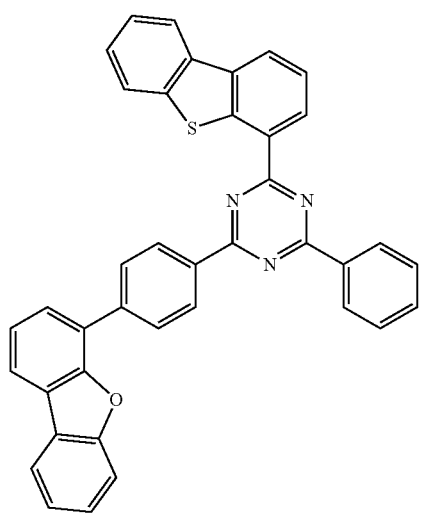
6-62
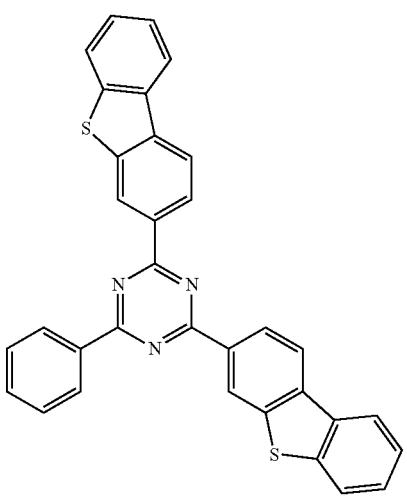

-continued
6-63
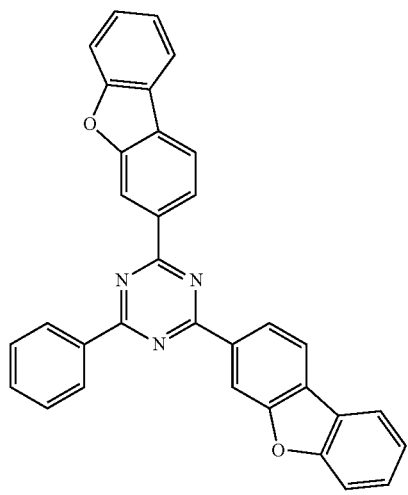
6-64
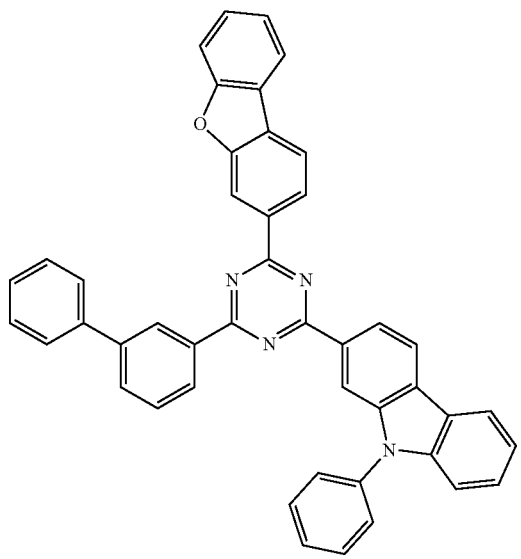
6-65
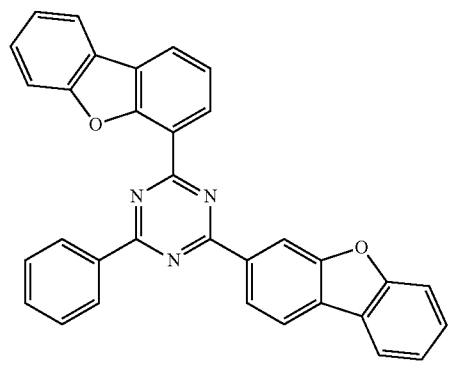
6-66
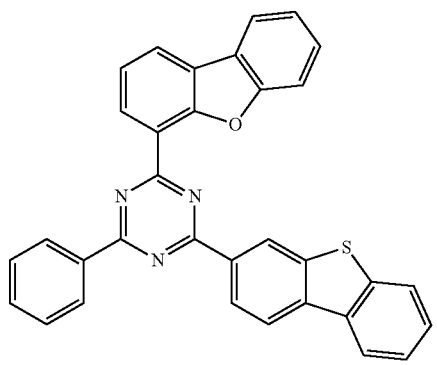
6-67
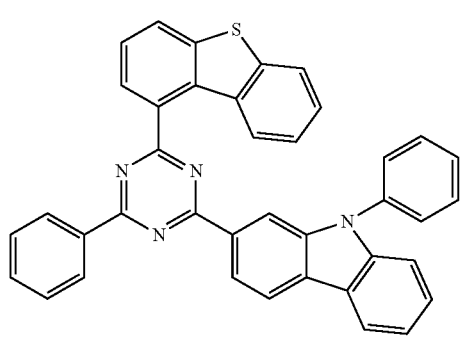
6-68
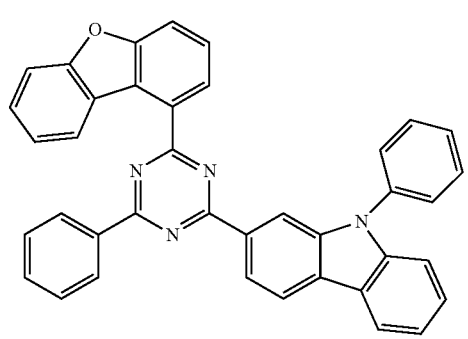

6-69
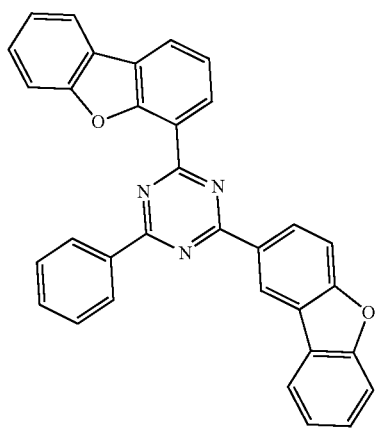
6-70
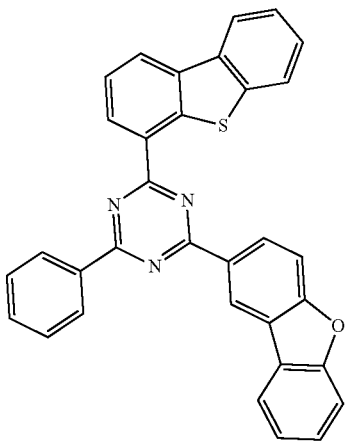
6-71
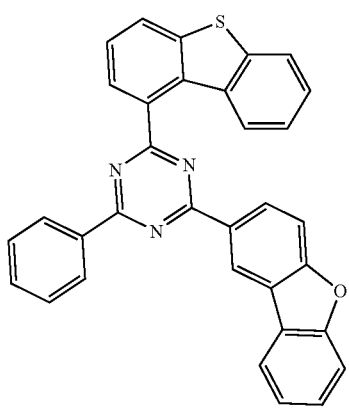
6-72
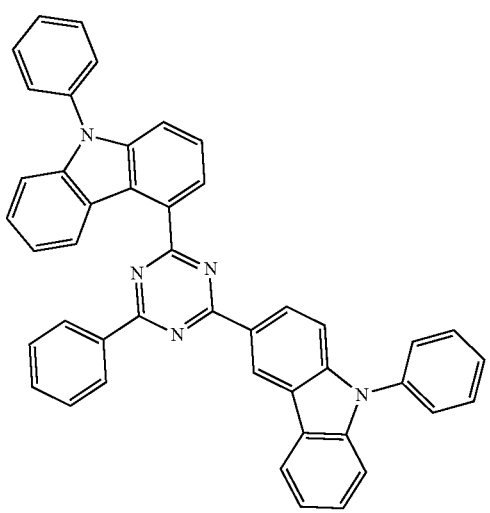
6-73
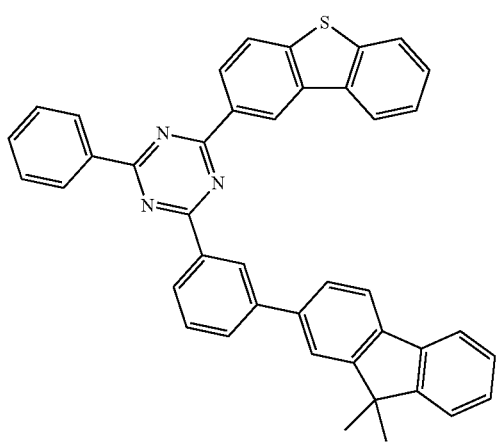

6-74
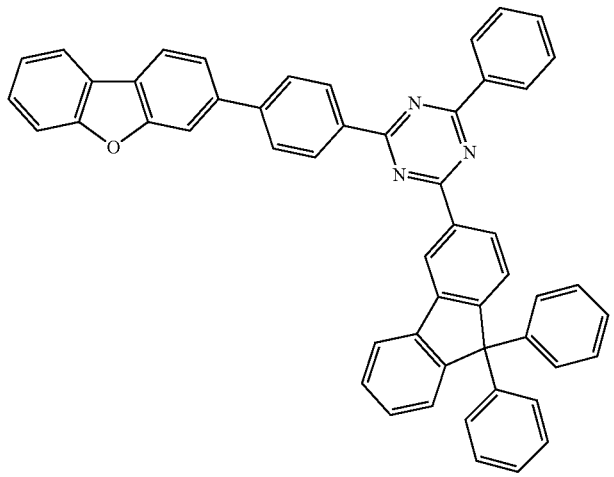
6-75
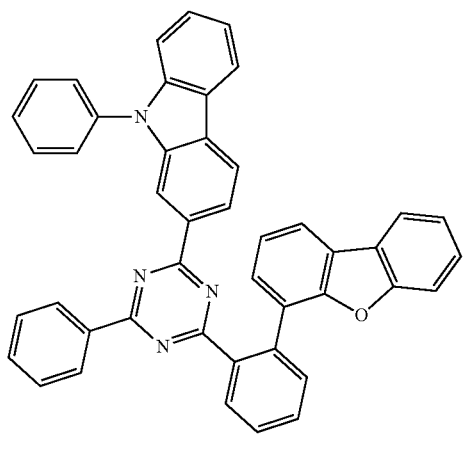
6-76
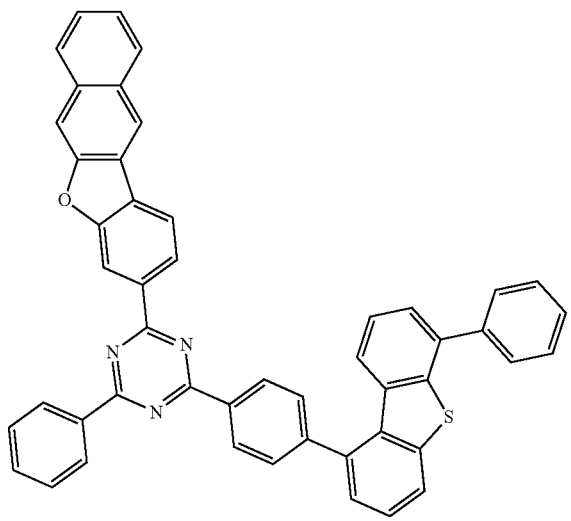
6-77
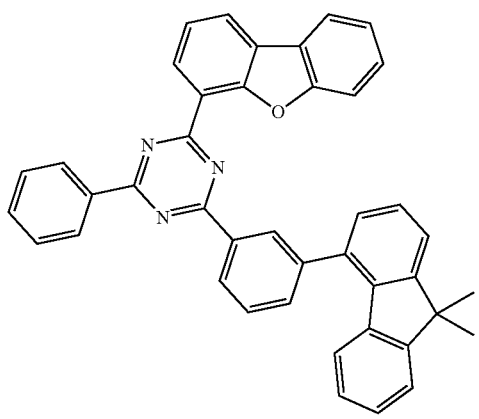
6-78
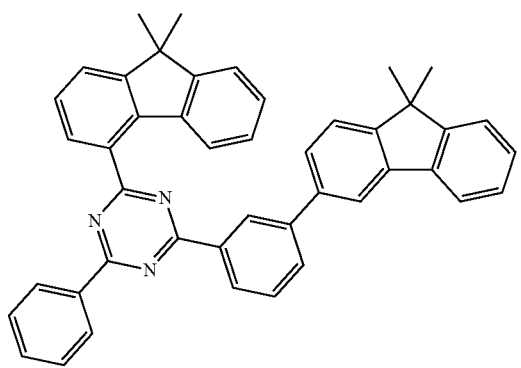

-continued
6-79
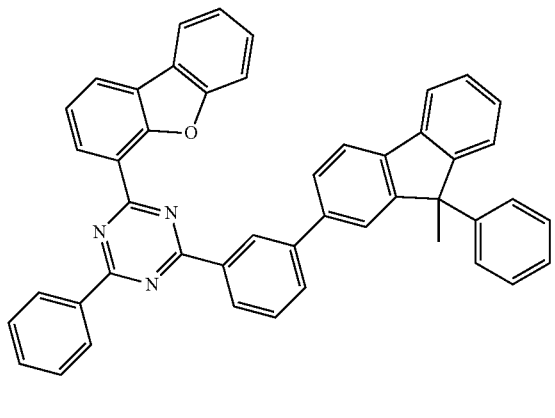
6-80
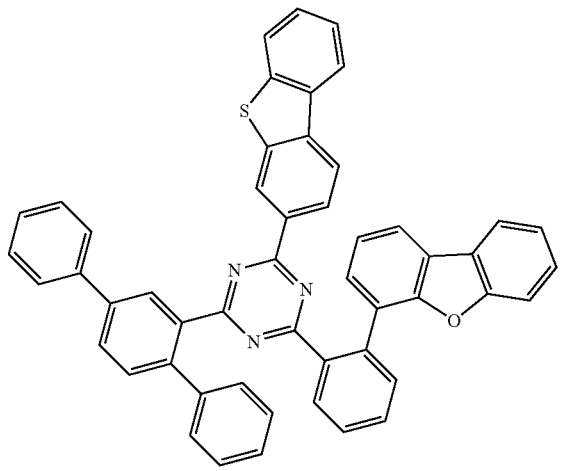
6-81
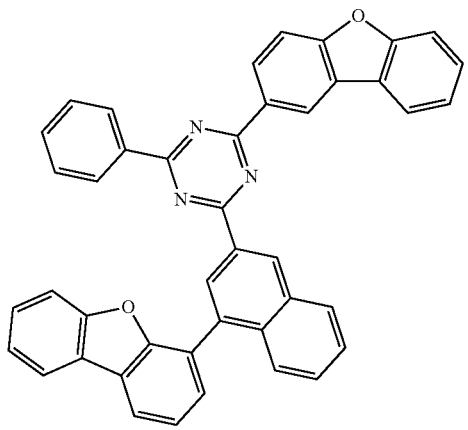
6-82
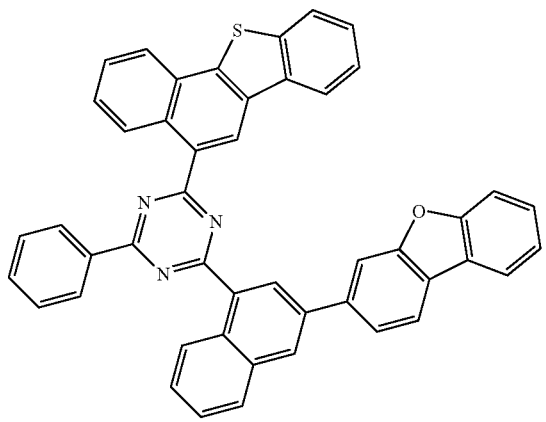
6-83
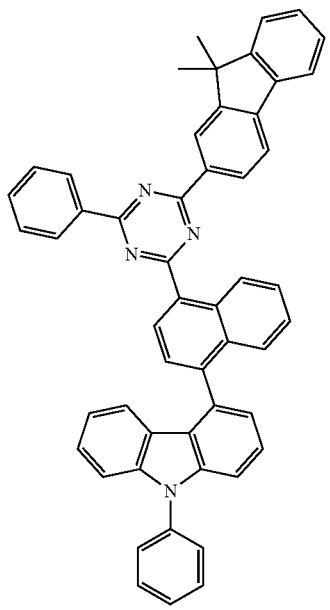
6-84
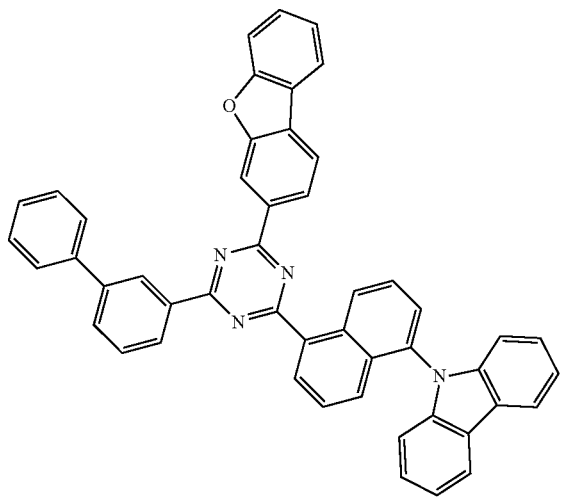

-continued
6-85
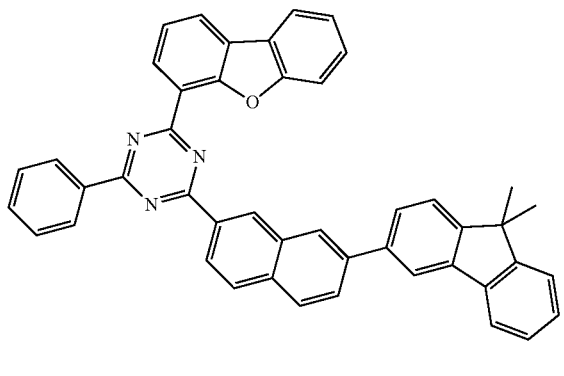
6-86
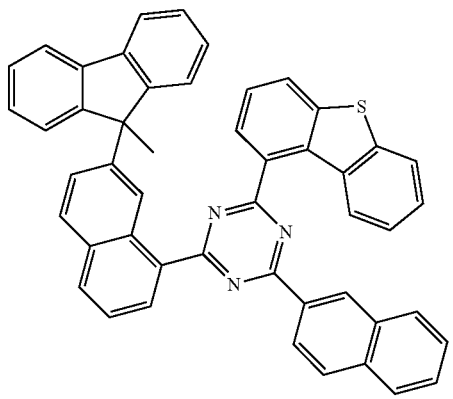
6-87
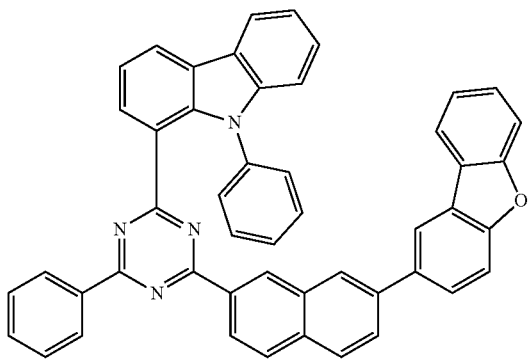
6-88
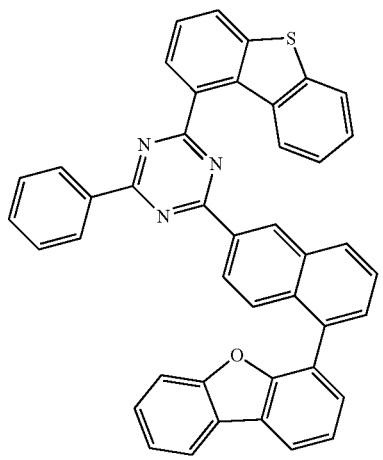
6-89
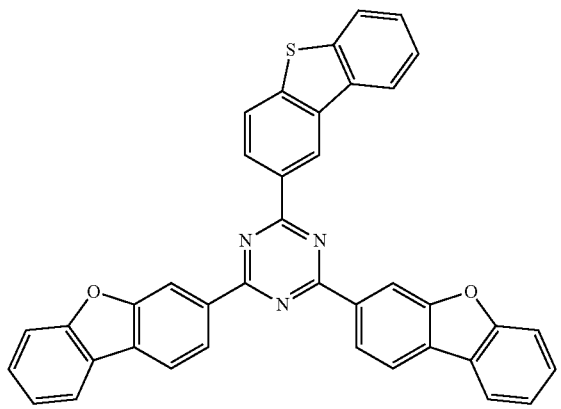
6-90
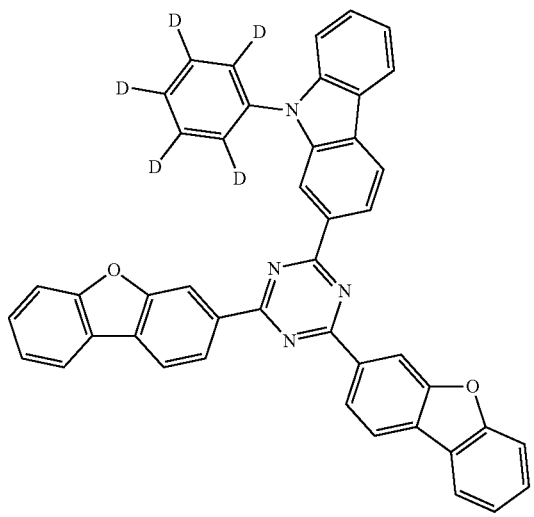

6-91
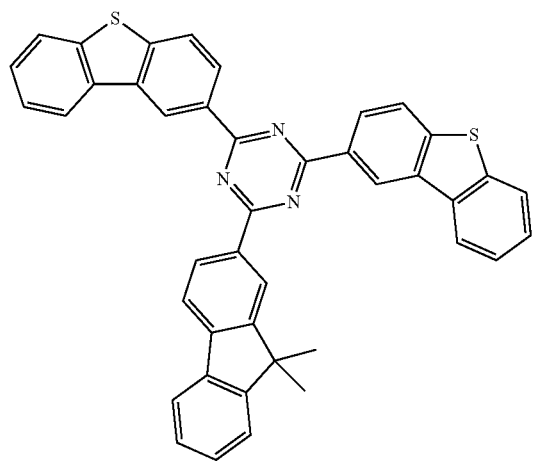
6-92
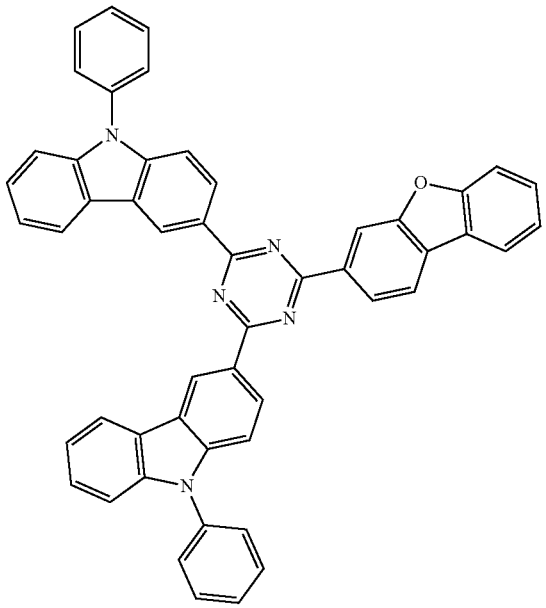
6-93
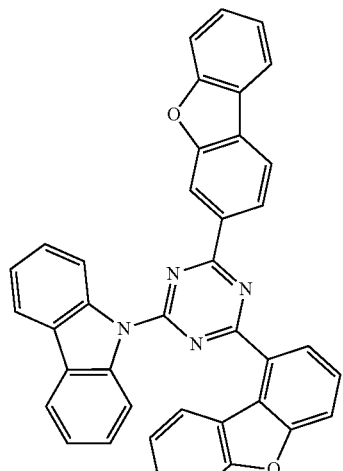
6-94
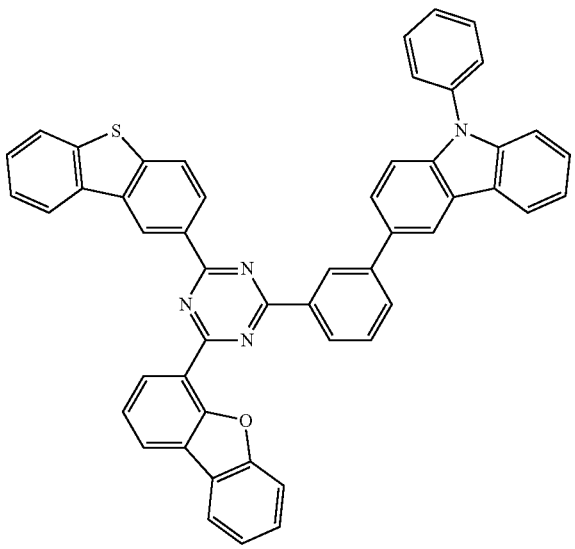

-continued
6-95
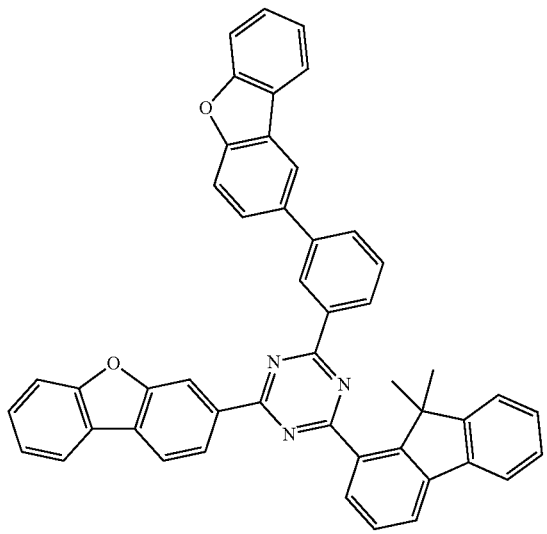
6-96
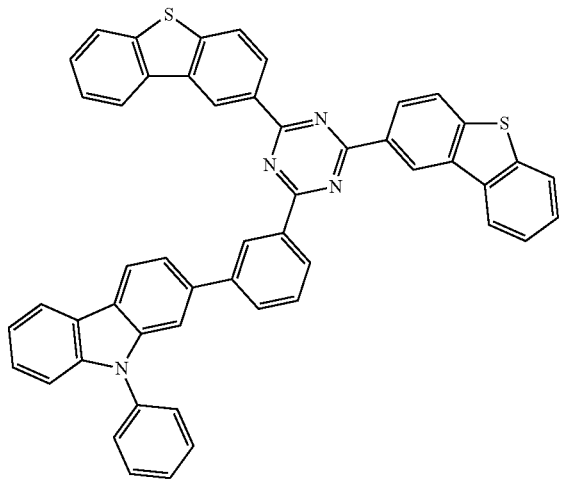
6-97
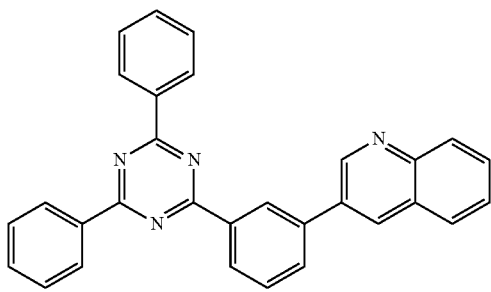
6-98
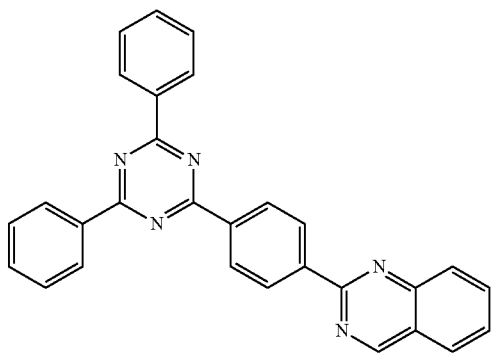
6-99
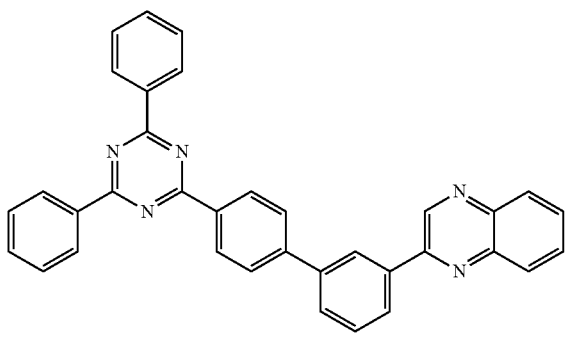
6-100
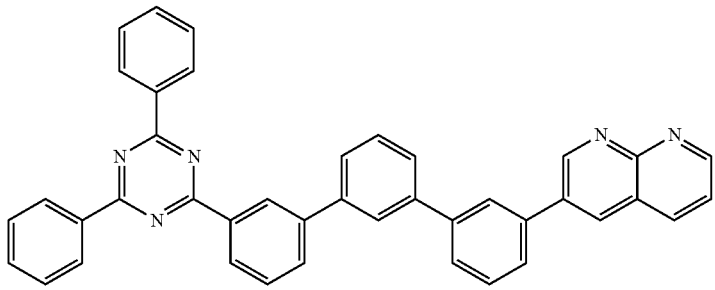

-continued
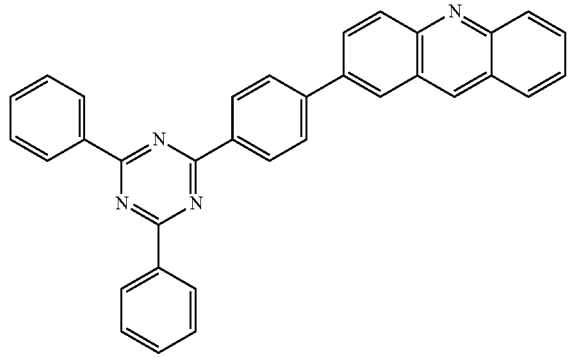
6-101
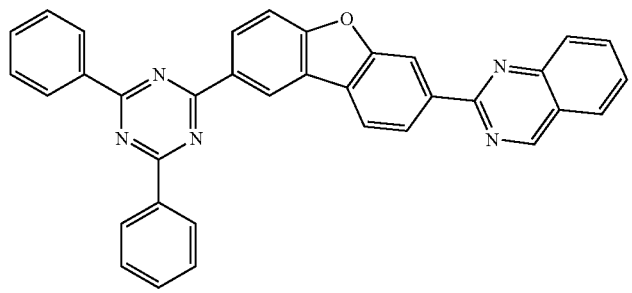
6-102
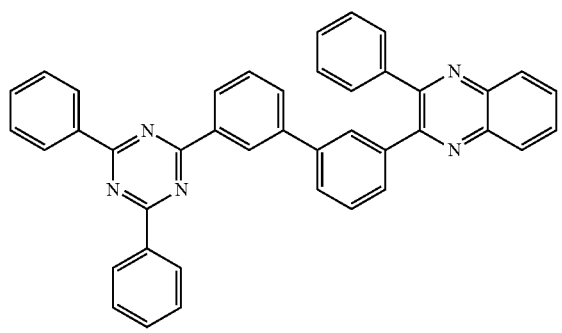
6-103
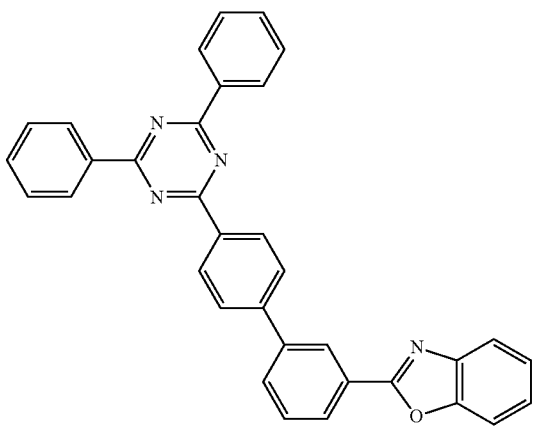
6-104
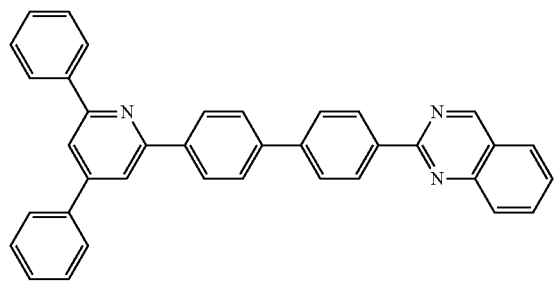
6-105
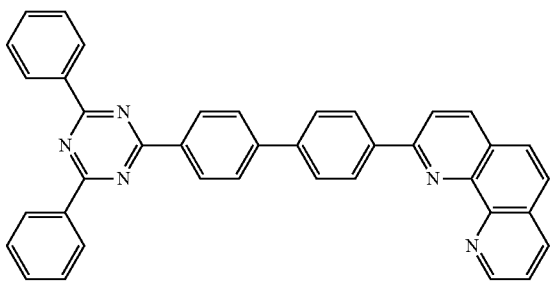
6-106

-continued
6-107
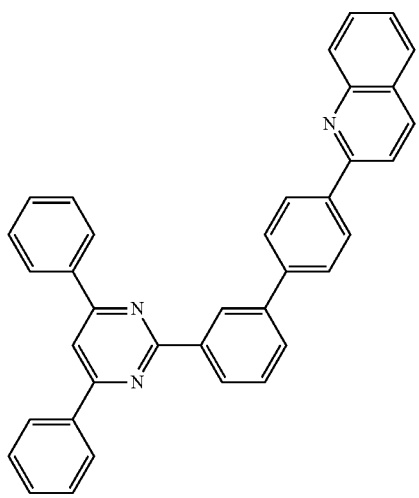
6-108
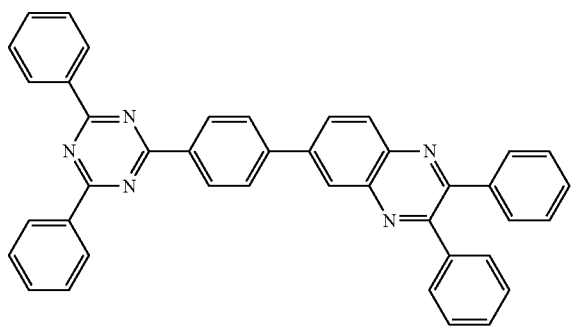
6-109
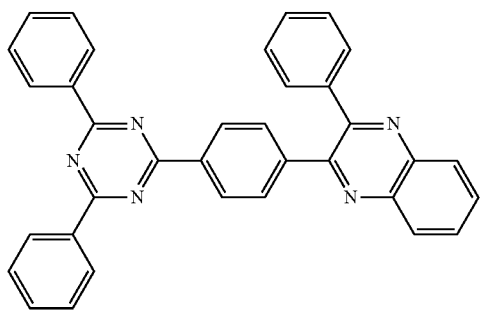
6-110
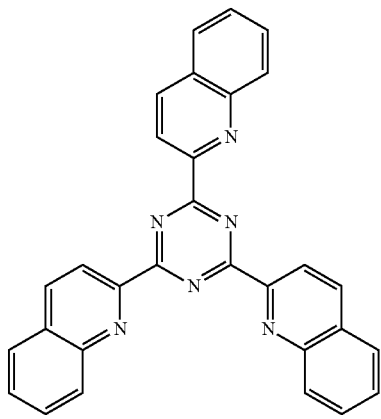
6-111
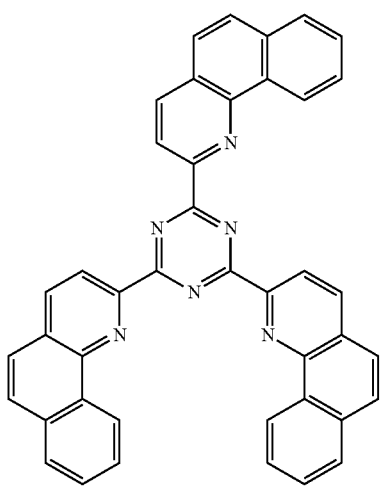
6-112
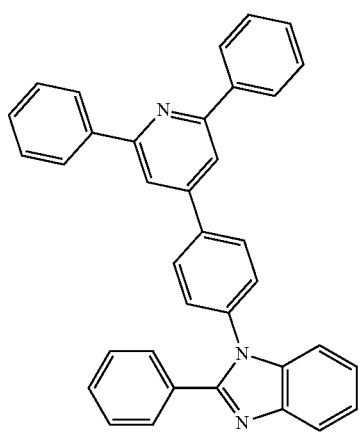

-continued
6-113
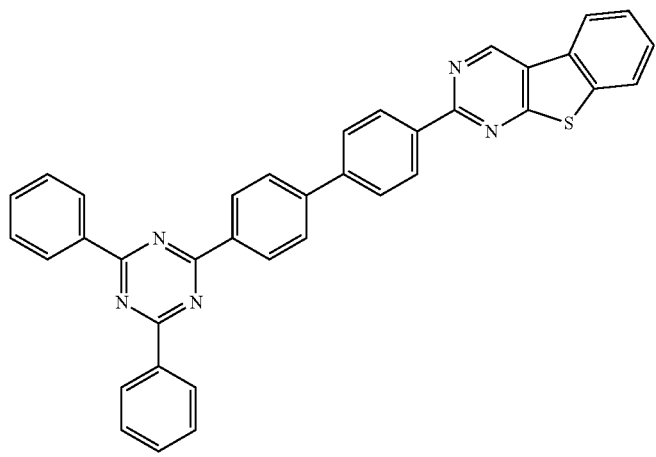
6-114
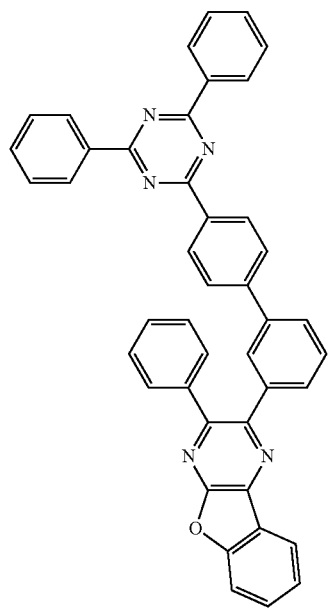
6-115
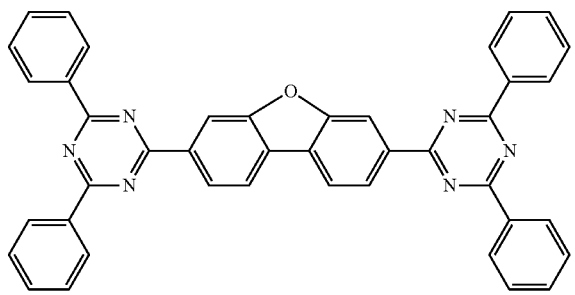
6-116
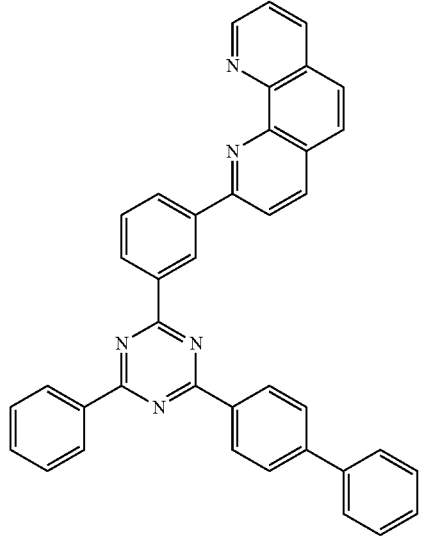
6-117
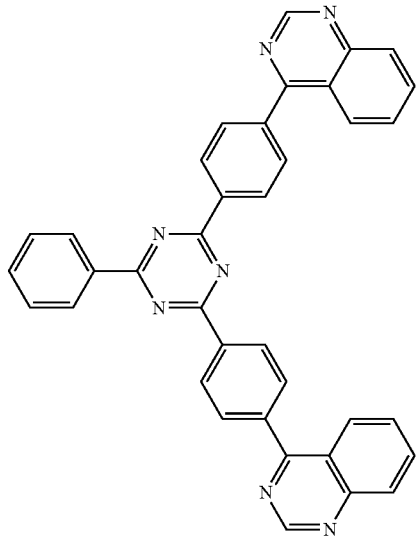

-continued
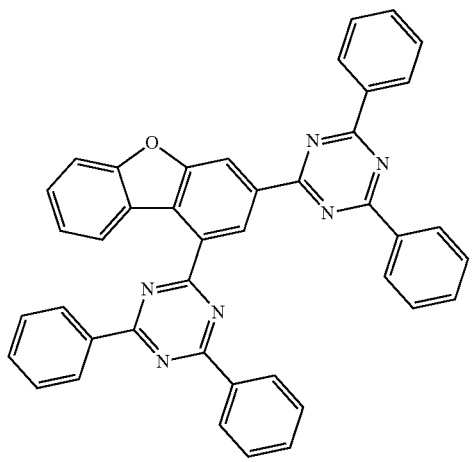
6-118
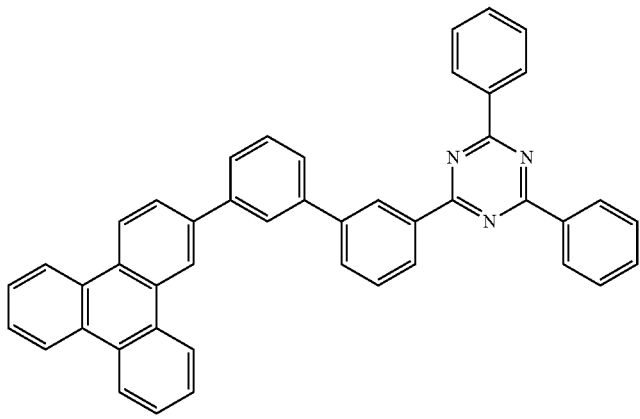
6-119
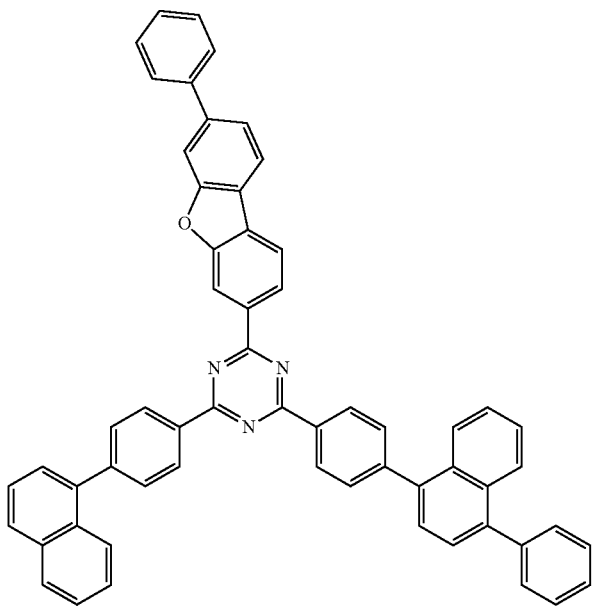
6-120

-continued
205
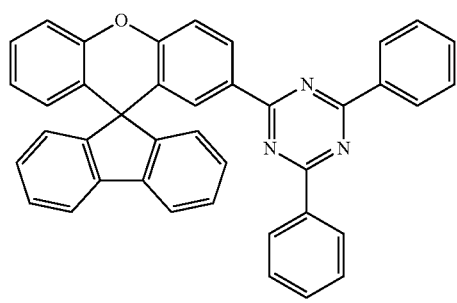
6-121
206
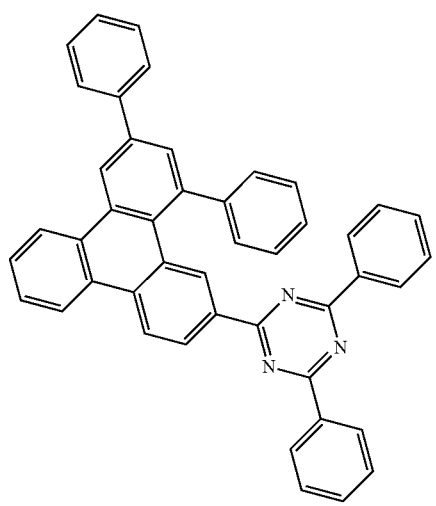
6-122
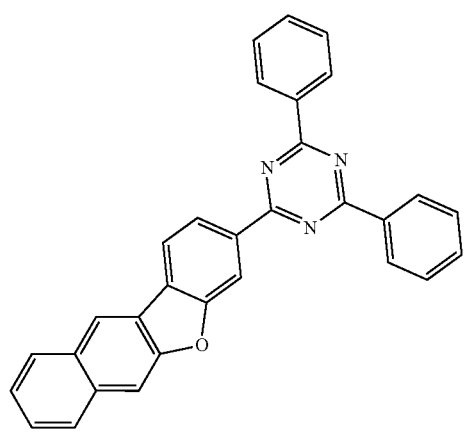
6-123
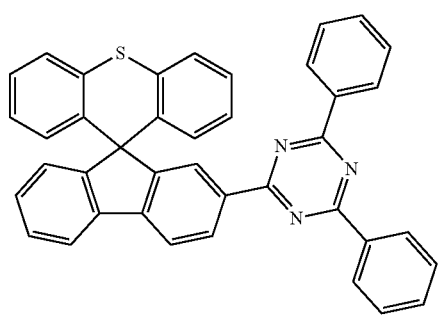
6-124
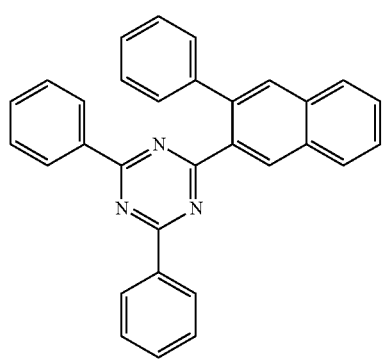
N-1
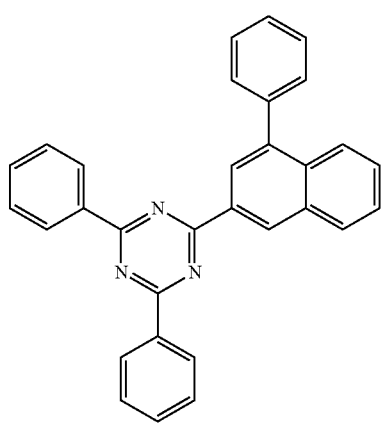
N-2

-continued
N-3
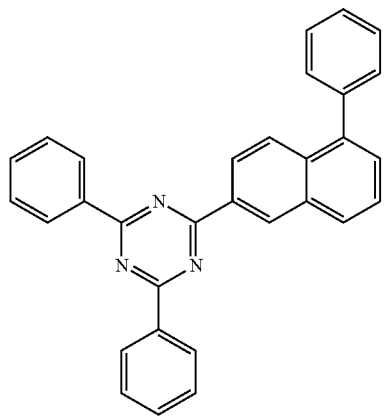
N-4
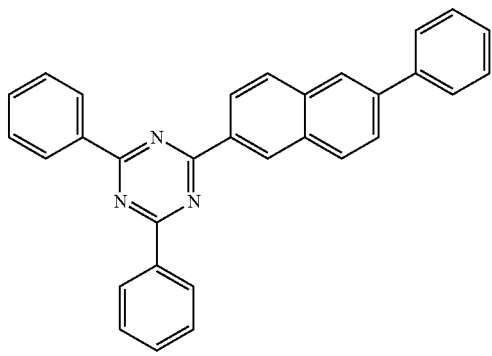
N-5
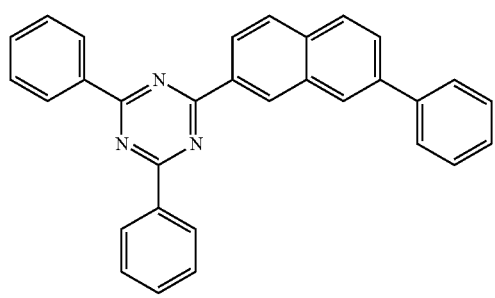
N-6
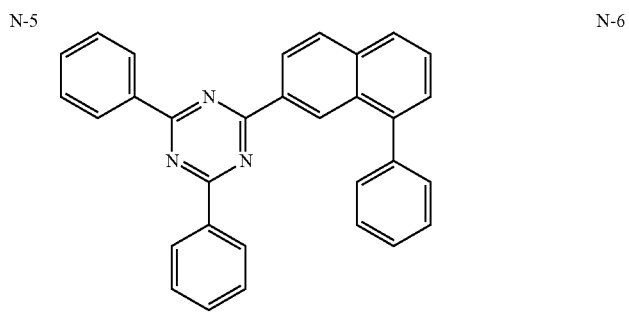
N-7
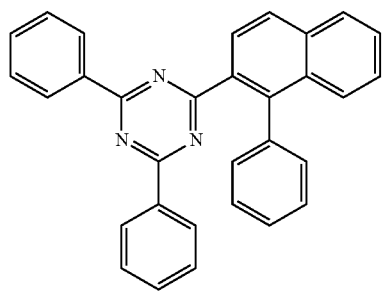
N-8
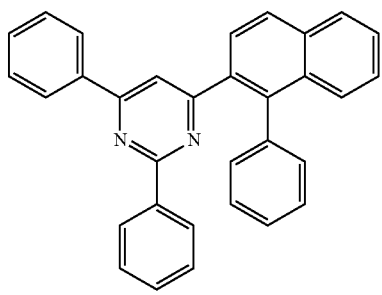
N-9
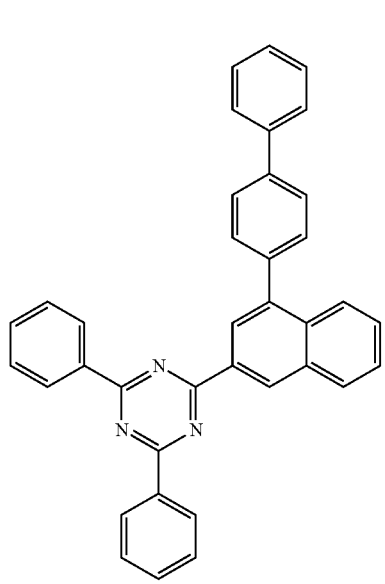
N-10
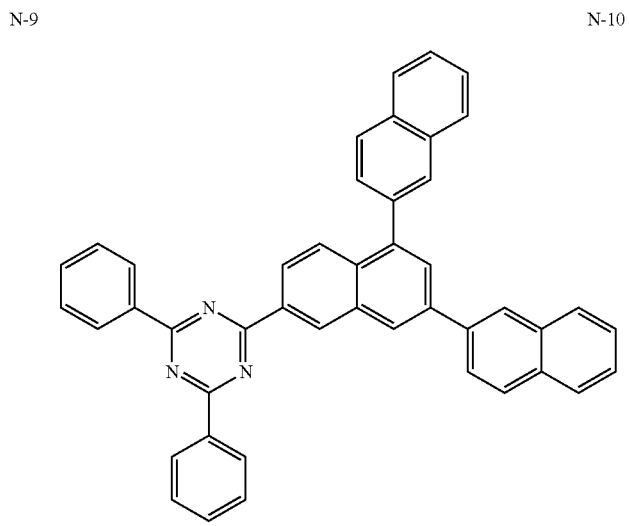

-continued
N-11
N-12
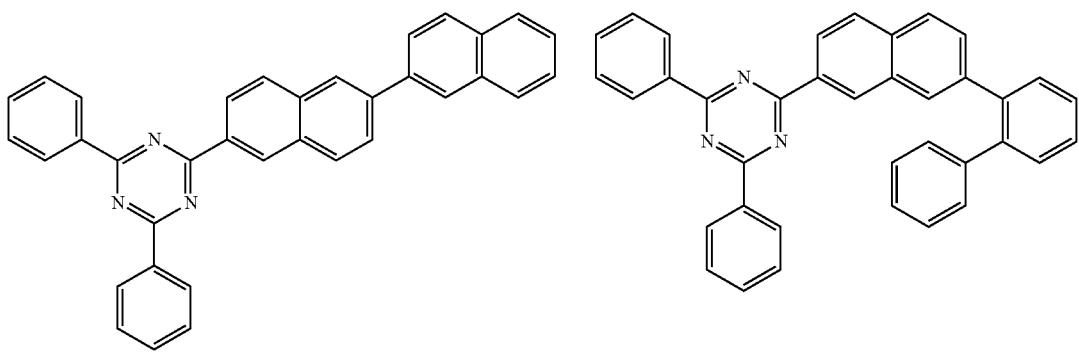
N-13
N-14
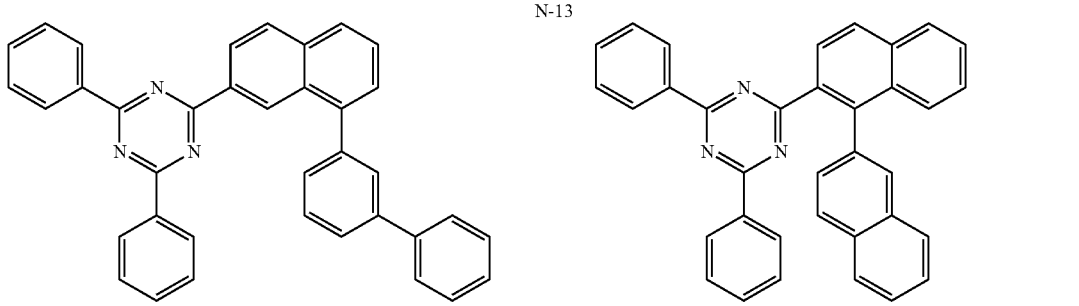
N-15
N-16
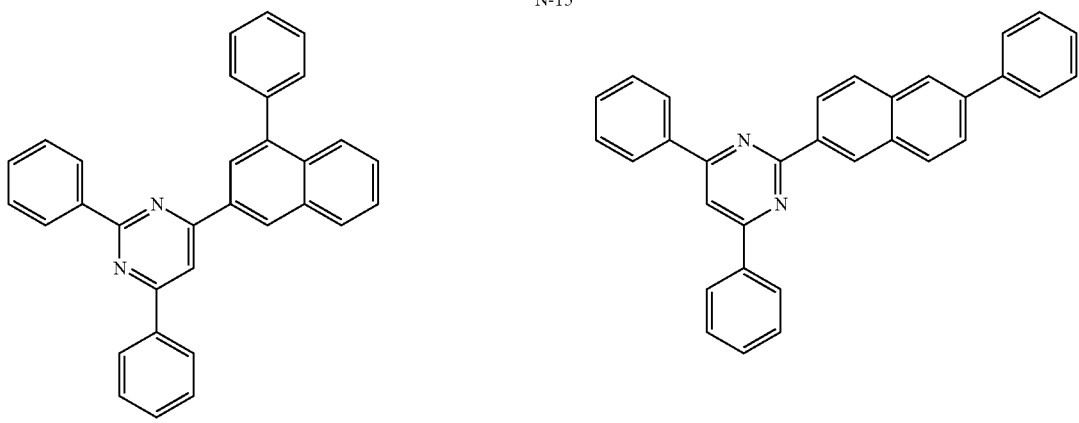
N-17
N-18
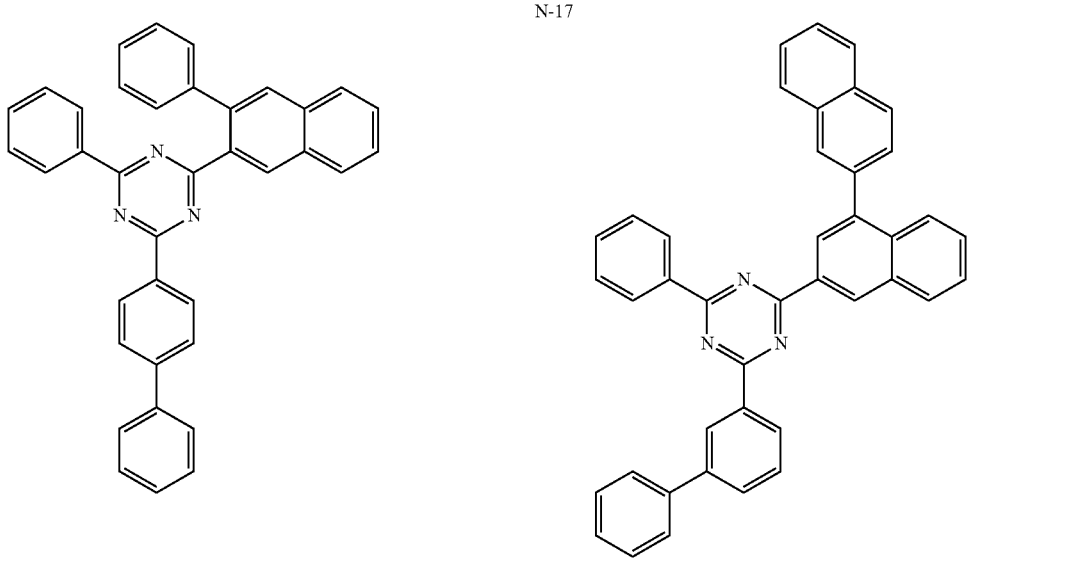

-continued
N-19
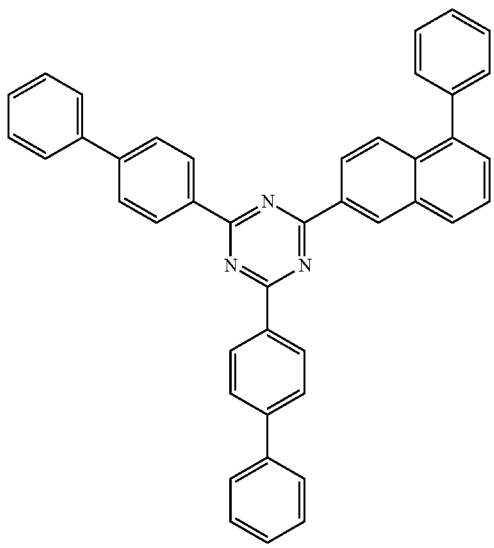
N-20
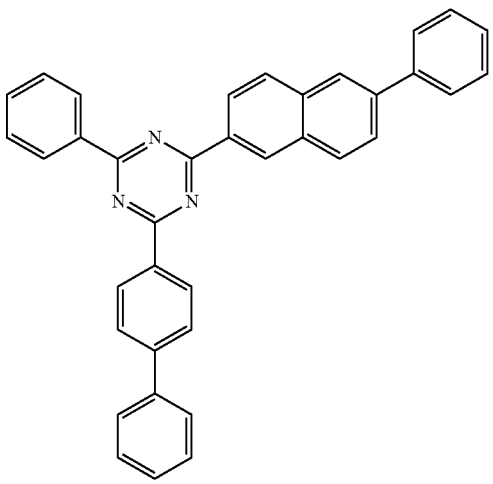
N-21
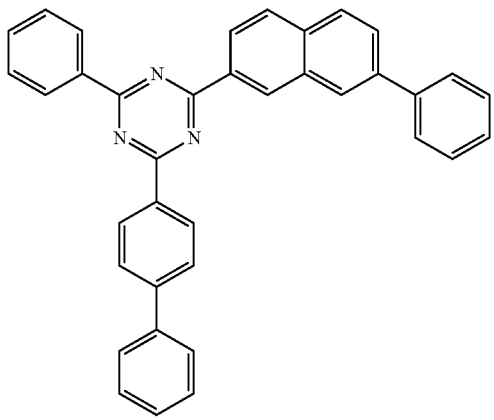
N-22
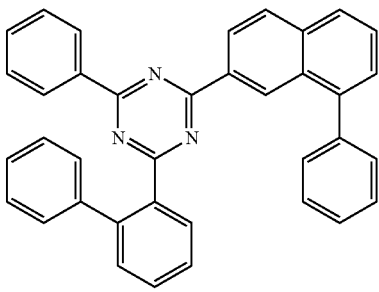
N-23
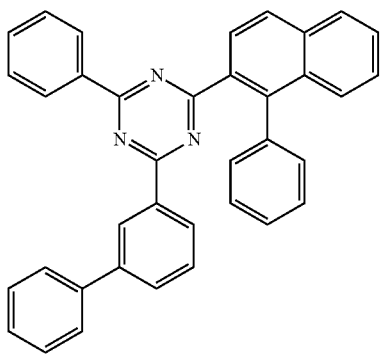
N-24
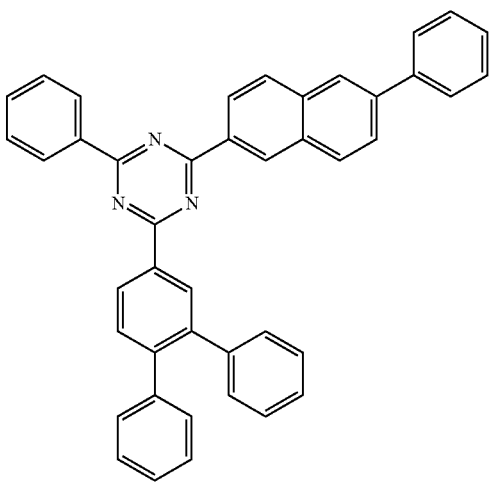

-continued
N-25
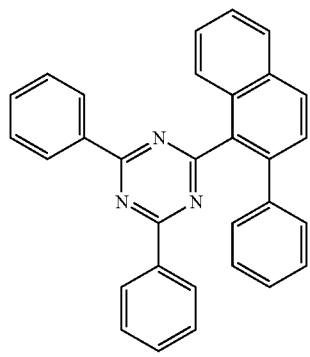
N-26
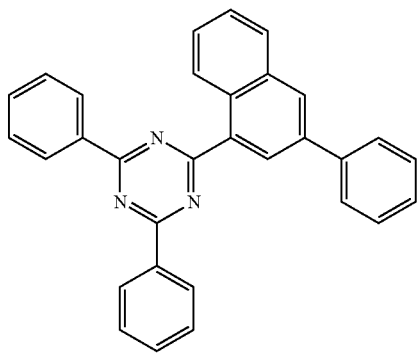
N-27
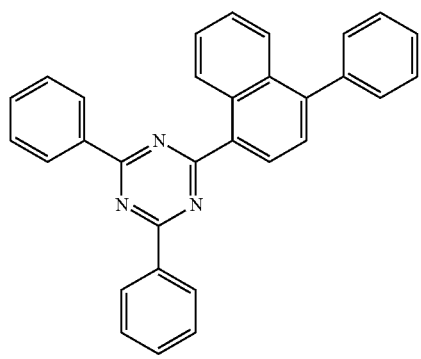
N-28
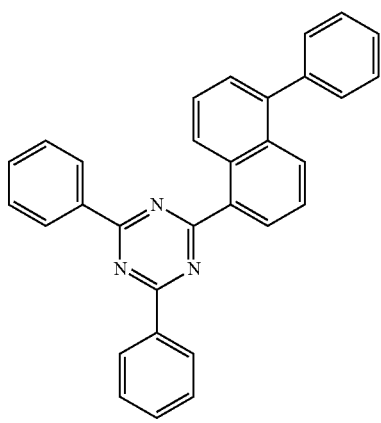
N-29
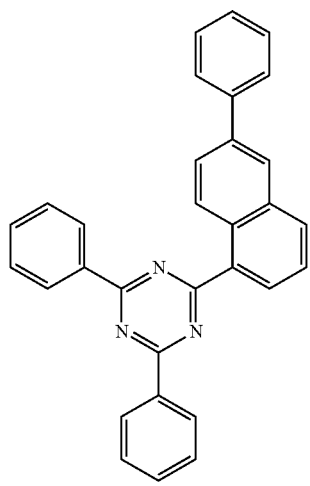
N-30
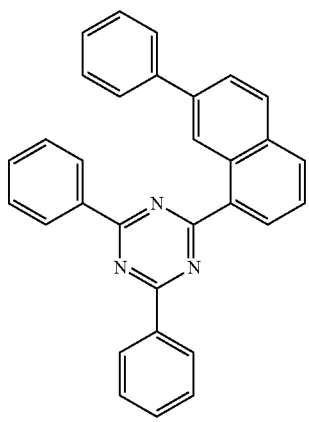
N-31
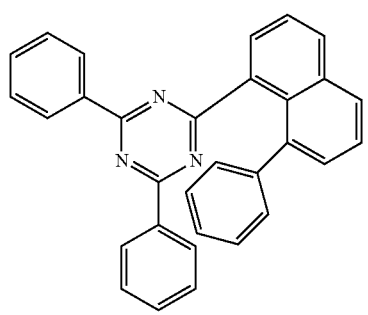
N-32
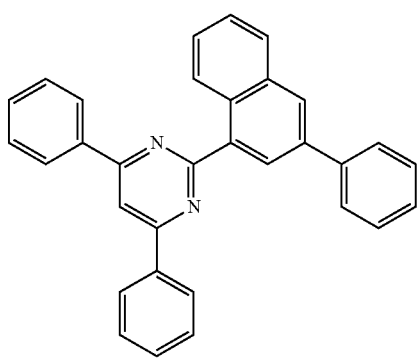

-continued
N-33
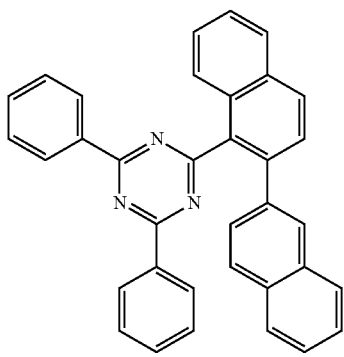
N-34
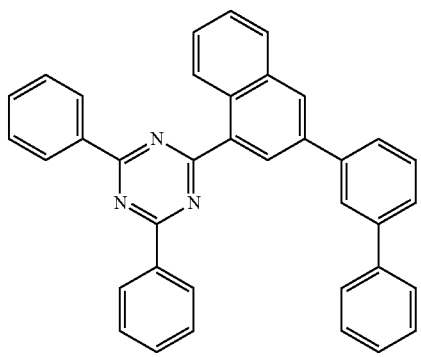
N-35
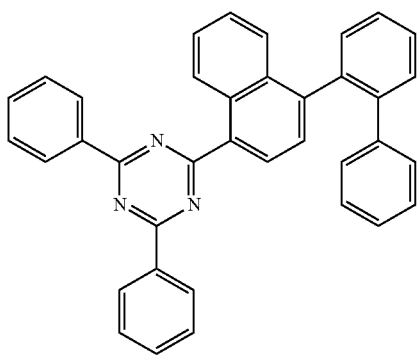
N-36
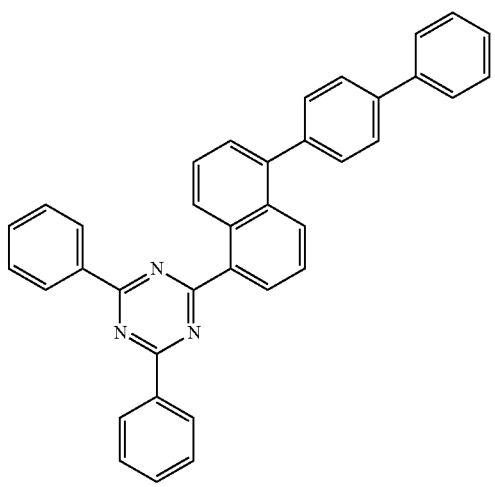
N-37
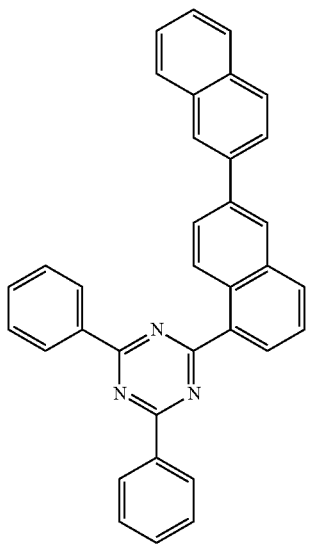
N-38
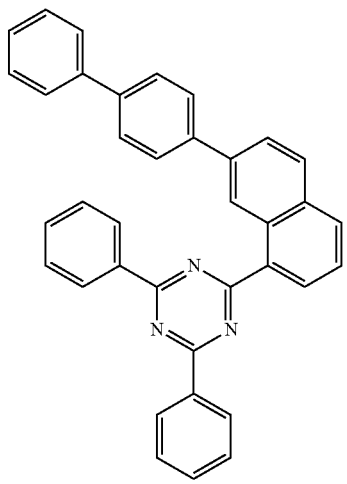

-continued
N-39
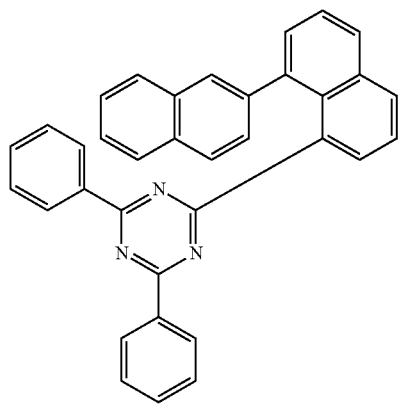
N-40
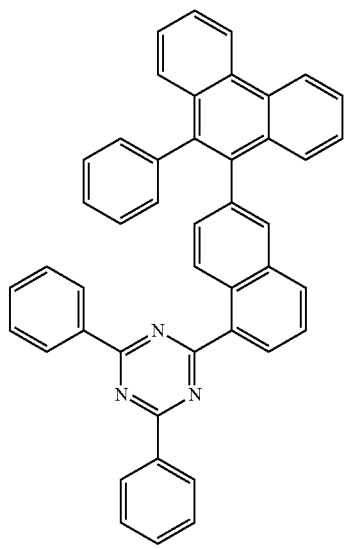
N-41
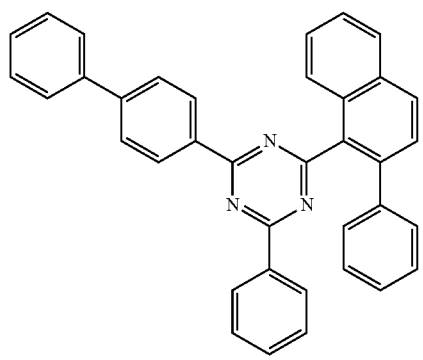
N-42
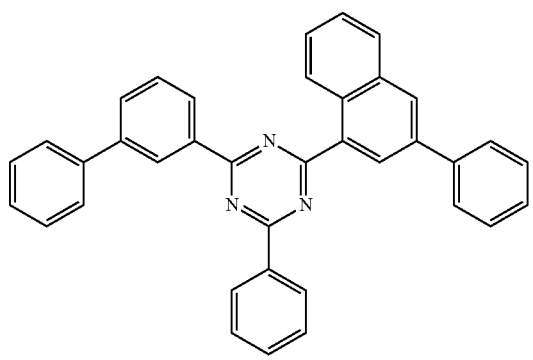
N-43
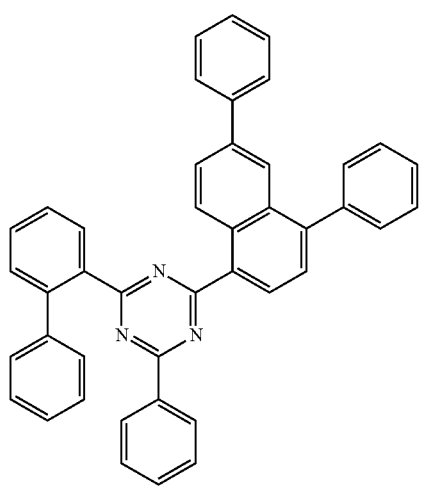

N-44
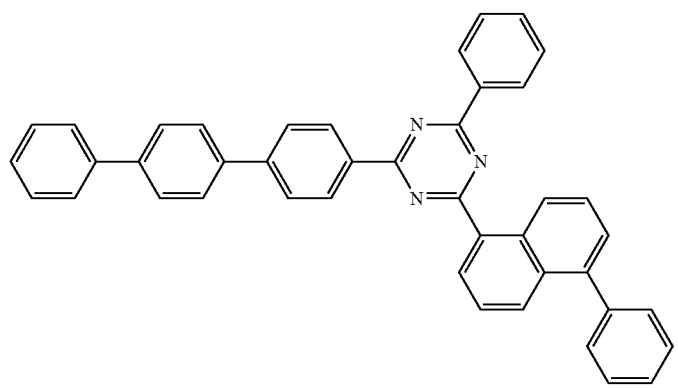
N-45
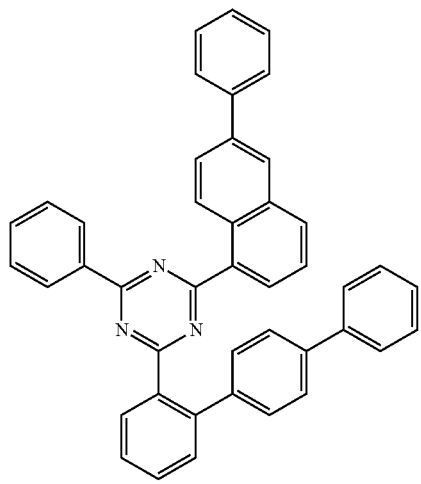
N-46
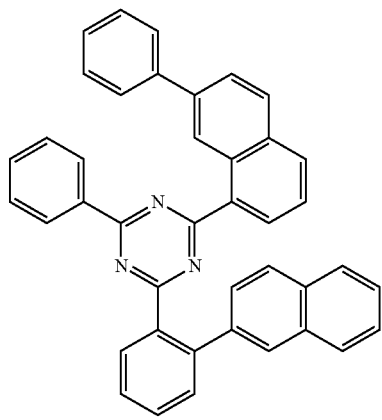
N-47
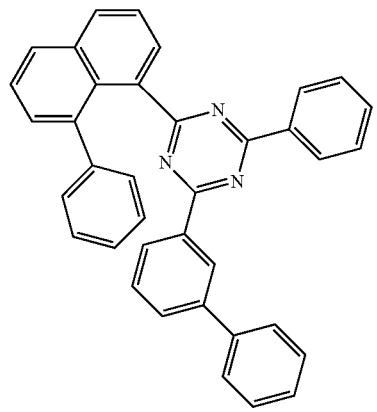
N-48
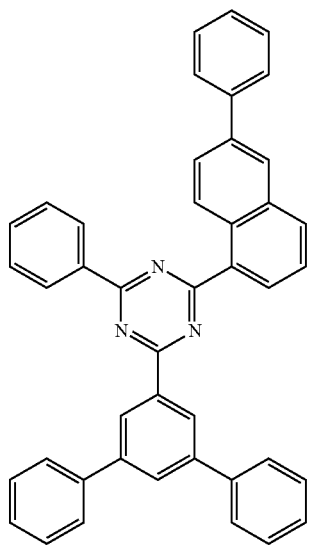

221                                        222
-continued
N-49                                              N-50
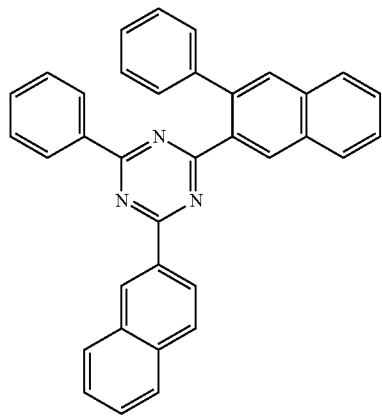                       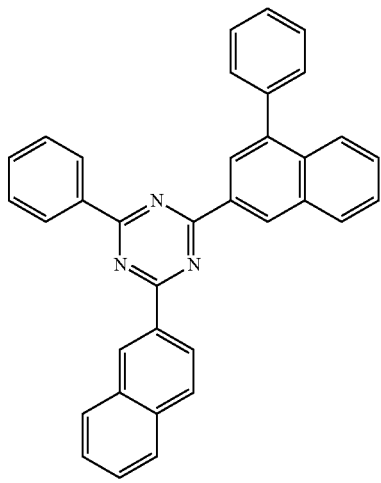
N-51                                              N-52
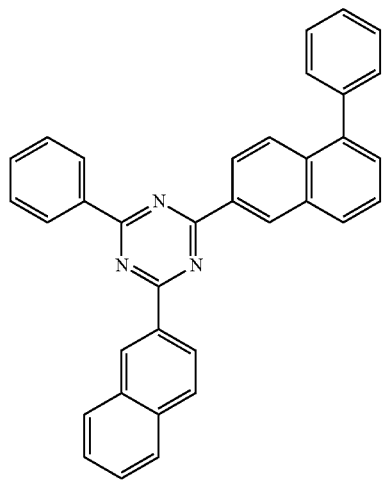                       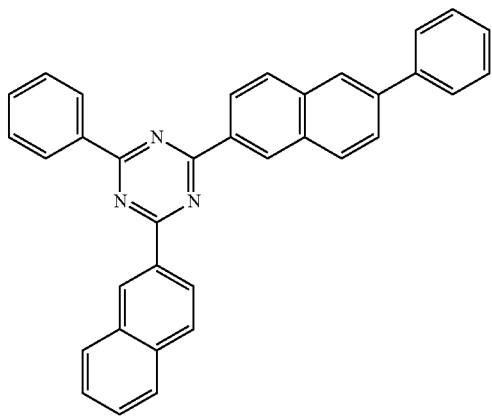
N-53                                              N-54
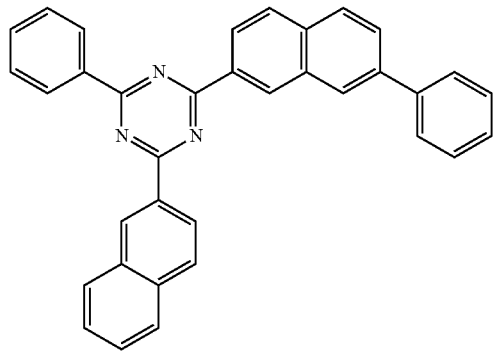                       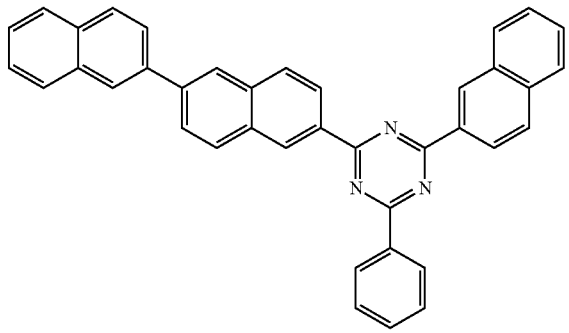

-continued
N-55
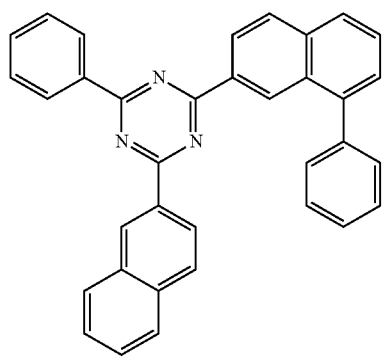
N-56
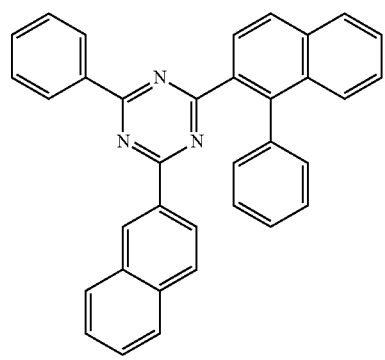
N-57
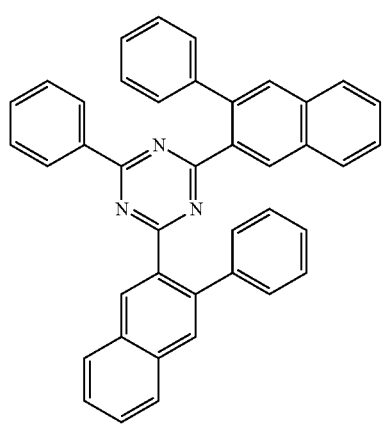
N-58
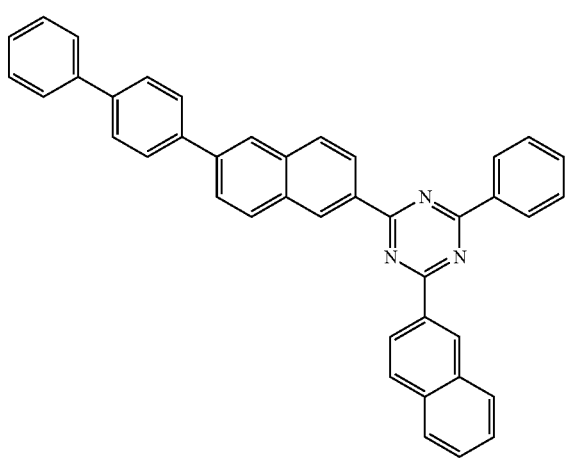
N-59
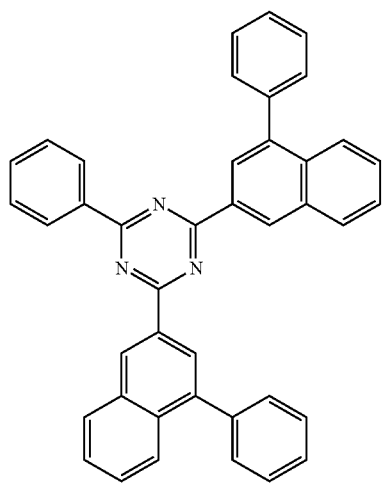
N-60
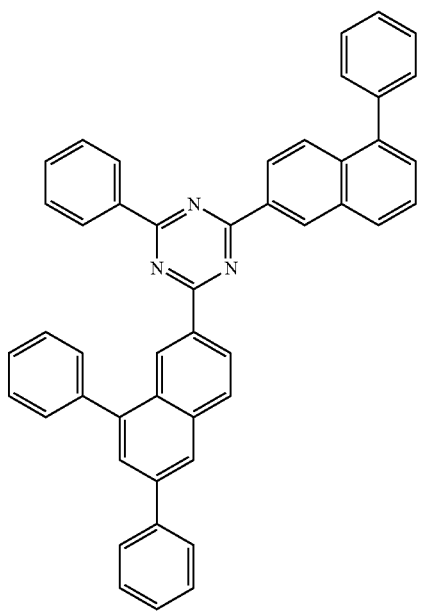

-continued
N-61
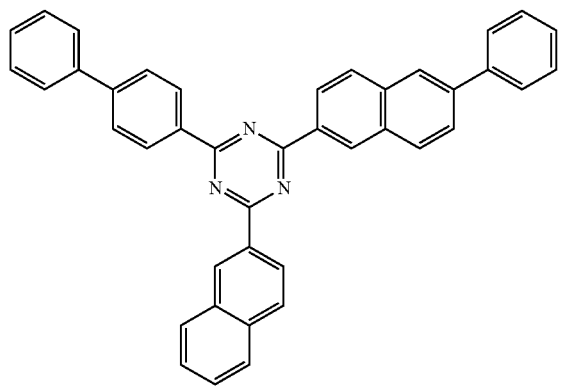
N-62
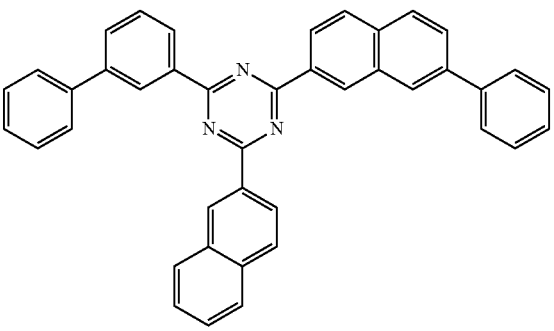
N-63
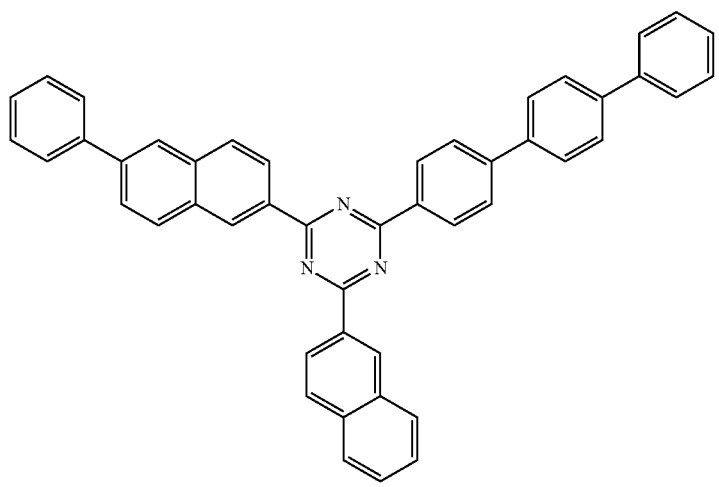
N-64
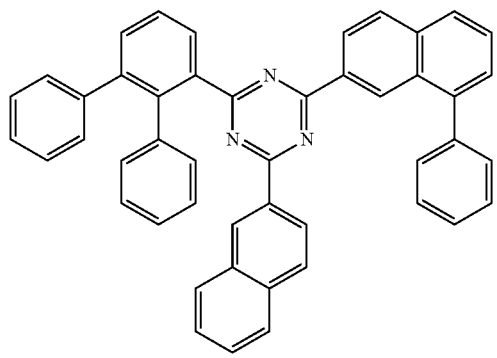
N-65
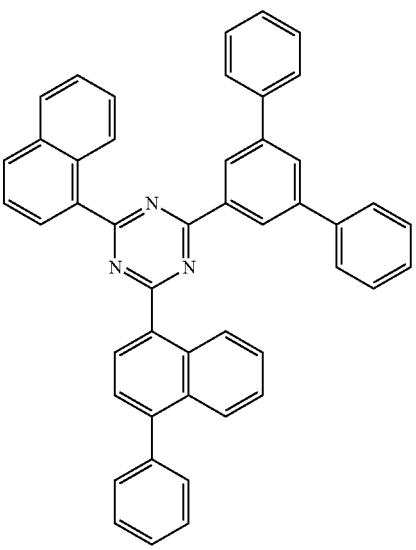

N-66
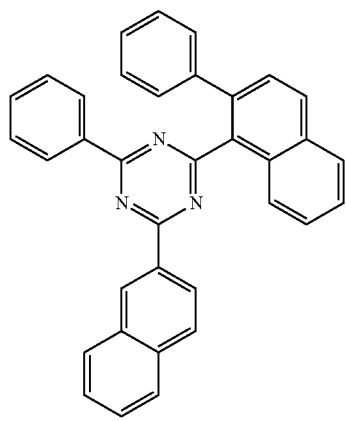
N-67
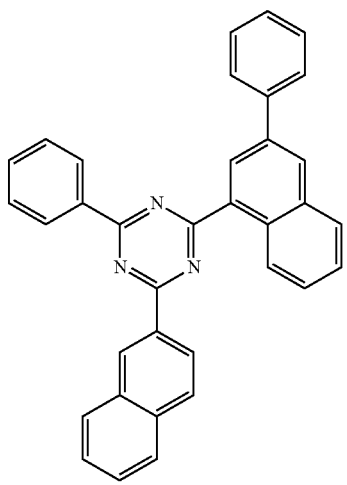
N-68
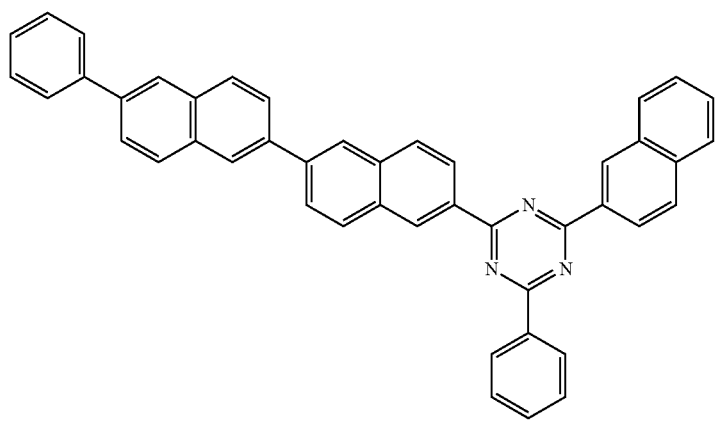
N-69
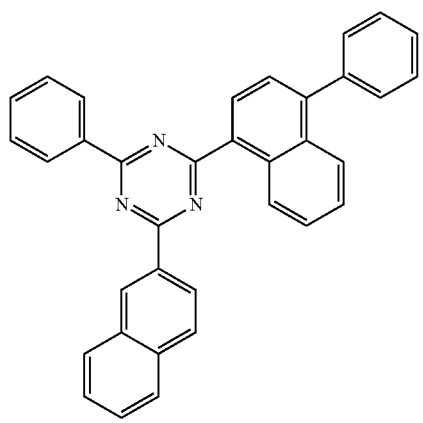
N-70
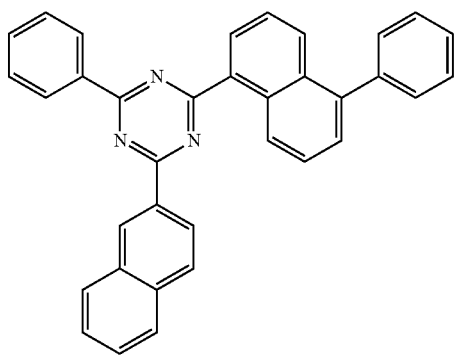

-continued
N-71
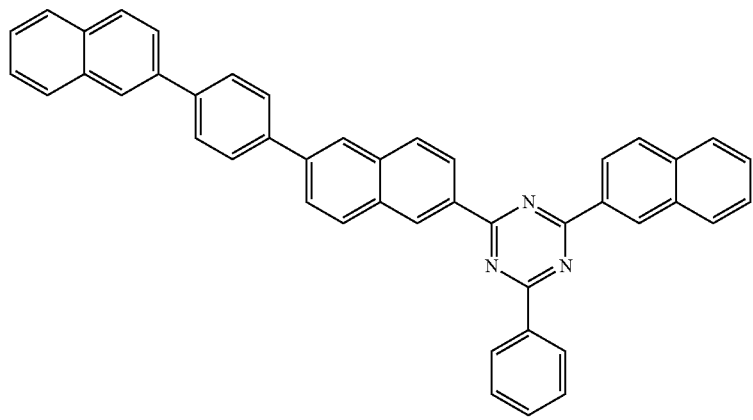
N-72
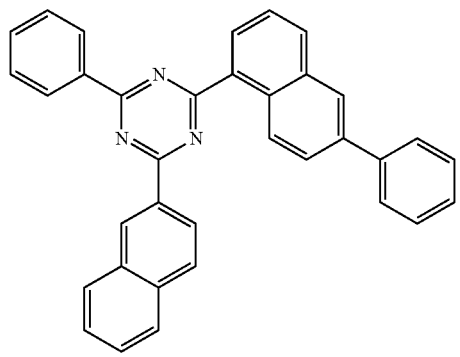
N-73
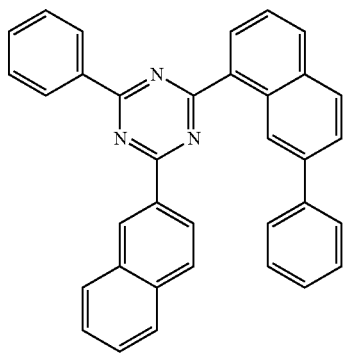
N-74
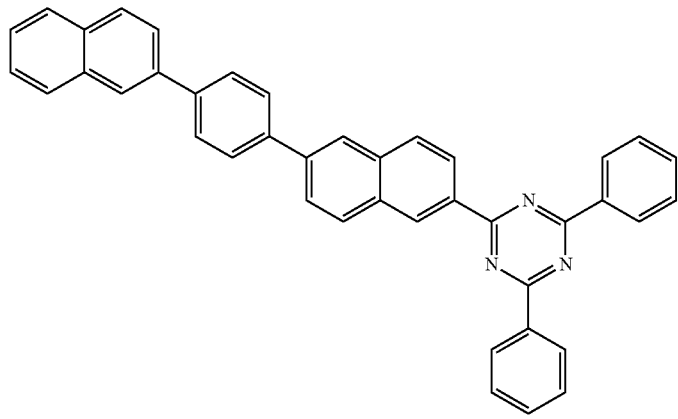
N-75
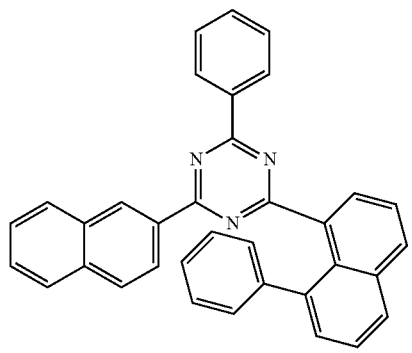
N-76
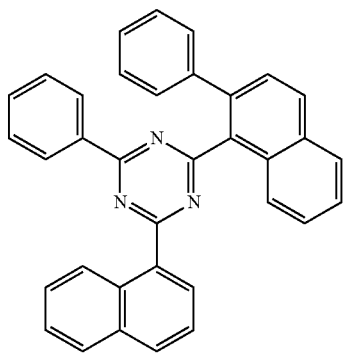

-continued
N-77
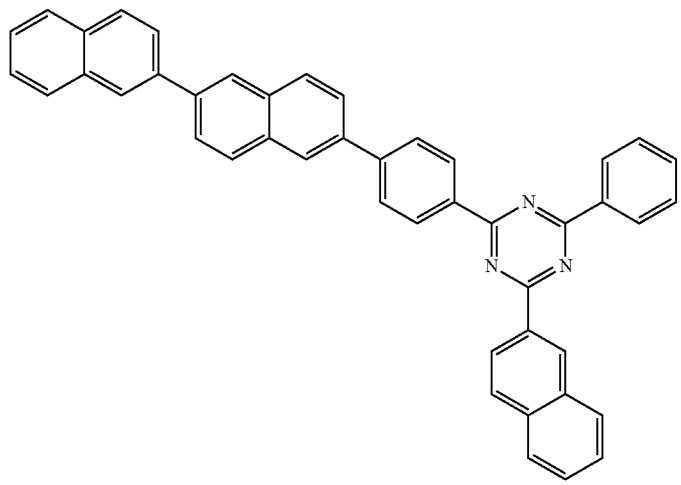
N-78
N-79
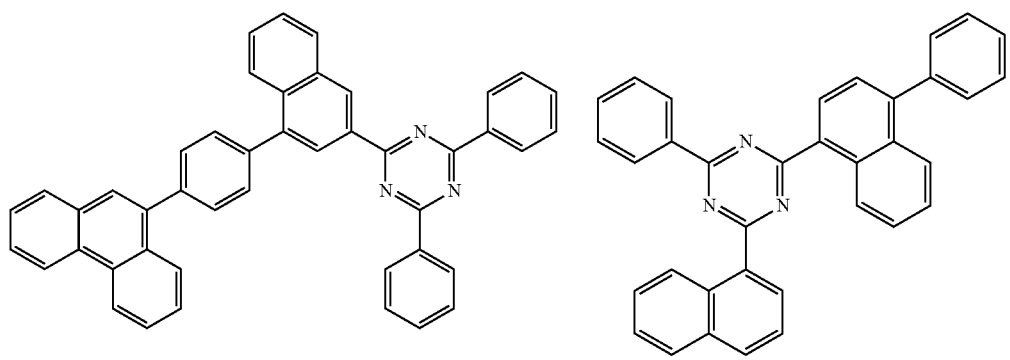
N-80
N-81
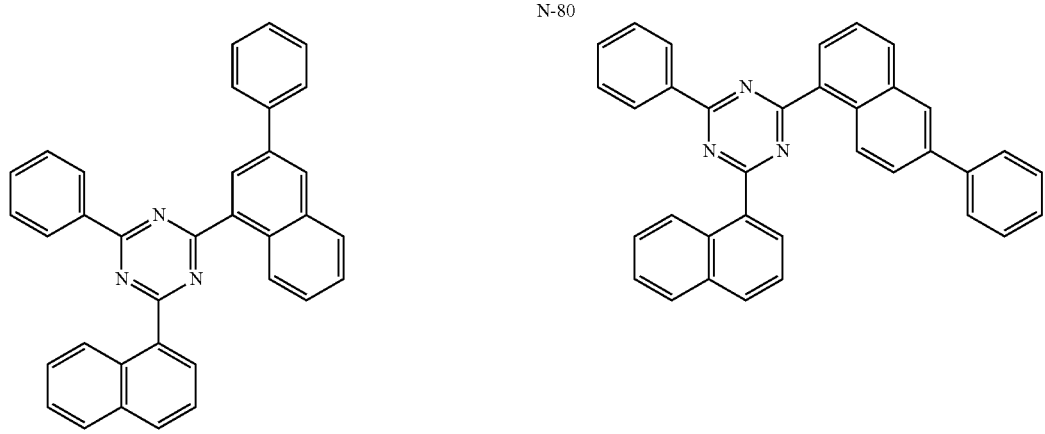
N-82
N-83
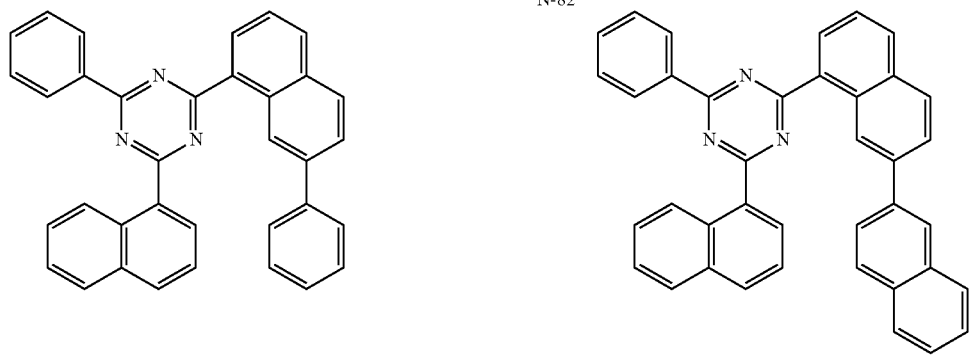

-continued
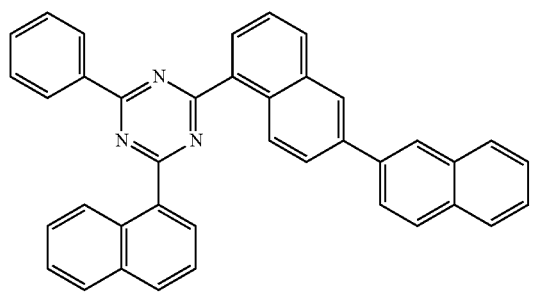
N-84
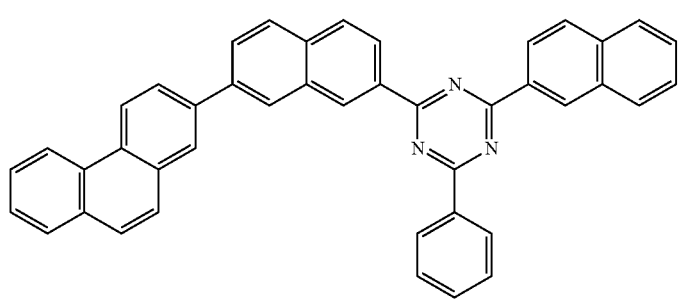
N-85
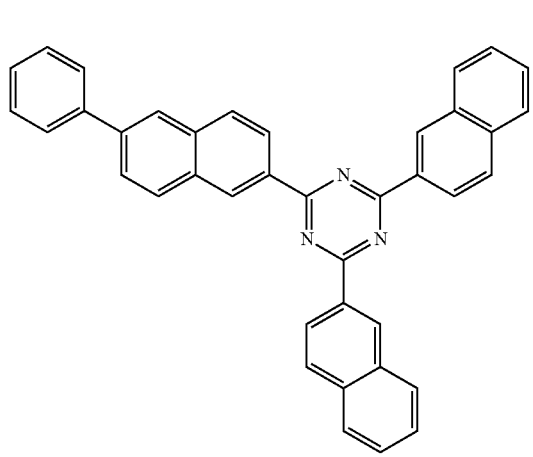
N-86
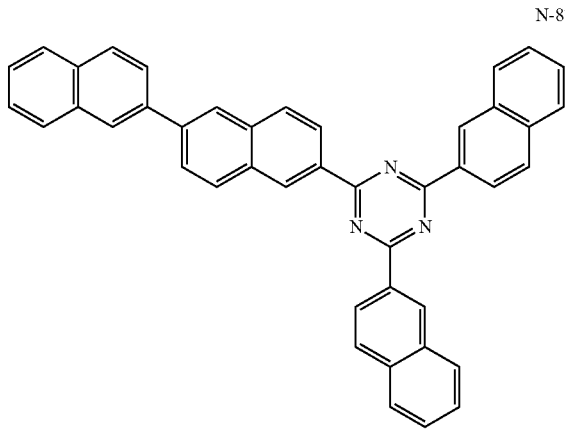
N-87
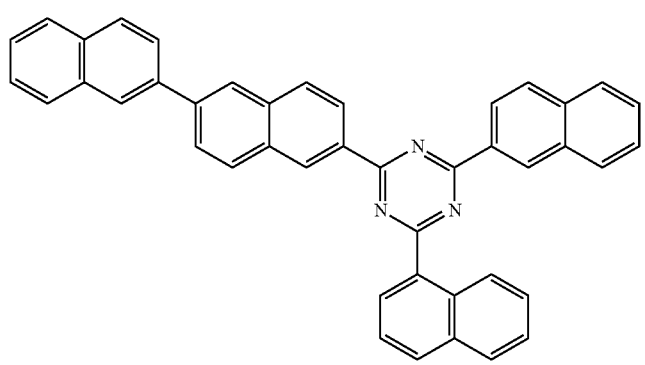
N-88

N-89
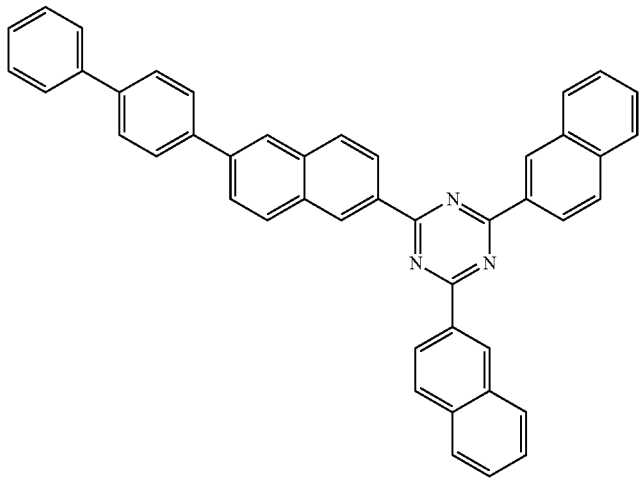
N-90
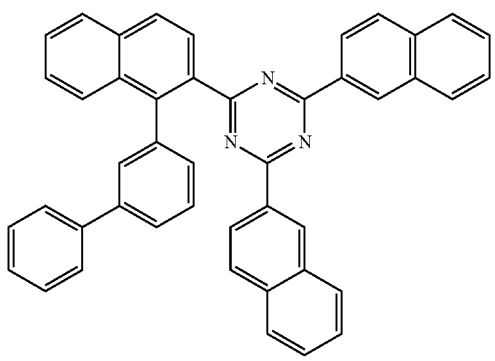
N-91
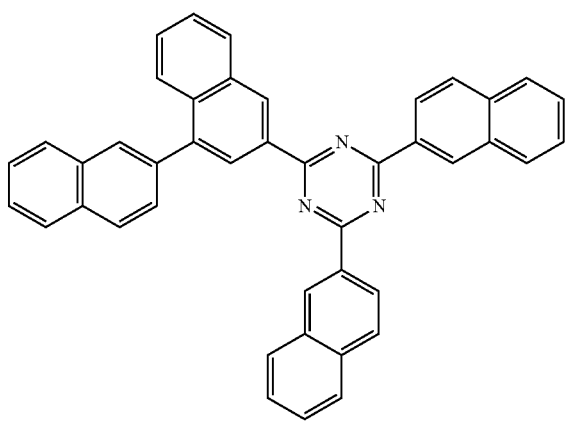
N-92
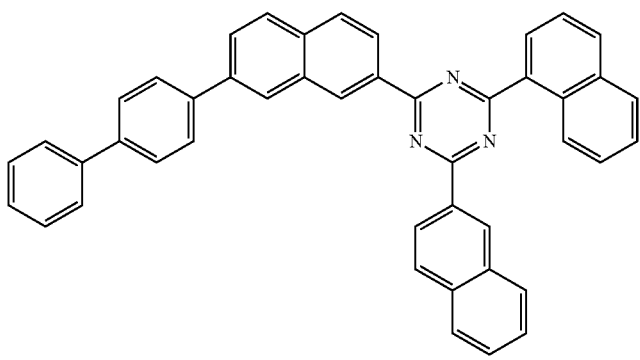

N-93
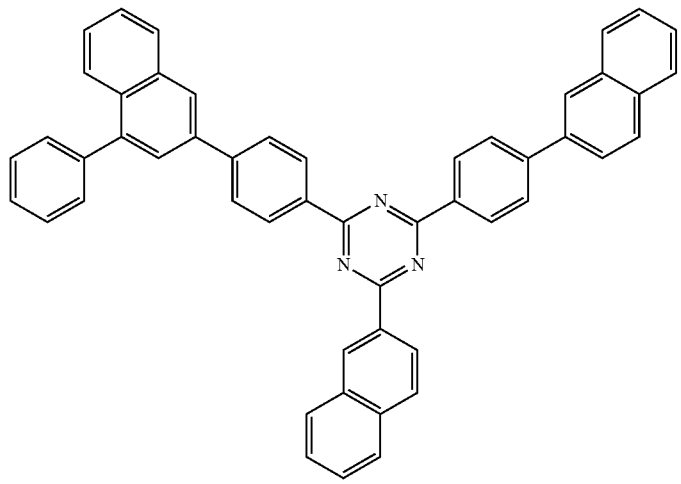
N-94
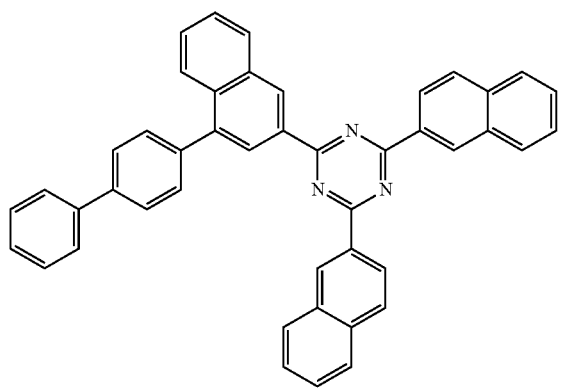
N-95
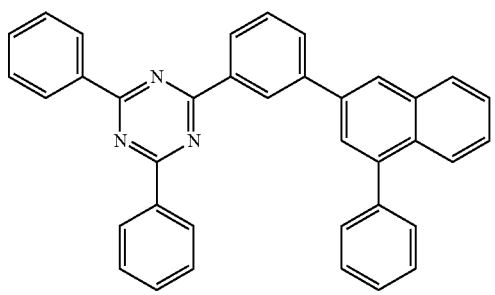
N-96
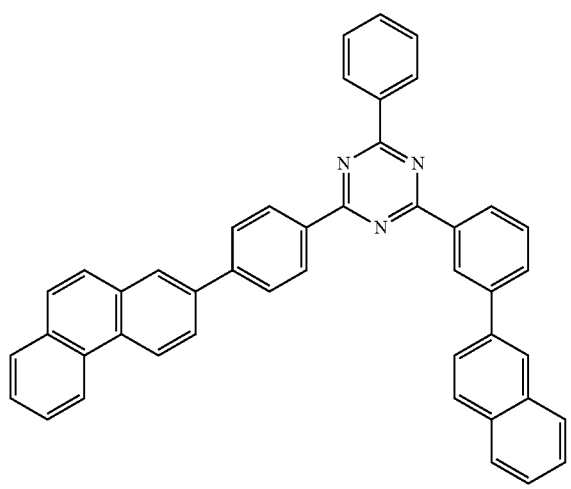

-continued
N-97
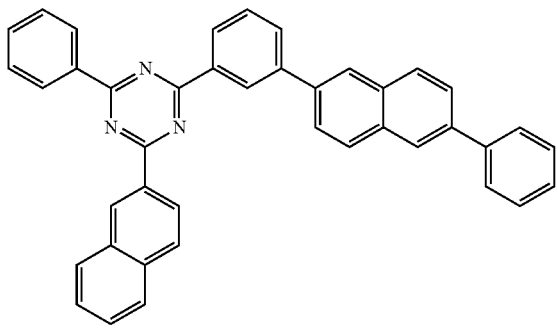
N-98
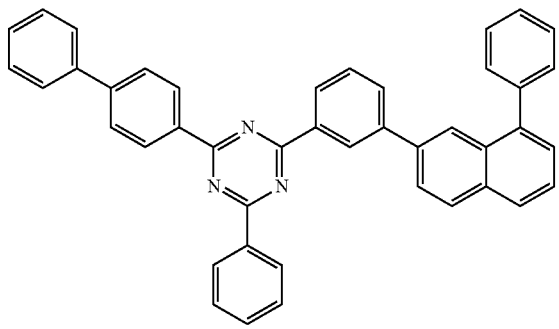
N-99
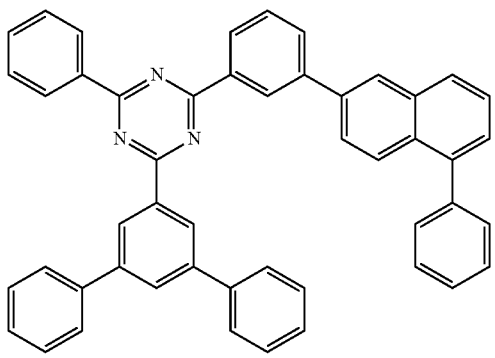
N-100
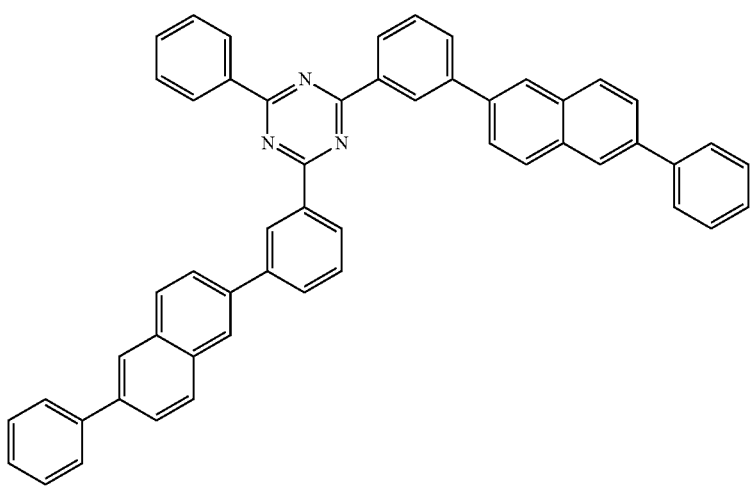

-continued
N-101
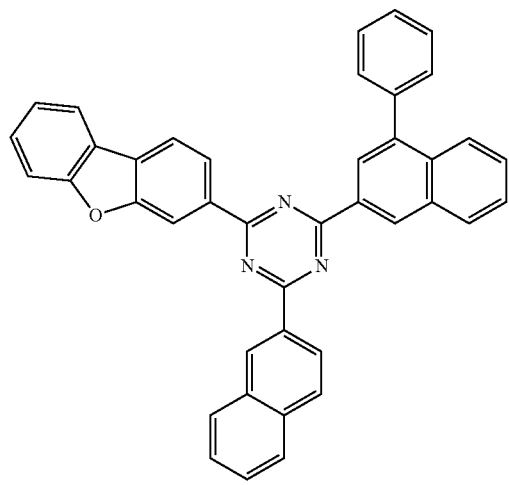
N-102
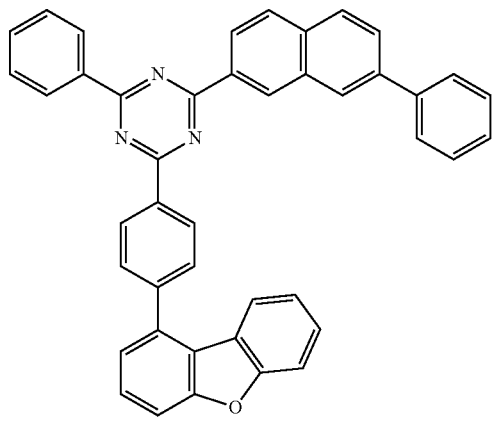
N-103
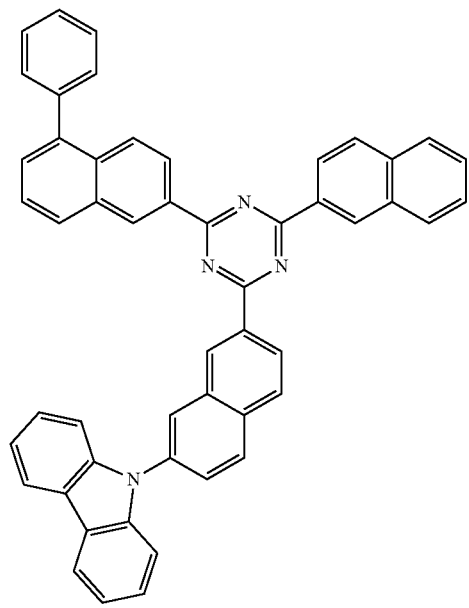
N-104
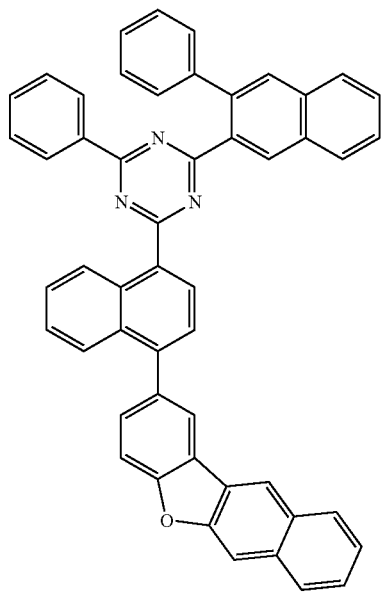
N-105
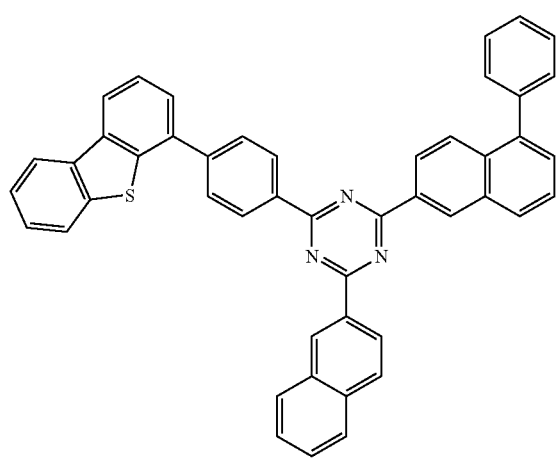
N-106
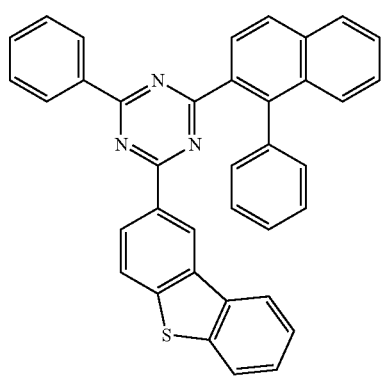

-continued
N-107
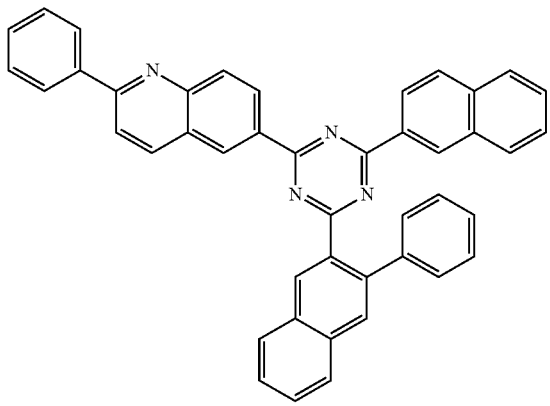
N-108
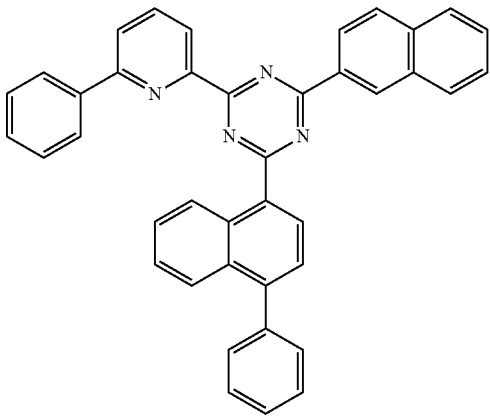
N-109
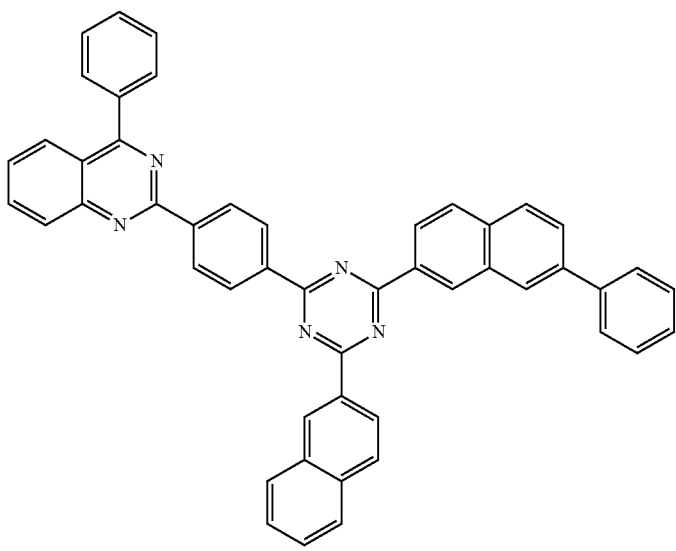
N-110
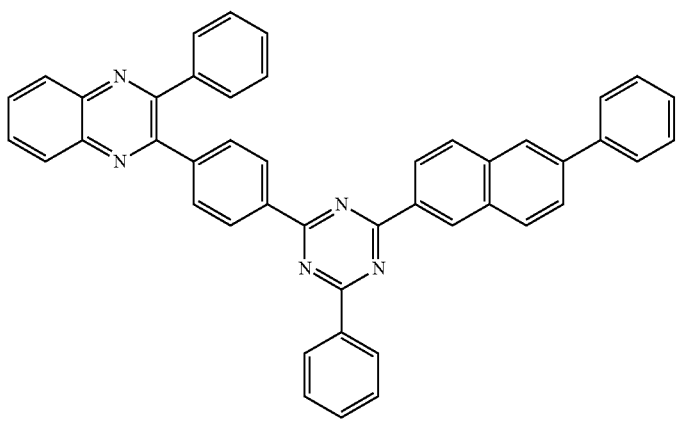

-continued
N-111
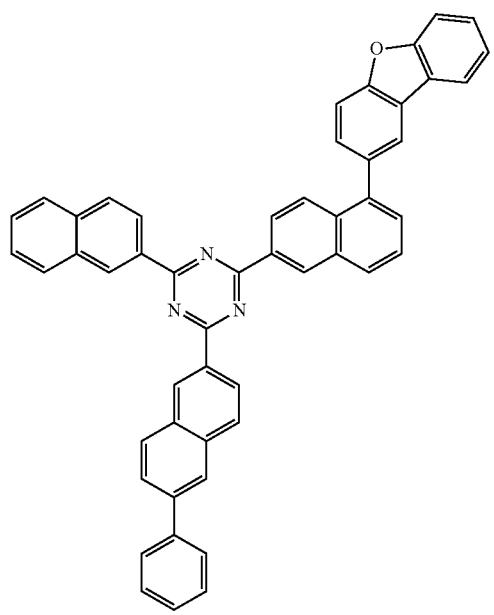
N-112
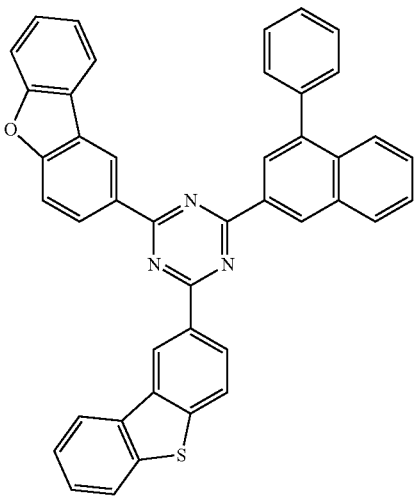
N-113
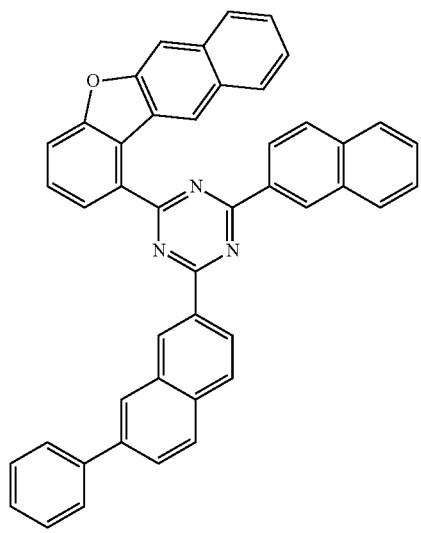
N-114
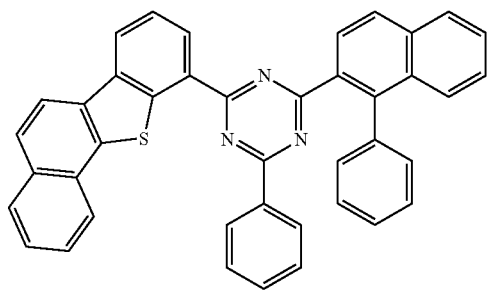

-continued
N-115
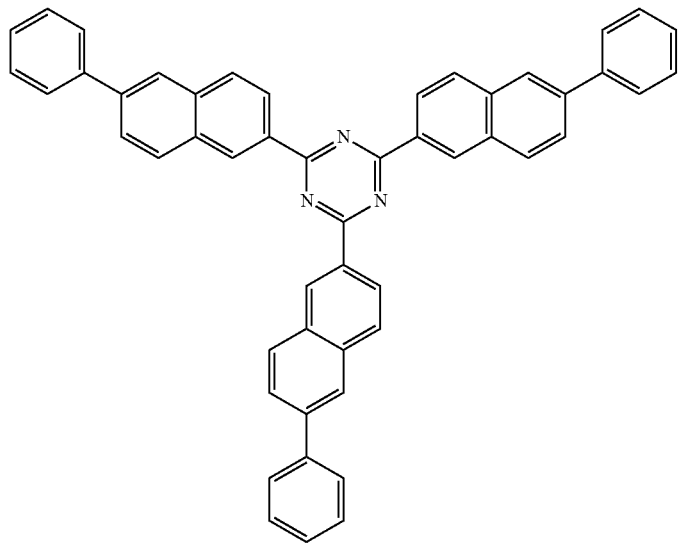
N-116
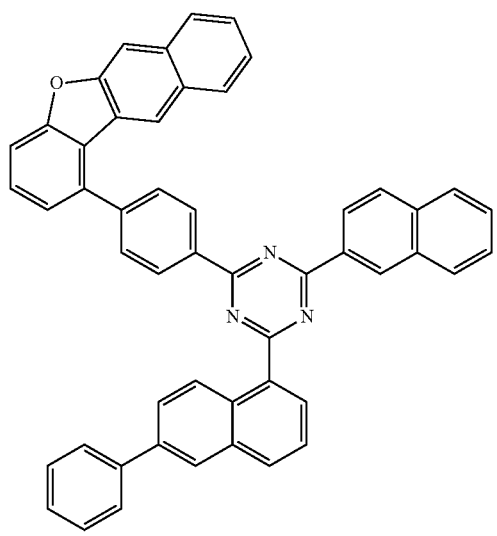
N-117
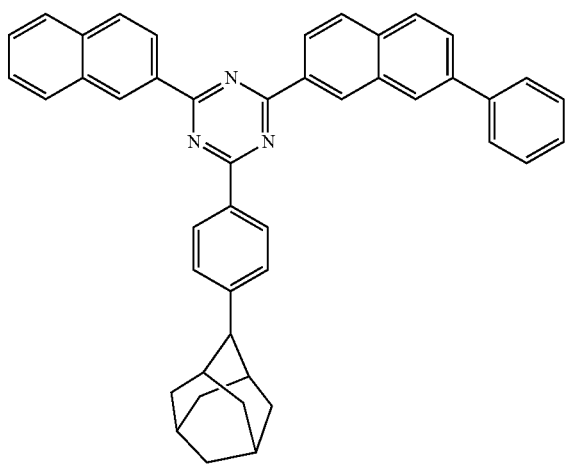
N-118
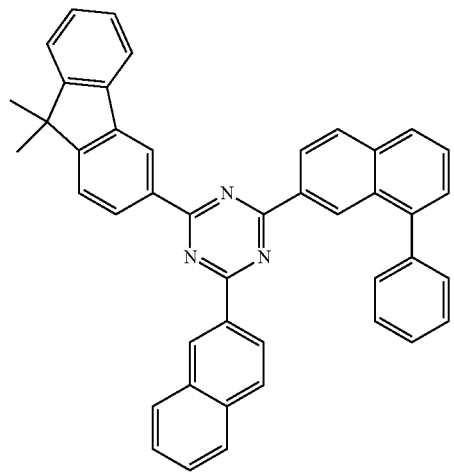
N-119
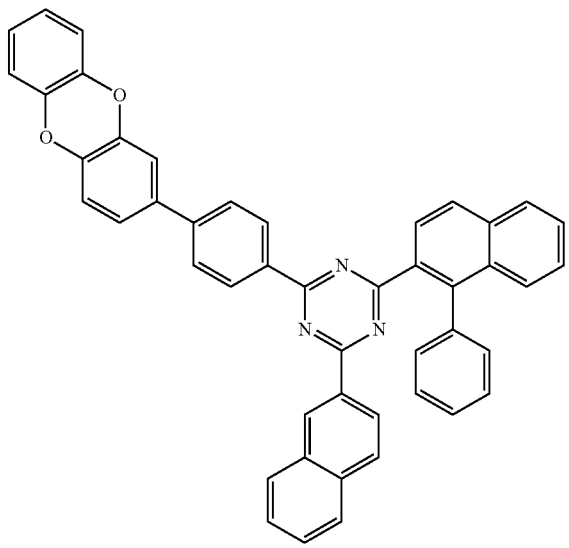

-continued
N-120
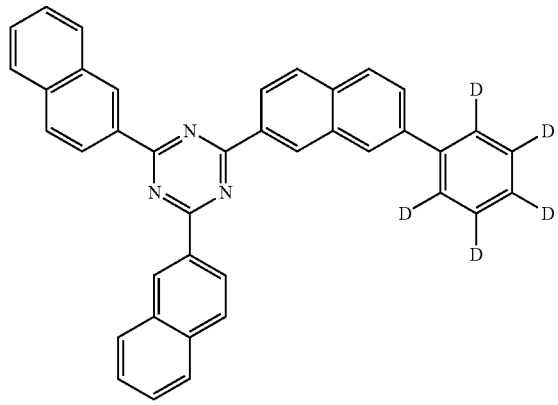
N-121
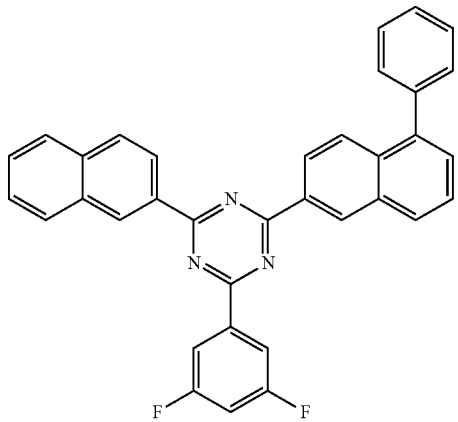
N-122
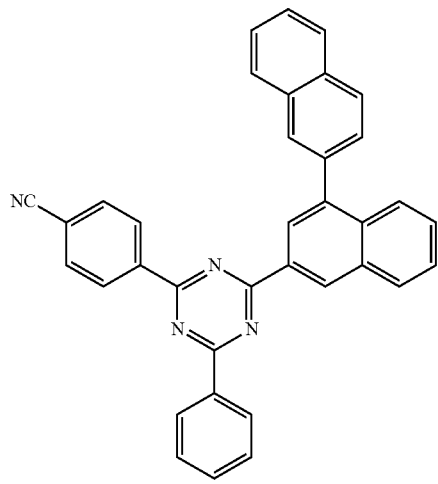
N-123
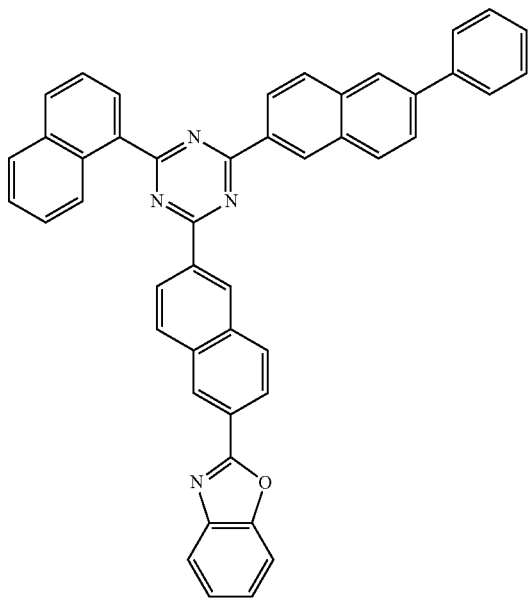
N-124
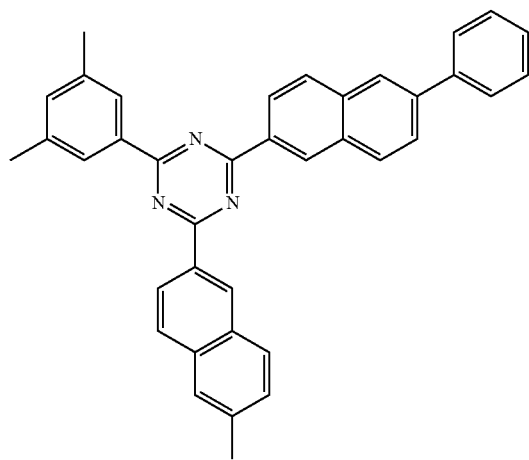
N-125
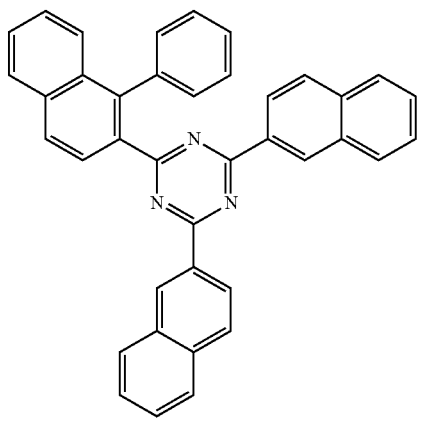

-continued
N-126
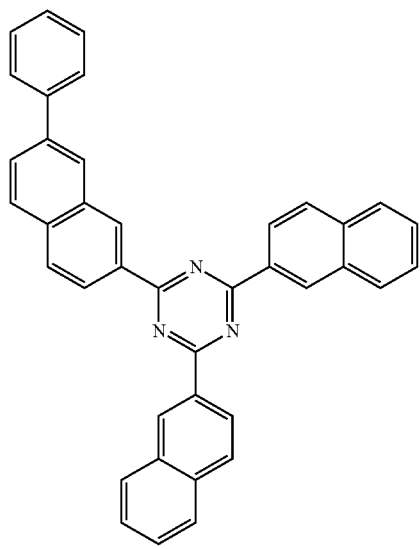
N-127
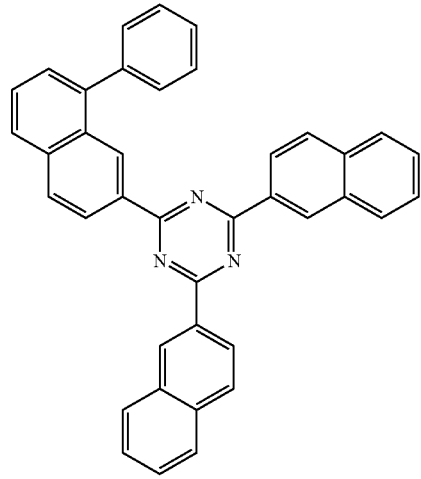
N-128
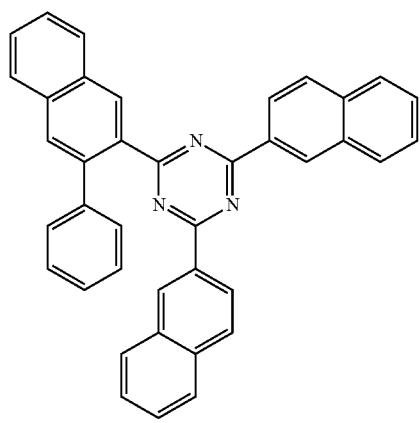
N-129
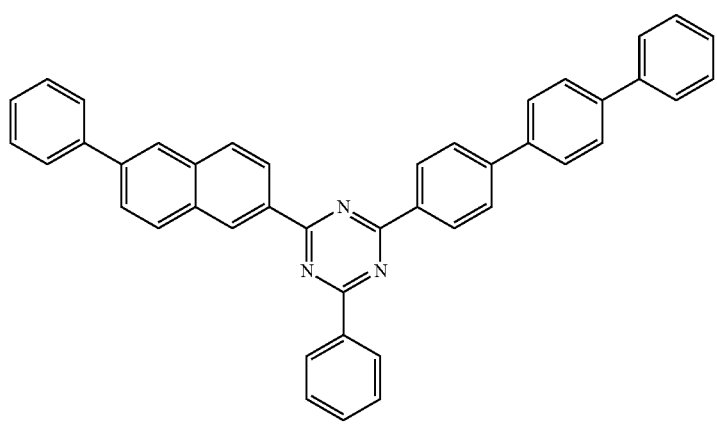

N-130
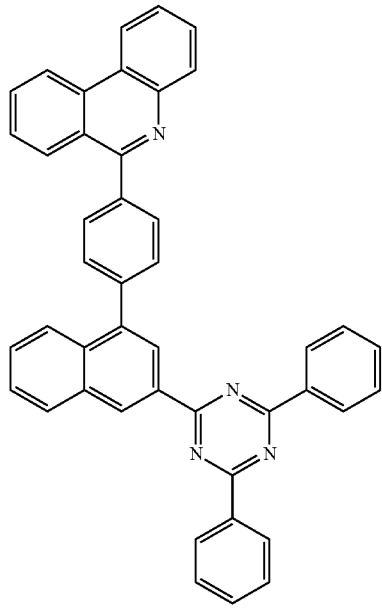
N-131
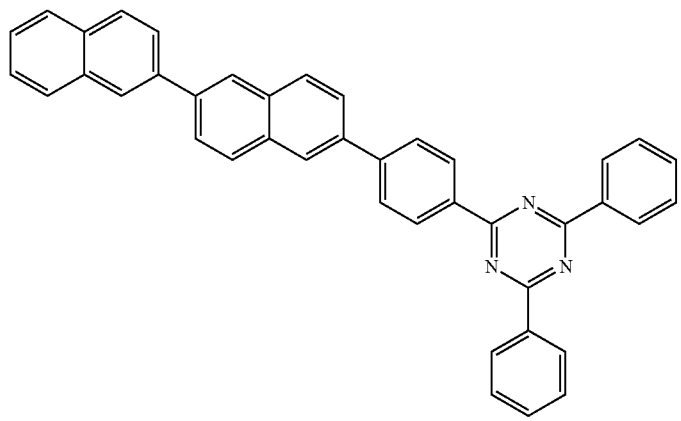
N-132
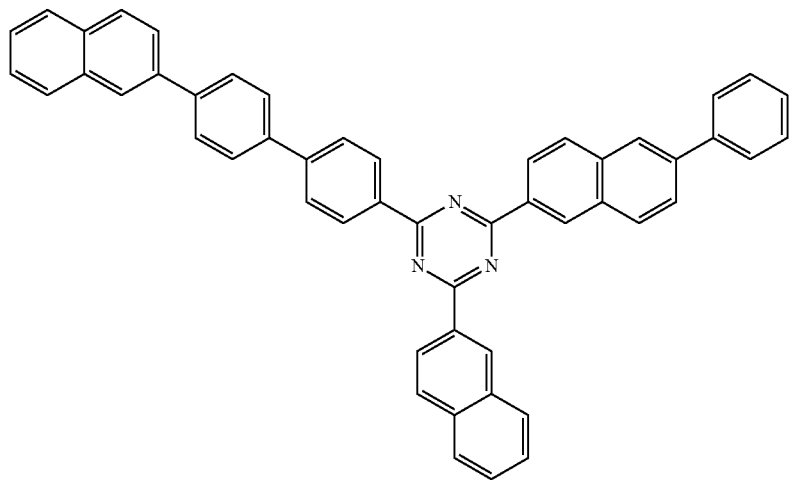

N-133
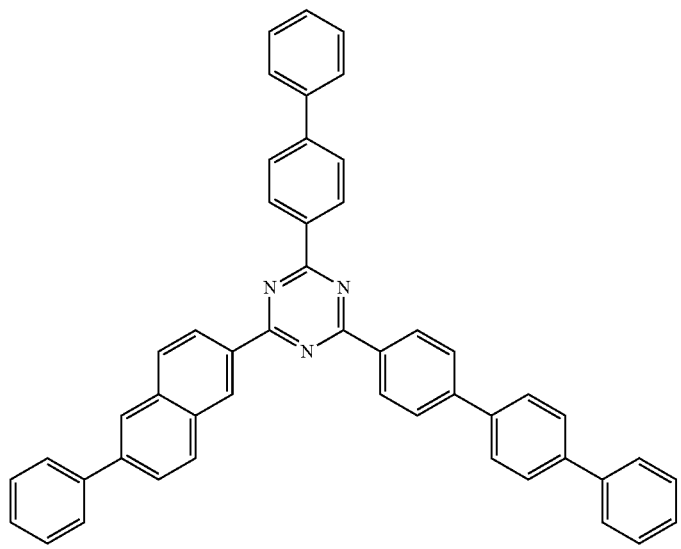
N-134
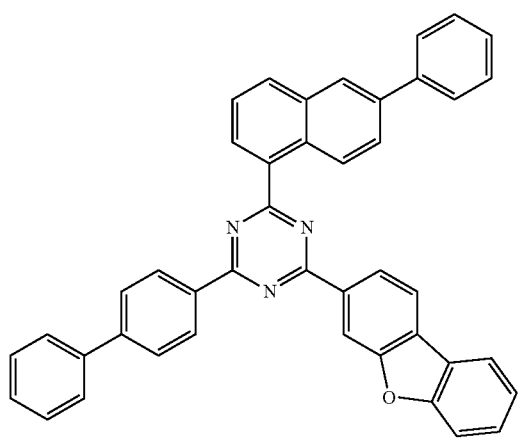
N-135
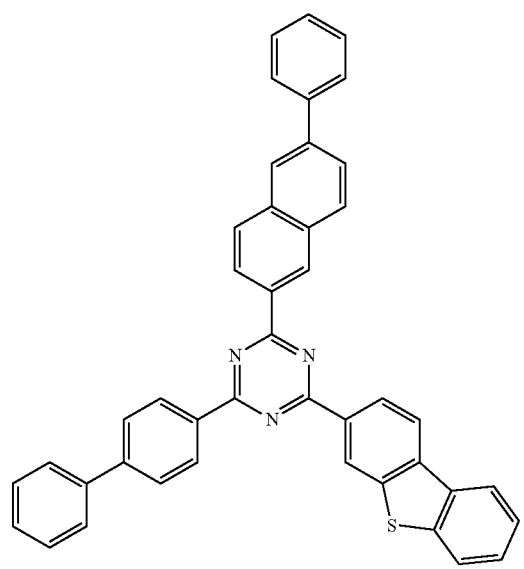

-continued
N-136
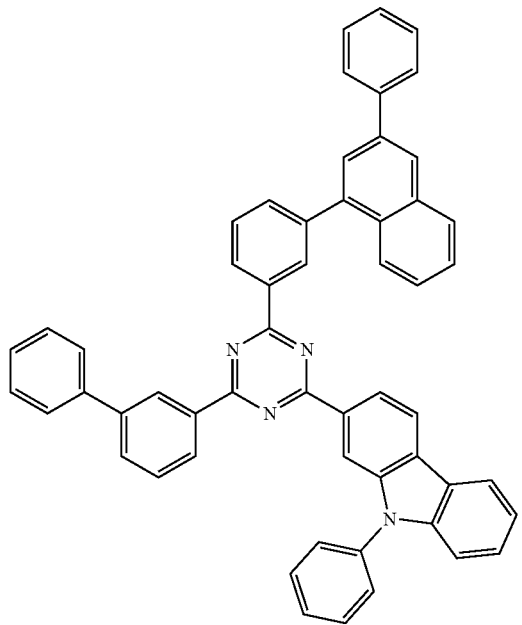
N-137
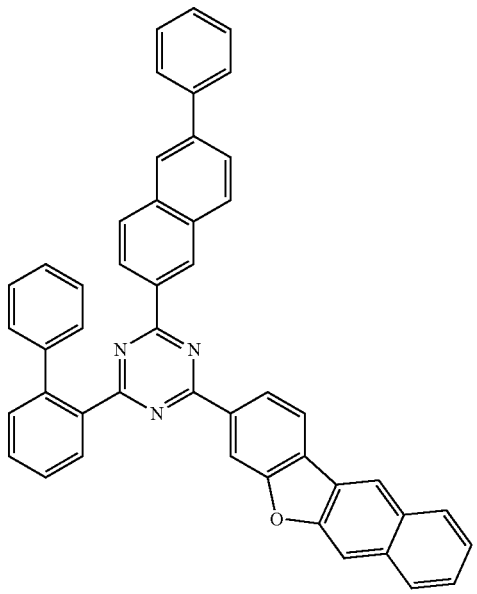
N-138
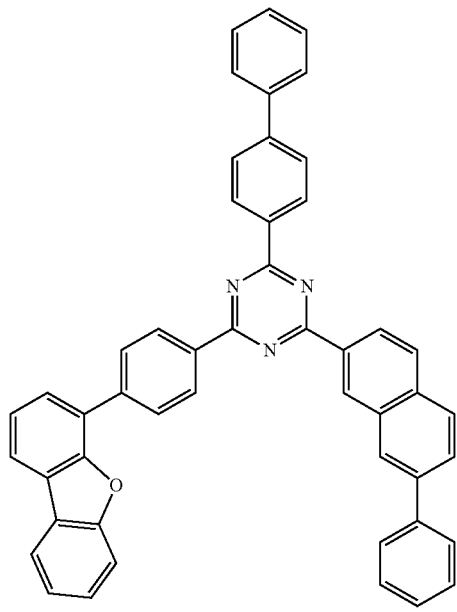
N-139
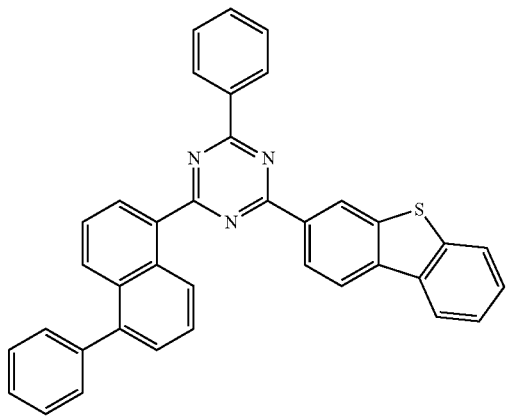

N-140
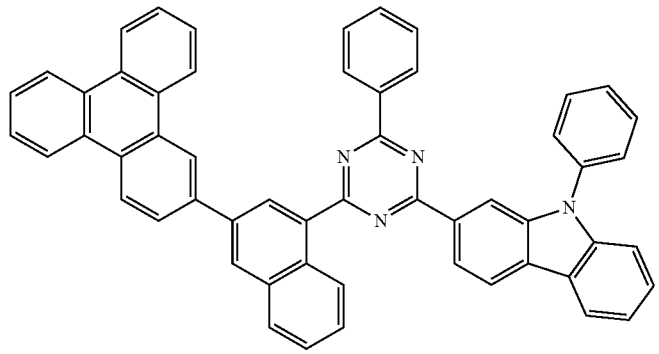
N-141 N-142
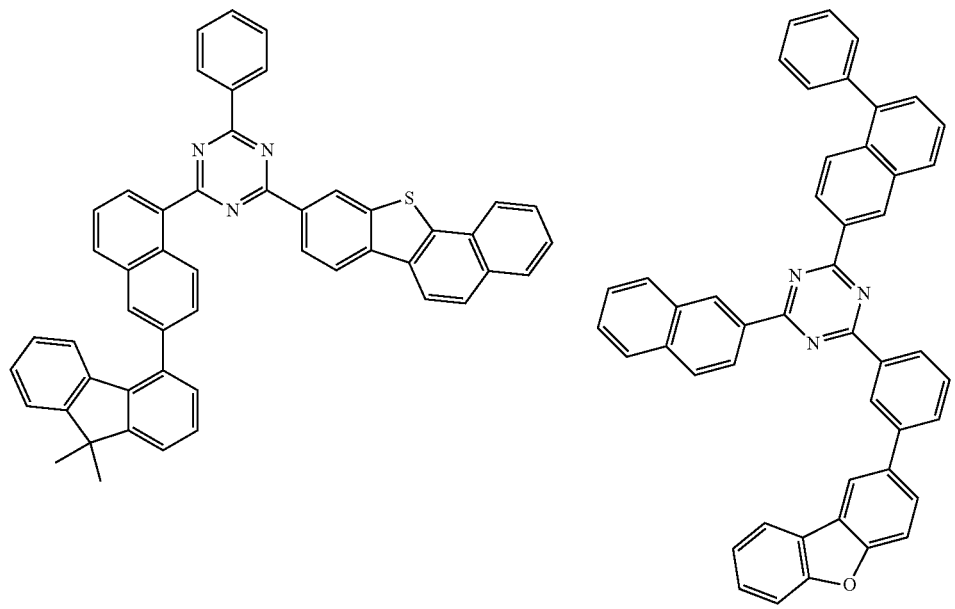
N-143 N-144
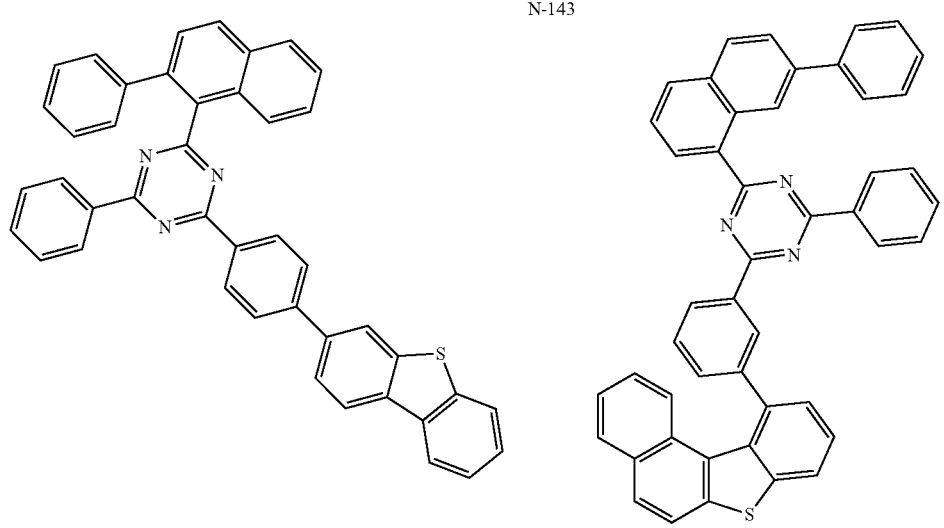

-continued

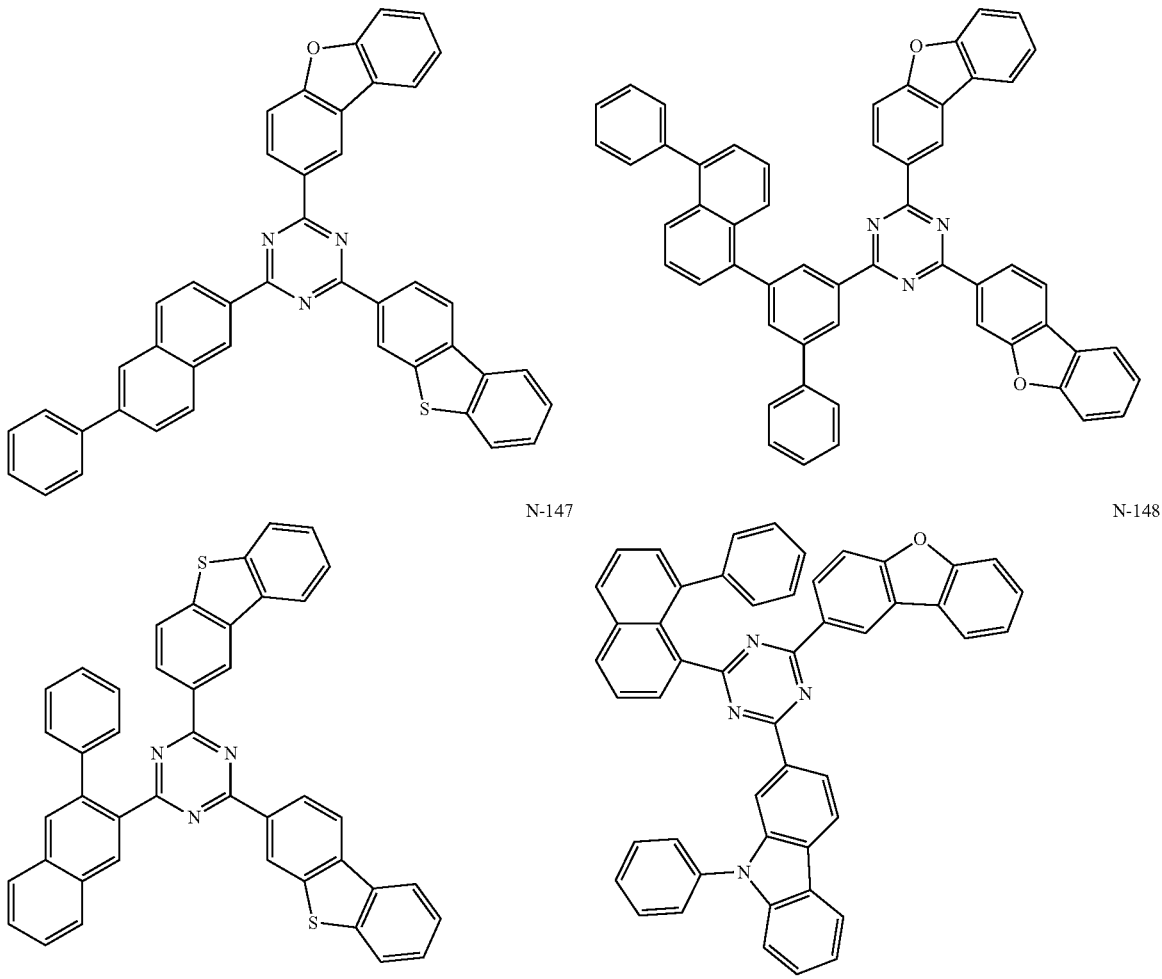

Referring to FIG. 1, the organic electronic element (100) according to the present invention includes a first electrode (110), a second electrode (170), and an organic material layer including a single compound or 2 or more compounds represented by Formula 1 between the first electrode (110) and the second electrode (170). In this case, the first electrode (110) may be an anode, and the second electrode (170) may be a cathode. In the case of an inverted type, the first electrode may be a cathode and the second electrode may be an anode.

Figure 2:
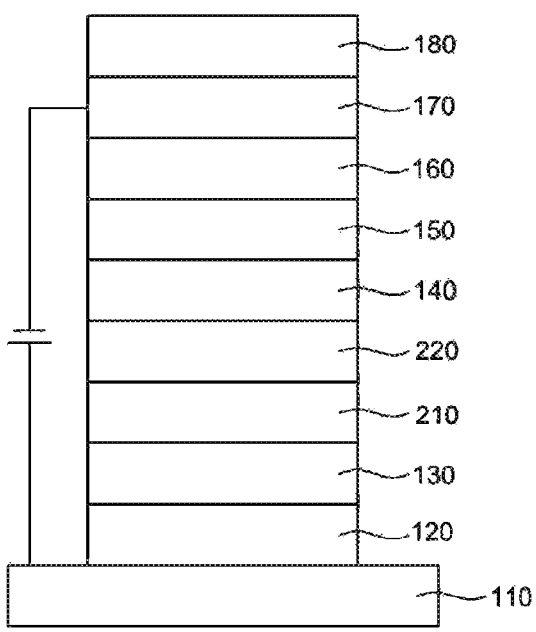

The organic material layer may sequentially include a hole injection layer (120), a hole transport layer (130), an emitting layer (140), an electron transport layer (150), and an electron injection layer (160) on the first electrode (110). In this case, the remaining layers except for the emitting layer (140) may not be formed. It may further include a hole blocking layer, an electron blocking layer, an emitting-auxiliary layer (220), a buffer layer (210), etc. and the electron transport layer (150) and the like may serve as a hole blocking layer. (See FIG. 2)

Also, the organic electronic element according to an embodiment of the present invention may further include a protective layer or a light efficiency enhancing layer (180). The light efficiency enhancing layer may be formed on one of both surfaces of the first electrode not in contact with the organic material layer or on one of both surfaces of the second electrode not in contact with the organic material layer. The compound according to an embodiment of the present invention applied to the organic material layer may be used as a host or dopant of the hole injection layer (120), the hole transport layer (130), the emitting-auxiliary layer (220), electron transport auxiliary layer, the electron transport layer (150), and an electron injection layer (160), the emitting layer (140) or as a material for the light efficiency enhancing layer. Preferably, for example, the compound according to Formula 1 of the present invention may be used as a material of the hole transport layer.

Figure 3:
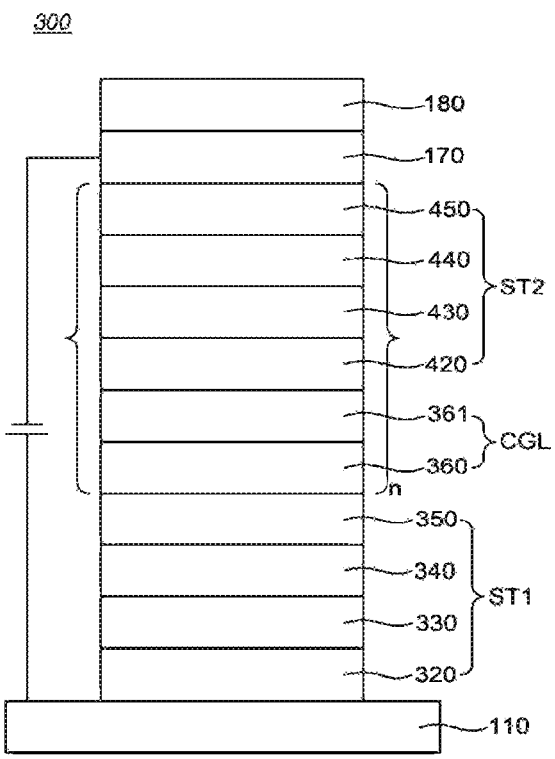
Figure 4:
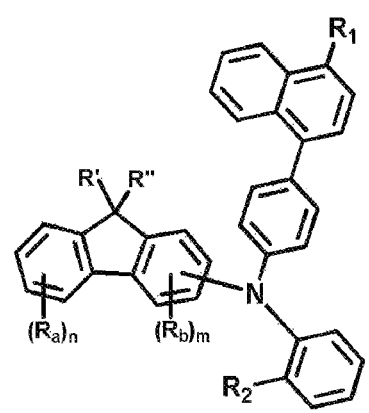
FIG. 4 is a Formula according to an aspect of the present invention.

The organic material layer may include 2 or more stacks including a hole transport layer, an emitting layer and an electron transport layer sequentially formed on the anode, further include a charge generation layer formed between the 2 or more stacks (see FIG. 3).

Otherwise, even with the same core, the band gap, electrical characteristics, interface characteristics, etc. may vary depending on which position the substituent is bonded to, therefore the choice of core and the combination of sub-substituents bound thereto are also very important, and in particular, when the optimal combination of energy levels and T1 values and unique properties of materials (mobility, interfacial characteristics, etc.) of each organic material layer is achieved, a long lifespan and high efficiency can be achieved at the same time.

The organic electroluminescent device according to an embodiment of the present invention may be manufactured using a PVD (physical vapor deposition) method. For example, depositing a metal or a metal oxide having conductivity or an alloy thereof on a substrate to form an anode, and after forming an organic material layer including the hole injection layer(120), the hole transport layer(130), the emitting layer(140), the electron transport layer(150) and the electron injection layer(160) thereon, it can be prepared by depositing a material that can be used as a cathode thereon.

Also, in the present invention, the organic material layer is formed by any one of a spin coating process, a nozzle printing process, an inkjet printing process, a slot coating process, a dip coating process, and a roll-to-roll process, and the organic material layer provides an organic electronic element comprising the compound as an electron transport material.

As another specific example, the same or different compounds of the compound represented by Formula 1 are mixed and used in the organic material layer.

Also, the present invention provides a hole transport layer composition comprising the compound represented by Formula 1, and provides an organic electronic element including the hole transport layer.

Also, the present invention provides an electronic device comprising a display device including the organic electronic element; and a control unit for driving the display device;

In another aspect, the organic electronic element is at least one of an organic electroluminescent device, an organic solar cell, an organic photoreceptor, an organic transistor, and a device for monochromatic or white lighting. At this time, the electronic device may be a current or future wired/wireless communication terminal, and covers all kinds of electronic devices including mobile communication terminals such as mobile phones, a personal digital assistant (PDA), an electronic dictionary, a point-to-multipoint (PMP), a remote controller, a navigation unit, a game player, various kinds of TVs, and various kinds of computers.

Hereinafter, with reference to the structure of Formula 1, the effect according to the structure of the skeleton of the compound of the present invention will be described in more detail.

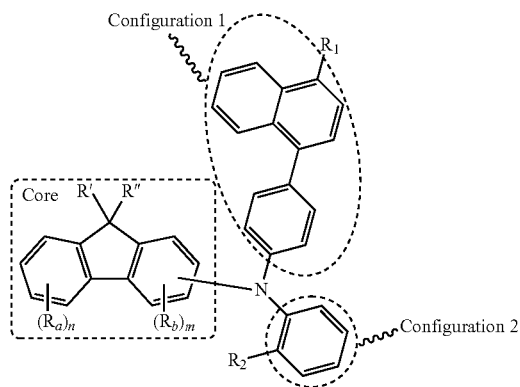

Formula 1

The compound represented by Formula 1 of the present invention may be used as a hole transport layer between the emitting layer and the hole injection layer, when used as a hole transport layer, it is easy to control the rate and amount of hole injection into the emitting layer or the emitting auxiliary layer, and excellent device properties can be exhibited by improving efficiency and lifespan.

In the compound represented by Formula 1 of the present invention, fluorenyl group is a major substituent that determines HOMO (highest occupied molecular orbital) and intermolecular packing when forming a thin film.

Also, in Formula 1 of the present invention, the substituent in the para-position of Configuration 1 and the substituent in the ortho-position of Configuration 2 may be preferably a $C_6$-$C_{25}$ aryl group, more preferably a $C_6$ aryl group (phenyl), due to this, it is possible to control the microscopic properties of the compound structure (HOMO level, stericity, intermolecular distance, T1-BDE).

More specifically, the triplet bond dissociation energy (T1-BDE) value of the molecule exceeds 15.0 kcal/mol, preferably 17.0 kcal/mol, more preferably 17.5 kcal/mol, thereby maximizing the lifespan of the device due to the increase in stability of the compound itself.

Also, in the comparison of similar cores, the luminous efficiency and driving voltage of the element can be improved by increasing the charge mobility by making the average distance between molecules to have a value lower than that of the comparative compound.

It is possible to improve the electrical properties of the element by finely adjusting the properties of the compound so as to achieve optimum efficiency as a hole transport layer through the $R_1$ and $R_2$ substituents having limited substitution positions in the monoamine compound having a fluorenyl core.

Triplet bond dissociation energy (Weakest bond dissociation energy at the first triplet excited state, T1-BDE) is a value calculated through bond dissociation energy in a single molecule, Bond-Dissociation Energy (BDE) is a calculation of the binding energy for acyclic bonds within a molecule. To this end, the electrical potential energy of the target molecule is calculated, and the electrical potential energy for each is calculated by dividing it into 2 radical molecules based on the acyclic bond, and the bond dissociation energy can be expressed as follows.

$$E_{BD} = E_A^{rad} + E_B^{rad} - E_{AB}^{mol}$$

Here, all calculations to obtain the triplet bond dissociation energy proceed to the electrically neutral triplet excited state. In this case, time dependent density functional theory (TD-DFT) was applied to optimize the molecular structure to the triplet excited state.

Molecular dynamics simulation was carried out in a total of four steps, and the first step was carried out at a temperature of 10 Kelvin under conditions of constant volume according to Brownian mechanics. The second step proceeds according to Brownian mechanics as well, but at a temperature of 100 Kelvin under constant atmospheric pressure (1.01325 bar). After that, in the third step, molecular dynamics according to the force field is calculated, and in the same way, it proceeds by 0.1 nanoseconds (ns) at a constant pressure (atmospheric pressure) and temperature (room temperature). Finally, under the same conditions as the third step (atmospheric pressure, room temperature), the molecular dynamics process is performed in units of 2 femtoseconds (fs), and the simulation is performed until a certain amount of time is required. In this case, the predetermined time means a time period for the amorphous solid structure to sufficiently reach an equilibrium state, preferably from several hundred nanoseconds to several thousand nanoseconds, more preferably from 100 nanoseconds to 150 nanoseconds, and even more preferably 120 nanoseconds. After that, structural data at the final time point are extracted, and some monomolecules are extracted (sampling) from the corresponding structure. The single-point energy calculation for a single molecule extracted through quantum mechanics simulation is carried out, and the bond dissociation energy for the acyclic bond within the molecule is calculated. All the obtained bond dissociation energy values are taken to form a bond dissociation energy set G={E1 ... EN}, and the average value of the bond dissociation energy set is used as an indicator of the bond dissociation energy of the solid state material.

In the present invention, the unit of the average bond dissociation energy value in the amorphous solid phase is eV, and can be converted to kcal/mol unit by multiplying the eV value by 23.061.

Assuming that the molecules in the amorphous solid state are sufficiently uniformly distributed, the average distance between molecules in amorphous solid is expressed as the following equation.

$$\bar{d} = \sqrt[3]{V/N}$$

where $\bar{d}$ is the average distance between molecules, V is the volume of the amorphous solid, and N is the number of molecules in the amorphous solid.

Here, the molecular dynamics simulation was carried out by arranging a certain number of [128] monomolecules in a unit cell with periodic repeat boundary conditions (PBC), so in the above equation, the volume and the number of molecules can be set as the volume in the PBC region (Bulk volume) and the number of molecules present therein [128], respectively.

Intermolecular distance and charge mobility are important correlation factors for explaining the progress of the compound of Formula 1 of the present invention, hereinafter, charge mobility will be described.

In the generalized effective medium model (GE MM), the charge mobility for a uniform medium can be obtained from the analytical solution of the Master equation according to the effective medium approximation, and the equation is expressed as follows.

$$\mu = \frac{e\beta M \langle H_{ab} \rangle}{n\hbar\sqrt{\lambda}} \sqrt{\frac{\pi\beta}{1 + \frac{\beta\sigma^2}{\lambda}}} \exp[-C((\beta\sigma)^2 - \beta\lambda)]$$

Here, e is the amount of charge, $\beta$ is a thermodynamic constant given by the Boltzmann constant and the reciprocal of temperature ($1/k_BT$), M is average number of nearest-neighbor molecules, $H_{ab}$ is the charge transfer matrix element, n is the charge transfer dimension (n=3 in 3D), $\hbar$ is the Planck constant, $\lambda$ is the reorganization energy, $\sigma$ is a disorder parameter, C is the correction constant. Therefore, the charge mobility has the following proportional relationship.

$$\mu \propto \frac{\langle H_{ab}^2 \rangle}{\sqrt{\lambda + \beta\sigma^2}} \exp(-\beta\lambda)$$

If it is assumed that the molecules in the amorphous solid state are sufficiently uniformly distributed ($\sigma \ll 1$), the charge transfer matrix element ($H_{ab}$) between each dimer is constant sn the above proportional expression can be expressed as follows.

$$\mu \propto \frac{H_{ab}^2}{\sqrt{\lambda}} \exp(-\beta\lambda)$$

In this case, it is known a priori that the charge transfer matrix element has a proportional relationship with the intermolecular distance as follows.

$$H_{ab} \propto \exp(-\eta/2r)$$

where $\eta$ is the decay constant and r is the intermolecular distance. Therefore, for a uniform medium, the charge mobility has a relationship that is proportional to the exponential decay with respect to the intermolecular distance, and as the intermolecular distance is shorter, the charge mobility tends to increase.

The density of the highest occupied molecular orbital states (HOMO) undergoes molecular dynamics simulation to obtain an amorphous solid structure in an equilibrium state. After that, single-point energy (SPE) is calculated by extracting a single molecule in the last state to calculate the HOMO level of each molecule. The calculated HOMO level is histogram plotted to obtain a HOMO distribution, and the median and full-width at half-maximum are obtained by fitting the distribution with a Gaussian function.

Figure 5:
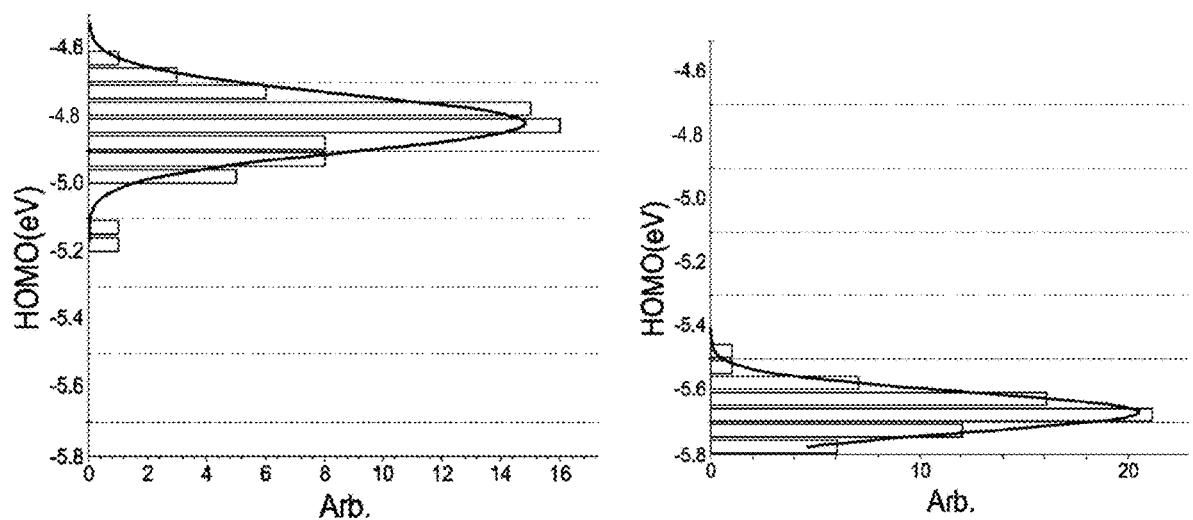
FIG. 5 is an exemplary diagram of HOMO DOS.
Figure 5:
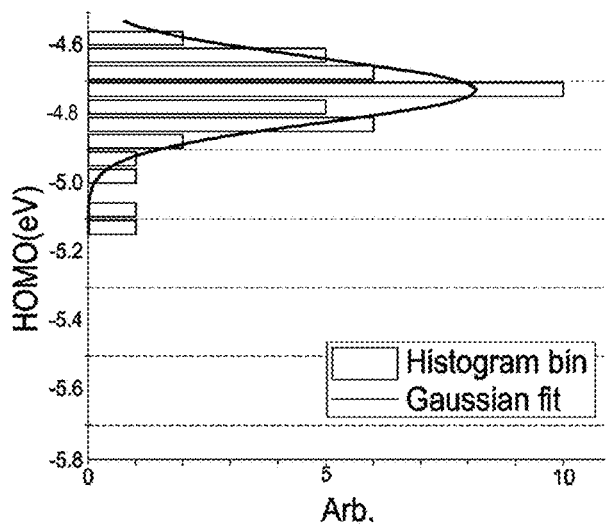

In detail, unlike an ideal gaseous state, molecules in an amorphous solid state are transformed the conformation due to interactions between different molecules. Due to this, the shape that a molecule can have is given as a Gaussian distribution function. Accordingly, the HOMO and LUMO levels of each molecule also exist in a Gaussian distribution instead of a single value, and in particular, the HOMO level distribution is defined as Density of the highest occupied molecular orbital states (HOMO DOS). Therefore, the HOMO level of the molecule in the amorphous solid state is defined as the full-width at half-maximum (FWHM) and the median of the normalized HOMO DOS (refer to FIG. 5).

Meanwhile, according to Marcus theory, the charge transfer rate (CTR) between two different molecules has the following proportional relationship.

$$k \propto \exp\left(-\frac{(\lambda + \Delta G)^2}{4\lambda k_B T}\right)$$

Figure 6:
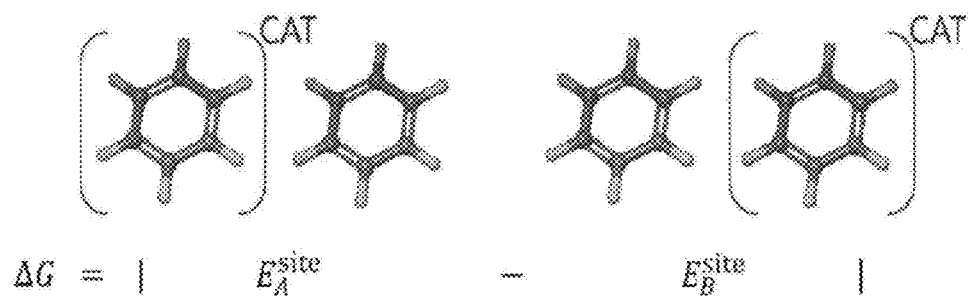
FIG. 6 is an exemplary diagram of state energy.

Here, k is the charge transfer rate, $\lambda$ is the rearrangement energy, $\Delta G$ is the site energy difference (SED), $k_B$ is the Boltzmann constant, T is the absolute temperature. Here, the smaller $\Delta G$, the higher the charge transfer rate. If a hole is transported, $\Delta G$ corresponds to the energy difference between the two states in which the monomolecules constituting the biomolecules exist as positive ions, respectively (refer to FIG. 6)

That is, $\Delta G$ approximately corresponds to the difference in the ionization potential of each molecule, which can be expressed as the difference in the absolute value of the HOMO level of each molecule according to Koopmans' theorem.

Therefore, comparing the HOMO DOS of different amorphous solids, the overlapping region is the region where Ä $\Delta G=0$, that is, the region where the charge transfer rate is maximized. Since HOMO DOS follows a normalized Gaussian distribution, the area of the overlapping region has a value of from 0 to 1, and it can be seen that the higher the value, the better the charge injection characteristics between different layers. In general, the wider the full-width at half-maximum of the DOS, the wider the area overlapped with other layers, so it can be seen that the injection characteristics are advantageous.

All the above calculations were made through molecular simulation (Gaussian09 Rev. C.01, Schrodinger Materials Science Suite 4.1.161), and the Desmond package was used for molecular dynamics simulation. By extracting a single molecule from the structure obtained through molecular dynamics simulation, quantum chemical properties based on the first principle were calculated under the conditions of B3LYP/6-31G(d) or B3LYP/6-31G*, Gaussian and Jaguar packages were used in this process.

Hereinafter, a synthesis example of the compound represented by Formula 1 of the present invention and a manufacturing example of an organic electric device of the present invention will be described in detail with reference to Examples, but the present invention is not limited to the following Examples.

SYNTHESIS EXAMPLE 1

Synthesis of Formula 1

The compound (final product) represented by Formula 1 according to the present invention is synthesized as shown in Reaction Scheme 1, but is not limited thereto. Here, Hal is I, Br or Cl.

Wherein $R_1$, $R_2$, R', R", $R_a$, $R_b$, m and n are the same as defined above.

An example of Sub 1 is as follows, but is not limited thereto. Table 1 below shows FD-MS (Field Desorption-Mass Spectrometry) values of some compounds belonging to Sub 1.

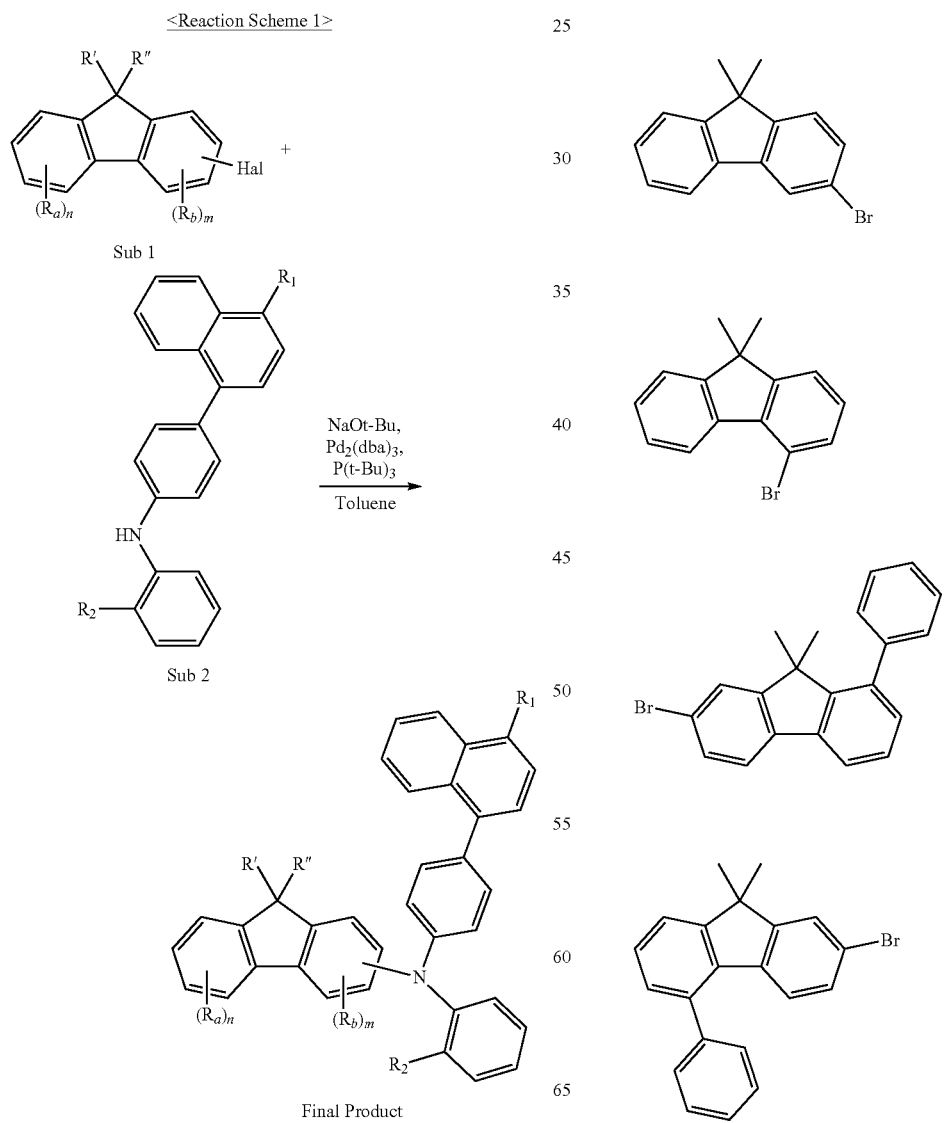

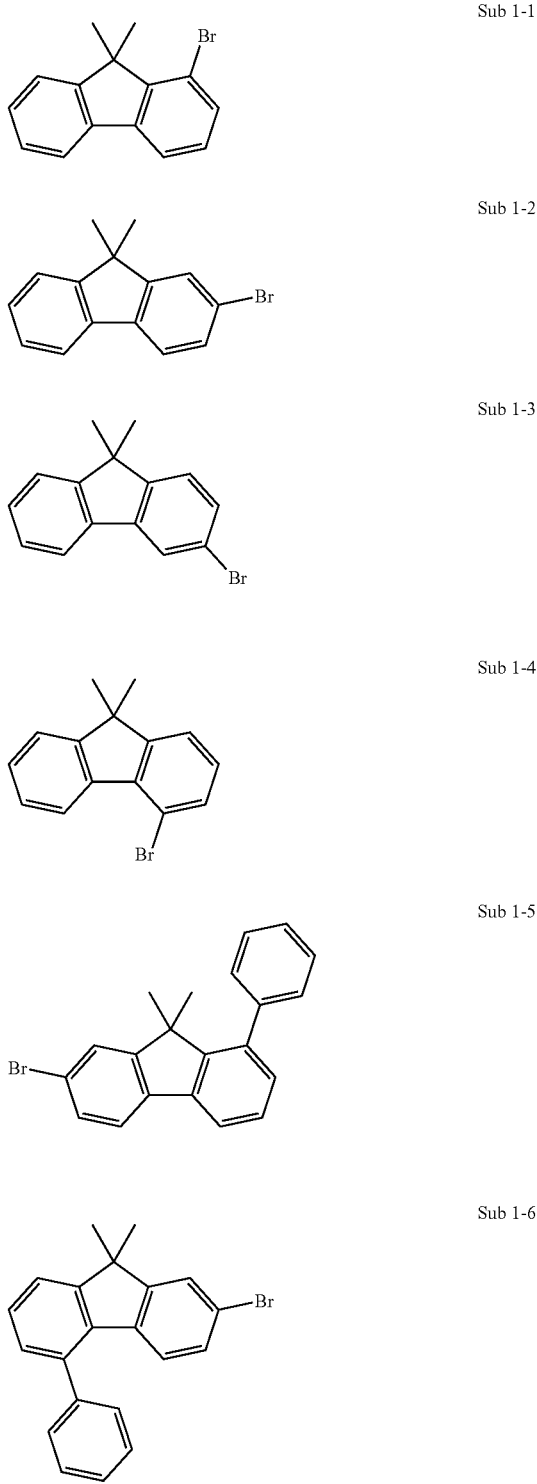

279
-continued
Sub 1-7
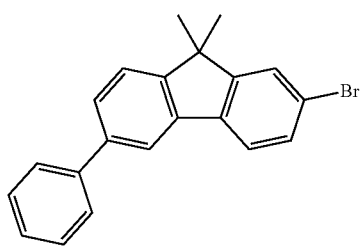
Sub 1-8
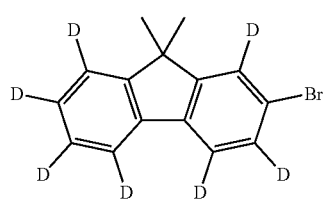
Sub 1-9
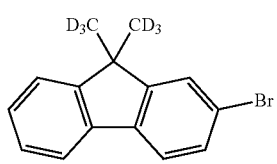
Sub 1-10
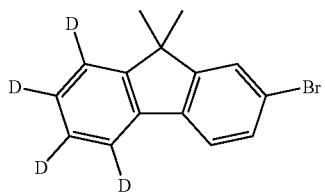
Sub 1-11
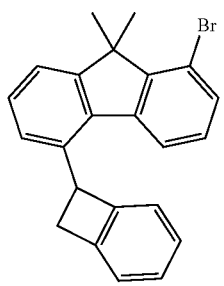
Sub 1-12
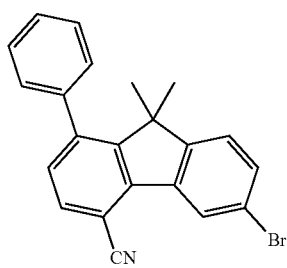
280
-continued
Sub 1-13
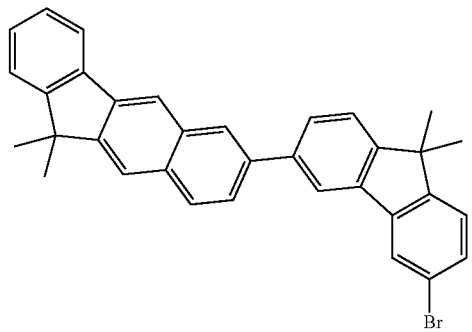
Sub 1-14
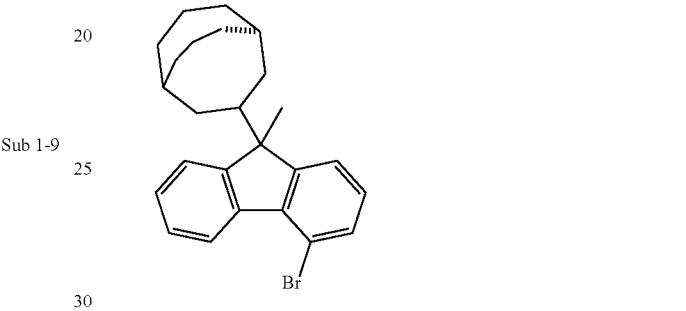
Sub 1-15
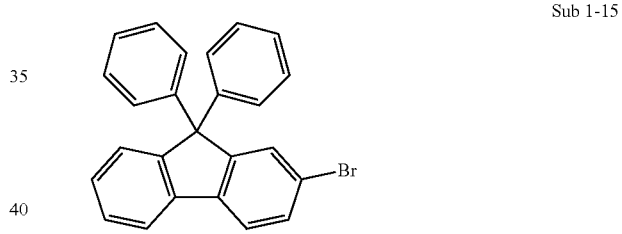
Sub 1-16
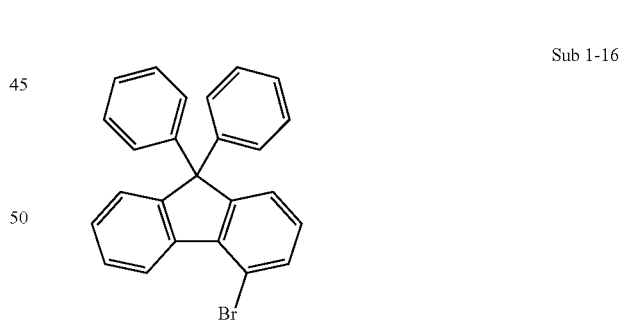
Sub 1-17
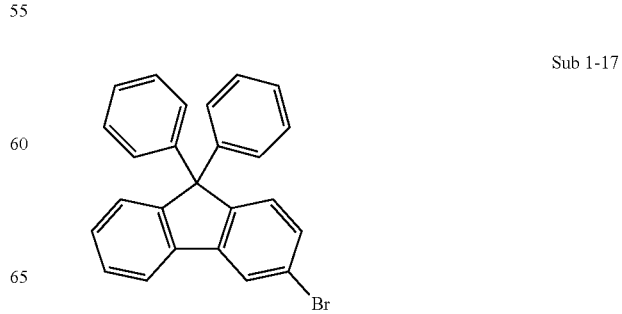

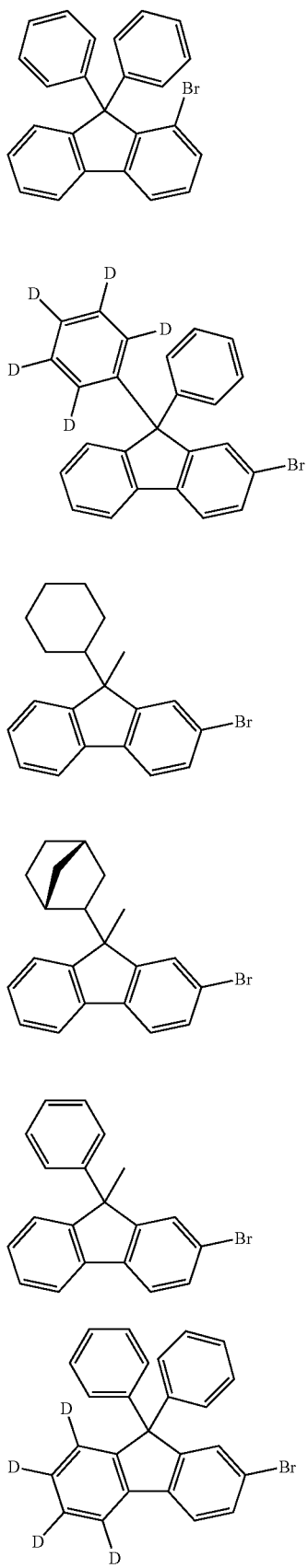
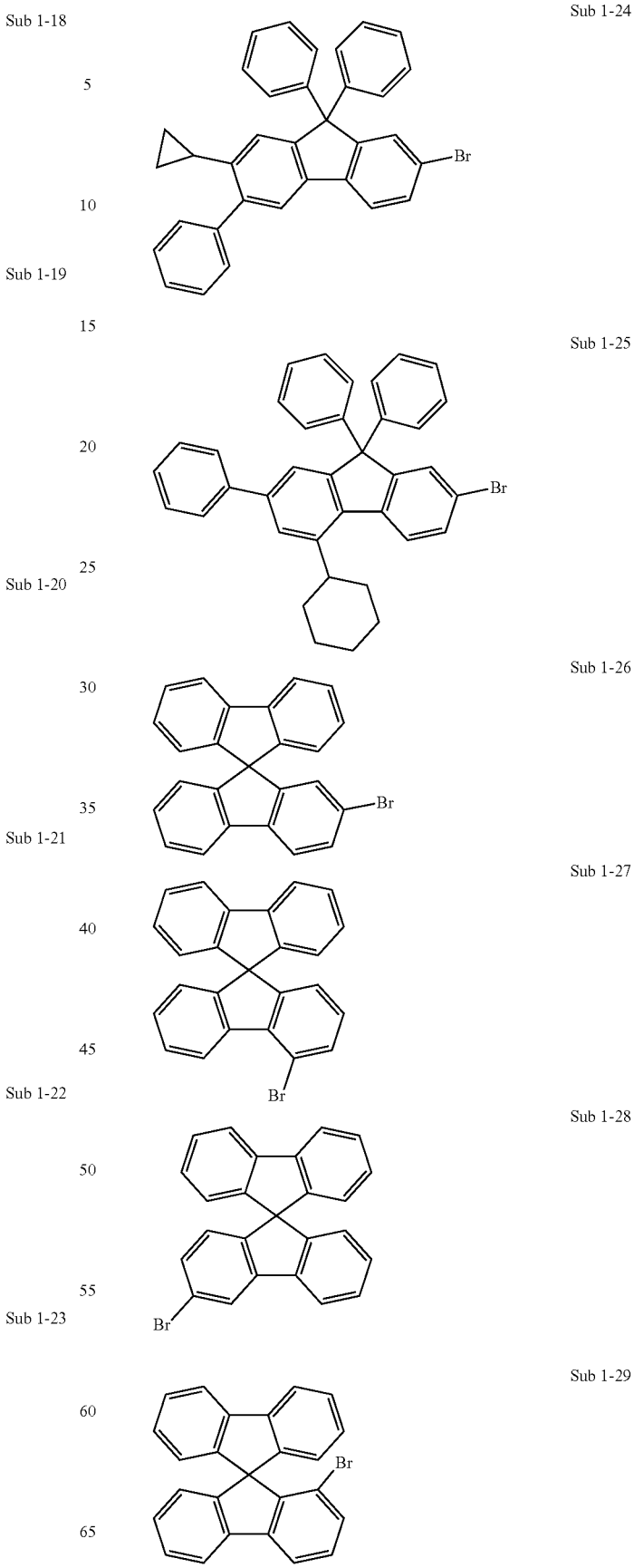

-continued
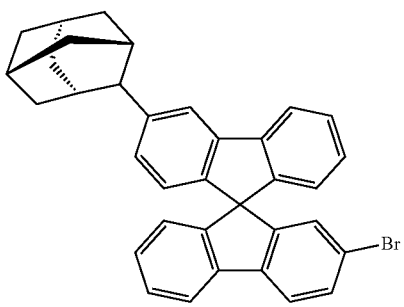
Sub 1-30
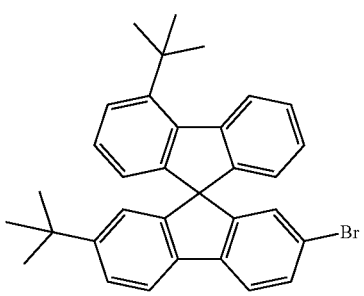
Sub 1-31
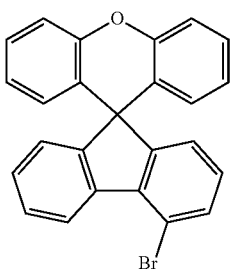
Sub 1-32
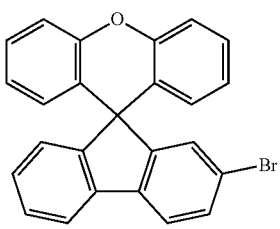
Sub 1-33
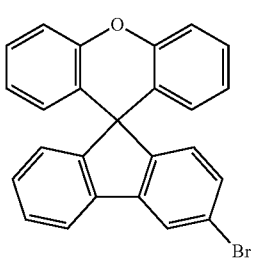
Sub 1-34
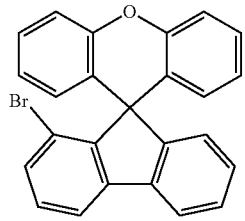
Sub 1-35
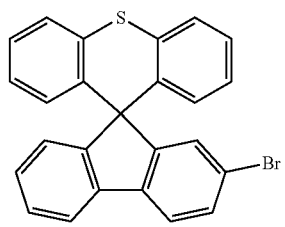
Sub 1-36
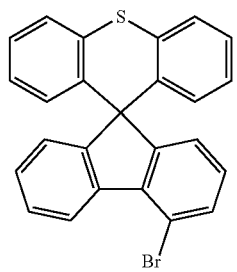
Sub 1-37
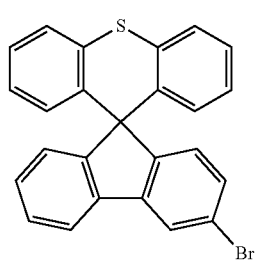
Sub 1-38
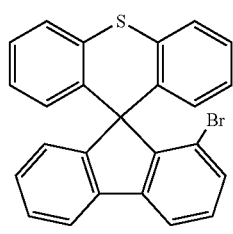
Sub 1-39

TABLE 1

| compound | FD-MS | compound | FD-MS |
|---|---|---|---|
| Sub 1-1 | m/z = 272.02($C_{15}H_{13}Br$ = 273.17) | Sub 1-2 | m/z = 272.02($C_{15}H_{13}Br$ = 273.17) |
| Sub 1-3 | m/z = 272.02($C_{15}H_{13}Br$ = 273.17) | Sub 1-4 | m/z = 272.02($C_{15}H_{13}Br$ = 273.17) |
| Sub 1-5 | m/z = 348.05($C_{21}H_{17}Br$ = 349.27) | Sub 1-6 | m/z = 348.05($C_{21}H_{17}Br$ = 349.27) |
| Sub 1-7 | m/z = 348.05($C_{21}H_{17}Br$ = 349.27) | Sub 1-8 | m/z = 279.06($C_{15}H_6D_7Br$ = 280.22) |
| Sub 1-9 | m/z = 278.06($C_{15}H_7D_6Br$ = 279.21) | Sub 1-10 | m/z = 276.05($C_{15}H_9D_4Br$ = 2772) |
| Sub 1-11 | m/z = 374.07($C_{23}H_{19}Br$ = 375.31) | Sub 1-12 | m/z = 373.05($C_{25}H_{16}BrN$ = 374.28) |
| Sub 1-13 | m/z = 514.13($C_{34}H_{27}Br$ = 515.49) | Sub 1-14 | m/z = 408.15($C_{25}H_{29}Br$ = 409.41) |
| Sub 1-15 | m/z = 396.05($C_{25}H_{17}Br$ = 397.32) | Sub 1-16 | m/z = 396.05($C_{25}H_{17}Br$ = 397.32) |
| Sub 1-17 | m/z = 396.05($C_{25}H_{17}Br$ = 397.32) | Sub 1-18 | m/z = 396.05($C_{25}H_{17}Br$ = 397.32) |
| Sub 1-19 | m/z = 401.08($C_{25}H_{12}D_5Br$ = 402.35) | Sub 1-20 | m/z = 340.08($C_{20}H_{21}Br$ = 341.29) |
| Sub 1-21 | m/z = 352.08($C_{21}H_{21}Br$ = 353.3) | Sub 1-22 | m/z = 334.04($C_{20}H_{15}Br$ = 335.24) |
| Sub 1-23 | m/z = 400.08($C_{25}H_{13}D_4Br$ = 401.34) | Sub 1-24 | m/z = 512.11($C_{34}H_{25}Br$ = 513.48) |
| Sub 1-25 | m/z = 554.16($C_{37}H_{31}Br$ = 555.56) | Sub 1-26 | m/z = 394.04($C_{25}H_{15}Br$ = 395.3) |
| Sub 1-27 | m/z = 394.04($C_{25}H_{15}Br$ = 395.3) | Sub 1-28 | m/z = 394.04($C_{25}H_{15}Br$ = 395.3) |
| Sub 1-29 | m/z = 394.04($C_{25}H_{15}Br$ = 395.3) | Sub 1-30 | m/z = 528.15($C_{35}H_{29}Br$ = 529.52) |
| Sub 1-31 | m/z = 410.03($C_{25}H_{15}BrO$ = 411.3) | Sub 1-32 | m/z = 410.03($C_{25}H_{15}BrO$ = 411.3) |
| Sub 1-33 | m/z = 410.03($C_{25}H_{15}BrO$ = 411.3) | Sub 1-34 | m/z = 410.03($C_{25}H_{15}BrO$ = 411.3) |
| Sub 1-35 | m/z = 410.03($C_{25}H_{15}BrO$ = 411.3) | Sub 1-36 | m/z = 426.01($C_{25}H_{15}BrS$ = 427.36) |
| Sub 1-37 | m/z = 426.01($C_{25}H_{15}BrS$ = 427.36) | Sub 1-38 | m/z = 426.01($C_{25}H_{15}BrS$ = 427.36) |
| Sub 1-39 | m/z = 426.01($C_{25}H_{15}BrS$ = 427.36) | | |

II. Example of Sub 2

Sub 2 of Reaction Scheme 1 may be synthesized as shown in Reaction Scheme 2 below, but is not limited thereto.

The Sub 2-I may be synthesized by Reaction Scheme 3, but is not limited thereto.

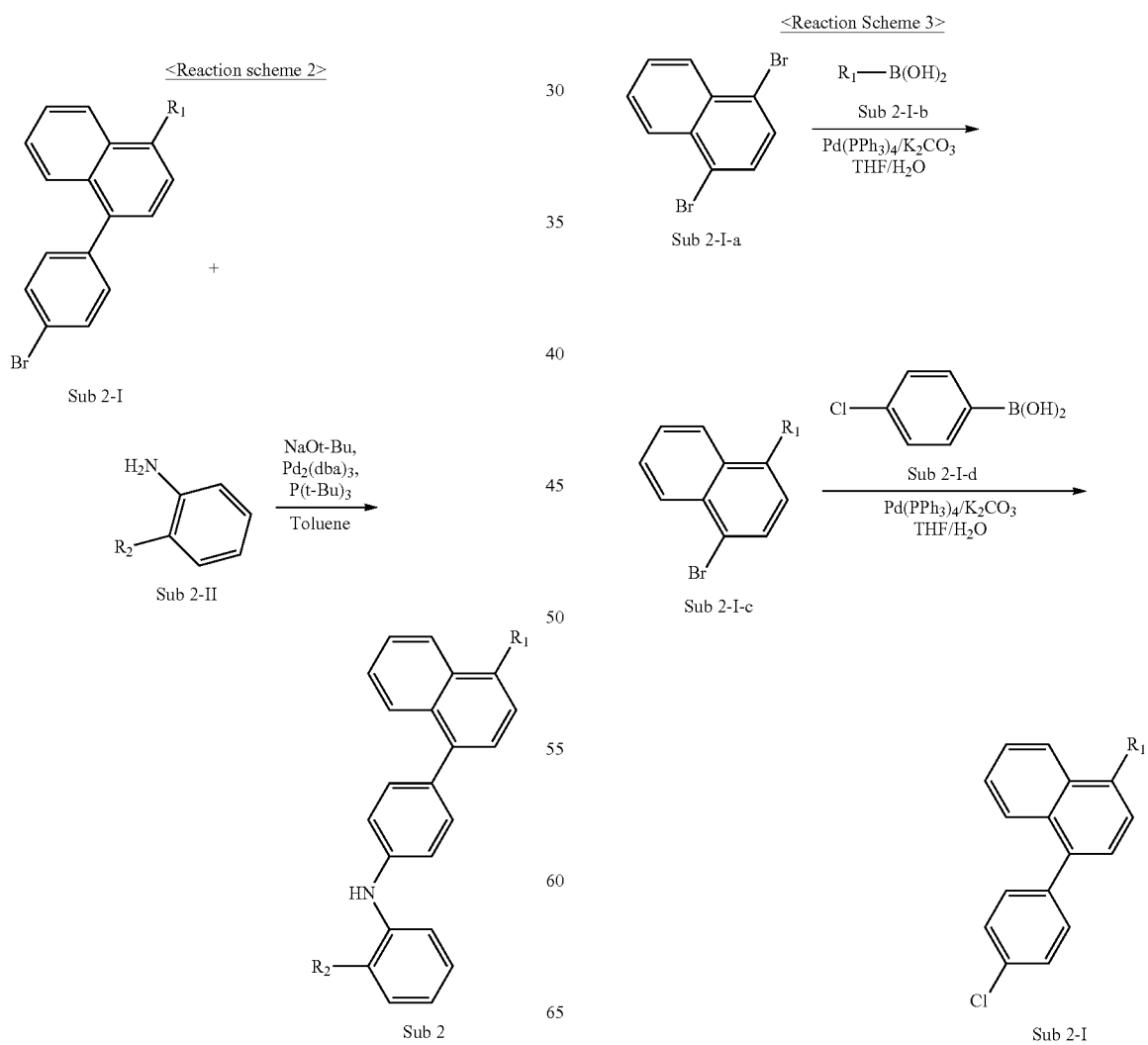

1. Synthesis Example of Sub 2-1

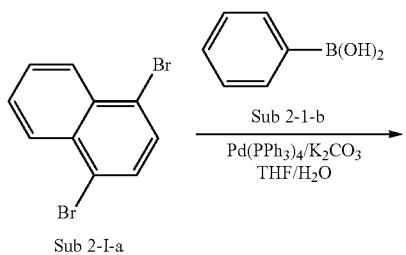

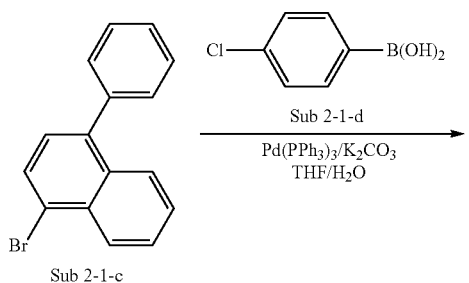

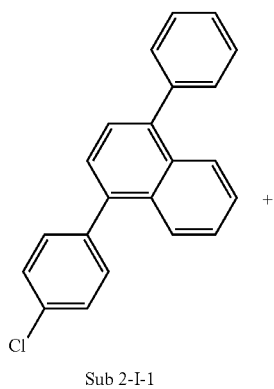

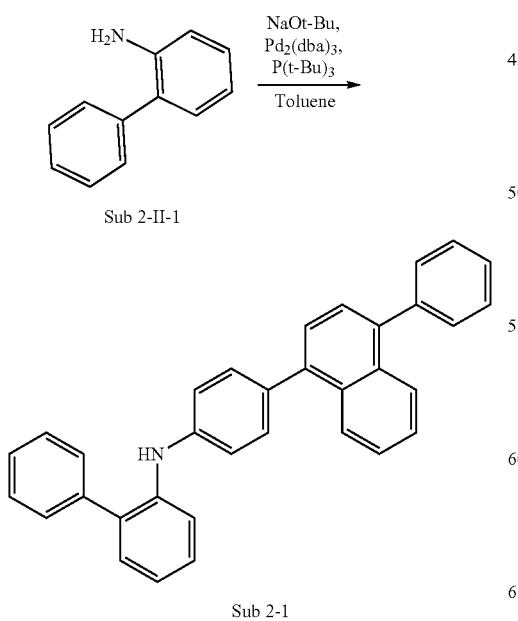

(1) Synthesis Example of Sub 2-1-c

Sub 2-1-b (14.9 g, 122.4 mmol), Pd(PPh$_3$)$_4$ (0.05 equiv.), K$_2$C$_3$ (3 equiv.), THF/H$_2$O (408 ml/204 ml) were added to Sub 2-1-a (35 g, 122.4 mmol), and refluxed for 12 hours. When the reaction is completed, the temperature of the reactant is cooled to room temperature, and THF is removed. It was extracted with MC and washed with water. After the organic layer was dried over MgSO$_4$ and concentrated, the resulting organic material was separated using a silicagel column to obtain 29.5 g of Sub 2-1-c. (Yield: 85.1%)

(2) Synthesis Example of Sub 2-I-1

Sub 2-1-d (16.3 g, 104.2 mmol), Pd(PPh$_3$)$_4$ (0.05 equiv.), K$_2$CO$_3$ (3 equiv.), THF/H$_2$O (347 ml/174 ml) were added to Sub 2-1-c (29.5 g, 104.2 mmol) synthesized in the above synthesis example, and 26.7 g of Sub 2-I-1 was obtained using the above synthesis method. (Yield: 81.4%)

(3) Synthesis Example of Sub 2-1

Sub 2-I-1 (26.7 g, 84.8 mmol) was added to toluene (869 ml), Sub 2-II-1 (15.1 g, 89.1 mmol), Pd$_2$(dba)$_3$ (0.03 equiv), P(t-Bu))$_3$ (0.06 equiv), NaOt-Bu (3 equiv) were added and stirred at 100° C. When the reaction was completed, the mixture was extracted with CH$_2$Cl$_2$ and water, the organic layer was dried over MgSO$_4$, concentrated, and the resulting compound was recrystallized by silicagel column to obtain 31.2 g of Sub 2-1. (Yield: 82.3%)

2. Synthesis Example of Sub 2-4

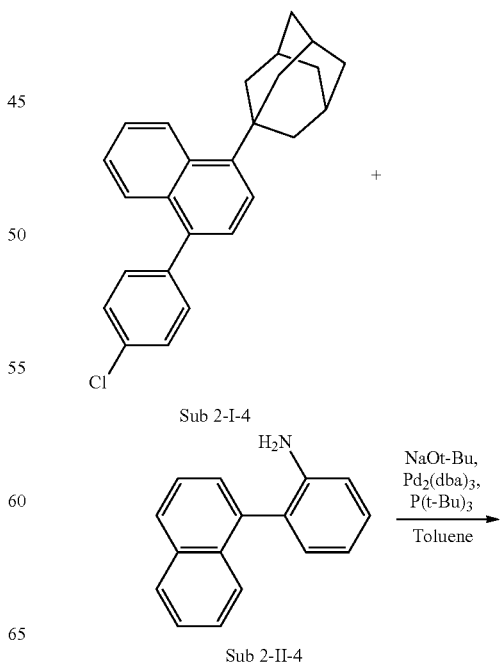

-continued

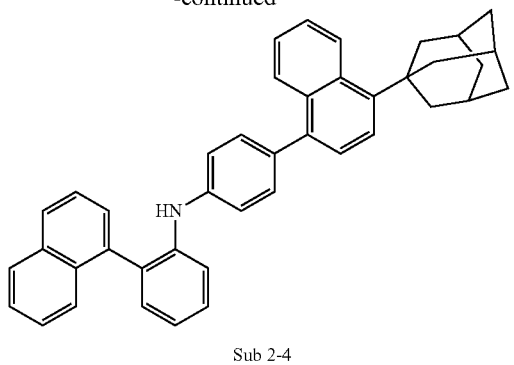

Sub 2-4

Sub 2-II-4 (15.4 g, 70.4 mmol), Pd₂(dba)₃ (0.03 equiv), P(t-Bu)₃ (0.06 equiv), NaOt-Bu (3 equiv.) and Toluene (687 ml) were added to Sub 2-I-4 (25 g, 67 mmol) and Sub 2-4 30.1 g (yield: 80.7%) was obtained by using Sub 2-1 synthesis method.

3. Synthesis Example of Sub 2-5

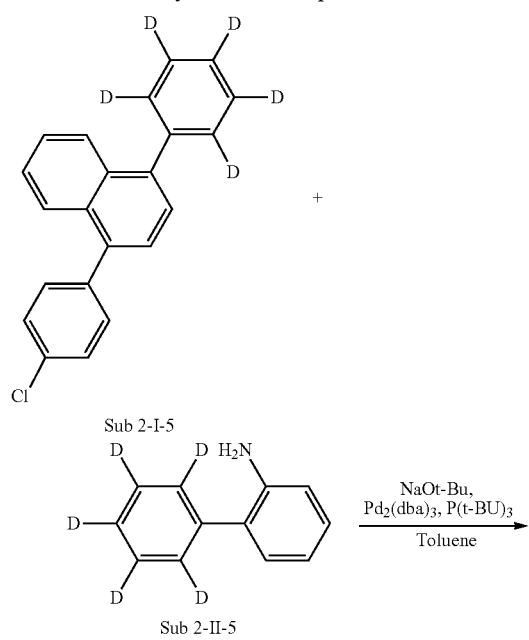

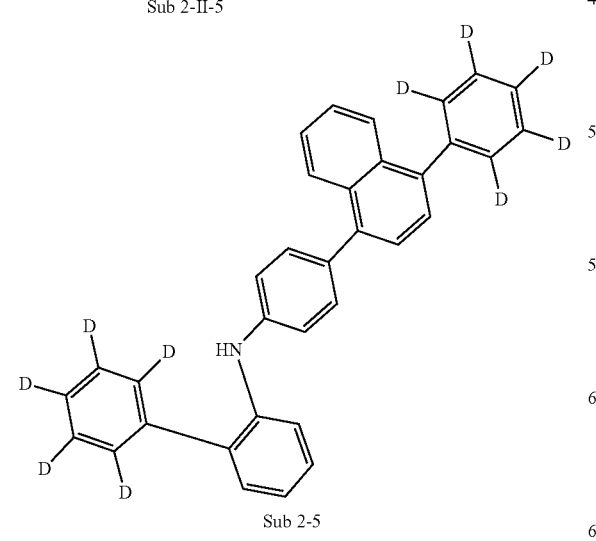

Sub 2-5

Sub 2-II-5 (12.6 g, 72.2 mmol), Pd₂(dba)₃ (0.03 equiv.), P(t-Bu)₃ (0.06 equiv.), NaOt-Bu (3 equiv.), Toluene (705 ml) were added to Sub 2-I-5 (22 g, 68.8 mmol), and 25.5 g (yield: 81%) of Sub 2-5 was obtained by using Sub 2-1 synthesis method.

4. Synthesis Example of Sub 2-19

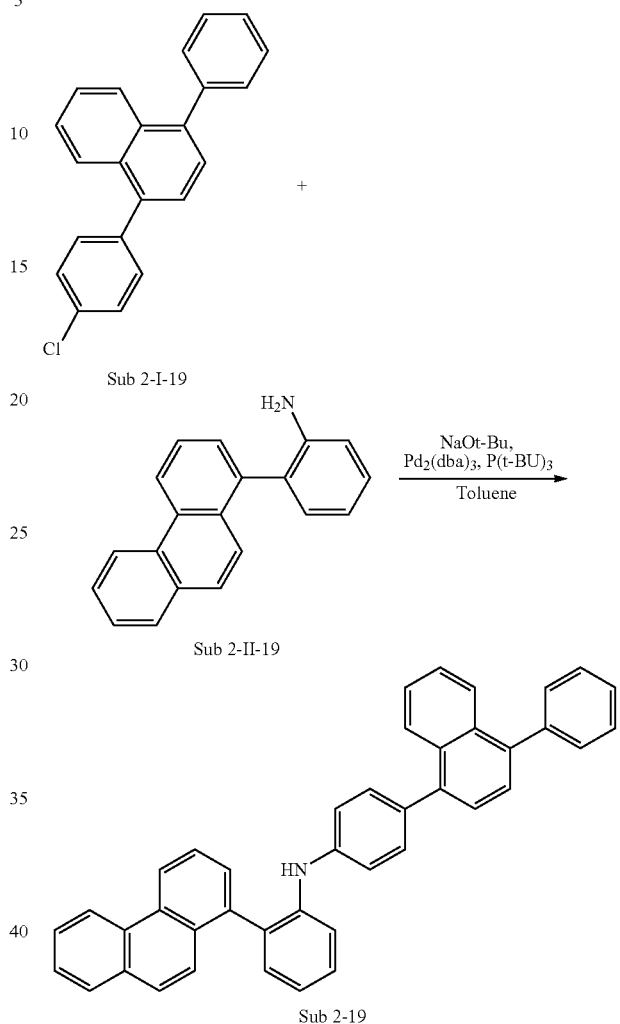

Sub 2-19

Sub 2-II-19 (20.6 g, 76.7 mmol), Pd₂(dba)₃ (0.03 equiv.), P(t-Bu)₃ (0.06 equiv.), NaOt-Bu (3 equiv.), Toluene (749 ml) were added to Sub 2-I-19 (23 g, 73.1 mmol), and 32.2 g (yield: 80.5%) of Sub 2-19 was obtained by using Sub 2-1 synthesis method.

5. Synthesis example of Sub 2-28

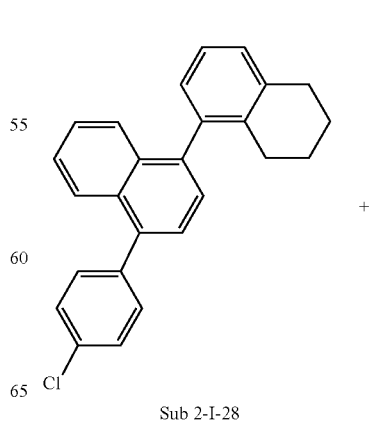

Sub 2-I-28

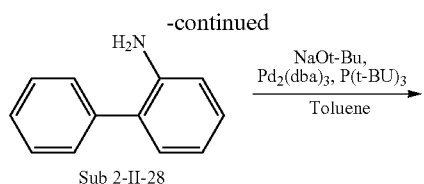

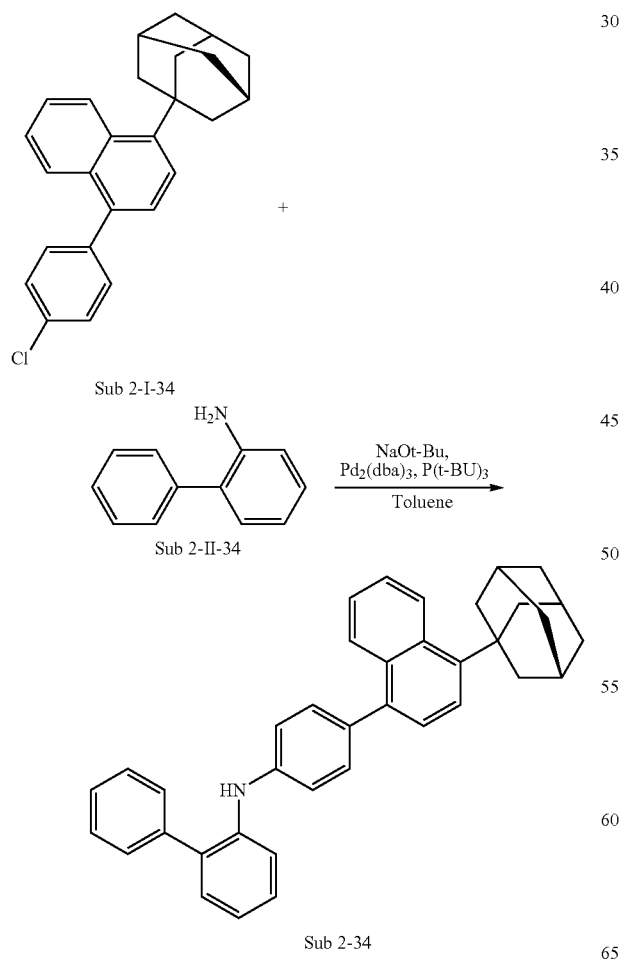

Sub 2-II-28 (9.2 g, 54.1 mmol), Pd$_2$(dba)$_3$ (0.03 equiv.), P(t-Bu)$_3$ (0.06 equiv.), NaOt-Bu (3 equiv.), Toluene (528 ml) were added to Sub 2-I-28 (19 g, 51.5 mmol) and 19.5 g (yield: 75.6%) of Sub 2-28 was obtained by using Sub 2-1 synthesis method.

6. Synthesis Example of Sub 2-34

Sub 2-II-34 (9.5 g, 56.3 mmol), Pd$_2$(dba)$_3$ (0.03 equiv.), P(t-Bu)$_3$ (0.06 equiv.), NaOt-Bu (3 equiv.), Toluene (550 ml) were added to Sub 2-I-34 (20 g, 53.6 mmol) and 19.3 g (yield: 71%) of Sub 2-34 was obtained by using Sub 2-1 synthesis method.

Meanwhile, the compound belonging to Sub 2 may be a compound as follows, but is not limited thereto, and Table 2 below shows the FD-MS values of the compound belonging to Sub 2.

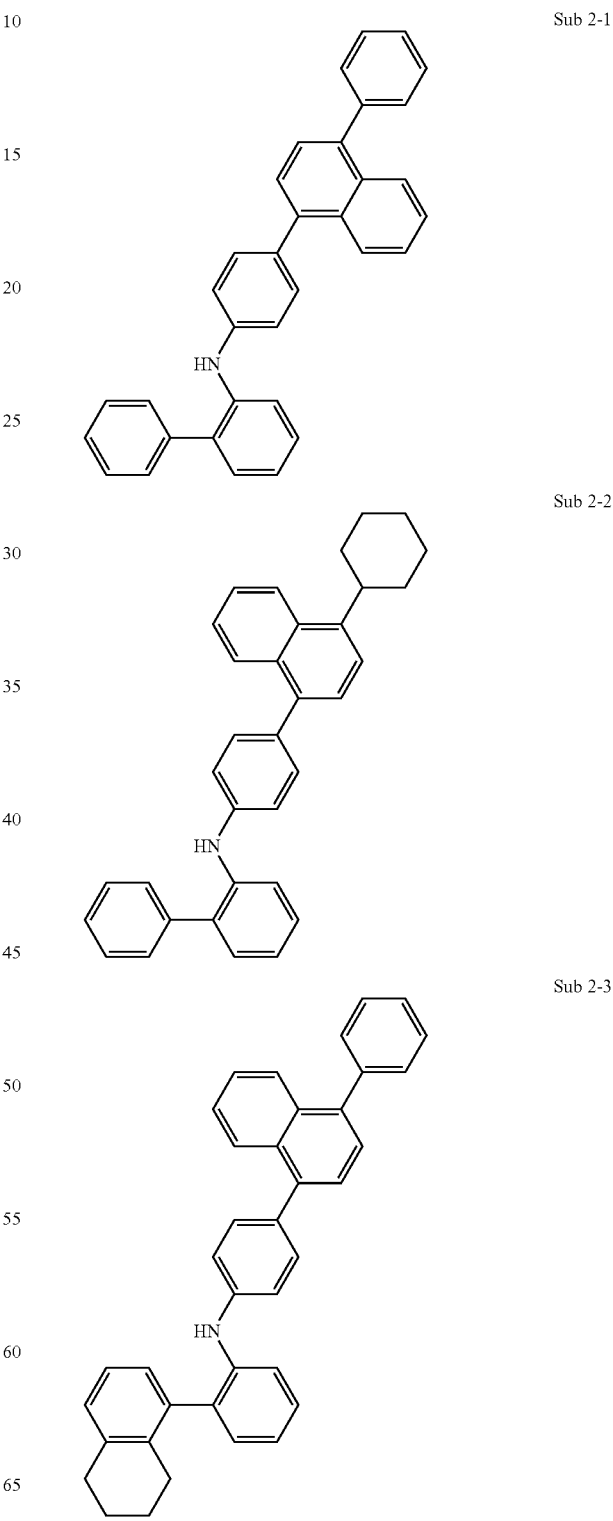

Sub 2-4
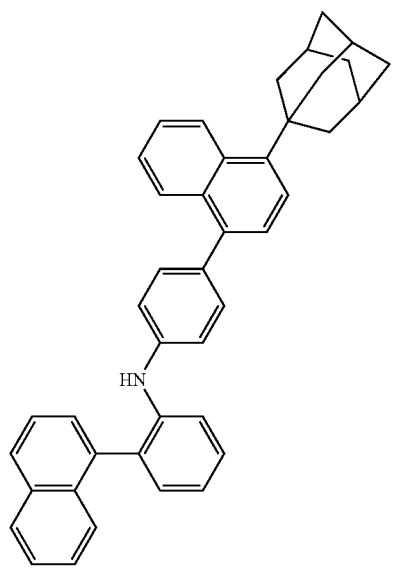
Sub 2-7
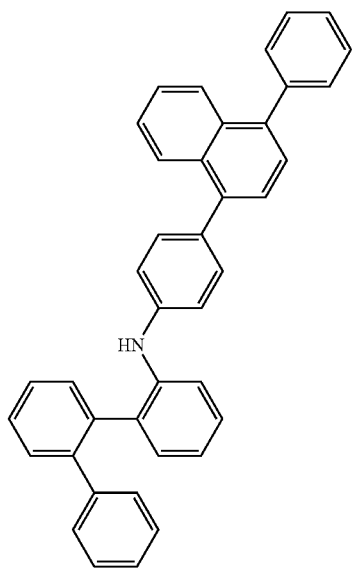
Sub 2-5
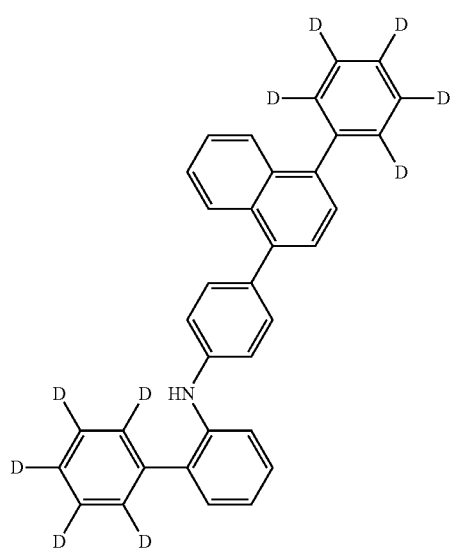
Sub 2-8
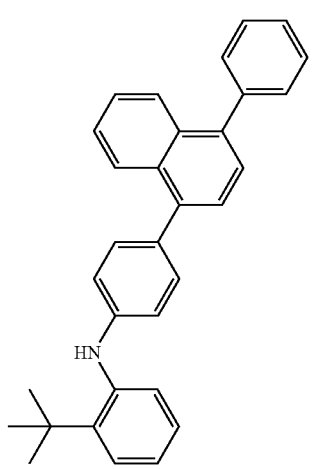
Sub 2-6
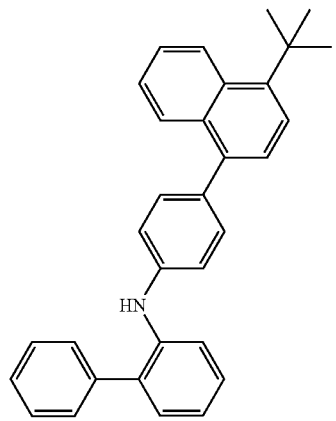
Sub 2-9
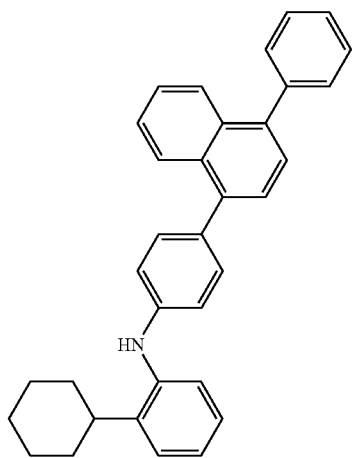

Sub 2-10
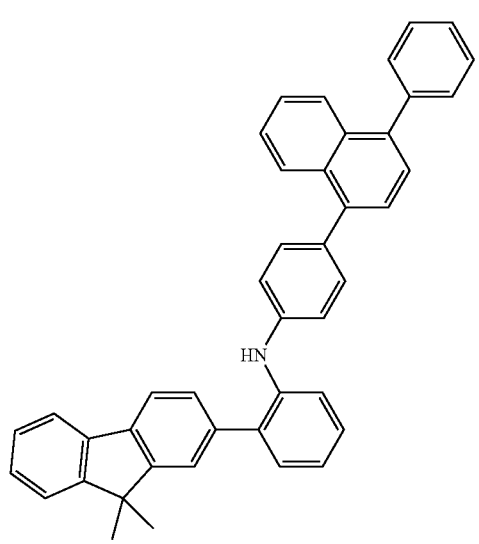
Sub 2-11
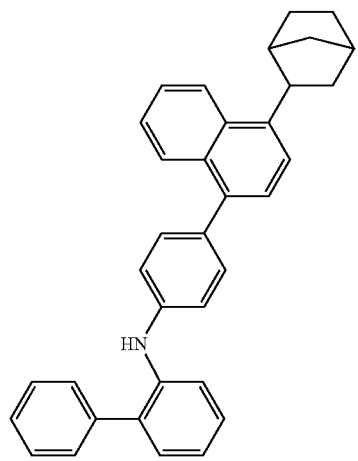
Sub 2-12
Sub 2-13
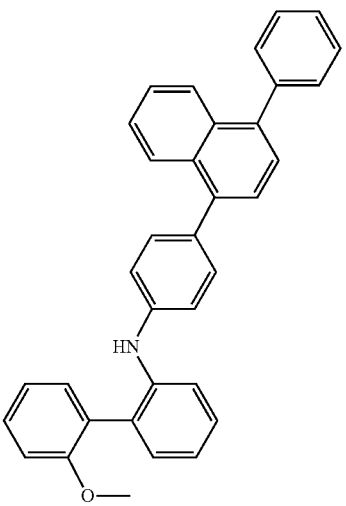
Sub 2-14
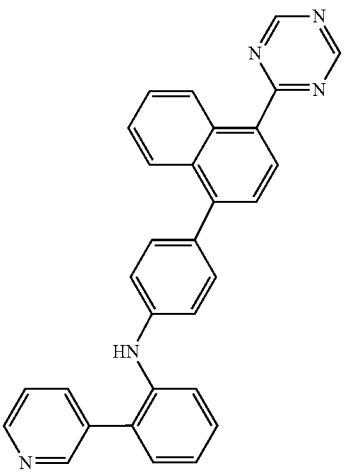
Sub 2-15
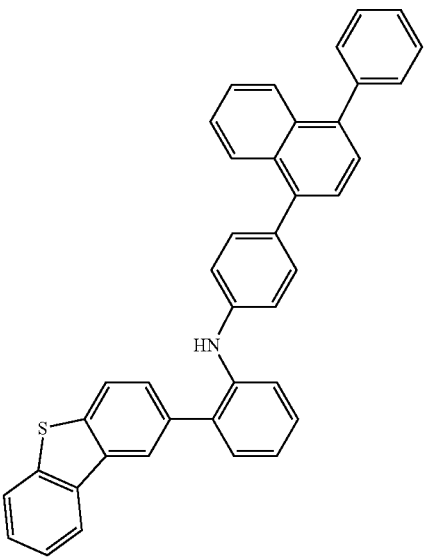

Sub 2-16
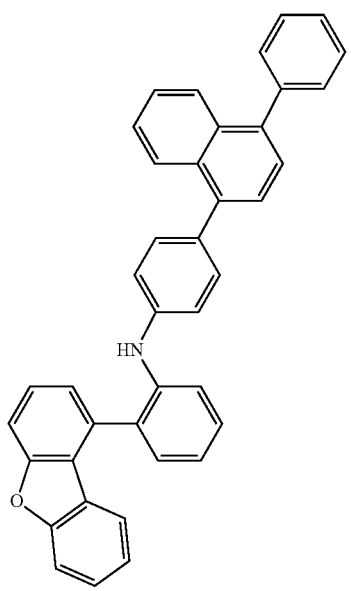
Sub 2-19
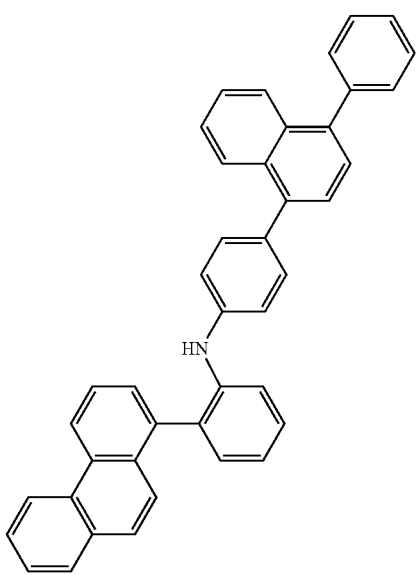
Sub 2-17
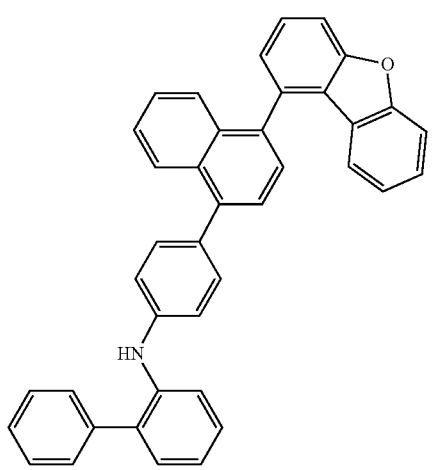
Sub 2-20
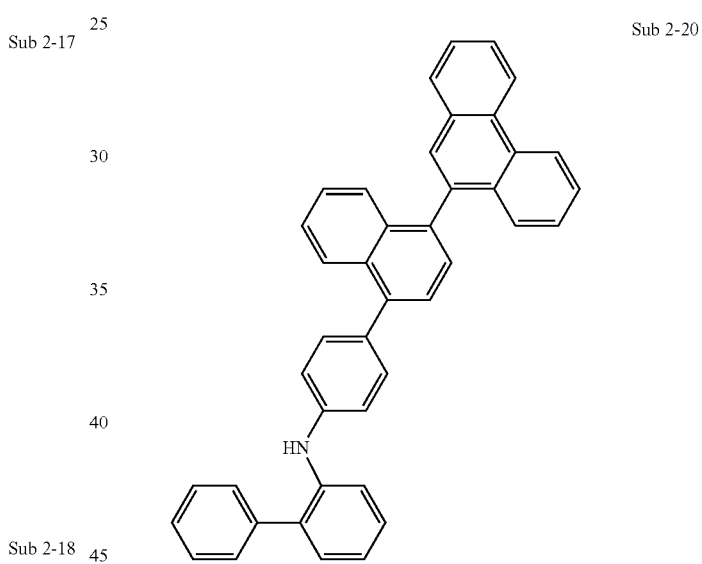
Sub 2-18
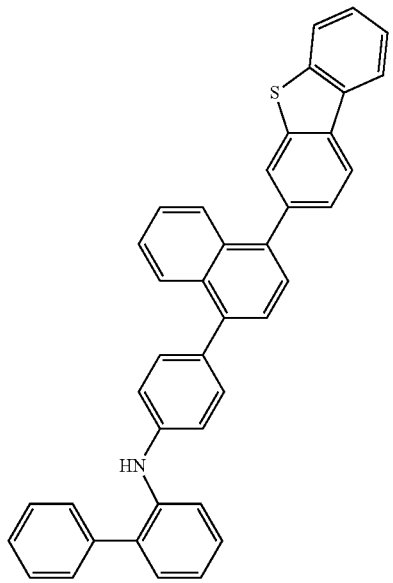
Sub 2-21
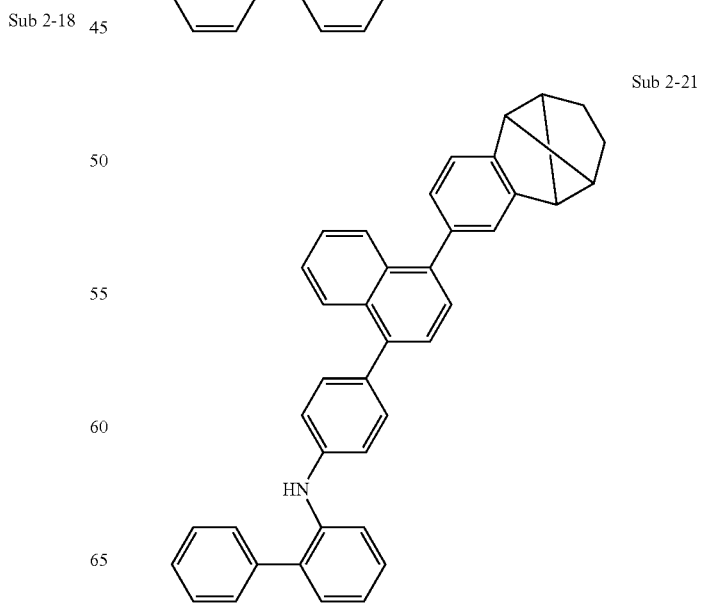

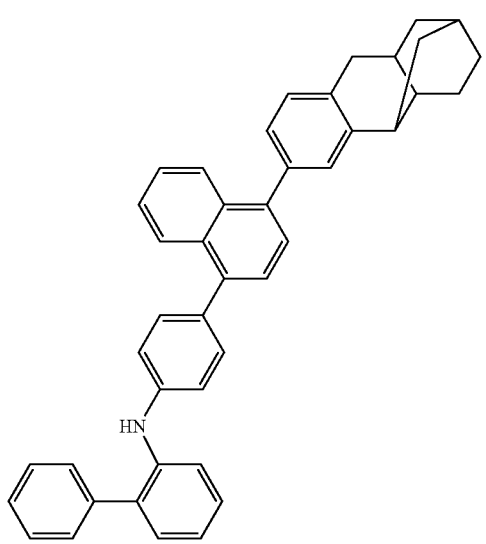
Sub 2-22
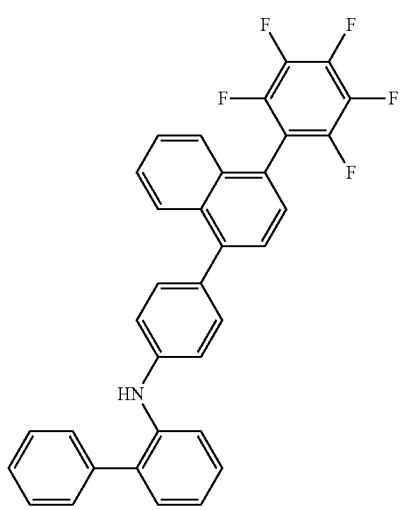
Sub 2-23
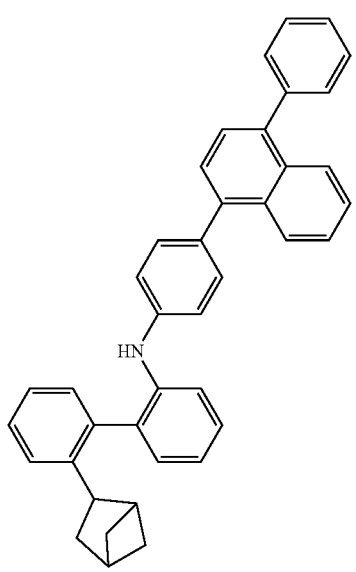
Sub 2-24
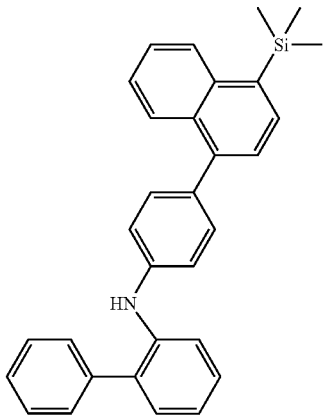
Sub 2-25
Sub 2-26
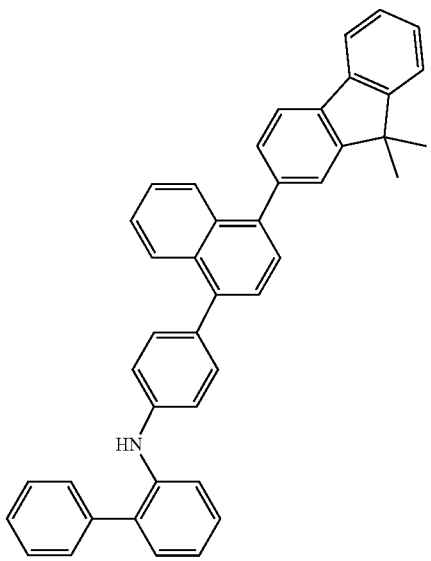
Sub 2-27

Sub 2-28 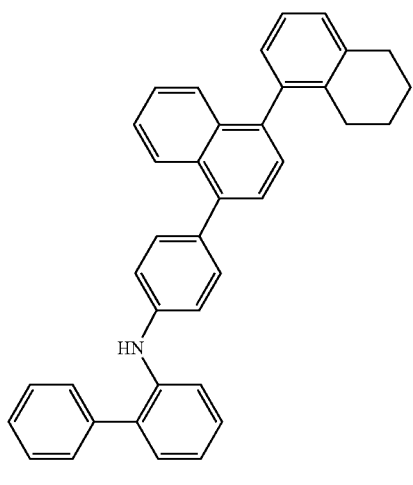
Sub 2-29 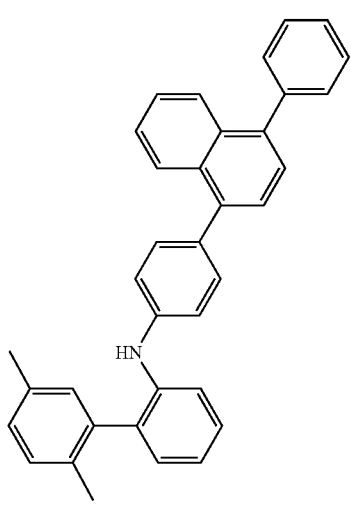
Sub 2-30 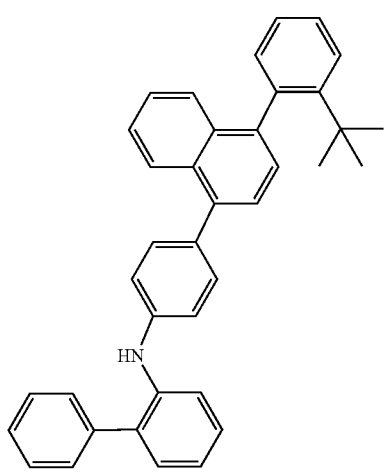
Sub 2-31 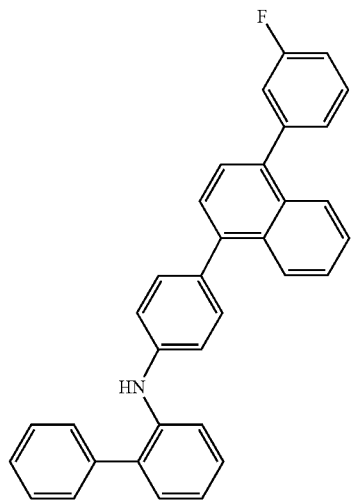
Sub 2-32 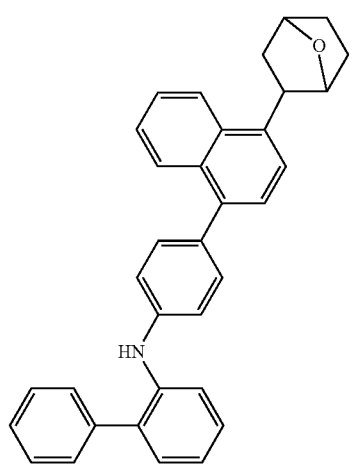
Sub 2-33 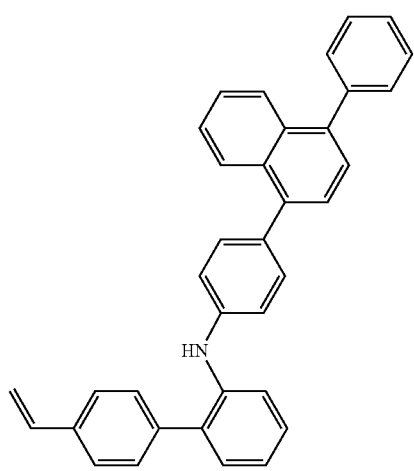

-continued

Sub 2-34

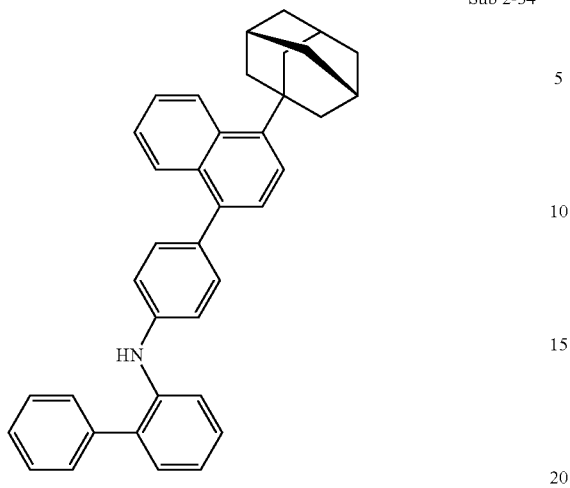

Sub 2-35

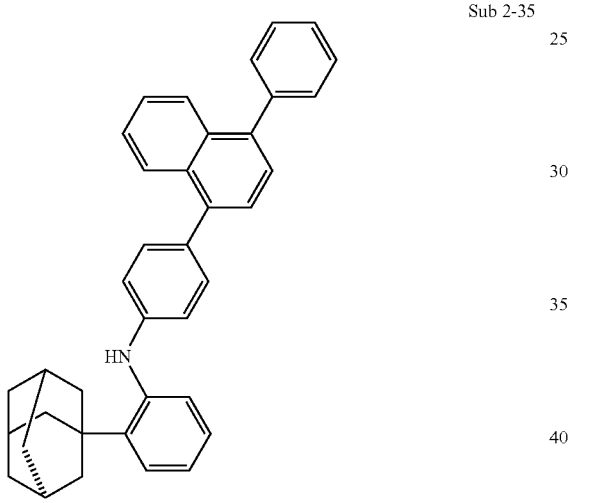

TABLE 2

| compound | FD-MS | compound | FD-MS |
| --- | --- | --- | --- |
| Sub 2-1 | m/z = 447.2($C_{34}H_{25}N$ = 447.58) | Sub 2-2 | m/z = 453.25($C_{34}H_{31}N$ = 453.63) |
| Sub 2-3 | m/z = 501.25($C_{38}H_{31}N$ = 501.67) | Sub 2-4 | m/z = 555.29($C_{42}H_{37}N$ = 555.77) |
| Sub 2-5 | m/z = 457.26($C_{34}H_{15}D_{10}N$ = 457.64) | Sub 2-6 | m/z = 427.23($C_{32}H_{29}N$ = 427.59) |
| Sub 2-7 | m/z = 523.23($C_{40}H_{29}N$ = 523.68) | Sub 2-8 | m/z = 427.23($C_{32}H_{29}N$ = 427.59) |
| Sub 2-9 | m/z = 453.25($C_{34}H_{31}N$ = 453.63) | Sub 2-10 | m/z = 563.26($C_{43}H_{33}N$ = 563.74) |
| Sub 2-11 | m/z = 465.25($C_{35}H_{31}N$ = 465.64) | Sub 2-12 | m/z = 397.18($C_{30}H_{23}N$ = 397.52) |
| Sub 2-13 | m/z = 477.21($C_{35}H_{27}NO$ = 477.61) | Sub 2-14 | m/z = 451.18($C_{30}H_{21}N_5$ = 451.53) |
| Sub 2-15 | m/z = 553.19($C_{40}H_{27}NS$ = 553.72) | Sub 2-16 | m/z = 537.21($C_{40}H_{27}NO$ = 537.66) |
| Sub 2-17 | m/z = 537.21($C_{40}H_{27}NO$ = 537.66) | Sub 2-18 | m/z = 553.19($C_{40}H_{27}NS$ = 553.72) |
| Sub 2-19 | m/z = 547.23($C_{42}H_{29}N$ = 547.7) | Sub 2-20 | m/z = 547.23($C_{42}H_{29}N$ = 547.7) |
| Sub 2-21 | m/z = 525.25($C_{40}H_{31}N$ = 525.7) | Sub 2-22 | m/z = 567.29($C_{43}H_{37}N$ = 567.78) |
| Sub 2-23 | m/z = 537.15($C_{34}H_{20}F_5N$ = 537.53) | Sub 2-24 | m/z = 527.26($C_{40}H_{33}N$ = 527.71) |
| Sub 2-25 | m/z = 443.21($C_{31}H_{29}NSi$ = 443.67) | Sub 2-26 | m/z = 453.25($C_{34}H_{31}N$ = 453.63) |
| Sub 2-27 | m/z = 563.26($C_{43}H_{33}N$ = 563.74) | Sub 2-28 | m/z = 501.25($C_{38}H_{31}N$ = 501.67) |
| Sub 2-29 | m/z = 475.23($C_{36}H_{29}N$ = 475.64) | Sub 2-30 | m/z = 503.26($C_{38}H_{33}N$ = 503.69) |
| Sub 2-31 | m/z = 467.22($C_{34}H_{29}NO$ = 467.61) | Sub 2-32 | m/z = 473.21($C_{36}H_{27}N$ = 473.62) |
| Sub 2-33 | m/z = 473.21($C_{36}H_{27}N$ = 473.62) | Sub 2-34 | m/z = 505.28($C_{38}H_{35}N$ = 505.71) |
| Sub 2-35 | m/z = 505.28($C_{38}H_{35}N$ = 505.71) | | |

II. Synthesis Example of Final Products

1. Synthesis Example of P-2

2. Synthesis Example of P-6

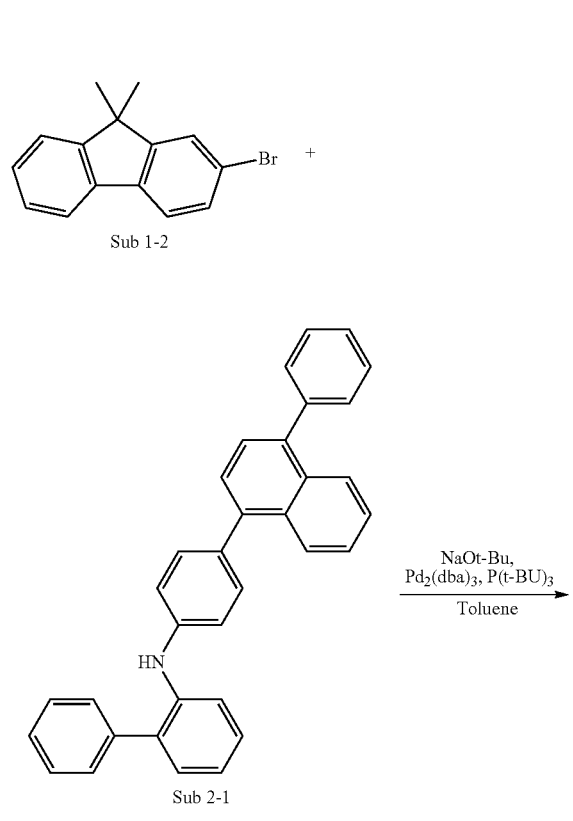

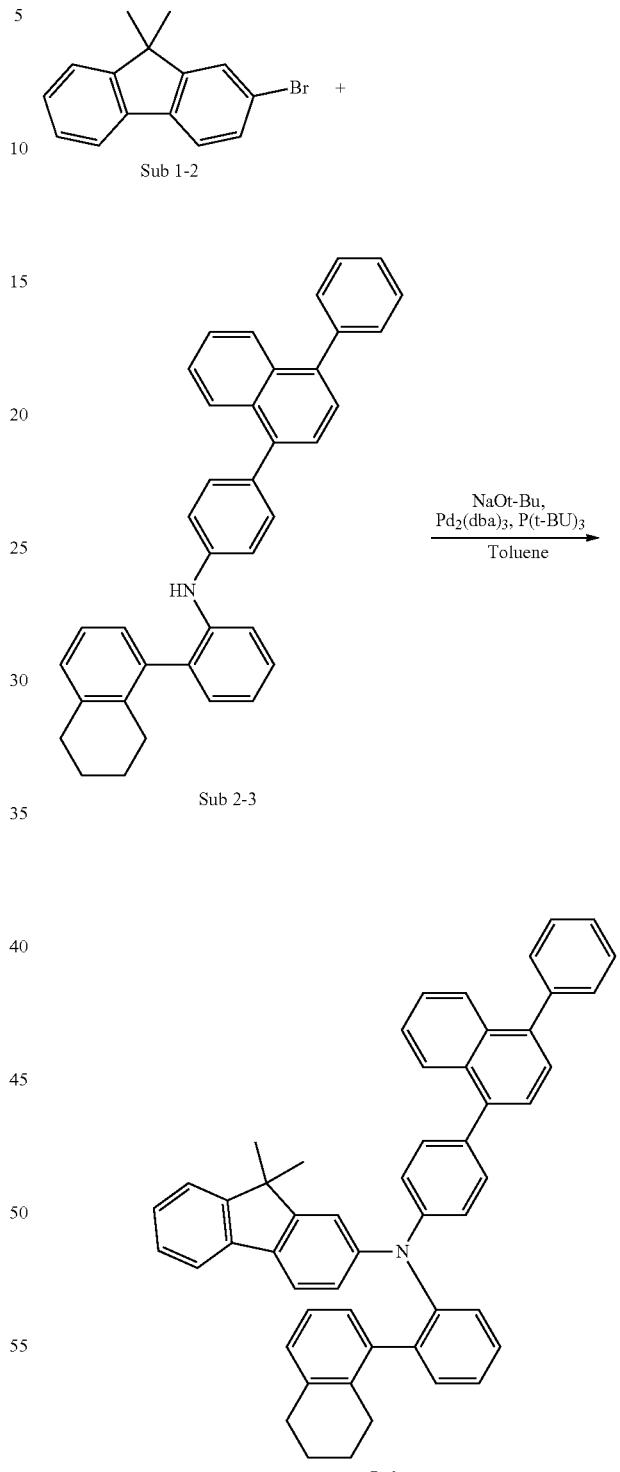

Sub 1-2 (30 g, 109.8 mmol) was added to toluene (1126 ml), and Sub 2-1 (51.6 g, 115.3 mmol), Pd$_2$(dba)$_3$ (0.03 equiv.), P(t-Bu)$_3$ (0.06 equiv.), NaOt-Bu (3 equiv.) were added and stirred at 100° C. When the reaction was completed, the mixture was extracted with CH$_2$C$_{12}$ and water, the organic layer was dried over MgSO$_4$, concentrated, and the resulting compound was recrystallized by silicagel column to obtain 59.7 g of P-2. (Yield: 85%)

Sub 2-3 (40.5 g, 80.7 mmol), Pd$_2$(dba)$_3$ (0.03 equiv.), P(t-Bu)$_3$ (0.06 equiv.), NaOt-Bu (3 equiv.) and Toluene (788 ml) were added to Sub 1-2 (21 g, 76.9 mmol), and 42.1 g (yield: 79%) of product P-6 was obtained by using P-2 synthesis method.

3. Synthesis Example of P-18

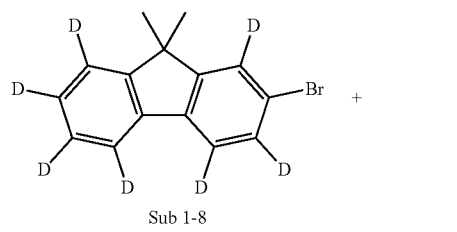

Sub 1-8

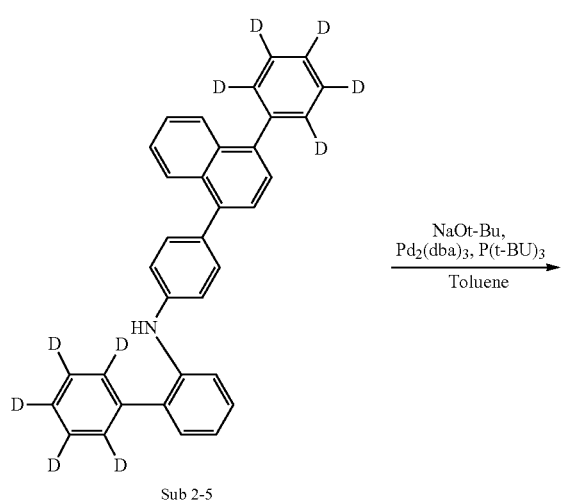

Sub 2-5

P-18

4. Synthesis Example of P-23

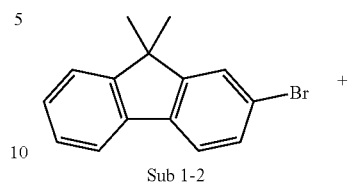

Sub 1-2

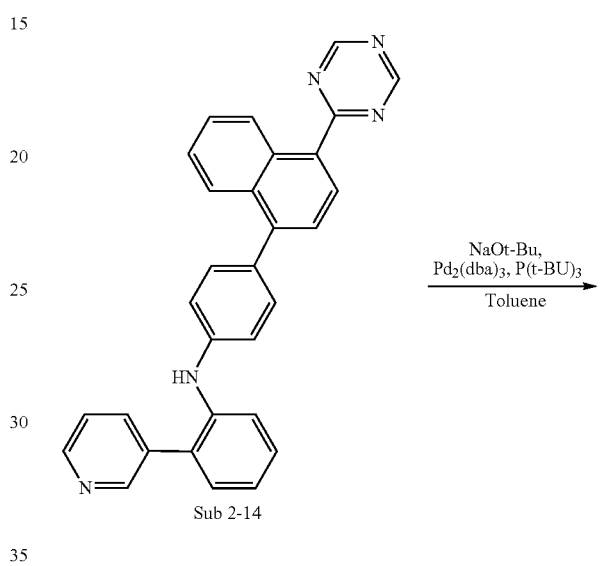

Sub 2-14

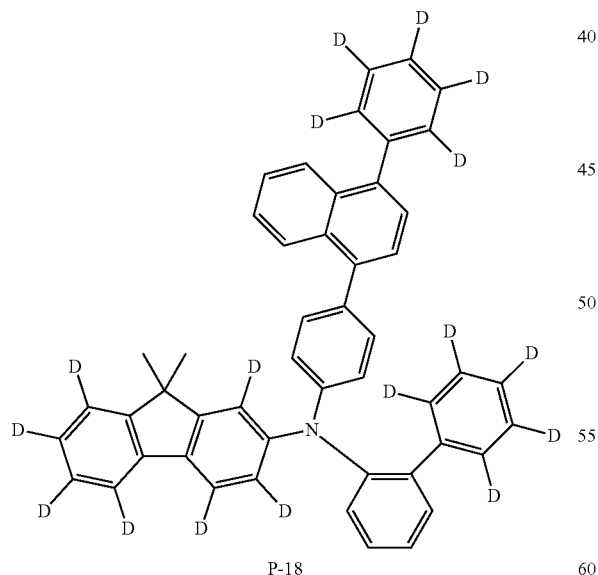

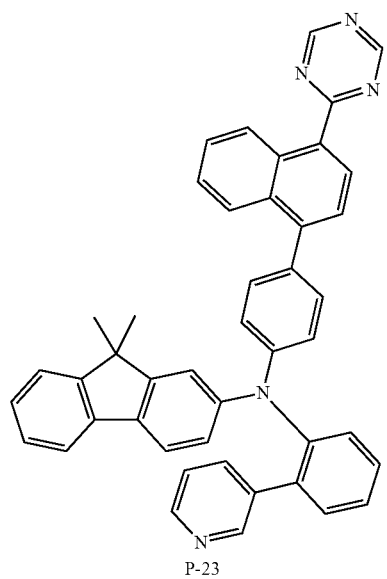

P-23

Sub 2-5 (42.9 g, 96.7 mmol), Pd$_2$(dba)$_3$ (0.03 equiv.), P(t-Bu)$_3$ (0.06 equiv.), NaOt-Bu (3 equiv.), Toluene (914 ml) were added to Sub 1-8 (25 g, 89.2 mmol), and 48.1 g (yield: 82%) of product P-18 was obtained by using P-2 synthesis method.

Sub 2-14 (26 g, 57.7 mmol), Pd$_2$(dba)$_3$ (0.03 equiv.), P(t-Bu)$_3$ (0.06 equiv.), NaOt-Bu (3 equiv.), Toluene (563 ml) were added to Sub 1-2 (15 g, 54.9 mmol), and 25.5 g (yield: 72%) of product P-23 was obtained by using P-2 synthesis method.

5. Synthesis Example of P-26

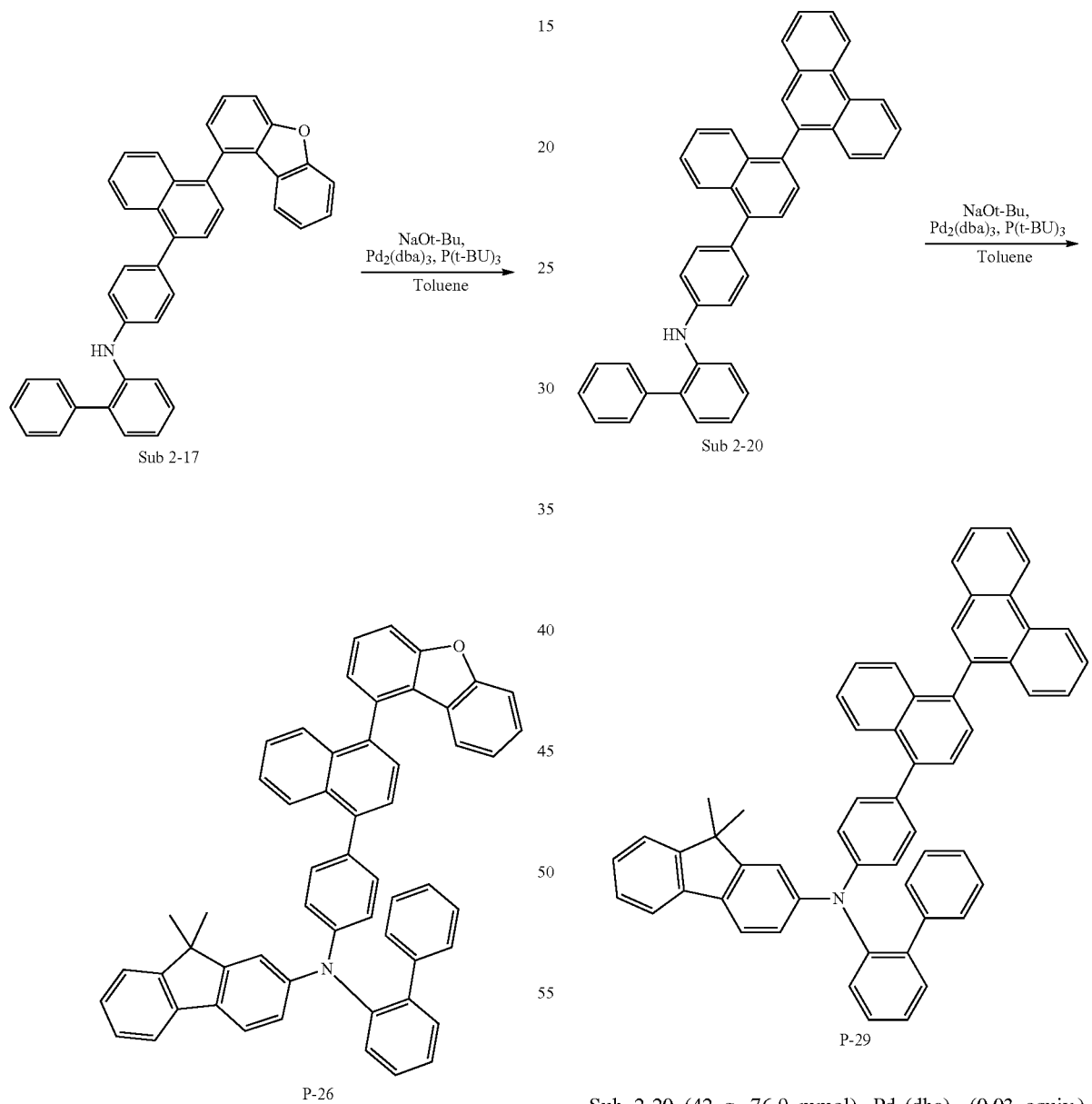

Sub 2-17 (35.1 g, 65.3 mmol), Pd₂(dba)₃ (0.03 equiv.), P(t-Bu)₃ (0.06 equiv.), NaOt-Bu (3 equiv.), Toluene (638 ml) were added to Sub 1-2 (17 g, 62.2 mmol), and 32.3 g (yield: 71%) of product P-26 was obtained by using P-2 synthesis method.

6. Synthesis Example of P-29

Sub 2-20 (42 g, 76.9 mmol), Pd₂(dba)₃ (0.03 equiv.), P(t-Bu)₃ (0.06 equiv.), NaOt-Bu (3 equiv.), Toluene (750 ml) were added to Sub 1-2 (20 g, 73.2 mmol), and 40.9 g (yield: 74%) of product P-29 was obtained by using P-2 synthesis method.

7. Synthesis Example of P-44

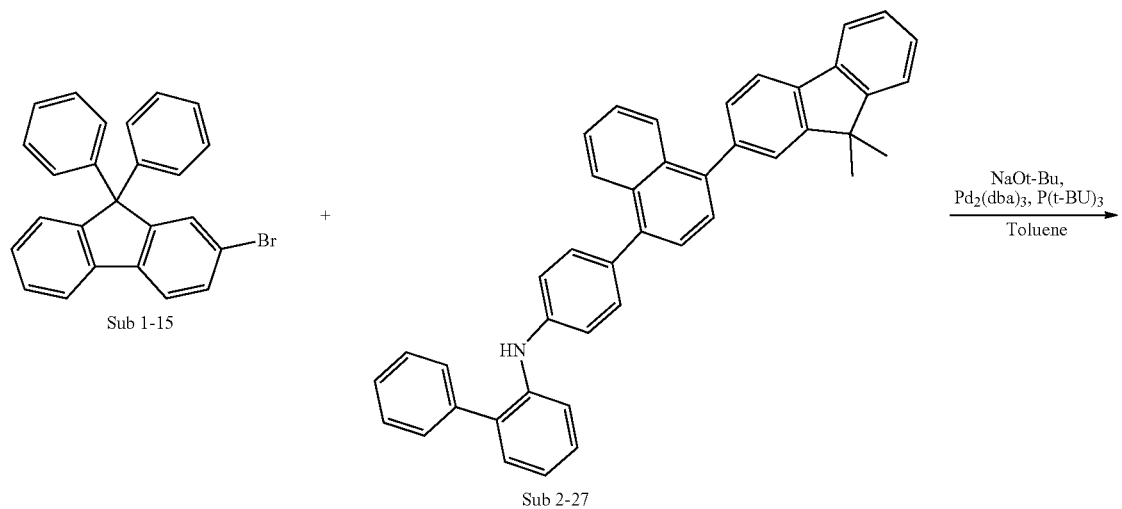
Sub 2-27 (28.3 g, 50.2 mmol), Pd$_2$(dba)$_3$ (0.03 equiv.), P(t-Bu)$_3$ (0.06 equiv.), NaOt-Bu (3 equiv.), Toluene (490 ml) were added to Sub 1-15 (19 g, 47.8 mmol), and 31 g (yield: 73.5%) of product P-44 was obtained by using P-2 synthesis method.
8. Synthesis Example of P-56
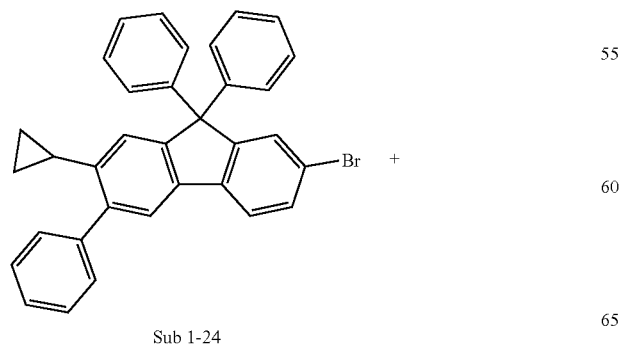

-continued
9. Synthesis Example of P-61
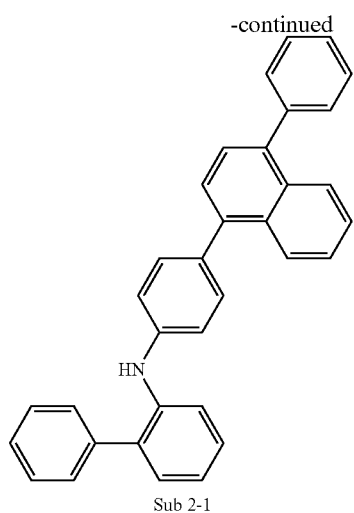
Sub 2-1
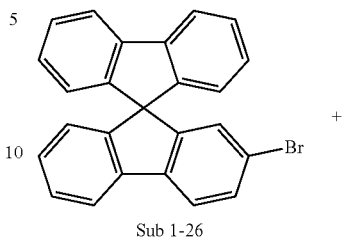
Sub 1-26
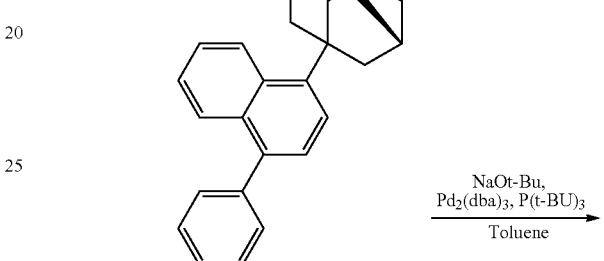
Sub 2-34
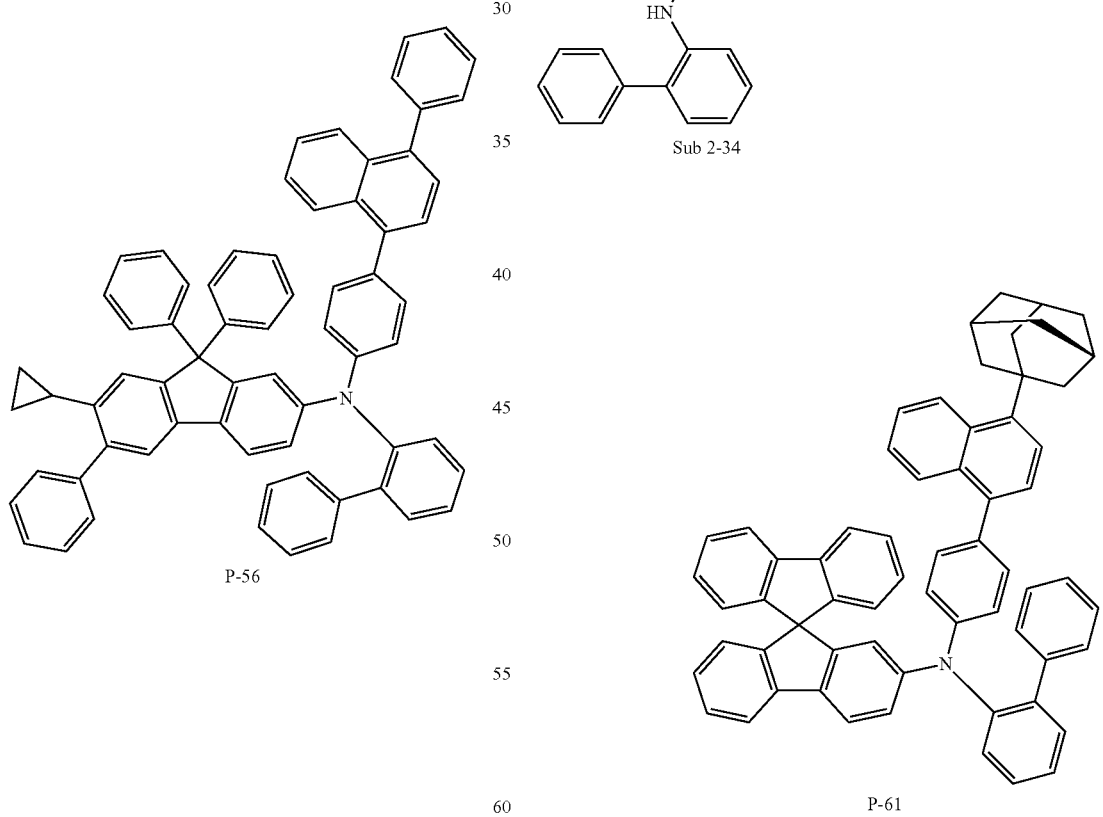
P-56
P-61
Sub 2-1 (12 g, 26.6 mmol), Pd$_2$(dba)$_3$ (0.03 equiv.), P(t-Bu)$_3$ (0.06 equiv.), NaOt-Bu (3 equiv.), Toluene (260 ml) were added to Sub 1-24 (13 g, 25.3 mmol), and 15.4 g (yield: 69%) of product P-56 was obtained by using P-2 synthesis method.
Sub 2-34 (21.5 g, 42.5 mmol), Pd$_2$(dba)$_3$ (0.03 equiv.), P(t-Bu)$_3$ (0.06 equiv.), NaOt-Bu (3 equiv.), Toluene (415 ml) were added to Sub 1-26 (16 g, 40.5 mmol), and 24 g (yield: 72.4%) of product P-61 was obtained by using P-2 synthesis method.

10. Synthesis Example of P-64

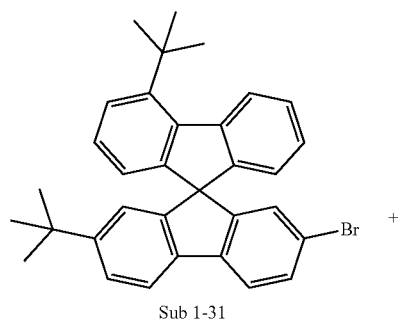
Sub 1-31

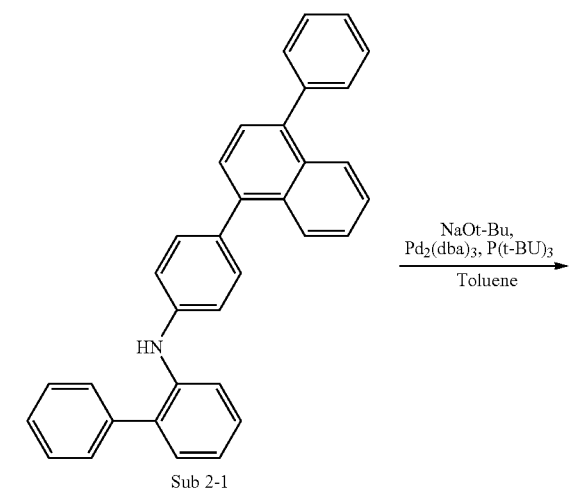
Sub 2-1

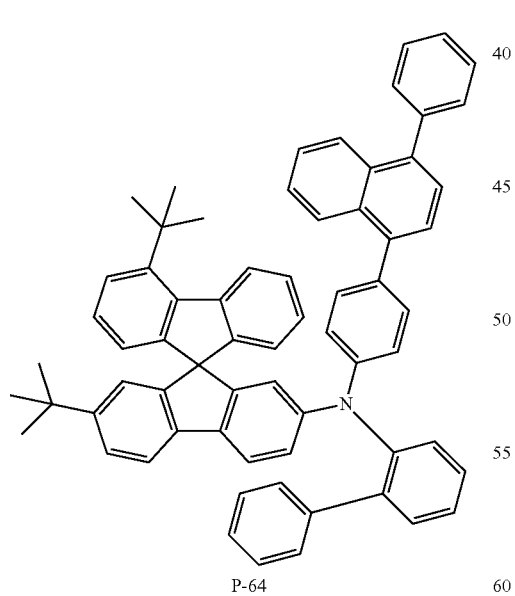
P-64

Sub 2-1 (17.1 g, 38.3 mmol), Pd$_2$(dba)$_3$ (0.03 equiv.), P(t-Bu)$_3$ (0.06 equiv.), NaOt-Bu (3 equiv.), Toluene (374 ml) were added to Sub 1-31 (18.5 g, 36.5 mmol), and 25.5 g (yield: 80%) of product P-64 was obtained by using P-2 synthesis method.

11. Synthesis Example of P-69

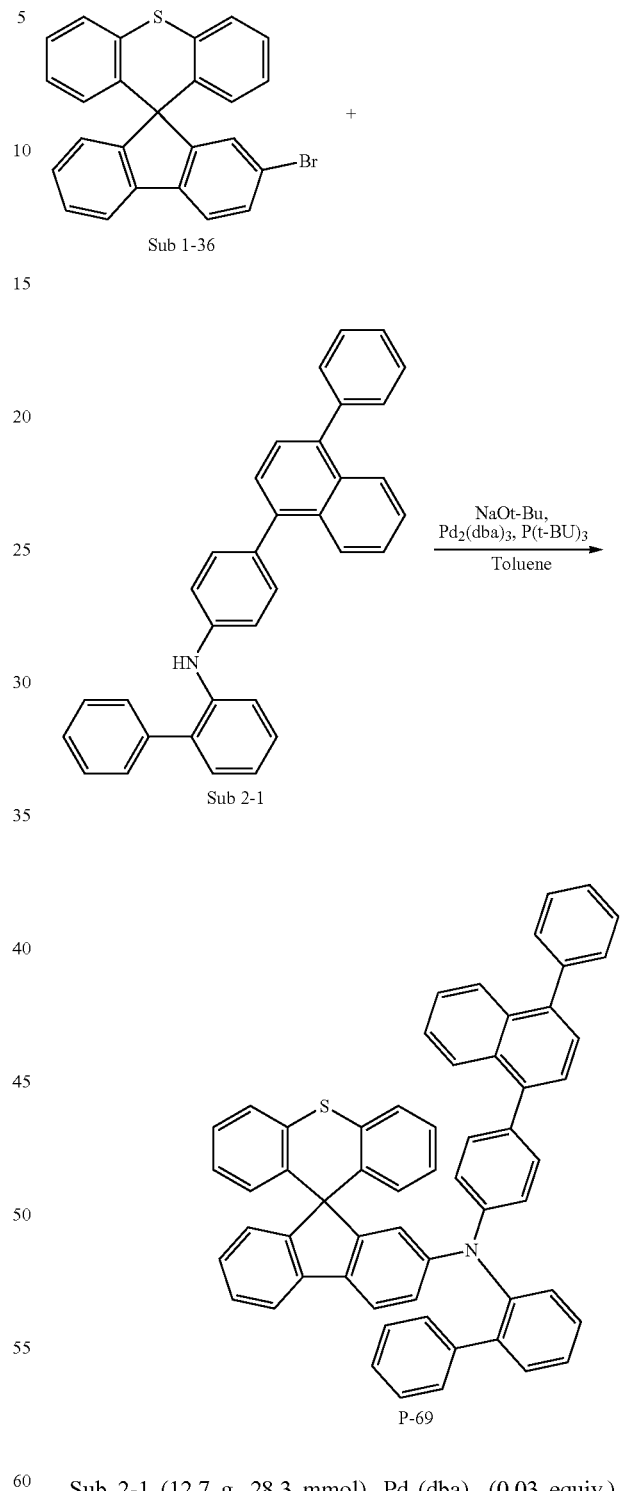

Sub 2-1 (12.7 g, 28.3 mmol), Pd$_2$(dba)$_3$ (0.03 equiv.), P(t-Bu)$_3$ (0.06 equiv.), NaOt-Bu (3 equiv.), Toluene (276 ml) were added to Sub 1-36 (11.5 g, 26.9 mmol), and 14.6 g (yield: 68.5%) of product P-69 was obtained by using P-2 synthesis method.

Table 3 shows the FD-MS values of some compounds belonging to the Final Product.

TABLE 3

| compound | FD-MS | compound | FD-MS |
|---|---|---|---|
| P-1 | m/z = 639.29($C_{49}H_{37}N$ = 639.84) | P-2 | m/z = 639.29($C_{49}H_{37}N$ = 639.84) |
| P-3 | m/z = 639.29($C_{49}H_{37}N$ = 639.84) | P-4 | m/z = 639.29($C_{49}H_{37}N$ = 639.84) |
| P-5 | m/z = 645.34($C_{49}H_{43}N$ = 645.89) | P-6 | m/z = 693.34($C_{53}H_{43}N$ = 693.93) |
| P-7 | m/z = 747.39($C_{57}H_{49}N$ = 748.03) | P-8 | m/z = 649.36($C_{49}H_{27}D_{10}N$ = 649.9) |
| P-9 | m/z = 619.32($C_{47}H_{41}N$ = 619.85) | P-10 | m/z = 71 5.32($C_{55}H_{41}N$ = 715.94) |
| P-11 | m/z = 715.32($C_{55}H_{41}N$ = 715.94) | P-12 | m/z = 71 5.32($C_{55}H_{41}N$ = 715.94) |
| P-13 | m/z = 715.32($C_{55}H_{41}N$ = 715.94) | P-14 | m/z = 61 9.32($C_{47}H_{41}N$ = 619.85) |
| P-15 | m/z = 645.34($C_{49}H_{43}N$ = 645.89) | P-16 | m/z = 755.36($C_{58}H_{45}N$ = 756.01) |
| P-17 | m/z = 657.34($C_{50}H_{43}N$ = 657.9) | P-18 | m/z = 656.4($C_{49}H_{20}D_{17}N$ = 656.95) |
| P-19 | m/z = 589.28($C_{45}H_{35}N$ = 589.78) | P-20 | m/z = 669.3($C_{50}H_{39}NO$ = 669.87) |
| P-21 | m/z = 645.33($C_{49}H_{31}D_6N$ = 645.88) | P-22 | m/z = 643.32($C_{49}H_{33}D_4N$ = 643.87) |
| P-23 | m/z = 643.27($C_{45}H_{33}N_5$ = 643.79) | P-24 | m/z = 729.3($C_{55}H_{39}NO$ = 729.92) |
| P-25 | m/z = 745.28($C_{55}H_{39}NS$ = 745.98) | P-26 | m/z = 729.3($C_{55}H_{39}NO$ = 729.92) |
| P-27 | m/z = 729.3($C_{55}H_{39}NO$ = 729.92) | P-28 | m/z = 739.32($C_{57}H_{41}N$ = 739.96) |
| P-29 | m/z = 739.32($C_{57}H_{41}N$ = 739.96) | P-30 | m/z = 717.34($C_{55}H_{43}N$ = 717.96) |
| P-31 | m/z = 729.25($C_{49}H_{32}F_5N$ = 729.79) | P-32 | m/z = 741.34($C_{57}H_{43}N$ = 741.98) |
| P-33 | m/z = 741.34($C_{57}H_{43}N$ = 741.98) | P-34 | m/z = 740.32($C_{56}H_{40}N2$ = 740.95) |
| P-35 | m/z = 881.4($C_{68}H_{51}N$ = 882.16) | P-36 | m/z = 855.48($C_{65}H_{61}N$ = 856.21) |
| P-37 | m/z = 763.32($C_{59}H_{41}N$ = 763.98) | P-38 | m/z = 763.32($C_{59}H_{41}N$ = 763.98) |
| P-39 | m/z = 813.34($C_{63}H_{43}N$ = 814.04) | P-40 | m/z = 763.32($C_{59}H_{41}N$ = 763.98) |
| P-41 | m/z = 759.33($C_{56}H_{45}NSi$ = 760.07) | P-42 | m/z = 768.36($C_{59}H_{36}D_5N$ = 769.01) |
| P-43 | m/z = 769.37($C_{59}H_{47}N$ = 770.03) | P-44 | m/z = 879.39($C_{68}H_{49}N$ = 880.15) |
| P-45 | m/z = 707.36($C_{54}H_{45}N$ = 707.96) | P-46 | m/z = 719.36($C_{55}H_{45}N$ = 719.97) |
| P-47 | m/z = 755.36($C_{58}H_{45}N$ = 756.01) | P-48 | m/z = 729.34($C_{56}H_{43}N$ = 729.97) |
| P-49 | m/z = 819.39($C_{63}H_{49}N$ = 820.09) | P-50 | m/z = 781.31($C_{59}H_{40}FN$ = 781.97) |
| P-51 | m/z = 783.35($C_{59}H_{45}NO$ = 784.02) | P-52 | m/z = 863.36($C_{67}H_{45}N$ = 864.1) |
| P-53 | m/z = 767.35($C_{59}H_{37}D_4N$ = 768.01) | P-54 | m/z = 921.43($C_{71}H_{55}N$ = 922.23) |
| P-55 | m/z = 789.34($C_{61}H_{43}N$ = 790.02) | P-56 | m/z = 879.39($C_{68}H_{49}N$ = 880.15) |
| P-57 | m/z = 761.31($C_{59}H_{39}N$ = 761.97) | P-58 | m/z = 761.31($C_{59}H_{39}N$ = 761.97) |
| P-59 | m/z = 761.31($C_{59}H_{39}N$ = 761.97) | P-60 | m/z = 761.31($C_{59}H_{39}N$ = 761.97) |
| P-61 | m/z = 819.39($C_{63}H_{49}N$ = 820.09) | P-62 | m/z = 819.39($C_{63}H_{49}N$ = 820.09) |
| P-63 | m/z = 895.42($C_{69}H_{53}N$ = 896.19) | P-64 | m/z = 873.43($C_{67}H_{55}N$ = 874.18) |
| P-65 | m/z = 777.3($C_{59}H_{39}NO$ = 777.97) | P-66 | m/z = 777.3($C_{59}H_{39}NO$ = 777.97) |
| P-67 | m/z = 777.3($C_{59}H_{39}NO$ = 777.97) | P-68 | m/z = 777.3($C_{59}H_{39}NO$ = 777.97) |
| P-69 | m/z = 793.28($C_{59}H_{39}NS$ = 794.03) | P-70 | m/z = 793.28($C_{59}H_{39}NS$ = 794.03) |
| P-71 | m/z = 793.28($C_{59}H_{39}NS$ = 794.03) | P-72 | m/z = 793.28($C_{59}H_{39}NS$ = 794.03) |

Manufacturing Evaluation of Organic Electronic Element

[Example 1] Green Organic Light Emitting Device (Hole Transport Layer)

After vacuum deposition of N1-(naphthalen-2-yl)-N4,N4-bis(4-(naphthalen-2-yl)phenyl)amino)phenyl)-N1-phenyl-benzene-1,4-diamine (hereinafter abbreviated as 2-TANA) to a thickness of 60 nm on the ITO layer (anode) formed on the glass substrate to form a hole injection layer, the compound P-1 of the present invention represented by Formula 1 was vacuum-deposited on the hole injection layer to a thickness of 60 nm to form a hole transport layer.

Then, an emitting layer having a thickness of 30 nm was formed on the hole transport layer using 4,4'-N,N'-dicarbazole-biphenyl (hereinafter abbreviated as CBP) as a host and tris(2-phenylpyridine)-iridium (hereinafter abbreviated as Ir(ppy)$_3$) as a dopant in a weight ratio of 90:10.

Then, (1,1'-biphenyl-4-olato)bis(2-methyl-8-quinolinolato)aluminum (hereinafter abbreviated as BAlq) was deposited to a thickness of 5 nm on the emitting layer to form a hole blocking layer, and Tris(8-quinolinol)aluminum (hereinafter Alq$_3$) was deposited to a thickness of 40 nm on the hole blocking layer to form an electron transport layer.

Thereafter, LiF was deposited to a thickness of 0.2 nm to form an electron injection layer, and then Al was deposited to a thickness of 150 nm to form a cathode, thereby manufacturing an organic electroluminescent device.

[Example 2] to [Example 18]

An organic electroluminescent device was manufactured in the same manner as in Example 1, except that the compound of the present invention described in Table 4 was used instead of the compound P-1 of the present invention as the hole transport layer material.

Comparative Example 1

An organic electroluminescent device was manufactured in the same manner as in Example 1, except that N,N'-Bis (1-naphthalenyl)-N,N'-bis-phenyl-(1,1'-biphenyl)-4,4'-diamine (hereinafter abbreviated as NPB) was used as the hole transport layer material.

[Comparative Example 2] to [Comparative Example 6]

An organic electroluminescent device was manufactured in the same manner as in Example 1, except that one of Comparative Compounds 1 to 5 was used as the hole transport layer material.

Comparative Compound 1 Comparative Compounds 2 Comparative Compounds 3

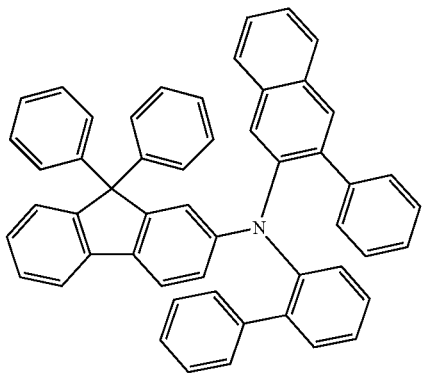

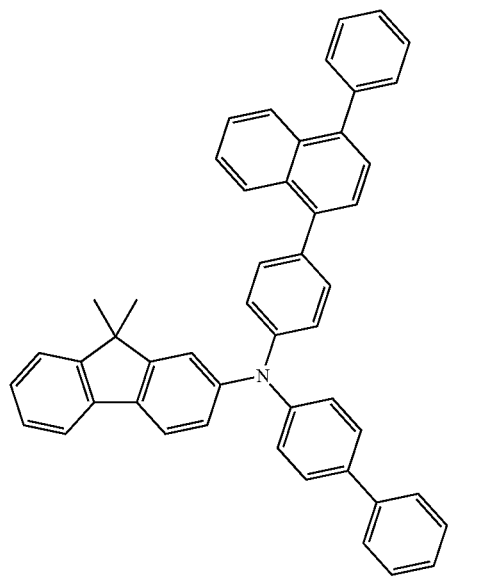

Comparative Compound 4 Comparative Compounds 5

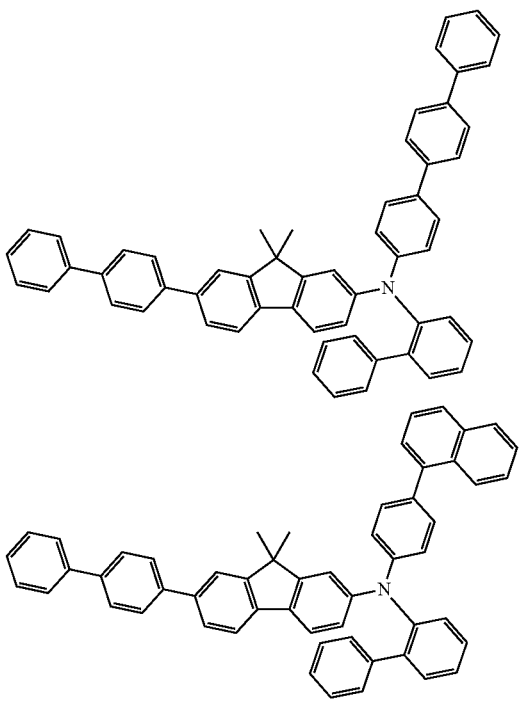

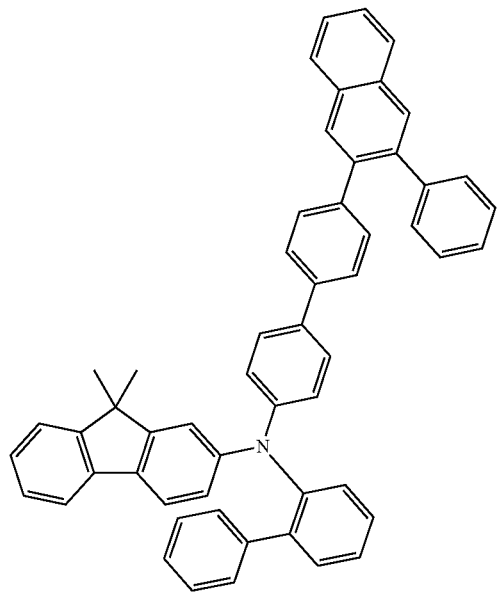

By applying a forward bias DC voltage to the organic electroluminescent devices of Examples 1 to 18 and Comparative Examples 1 to 6 prepared in this way, Electroluminescence (EL) characteristics were measured with PR-650 from photo research, and as a result of the measurement, the T95 lifetime was measured using a lifetime measuring device manufactured by McScience at 5000 cd/m² standard luminance. Table 4 below shows the device fabrication and evaluation results.

Hereinafter, with reference to the structure of Formula 1, element data and inventive step according to the skeleton structure of the compound of the present invention will be described together.

Formula 1

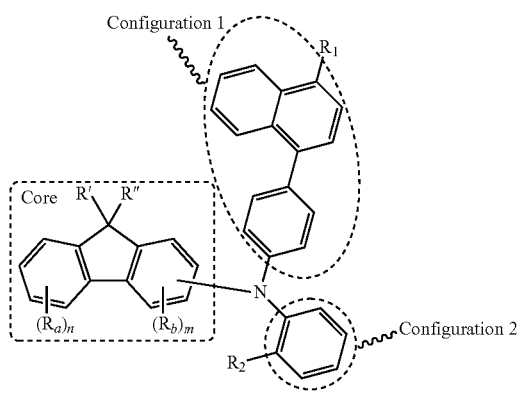

parative Example 1 manufactured using NPB mainly used as a hole transport layer material have been improved, and Compared to Comparative Examples 1 to 6, when the compound according to Formula 1 of the present invention was used as a material for the hole transport layer, the luminous efficiency and lifespan of the organic light emitting device were increased, and the driving voltage was slightly lowered, thereby further improving the electrical properties of the element.

Comparative Compounds 1 to 5 are the same as the compounds of the present invention in that the fluorenyl group is substituted with the core in the tertiary amine compound, but Comparative Compounds 1 to 5 differ in that they are not identical in composition to Configurations 1 and 2 of Formula 1 of the present invention, or do not have $R_1$ and $R_2$ substituents at specific substitution positions based on Configurations 1 and 2 at the same time. That is, the compounds of the examples of the present invention present

TABLE 4

| | compound | Voltage | Current Density (mA/cm$^2$) | Brightness (cd/m$^2$) | Efficiency (cd/A) | T(95) | CIE X | CIE Y |
|---|---|---|---|---|---|---|---|---|
| comparative example(1) | NPB | 6.0 | 24.5 | 5000 | 20.4 | 58.9 | 0.31 | 0.61 |
| comparative example(2) | comparative compound 1 | 5.2 | 17.4 | 5000 | 28.8 | 85.0 | 0.32 | 0.61 |
| comparative example(3) | comparative compound 2 | 5.3 | 18.2 | 5000 | 27.5 | 80.9 | 0.32 | 0.61 |
| comparative example(4) | comparative compound 3 | 5.4 | 18.9 | 5000 | 26.4 | 80.3 | 0.32 | 0.60 |
| comparative example(5) | comparative compound 4 | 5.3 | 18.5 | 5000 | 27.1 | 81.8 | 0.32 | 0.60 |
| comparative example(6) | comparative compound 5 | 5.3 | 17.9 | 5000 | 28.0 | 82.6 | 0.32 | 0.60 |
| example(1) | P-1 | 5.1 | 11.7 | 5000 | 42.7 | 108.3 | 0.32 | 0.61 |
| example(2) | P-2 | 5.0 | 11.2 | 5000 | 44.8 | 110.4 | 0.32 | 0.61 |
| example(3) | P-3 | 5.1 | 11.9 | 5000 | 41.9 | 107.9 | 0.33 | 0.60 |
| example(4) | P-4 | 5.1 | 12.2 | 5000 | 41.0 | 107.2 | 0.33 | 0.61 |
| example(5) | P-7 | 5.2 | 13.8 | 5000 | 36.3 | 101.3 | 0.33 | 0.61 |
| example(6) | P-8 | 5.0 | 11.3 | 5000 | 44.1 | 109.5 | 0.33 | 0.60 |
| example(7) | P-11 | 5.2 | 13.6 | 5000 | 36.7 | 101.8 | 0.33 | 0.61 |
| example(8) | P-18 | 5.1 | 12.5 | 5000 | 40.0 | 106.4 | 0.33 | 0.61 |
| example(9) | P-21 | 5.0 | 11.5 | 5000 | 43.6 | 109.0 | 0.33 | 0.63 |
| example(10) | P-23 | 5.2 | 13.3 | 5000 | 37.5 | 102.7 | 0.33 | 0.62 |
| example(11) | P-28 | 5.1 | 12.9 | 5000 | 38.7 | 104.6 | 0.33 | 0.63 |
| example(12) | P-37 | 5.1 | 13.2 | 5000 | 37.9 | 103.3 | 0.33 | 0.62 |
| example(13) | P-56 | 5.2 | 14.9 | 5000 | 33.5 | 98.4 | 0.33 | 0.63 |
| example(14) | P-57 | 5.2 | 14.0 | 5000 | 35.6 | 100.5 | 0.33 | 0.62 |
| example(15) | P-61 | 5.2 | 15.1 | 5000 | 33.1 | 97.8 | 0.33 | 0.62 |
| example(16) | P-64 | 5.2 | 14.2 | 5000 | 35.2 | 100.1 | 0.33 | 0.63 |
| example(17) | P-66 | 5.2 | 14.5 | 5000 | 34.4 | 99.2 | 0.33 | 0.63 |
| example(18) | P-69 | 5.2 | 14.8 | 5000 | 33.8 | 98.9 | 0.33 | 0.62 |

As can be seen from Table 4, when a green organic electroluminescent device is manufactured using the compound represented by Formula 1 of the present invention as a hole transport layer material, it is possible to improve the driving voltage, luminous efficiency and lifespan of the organic electronic element compared to Comparative Examples using Comparative Compounds 1 to 6 having similar basic skeletons to the compound of the present invention. That is, the electrical properties of the element of Comparative Examples 2 to 6 prepared using Comparative Compounds 1 to 5 in which an amine group is substituted in the fluorenyl group core rather than the element of Comparative Example 1 manufactured using NPB mainly used as a hole transport layer material have been improved, and Compared to Comparative Examples 1 to 6, when the compound according to Formula 1 of the present invention was used as a material for the hole transport layer, the luminous efficiency and lifespan of the organic light emitting device were increased, and the driving voltage was slightly lowered, thereby further improving the electrical properties of the element.

Configurations 1 and 2, of the fluorenyl group and the substituent of the amine group on the monoamine basic skeleton, and are compounds having a substituent at a specific substitution position, such as $R_1$ and $R_2$ in each of Configurations 1 and 2.

Table 5 is data obtained by measuring quantum mechanical triplet bond dissociation energies (hereinafter, T1-BDE) of amorphous solid-phase molecules of the compounds of the present invention having similar compound structures and Comparative Compounds 1 to 5 using molecular simulation.

TABLE 5

| | T1-BDE (Kcal/mol) |
|---|---|
| P-1 | 17.698 |
| P-37 | 17.630 |
| P-57 | 18.362 |
| comparative compound 1 | 9.043 |
| comparative compound 2 | 10.284 |
| comparative compound 3 | 14.187 |
| comparative compound 4 | 14.725 |
| comparative compound 5 | 13.939 |

In Table 5, it can be seen that the T1-BDE values of the compounds P-1, P-37 and P-57 of the present invention are higher than those of Comparative Compounds 1 to 5. In organic electronic elements, the lower the crystallinity of the thin film, the more an amorphous state can be created, and this amorphous state can reduce grain boundaries and speed up the mobility of charges and holes through isotropic and homogeneous properties. However, depending on the structure of the molecule, even in the same amorphous state, the quantum mechanical average dissociation energy of a solid-state molecule in the amorphous state may be different due to intermolecular interactions in the solid-state, and the higher the value, the higher the stability of the compound itself. Therefore, it is judged that when the compound of the present invention is used as a hole transport layer of an organic electronic element, the stability of electrons passing through the emitting layer is significantly higher than that of Comparative Examples using Comparative Compounds 1 to 5, which have similar basic skeletons to the compound of the present invention, therefore the lifetime of the element is maximized.

Also, it can be seen from Tables 6 and 7, even with the same configuration, the difference in effects according to the limitations of the substituents corresponding to Configurations 1 and 2 of Formula 1 of the present invention can be confirmed. Table 6 is a table showing the average distance between molecules of the compound P-1 of the present invention and Comparative Compounds 1, 3 to 5, and Table 7 is data comparing the average distance between molecules of the compound P-37 of the present invention and the comparative compound 2.

TABLE 6

| | average distance between molecules (Å) |
|---|---|
| P-1 | 9.956 |
| comparative compound 1 | 10.359 |
| comparative compound 3 | 9.965 |
| comparative compound 4 | 10.476 |
| comparative compound 5 | 10.352 |

TABLE 7

| | average distance between molecules (Å) |
|---|---|
| P-37 | 10.507 |
| comparative compound 2 | 10.553 |

Referring to Table 6, it can be seen that the average intermolecular distance of compound P-1 of the present invention represents a value smaller than the average intermolecular distance of Comparative Compounds 1, 3 to 5, furthermore, it can be confirmed that the average distance between molecules is 9.956 Å, which is smaller than that of Comparative Compound 3, which has the same molecular weight as Compound P-1. Through this, in Formula 1 of the present invention, $R_1$ and $R_2$ in Components 1 and 2 are respectively substituted at specific positions, so that the intermolecular distance is closer when the compound of the present invention is in an amorphous solid state than the comparative compounds, accordingly, it is judged that the efficiency and driving of the device are remarkably improved as the charge balance of the entire device is improved because the movement of the charge is relatively fast. As described above, referring to Table 7, it can be seen that the average intermolecular distance of the compound P-37 of the present invention gives a small value compared to the comparative compound 2, and the above-described effects can be obtained through the compound of the example of the present invention.

Additionally, Table 8 is data comparing the HOMO dos w of the compound P-1 of the present invention and the comparative compound 1.

TABLE 8

| | HOMO dos w (eV) |
|---|---|
| P-1 | 0.172 |
| Comparative example 1 | 0.119 |

Referring to Table 8, the HOMO dos w of the compound P-1 of the present invention shows a value of 0.172 eV, and the comparative compound 1 shows a value of 0.119 eV. It means as the value increases, the charge injection characteristics between different layers are improved. Through this, it can be confirmed that even if the compound skeleton of the present compound P-1 and the comparative compound 1 is very similar and the molecular weight is the same, having a selective structure in which $R_1$ is substituted at the para position of component 1 and $R_2$ is substituted at the ortho position of component 2 as shown in Formula 1 of the present invention can further improve the performance of the device.

Additionally, in the evaluation results of the above-described element fabrication, the element characteristics in which the compound of the present invention is applied only to the hole transport layer has been described, but the compound of the present invention may be applied to the emitting auxiliary layer or both the hole transport layer and the emitting auxiliary layer may be applied. However, it is explained through the element results that the preferred layer of the compound of the present invention is a hole transport layer.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

BRIEF DESCRIPTION OF THE DRAWINGS 100, 200, 300: organic electronic element 110: the first electrode
120: hole injection layer 130: hole transport layer
140: emitting layer 150: electron transport layer
160: electron injection layer 170: second electrode
180: light efficiency enhancing Layer 210: buffer layer
220: emitting-auxiliary layer 320: first hole injection layer
330: first hole transport layer 340: first emitting layer
350: first electron transport layer 360: first charge generation layer
361: second charge generation layer 420: second hole injection layer
430: second hole transport layer 440: second emitting layer
450: second electron transport layer CGL: charge generation layer
ST1: first stack ST2: second stack

What is claimed is:

1. A compound represented by Formula 2:

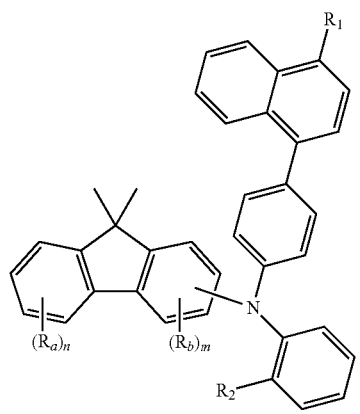

Formula 2 wherein:
1) $R_1$ is a $C_6$ aryl group;
2) $R_2$ is selected from a group consisting of an $C_6$-$C_{26}$ aryl group; fluorenyl group; $C_2$-$C_{30}$ heterocyclic group including at least one heteroatom of O, N, S, Si or P; fused ring group of a $C_3$-$C_{20}$ aliphatic ring and a $C_6$-$C_{30}$ aromatic ring; and $C_2$-$C_{10}$ alkenyl group;
3) $R_a$ and $R_b$ are the same or different from each other, and are each independently a hydrogen; deuterium; $C_6$-$C_{30}$ aryl group;
4) m is an integer of 0 to 3, n is an integer of 0 to 4,
5) Wherein the aryl group, heterocyclic group, fluorenyl group, aliphatic ring, fused ring group, and alkenyl group may be substituted with one or more substituents selected from the group consisting of deuterium; halogen; $C_6$-$C_{20}$ aryl group; and $C_6$-$C_{20}$ aryl group substituted with deuterium.

2. The compound of claim 1, wherein Formula 2 is represented by Formula 8:

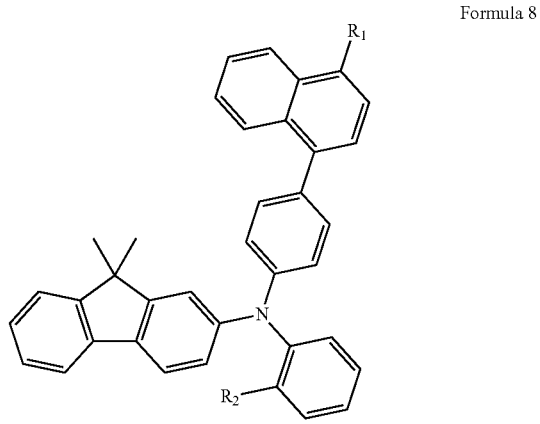

Formula 8 wherein $R_1$ and $R_2$ are the same as defined in claim 1.

3. The compound of claim 2, wherein $R_1$ and $R_2$ are each a $C_6$ aryl group.

4. The compound of claim 1, wherein the compound is a hole transport layer material.

5. A compound represented by any one of the following compounds:

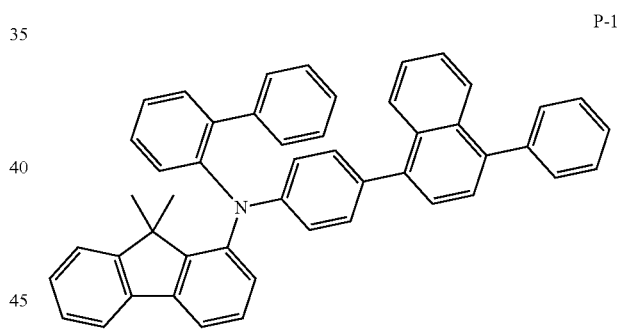

P-1

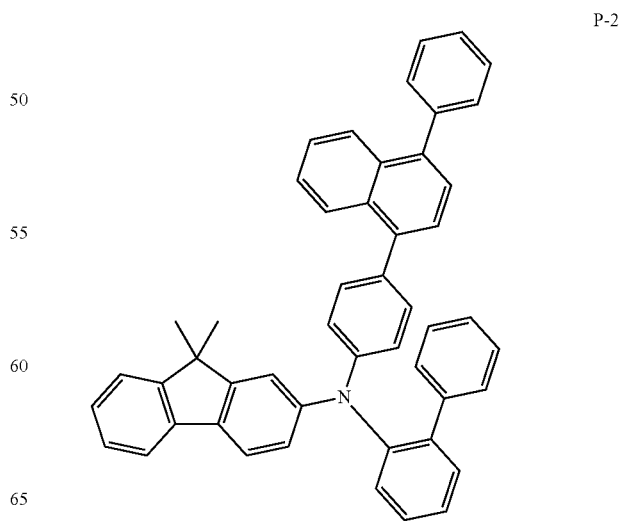

P-2

P-3
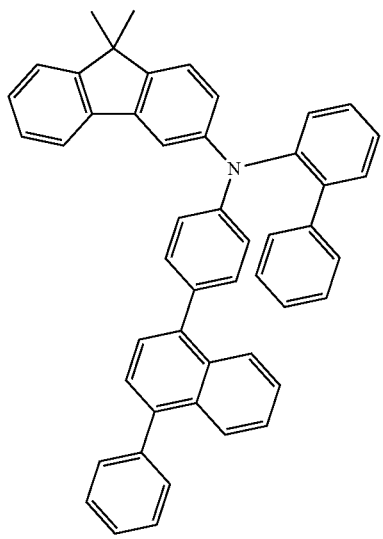
P-4
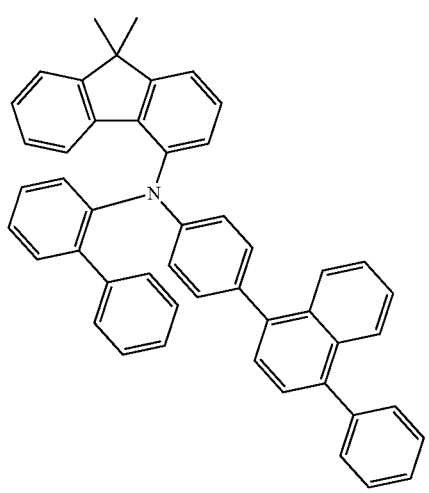
P-6
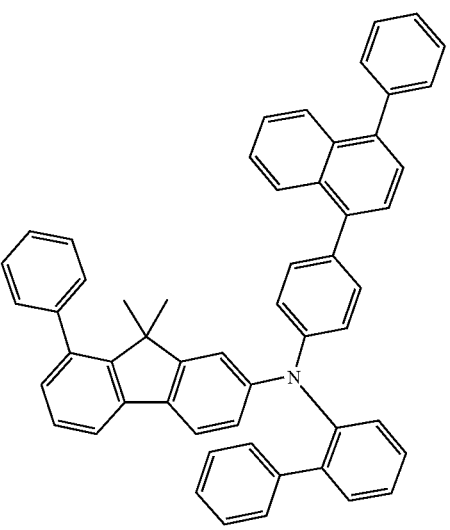
P-8
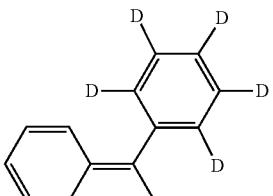
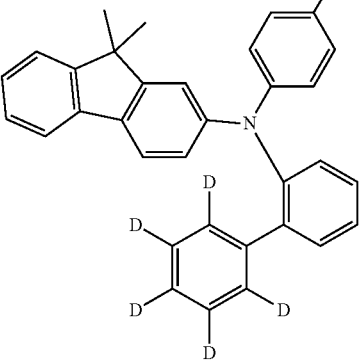
P-10

P-11
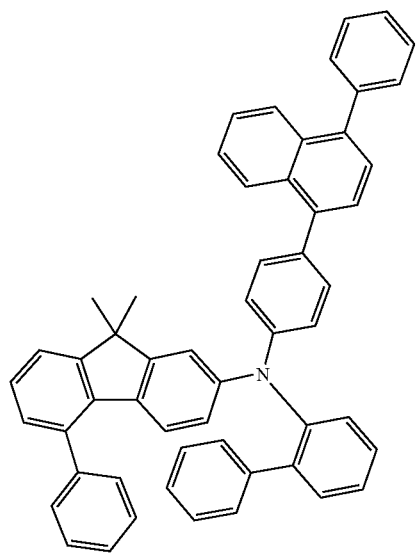
P-12
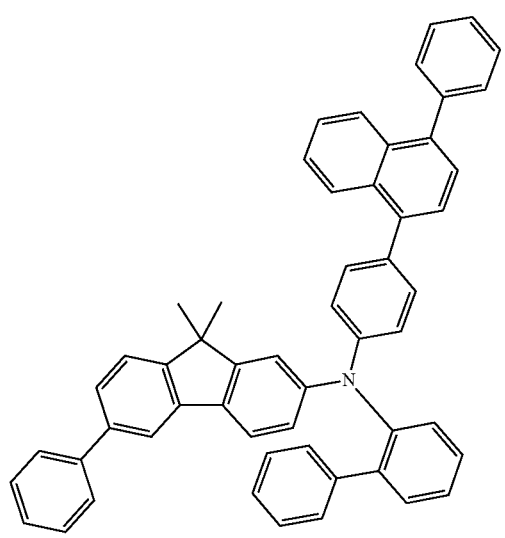
P-13
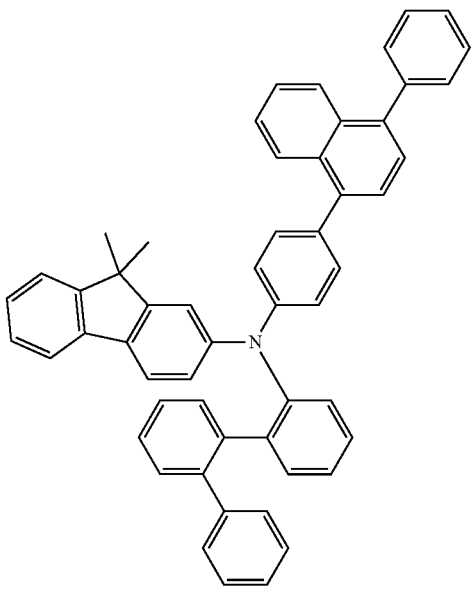
P-16
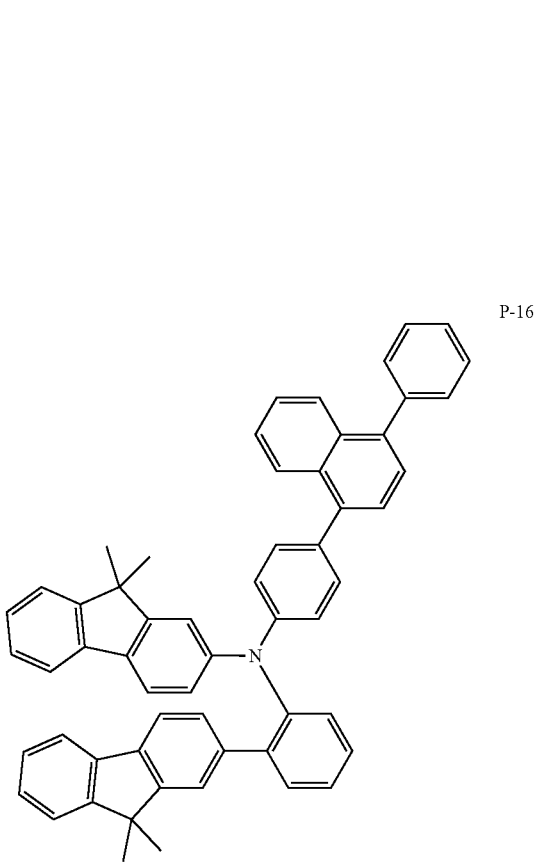

P-18
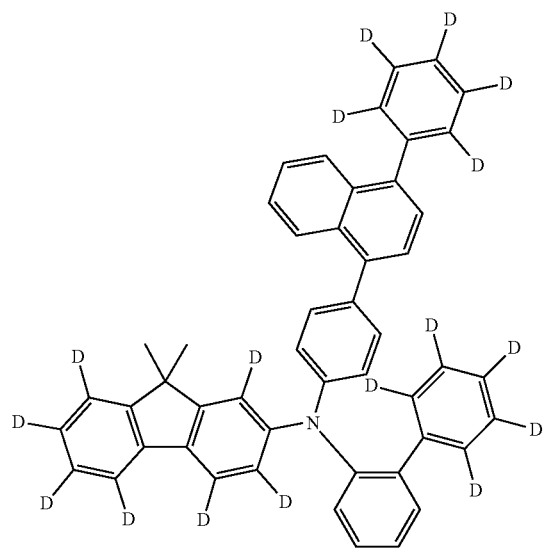
P-24
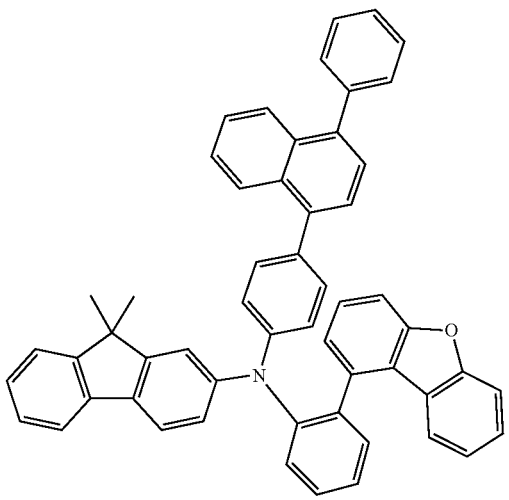
P-19
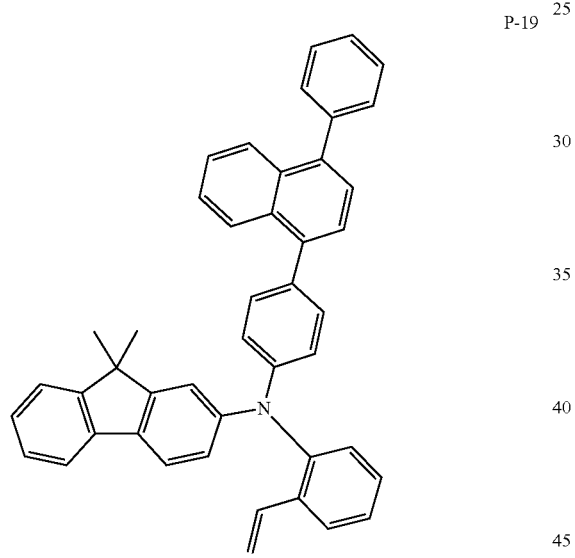
P-25
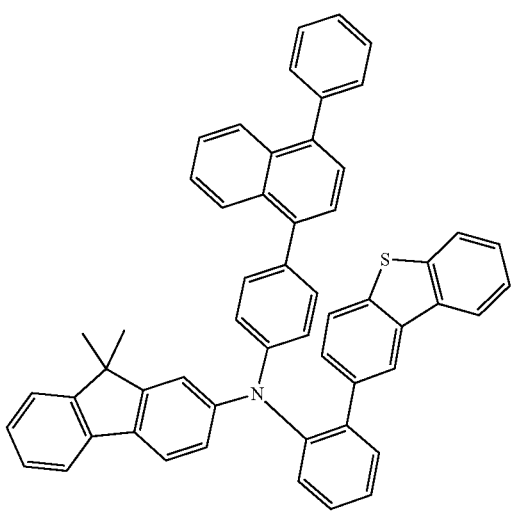
P-22
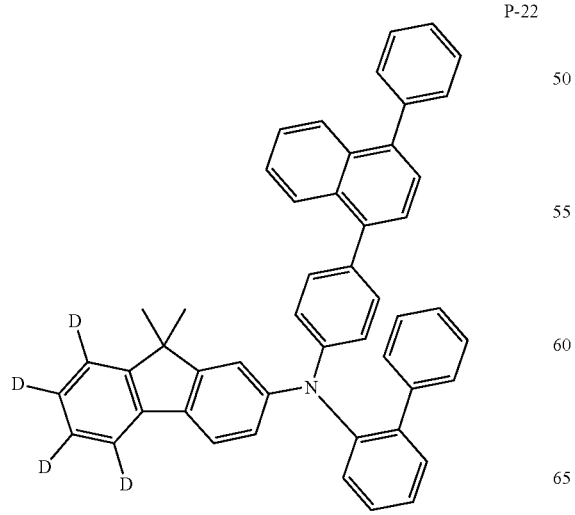
P-28
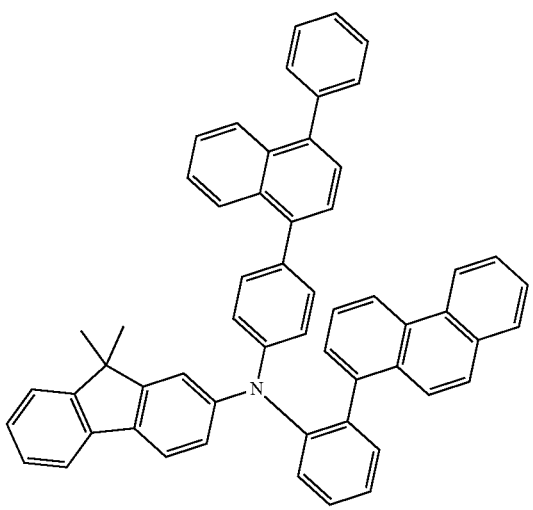

333
-continued

P-32

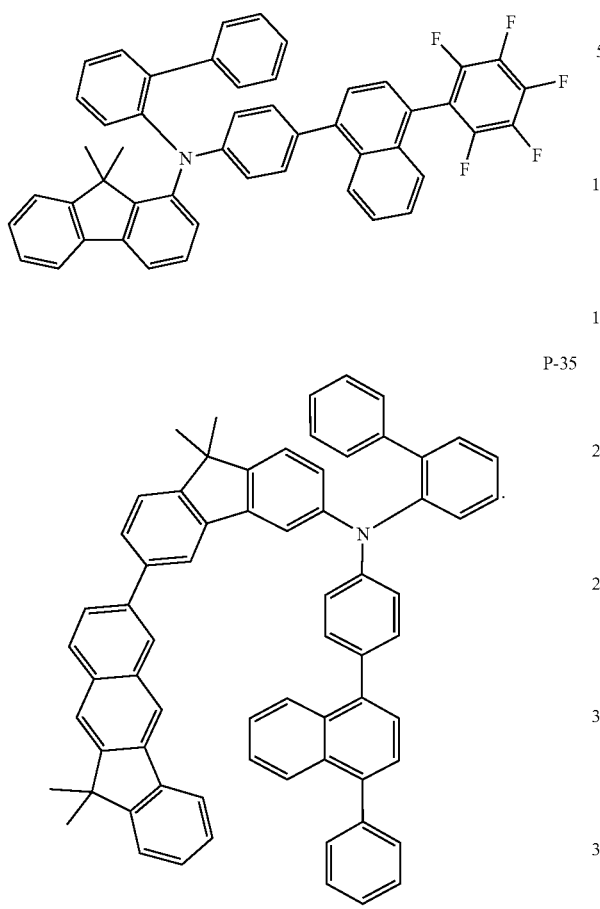

P-35

6. An organic electronic element comprising an anode, a cathode, and an organic material layer formed between the anode and the cathode, wherein the organic material layer comprises a single compound or 2 or more compounds according to claim 1.

7. The organic electronic element of claim 6, wherein the organic material layer comprises at least one of a hole injection layer, a hole transport layer, an emitting-auxiliary layer, an emitting layer, an electron transport auxiliary layer, an electron transport layer, and an electron injection layer.

8. The organic electronic element of claim 6, wherein the organic layer is a hole transport layer.

9. The organic electronic element of claim 7, wherein the emitting layer comprises at least one compound represented by any of Formulas 12 to 14:

Formula 12

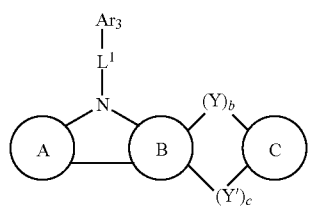

334
-continued

Formula 13

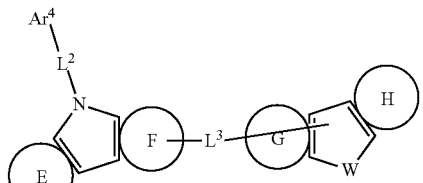

Formula 14

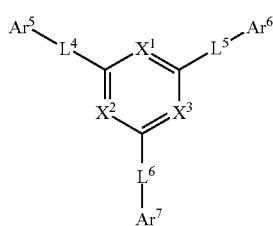

wherein:
1) $X^1$, $X^2$ and $X^3$ are each independently $C(R_3)$ or N, provided that at least 2 of $X^1$, $X^2$ and $X^3$ are N,
2) $R_3$ is selected from the group consisting of hydrogen; deuterium; halogen; a $C_6$-$C_{60}$ aryl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; $C_1$-$C_{50}$ alkyl group; a $C_2$-$C_{20}$ alkenyl group; a $C_2$-$C_{20}$ alkynyl group; a $C_1$-$C_{30}$ alkoxy group; and a $C_6$-$C_{30}$ aryloxy group,
3) Y and Y' are each independently O, S, $CR^eR^f$ or N-L'-$Ar^8$,
4) W is O, N, S, $CR^eR^f$ or N-L'-$Ar^8$,
5) Wherein $R^e$ and $R^f$ are each independently selected from the group consisting of hydrogen; deuterium; $C_6$-$C_{60}$ aryl group; fluorenyl group; $C_2$-$C_{60}$ heterocyclic group including at least one heteroatom of O, N, S, Si or P; fused ring group of a $C_3$-$C_{60}$ aliphatic ring and a $C_6$-$C_{60}$ aromatic ring; $C_1$-$C_{50}$ alkyl group; $C_2$-$C_{20}$ alkenyl group; $C_2$-$C_{20}$ alkynyl group; $C_1$-$C_{30}$ alkoxy group; and $C_6$-$C_{30}$ aryloxy group, or $R^e$ and $R^f$ may be bonded to each other to form a spiro ring,
6) $L^1$, $L^2$, $L^3$, $L^4$, $L^5$, $L^6$ and L' are each independently selected from the group consisting of a single bond; a $C_6$-$C_{60}$ arylene group; and a $C_2$-$C_{60}$ heterocyclic group including at least one heteroatom of O, N, S, Si or P,
7) $Ar^3$, $Ar^4$, $Ar^5$, $Ar^6$, $Ar^7$ and $Ar^8$ are each independently selected from the group consisting of $O_6$-$C_{60}$ aryl group; fluorenyl group; $C_2$-$C_{60}$ heterocyclic group including at least one heteroatom of O, N, S, Si or P; fused ring group of a $C_3$-$C_{60}$ aliphatic ring and a $C_6$-$C_{60}$ aromatic ring; $C_1$-$C_{60}$ alkyl group; $C_2$-$C_{20}$ alkenyl group; $C_2$-$C_{20}$ alkynyl group; $C_1$-$C_{30}$ alkoxy group; and $C_6$-$C_{30}$ aryloxy group,
8) Ring A, ring B and ring C are each independently a $C_6$-$C_{14}$ aryl group; or, ring A, ring B and ring C may be substituted with $R^1$,
9) E ring, F ring, G ring and H ring are each independently a $C_6$-$C_{20}$ aryl group; or $C_2$-$C_{20}$ heterocyclic group; or, E ring, F ring, G ring and H ring may be substituted with $R^2$,
10) Wherein $R^1$ and $R^2$ are each independently selected from the group consisting of a hydrogen; deuterium; halogen; cyano group; $C_6$-$C_{60}$ aryl group; $C_2$-$C_{60}$ heterocyclic group including at least one heteroatom of O, N, S, Si or P; fused ring group of a $C_3$-$C_{60}$ aliphatic ring and a $C_6$-$C_{60}$ aromatic ring; $C_1$-$C_{50}$ alkyl group; $C_2$-$C_{20}$ alkenyl group; $C_2$-$C_{20}$ alkynyl group; $C_1$-$C_{30}$ alkoxy group; and $C_6$-$C_{30}$ aryloxy group; -L''-N(R''')(R''); and adjacent groups can bond to form a ring, 11) Wherein L'' is selected from the group consisting of a single bond; a $C_6$-$C_{60}$ arylene group; a fluorenylene group; a $C_3$-$C_{60}$ aliphatic ring; a $C_2$-$C_{60}$ heterocyclic group including at least one heteroatom of O, N, S, Si or P; and a combination thereof, wherein R''' and R'' are each independently selected from the group consisting of $C_6$-$C_{60}$ aryl group; fluorenyl group; $C_3$-$C_{60}$ aliphatic ring; $C_2$-$C_{60}$ heterocyclic group including at least one heteroatom of O, N, S, Si or P; and a combination thereof, 12) B and c are each independently 0 or 1, provided that b+c≥1, 13) Wherein the aryl group, arylene group, heterocyclic group, fluorenyl group, fluorenylene group; aliphatic ring, fused ring group, alkyl group, alkenyl group, alkoxyl group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$~$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group; and the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

10. The organic electronic element of claim 9, wherein Formula 12 is represented by any one of Formulas 2-1 to 2-3:

Formula 2-1

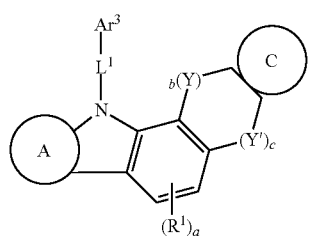

Formula 2-2

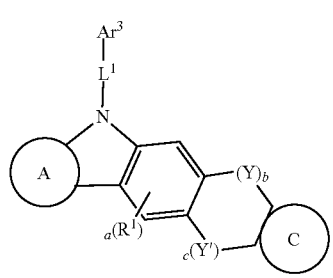

-continued

Formula 2-3

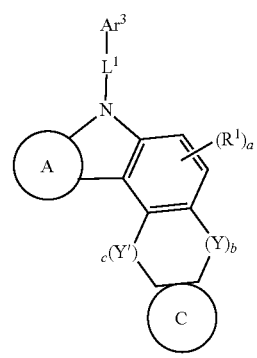

wherein:

1) A ring, C ring, Y, Y', b, c, $Ar^3$, $L^1$ and $R^1$ are the same as defined in claim 9, 2) a is an integer of 0 to 2.

11. The organic electronic element of claim 9, wherein the compound represented by Formula 12 is any one of the following compounds:

2-1

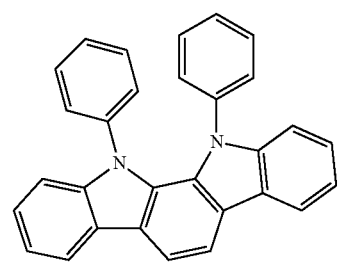

2-2

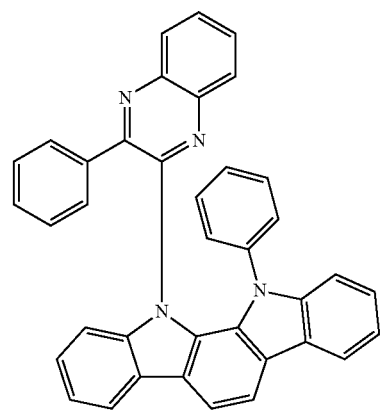

2-3

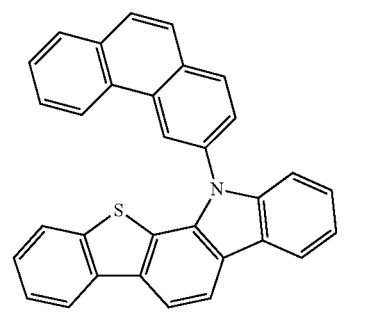

2-4
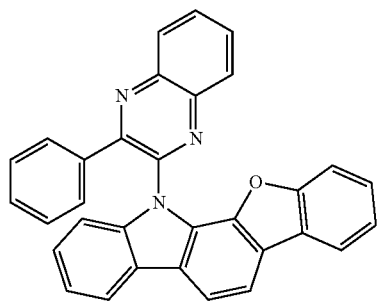
2-5
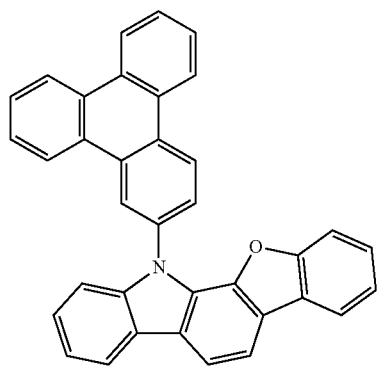
2-6
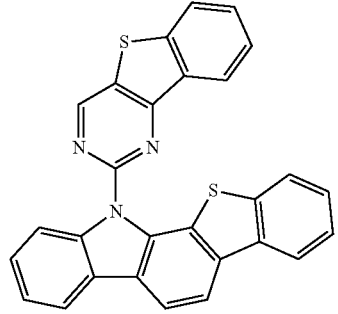
2-7
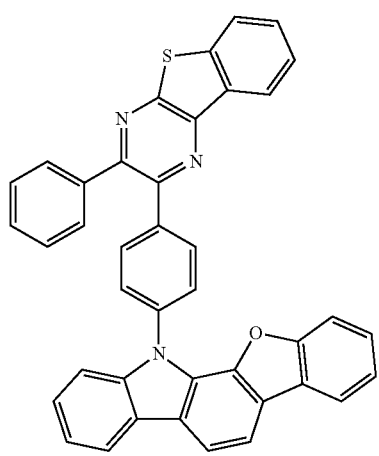
2-8
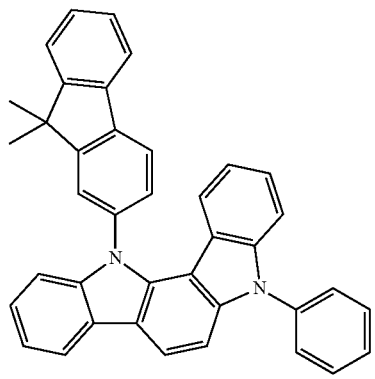
2-9
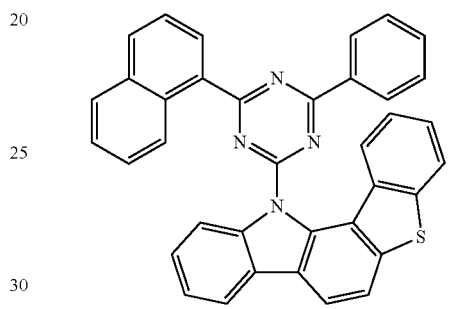
2-10
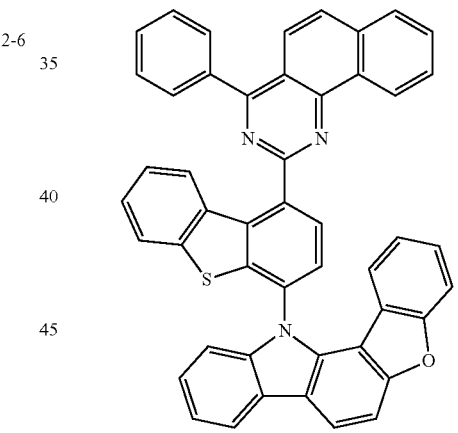
2-11
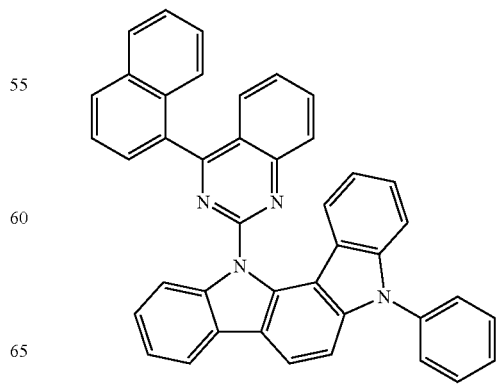

2-12
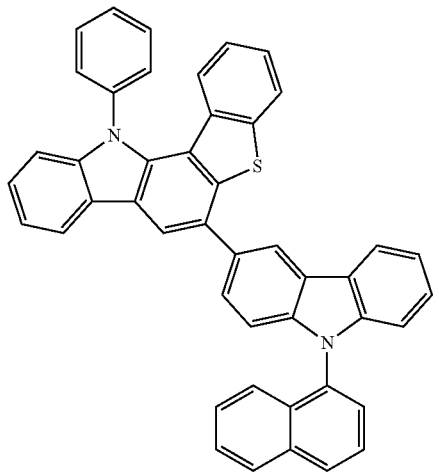
2-13
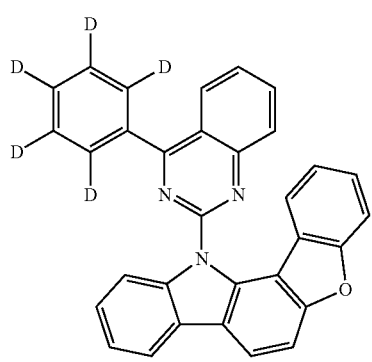
2-14
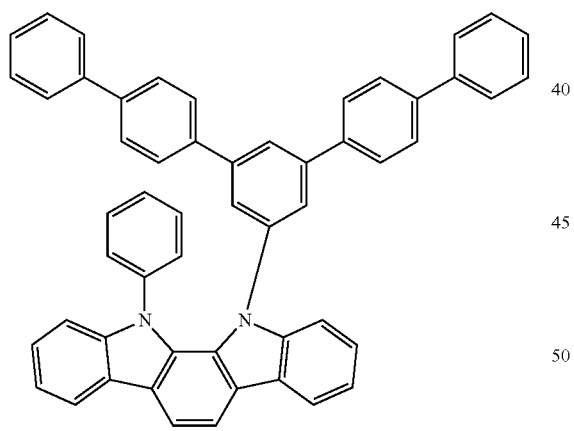
2-15
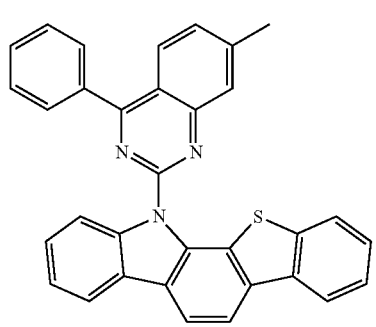
2-16
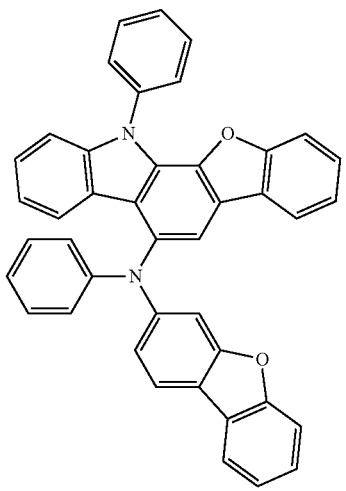
2-17
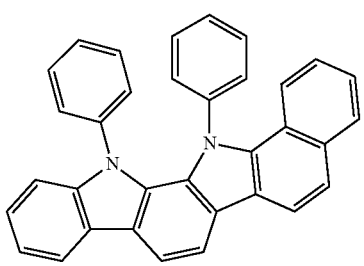
2-18
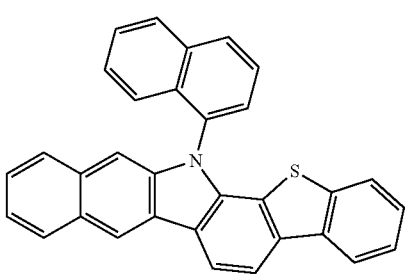
2-19
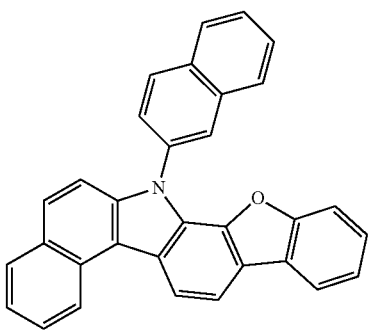

341
-continued
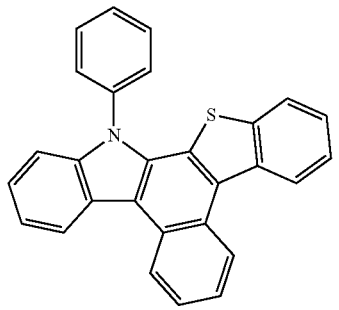
2-20
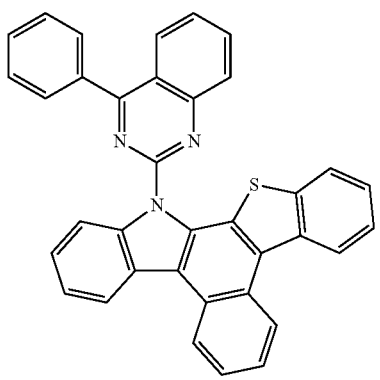
2-21
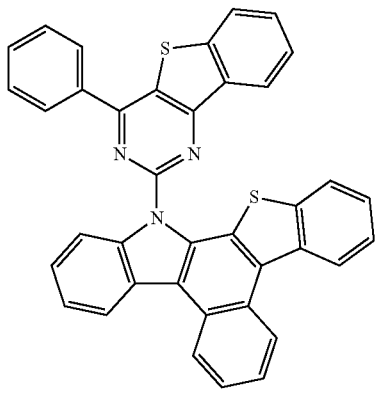
2-22
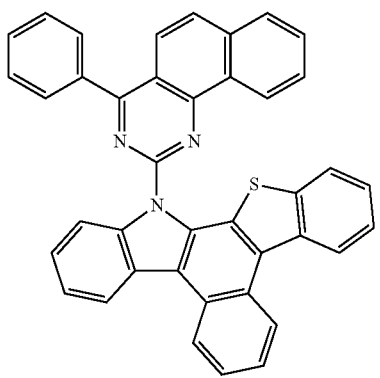
2-23
342
-continued
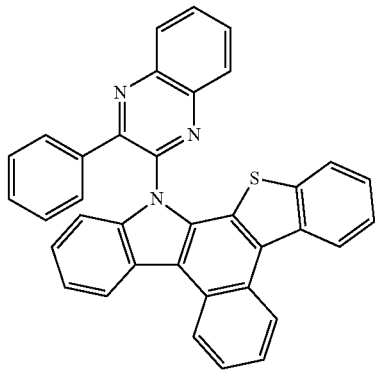
2-24
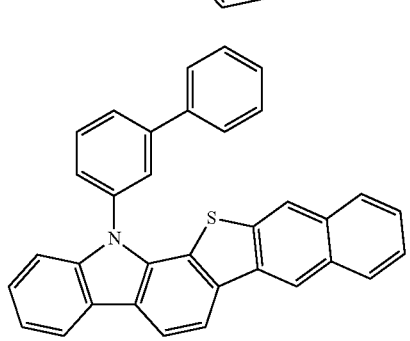
2-25
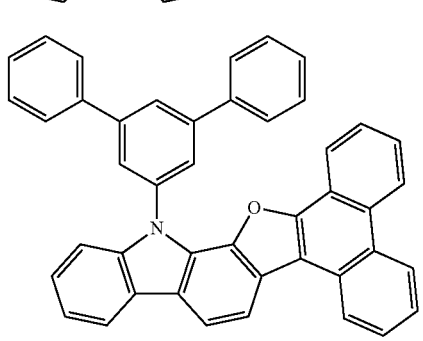
2-26
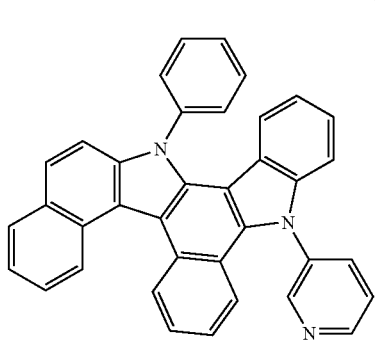
2-27
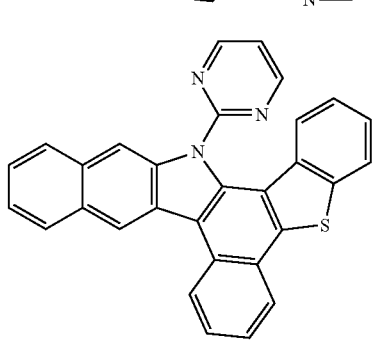
2-28

343 344
-continued -continued
2-29
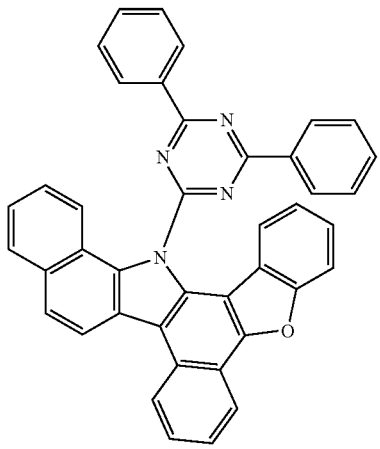
2-33
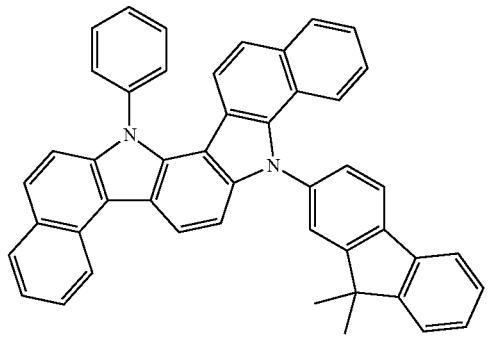
2-30
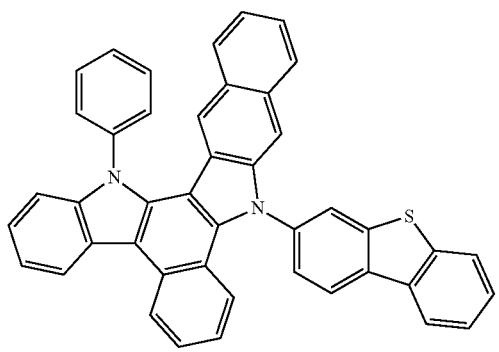
2-34
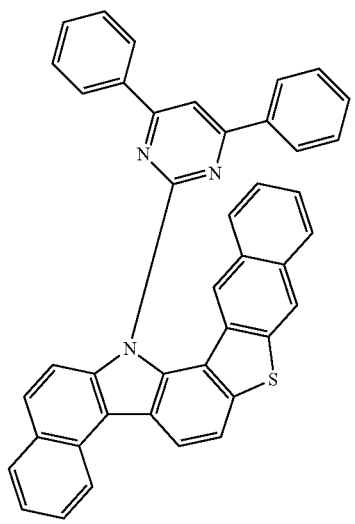
2-31
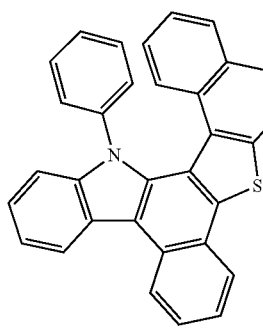
2-32
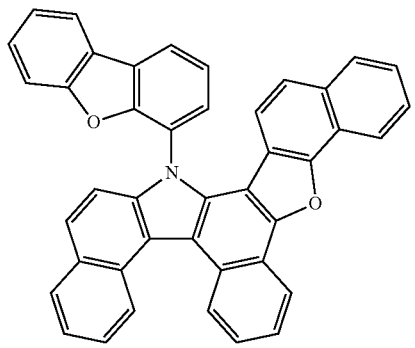
2-35
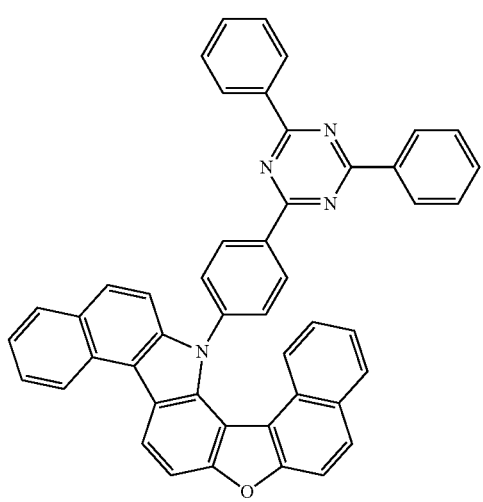

2-36
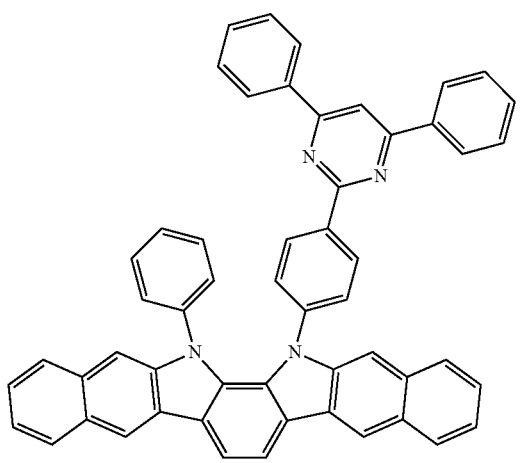
2-37
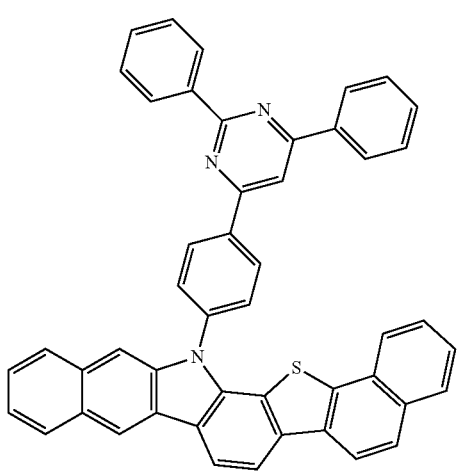
2-38
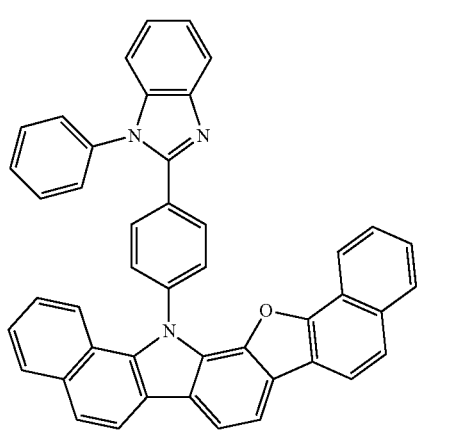
2-39
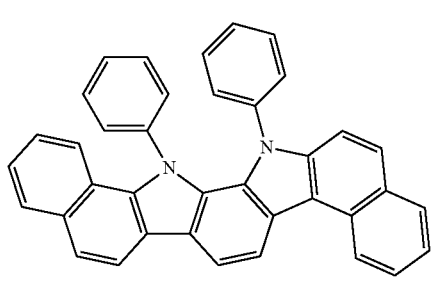
2-40
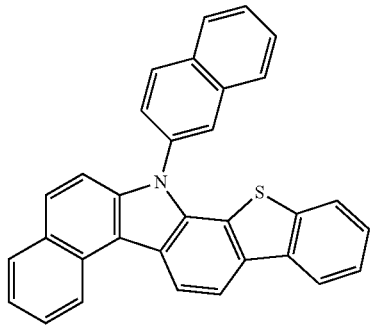
2-41
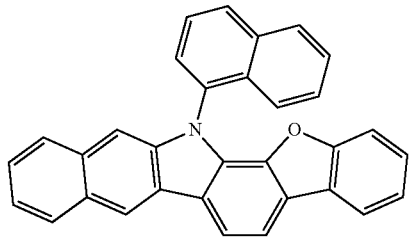
2-42
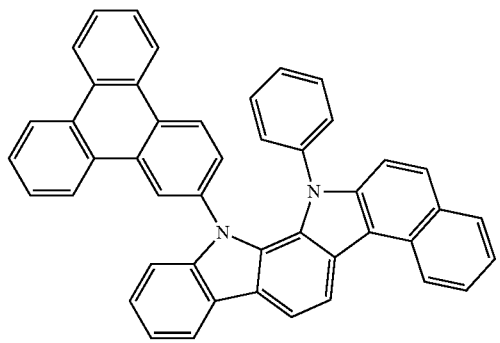
2-43
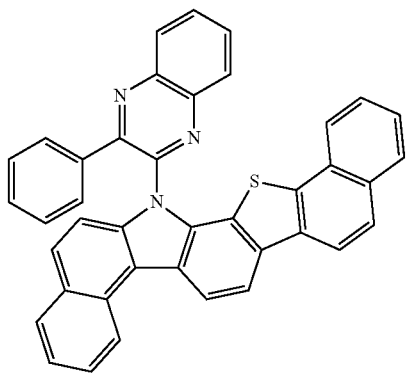
2-44
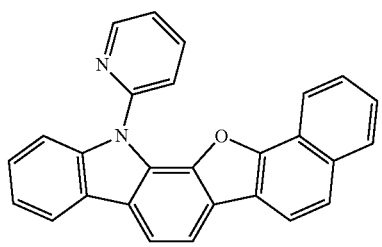

2-45
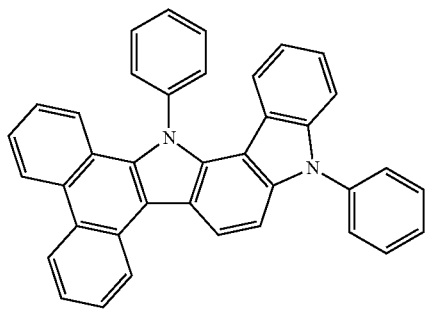
2-49
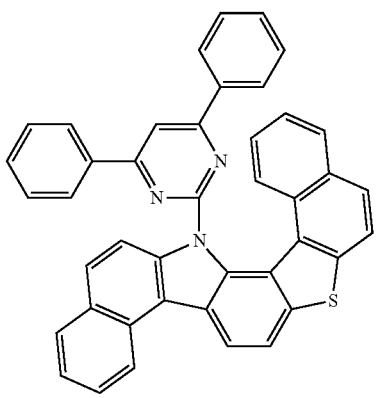
2-46
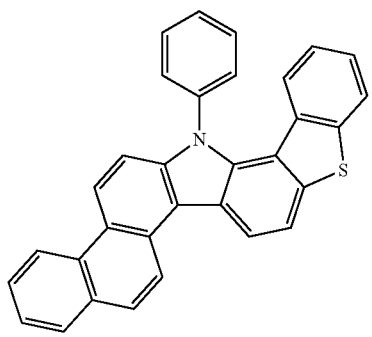
2-50
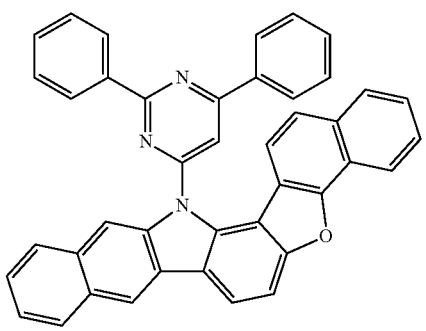
2-47
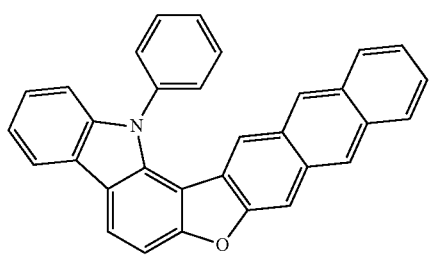
2-51
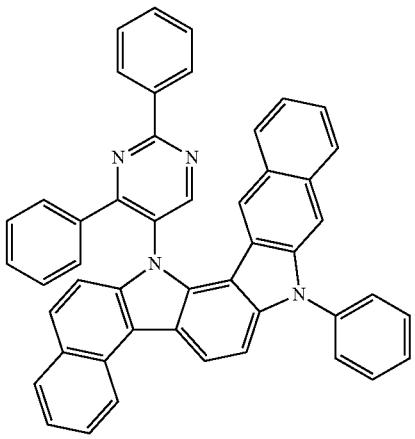
2-48
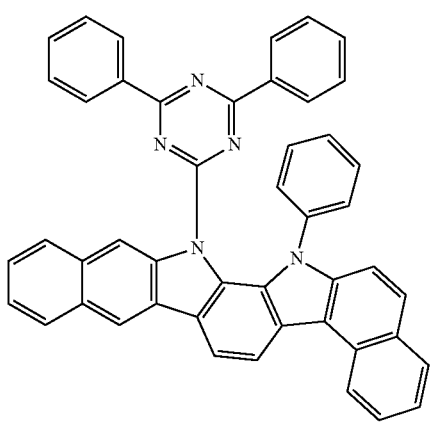
2-52
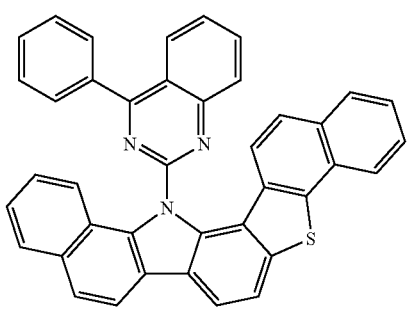

2-53
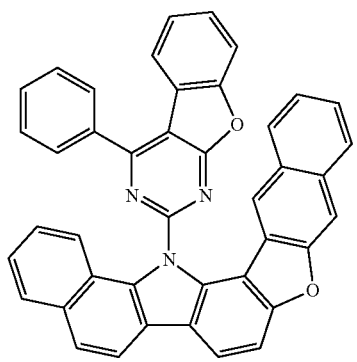
2-54
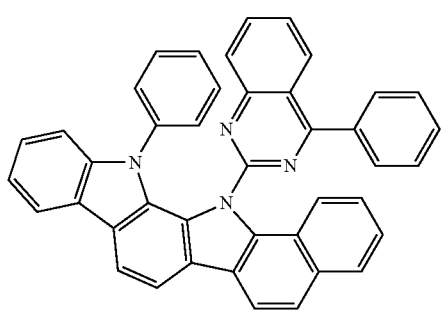
2-55
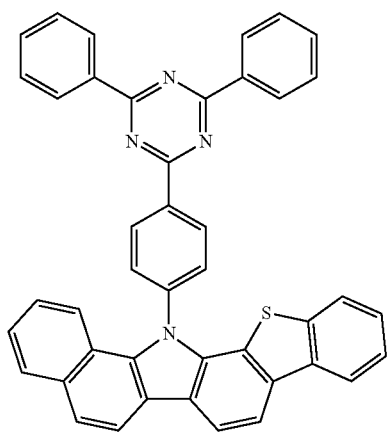
2-56
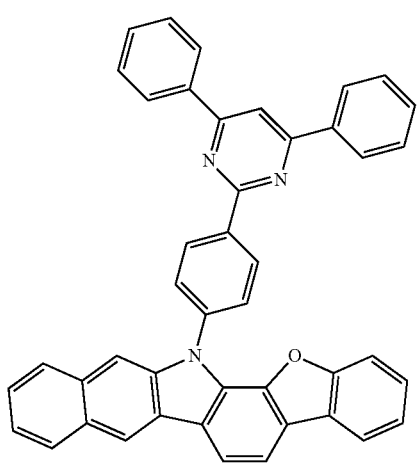
2-57
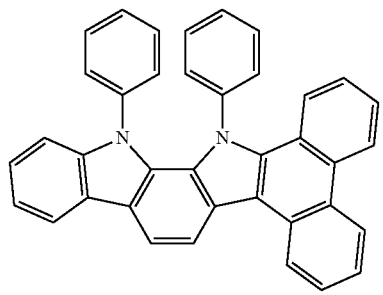
2-58
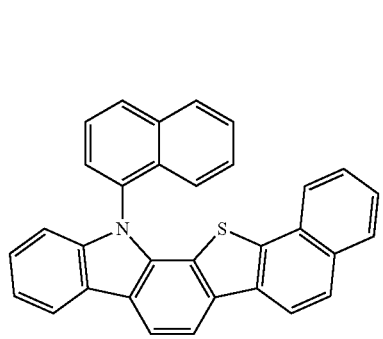
2-59
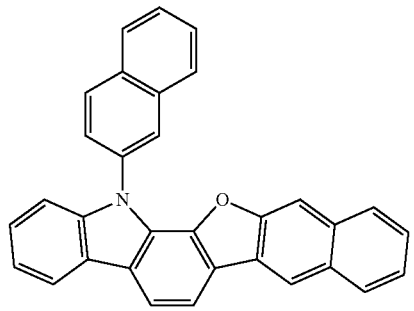
2-60
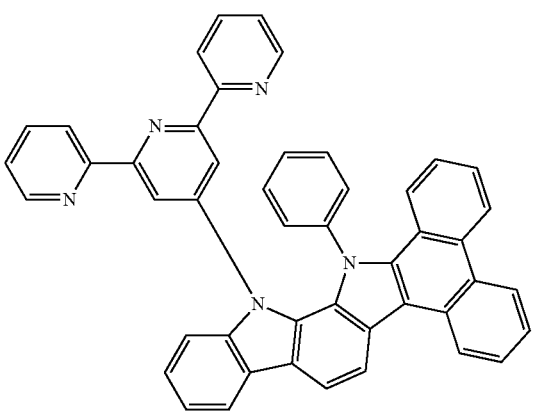

| 2-61 | 2-65 |
|---|---|
| 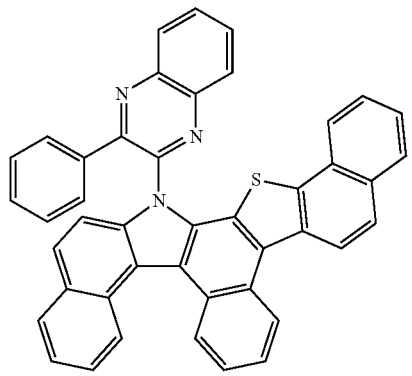 | 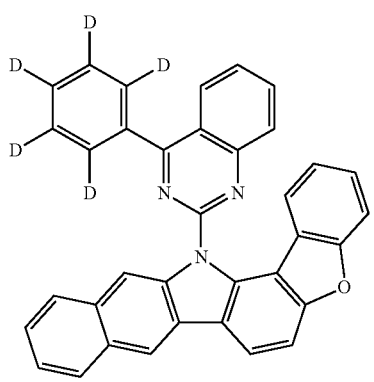 |
| 2-62 | 2-66 |
| 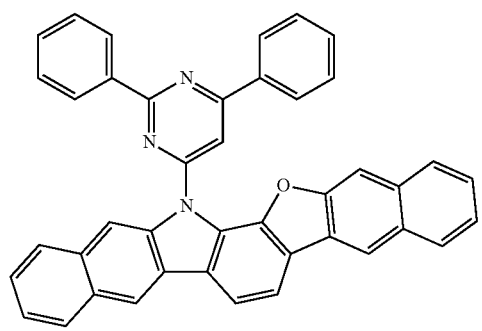 | 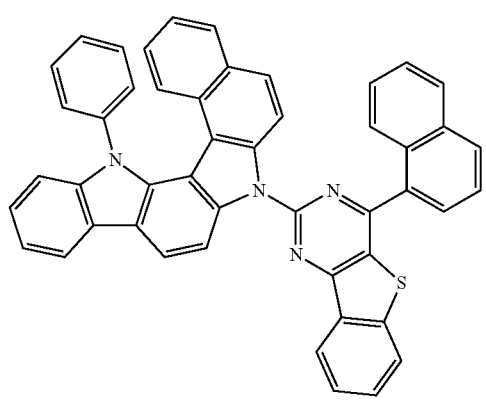 |
| 2-63 | 2-67 |
| 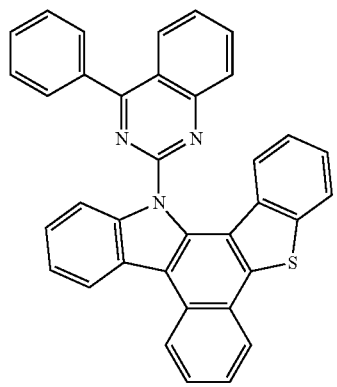 | 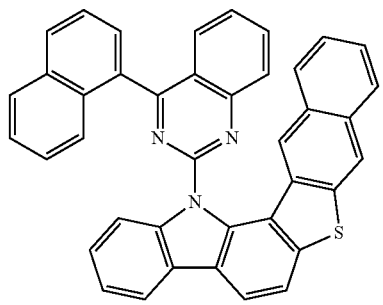 |
| 2-64 | 2-68 |
| 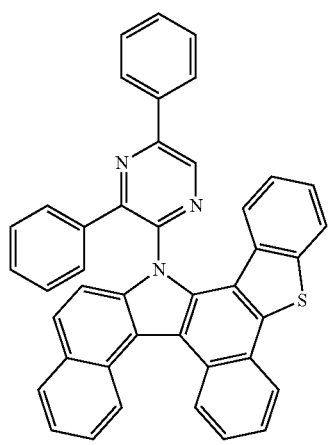 | 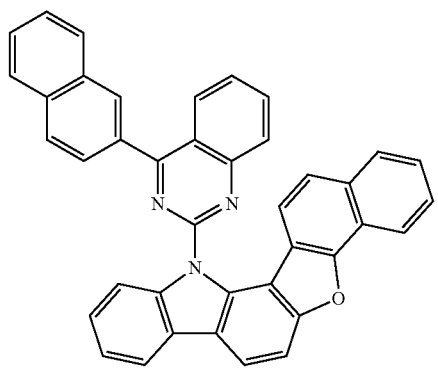 |

2-69
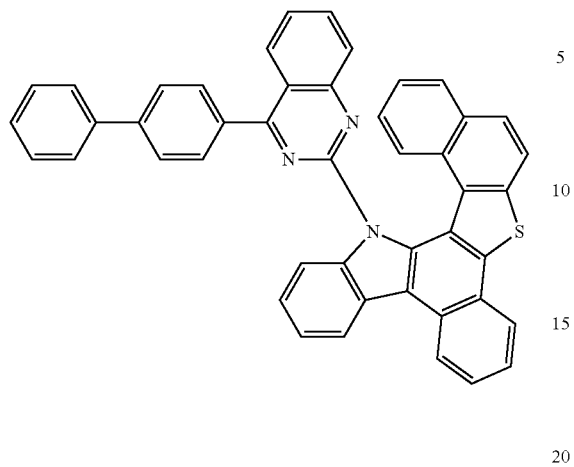
2-72
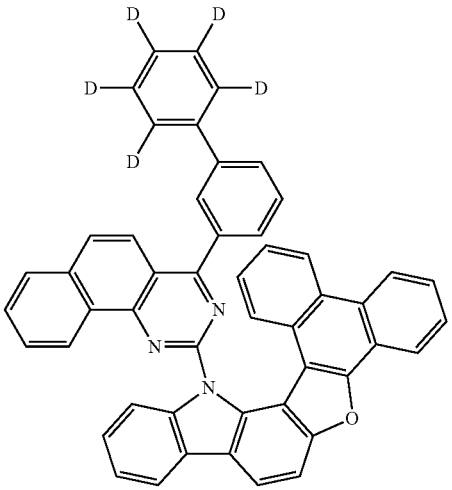
2-70
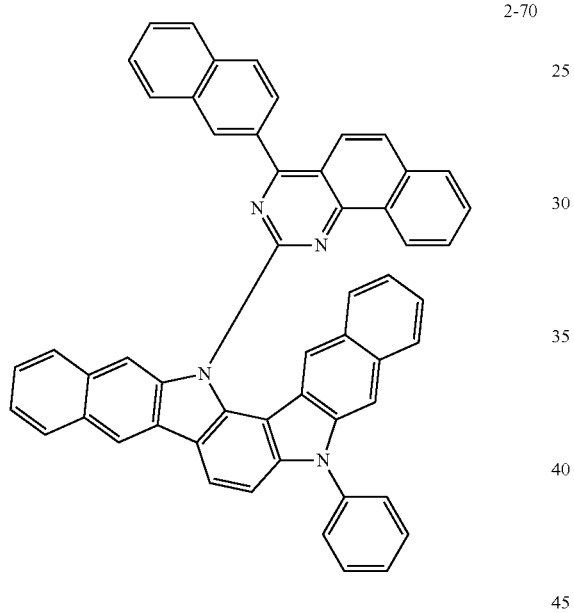
2-73
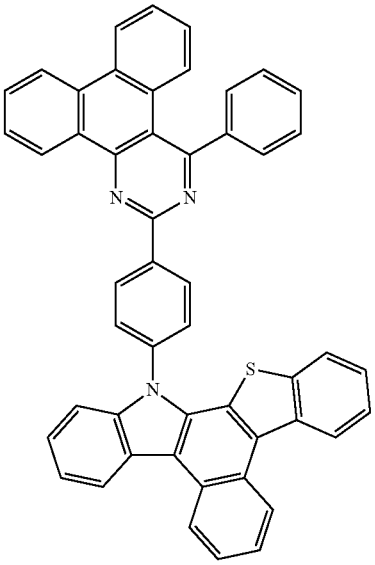
2-71
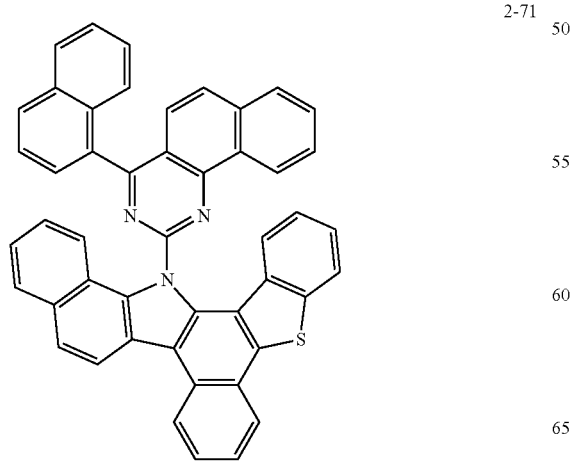
2-74
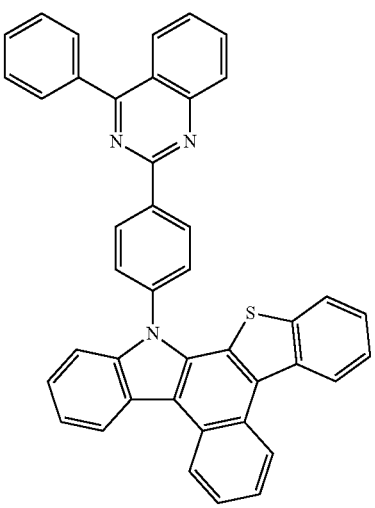

355
-continued
2-75
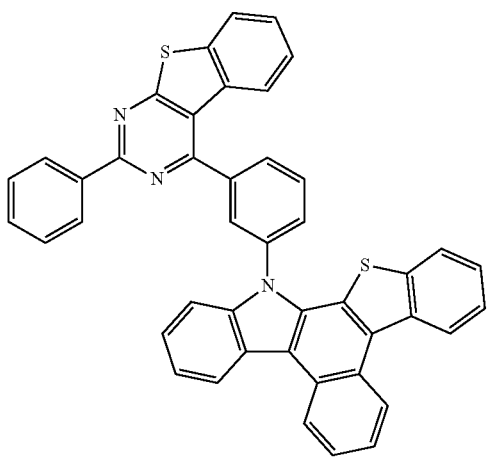
2-76
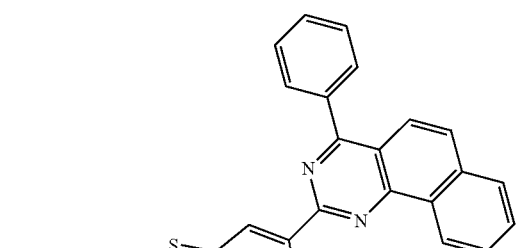
2-77
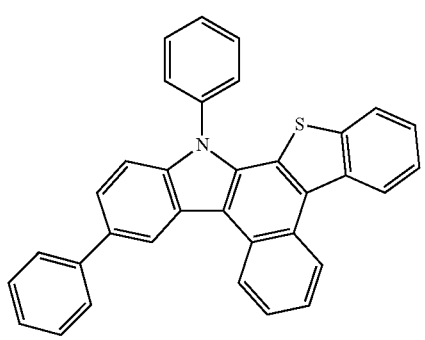
356
-continued
2-78
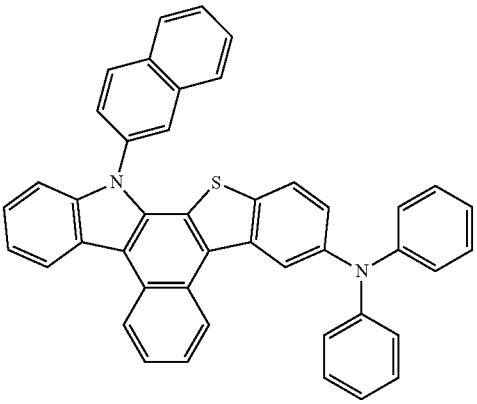
2-79
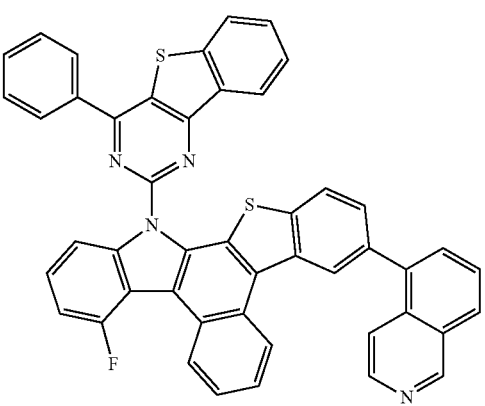
2-80
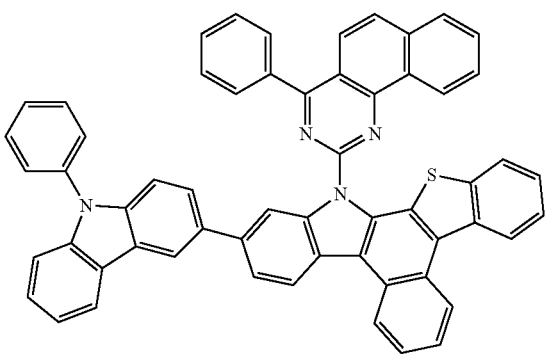
2-81
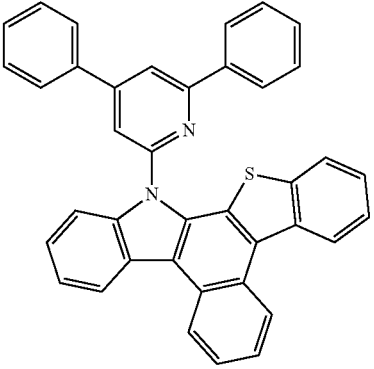

2-82
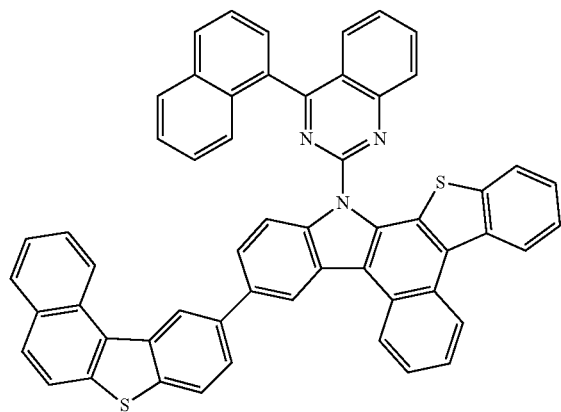
2-85
2-83
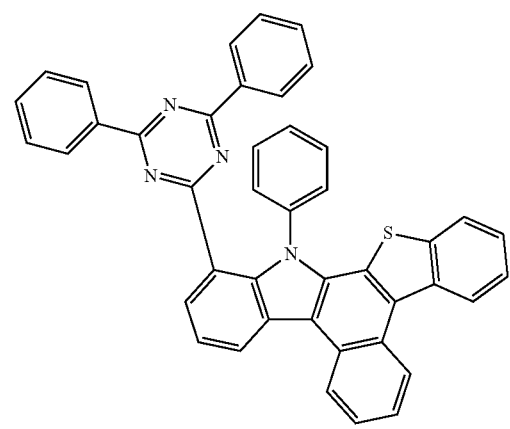
2-86
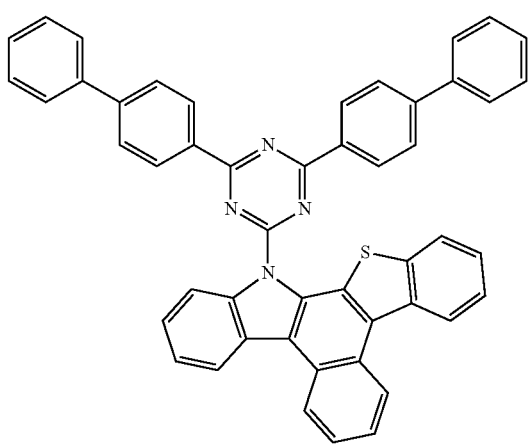
2-84
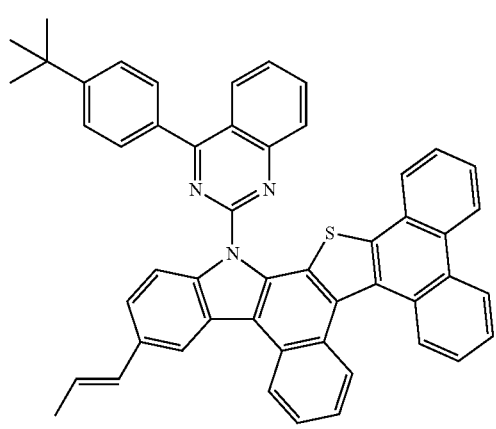
2-87
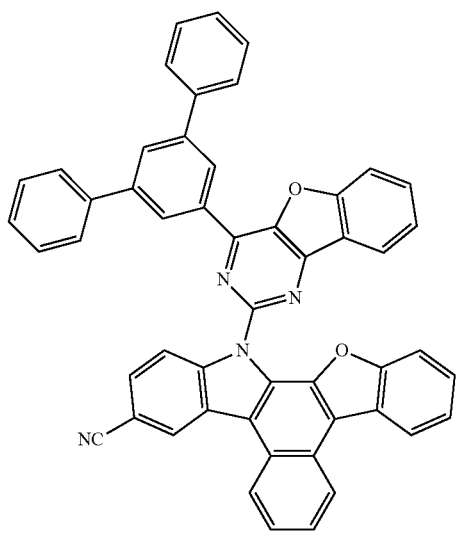

2-88
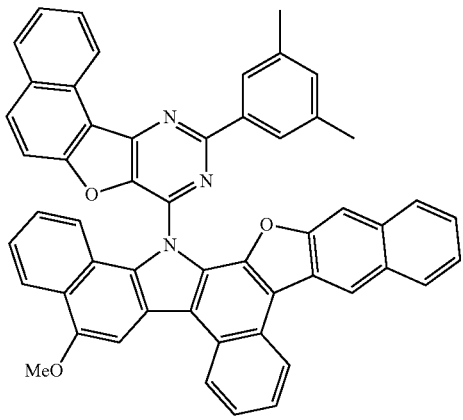
2-89
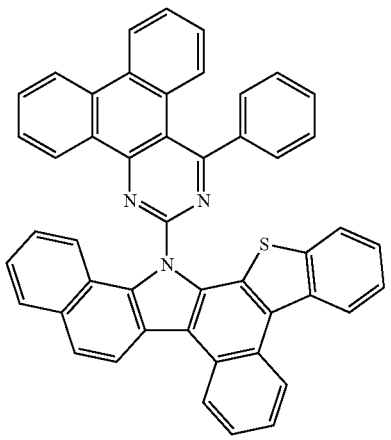
2-90
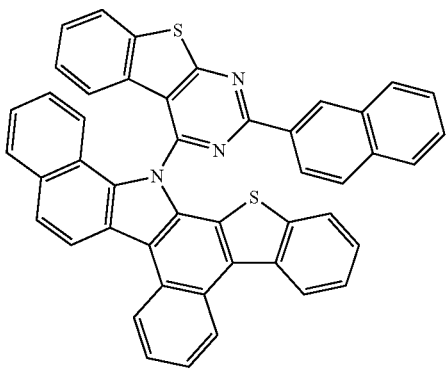
2-91
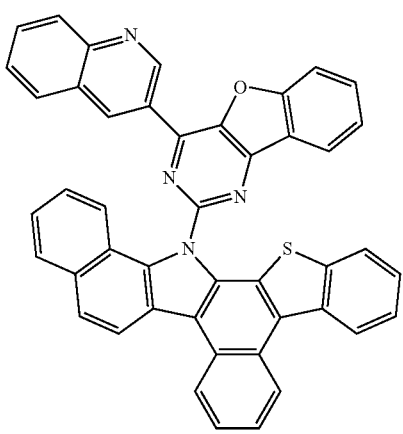
2-92
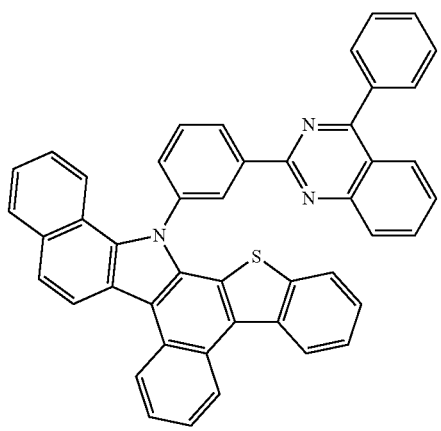
2-93
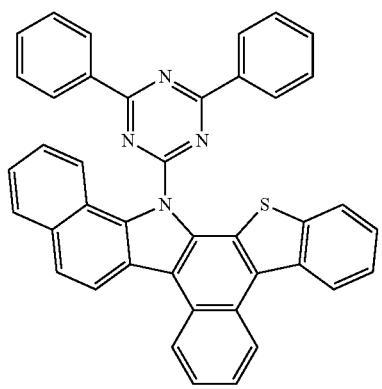
2-94
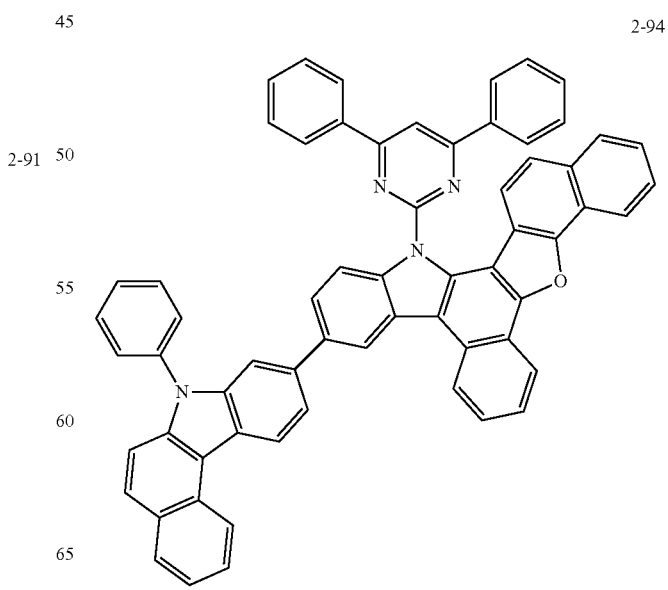

-continued
2-95
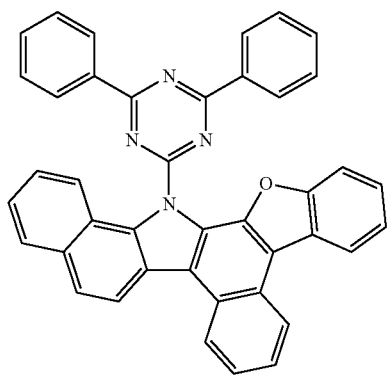
2-98
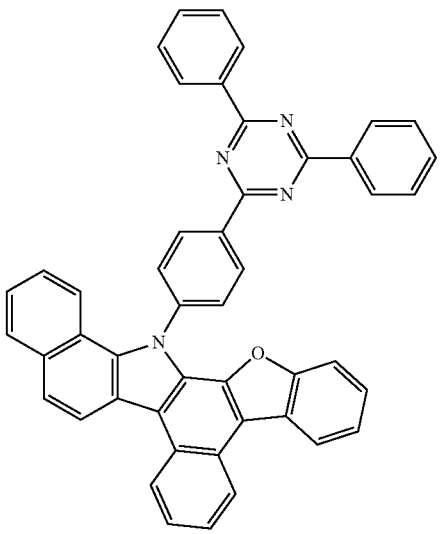
2-96
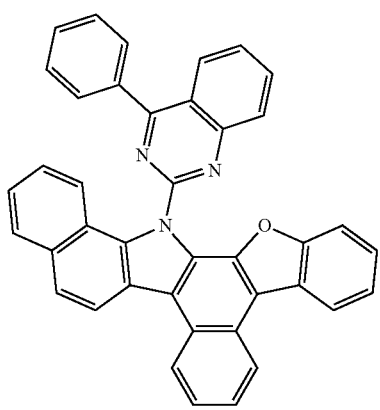
2-99
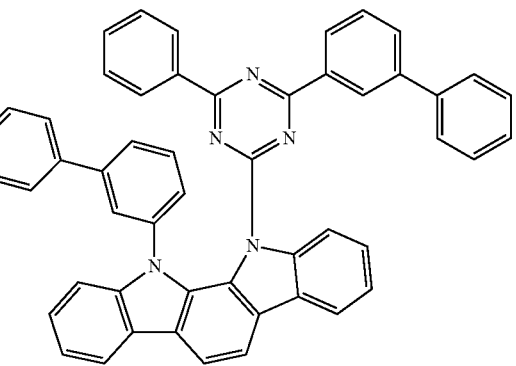
2-97
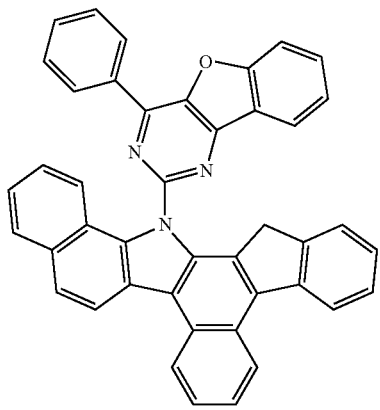
2-100

2-101
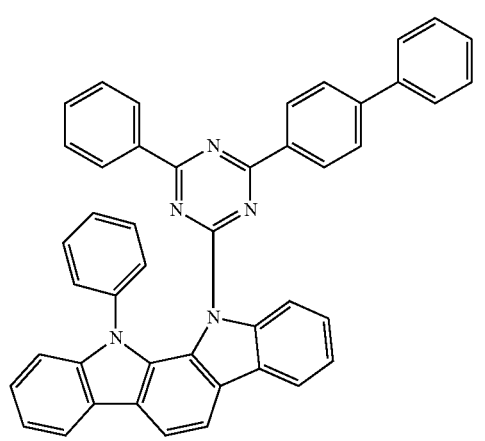
2-102
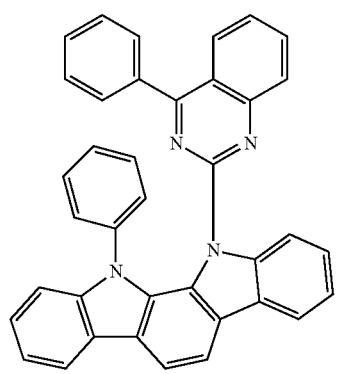
2-103
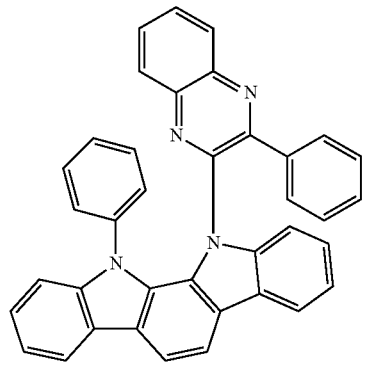
2-104
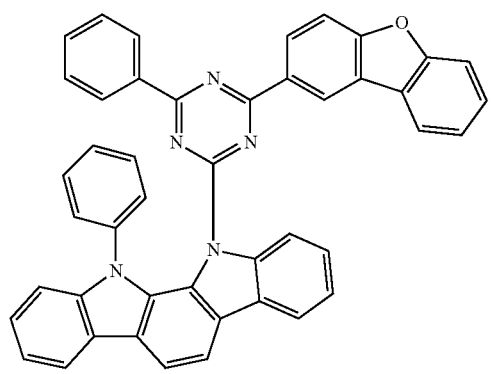
3-1
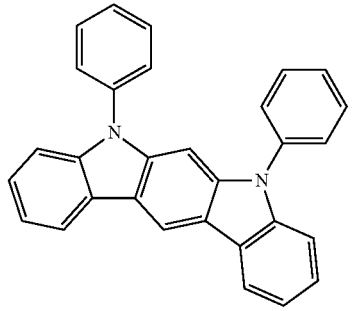
3-2
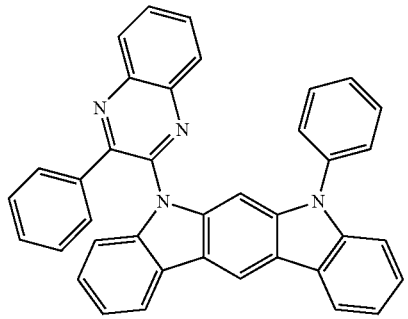
3-3
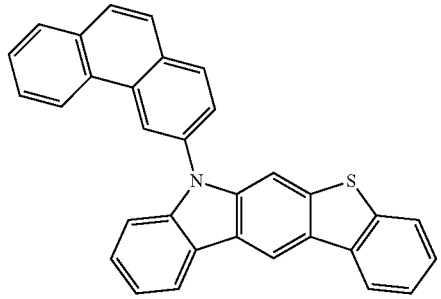
3-4
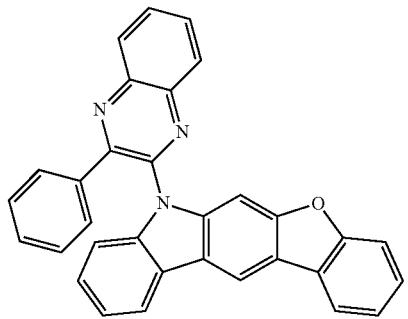
3-5
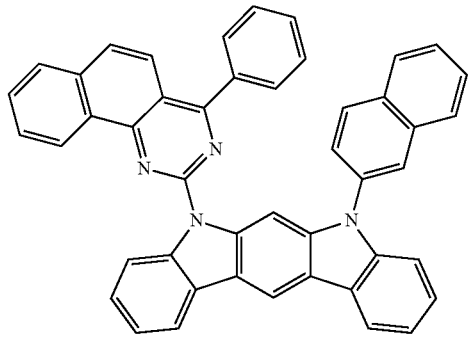

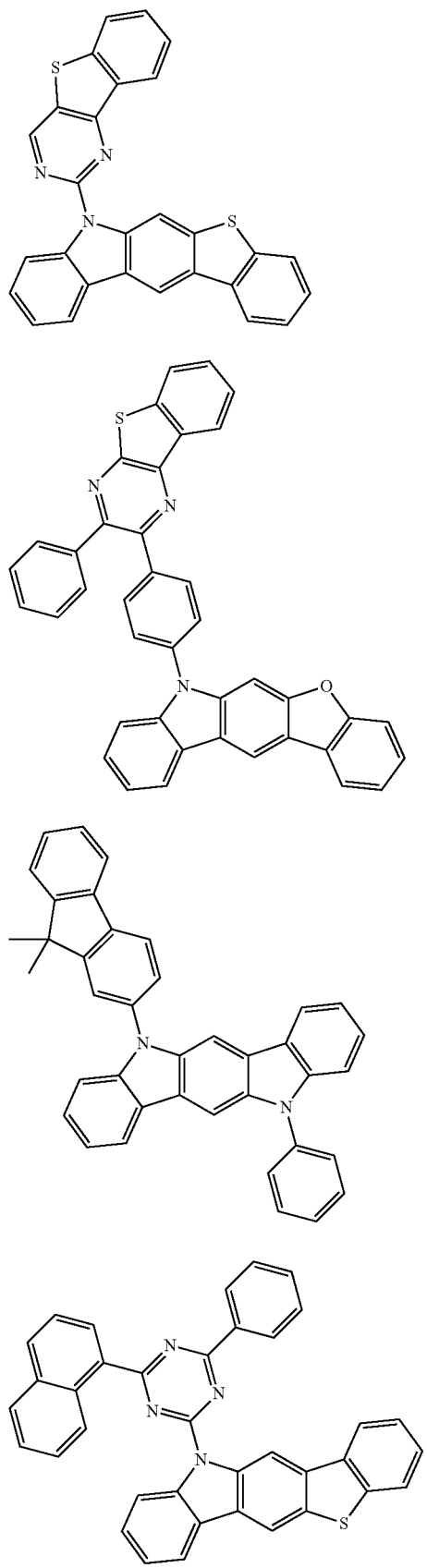
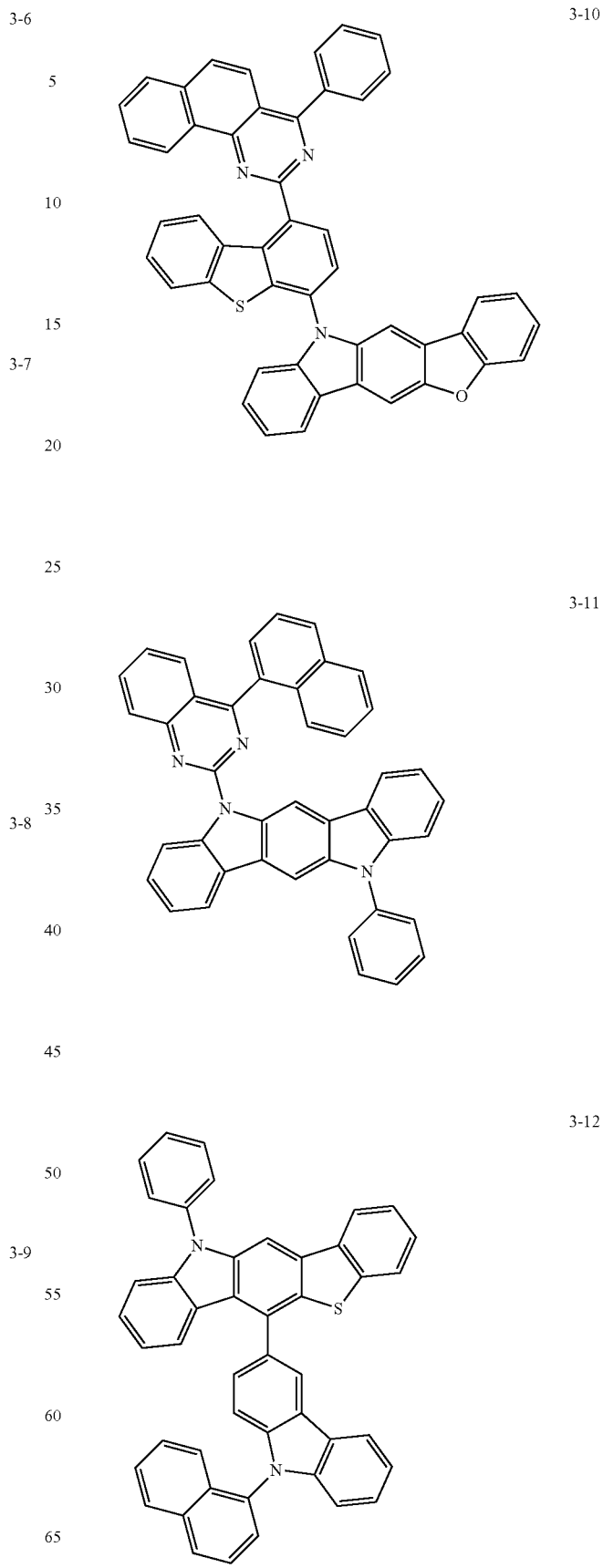

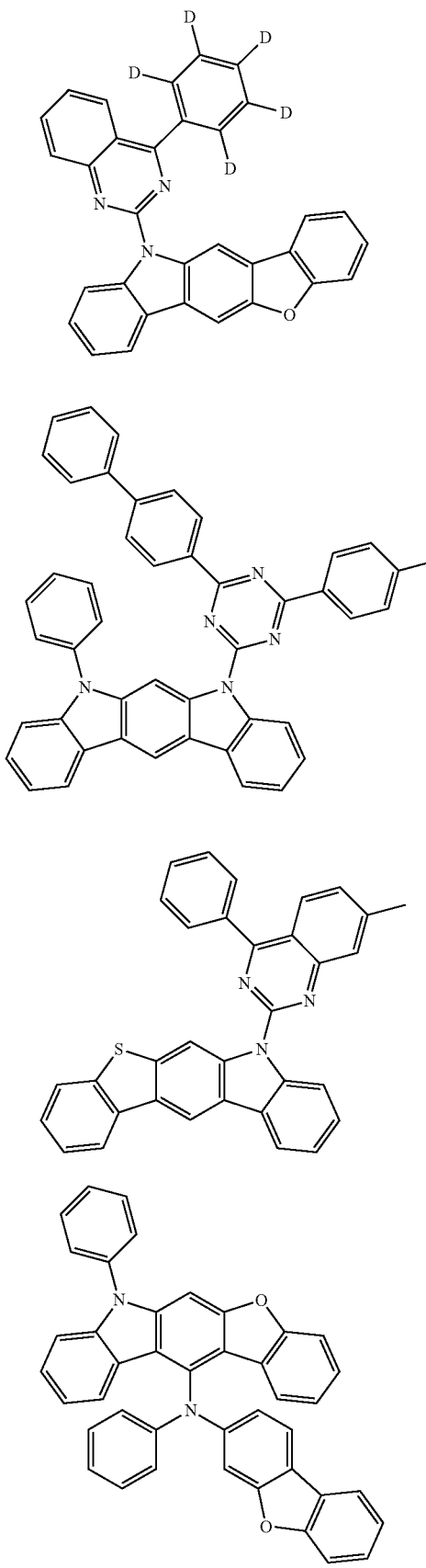
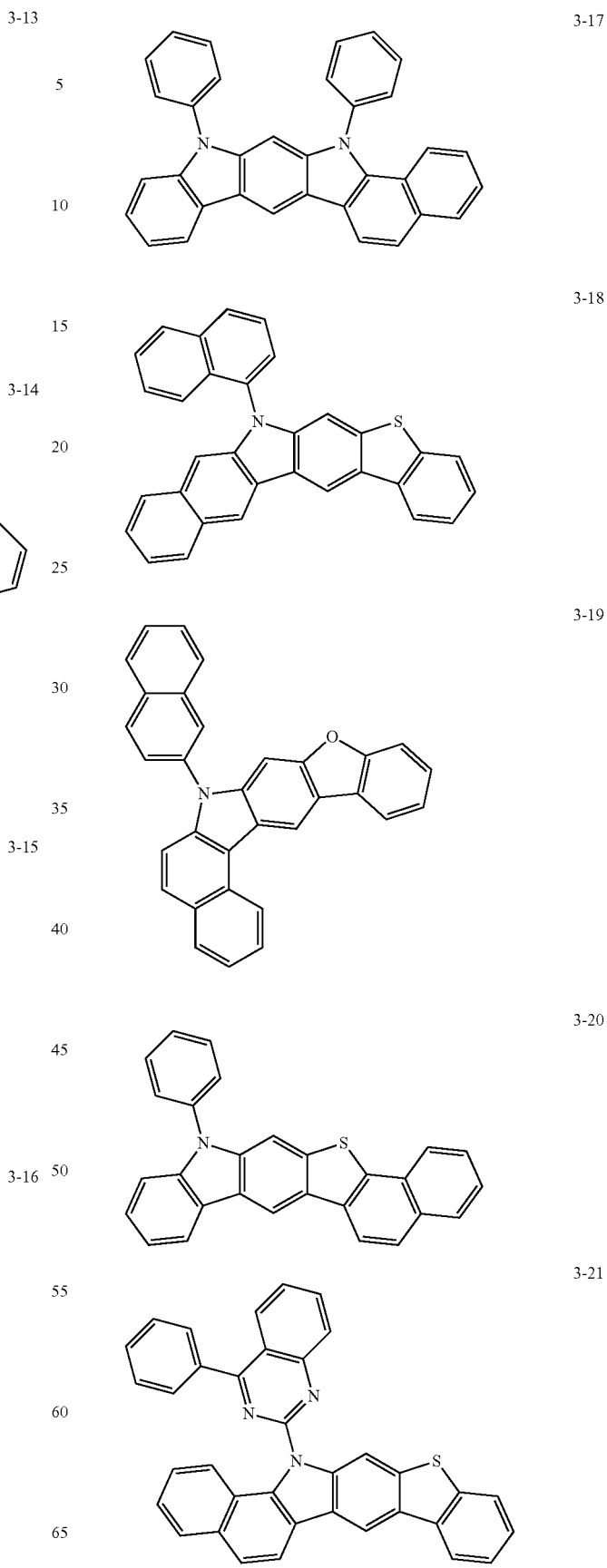

3-22
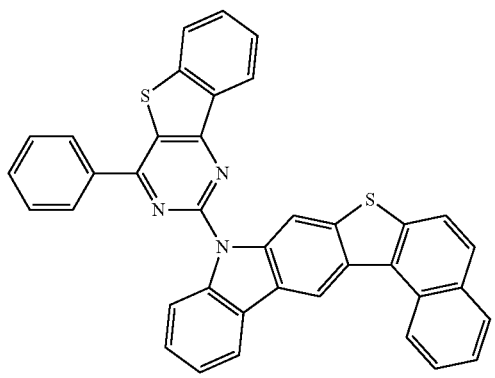
3-23
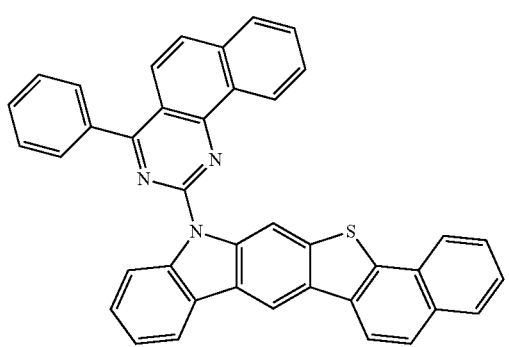
3-24
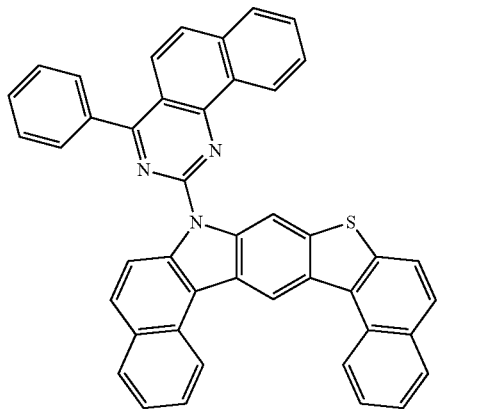
3-25
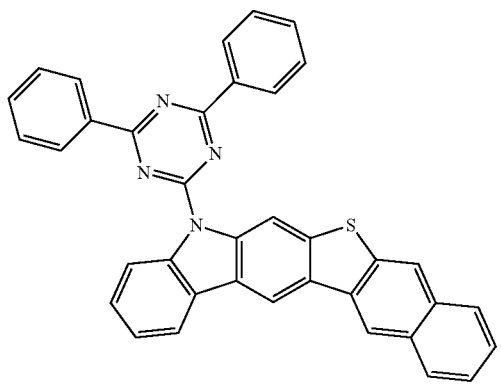
3-26
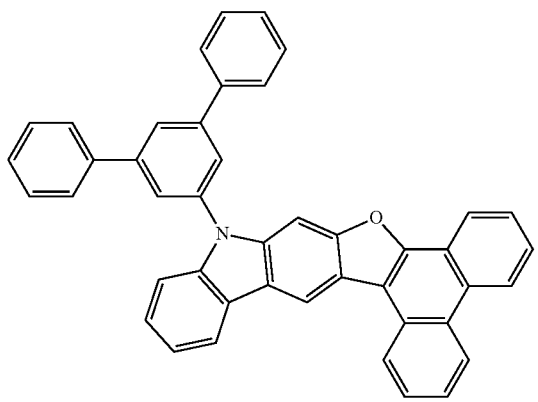
3-27
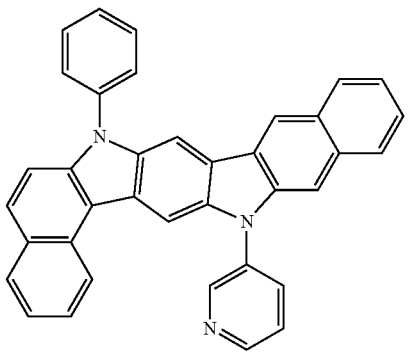
3-28
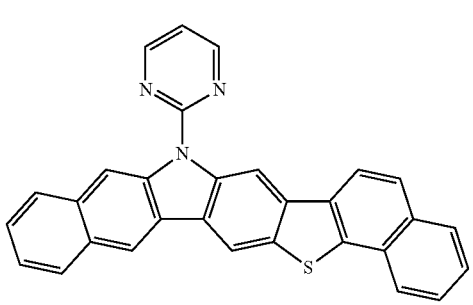
3-29
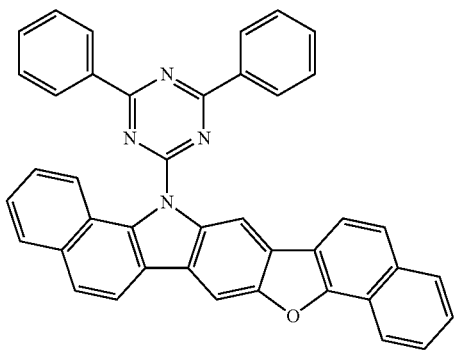

371
-continued
3-30
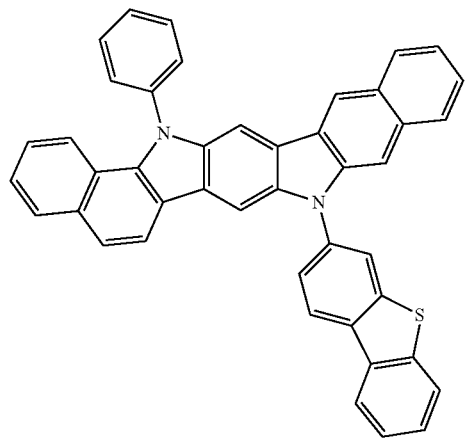
3-31
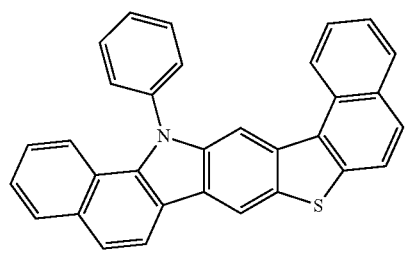
3-32
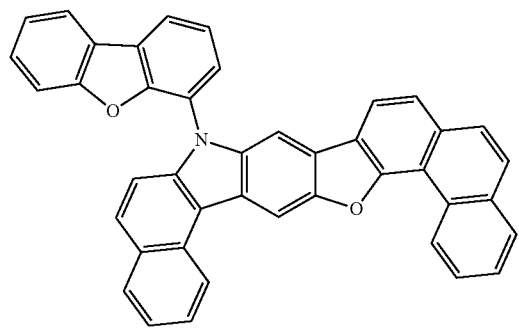
3-33
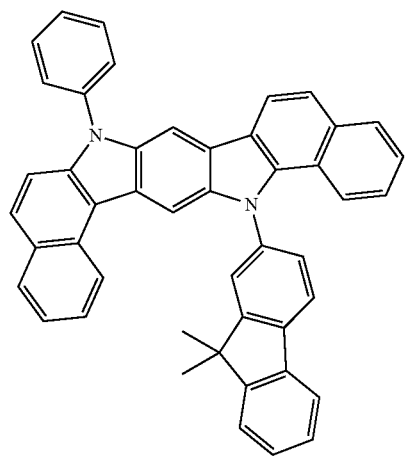
372
-continued
3-34
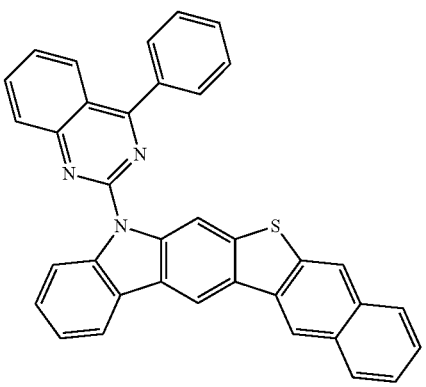
3-35
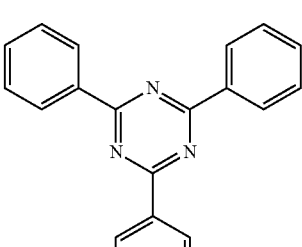
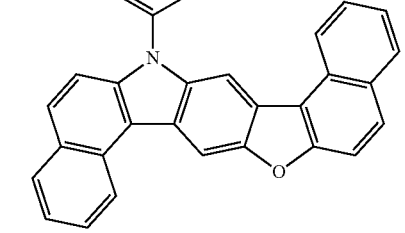
3-36
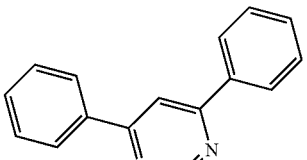
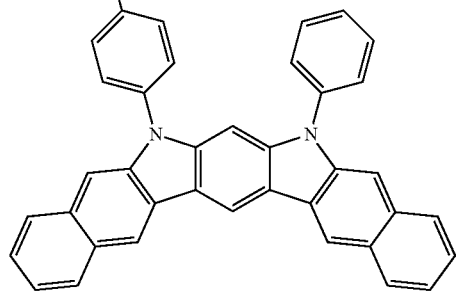

-continued
3-37
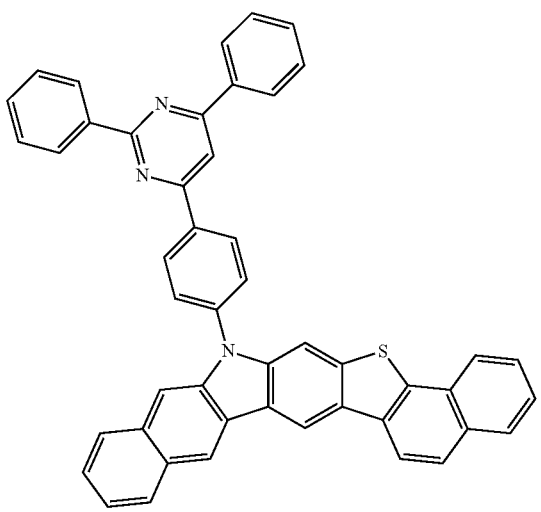
3-38
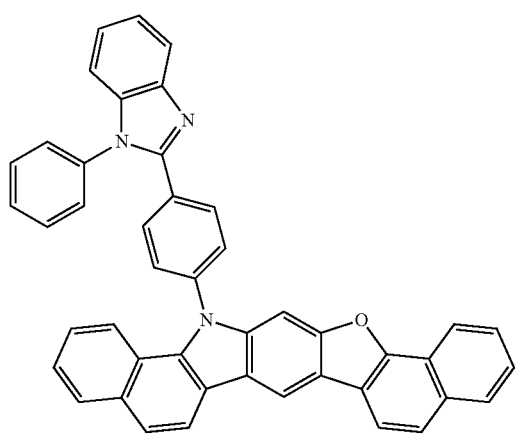
3-39
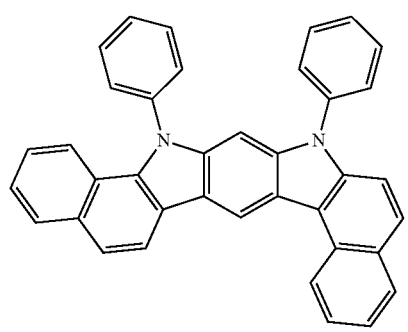
-continued
3-40
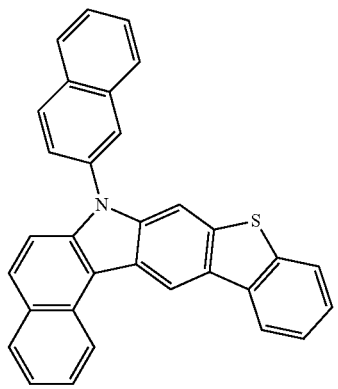
3-41
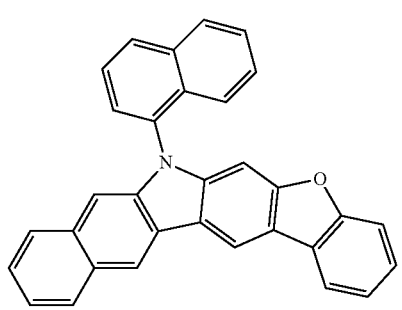
3-42
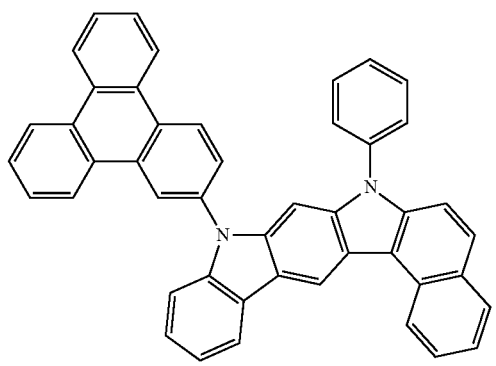
3-43
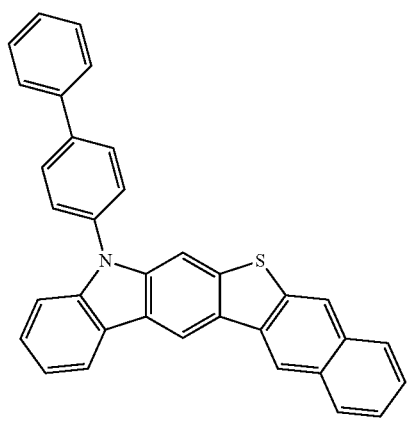

3-44
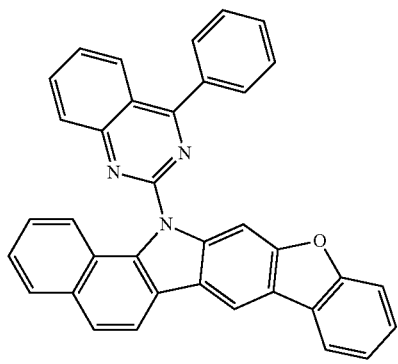
3-45
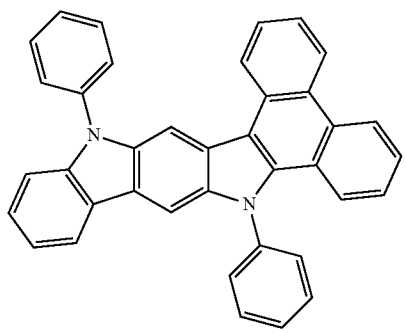
3-46
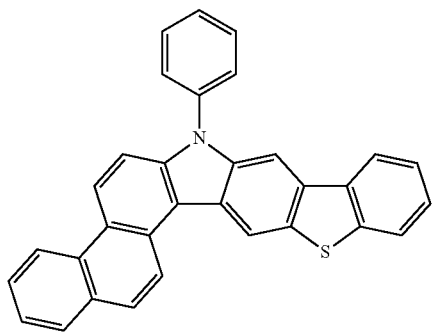
3-47
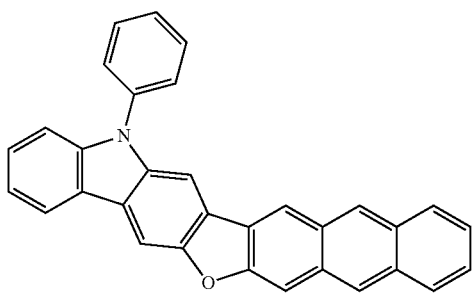
3-48
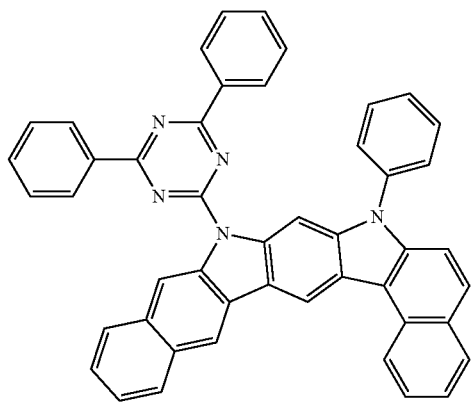
3-49
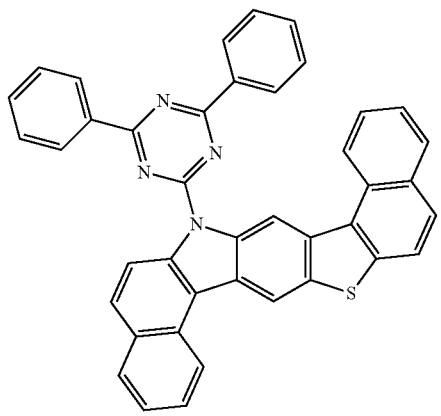
3-50
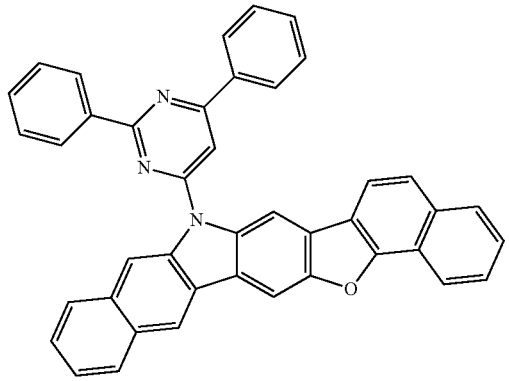

3-51
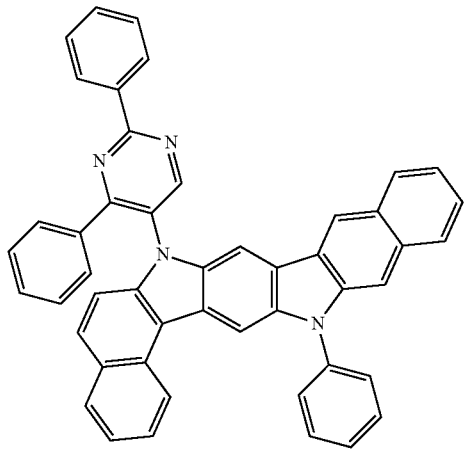
3-52
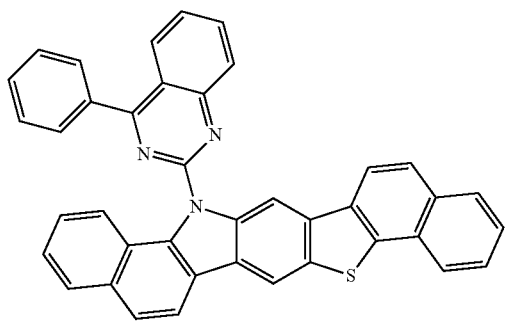
3-53
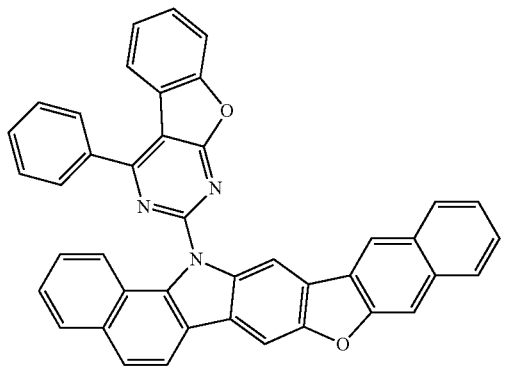
3-54
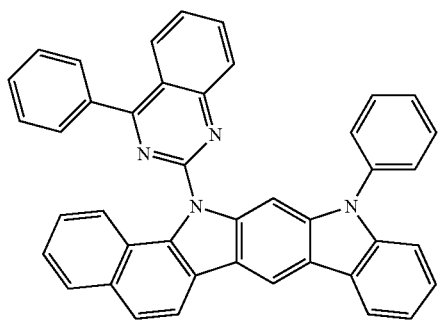
3-55
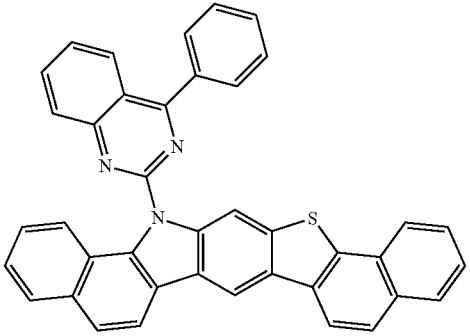
3-56
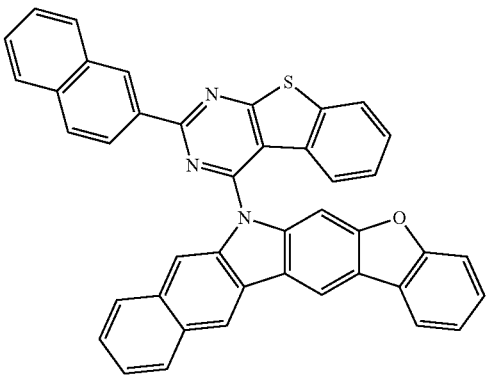
3-57
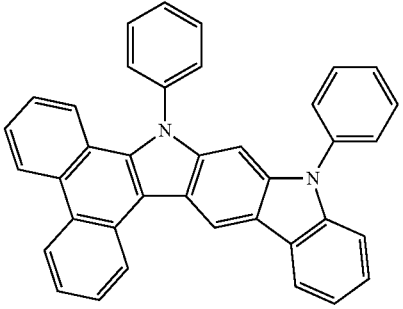
3-58
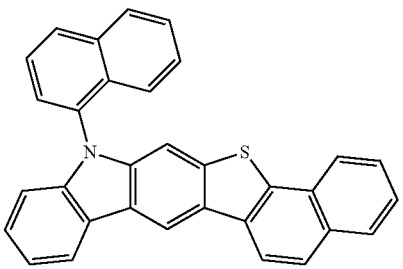

379
-continued
3-59
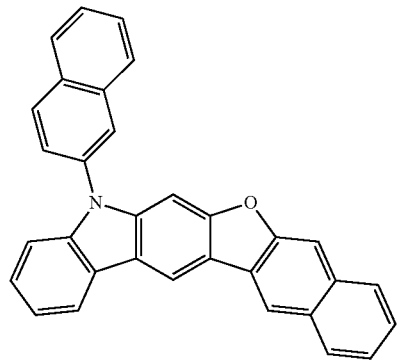
3-60
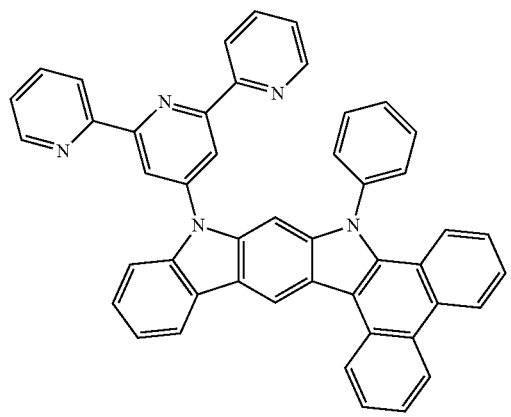
3-61
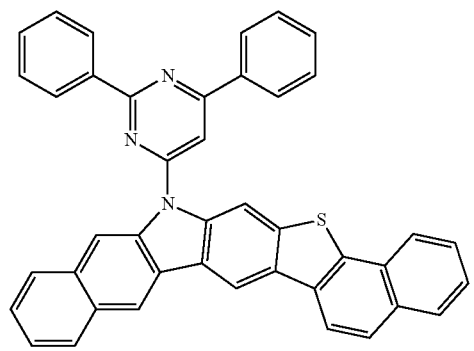
3-62
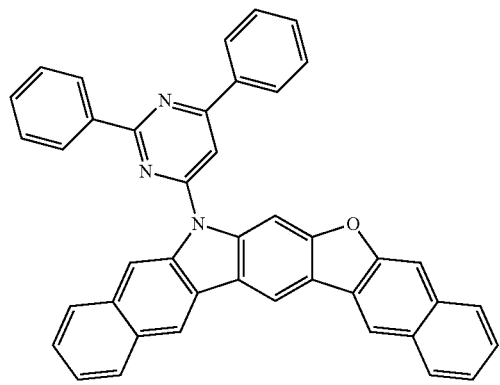
380
-continued
3-63
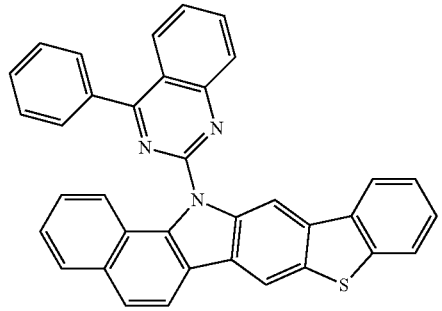
3-64
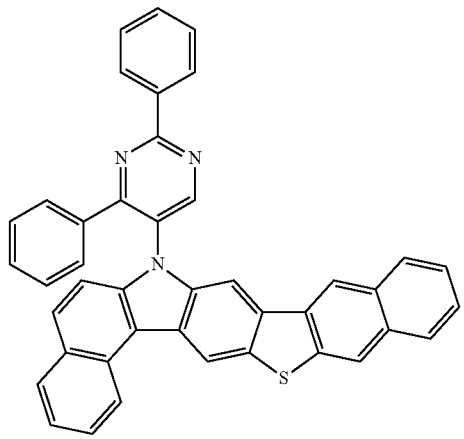
3-65
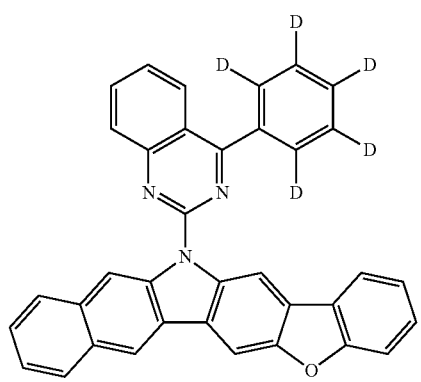
3-66
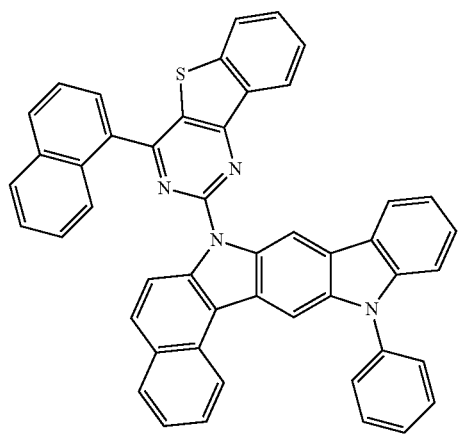

3-67
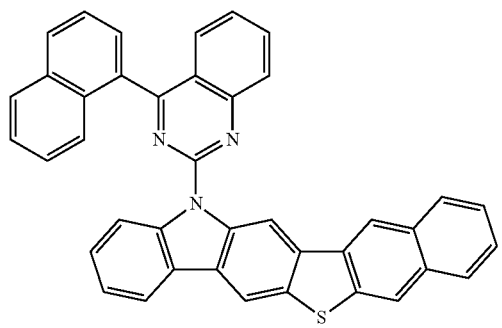
3-68
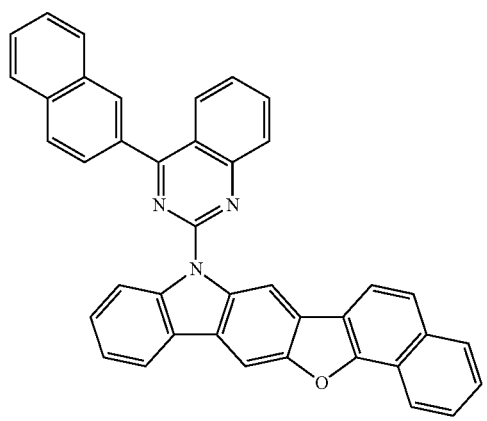
3-69
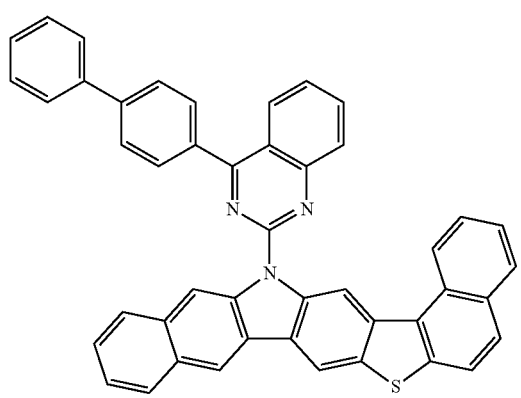
3-70
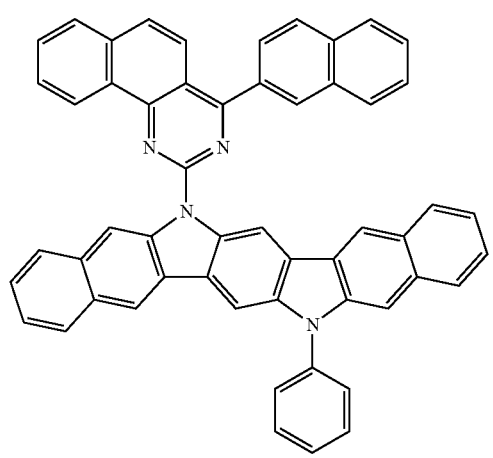
3-71
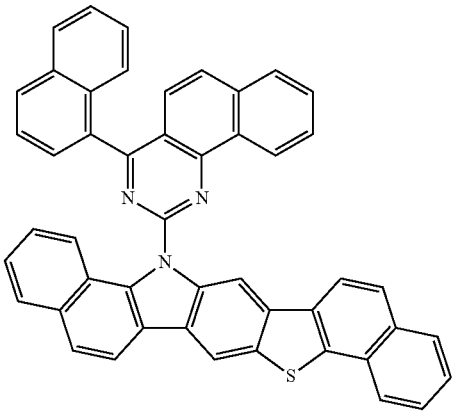
3-72
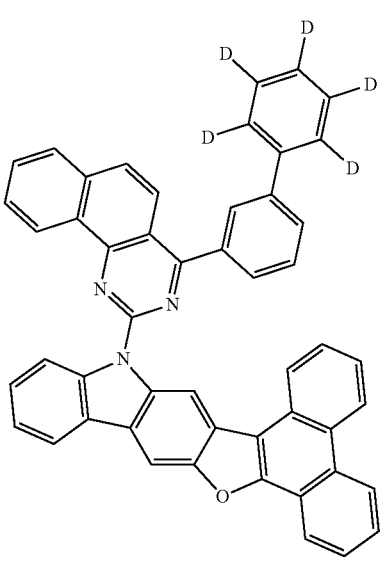
3-73
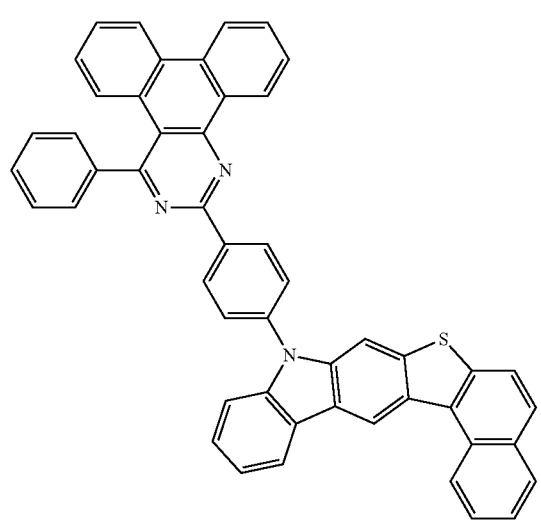

3-74
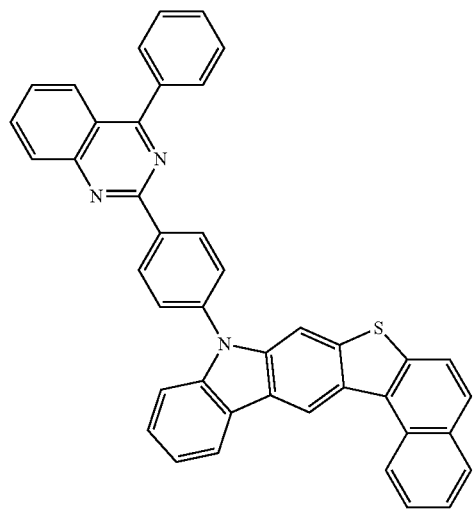
3-75
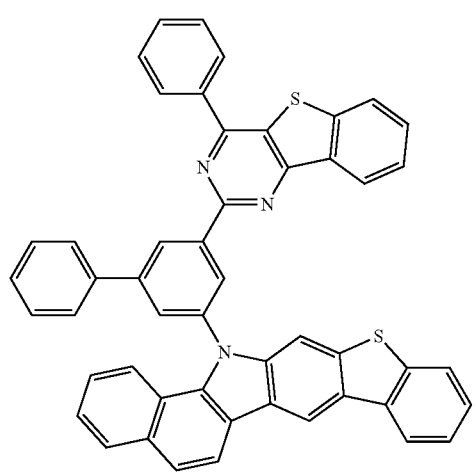
3-76
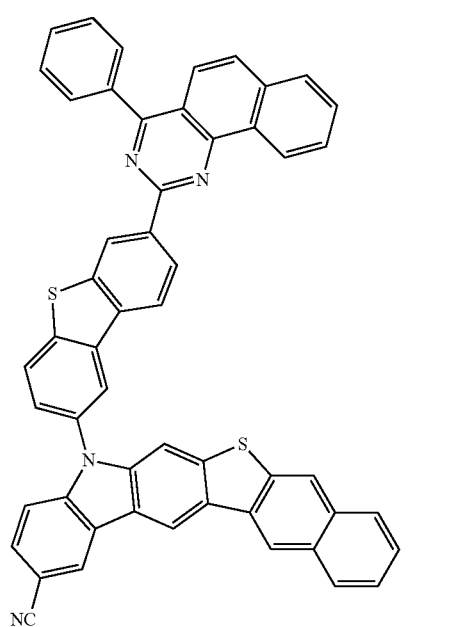
3-77
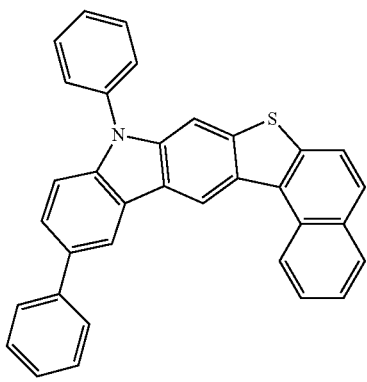
3-78
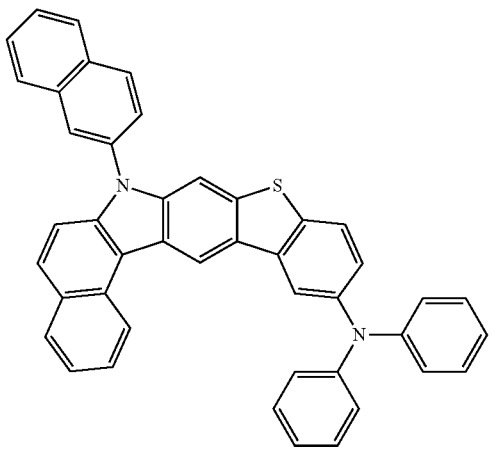
3-79
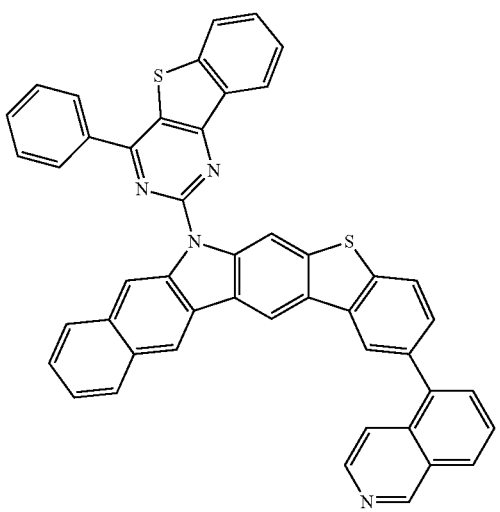

3-80
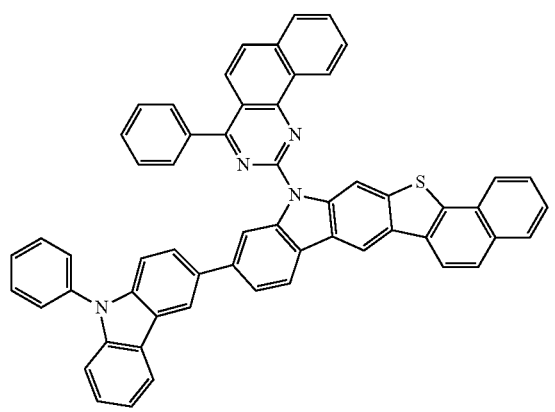
3-81
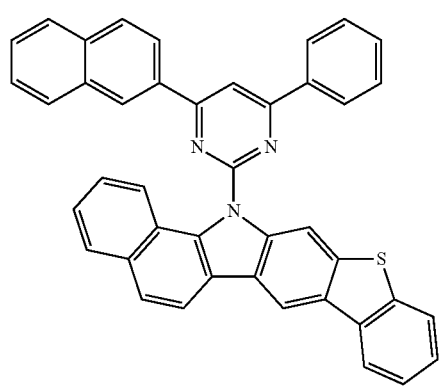
3-82
3-83
3-84
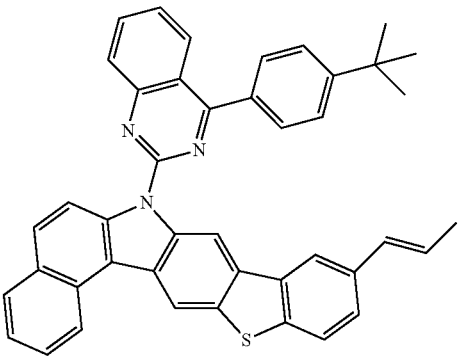
3-85
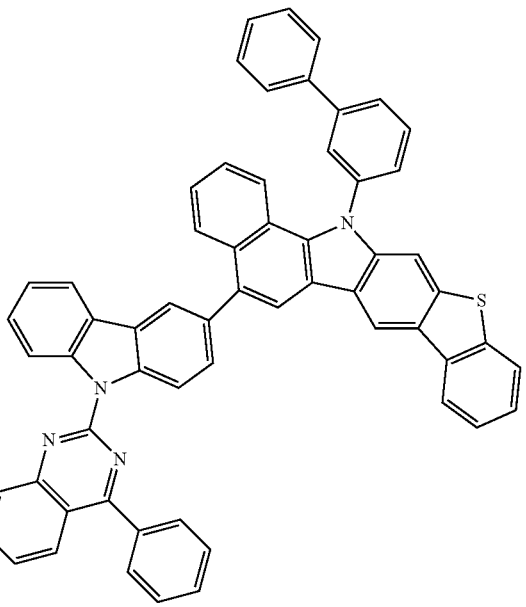
3-86
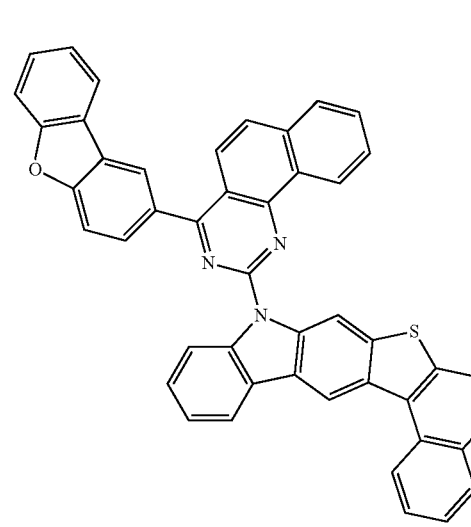

3-87
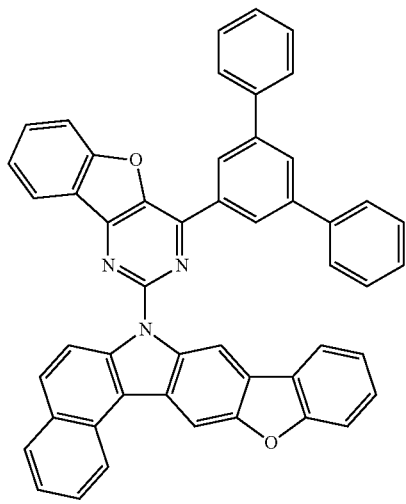
3-90
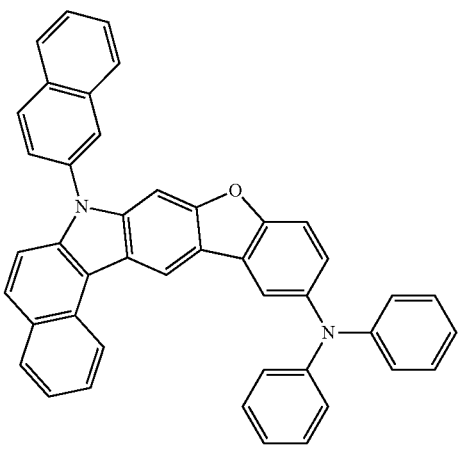
3-88
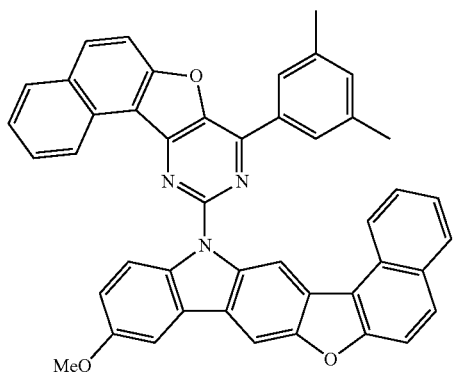
3-91
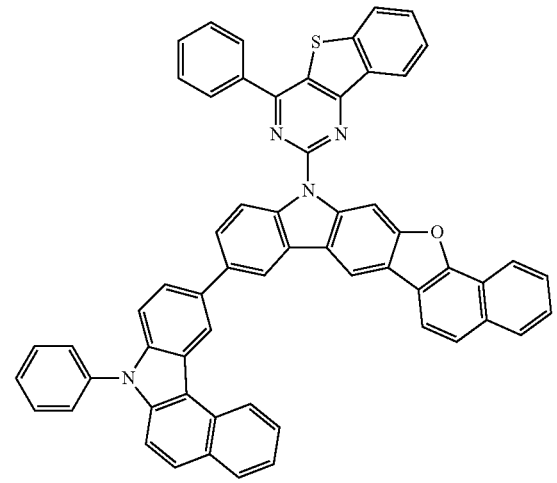
3-89
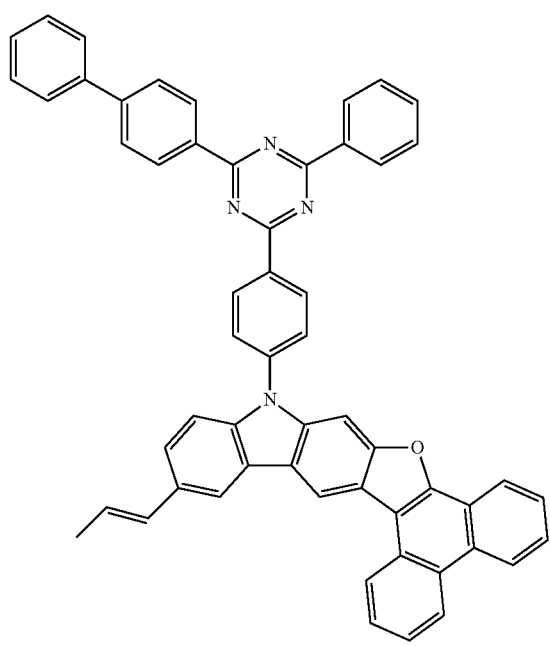
3-92
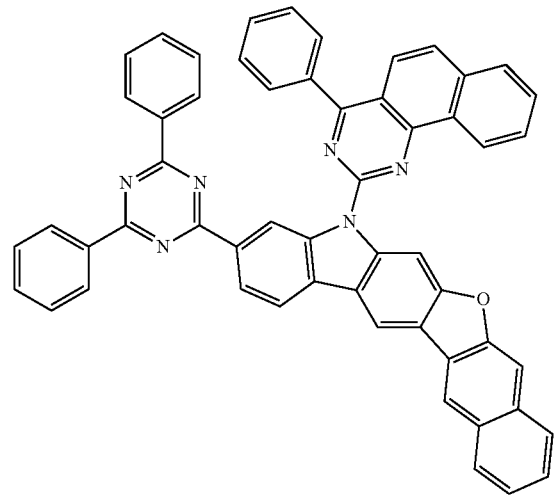

3-93
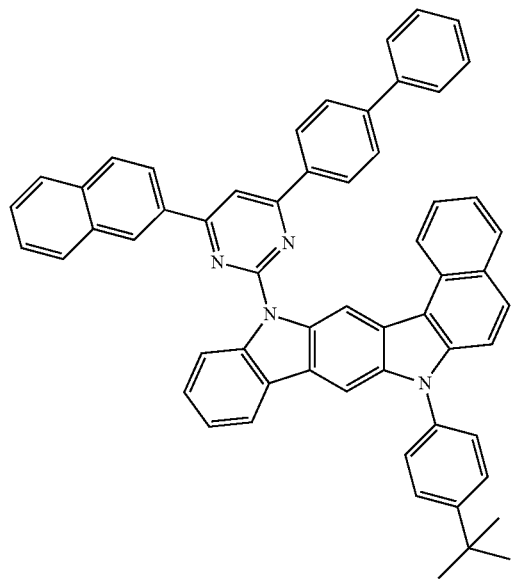
3-95
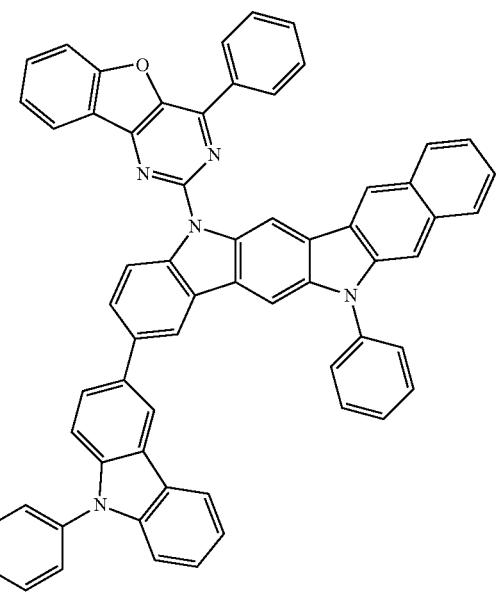
3-96
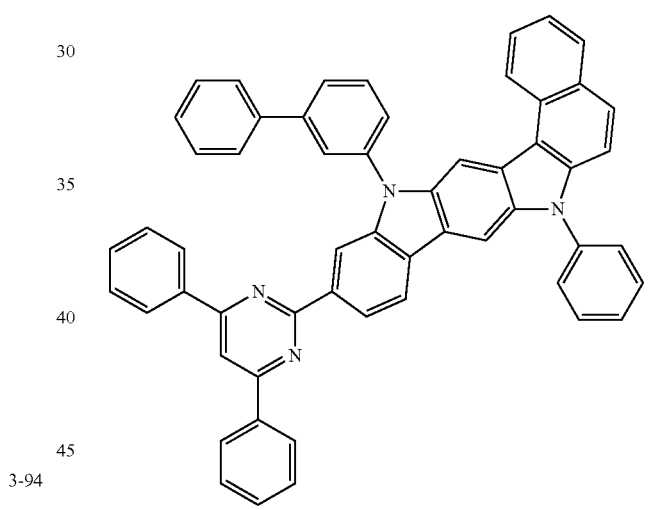
3-94
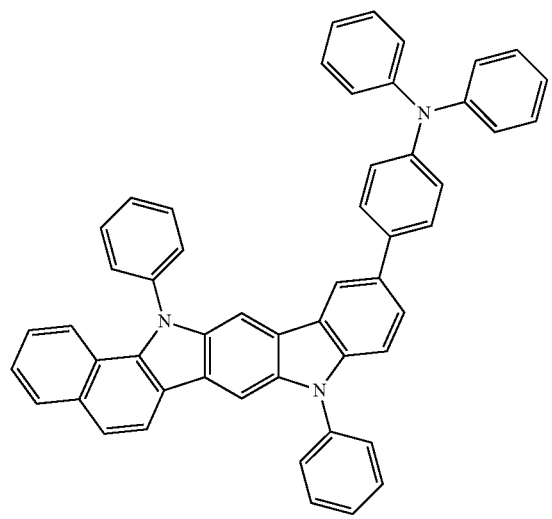
3-97
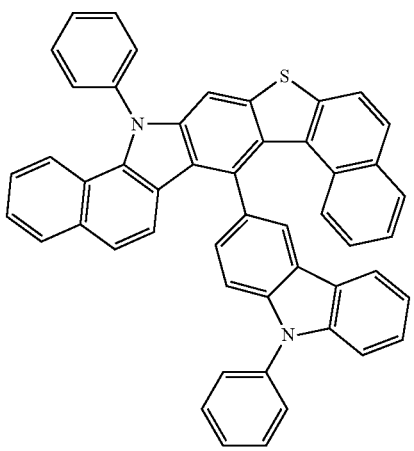

3-98
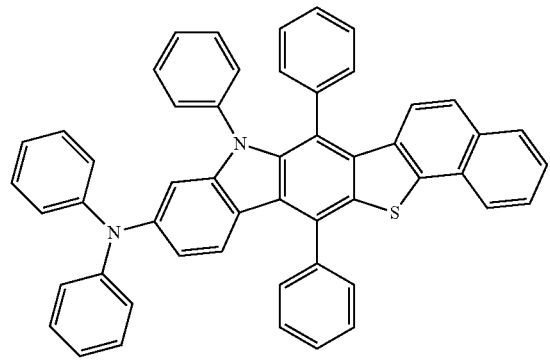
3-99
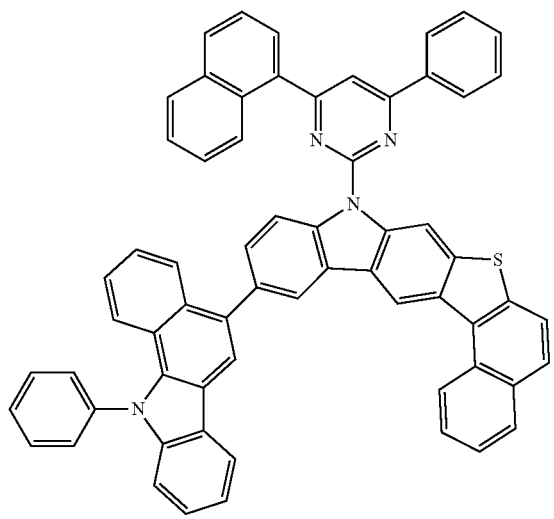
3-100
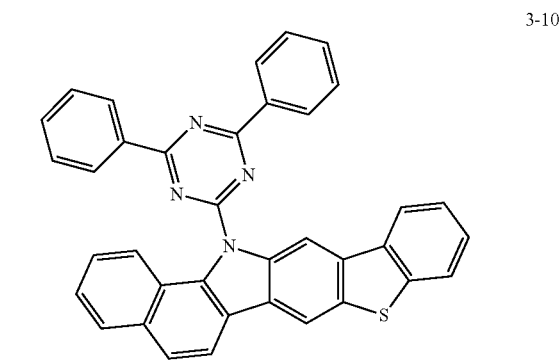
3-101
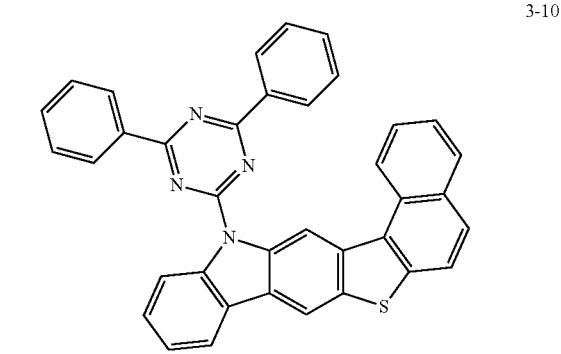
3-102
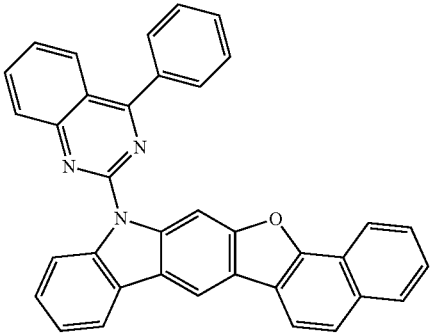
3-103
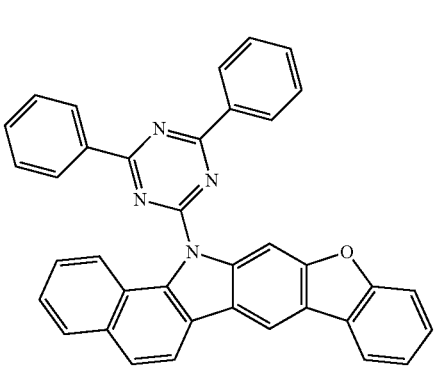
3-104
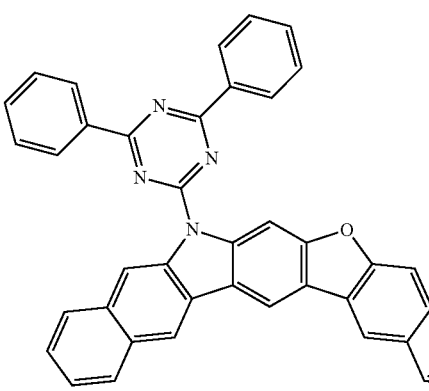
4-1
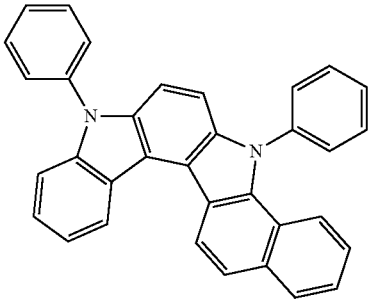

4-2
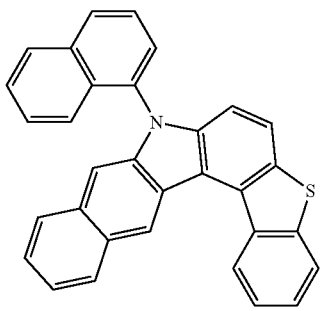
4-3
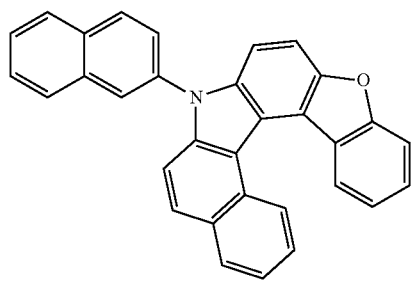
4-4
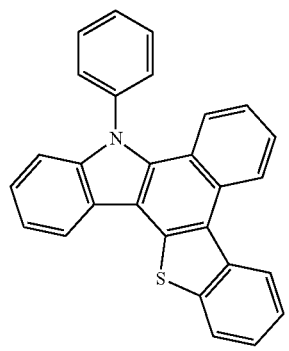
4-5
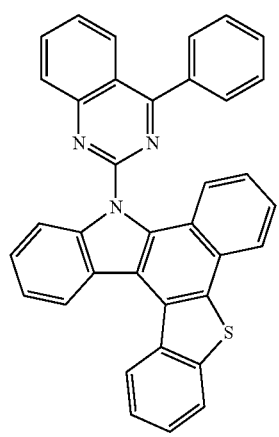
4-6
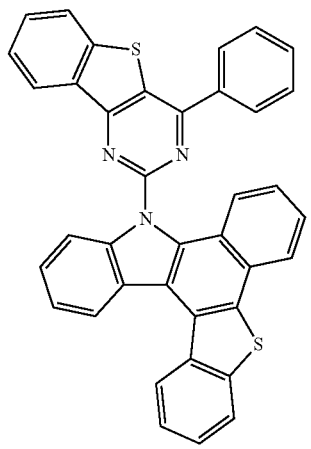
4-7
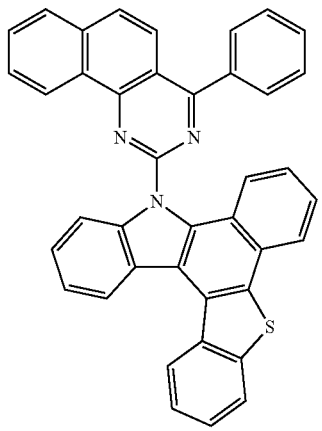
4-8
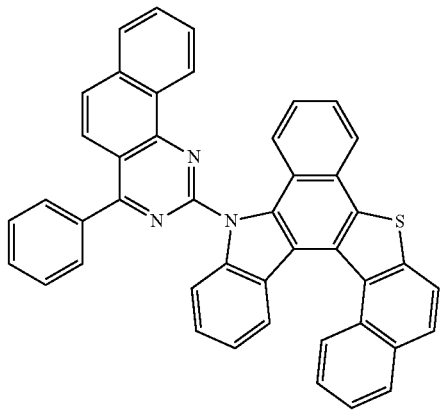

4-9
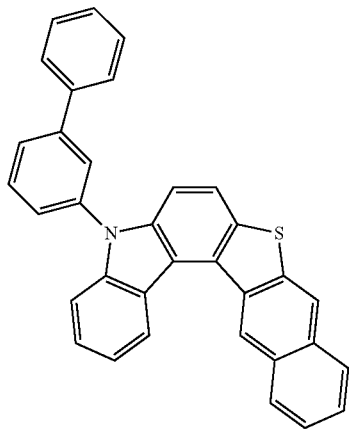
4-13
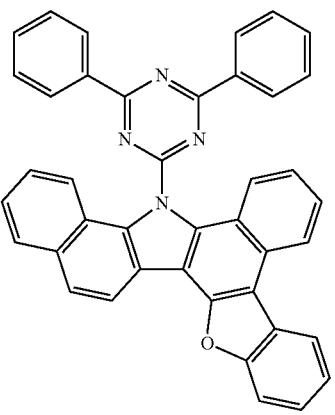
4-10
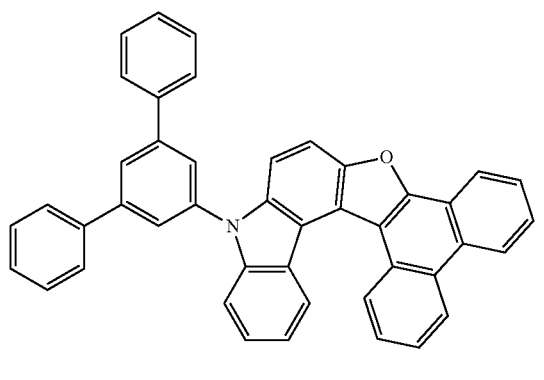
4-14
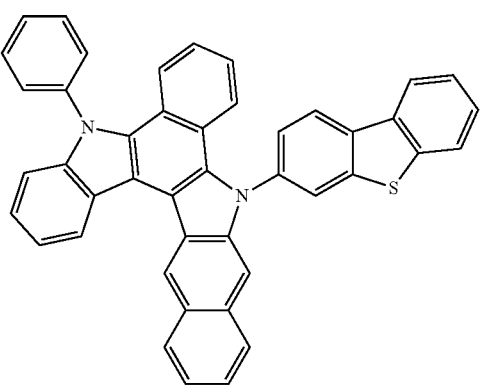
4-11
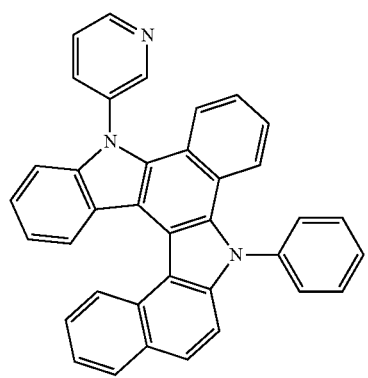
4-15
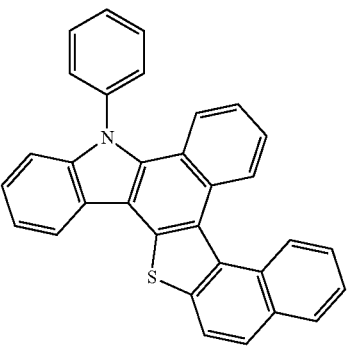
4-12
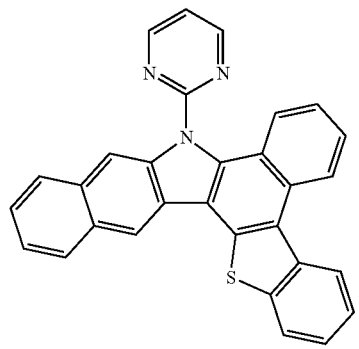
4-16
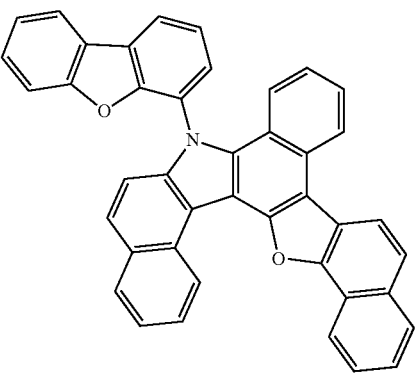

397
-continued
398
-continued
4-17
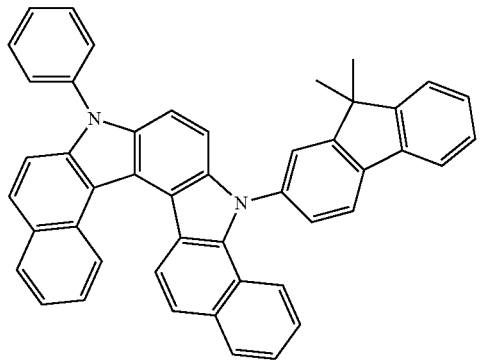
4-20
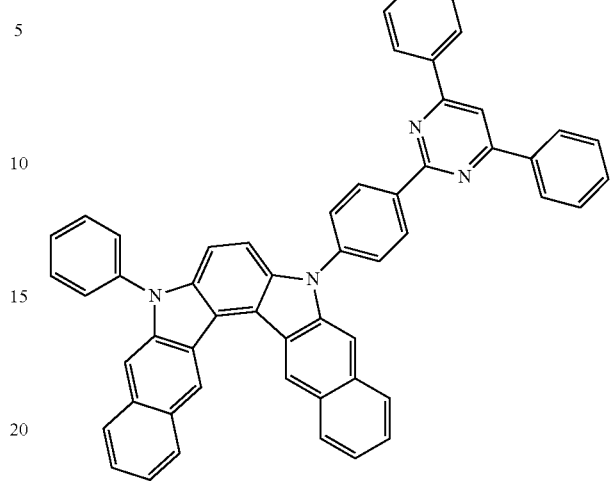
4-18
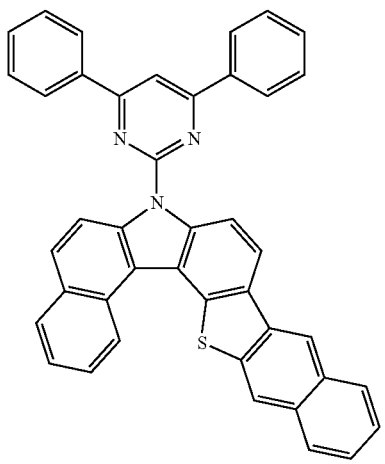
4-21
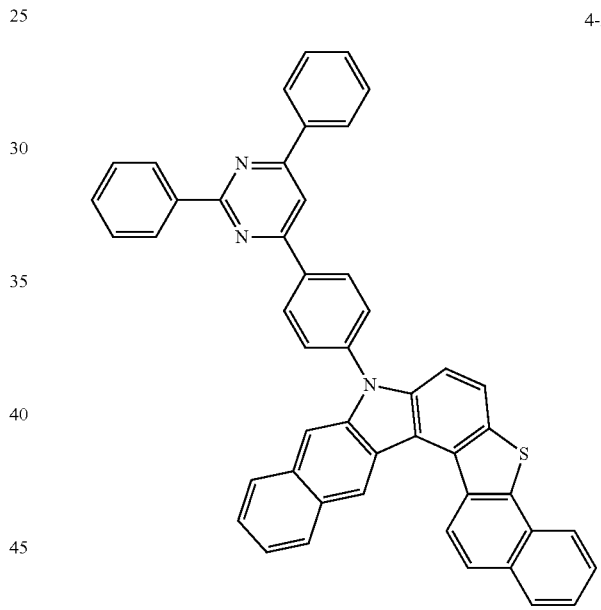
4-19
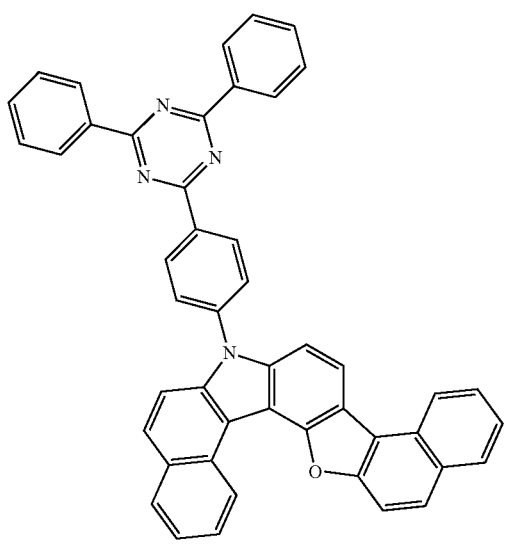
4-22
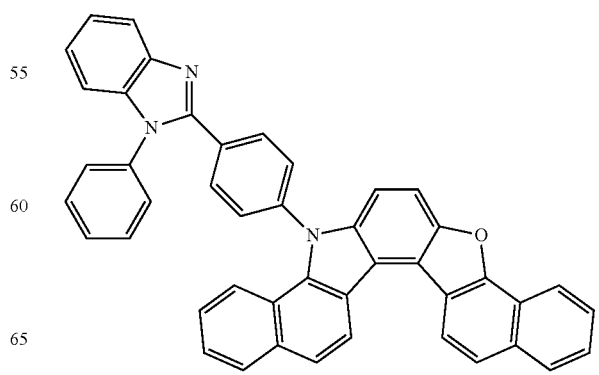

399
-continued
4-23
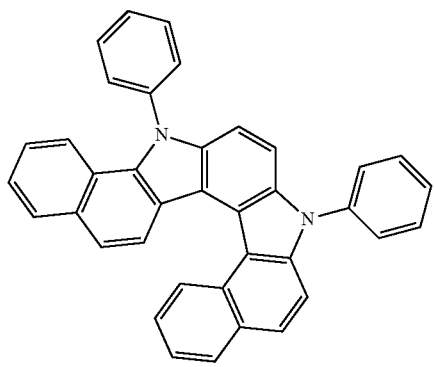
4-24
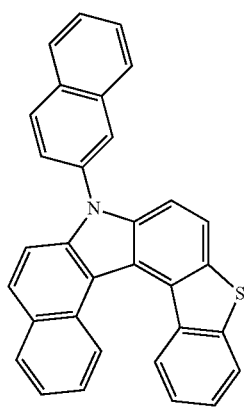
4-25
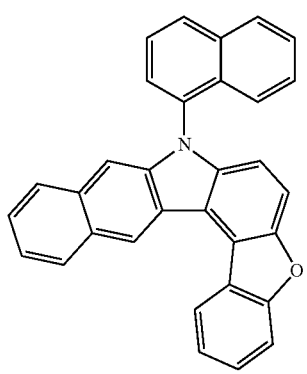
4-26
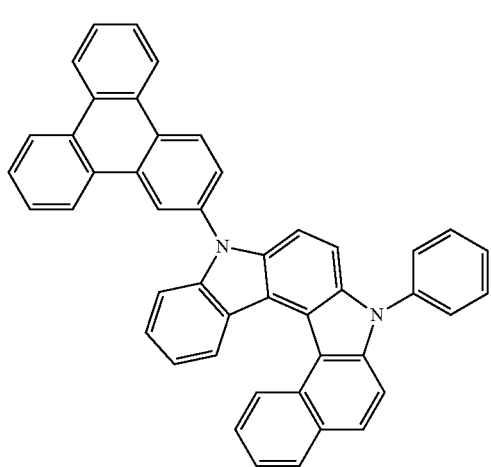
400
-continued
4-27
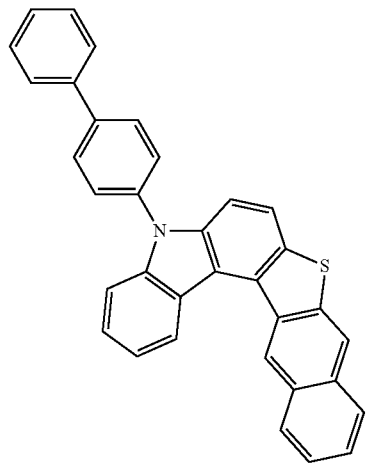
4-28
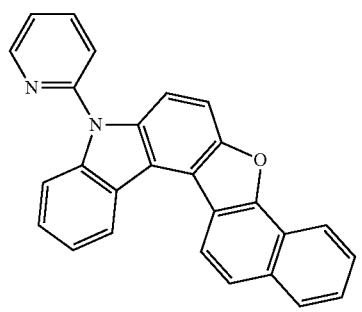
4-29
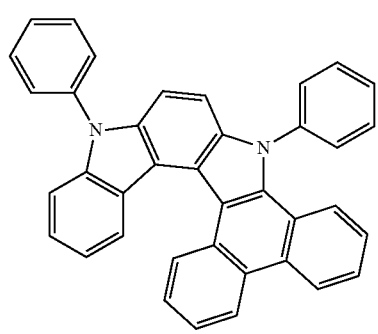
4-30
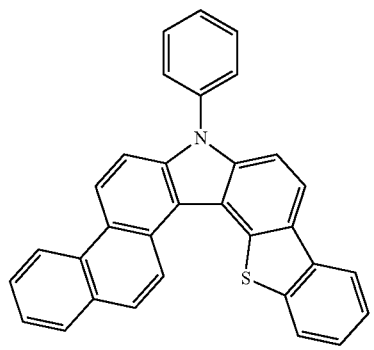

401
-continued
4-31
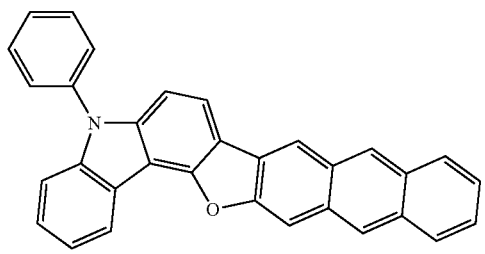
4-32
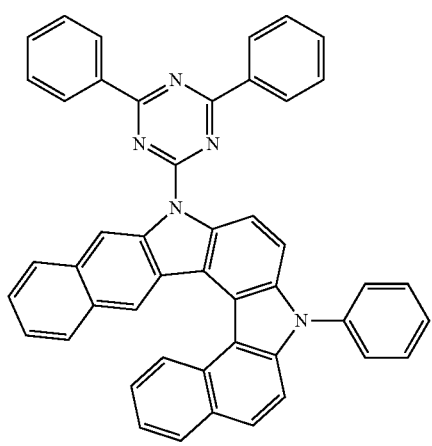
4-33
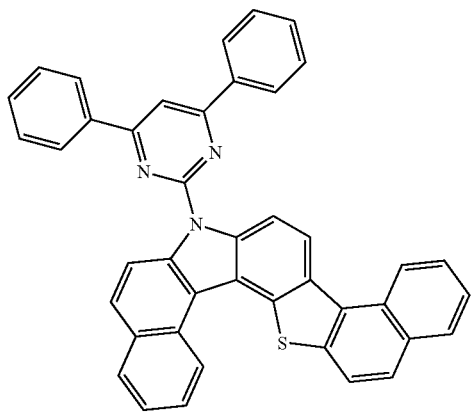
4-34
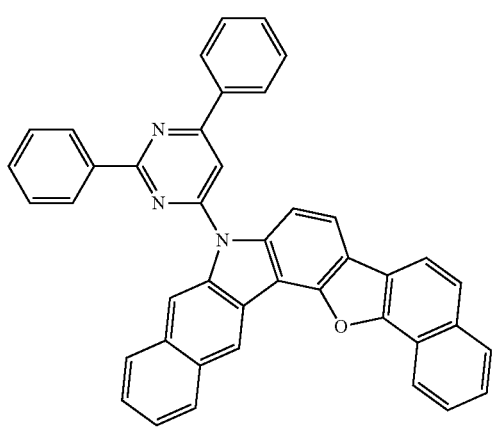
402
-continued
4-35
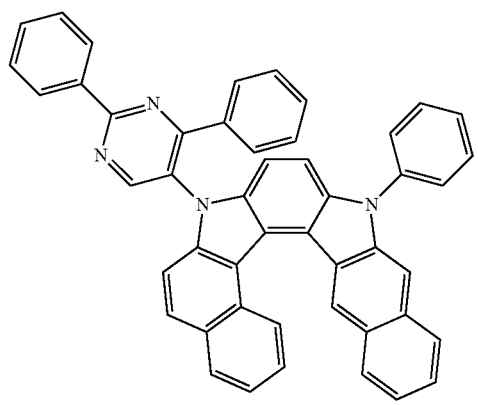
4-36
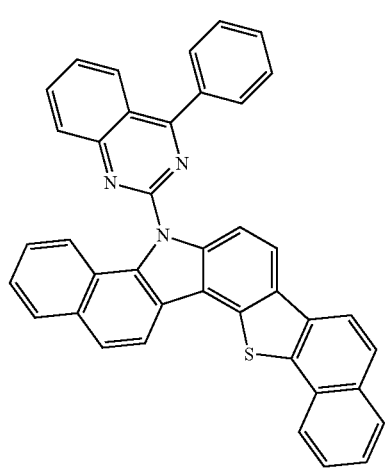
4-37
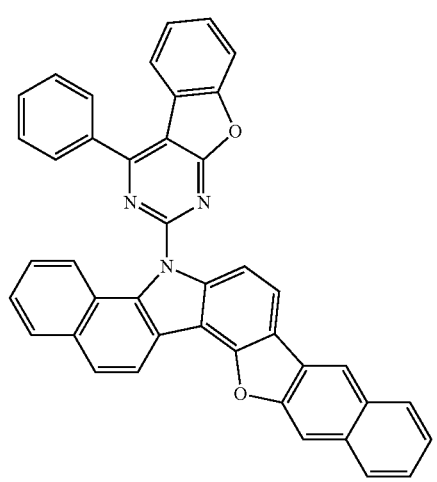

403
-continued
4-38
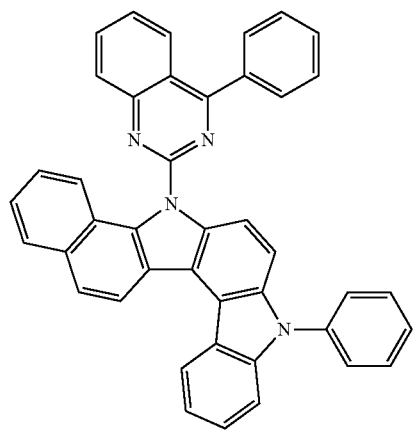
4-39
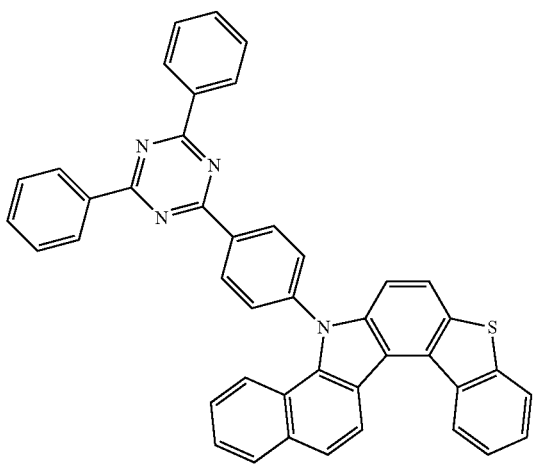
4-40
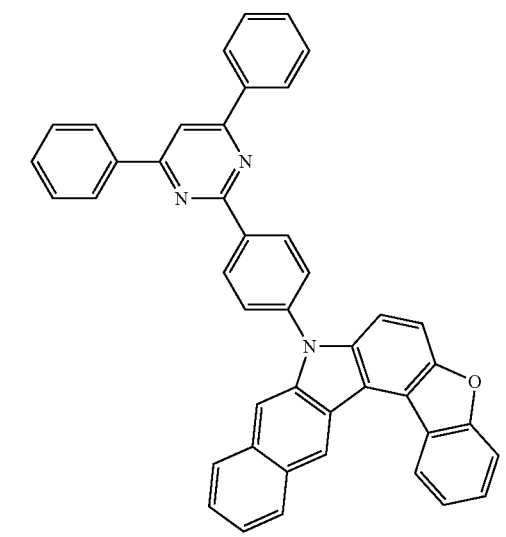
404
-continued
4-41
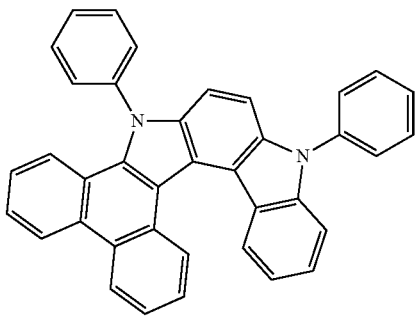
4-42
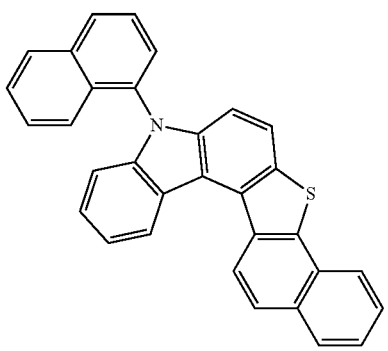
4-43
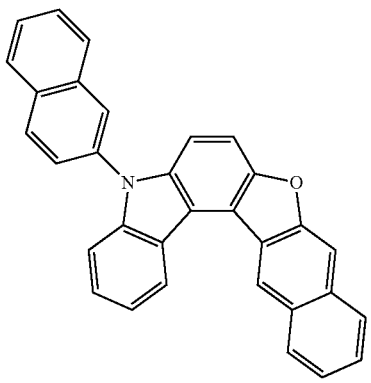
4-44
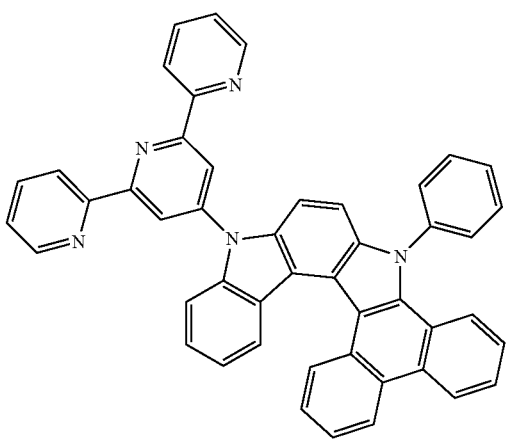

405
-continued
406
-continued
4-45
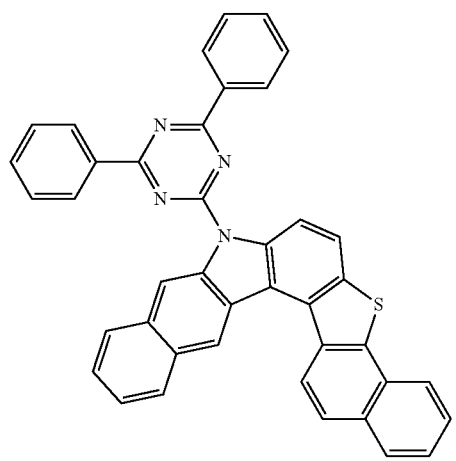
4-48
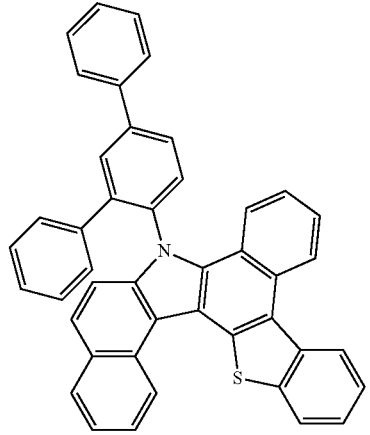
4-46
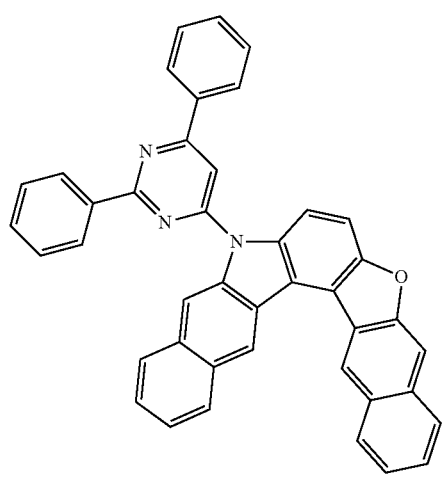
4-49
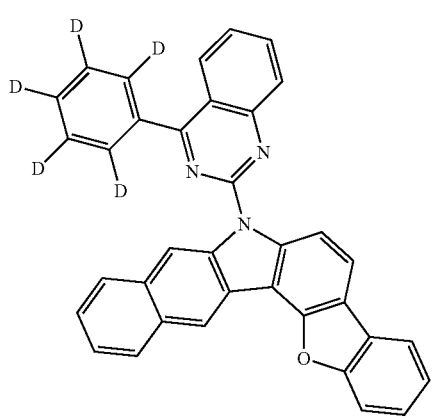
4-47
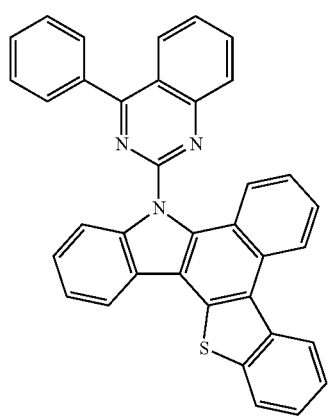
4-50
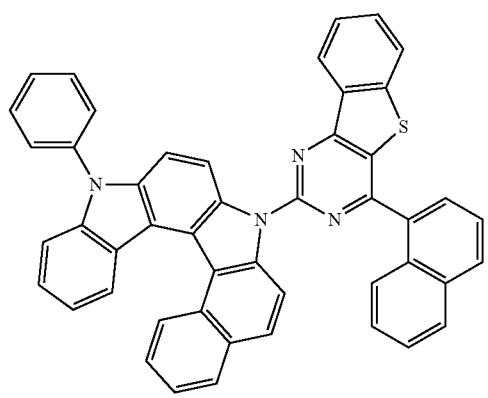

4-51
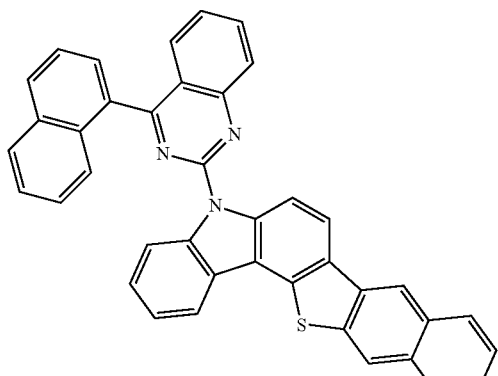
4-52
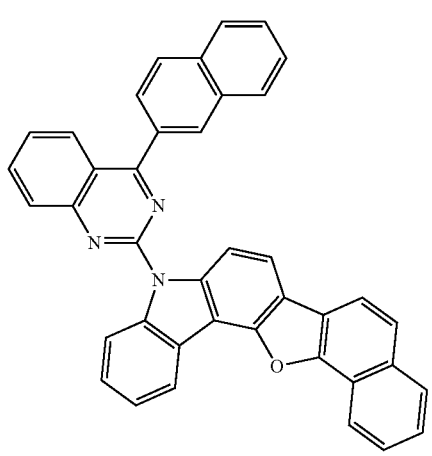
4-53
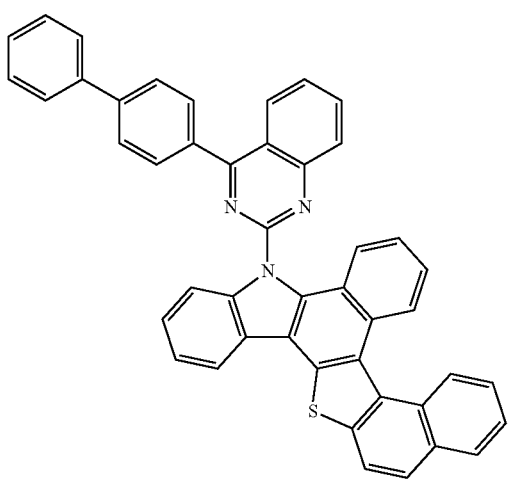
4-54
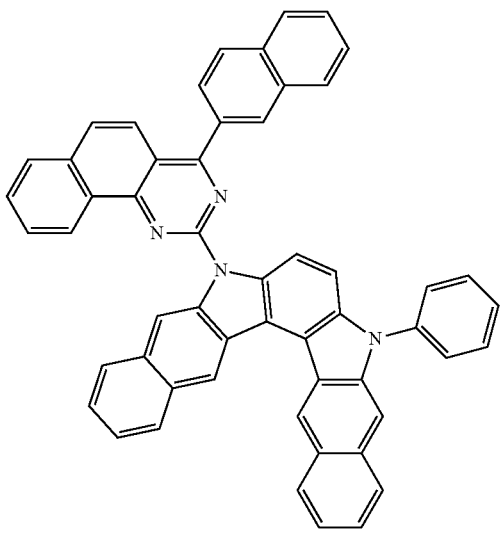
4-55
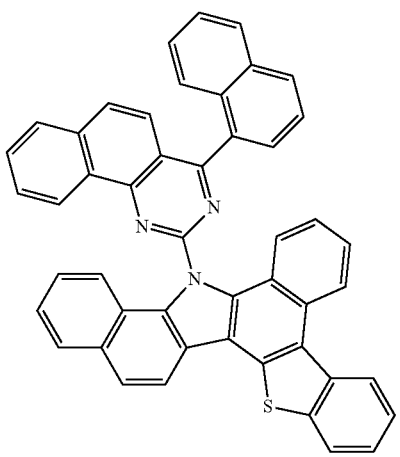
4-56
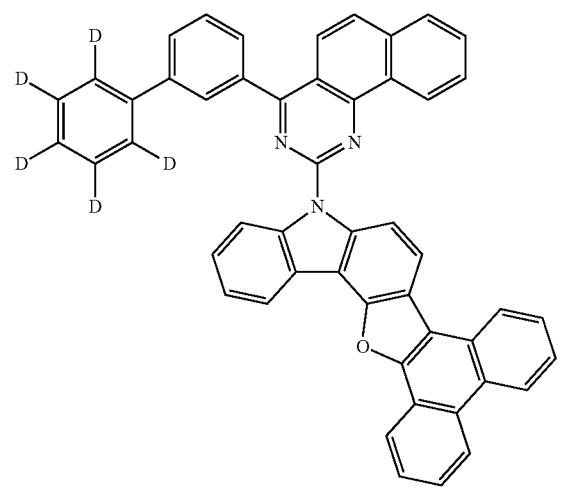

409
-continued
4-57
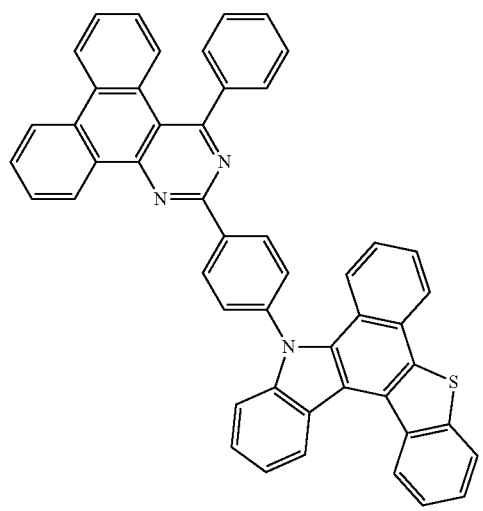
4-58
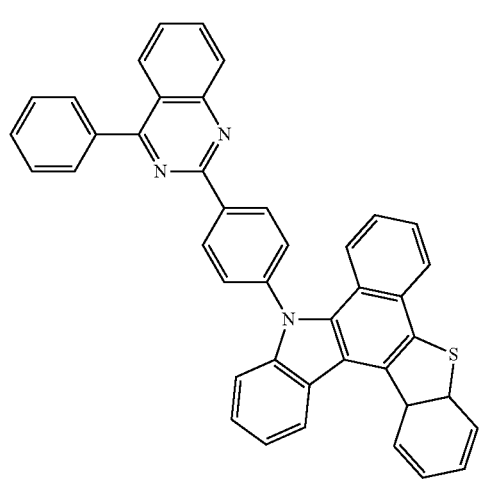
4-59
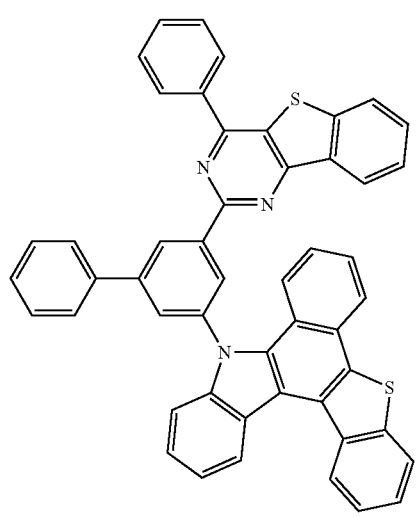
410
-continued
4-60
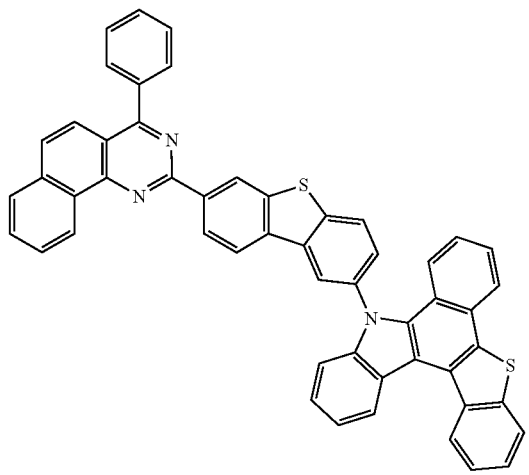
4-61
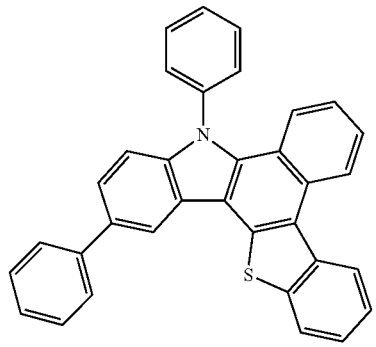
4-62
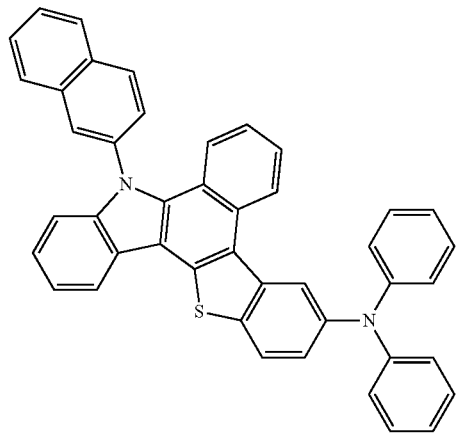

411
-continued
4-63
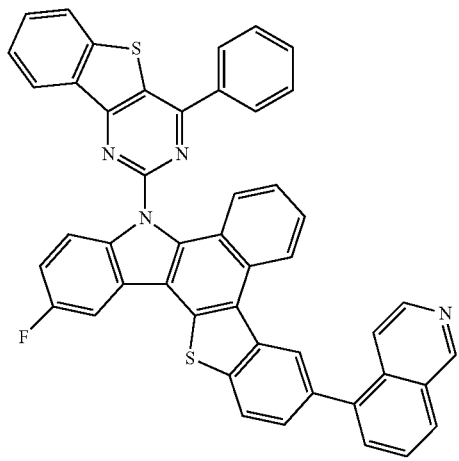
4-64
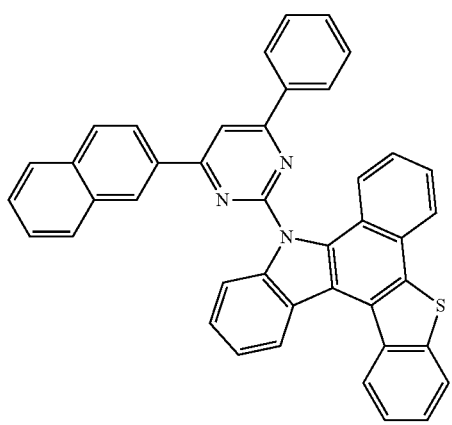
4-65
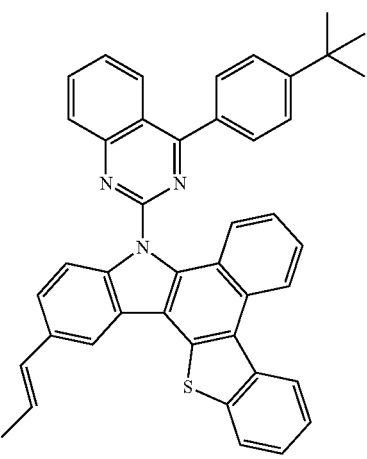
412
-continued
4-66
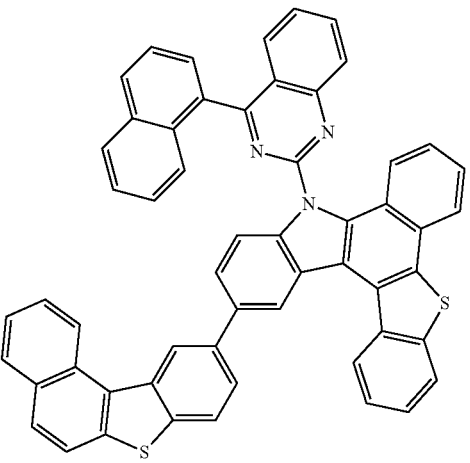
4-67
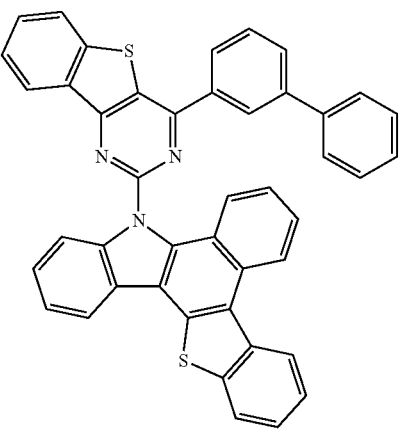
4-68

4-69
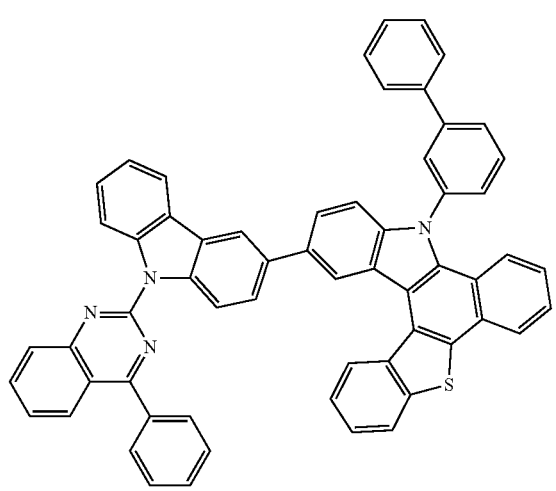
4-70
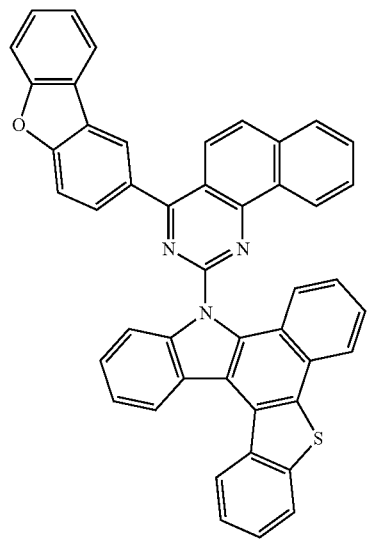
4-71
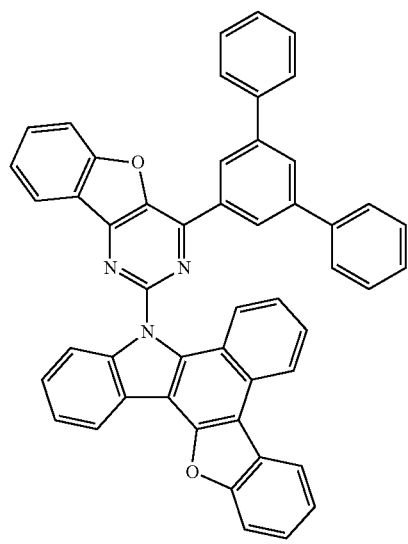
4-72
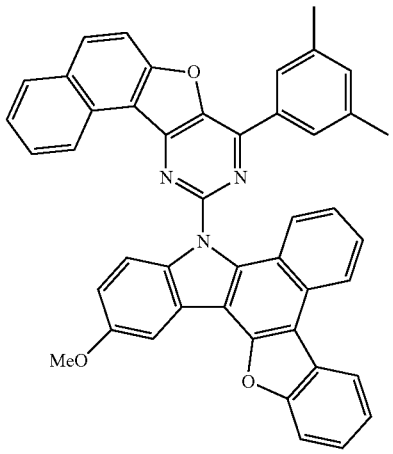
4-73
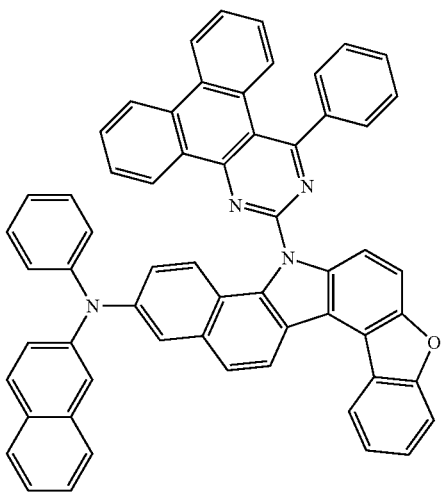
4-74
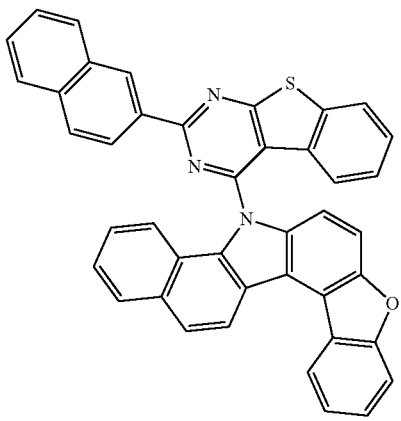

4-75
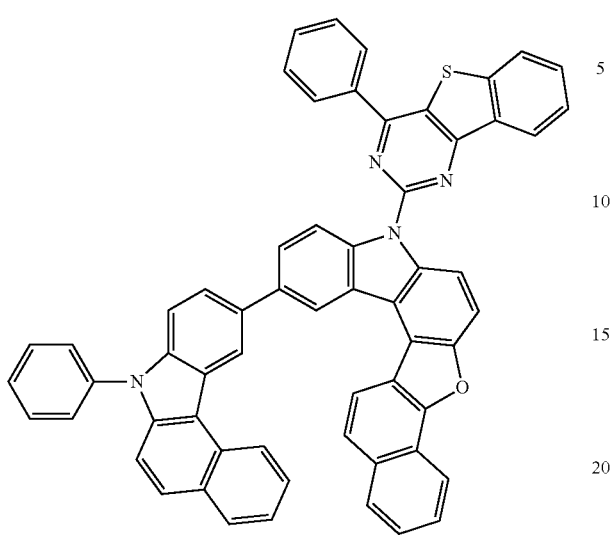
4-78
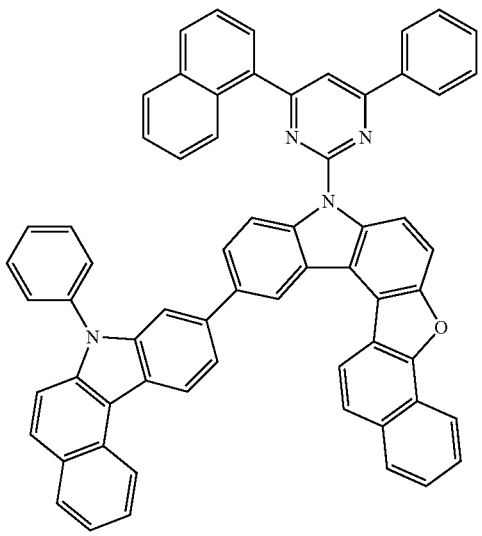
4-76
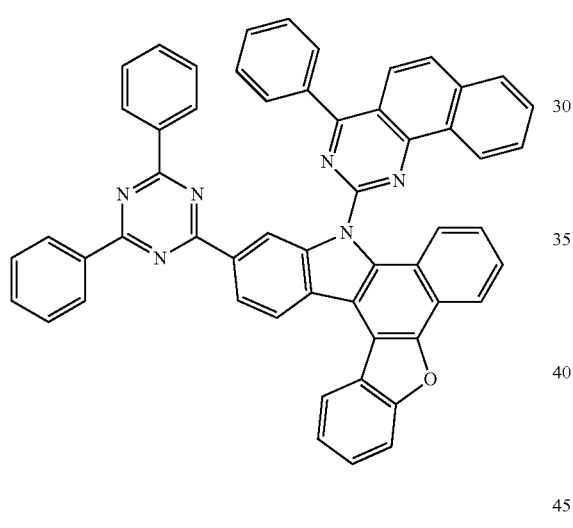
4-79
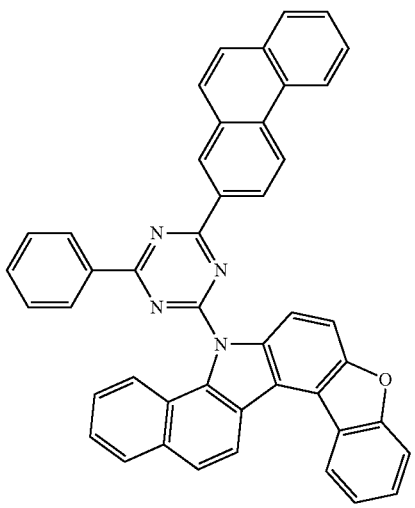
4-77
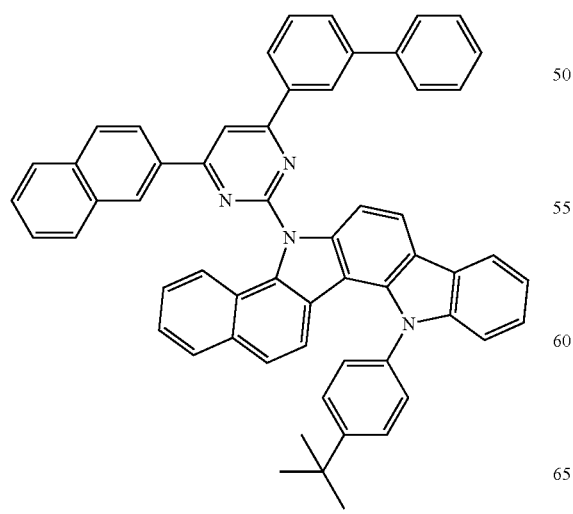
4-80
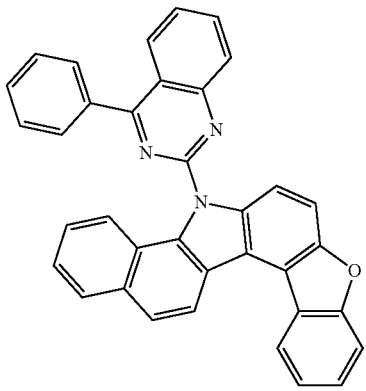

4-81
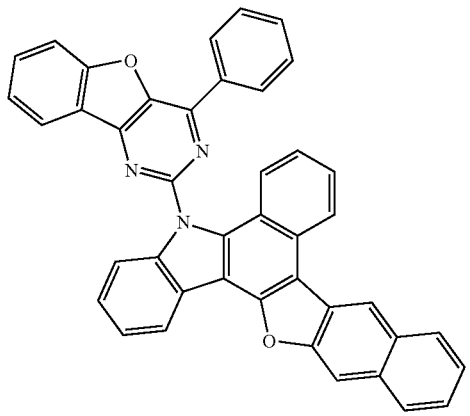
4-82
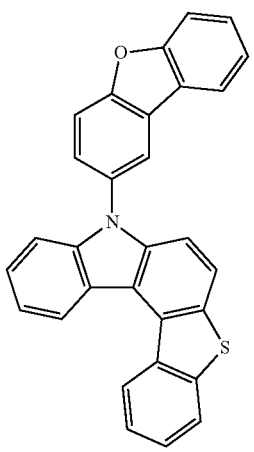
4-83
4-84
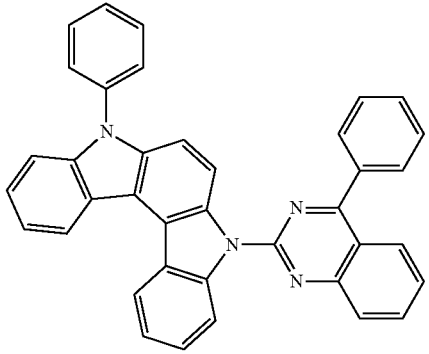
4-85
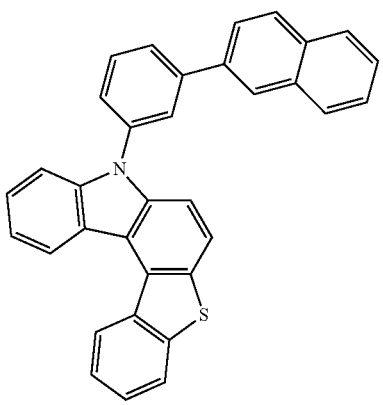
4-86
4-87
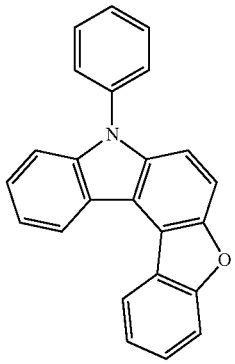

419
-continued
4-88
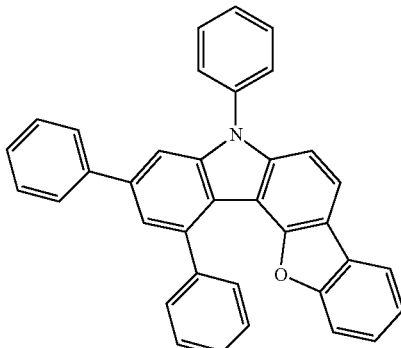
4-89
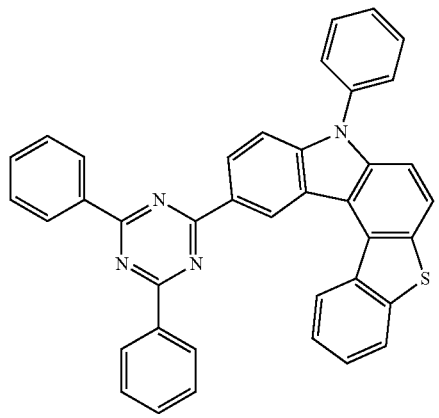
4-90
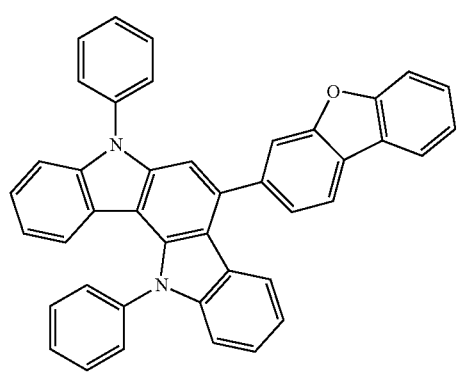
420
-continued
4-91
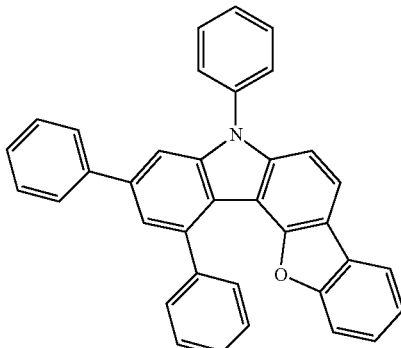
4-92
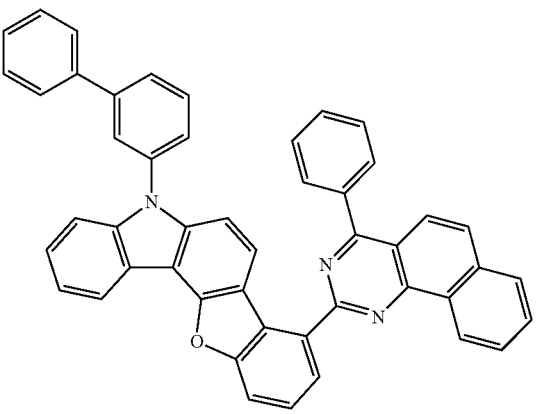
4-93
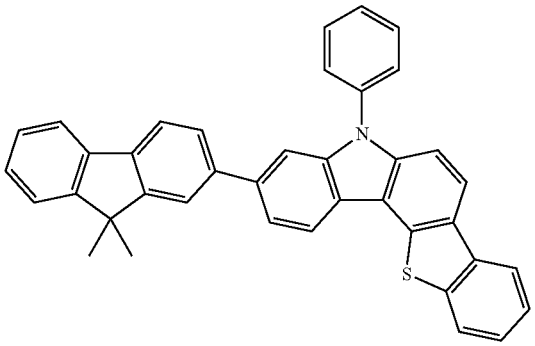
4-94
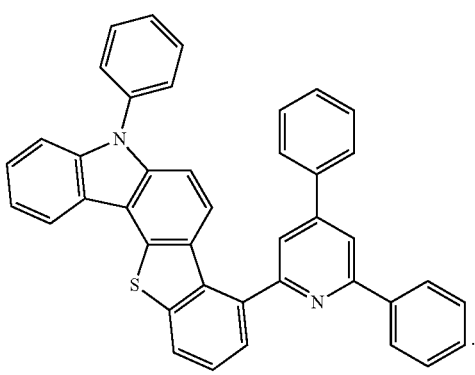
12. The organic electronic element of claim 9, wherein Formula 13 is represented by any one of Formulas 3-1 to 3-5:

Formula 3-1
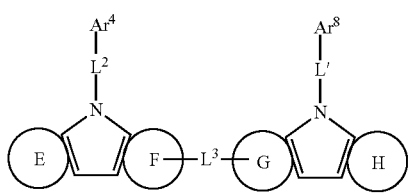
Formula 3-2
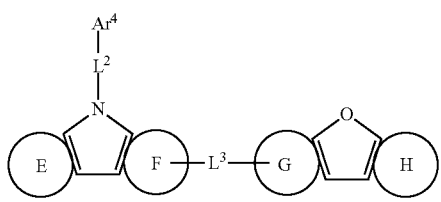
Formula 3-3
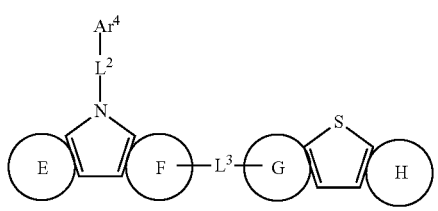
Formula 3-4
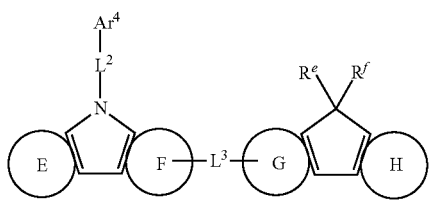
Formula 3-5
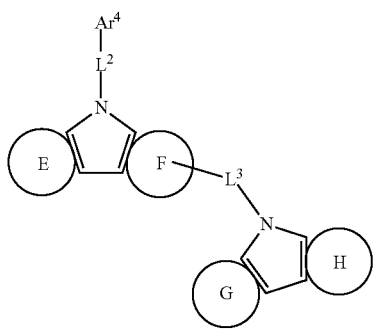
wherein E ring, F ring, G ring, H ring, $Ar^4$, $Ar^8$, $L^2$, $L^3$, L', $R^e$ and $R^f$ are the same as defined in claim 9.
13. The organic electronic element of claim 9, wherein the compound represented by Formula 13 is any one of the following compounds:
5-1
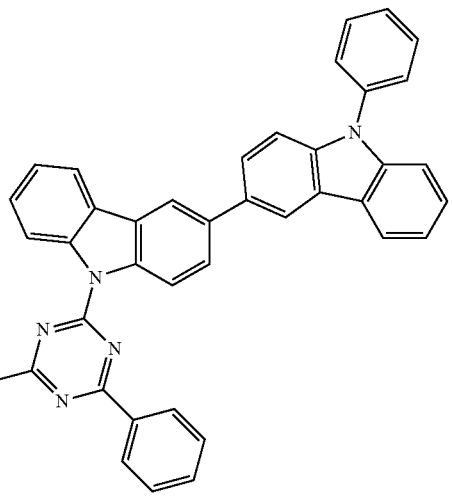
5-2
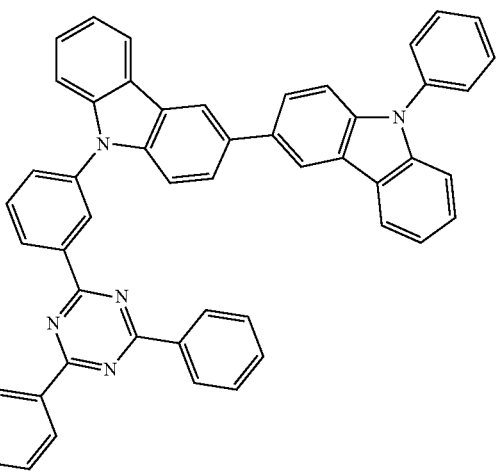
5-3
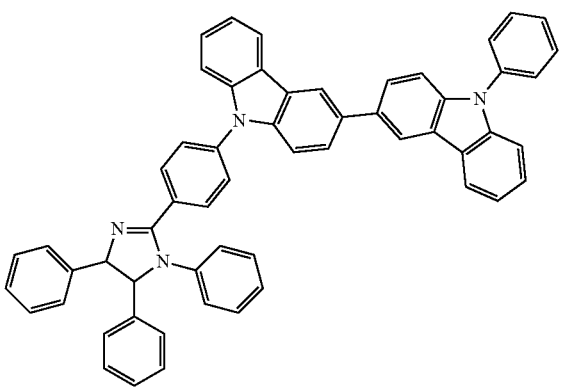

5-4
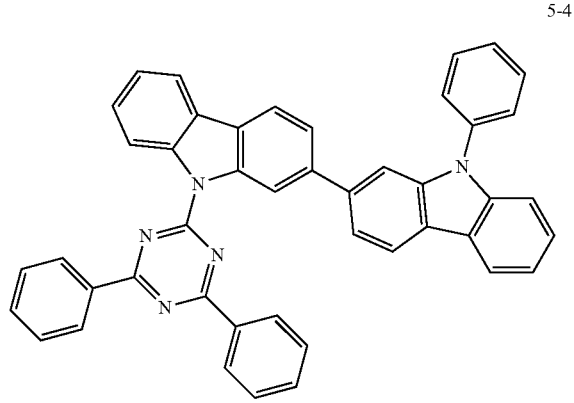
5-5
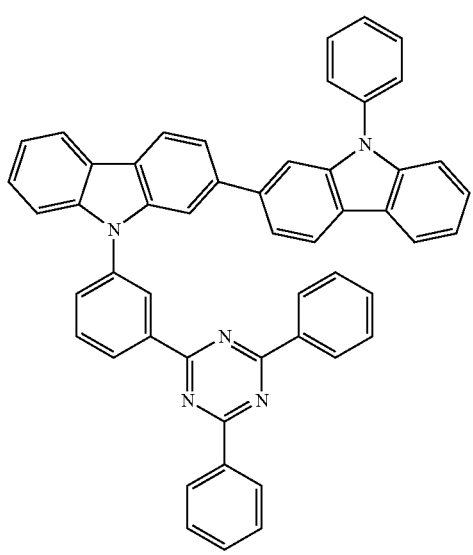
5-6
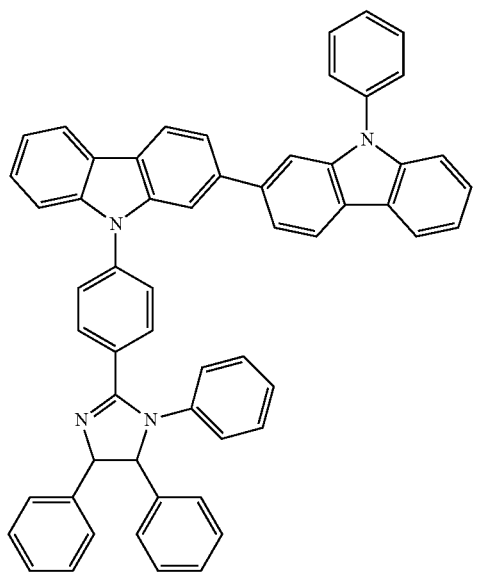
5-7
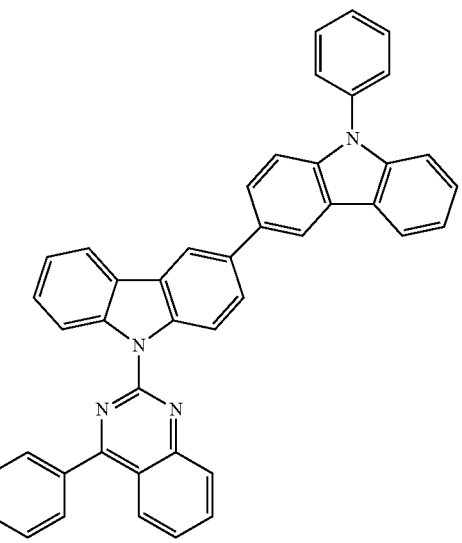
5-8
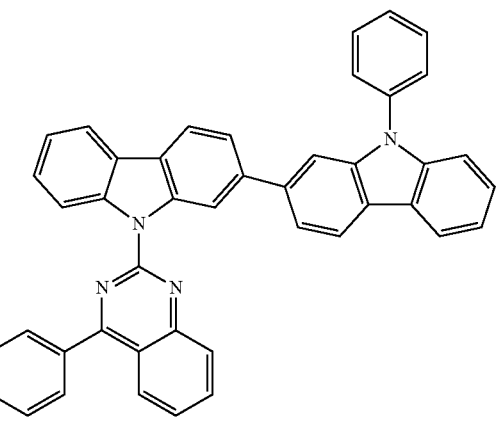
5-9
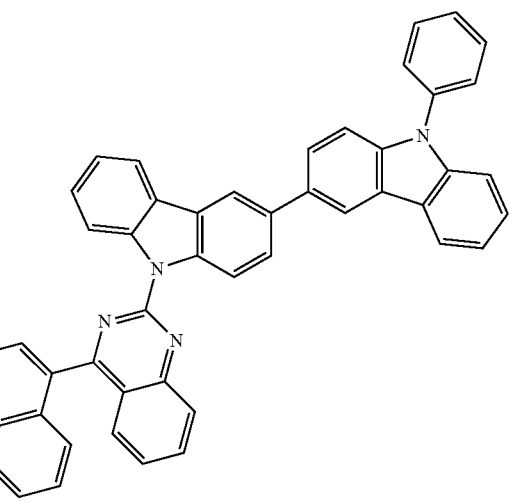

-continued
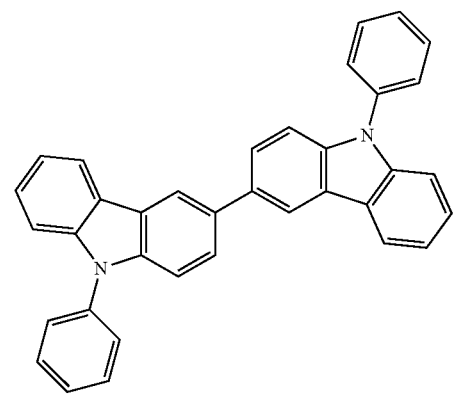
5-10
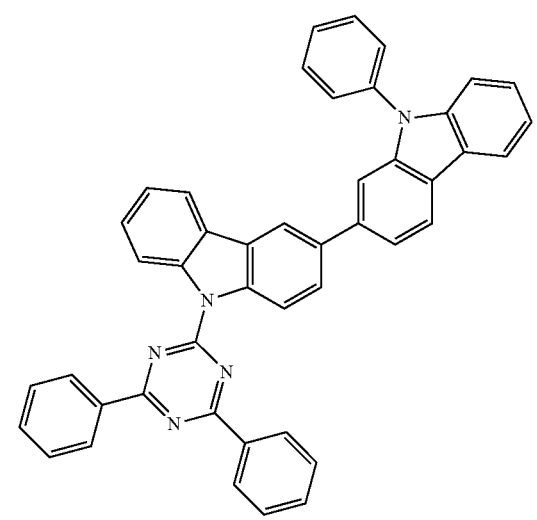
5-11
5-12
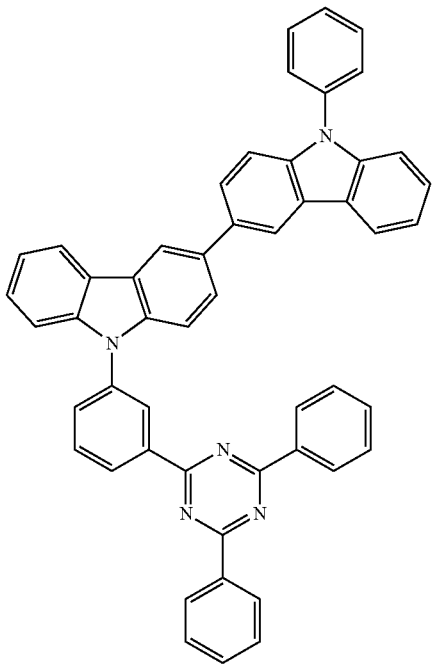
5-13
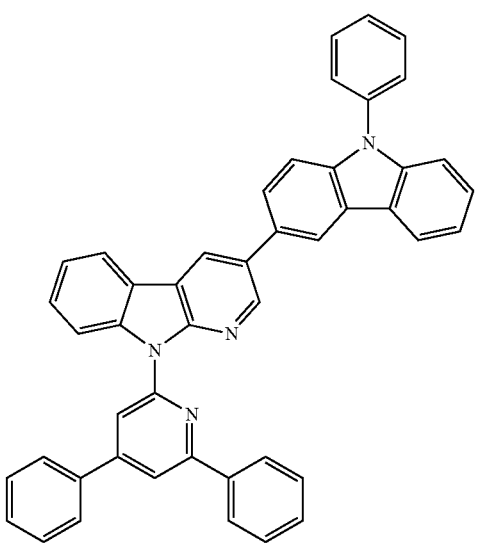
5-14

5-15
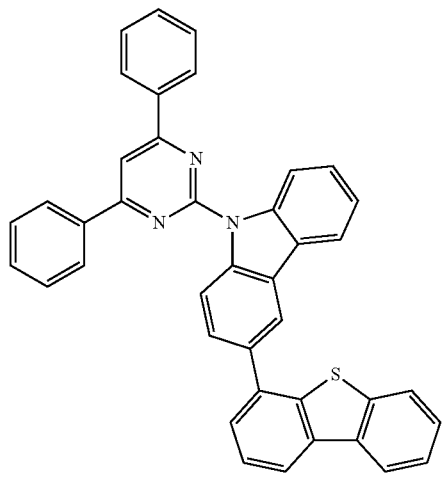
5-16
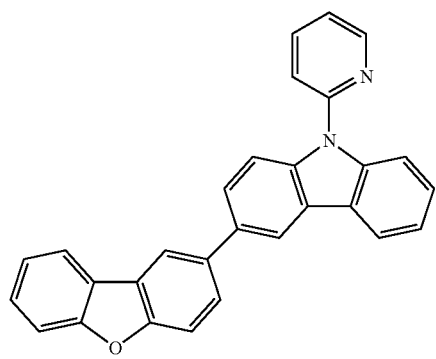
5-17
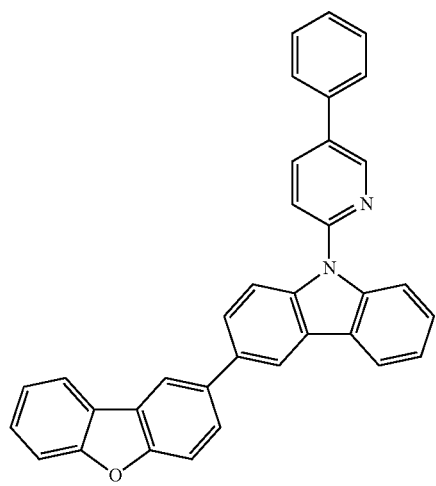
5-18
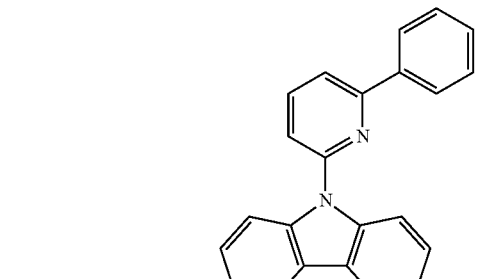
5-19
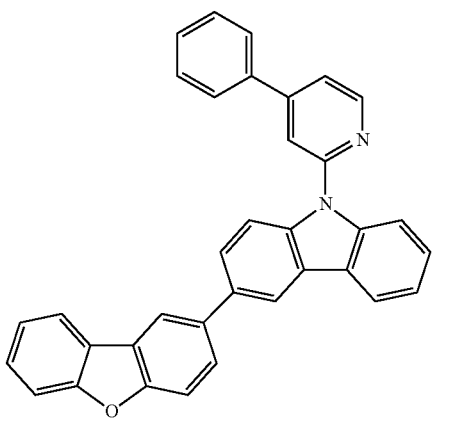
5-20
5-21
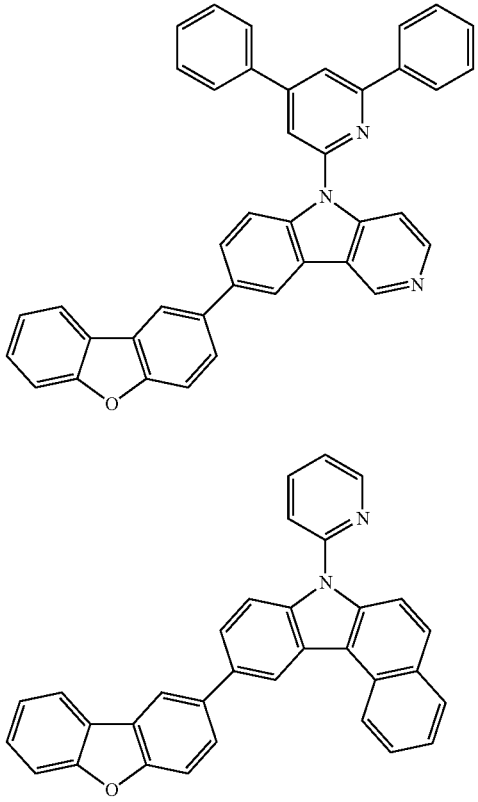

5-22
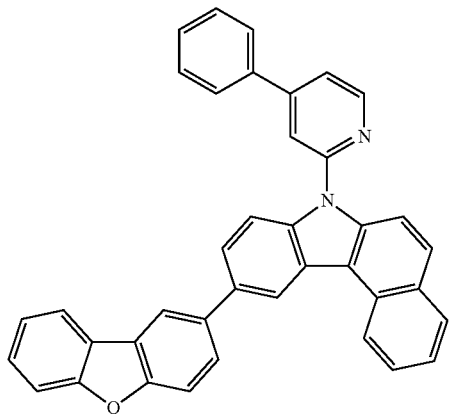
5-25
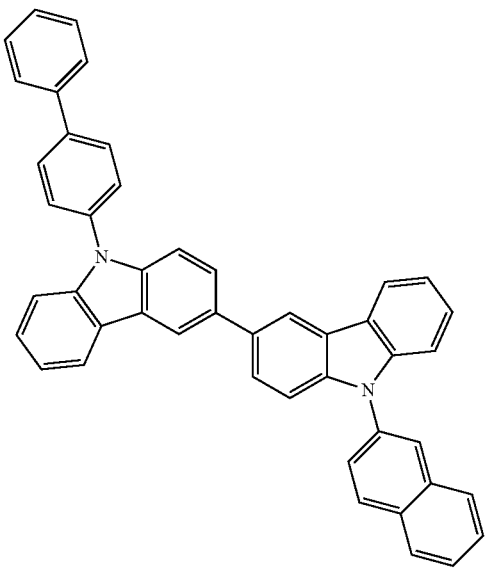
5-23
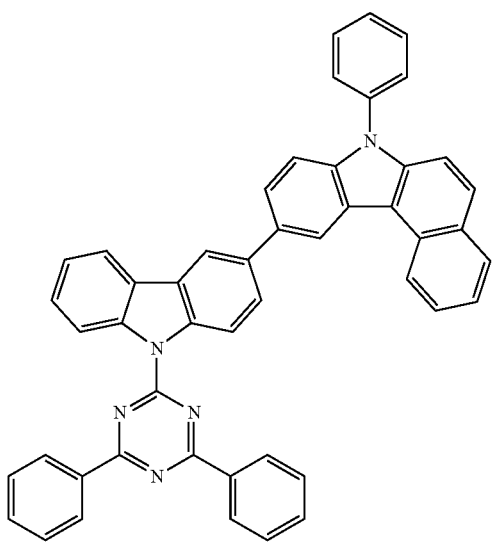
5-24
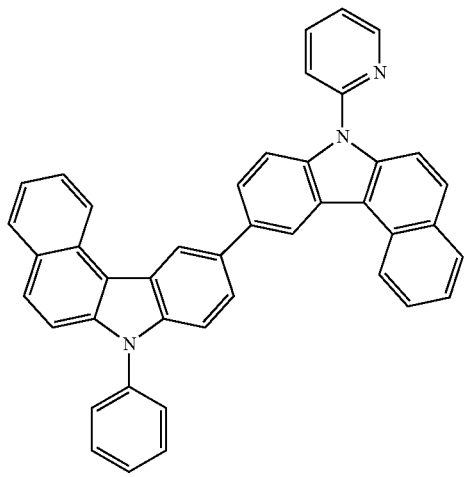
5-26
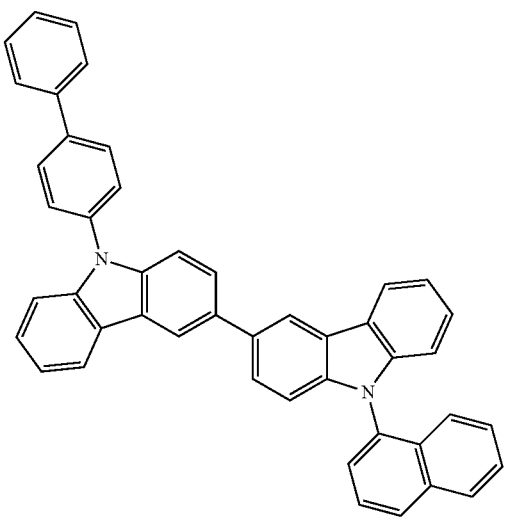

431
-continued
5-27
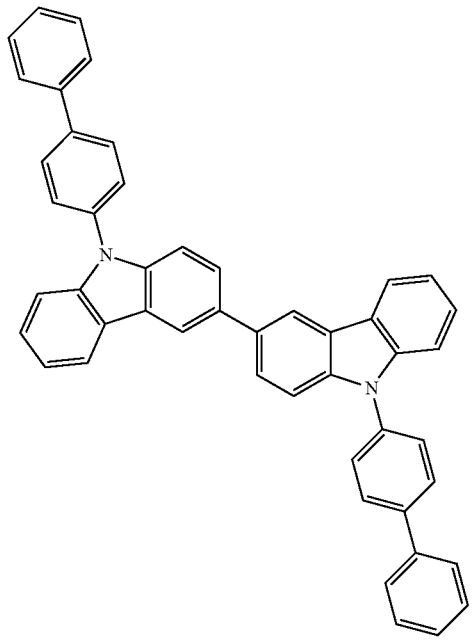
5-28
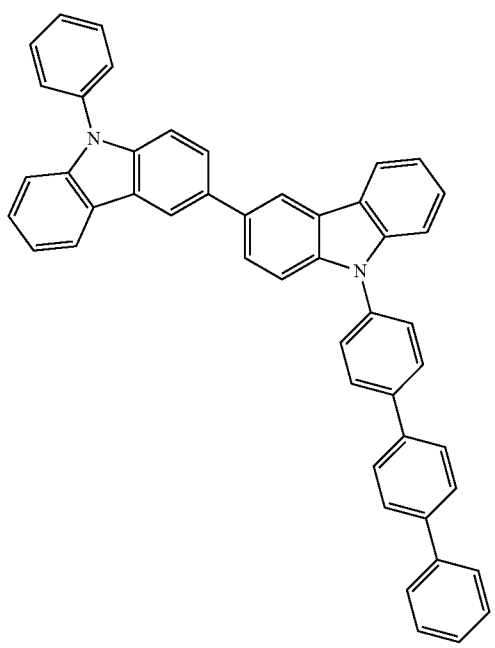
432
-continued
5-29
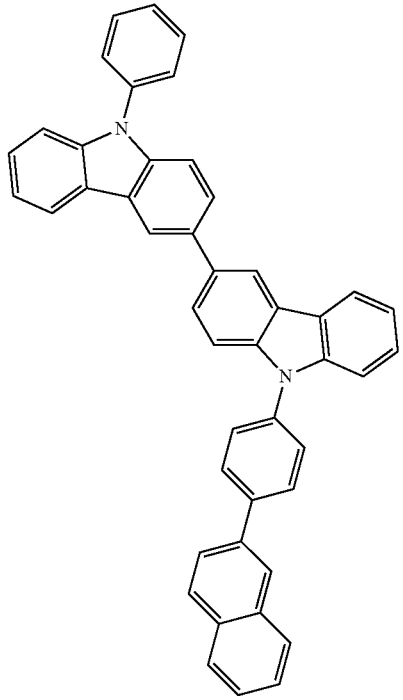
5-30
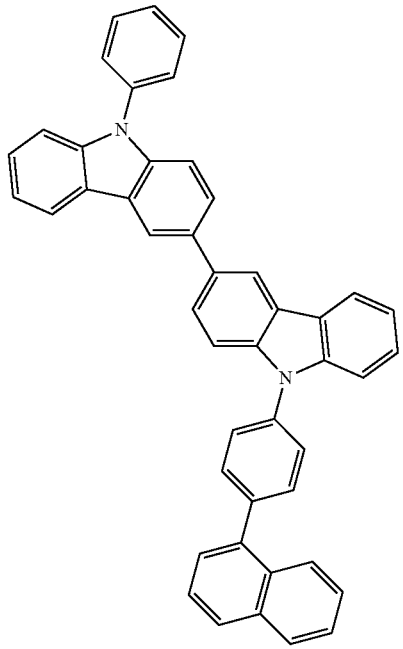

-continued
5-31
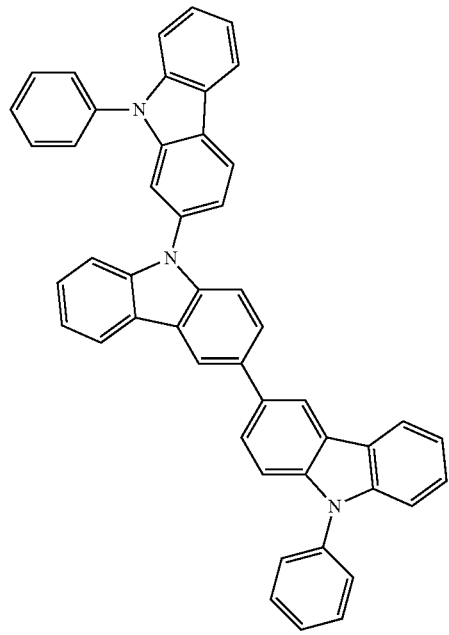
5-32
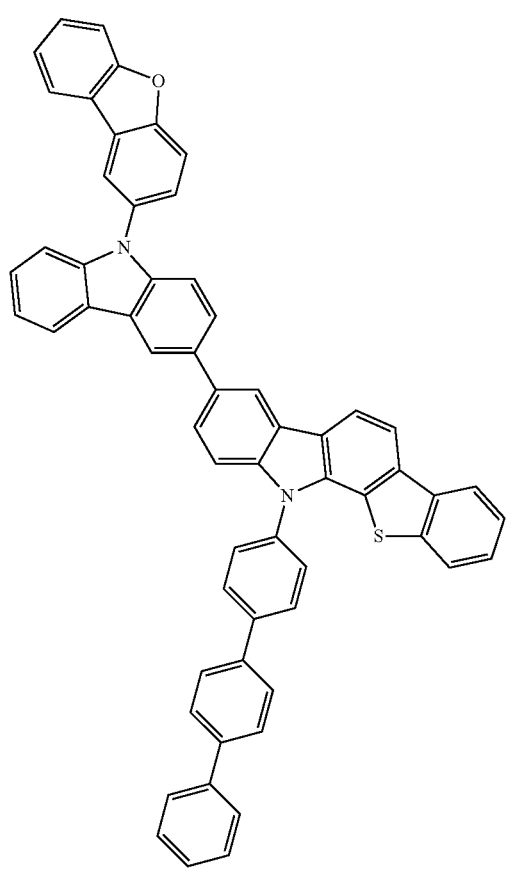
5-33
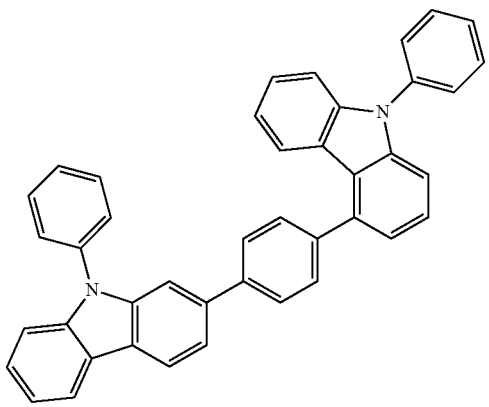
5-34
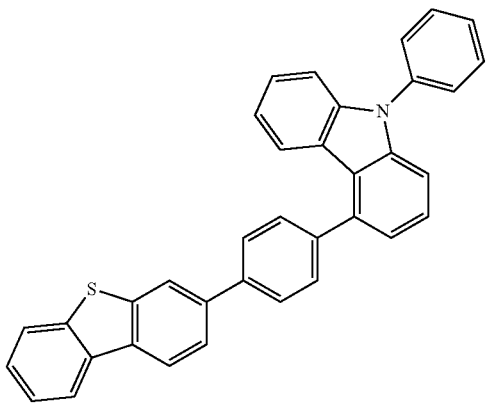
5-35
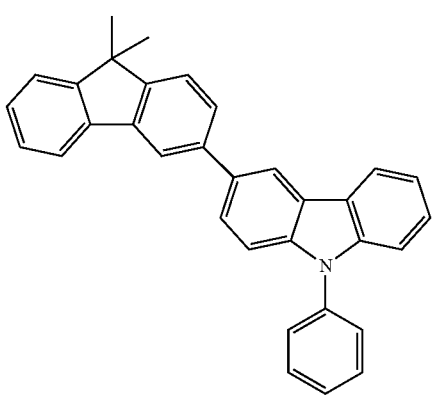

5-36
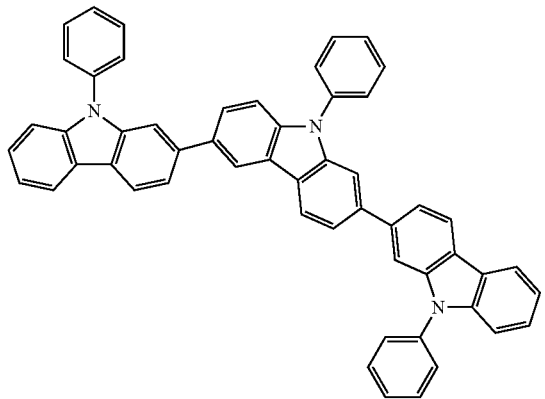
5-38
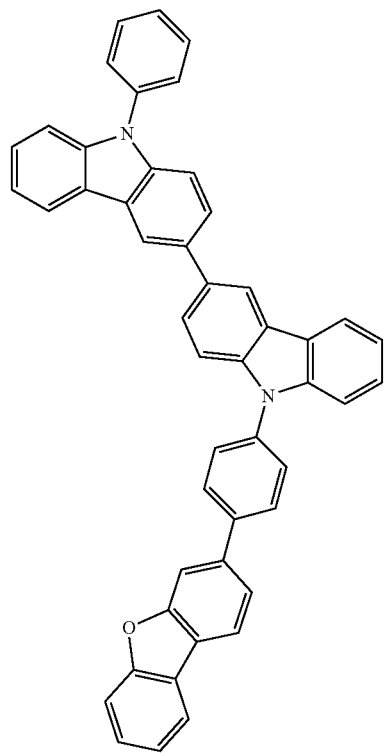
5-37
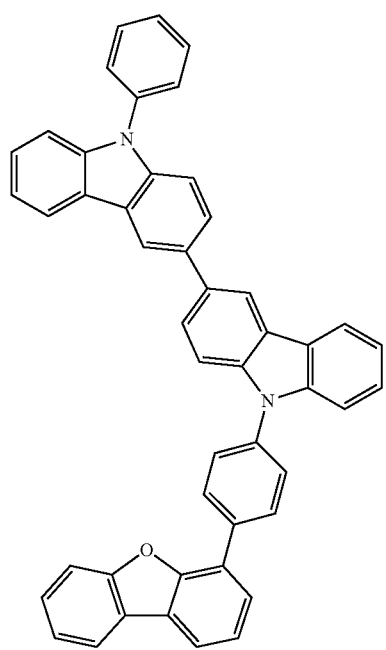
5-39
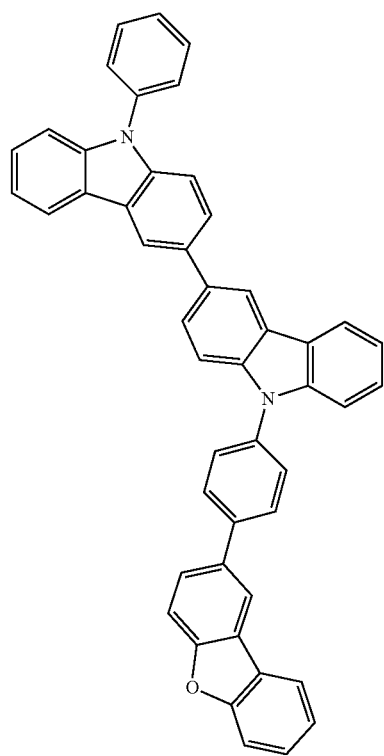

-continued
5-40
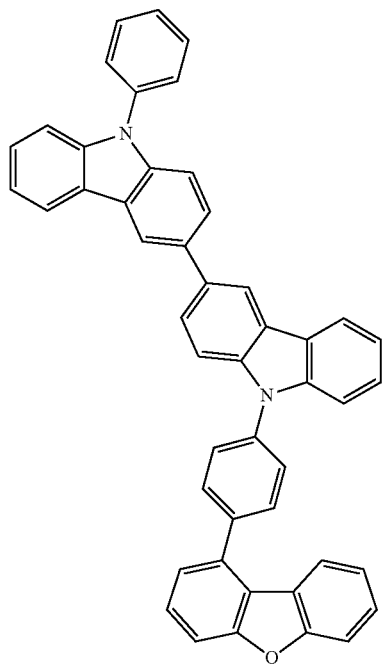
5-41
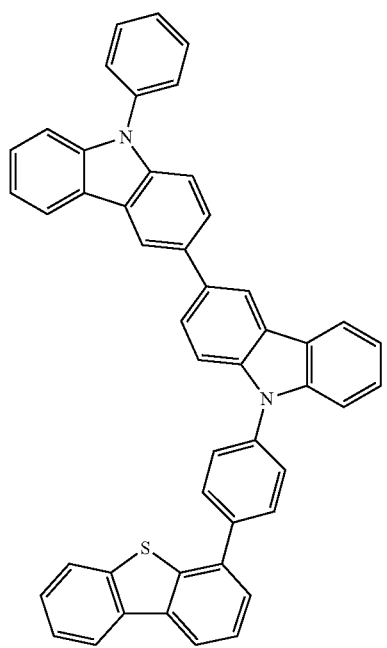
5-42
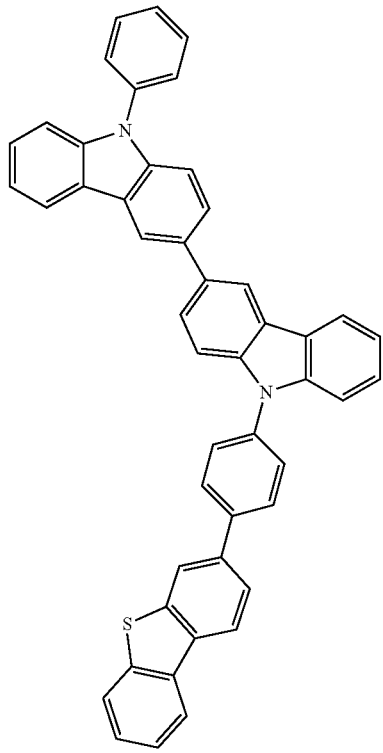
5-43
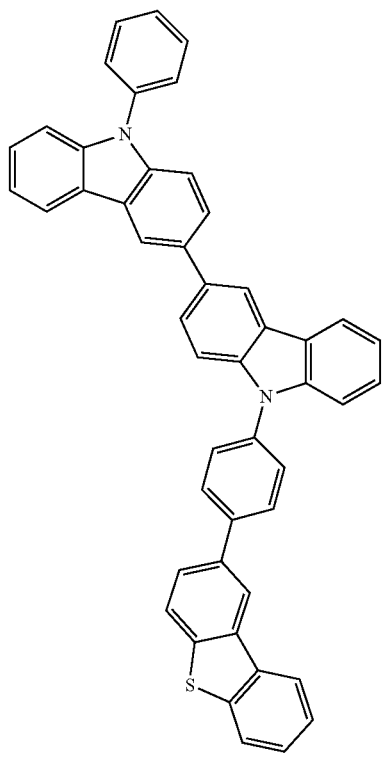

5-44
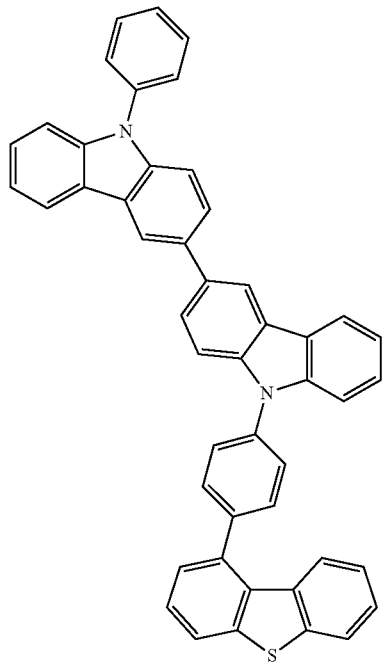
5-45
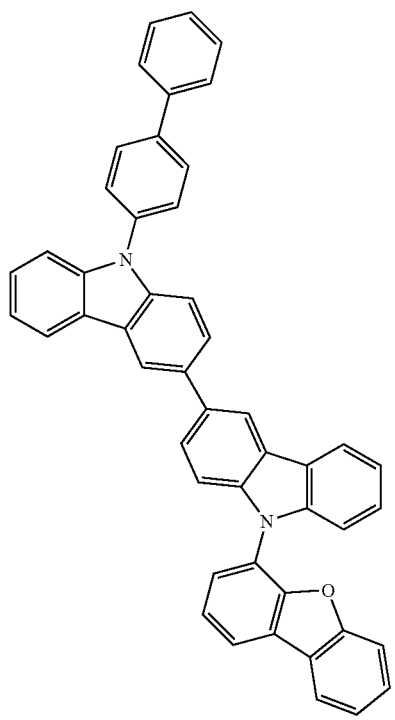
5-46
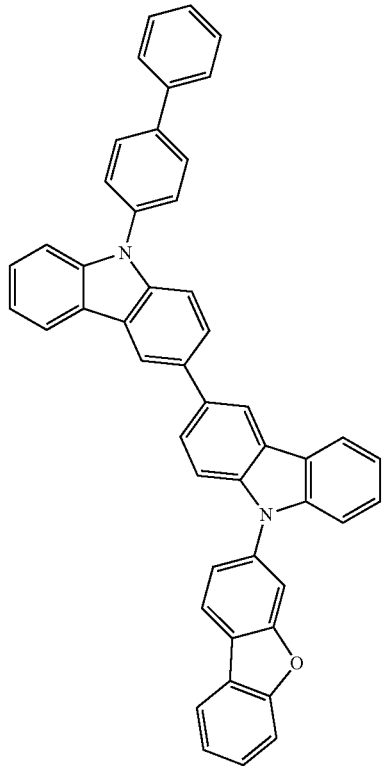
5-47
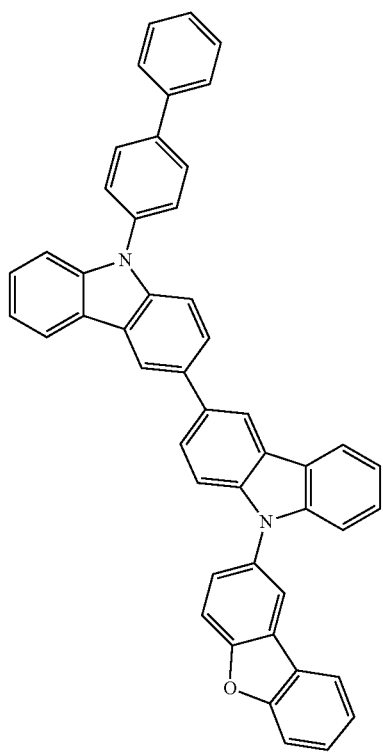

5-48
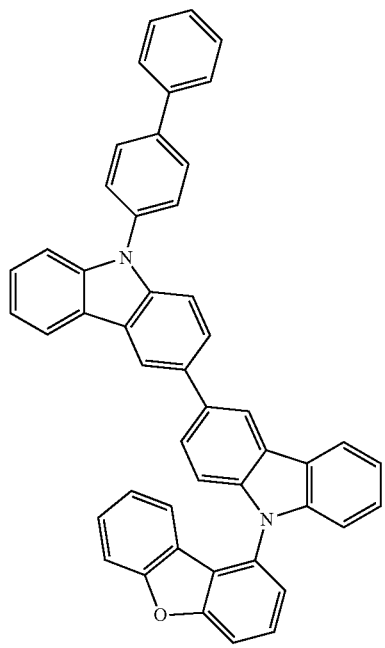
5-45
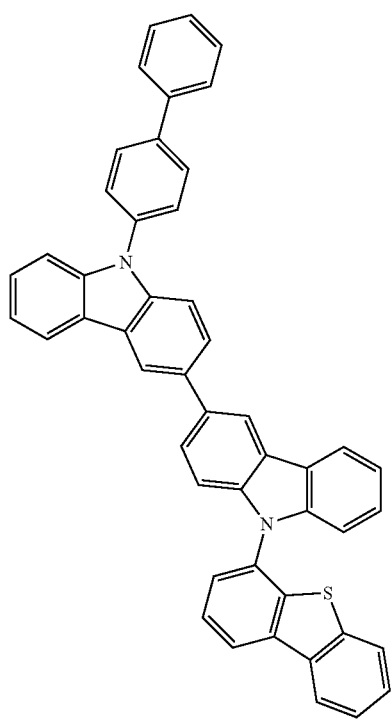
5-46
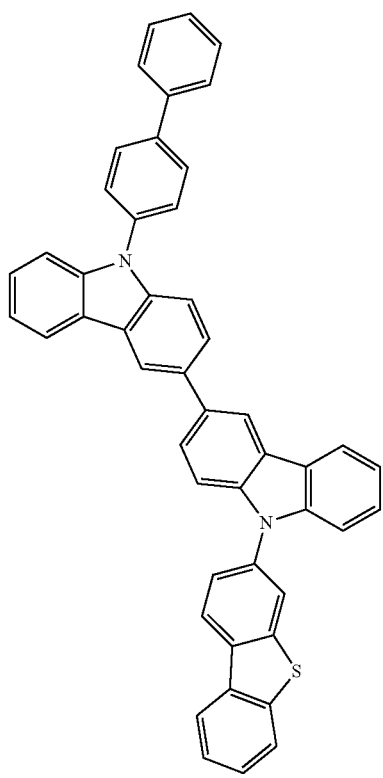
5-47
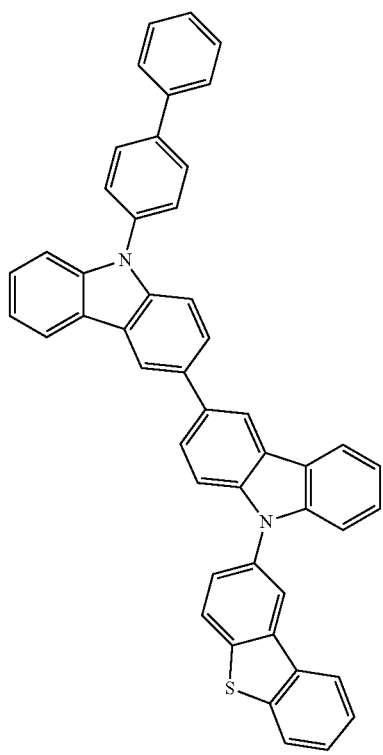

5-48
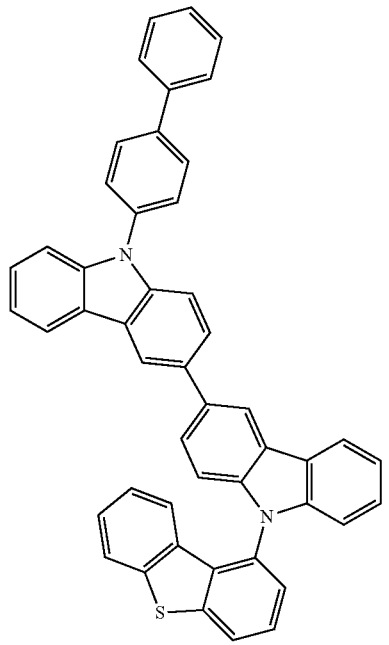
5-53
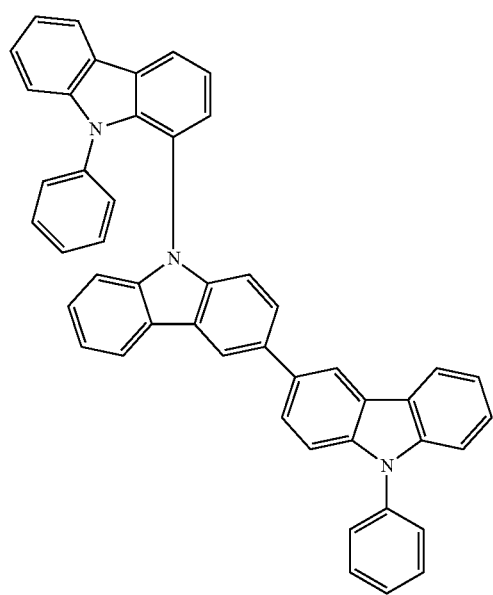
5-54
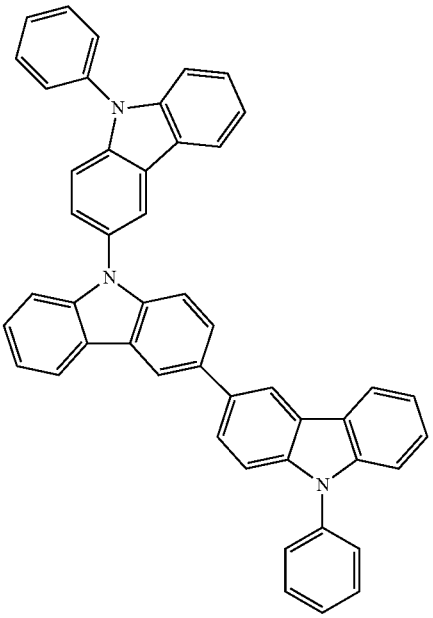
5-55
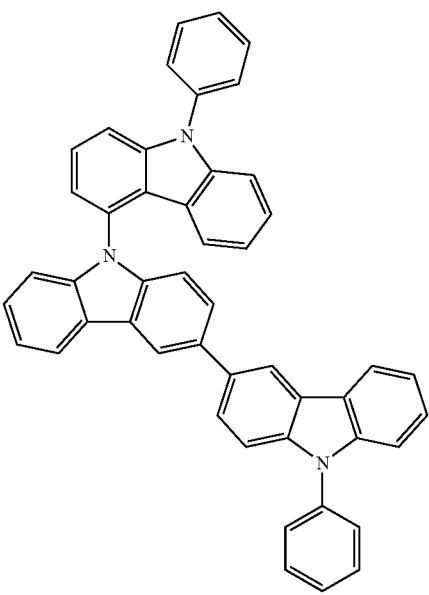

5-56
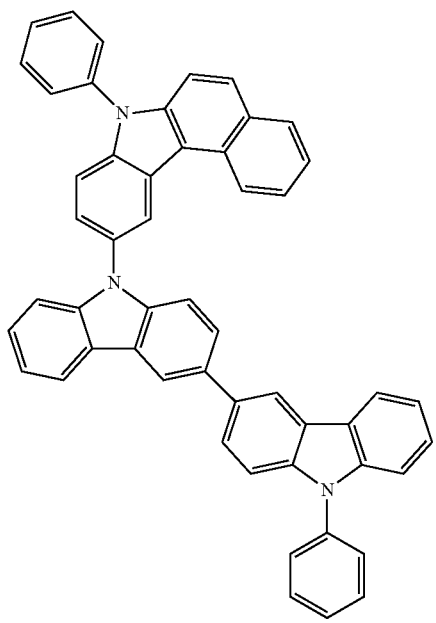
5-57
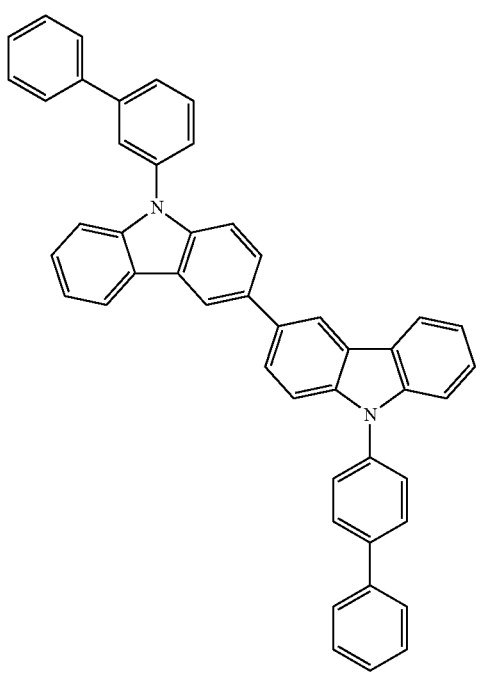
5-58
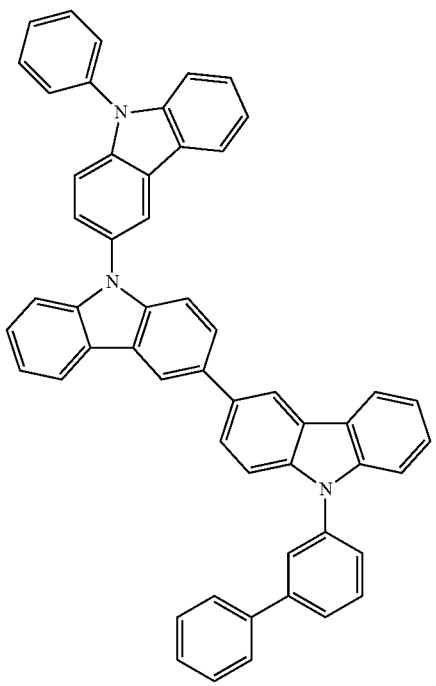
5-59
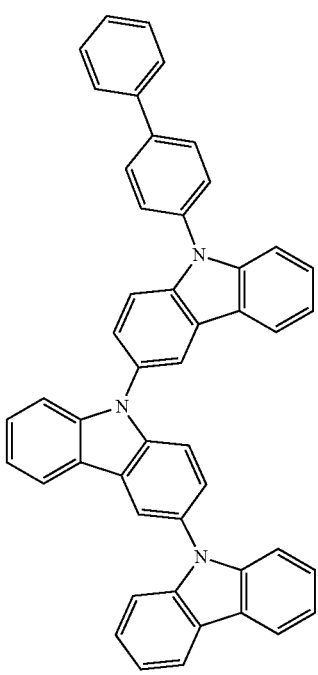

5-60
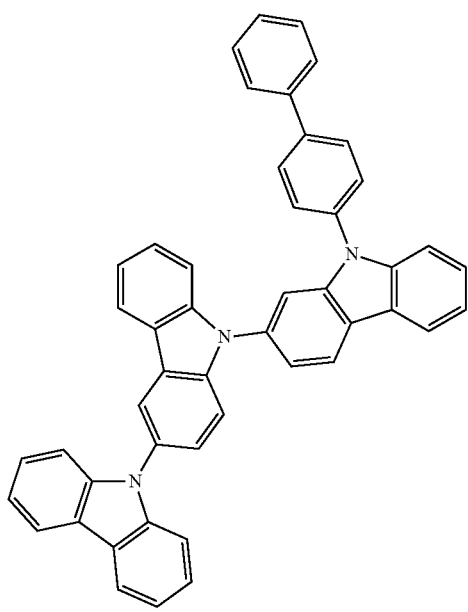
5-61
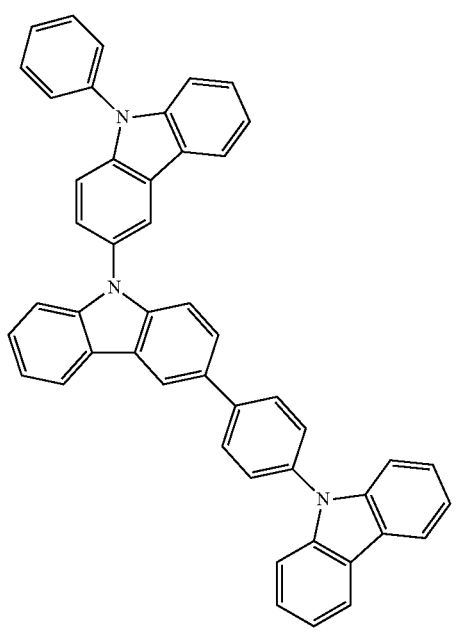
5-62
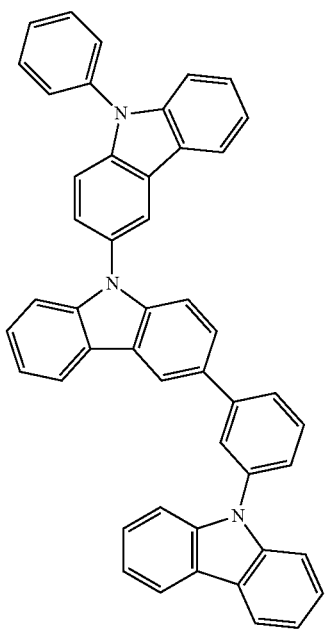
5-63
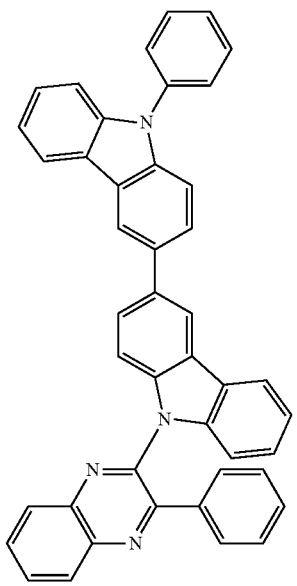

449
-continued
5-64
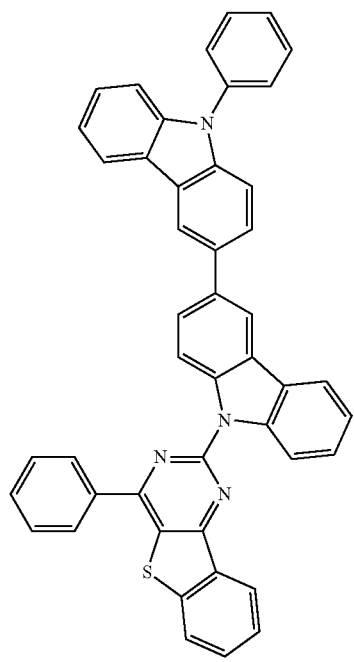
5-65
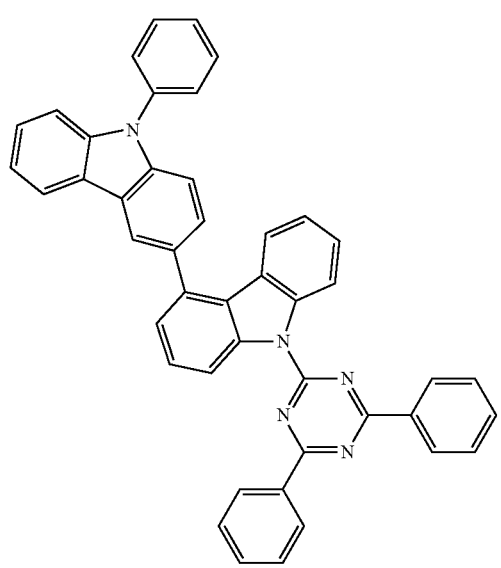
450
-continued
5-66
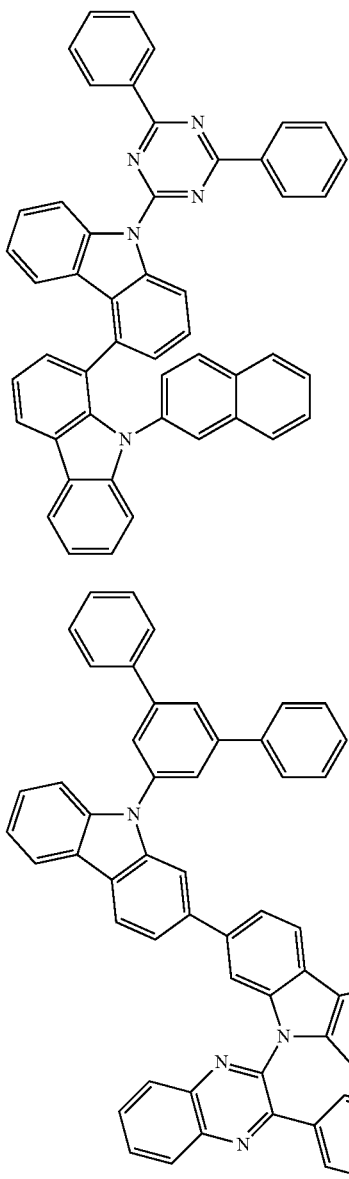
5-67
5-68

5-69
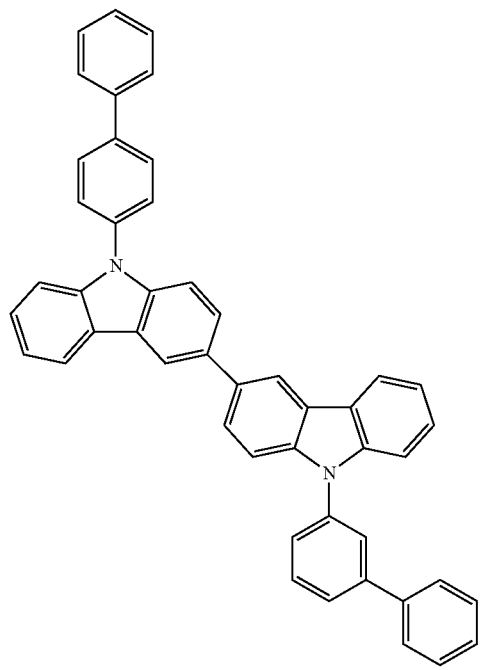
5-70
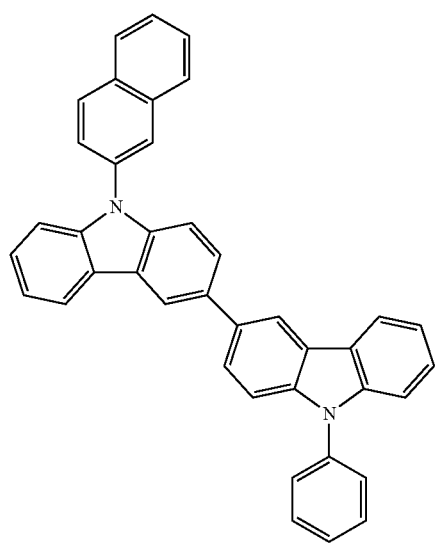
5-71
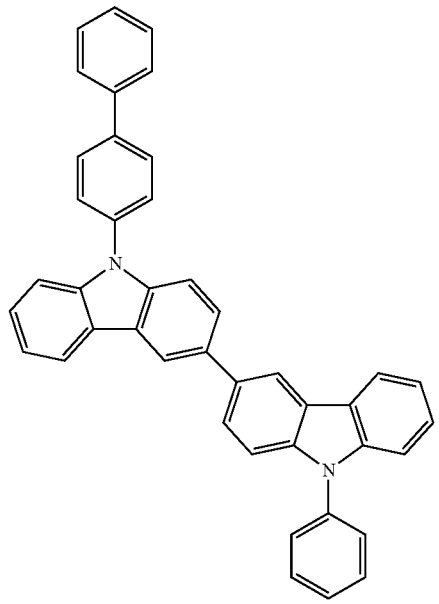
5-72
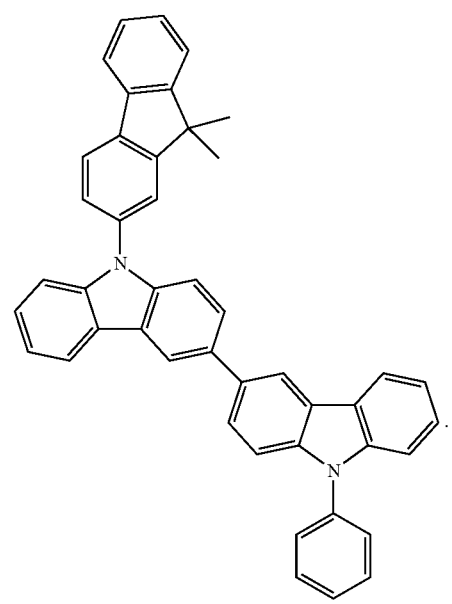
14. The organic electronic element of claim 9, wherein Formula 14 is represented by any one of Formulas 4-1 to 4-6:
Formula 4-1
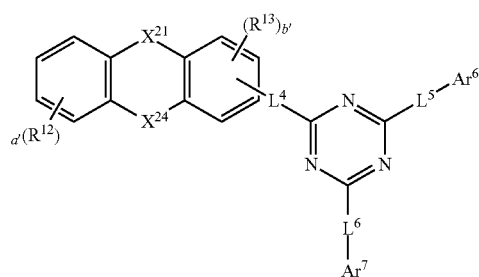

-continued

Formula 4-2

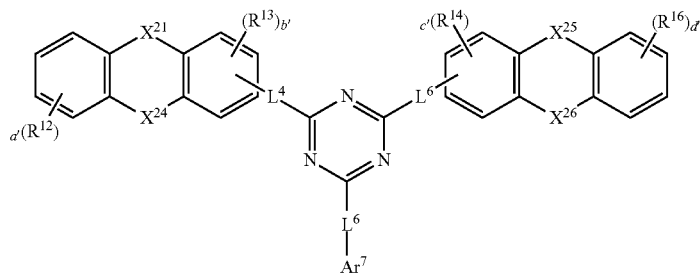

Formula 4-3

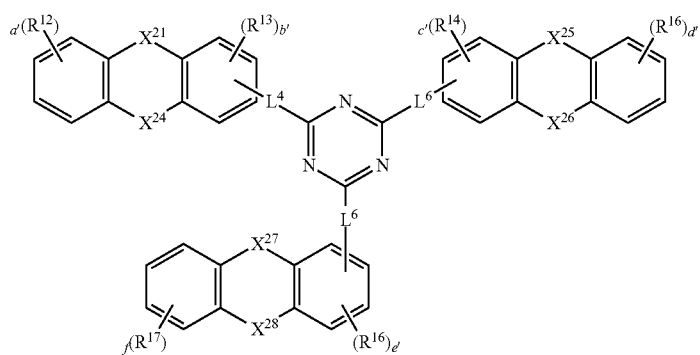

Formula 4-4

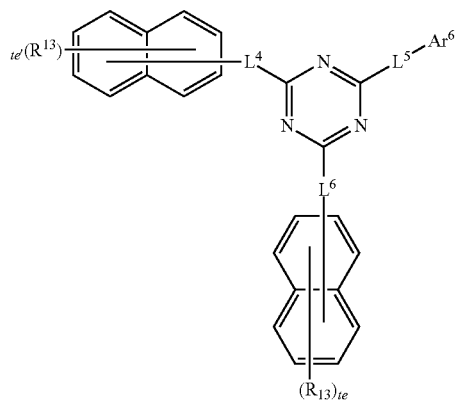

Formula 4-5

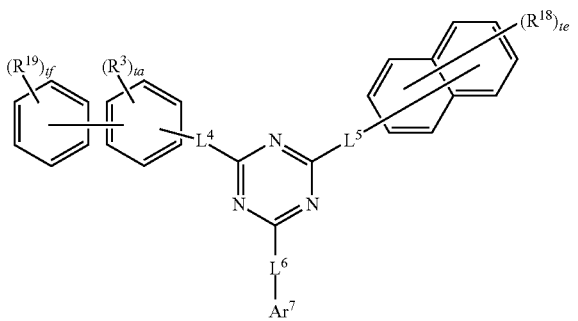

Formula 4-6

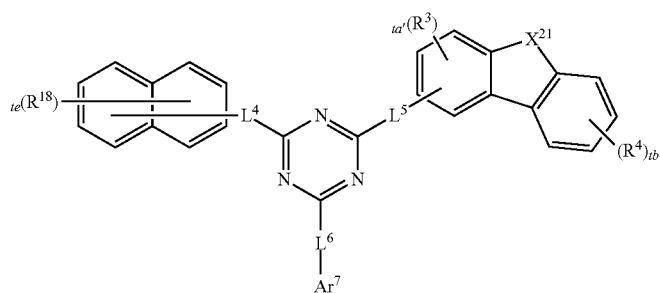

wherein:
1) $X^{21}$, $X^{25}$ and $X^{27}$ are each independently $NAr^{11}$, O, S or $C(R^{10})(R^{11})$,
2) $X^{24}$, $X^{26}$ and $X^{28}$ are each independently $NAr^{12}$, O, S, $C(R^{20})(R^{21})$ or a single bond,
3) wherein $Ar^{11}$ and $Ar^{12}$ are the same as the definition of $Ar^3$ in claim 9,
4) A', d' and f' are each independently an integer of 0 to 4, b', c', e' and ta' are each independently integer of 0 to 3,
5) $L^4$, $L^5$, $L^6$, $Ar^6$ and $Ar^7$ are the same as defined in claim 9,
6) To and tb are each independently integer of 0 to 4, to is an integer of 0 to 7, tf is an integer of 0 to 5,
7) $R^3$, $R^4$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ are the same or different from each other, and are each independently selected from the group consisting of hydrogen; deuterium; halogen; a silane group unsubstituted or substituted with a $C_1$-$C_{20}$ alkyl group or a $C_6$-$C_{20}$ aryl group; cyano group; nitro group; $C_1$-$C_{20}$ alkoxy group; $C_6$-$C_{20}$ aryloxy group; $C_1$-$C_{20}$ alkyl group; $C_2$-$C_{20}$ alkenyl group; $C_2$-$C_{20}$ alkynyl group; $C_6$-$C_{20}$ aryl group; fluorenyl group; $C_2$-$C_{20}$ heterocyclic group including at least one heteroatom of O, N, S, Si or P; and $C_3$-$C_{20}$ aliphatic ring; or adjacent groups may be bonded to each other to form a ring, or may be bonded to adjacent substituents to form a ring.

15. The organic electronic element of claim 9, wherein the compound represented by Formula 14 is any one of the following compounds:

6-1

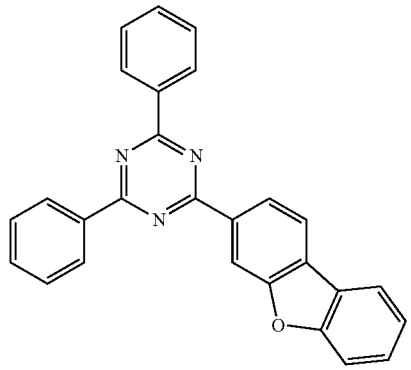

6-2

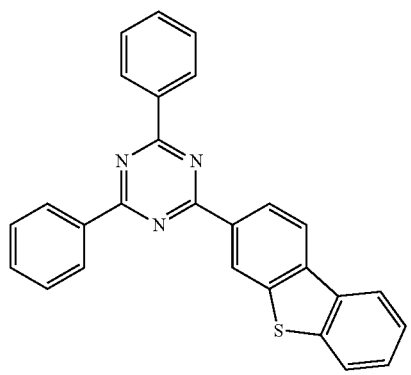

6-3

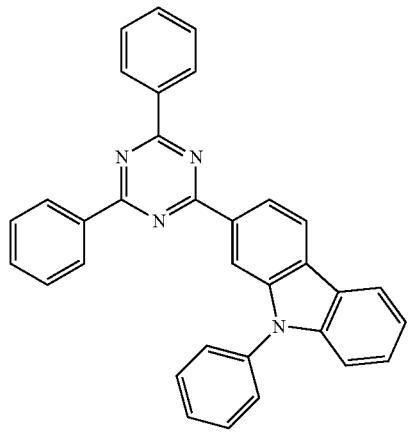

6-4

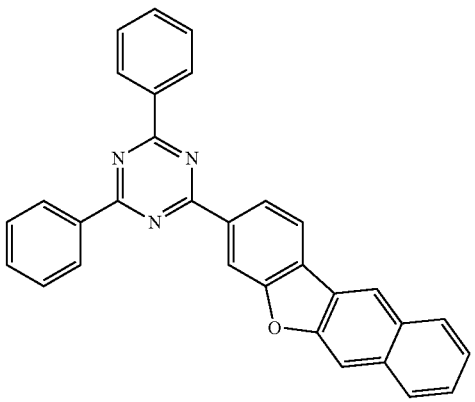

6-5

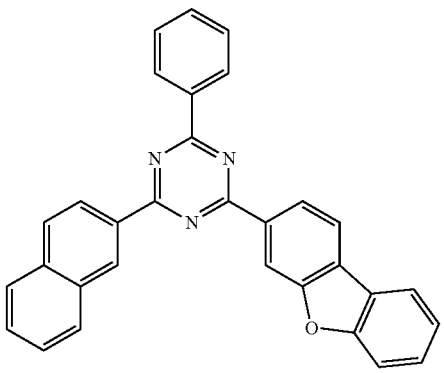

6-6

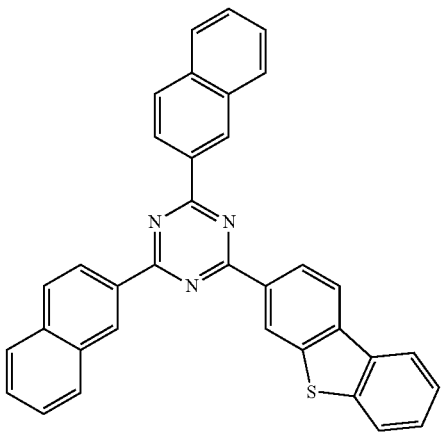

6-7
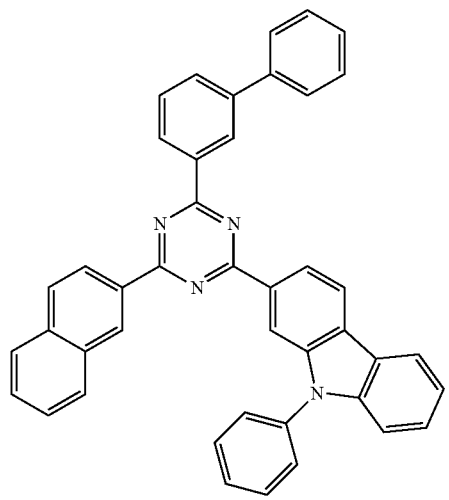
6-8
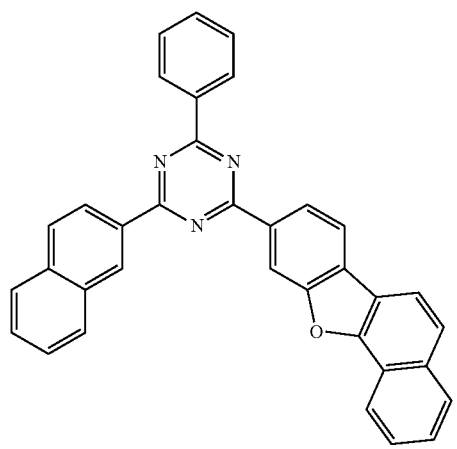
6-9
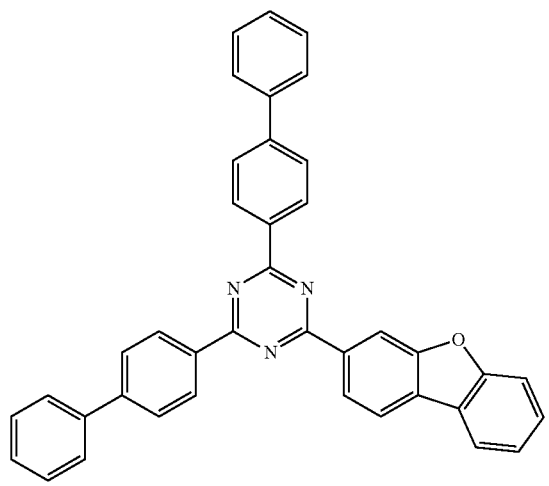
6-10
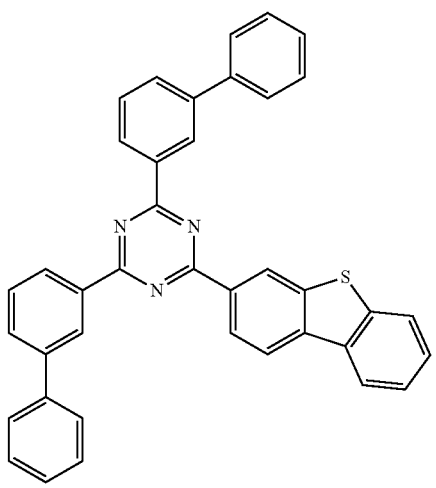
6-11
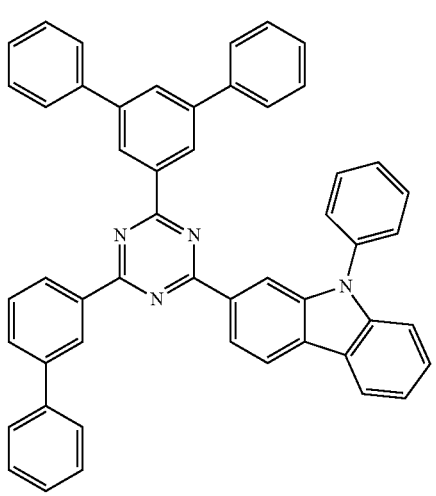
6-12
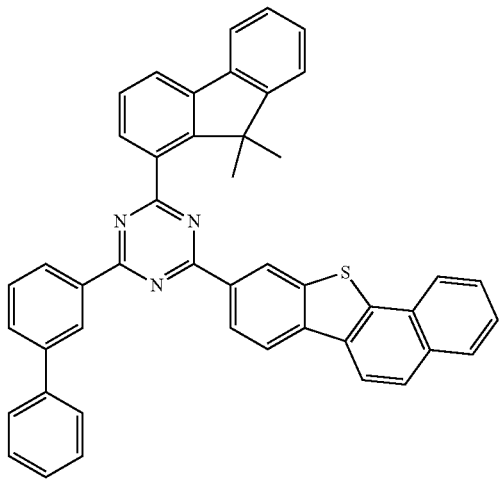

459
-continued
6-13
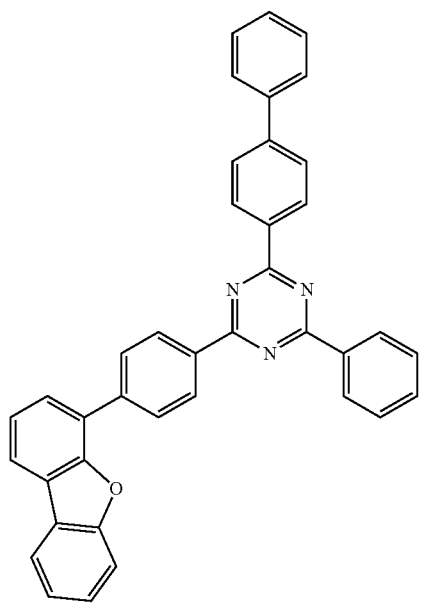
6-14
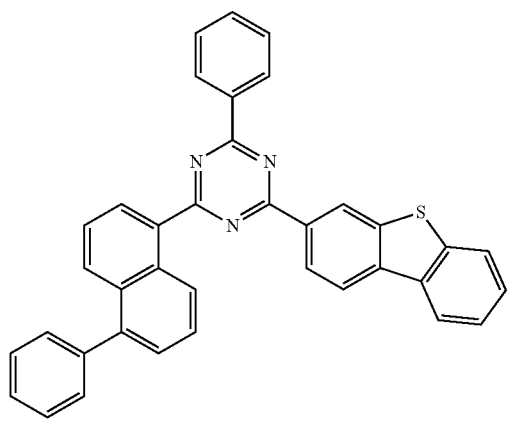
6-15
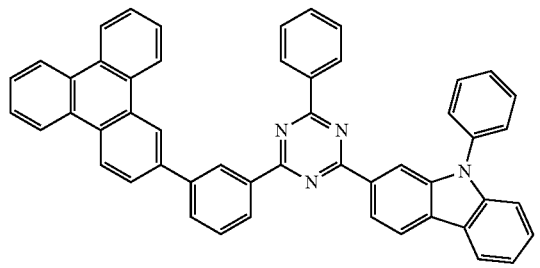
460
-continued
6-16
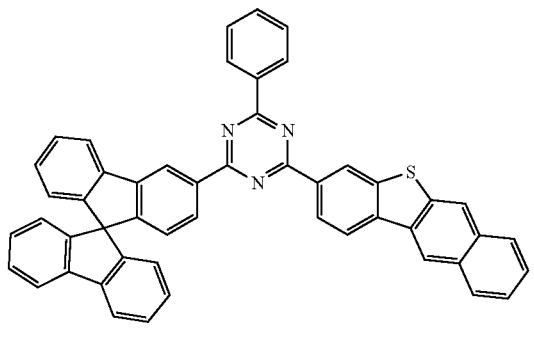
6-17
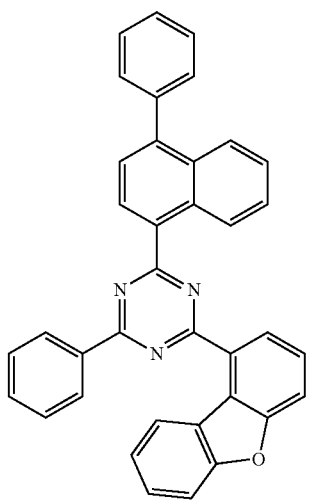
6-18
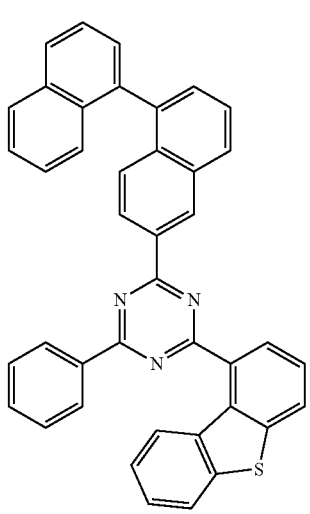

6-19
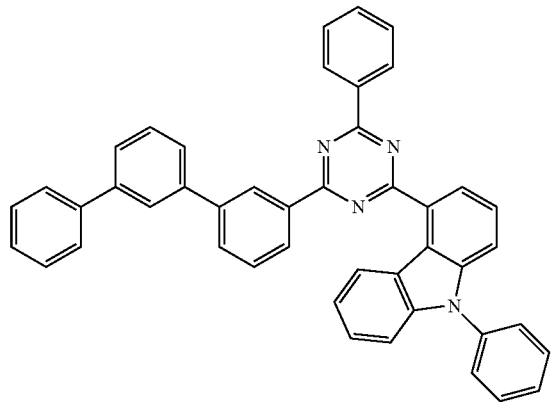
6-20
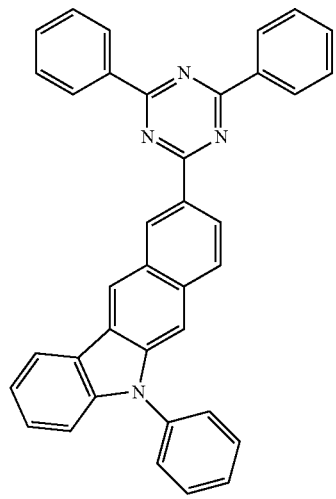
6-21
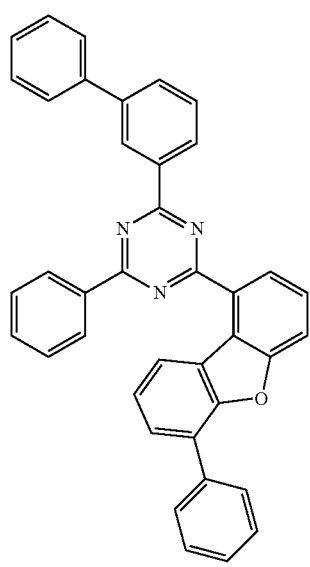
6-22
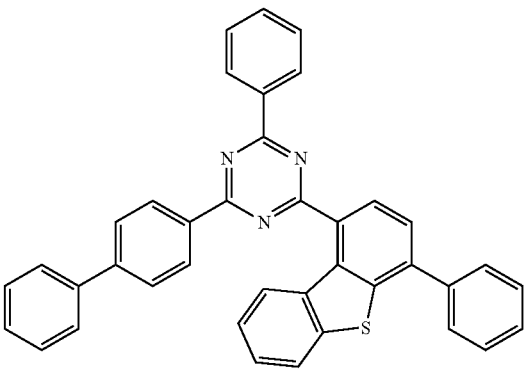
6-23
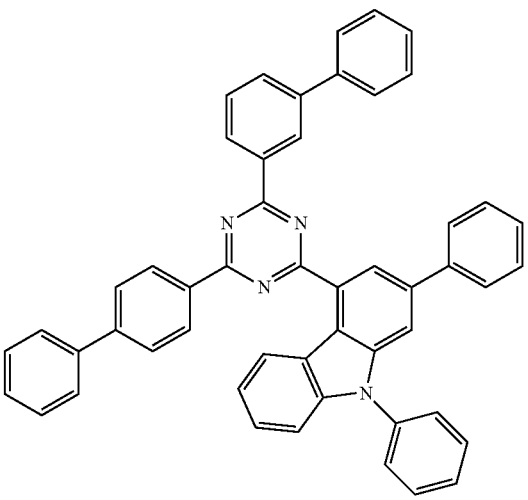
6-24
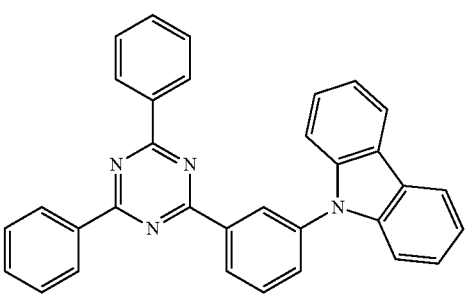
6-25
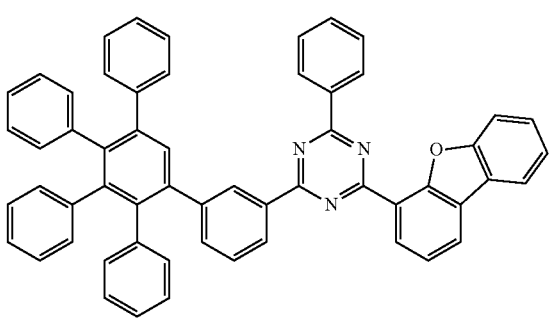

6-26
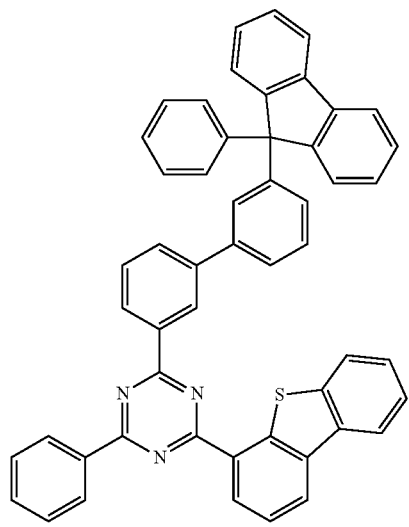
6-29
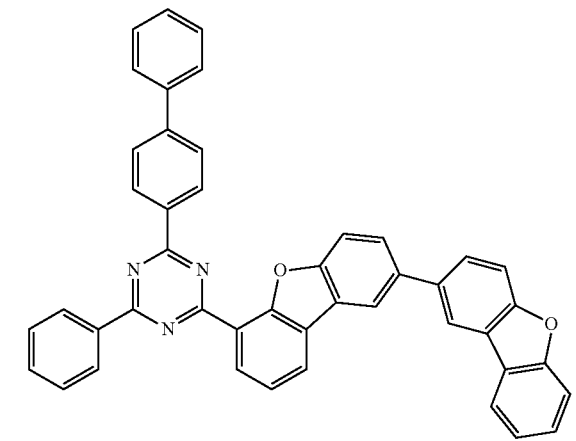
6-27
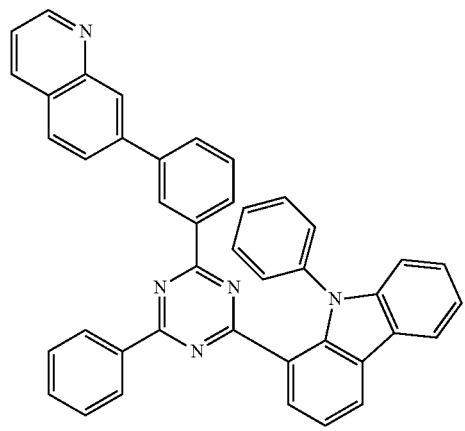
6-30
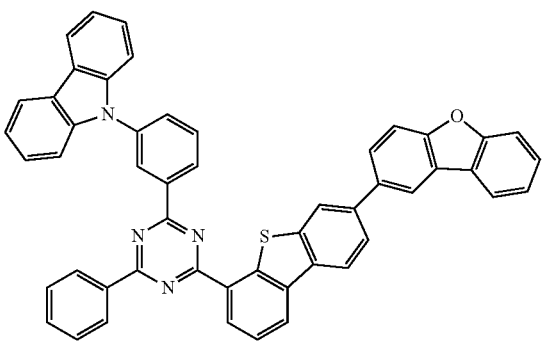
6-31
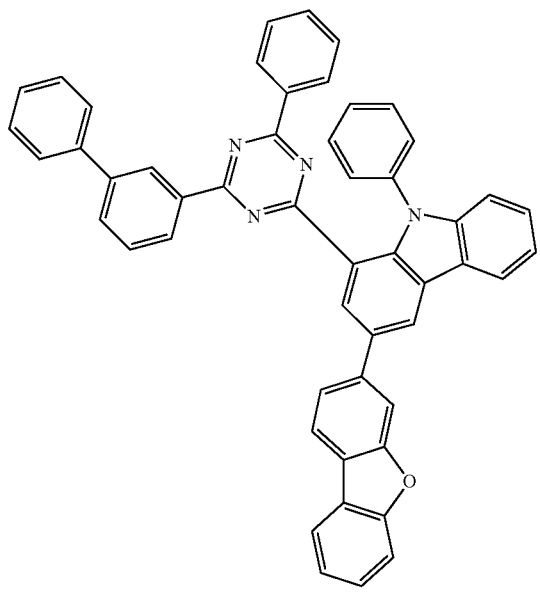
6-28
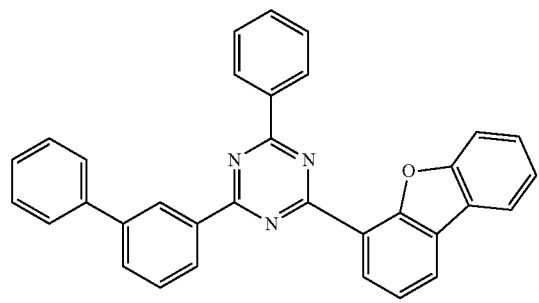

6-32
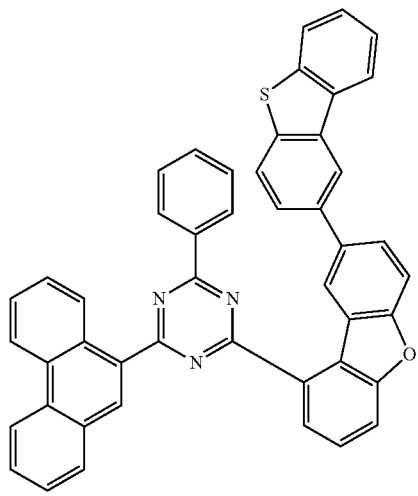
6-33
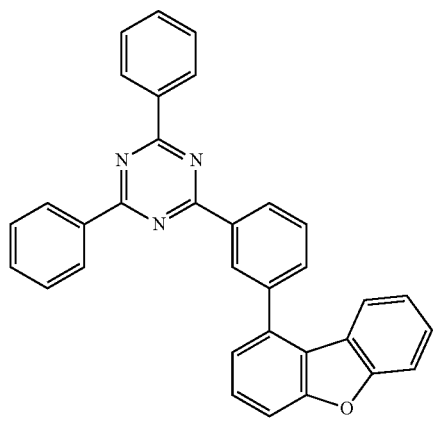
6-34
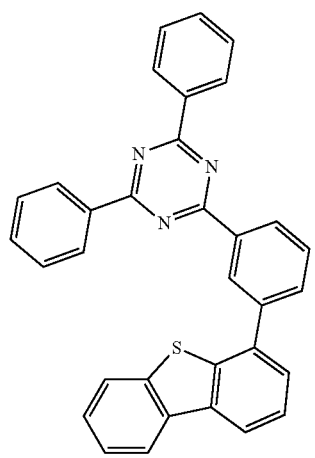
6-35
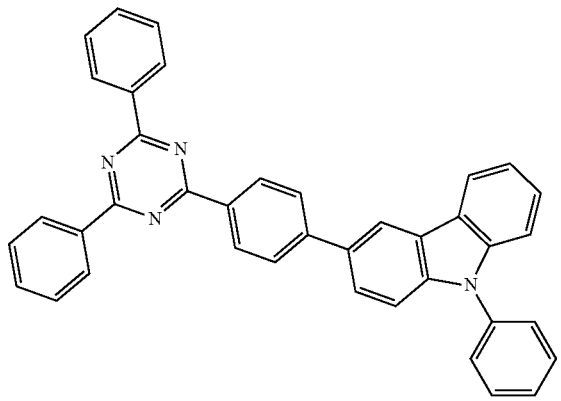
6-36
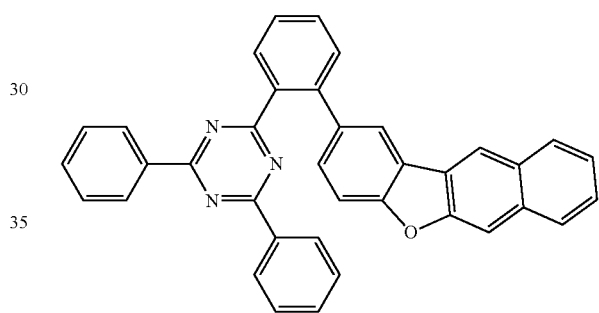
6-37
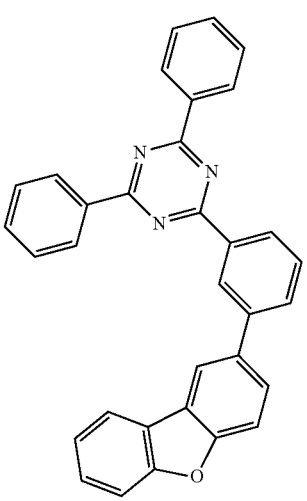

467
-continued
6-38
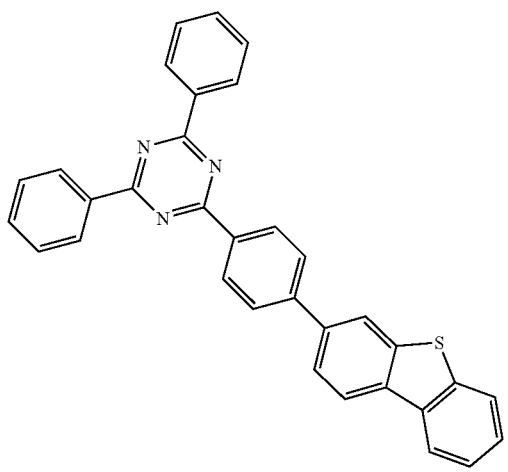
6-39
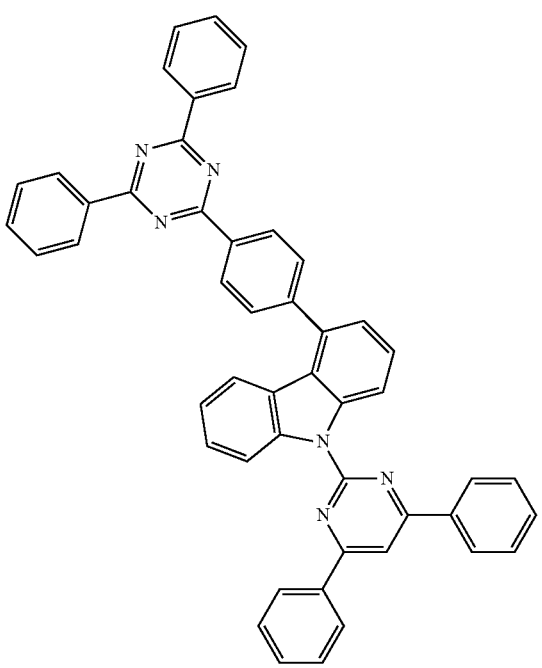
6-40
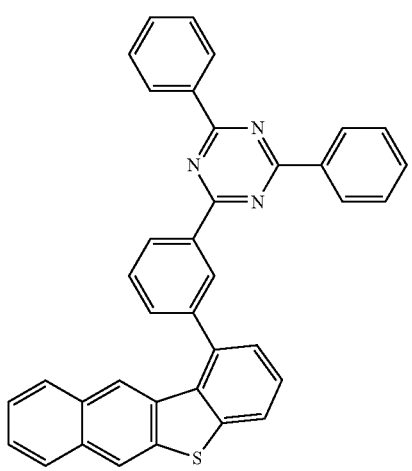
468
-continued
6-41
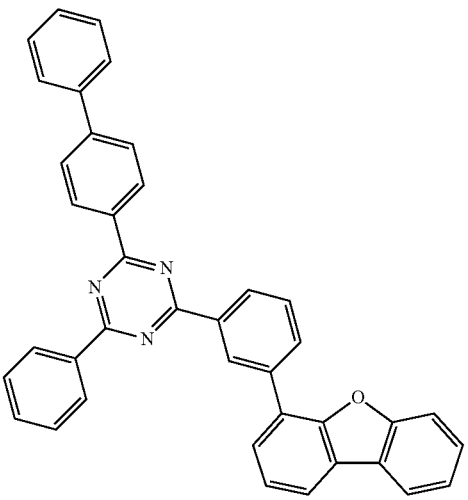
6-42
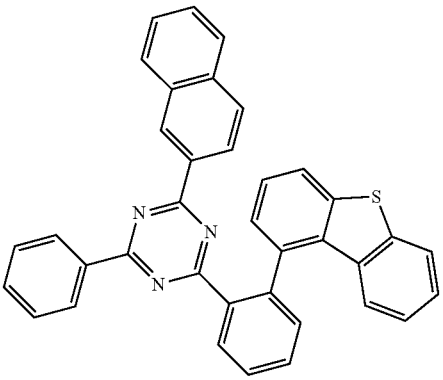
6-43
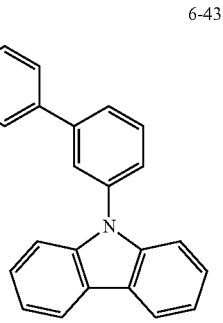

6-44
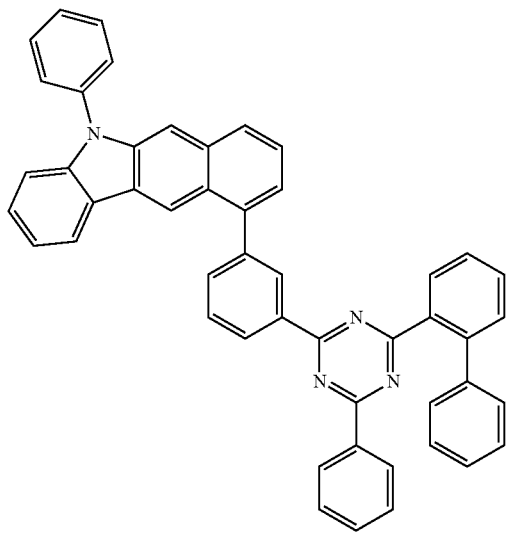
6-45
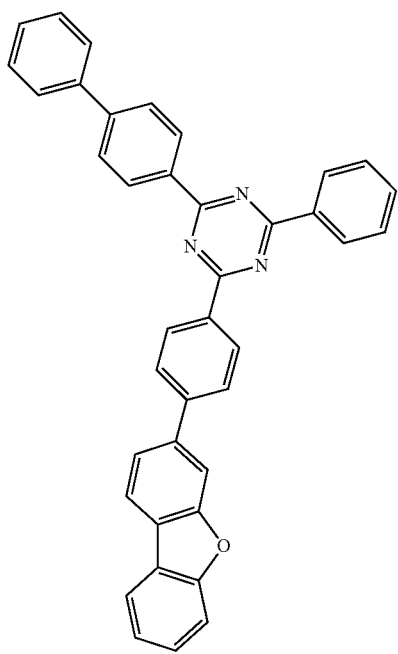
6-46
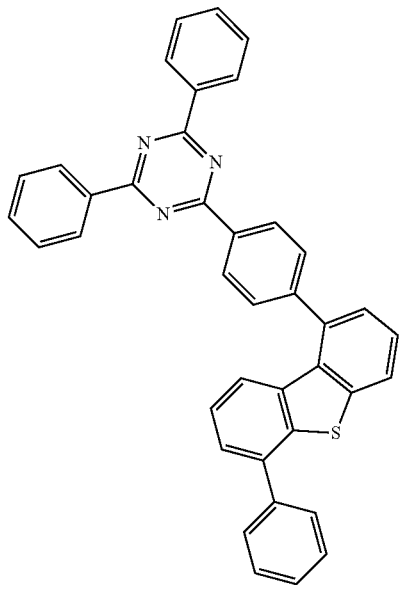
6-47
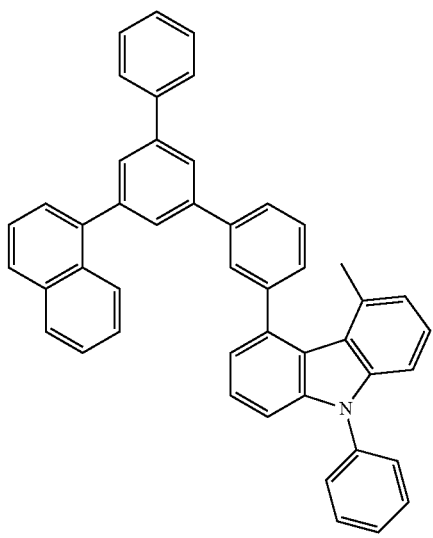
6-48
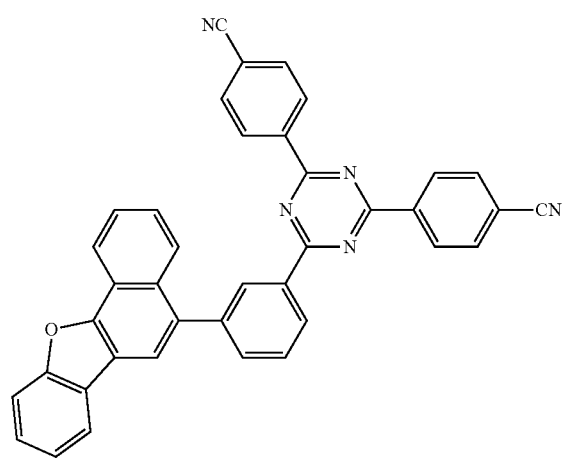

-continued
6-49
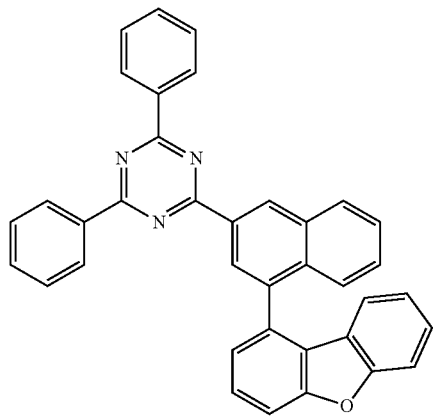
6-50
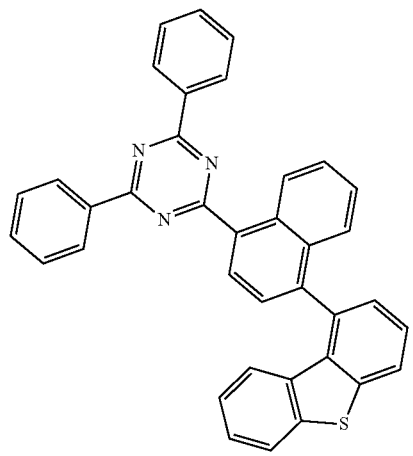
6-51
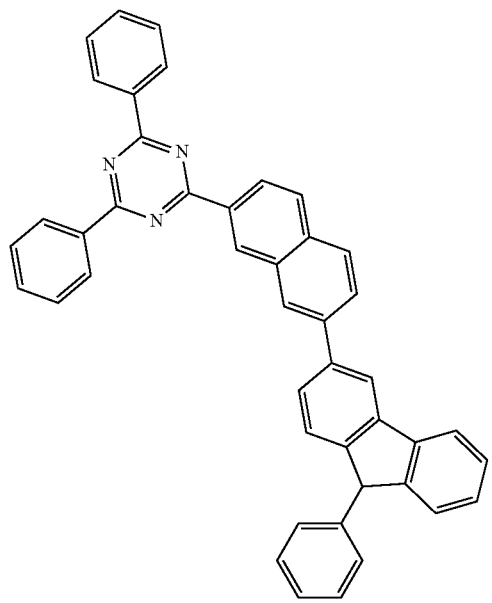
-continued
6-52
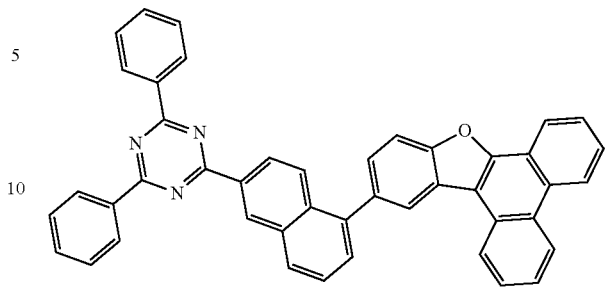
6-53
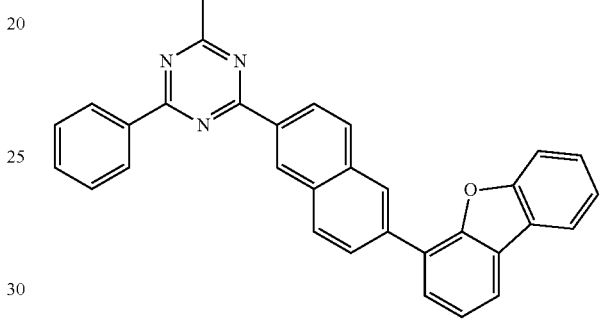
6-54
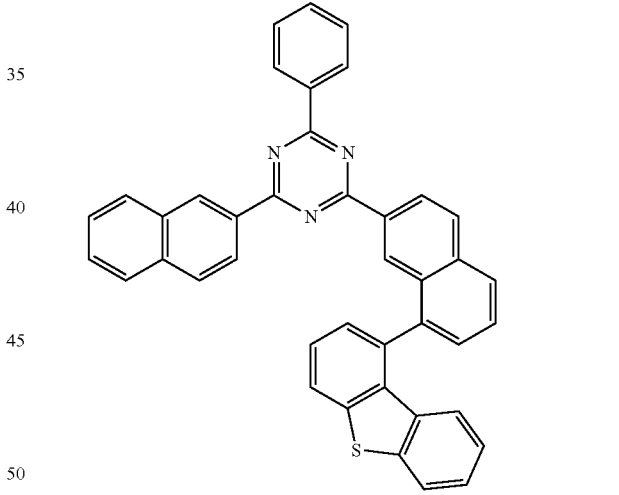
6-55
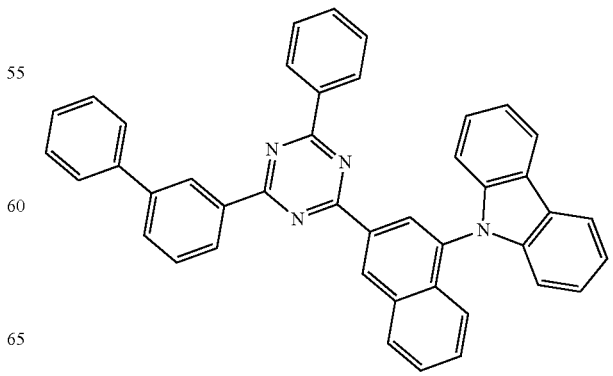

473
-continued
6-56
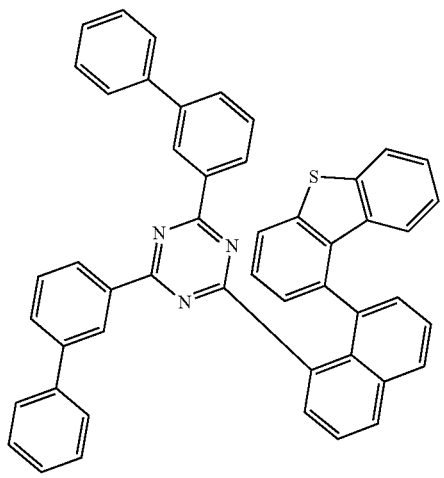
6-57
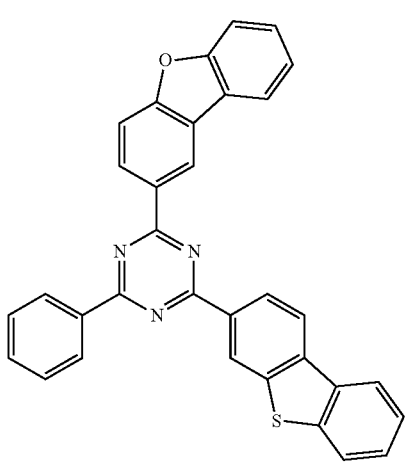
6-58
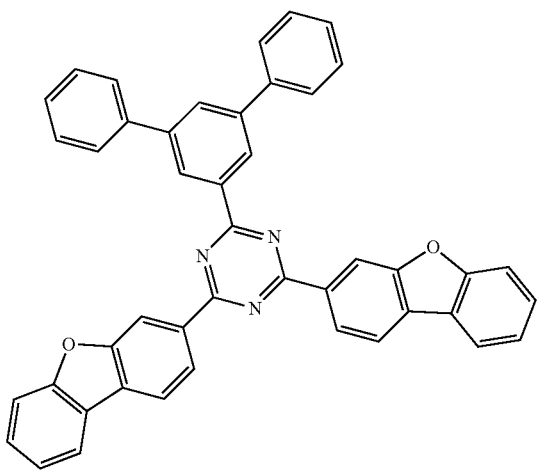
474
-continued
6-59
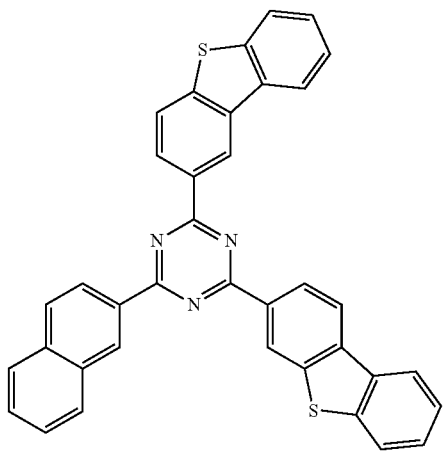
6-60
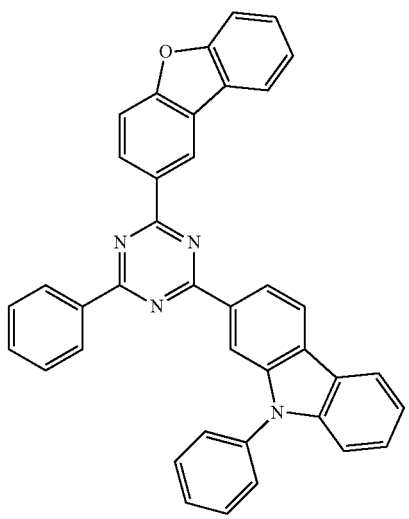
6-61
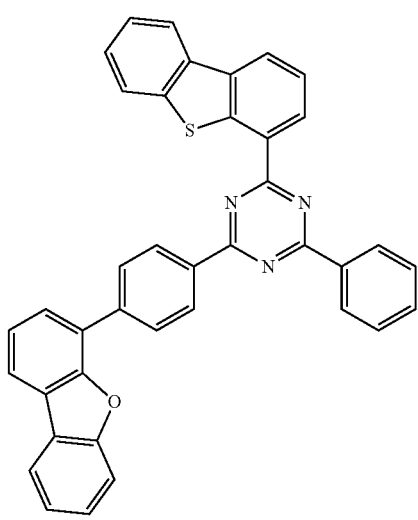

6-62
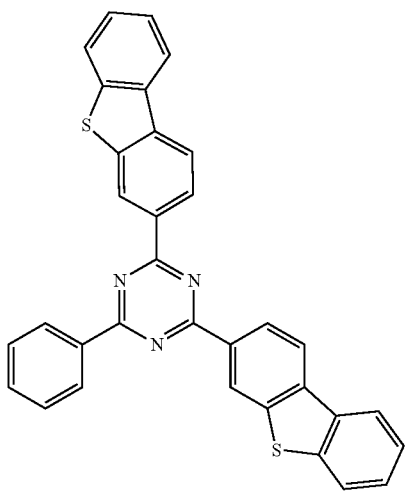
6-63
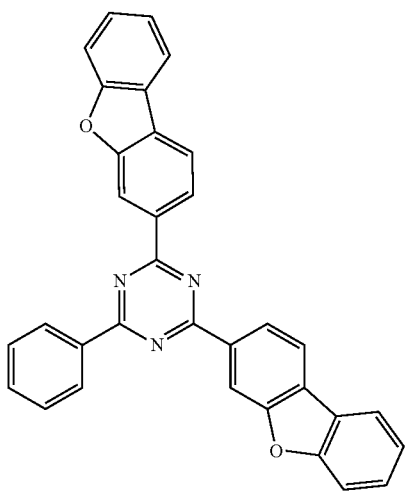
6-64
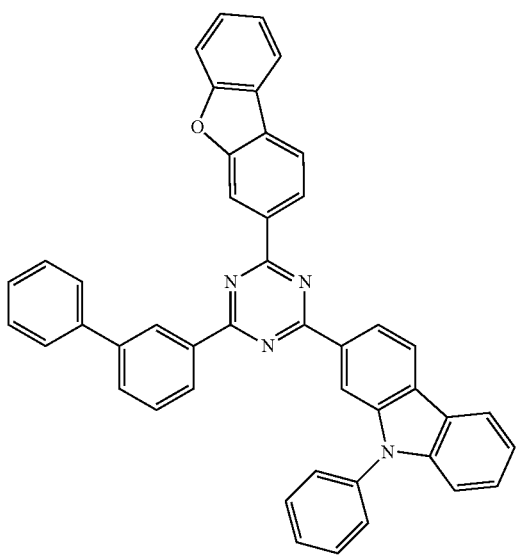
6-65
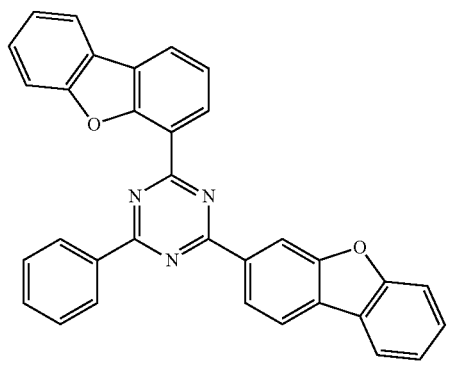
6-66
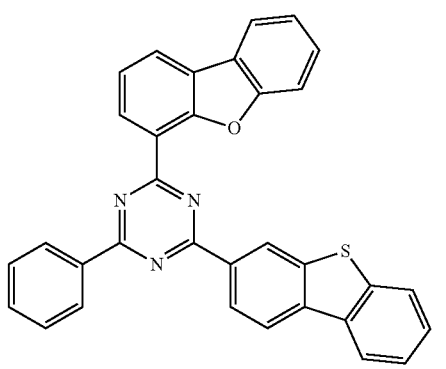
6-67
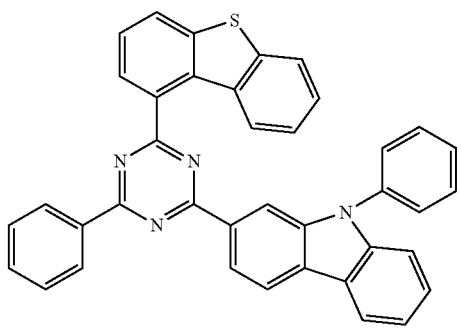
6-68
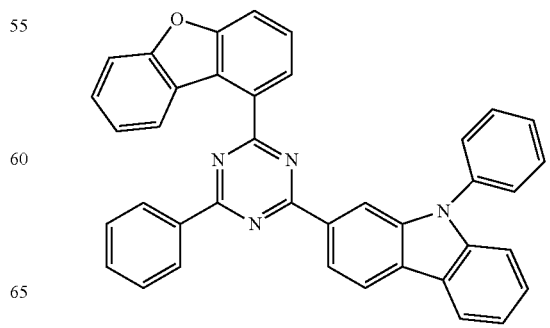

477
-continued
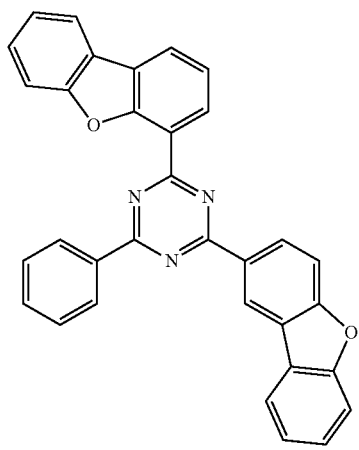
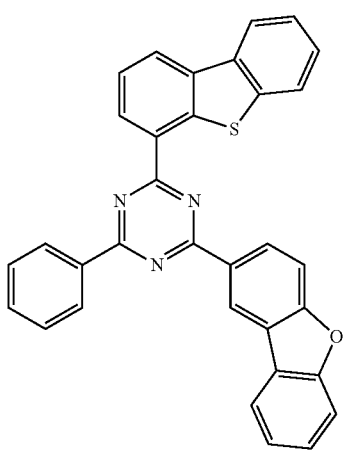
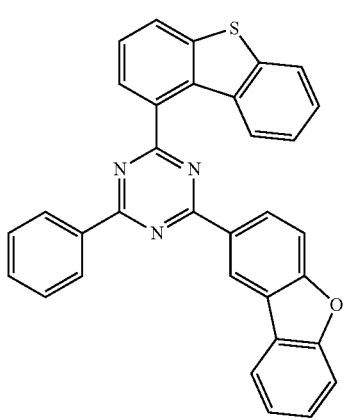
478
-continued
6-69
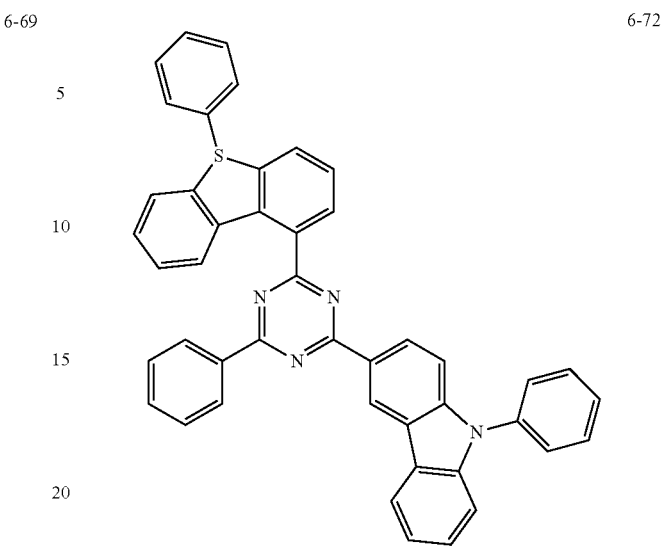
6-72
6-70
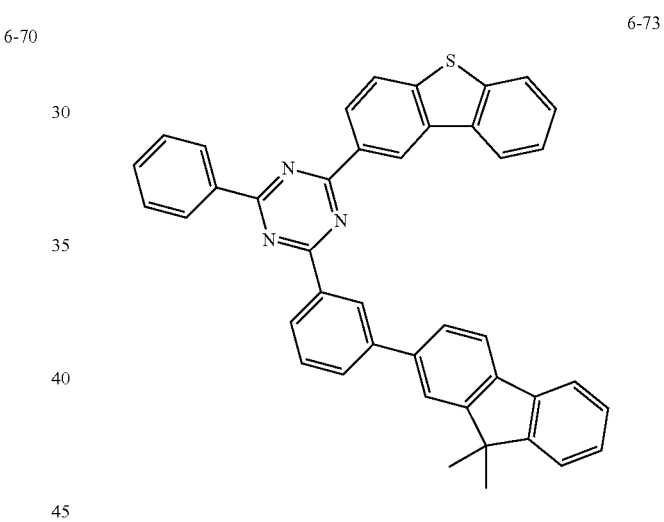
6-73
6-71
6-74
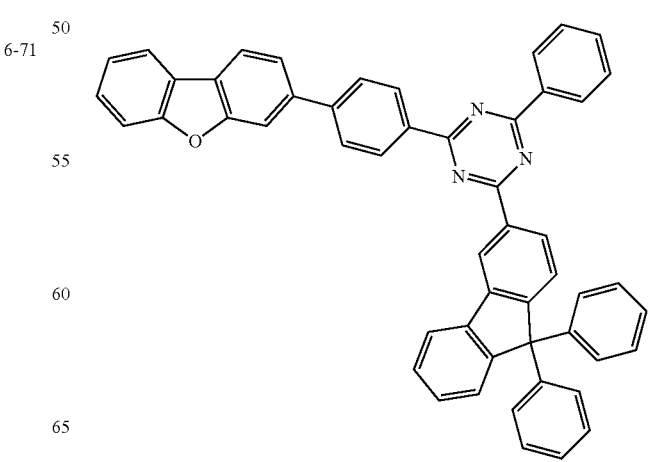

6-75
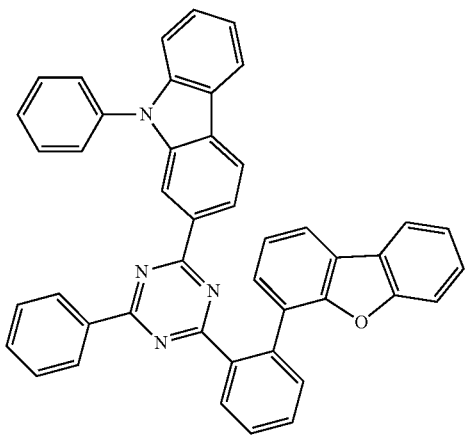
6-76
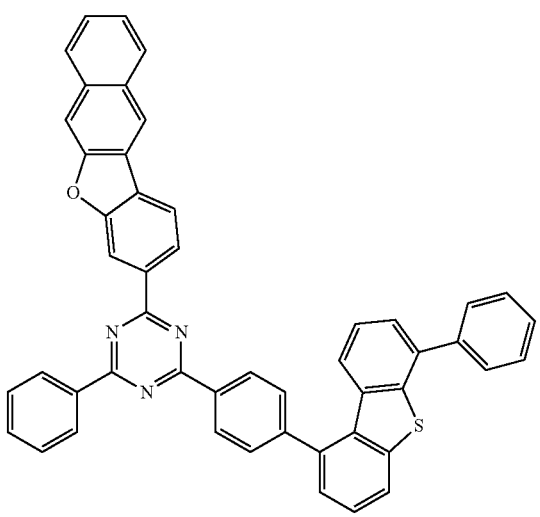
6-77
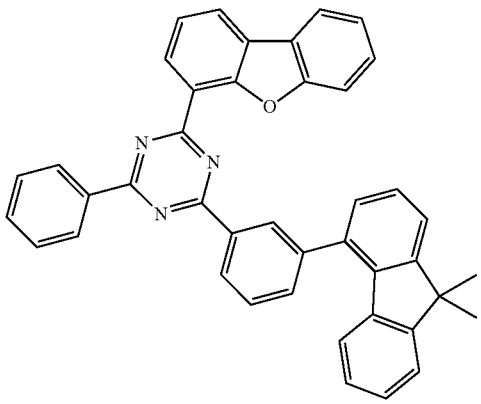
6-78
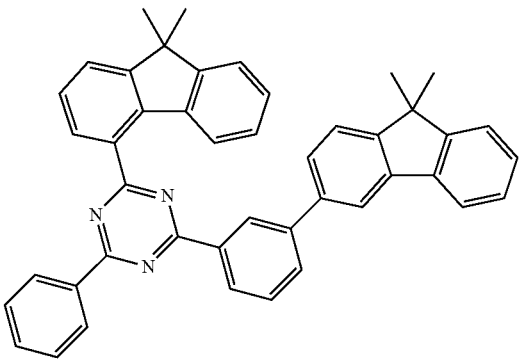
6-79
6-80
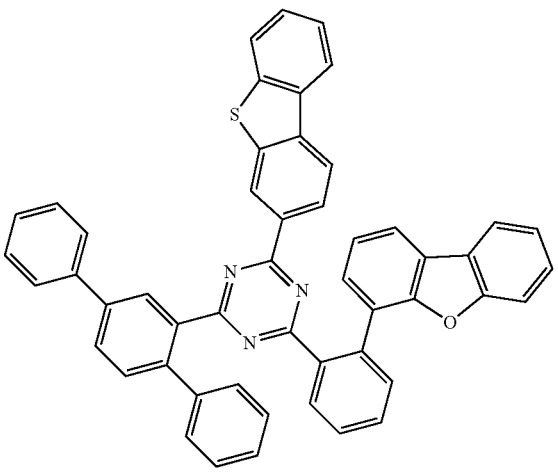

481
-continued
6-81
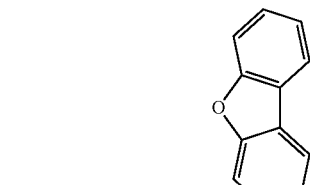
6-82
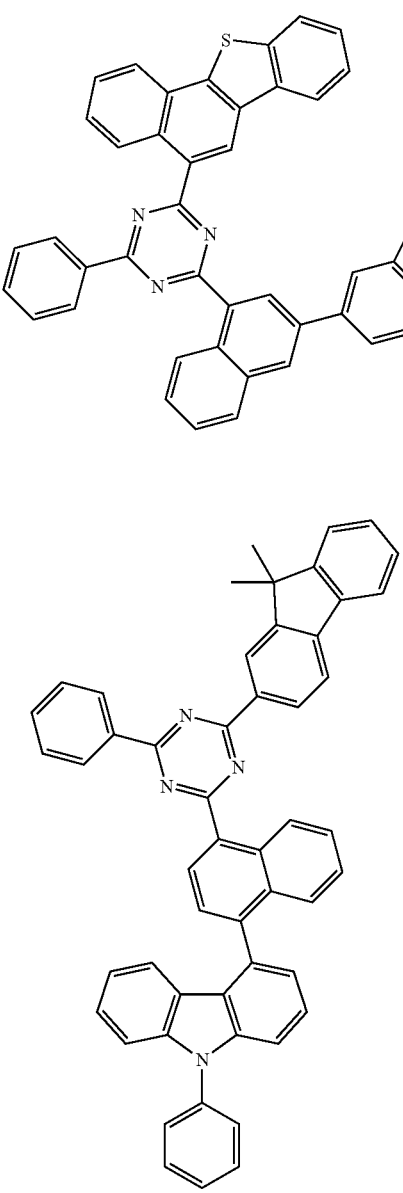
482
-continued
6-84
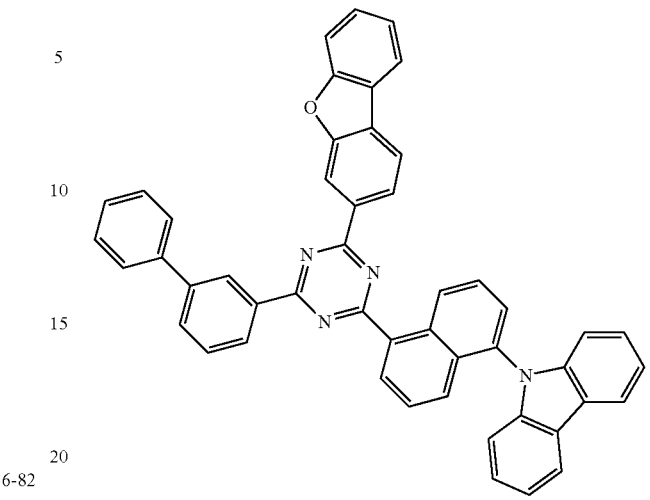
6-85
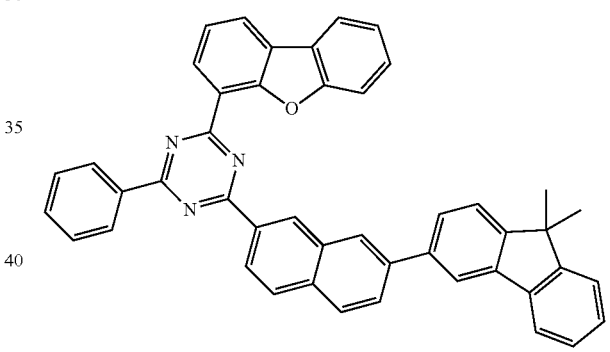
6-86
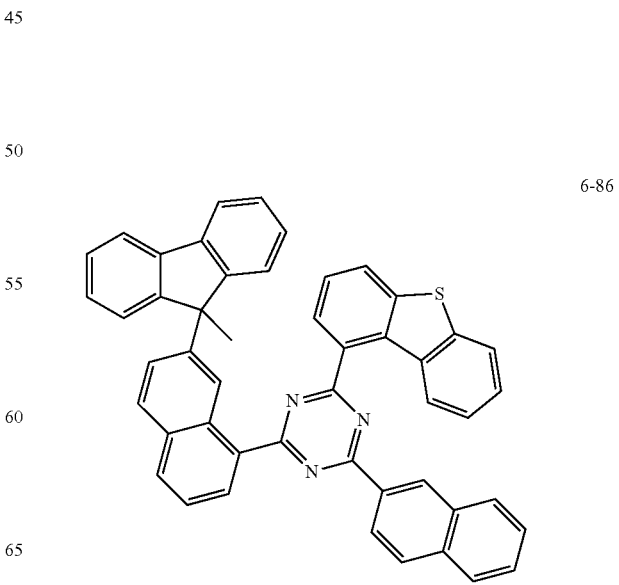

6-87
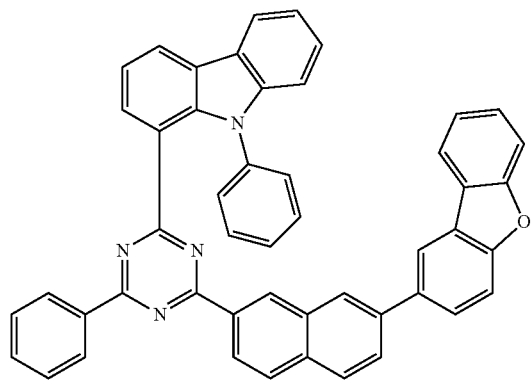
6-88
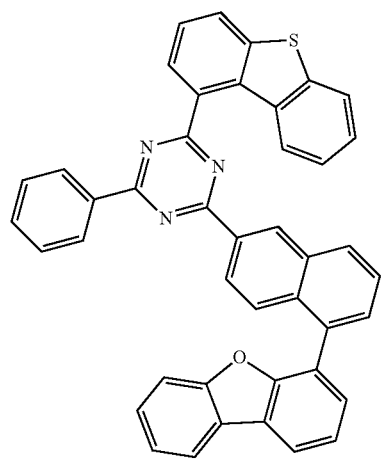
6-89
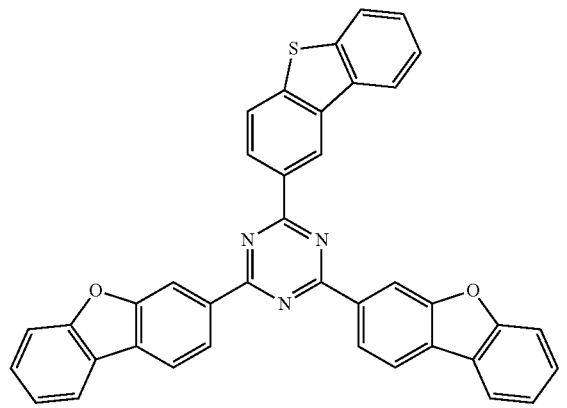
6-90
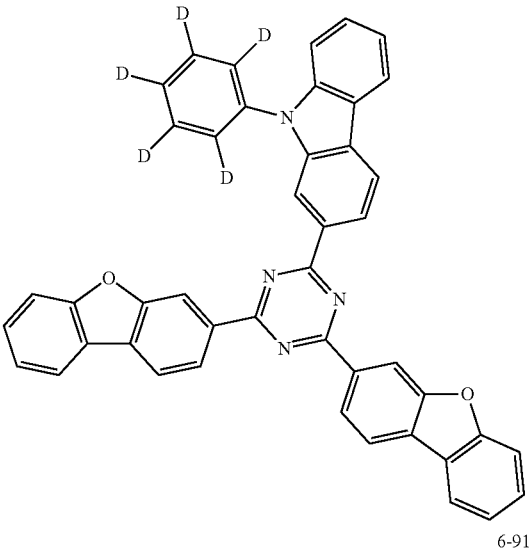
6-91
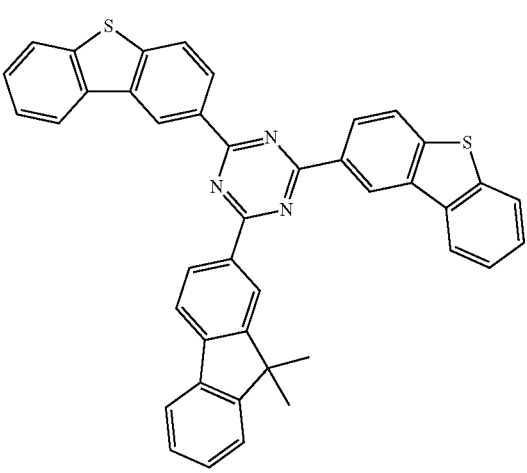
6-92
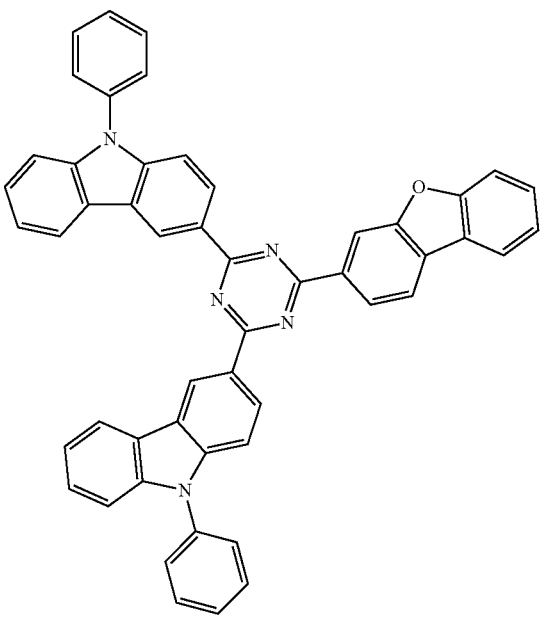

6-93
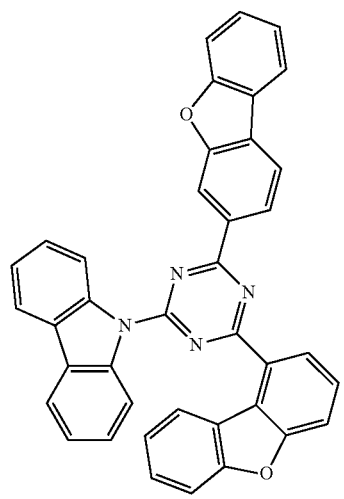
6-96
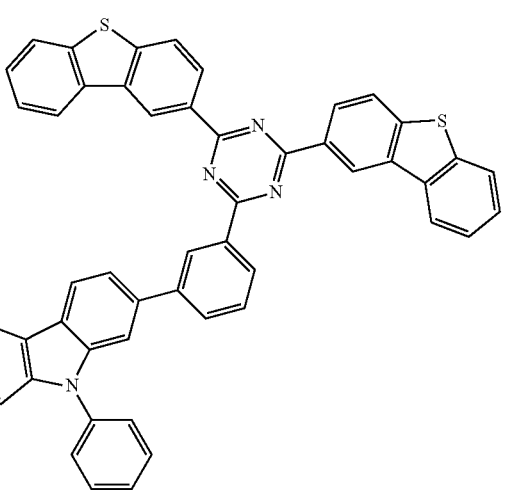
6-94
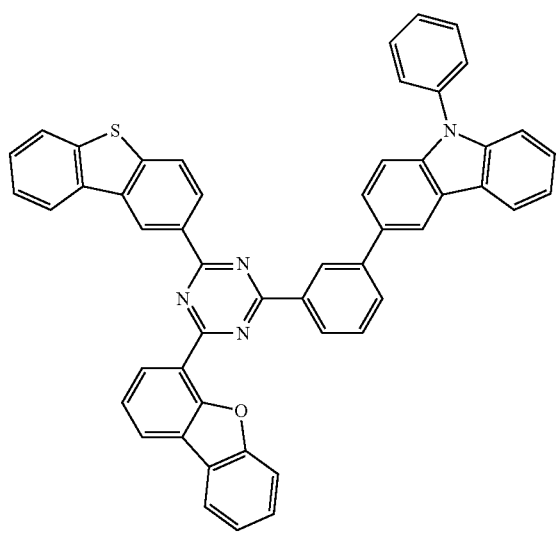
6-97
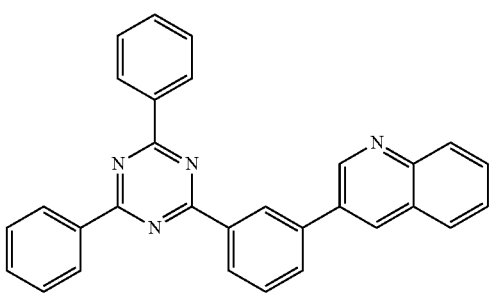
6-98
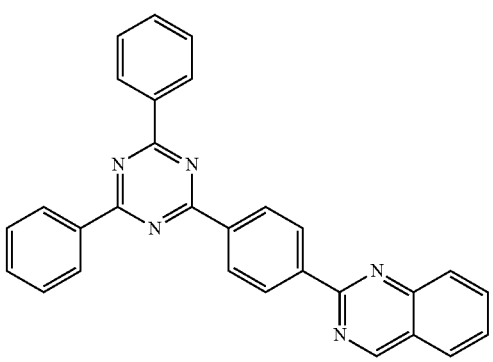
6-95
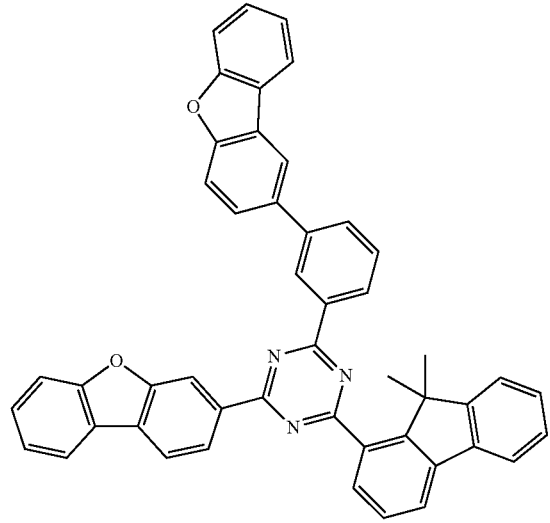
6-99
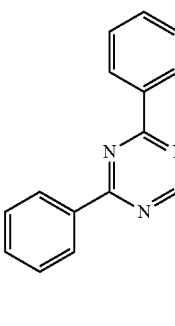

-continued
6-100
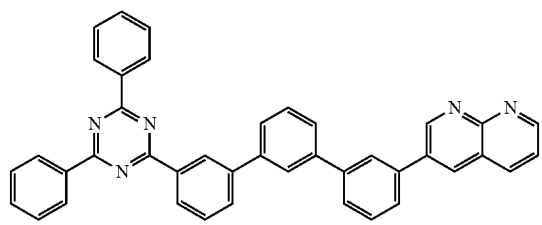
6-101
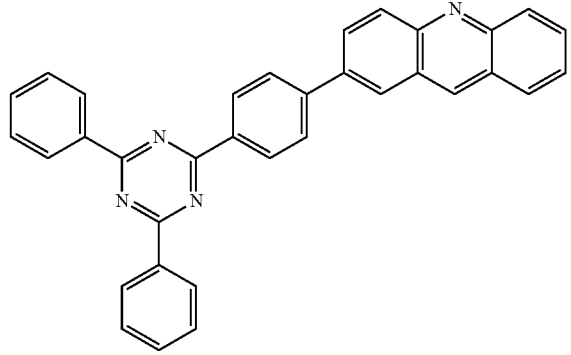
6-102
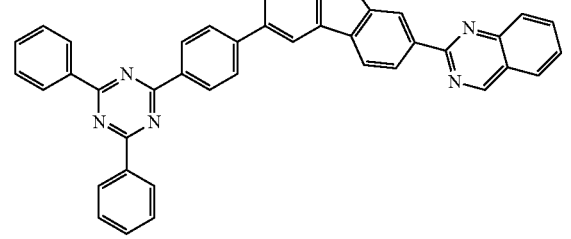
6-103
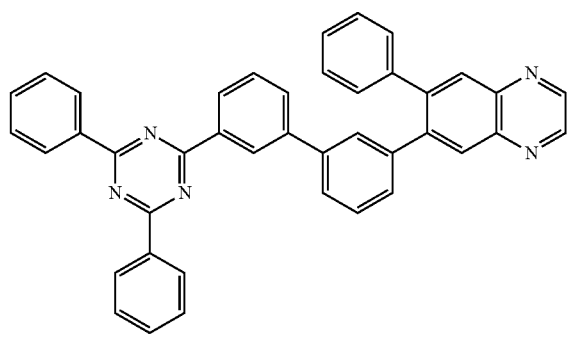
-continued
6-104
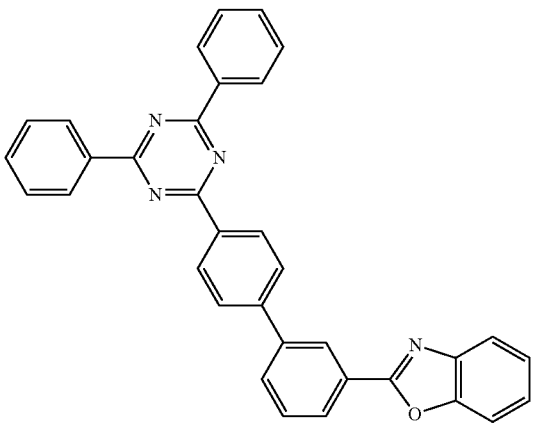
6-105
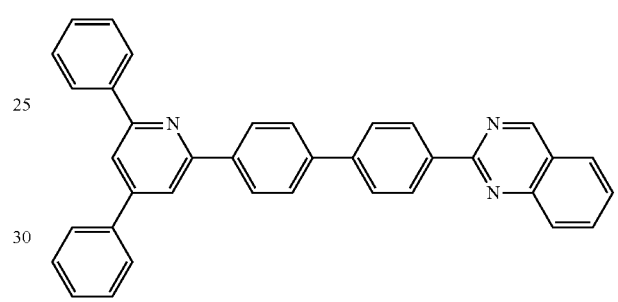
6-106
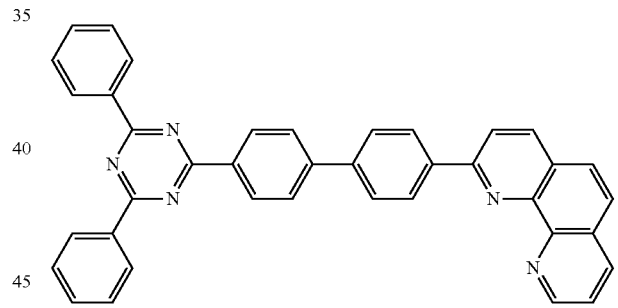
6-107
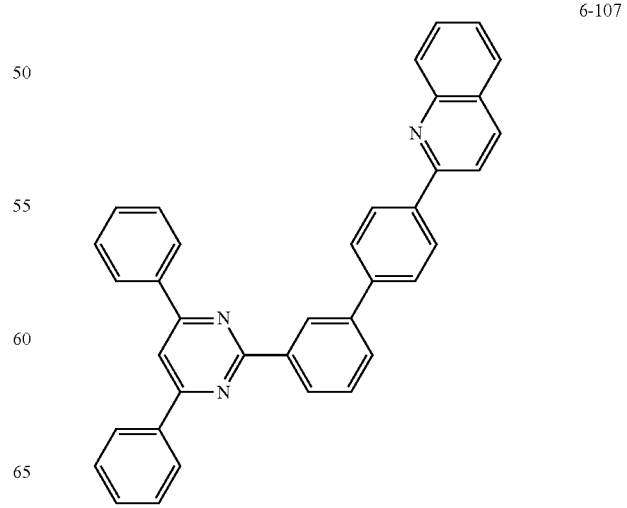

6-108
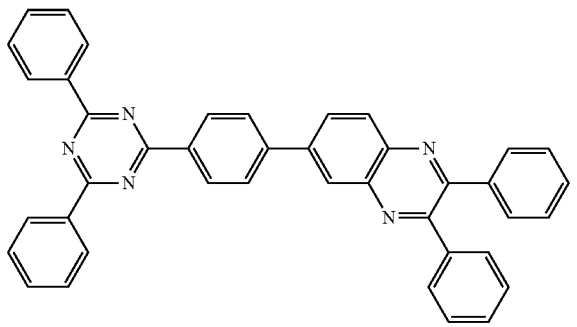
6-109
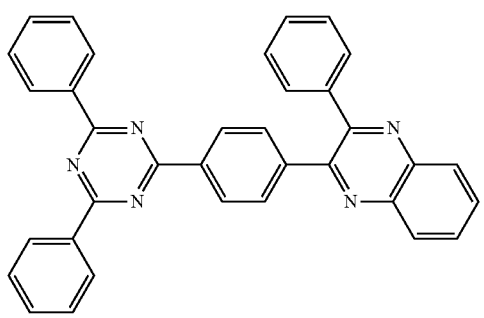
6-110
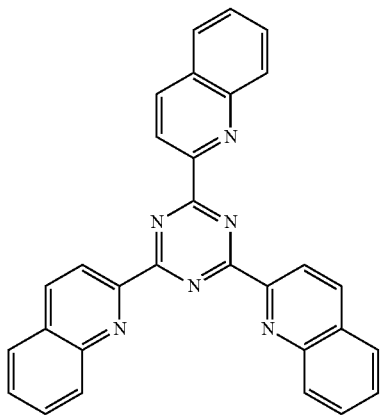
6-111
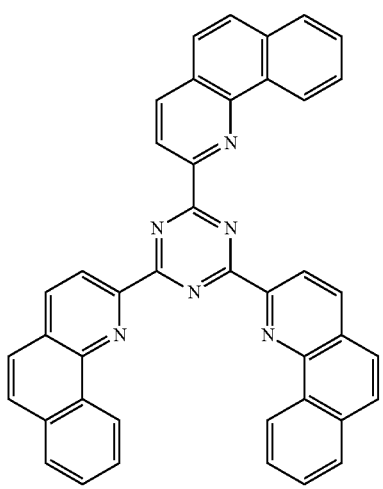
6-112
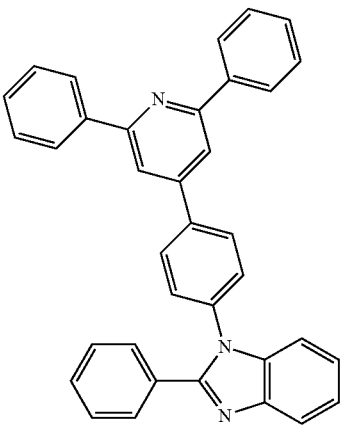
6-113
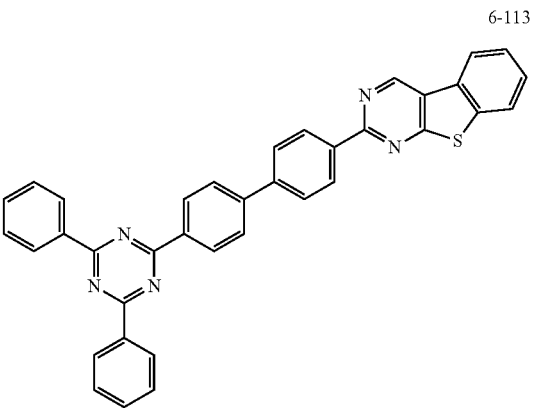
6-114
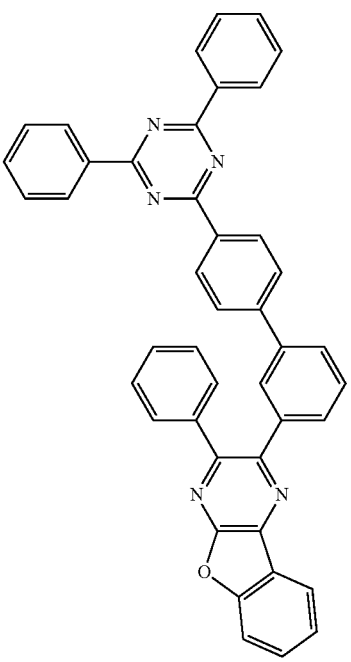

491
-continued
492
-continued
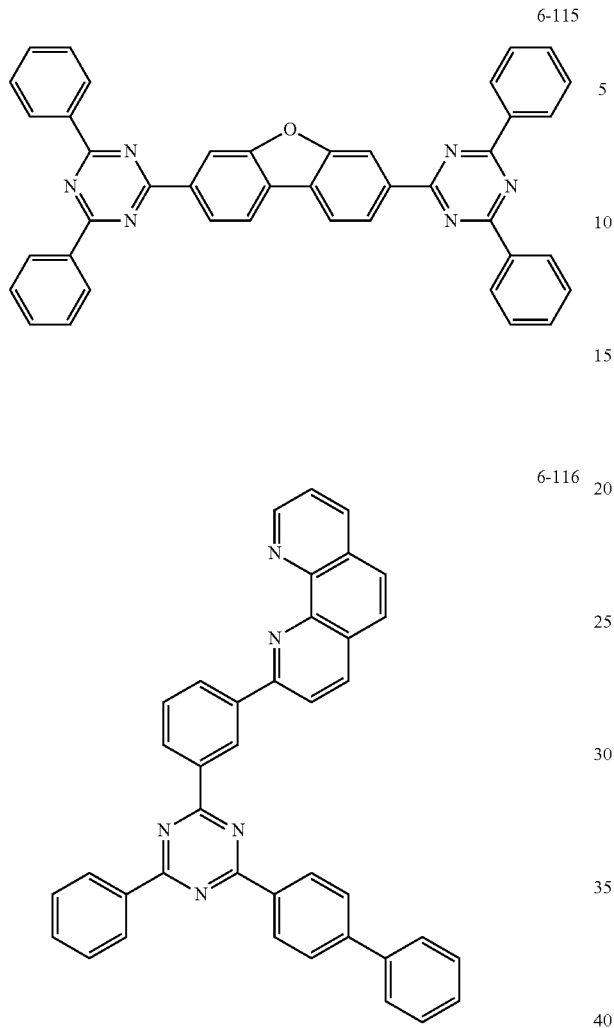
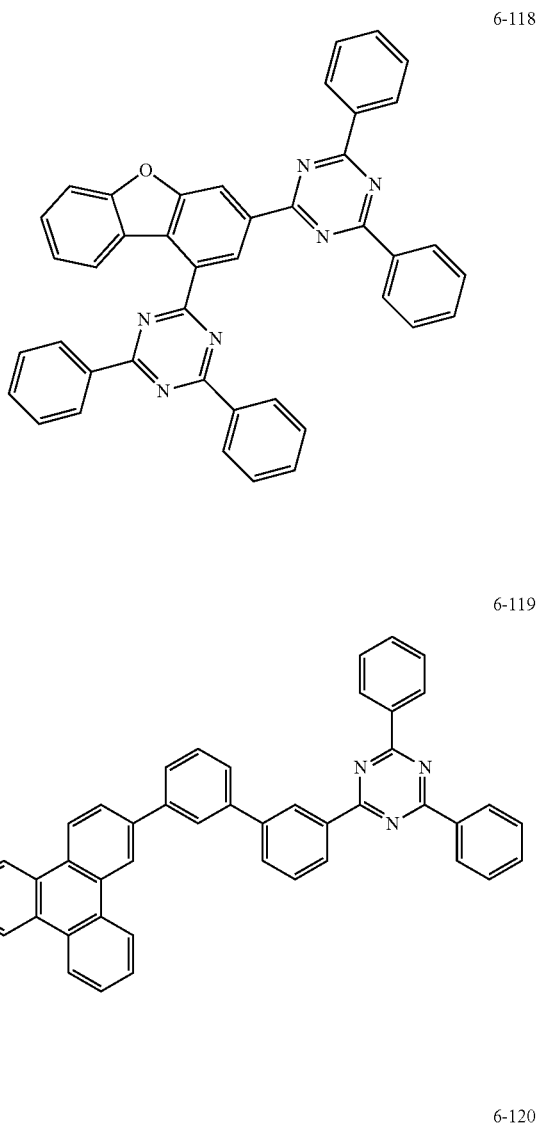
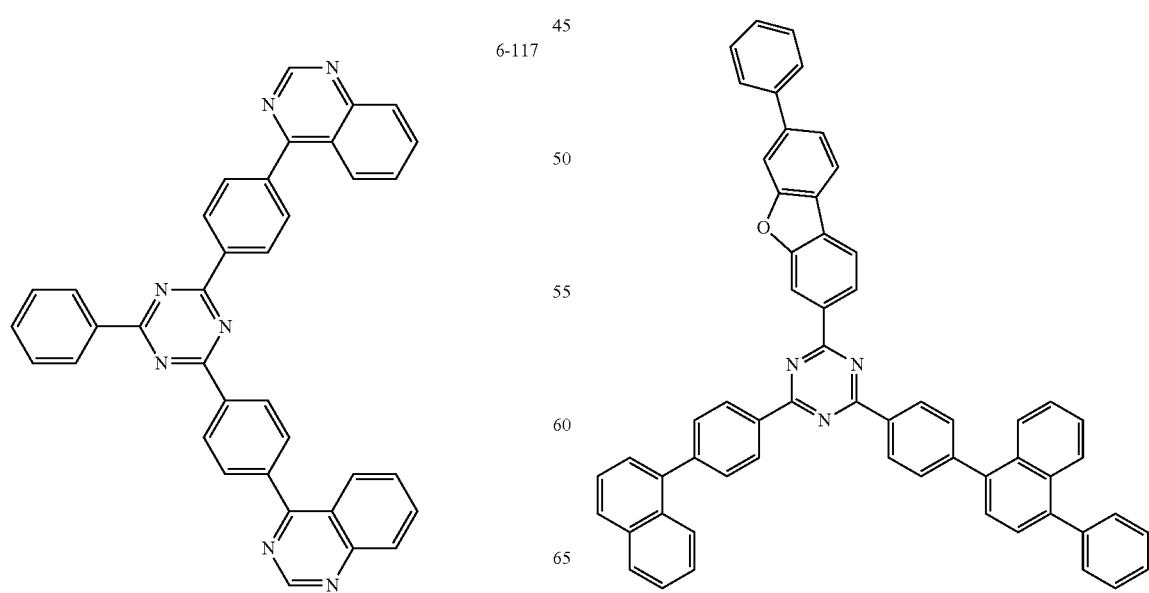

6-121
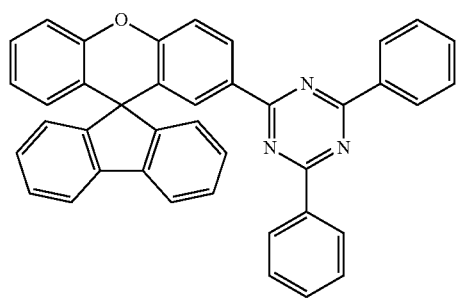
6-122
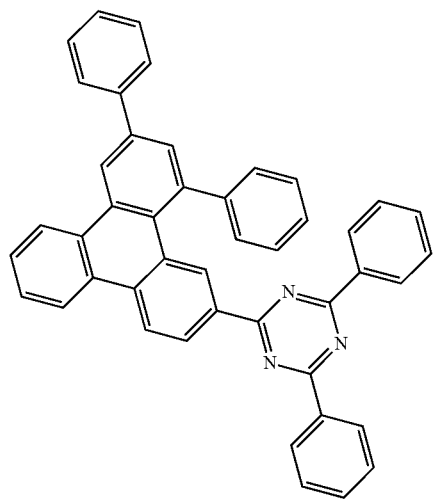
6-123
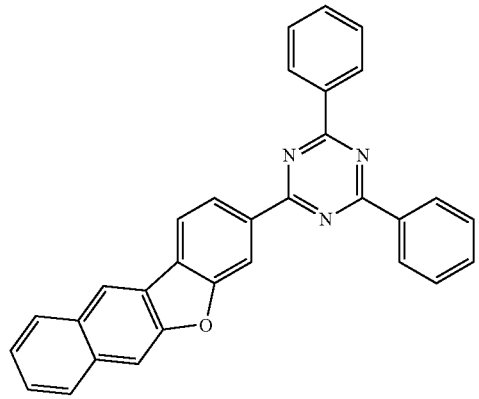
6-124
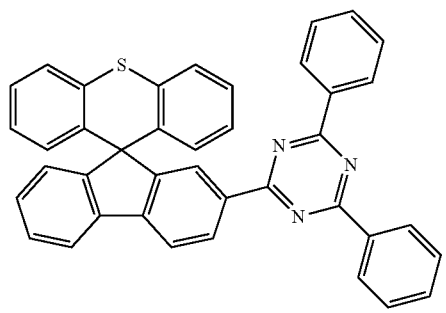
N-1
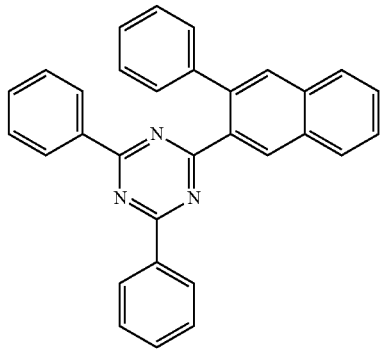
N-2
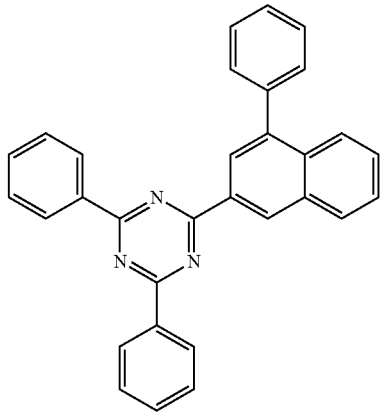
N-3
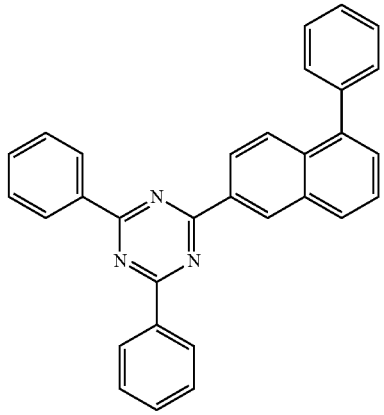
N-4
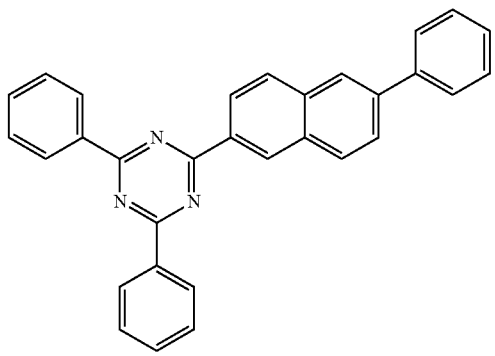

N-5
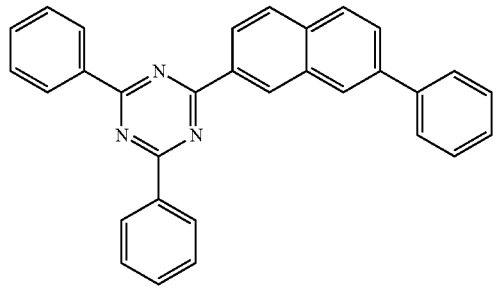
N-6
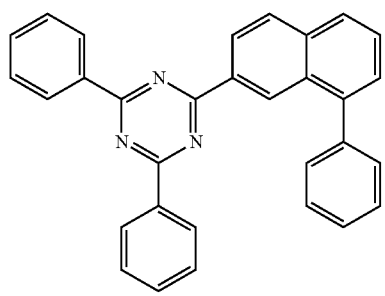
N-7
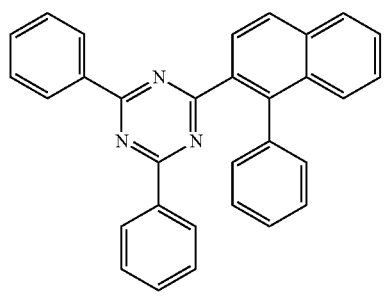
N-8
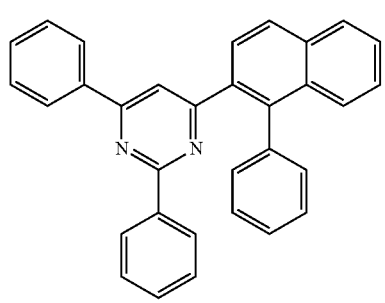
N-9
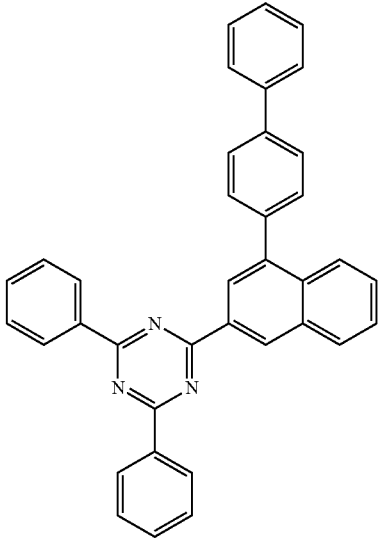
N-10
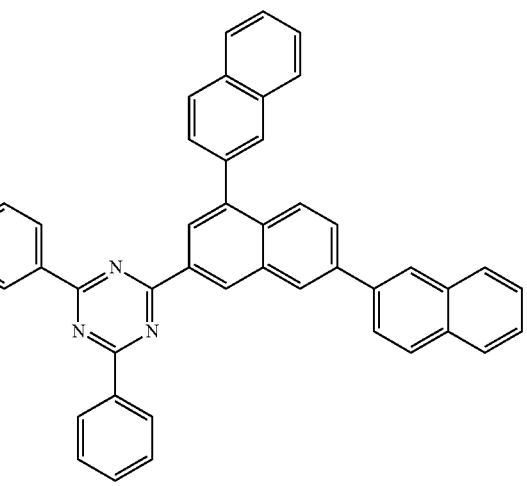
N-11
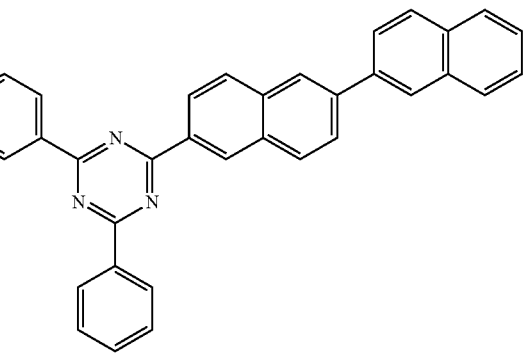

N-12
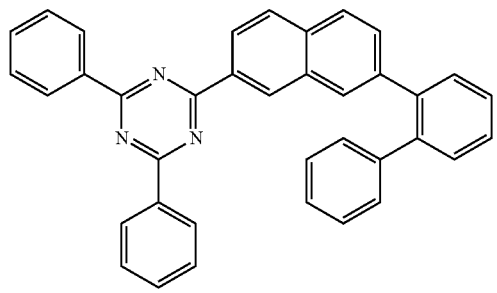
N-13
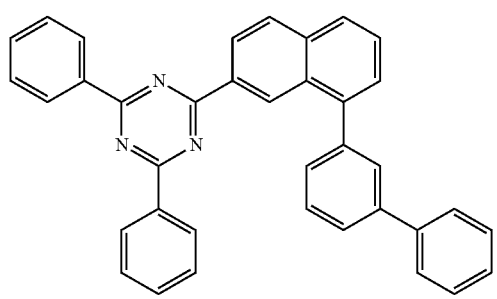
N-14
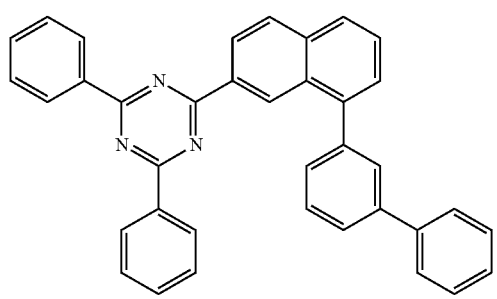
N-15
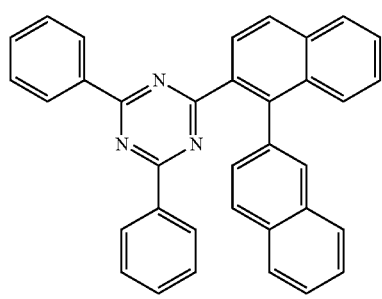
N-16
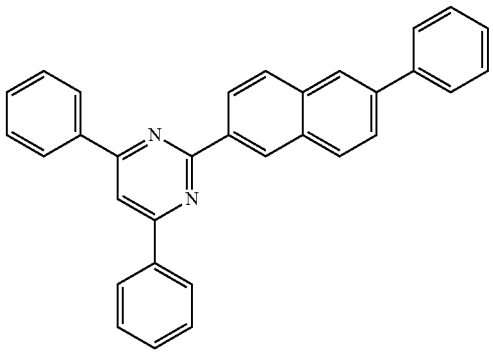
N-17
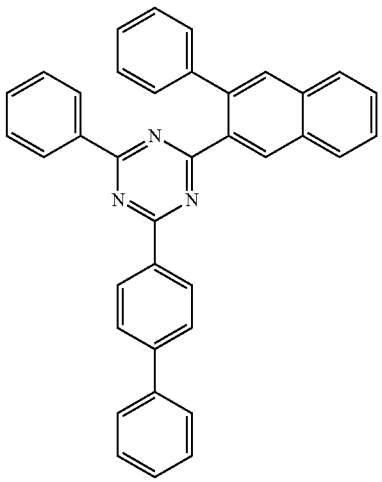
N-18
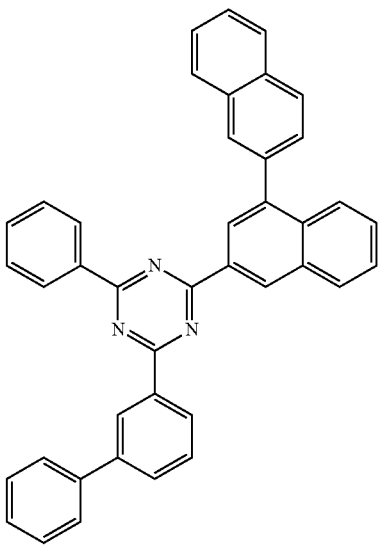

N-19
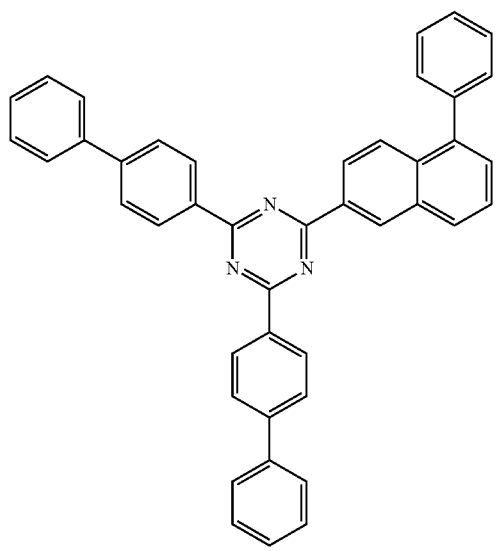
N-20
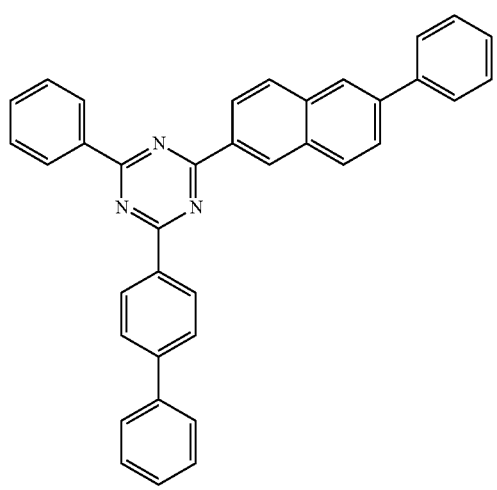
N-21
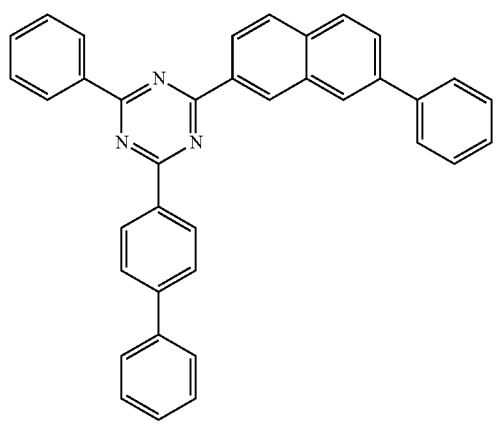
N-22
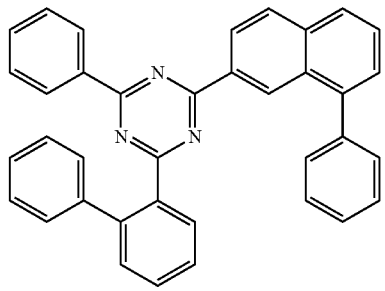
N-23
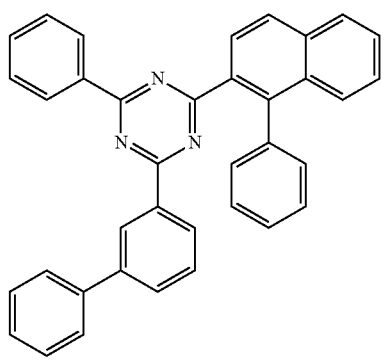
N-24
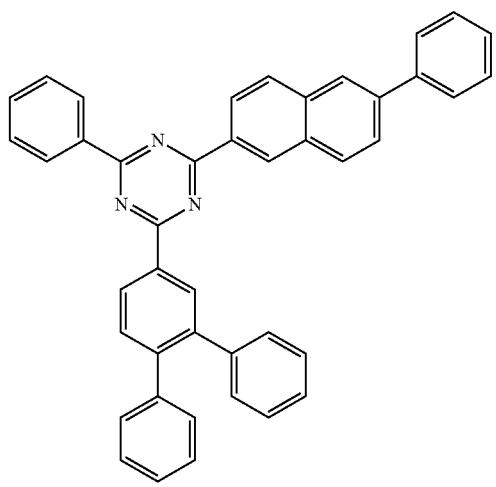
N-25
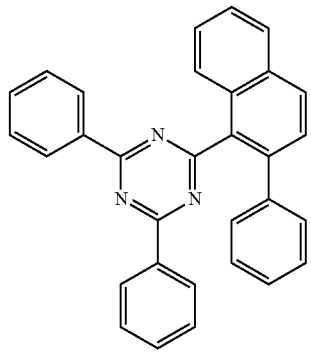

N-26
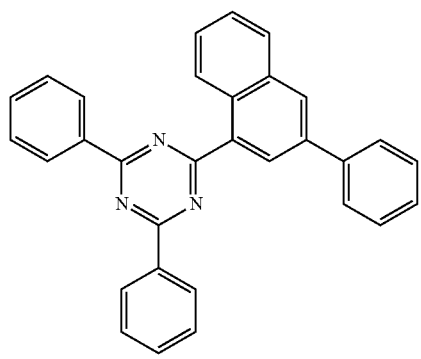
N-27
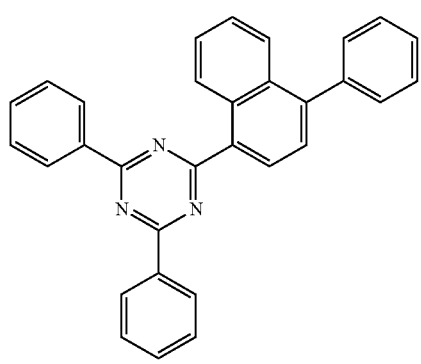
N-28
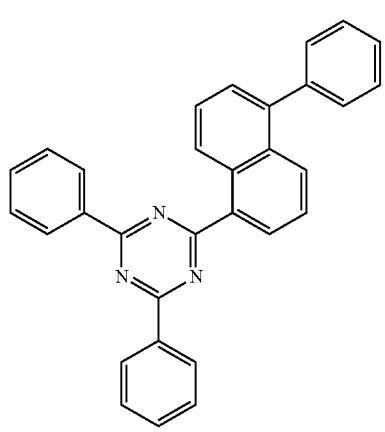
N-29
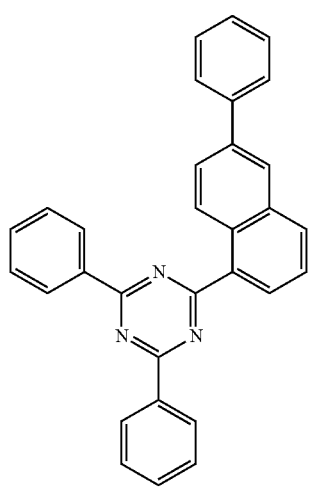
N-30
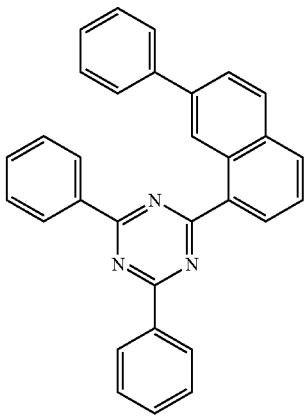
N-31
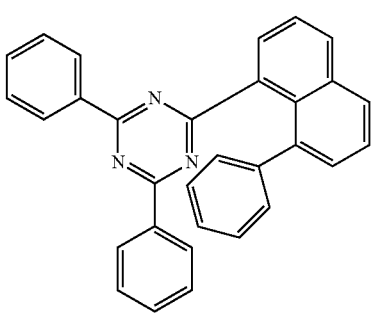
N-32
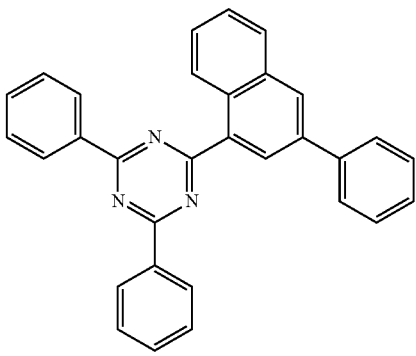
N-33
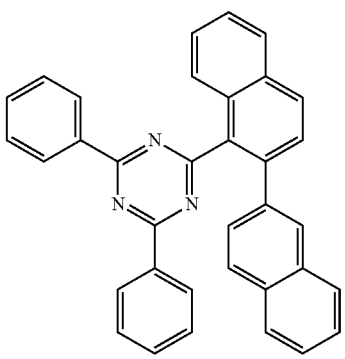

N-34
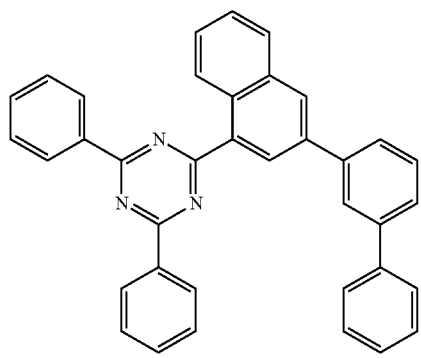
N-37
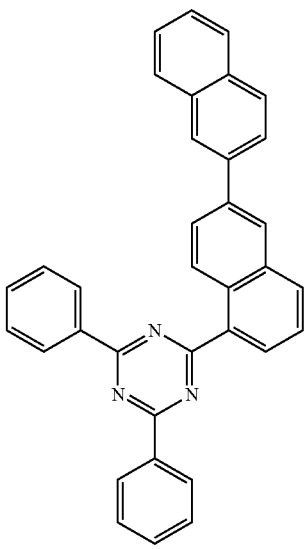
N-35
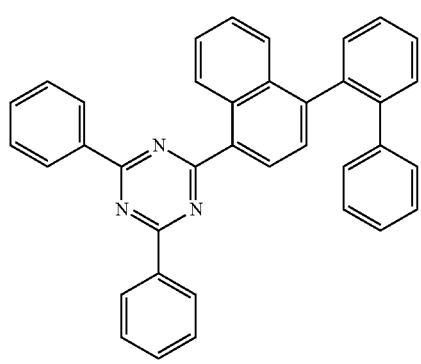
N-38
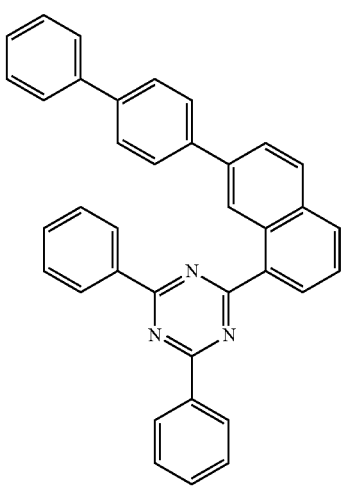
N-36
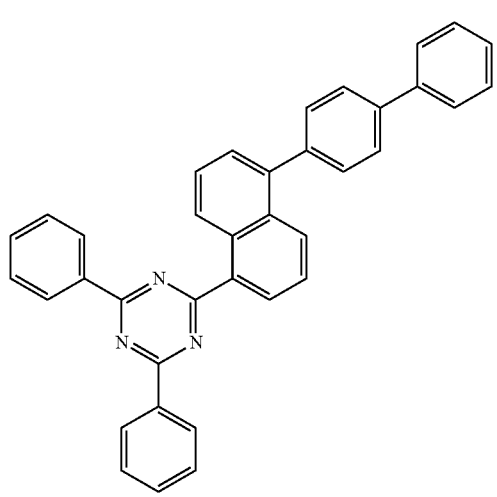
N-39
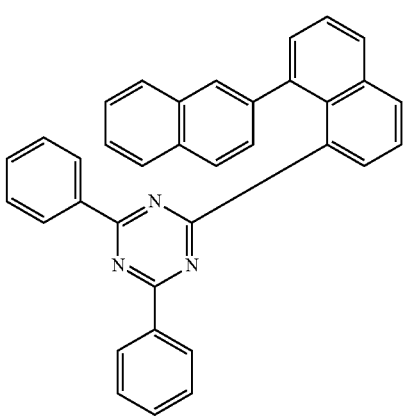

N-40
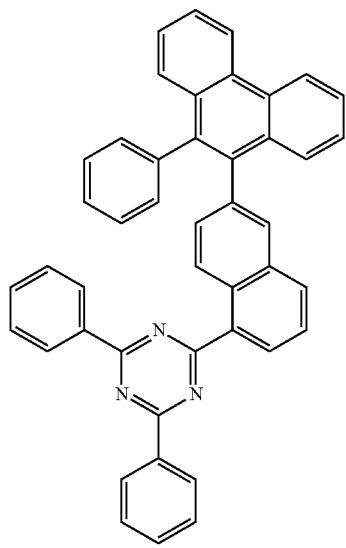
N-41
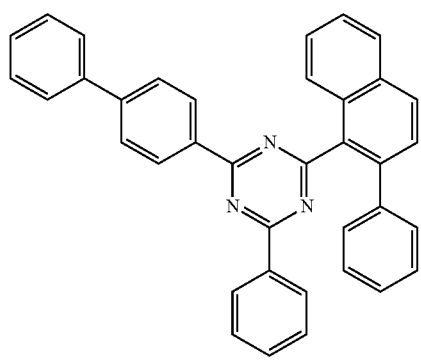
N-42
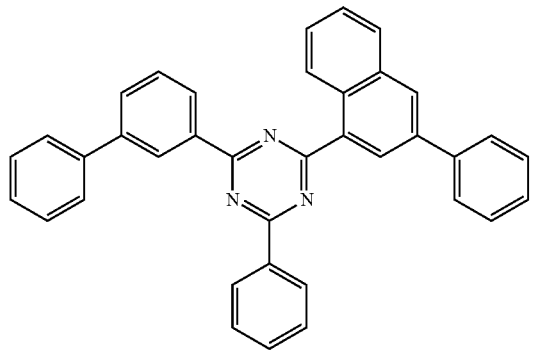
N-43
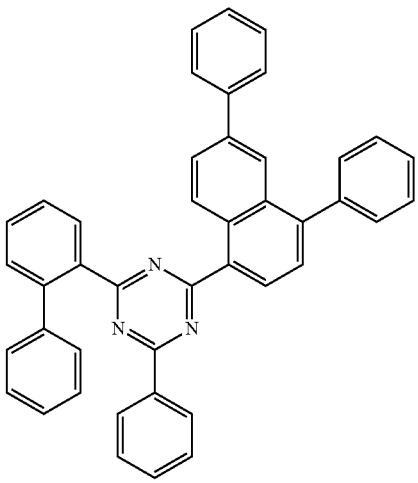
N-44
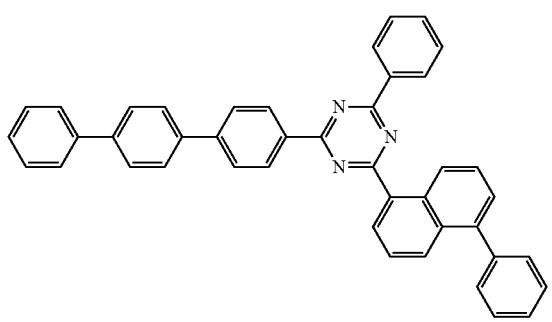
N-45
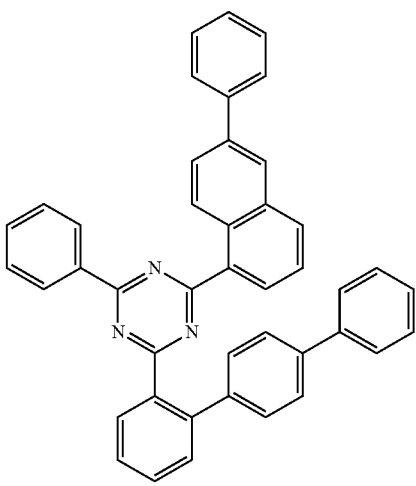

N-46
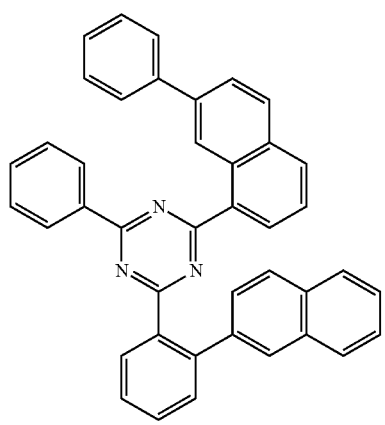
N-47
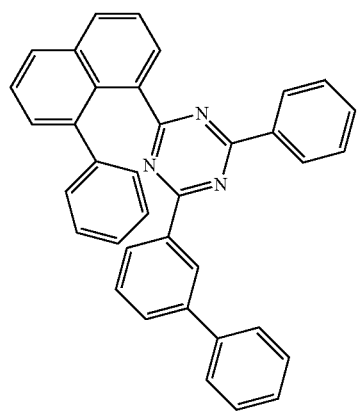
N-48
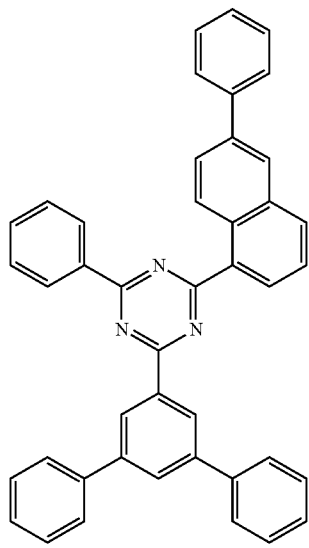
N-49
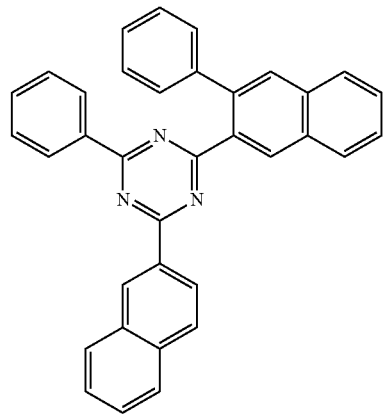
N-50
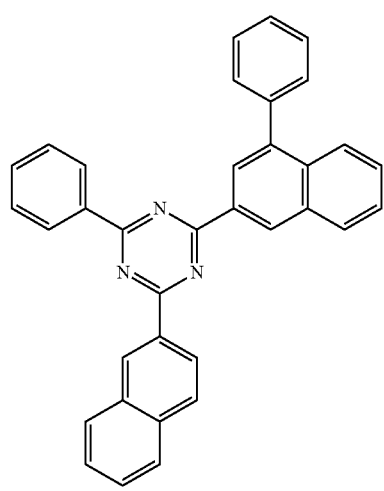
N-51
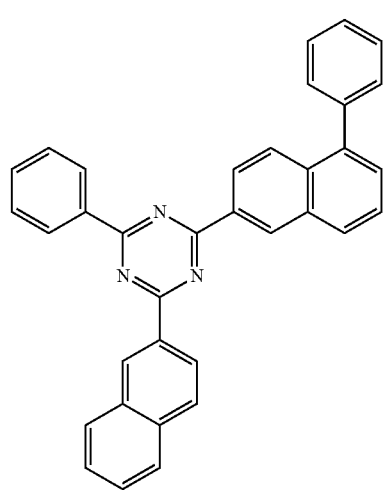

N-52
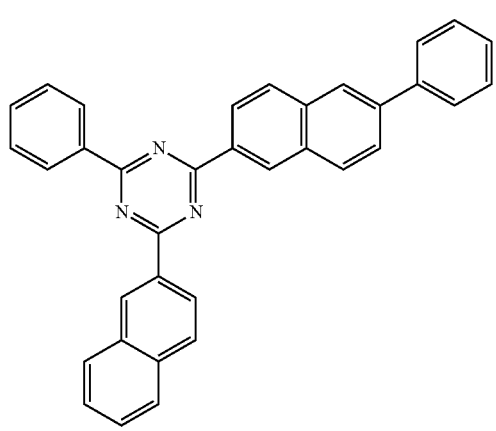
N-53
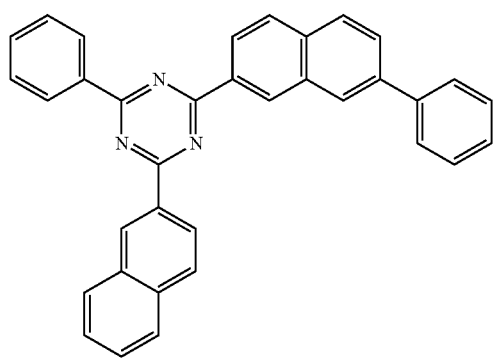
N-54
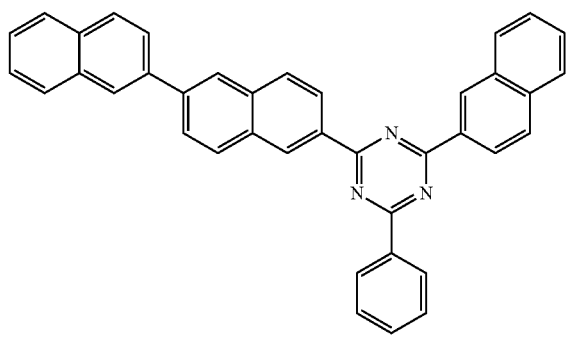
N-55
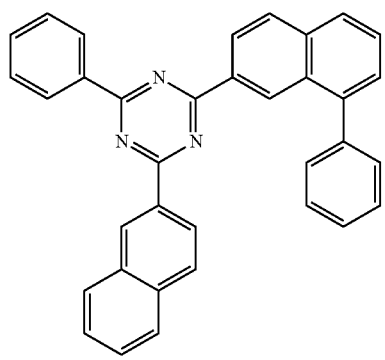
N-56
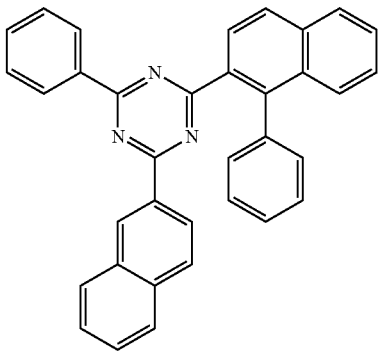
N-57
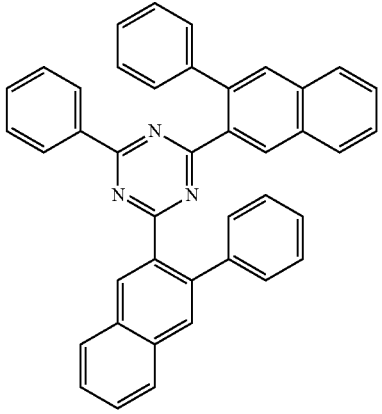
N-58
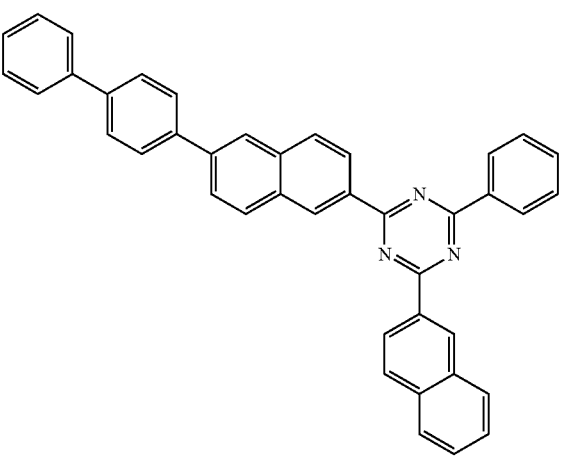

N-59
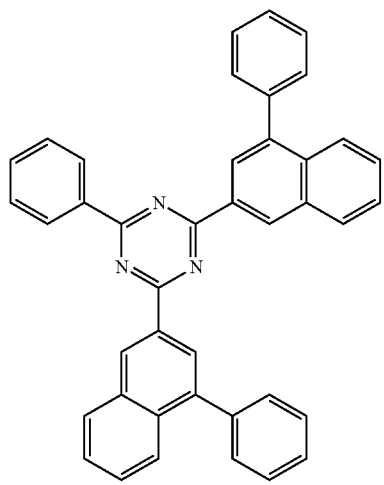
N-62
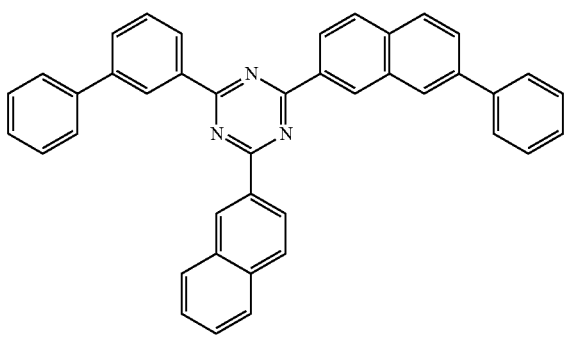
N-60
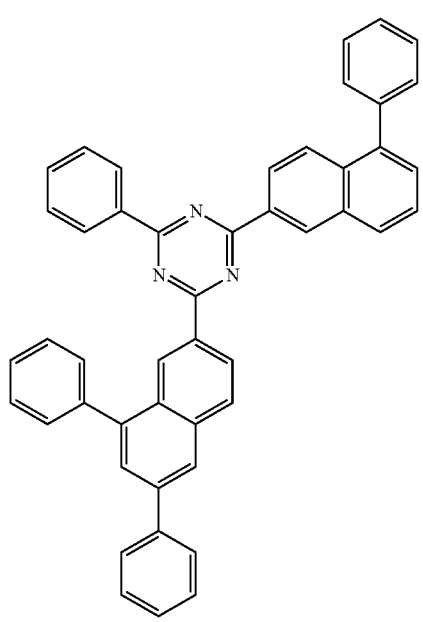
N-63
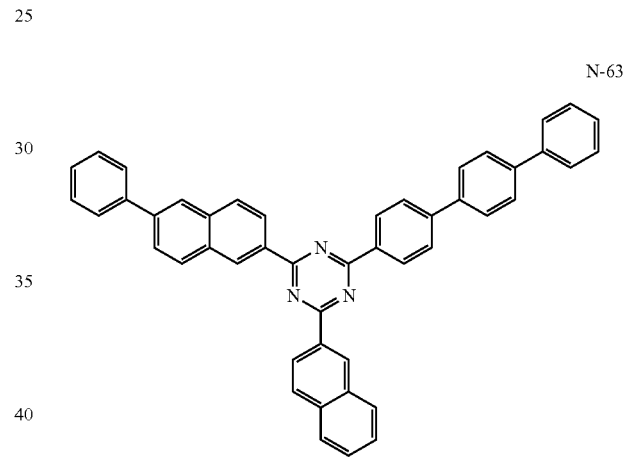
N-61
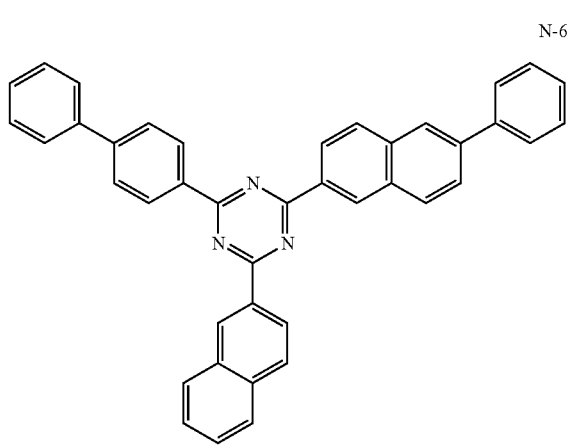
N-64
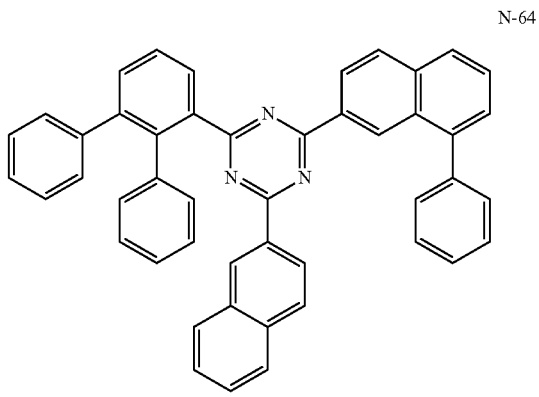

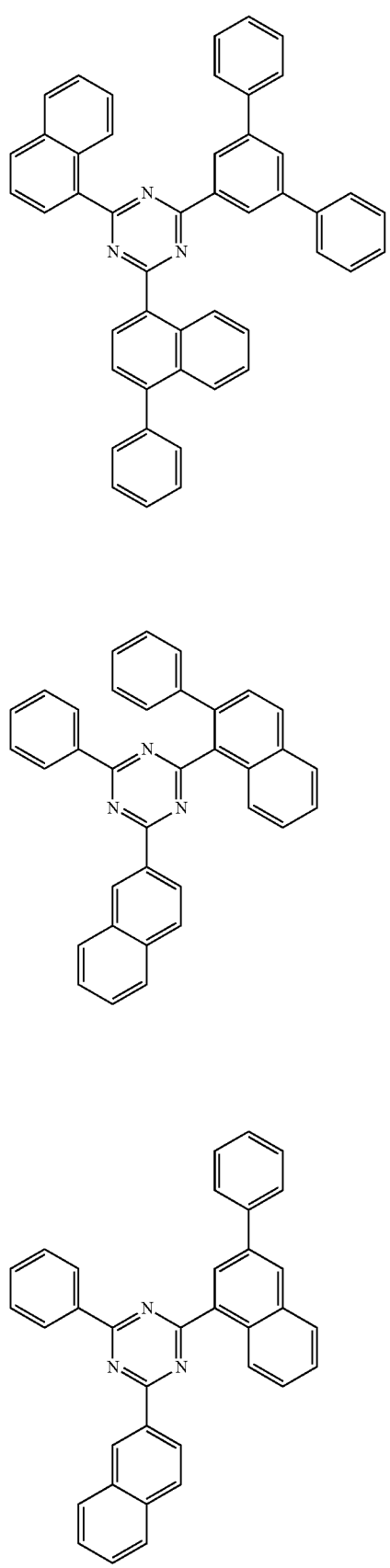
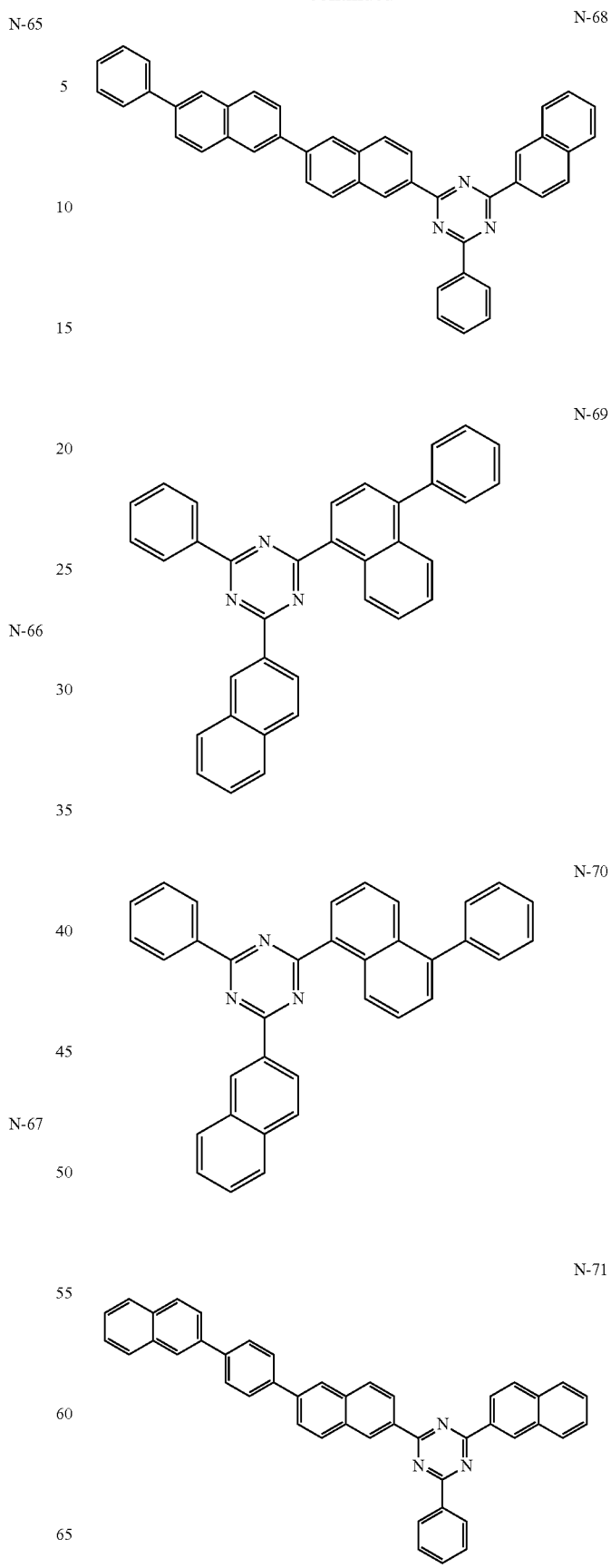

N-72
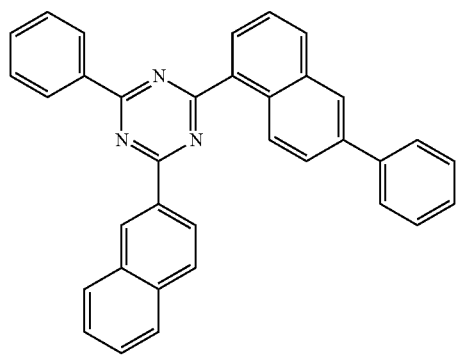
N-76
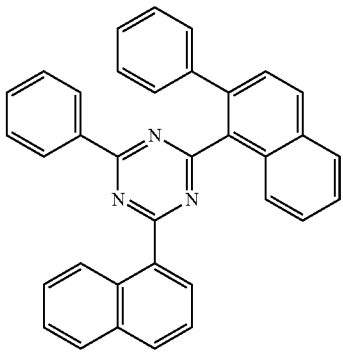
N-73
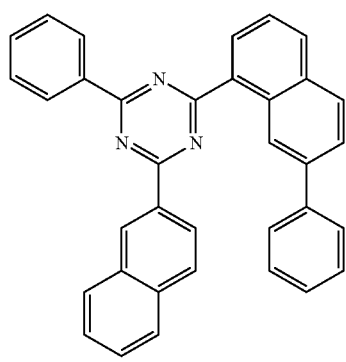
N-77
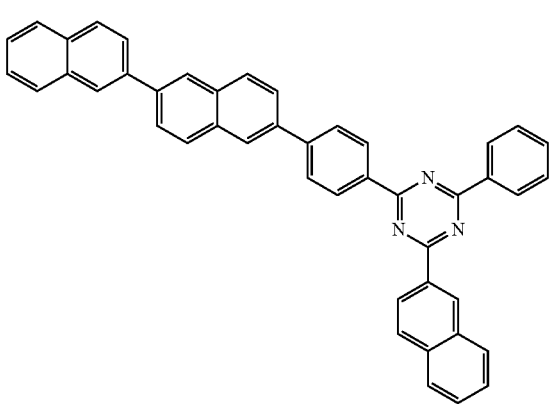
N-74
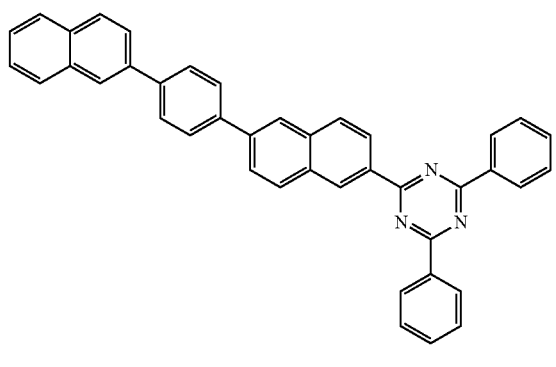
N-78
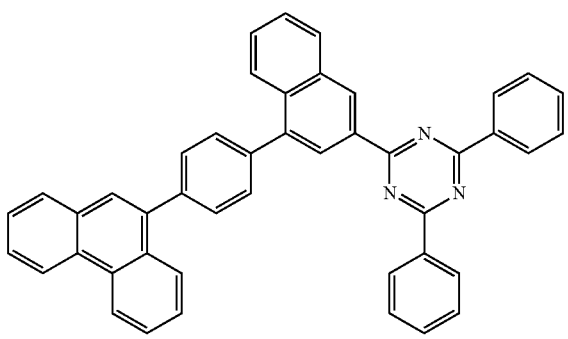
N-75
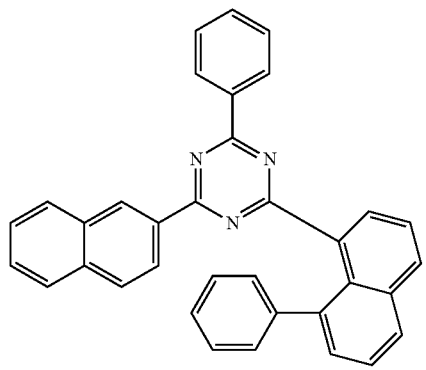
N-79
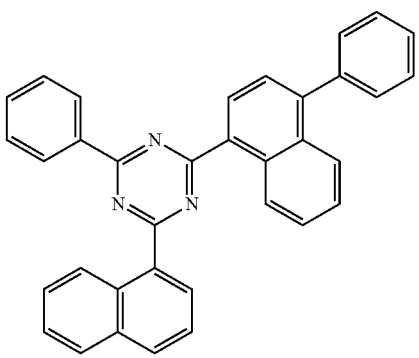

N-80
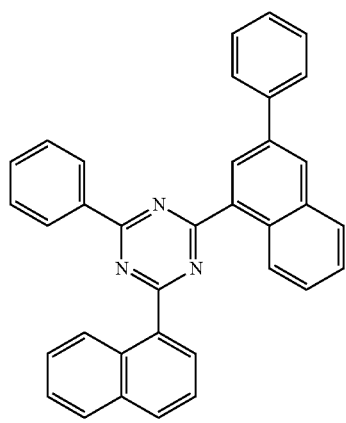
N-81
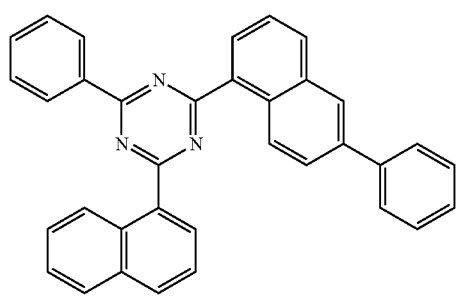
N-82
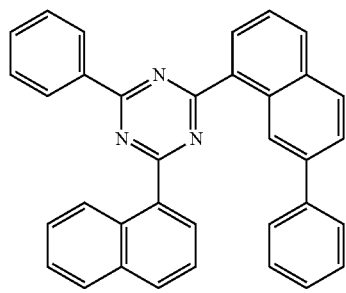
N-83
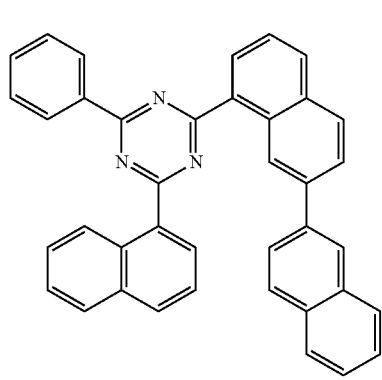
N-84
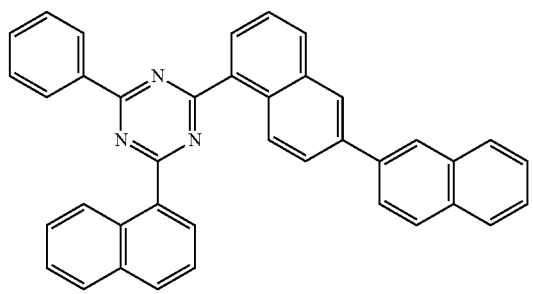
N-85
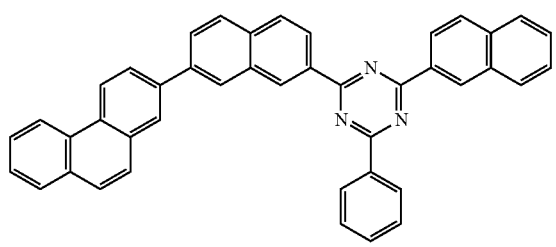
N-86
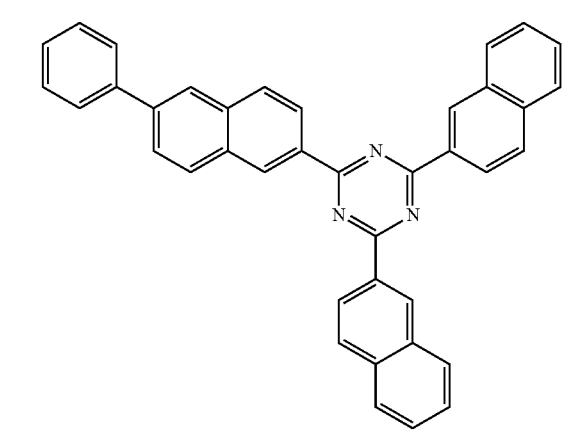
N-87
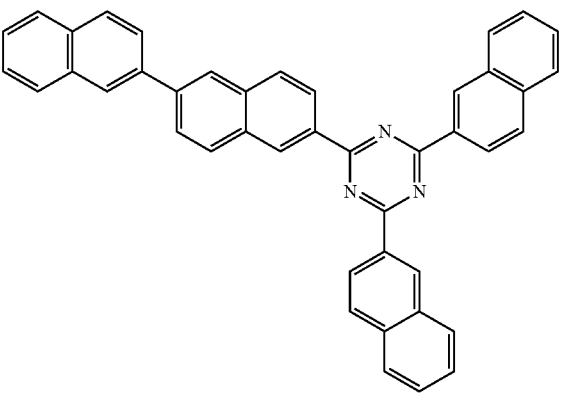

N-88
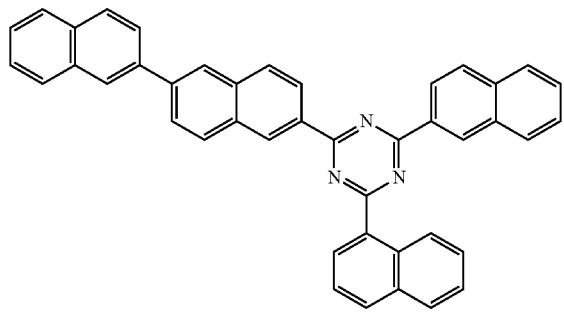
N-89
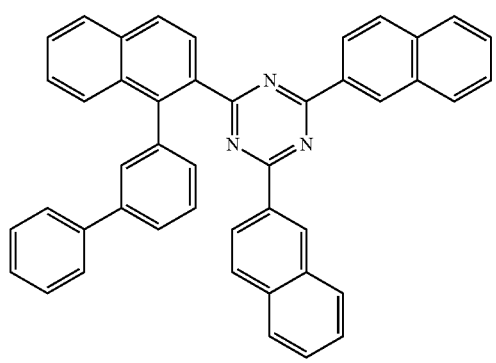
N-90
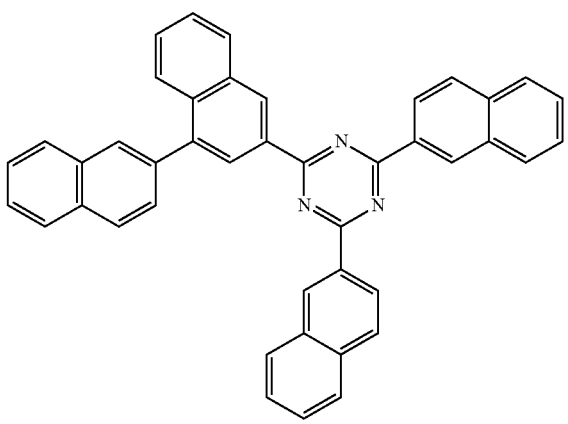
N-91
N-92
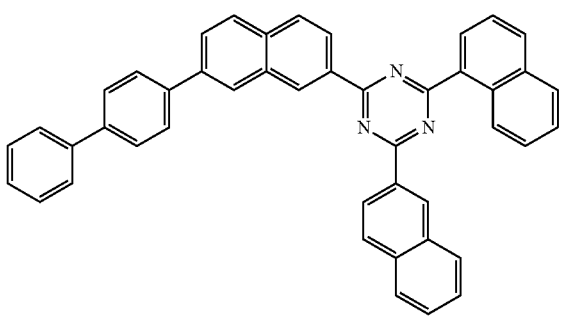
N-93
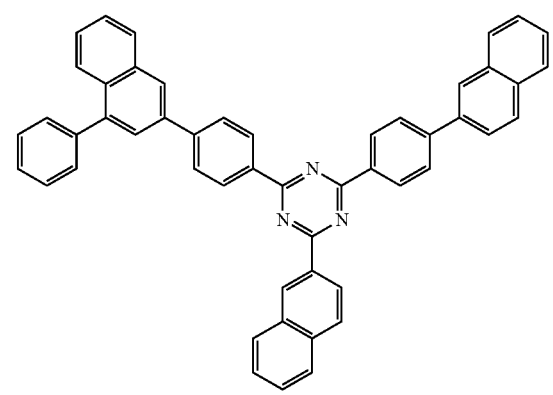
N-94
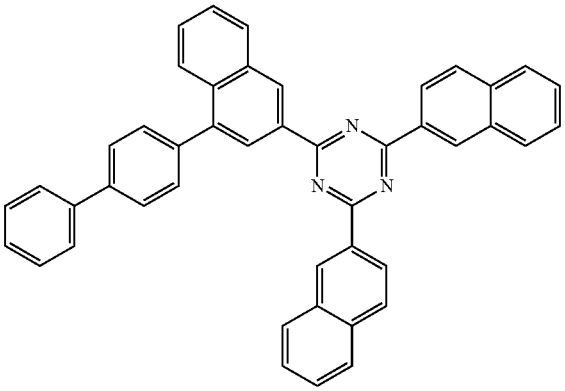
N-95
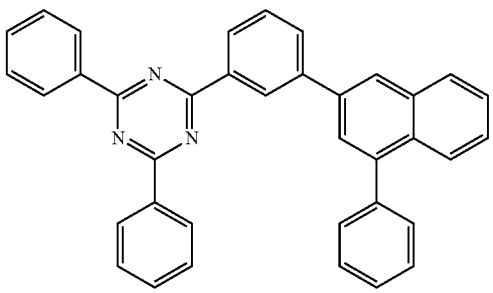

N-96
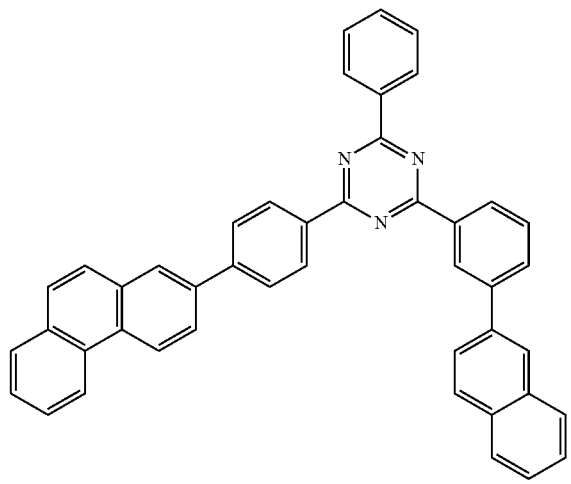
N-97
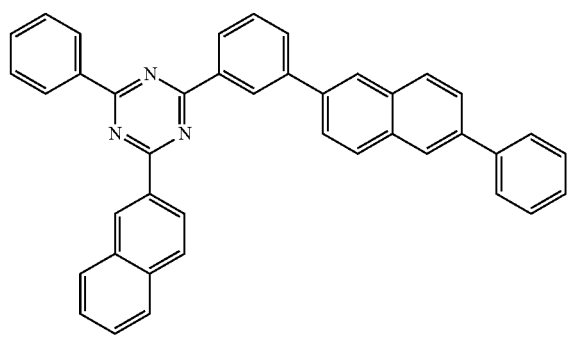
N-98
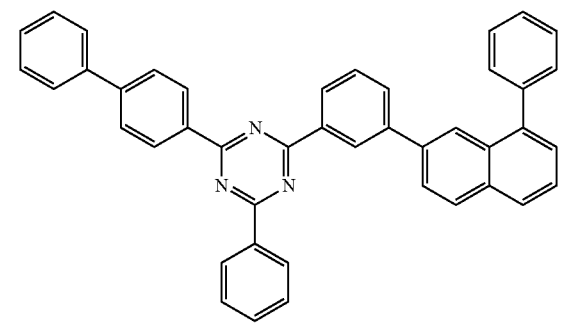
N-99
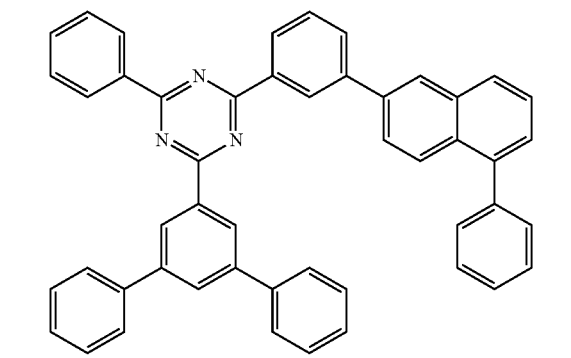
N-100
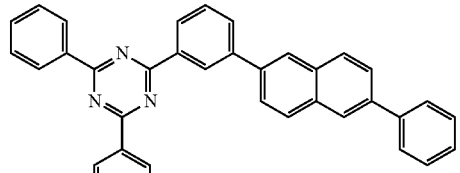
N-101
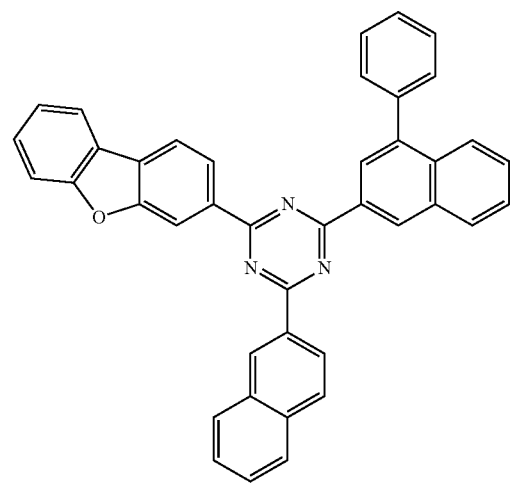
N-102
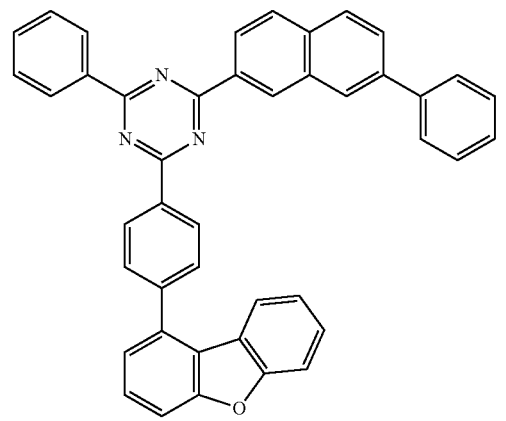

N-103
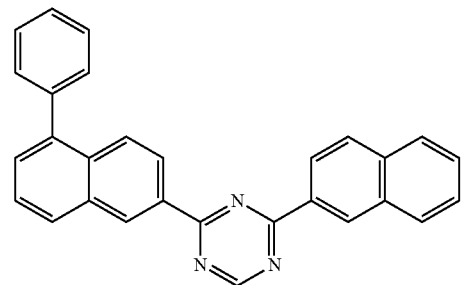
N-104
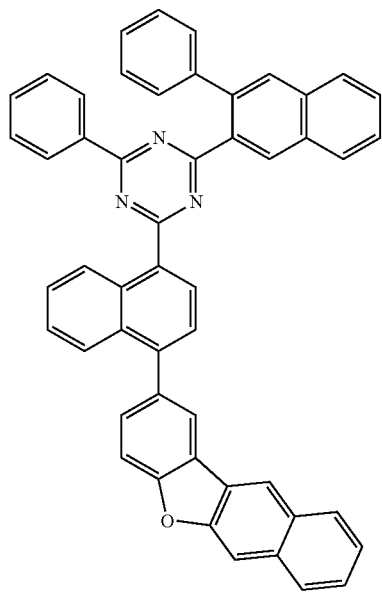
N-105
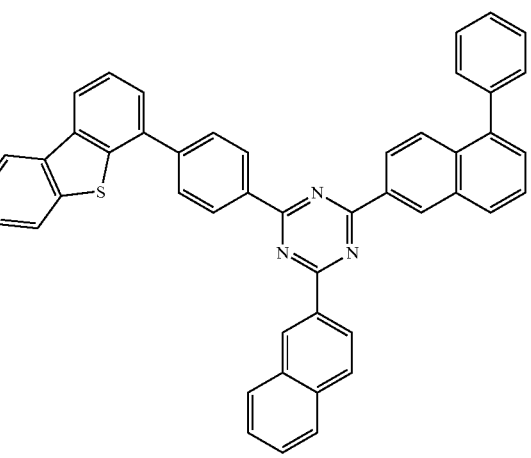
N-106
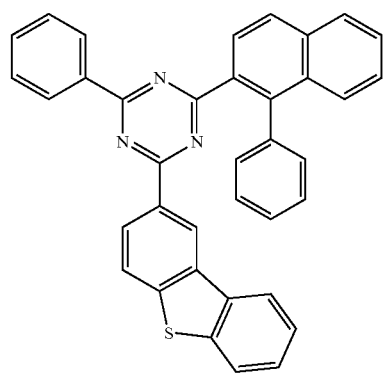
N-107
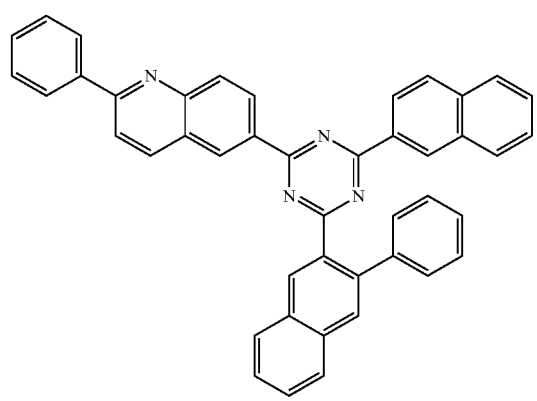
N-108
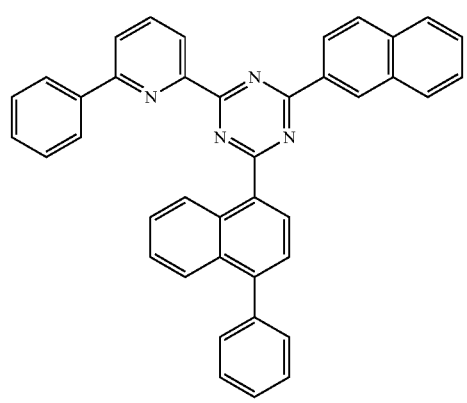
N-109
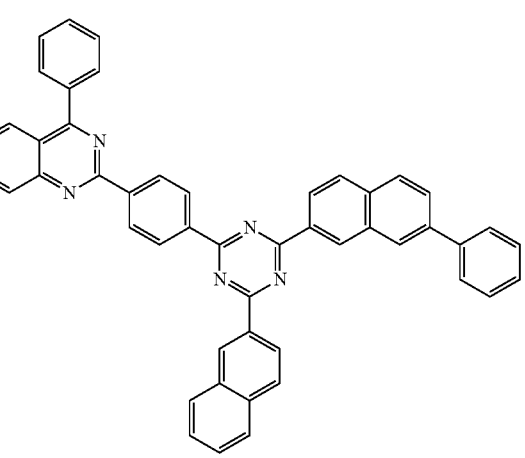

N-110
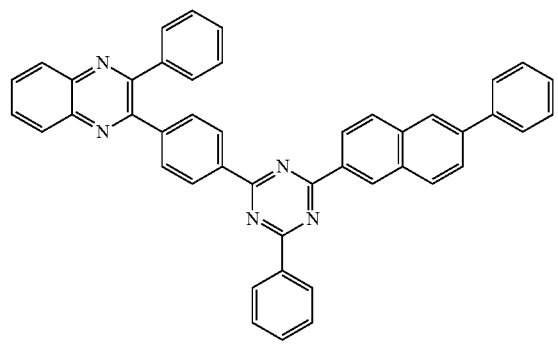
N-111
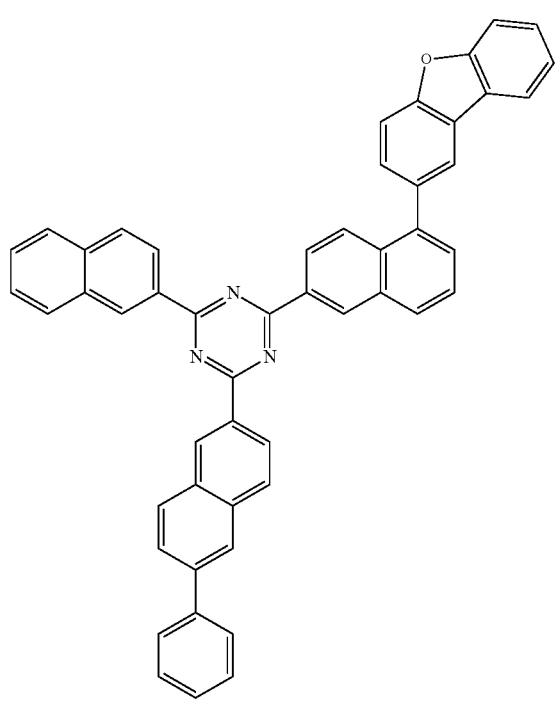
N-112
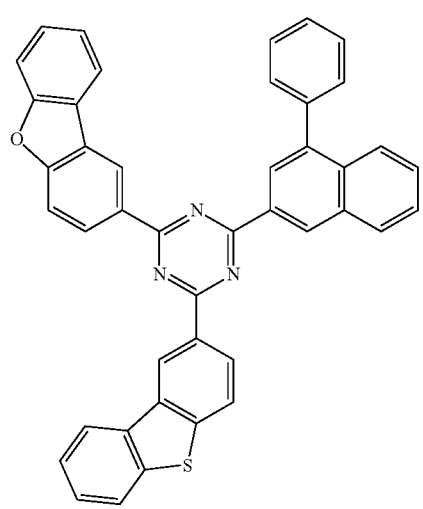
N-113
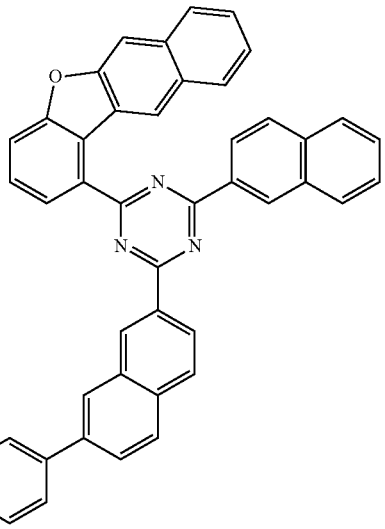
N-114
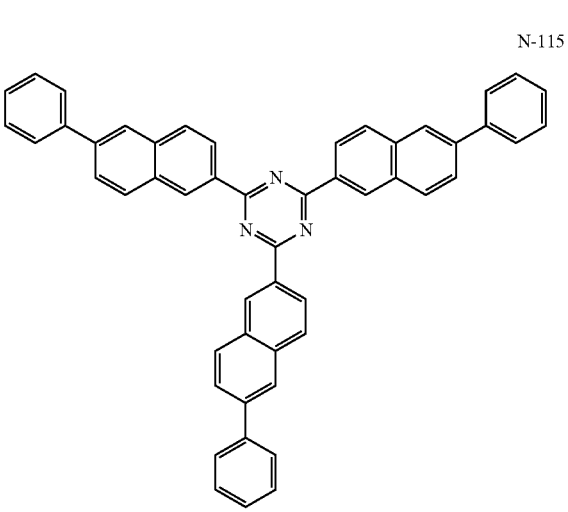
N-115

527
-continued
N-116
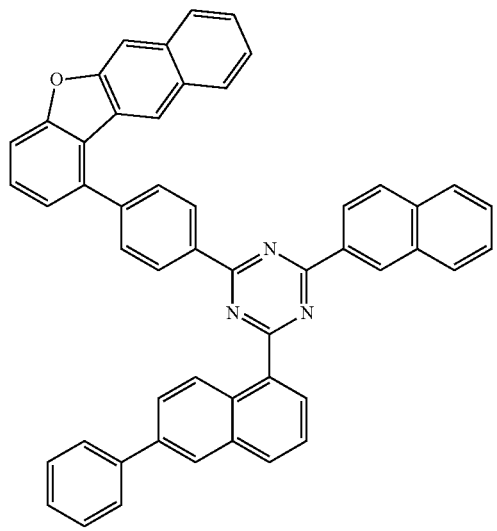
N-117
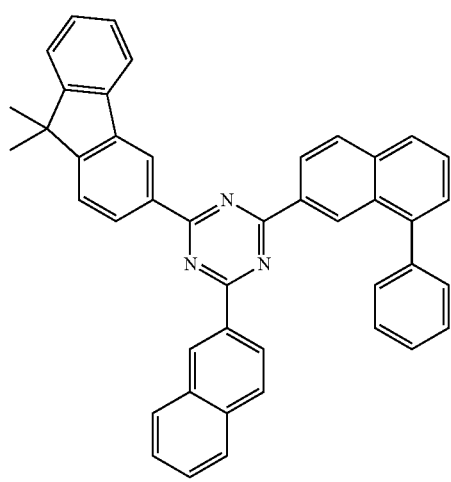
528
-continued
N-119
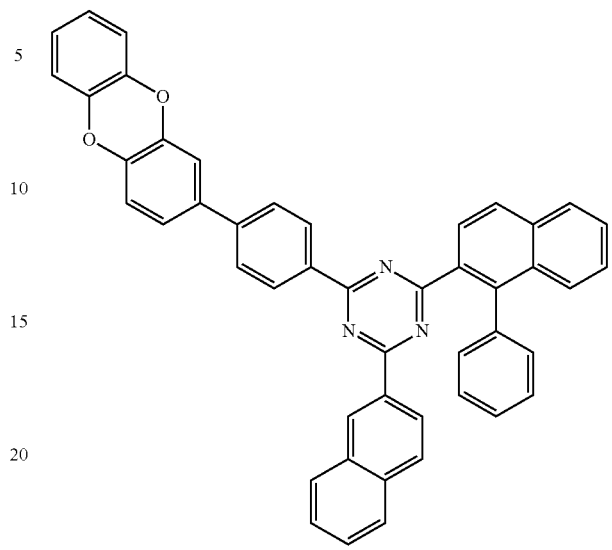
N-120
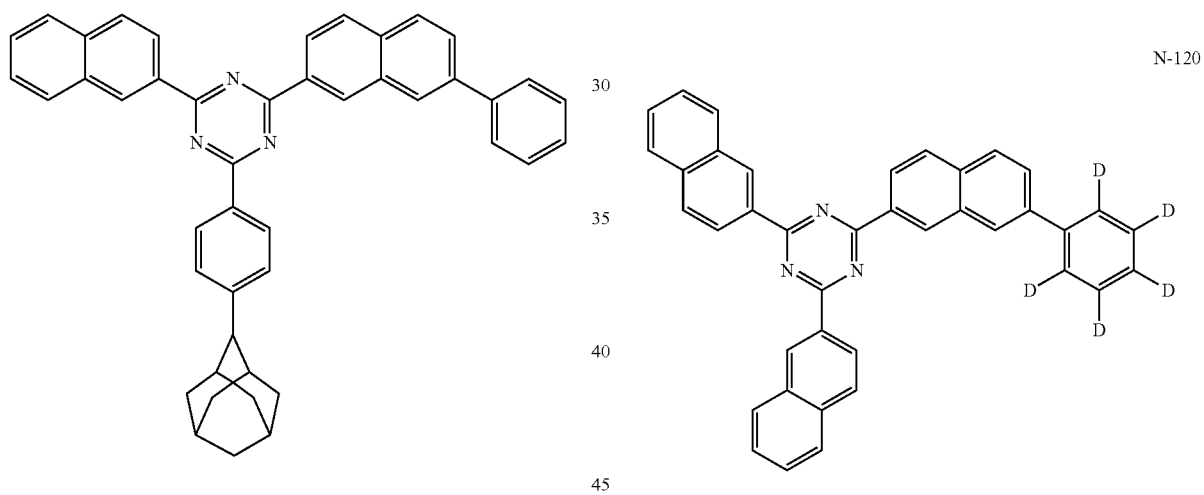
N-118
N-121
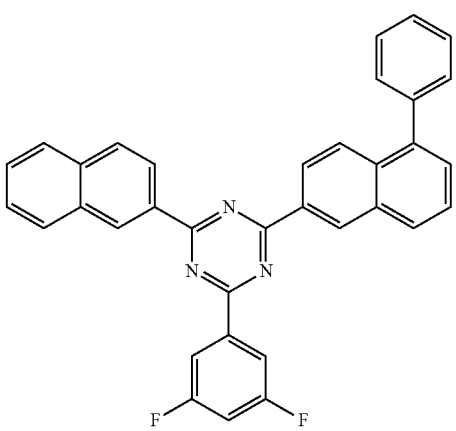

N-122
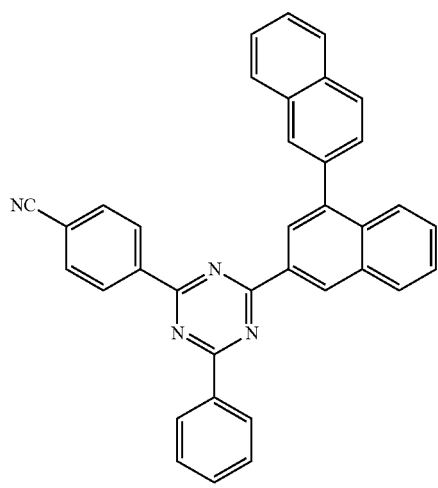
N-125
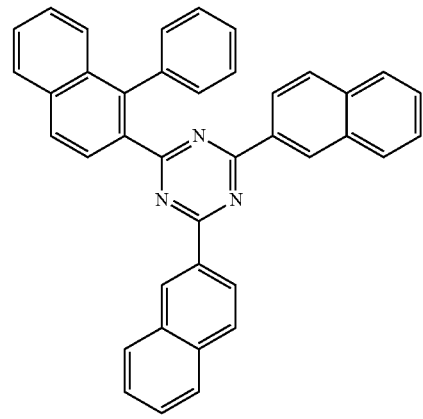
N-123
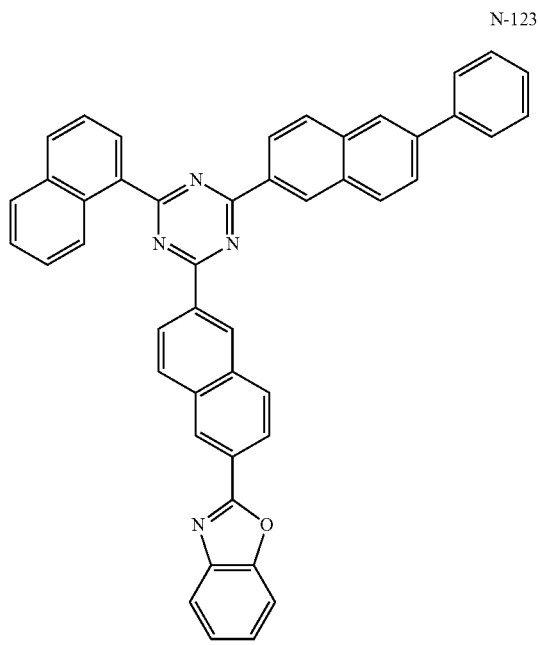
N-126
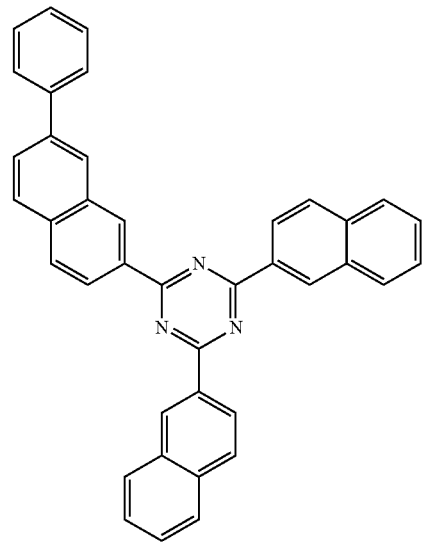
N-124
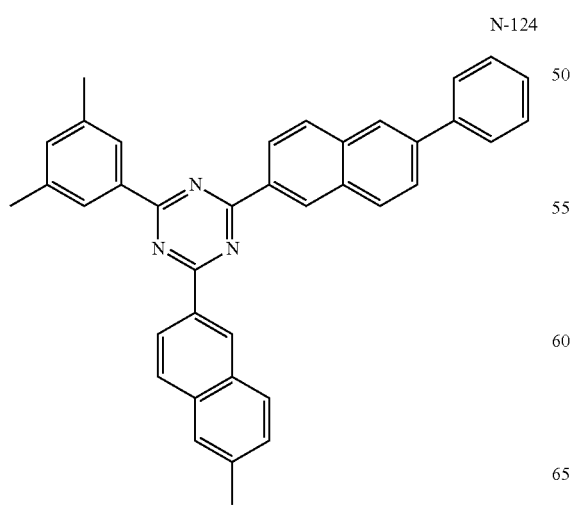
N-127
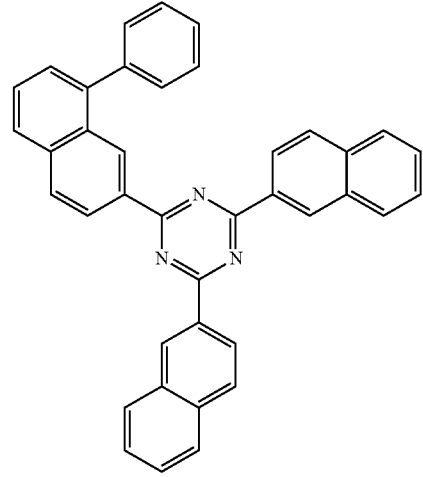

N-128
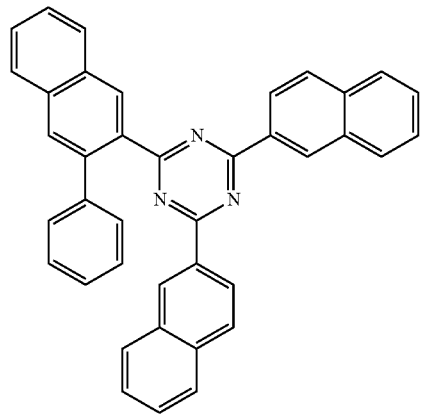
N-129
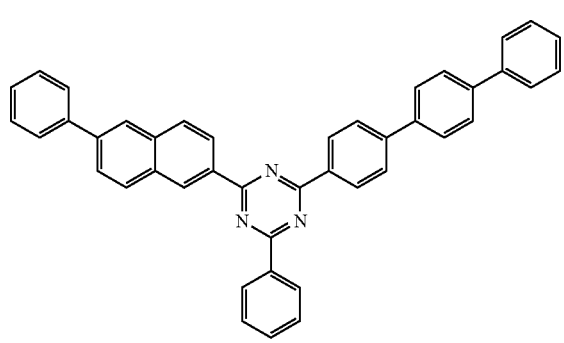
N-130
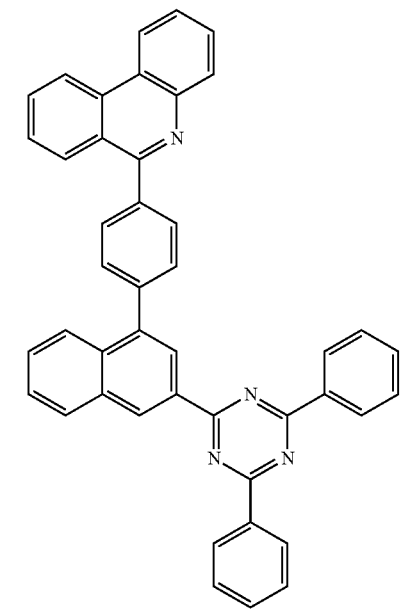
N-131
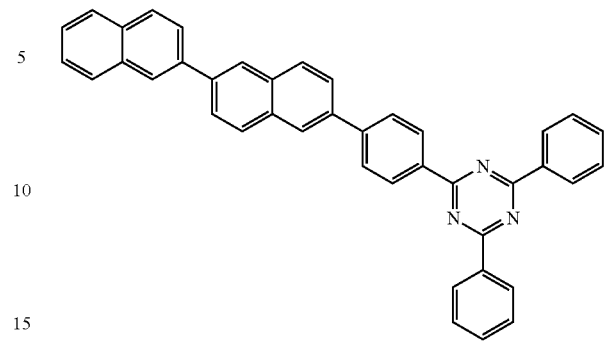
N-132
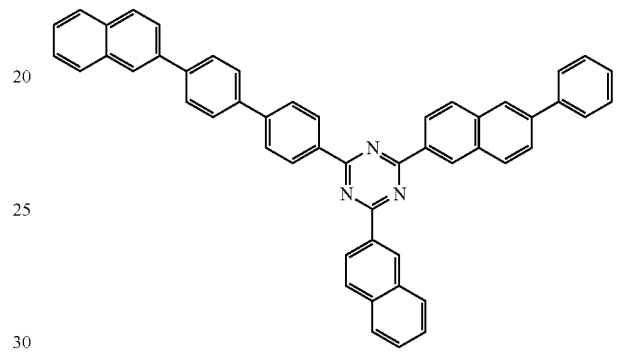
N-133
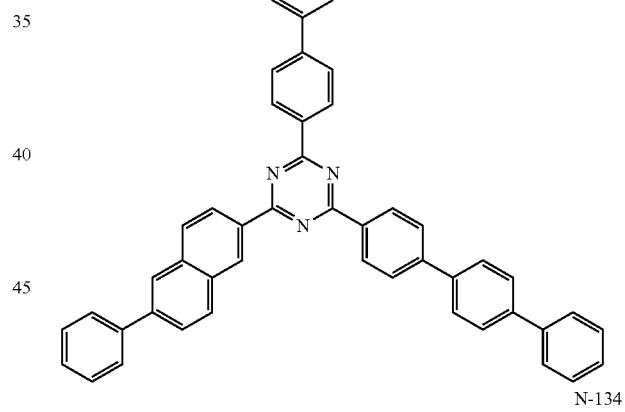
N-134
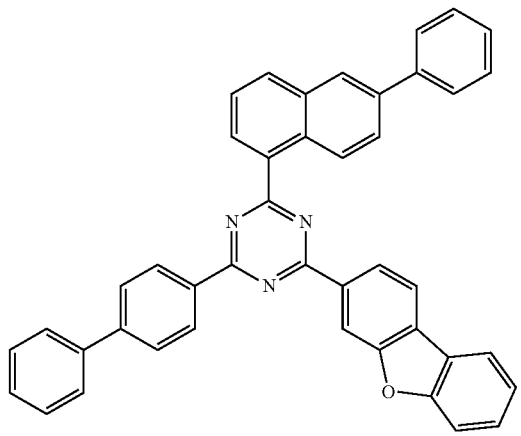

N-135
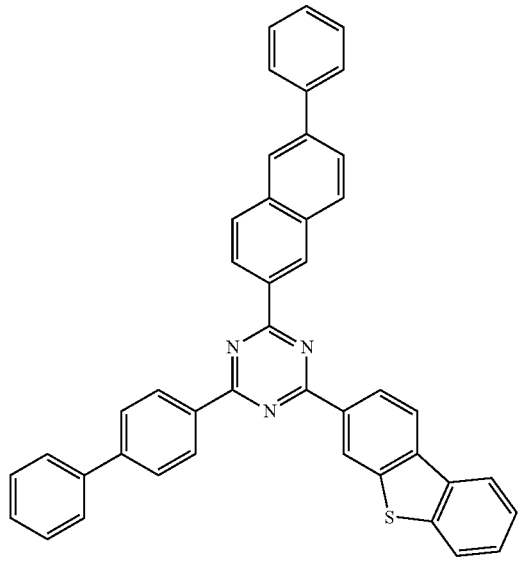
N-136
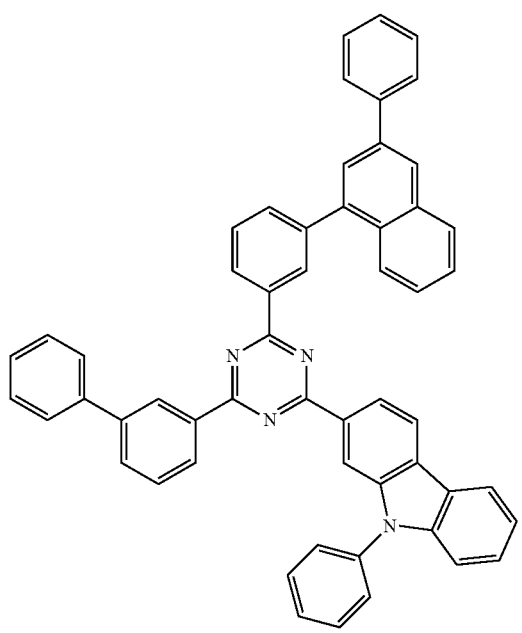
N-137
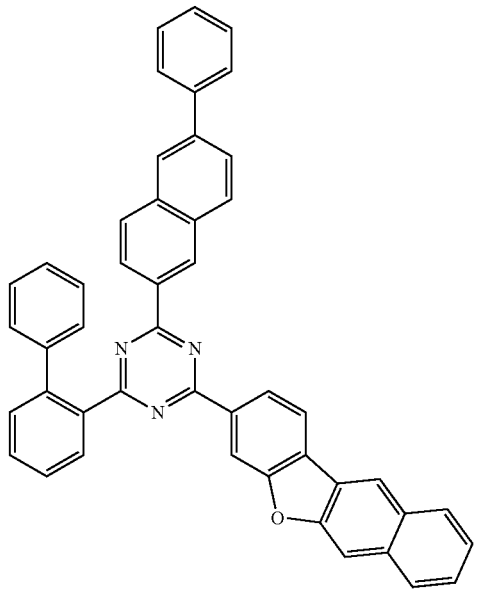
N-138
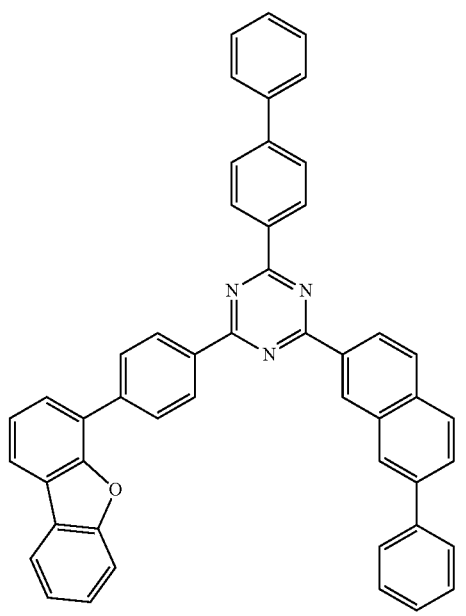
N-139
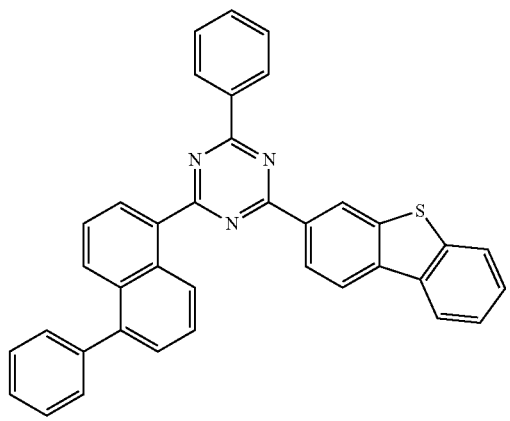

N-140
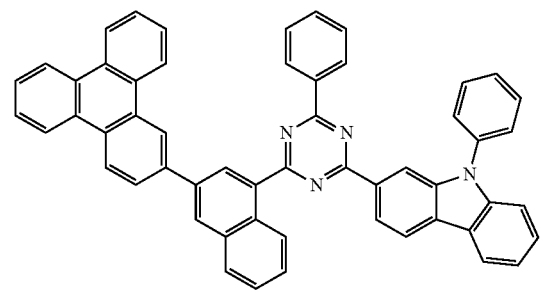
N-141
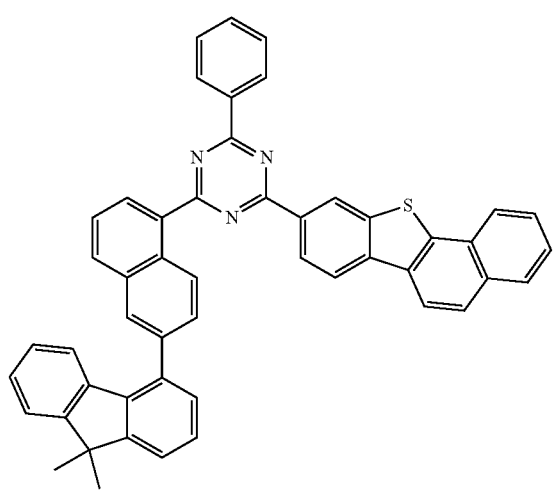
N-142
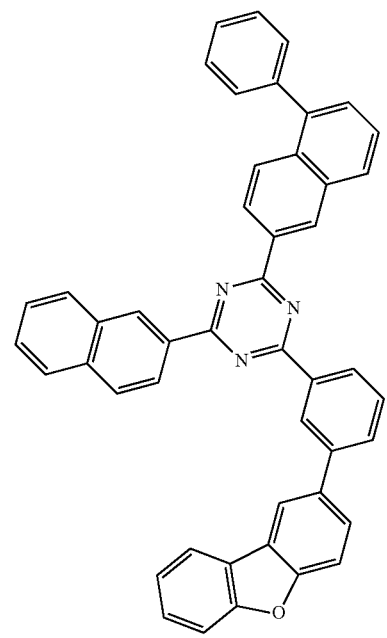
N-143
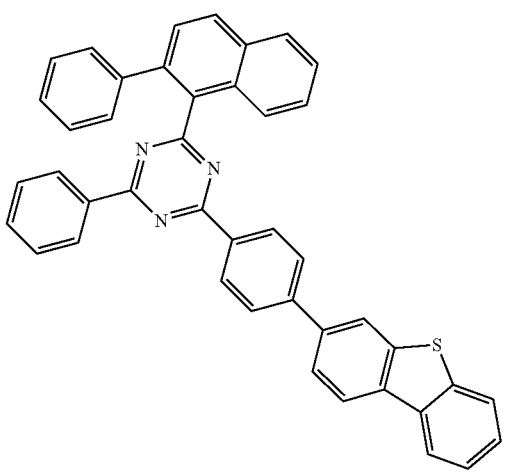
N-144
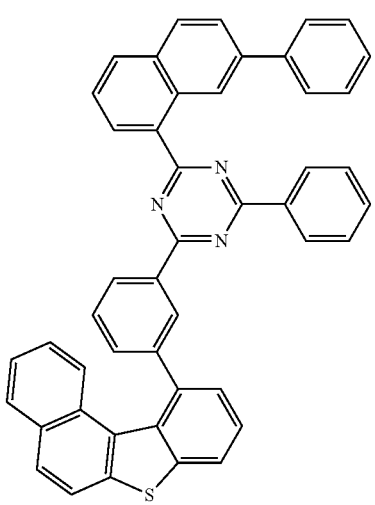
N-145
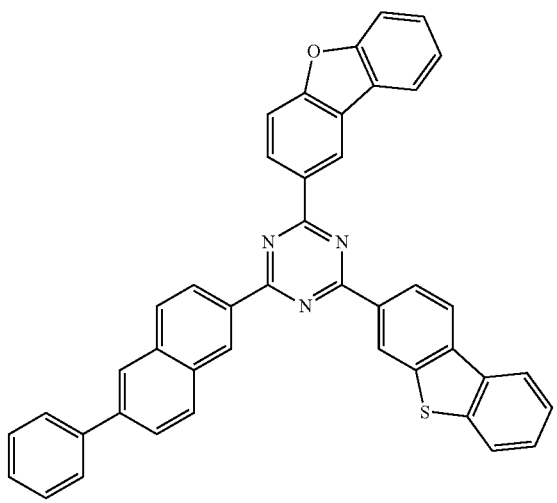

N-146

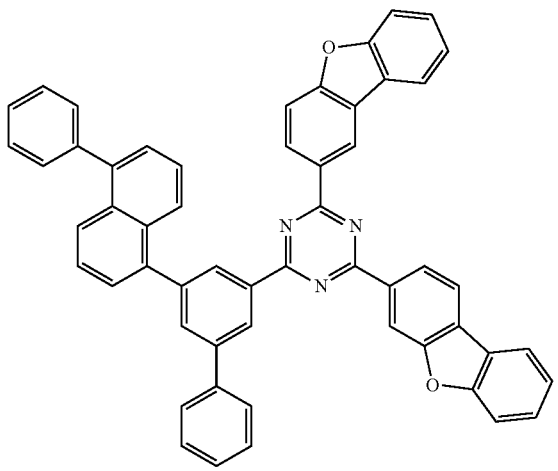

N-148

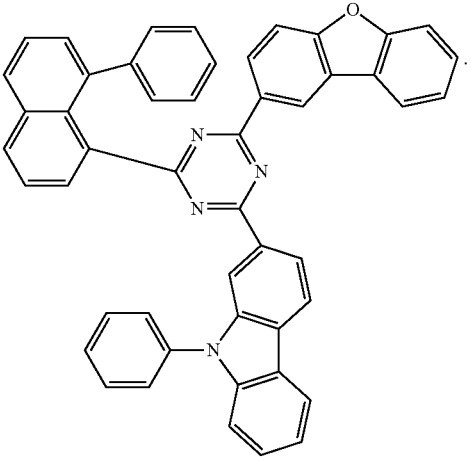

N-147

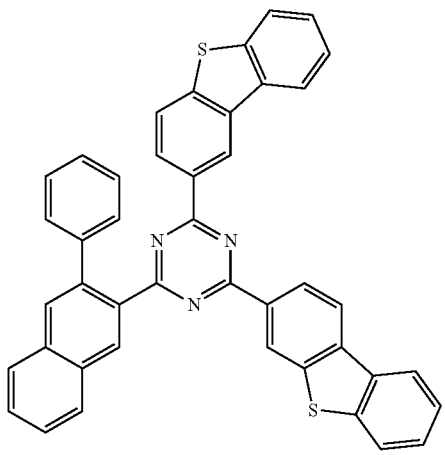

16. The organic electronic element of claim 6, further comprising a light efficiency enhancing layer formed on at least one surface opposite to the organic material layer among the surfaces of the anode and the cathode.

17. The organic electronic element of claim 6, wherein the organic material layer comprises 2 or more stacks including a hole transport layer, an emitting layer and an electron transport layer sequentially formed on the anode.

18. The organic electronic element of claim 17, wherein the organic material layer further comprises a charge generating layer formed between the 2 or more stacks.

19. An electronic device comprising: a display device including the organic electronic element of claim 6; and a control unit for driving the display device.

20. The electronic device of claim 19, wherein the organic electronic element is any one of an organic electroluminescent device (OLED), an organic solar cell, an organic photoreceptor (OPC), an organic transistor (organic TFT), and an element for monochromic or white illumination.

* * * * *